(12) United States Patent
Kuo et al.

(10) Patent No.: US 9,801,888 B2
(45) Date of Patent: Oct. 31, 2017

(54) PYRIMIDINE COMPOUNDS AS MTOR AND PI3K INHIBITORS

(71) Applicants: DEVELOPMENT CENTER FOR BIOTECHNOLOGY, New Taipei (TW); DCB-USA LLC, Wilmington, DE (US)

(72) Inventors: Mann-Yan Kuo, New Taipei (TW); Ying-Shuan Lee, New Taipei (TW); Paonien Chen, New Taipei (TW); Li Jung Chen, New Taipei (TW); Yann Yu Lu, New Taipei (TW); Yi-Ting Huang, New Taipei (TW); Hung-Yi Hsu, New Taipei (TW); Ping-Kuei Tsai, New Taipei (TW)

(73) Assignee: DEVELOPMENT CENTER FOR BIOTECHNOLOGY, New Taipei (TW)

( * ) Notice: Subject to any disclaimer, the term of this patent is extended or adjusted under 35 U.S.C. 154(b) by 0 days.

(21) Appl. No.: 15/002,806

(22) Filed: Jan. 21, 2016

(65) Prior Publication Data
US 2016/0136176 A1 May 19, 2016

Related U.S. Application Data

(60) Division of application No. 14/192,301, filed on Feb. 27, 2014, now Pat. No. 9,315,491, which is a continuation-in-part of application No. 13/519,535, filed as application No. PCT/IB2010/003347 on Dec. 27, 2010, now abandoned.

(60) Provisional application No. 61/290,437, filed on Dec. 28, 2009.

(51) Int. Cl.
| | |
|---|---|
| *A61K 31/5377* | (2006.01) |
| *A61K 31/541* | (2006.01) |
| *C07D 413/04* | (2006.01) |
| *C07D 413/14* | (2006.01) |
| *C07D 417/14* | (2006.01) |
| *C07D 403/12* | (2006.01) |
| *C07D 401/14* | (2006.01) |
| *C07D 239/47* | (2006.01) |
| *C07D 409/12* | (2006.01) |
| *C07D 413/12* | (2006.01) |
| *A61K 45/06* | (2006.01) |
| *C07D 401/04* | (2006.01) |

(52) U.S. Cl.
CPC ........ *A61K 31/5377* (2013.01); *A61K 31/541* (2013.01); *A61K 45/06* (2013.01); *C07D 239/47* (2013.01); *C07D 401/04* (2013.01); *C07D 401/14* (2013.01); *C07D 403/12* (2013.01); *C07D 409/12* (2013.01); *C07D 413/04* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 4,565,864 A | 1/1986 | Wade | |
| 5,250,530 A | 10/1993 | Giencke et al. | |
| 5,420,129 A | 5/1995 | Breu et al. | |
| 7,423,148 B2 | 9/2008 | Nuss et al. | |
| 2008/0280889 A1 | 11/2008 | Bilodeau et al. | |
| 2009/0156601 A1 | 6/2009 | McDonald et al. | |

FOREIGN PATENT DOCUMENTS

| | | |
|---|---|---|
| WO | 00/43385 | 7/2000 |
| WO | 01/81338 A1 | 11/2001 |
| WO | 2007/066099 A1 | 6/2007 |
| WO | 2008/023159 A1 | 2/2008 |
| WO | 2008/032086 A1 | 3/2008 |
| WO | 2008/098058 A1 | 8/2008 |
| WO | 2009/019656 A1 | 2/2009 |

OTHER PUBLICATIONS

Michael J. Berridge et al., "Inositol trisphosphate, a novel second messenger in cellular signal transduction," Nature, vol. 312, No. 22, Nov. 1984, pp. 315-321.
Communication dated Dec. 10, 2014, issued by the Intellectual Property Office of Singapore in Singapore Application No. 2012044517.
Felix Kopp et al., "Functionalization of Unprotected Uracil Derivatives using the Halogen-Magnesium Exchange," Organic Letters, 2007, vol. 9, No. 9, pp. 1639-1641.
International Search Report of PCT/IB10/03347, dated Jun. 14, 2011.
John A. Montgomery et al., "Analogs of 5'-Deoxy-5'-(methylthio)adenosine," J. Med. Chem., 1974, vol. 17, No. 11, pp. 1197-1207.

(Continued)

*Primary Examiner* — Samantha Shterengarts
(74) *Attorney, Agent, or Firm* — Sughrue Mion, PLLC

(57) ABSTRACT

The present invention relates to pyrimidine compounds of formula (I):

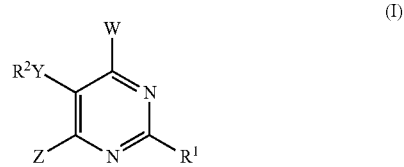

which are useful in treating mTOR kinase- or PI3K kinase-related diseases.

10 Claims, No Drawings

(56) References Cited

OTHER PUBLICATIONS

John Hannah et al., "Carba-acyclonucleoside Antiherpetic Agents," J. of Heterocyclic Chemistry, 1989, 1261-1271.
Office Action dated Apr. 24, 2014 from the European Patent Office in European Application No. 10 840 651.3.
Reinhold Zimmer et al. "Preparation of Pyrimidine-N-oxides by Condensation of Functionalized Enamides with Hydroxylamine Hydrochloride", Synlett, 2010, No. 12, Jul. 1, 2010 (Jul. 1, 2010), p. 1793-1796.
S B Gashev et al: "Aminomethylation of substituted 5-hydroxypyrimidines", Chemistry of Heterocyclic Compounds, Jan. 1, 1980 (Jan. 1, 1980), pp. 532-534.
Extended European Search Report dated Apr. 25, 2013 in European Application No. 10840651.3.
Tilman Lechel et al., "5-Alkoxypyrimidine Derivatives from [beta]-Alkoxy [beta]-Keto Enamides and Ammonium Salts", European Journal of Organic Chemistry, 2010, No. 13, May 1, 2010 (May 1, 2010), pp. 2555-2564.
Tilman Lechel et al., "A Concise Synthesis of Alkoxy-Substituted Pyrimidine Derivatives Based upon a Three-Component Access to Functionalized Enamides", Synlett, 2009, No. 07, Apr. 1, 2009 (Apr. 1, 2009), p. 1059-1062.
Yasutomi Nishizuka, "Turnover of Inositol Phospholipids and Signal Transduction," Science, vol. 225, No. 21, Sep. 1984, pp. 1365-1370.

PYRIMIDINE COMPOUNDS AS MTOR AND PI3K INHIBITORS

CROSS REFERENCE TO RELATED APPLICATIONS

This application is a divisional of U.S. application Ser. No. 14/192,301 filed Feb. 27, 2014, which is a continuation-in-part of U.S. application Ser. No. 13/519,535 filed Jun. 27, 2012, which is a 371 of PCT/M2010/003347 filed Dec. 27, 2010, which claims priority to U.S. Provisional Application No. 61/290,437 filed Dec. 28, 2009, the contents of all of which are incorporated herein by reference in their entirety.

FIELD OF THE INVENTION

The present invention relates to novel pyrimidine compounds and their use in treating PI3K kinase- and/or mTOR kinase-related diseases.

BACKGROUND OF THE INVENTION

The mammalian target of Rapamycin, mTOR, is a cell-signaling protein that regulates the response of tumor cells to nutrients and growth factors, as well as controlling tumor blood supply through effects on Vascular Endothelial Growth Factor, VEGF. Inhibitors of mTOR starve cancer cells and shrink tumors by inhibiting the effect of mTOR. There are two important effects as mTOR inhibitors bind to the mTOR kinase. First, mTOR is a downstream mediator of the PI3K/Akt pathway. The PI3K/Akt pathway is thought to be over-activated in numerous cancers and may account for the widespread response from various cancers to mTOR inhibitors. The over-activation of the upstream pathway would normally cause mTOR kinase to be over-activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is antiangiogenesis via the lowering of VEGF levels. These anticancer drugs have shown exceptional promise in cancer therapy and may change the way many types of cancer are treated.

Several studies have demonstrated that mTOR has a central role in controlling cell growth, proliferation and metabolism. mTOR regulates a wide range of cellular functions, including translation, transcription, mRNA turnover, protein stability, actin cytoskeletal organization and autophagy. mTOR is a member of the phosphoinositide kinase-related kinase (PIKK) family, but is not a phosphorylating phosphoinositide, a phosphorylate protein on serine or a threonine residue. There are two mTOR complexes in mammalian cells. mTOR complex I (mTORC1) is a raptor-mTOR complex, which mainly regulates cell growth in a rapamycin-sensitive manner, whereas mTOR complex II (mTORC2) is a rictor-mTOR complex, which regulates cytoskeletal organization in a rapamycin-insensitive manner. Kinase subunits of both mTORC1 and mTORC2 regulate cell growth and survival in response to nutrient and hormonal signals. mTORC1 is activated in response to growth factors or amino-acids. Amino-acid-signaling to mTORC1 is mediated by Rag GTPases, which cause amino-acid-induced relocalization of mTOR within the endomembrane system. Growth-factor-stimulated mTORC1 activation involves AKT1-mediated phosphorylation of TSC1-TSC2, which leads to the activation of the Rheb GTPase that potently activates the protein kinase activity of mTORC1. Activated mTORC1 up-regulates protein synthesis by phosphorylating key regulators of mRNA translation and ribosome synthesis. mTORC1 phosphorylates eIF4EBP1 and releases it from inhibiting the elongation initiation factor 4E (eIF4E). mTORC1 phosphorylates and activates S6K1 at Thr-421, which then promotes protein synthesis by phosphorylating PDCD4 and targeting it for degradation. mTORC2 is also activated by growth factors, but seems to be nutrient-insensitive. mTORC2 seems to function upstream of Rho GTPases to regulate the actin cytoskeleton, probably by activating one or more Rho-type guanine nucleotide exchange factors. mTORC2 promotes the serum-induced formation of stress-fibers or F-actin. mTORC2 plays a critical role in AKT1 Ser-473 phosphorylation, which may facilitate the phosphorylation of the activation loop of AKT1 on Thr-308 by PDK1, which is a prerequisite for full activation. mTORC2 regulates the phosphorylation of SGK1 at Ser-422. mTORC2 also modulates the phosphorylation of PRKCA on Ser-657.

With the recent discovery of rapamycin independent function of mTOR (by mTOR2) in phosphorylation AKT (at S473), which is important in regulation of cell survival and modulation of PKCα, which plays a major role in regulation of actin cytoskeletal organization, it is believed that inhibition of mTOR function by rapamycin is partial. Therefore, a small molecule designed to compete with ATP in the catalytic site of mTOR would be expected to inhibit all of the kinase-dependent functions of mTORC1 and mTORC2, unlike rapalogs that only target mTORC1. Here we describe the discovery of direct mTOR kinase inhibitors which can be used in the treatment of a variety of cancers, including breast, lung, kidney, prostate, blood, liver, and ovarian cancers, and lymphoma and other indications such as rheumatoid arthritis, hamartoma syndromes, transplant rejection, multiple sclerosis and immunosuppression.

Phosphatidylinositol (hereinafter abbreviated as "PI") is one of the phospholipids in cell membranes. In recent years it has become clear that PI also plays an important role in intracellular signal transduction. In particular, it is well recognized in the art that PI (4,5) bisphosphate (PI(4,5)P2) is degraded into diacylglycerol and inositol (1,4,5) triphosphate by phospholipase C to induce activation of protein kinase C and intracellular calcium mobilization, respectively [M. J. Berridge et al., Nature, 312, 315 (1984); Y. Nishizuka, Science, 225, 1365 (1984)].

PI3K was originally considered to be a single enzyme, but it has now been clarified that a plurality of subtypes is present in PI3K. Each subtype has its own mechanism for regulating activity. The PI3K family comprises at least 15 different enzymes sub-classified by structural homology and divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110α catalytic subunit which phosphorylates its lipid substrate. Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

Most if not all of the non-rapalog mTOR inhibitors described to date in the scientific literature were developed to inhibit other enzymes, especially class I PI3Ks. Because PI3K regulates mTOR activity, inhibitors that target both enzymes are generally not useful as research tools to study mTOR regulation or function. However, drugs that are dual PI3K/mTOR inhibitors might have a therapeutic advantage over single-target inhibitors in certain disease settings. PI3K inhibitors and mTOR inhibitors are expected to be novel types of medicaments useful against cell proliferation disorders, especially as carcinostatic agents. Thus, it would be advantageous to have new mTOR inhibitors and PI3K inhibitors as potential treatment regimens for mTOR kinase- and PI3K kinase-related diseases.

SUMMARY OF THE INVENTION

It has now been found that a series of novel pyrimidine compounds have activity as inhibitors of mTOR and PI3K. Accordingly, the present invention provides a compound of formula (I):

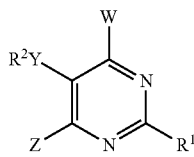

wherein
$R^1$ is selected from:
(i) a group of the following formula:

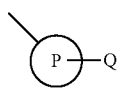

wherein
P is aryl or heteroaryl which is unsubstituted or substituted, wherein when P is a benzoimidazole group, said benzoimidazole group is attached to the pyrimidinyl group in formula (I) through its benzene ring;
Q is selected from —H, —OR, —SR, -Halo, —$NR_3R_4$, —OS(O)$_m$R, —OC(O)R, —OC(O)NHR, —S(O)$_m NR_3R_4$, —NRC(O)R, —NRS(O)$_m$R, —NRC(O)$NR_3R_4$, and —NRC(S)$NR_3R_4$, wherein each R, $R_3$, and $R_4$ is independently selected from H, $C_1$-$C_6$ alkyl, $C_3$-$C_{10}$ cycloalkyl and a 5- to 12-membered carbocyclic group, aryl or heteroaryl group, the group being unsubstituted or substituted; m is 1 or 2; or $R_3$ and $R_4$, which are the same or different, are each independently selected from H, $C_1$-$C_6$ alkyl which is unsubstituted or substituted, $C_3$-$C_{10}$ cycloalkyl which is unsubstituted or substituted, —C(O)R, —C(O)N(R)$_2$ and —S(O)$_m$R wherein R and m are as defined above, or $R_3$ and $R_4$ together with the nitrogen atom to which they are attached form a saturated 5-, 6- or 7-membered N-containing heterocyclic group which is unsubstituted or substituted; —C(O)R, —C(O)N(R)$_2$ and —S(O)$_m$R wherein R and m are as defined above;

Y is selected from —O—(CH$_2$)$_n$—, —S—(CH$_2$)$_n$—, and —S(O)$_m$(CH$_2$)$_n$— wherein m is 1 or 2, n is 0 or an integer of 1 to 3, and $R^2$ is selected from H or a 5- to 12-membered carbocyclic or heterocyclic group which is unsubstituted or substituted, and a group —$NR_3R_4$ wherein $R_3$ and $R_4$ are as defined above;

Z is selected from (i) halo, —(CH$_2$)$_s$—COOR, —(CH$_2$)$_s$CHO, —(CH$_2$)CH$_2$OR, —(CH$_2$)$_s$CONR$_3$R$_4$, —(CH$_2$)$_s$CH$_2$NR$_3$R$_4$, —NR$_3$R$_4$ and —O(CH$_2$)$_s$NR$_3$R$_4$ wherein s is 0 or an integer of 1 to 2 and wherein R, $R_3$ and $R_4$ are as defined above; (ii) substituted or unsubstituted heteroaryl, (iii) substituted or unsubstituted heterocyclyl, (iv) substituted or unsubstituted aryl, and (v) substituted or unsubstituted $C_1$-$C_6$-alkyl; and W is selected from (i) NR$_5$R$_6$, wherein R$_5$ and R$_6$ form, together with the N atom to which they are attached, a morpholine ring which is unsubstituted or substituted, (ii) substituted or unsubstituted heteroaryl, (iii) substituted or unsubstituted heterocyclyl, (iv) substituted or unsubstituted aryl, and (v) substituted or unsubstituted $C_1$-$C_6$-alkyl; or a stereoisomer, or a tautomer, or an N-oxide, or a pharmaceutically acceptable salt, or an ester, or a prodrug, or a hydrate, or a solvate thereof.

Provided herein are pharmaceutical compositions comprising the compound of formula (I), or a stereoisomer, or a tautomer, or an N-oxide, or a pharmaceutically acceptable salt, or an ester, or a prodrug, or a hydrate, or a solvate thereof, and a pharmaceutically acceptable carrier or diluent.

Further provided herein is a method for treating mTOR kinase-/PI3K kinase-related diseases, which comprises administering to a subject an effective amount of the compound of formula (I), or a stereoisomer, or a tautomer, or an N-oxide, or a pharmaceutically acceptable salt, or an ester, or a prodrug, or a hydrate, or a solvate thereof.

Additionally provided herein is a method for preparing the compound of formula (I), or a stereoisomer, or a tautomer, or an N-oxide, or a pharmaceutically acceptable salt, or an ester, or a prodrug, or a hydrate, or a solvate thereof.

DETAILED DESCRIPTION OF THE INVENTION

The present invention relates to a compound of formula (I):

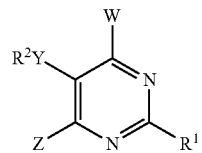

wherein
$R^1$ is selected from:
(i) a group of the following formula:

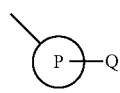

wherein P is aryl or heteroaryl which is unsubstituted or substituted, wherein when P is a benzoimidazole group, said benzoimidazole group is attached to the pyrimidinyl group in formula (I) through its benzene ring;

Q is selected from —H, —OR, —SR, -Halo, —NR$_3$R$_4$, —OS(O)$_m$R, —OC(O)R, —OC(O)NHR, —S(O)$_m$NR$_3$R$_4$, —NRC(O)R, —NRS(O)$_m$R, —NRC(O)NR$_3$R$_4$, and —NRC(S)NR$_3$R$_4$, wherein each R, R$_3$, and R$_4$ is independently selected from H, C$_1$-C$_6$ alkyl, C$_3$-C$_{10}$ cycloalkyl and a 5- to 12-membered carbocyclic group, aryl or heteroaryl group, the group being unsubstituted or substituted; m is 1 or 2; or R$_3$ and R$_4$, which are the same or different, are each independently selected from H, C$_1$-C$_6$ alkyl which is unsubstituted or substituted, C$_3$-C$_{10}$ cycloalkyl which is unsubstituted or substituted, —C(O)R, —C(O)N(R)$_2$ and —S(O)$_m$R wherein R and m are as defined above, or R$_3$ and R$_4$ together with the nitrogen atom to which they are attached form a saturated 5-, 6- or 7-membered N-containing heterocyclic group which is unsubstituted or substituted; —C(O)R, —C(O)N(R)$_2$ and —S(O)$_m$R wherein R and m are as defined above;

Y is selected from —O—(CH$_2$)$_n$—, —S—(CH$_2$)$_n$—, and —S(O)$_m$(CH$_2$)$_n$— wherein m is 1 or 2, n is 0 or an integer of 1 to 3, and R$^2$ is selected from H or a 5- to 12-membered carbocyclic or heterocyclic group which is unsubstituted or substituted, and a group —NR$_3$R$_4$ wherein R$_3$ and R$_4$ are as defined above;

Z is selected from (i) halo, —(CH$_2$)$_s$—COOR, —(CH$_2$)$_s$CHO, —(CH$_2$)$_s$CH$_2$OR, —(CH$_2$)$_s$CONR$_3$R$_4$, —(CH$_2$)$_s$CH$_2$NR$_3$R$_4$, —NR$_3$R$_4$ and —O(CH$_2$)$_s$NR$_3$R$_4$ wherein s is 0 or an integer of 1 to 2 and wherein R, R$_3$ and R$_4$ are as defined above; (ii) substituted or unsubstituted heteroaryl, (iii) substituted or unsubstituted heterocyclyl, (iv) substituted or unsubstituted aryl, and (v) substituted or unsubstituted C$_1$-C$_6$-alkyl; and W is selected from (i) NR$_5$R$_6$, wherein R$_5$ and R$_6$ form, together with the N atom to which they are attached, a morpholine ring which is unsubstituted or substituted, (ii) substituted or unsubstituted heteroaryl, (iii) substituted or unsubstituted heterocyclyl, (iv) substituted or unsubstituted aryl, and (v) substituted or unsubstituted C$_1$-C$_6$-alkyl; or a stereoisomer, or a tautomer, or an N-oxide, or a pharmaceutically acceptable salt, or an ester, or a prodrug, or a hydrate, or a solvate thereof.

Preferably, P is a heteroaryl group selected from:
(a) an indazole group which is unsubstituted or substituted;
(b) an indole group which is unsubstituted or substituted; and
(c) a benzoimidazole group of the formula

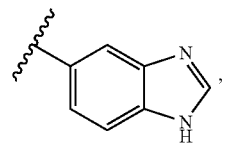 [SMILES: *c1ccc2[nH]cnc2c1]

which is unsubstituted or substituted.

A C$_1$-C$_6$ alkyl group is linear or branched. Preferably, the alkyl is a C$_1$-C$_4$ alkyl group. A C$_1$-C$_6$ alkyl group can be unsubstituted or substituted with one or more groups Z as defined above. Examples of a C$_1$-C$_6$ alkyl group include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

A halogen is F, Cl, Br or I. Preferably, it is F, Cl or Br. A C$_1$-C$_6$ alkyl group substituted by halogen may be denoted by the term "halo-C$_1$-C$_6$ alkyl," which means an alkyl group in which one or more hydrogen atoms are replaced by halo. A halo-C$_1$-C$_6$ alkyl group preferably contains one, two or three halo groups. A preferred halo-C$_1$-C$_6$ alkyl group is trifluoromethyl.

A C$_3$-C$_{10}$ cycloalkyl group may be saturated or unsaturated but a non-aromatic, and/or bridged, and/or non-bridged, and/or fused bicyclic group having 3 to 10 carbon atoms. The cycloalkyl group preferably has 3 to 8, more preferably has 3 to 6 carbon atoms. Examples of a C$_3$-C$_{10}$ cycloalkyl group include, but are not limited to, cyclopropyl, cyclobutyl, cyclopentyl, cyclopentenyl, cyclohexyl, cyclohexenyl, cyclohexadienyl, cycloheptyl, and cycloheptenyl. A C$_3$-C$_{10}$ cycloalkyl group can be unsubstituted or substituted with one or more groups Z as defined above.

An unsaturated 5- to 12-membered carbocyclic group is a 5-, 6-, 7-, 8-, 9-, 10-, 11- or 12-membered carbocyclic ring containing at least one unsaturated bond. It is a monocyclic or fused bicyclic ring system. The group is aromatic or non-aromatic, for instance a 5- to 12-membered aryl group. Examples of an unsaturated 5- to 12-membered carbocyclic group include, but are not limited to, phenyl, naphthyl, indanyl, indenyl and tetrahydronaphthyl groups. The group is unsubstituted or substituted with one or more groups Z as defined above.

An aryl group refers to a 5- to 12-membered, monovalent monocyclic aromatic group and/or monovalent polycyclic aromatic group that contains at least one aromatic carbon ring. Preferably, it is monocyclic or bicyclic. Examples of aryl groups include, but are not limited to, phenyl, naphthyl, fluorenyl, azulenyl, anthryl, phenanthryl, pyrenyl, biphenyl, and terphenyl. The group is unsubstituted or substituted with a group Z as defined above.

A saturated 5-, 6-, or 7-membered N-containing heterocyclic ring refers to a monovalent monocyclic non-aromatic ring system or monovalent polycyclic ring system that contains at least one N and the remaining ring atoms are carbon atoms. Examples of such heterocyclic ring include, but are not limited to, piperidine, piperazine, morpholine or pyrrolidine. The ring typically contains one nitrogen atom and either an additional N atom or an O atom, or no additional heteroatoms. The ring is unsubstituted or substituted on one or more ring carbon atoms and/or on any additional N atom present in the ring. Examples of suitable substituents include one or more groups Z as defined above and a C$_1$-C$_6$ alkyl group. When the ring is piperazine, it is typically unsubstituted or substituted, typically on the second ring nitrogen atom, by —C(O)R, —C(O)N(R)$_2$ or —S(O)$_m$R, or by C$_1$-C$_6$ alkyl which is unsubstituted or substituted by C$_1$-C$_6$ alkoxy or OH.

An unsaturated 5- to 12-membered heterocyclic group is typically heteroaryl. Heteroaryl can be a 5- to 12-membered aromatic group having 1, 2, 3, or 4 heteroatoms selected from O, N and S. Typically it contains one N atom and 0, 1, 2 or 3 additional heteroatoms selected from O, S and N. It may be, for example, furan, thiophene, pyrrole, indole, isoindole, pyrazole, imidazole, benzothiophene, benzothiazole, benzofuran, isoxazole, oxazole, oxadiazole, thiazole, isothiazole, thiadiazole, dihydroimidazole, pyridine, pyridine, quinoline, isoquinoline, quinoxaline, thienopyrazine, pyran, pyrimidine, pyridazine, pyrazine, triazine, triazole or tetrazole. The group can be unsubstituted or substituted with one or more groups Z as defined above.

Specific examples of the compounds of the invention include:
5-Ethoxy-2-(3-hydroxy-phenyl)-6-morpholin-4-yl-pyrimidine-4-carboxylic acid ethyl ester (MTR-0037)
5-Ethoxy-2-(4-hydroxy-3-methoxy-phenyl)-6-morpholin-4-yl-pyrimidine-4-carboxylic acid ethyl ester (MTR-0038)

5-Ethoxy-2-(3-fluoro-4-methoxy-phenyl)-6-morpholin-4-yl-pyrimidine-4-carboxylic acid ethyl ester (MTR-0039)
2-(3-Amino-phenyl)-5-ethoxy-6-morpholin-4-yl-pyrimidine-4-carboxylic acid ethyl ester (MTR-0040)
3-[4-(2-Dimethylamino-ethoxy)-5-methylsulfanyl-6-morpholin-4-yl-pyrimidin-2-yl]-phenol (MTR-0043)
3-[4-(2-Dimethylamino-ethoxy)-5-methylsulfanyl-6-morpholin-4-yl-pyrimidin-2-yl]-phenol (MTR-0046)
3-(5-Methoxy-4-morpholin-4-yl-pyrimidin-2-yl)-phenylamine (MTR-0047)
2-(3,5-Difluoro-phenyl)-5-ethoxy-6-morpholin-4-yl-pyrimidine-4-carboxylic acid ethyl ester (MTR-0053)
5-Ethoxy-2-(1H-indol-5-yl)-6-morpholin-4-yl-pyrimidine-4-carboxylic acid ethyl ester (MTR-0054)
5-Ethoxy-2-(1H-indol-6-yl)-6-morpholin-4-yl-pyrimidine-4-carboxylic acid ethyl ester (MTR-0055)
2-Benzo[1,3]dioxol-5-yl-5-ethoxy-6-morpholin-4-yl-pyrimidine-4-carboxylic acid ethyl ester (MTR-0056)
5-Ethoxy-2-(1H-indazol-4-yl)-6-morpholin-4-yl-pyrimidine-4-carboxylic acid ethyl ester (MTR-0057)
5-Ethoxy-2-(2-fluoro-3-methoxy-phenyl)-6-morpholin-4-yl-pyrimidine-4-carboxylic acid ethyl ester (MTR-0058)
2-{3-[3-(4-Chloro-3-trifluoromethyl-phenyl)-ureido]-phenyl}-5-ethoxy-6-morpholin-4-yl-pyrimidine-4-carboxylic acid ethyl ester (MTR-0059)
5-Ethoxy-6-morpholin-4-yl-2-[3-(3-phenyl-ureido)-phenyl]-pyrimidine-4-carboxylic acid ethyl ester (MTR-0060)
2-(4-Amino-phenyl)-5-ethoxy-6-morpholin-4-yl-pyrimidine-4-carboxylic acid ethyl ester (MTR-0068)
5-Ethoxy-6-morpholin-4-yl-2-[4-(3-phenyl-ureido)-phenyl]-pyrimidine-4-carboxylic acid ethyl ester (MTR-0069)
2-{4-[3-(4-Chloro-3-trifluoromethyl-phenyl)-ureido]-phenyl}-5-ethoxy-6-morpholin-4-yl-pyrimidine-4-carboxylic acid ethyl ester (MTR-0070)
4-(4-Chloro-5-methylsulfanyl-6-morpholin-4-yl-pyrimidin-2-yl)-phenylamine (MTR-0071)
2-(3-Hydroxy-phenyl)-5-methoxy-6-morpholin-4-yl-pyrimidine-4-carboxylic acid ethyl ester (MTR-0073)
5-(4-Chloro-5-methylsulfanyl-6-morpholin-4-yl-pyrimidin-2-yl)-1H-indole (MTR-0074)
2-(1H-Indazol-4-yl)-5-methoxy-6-morpholin-4-yl-pyrimidine-4-carboxylic acid ethyl ester (MTR-0075)
1-[4-(4-Chloro-5-methylsulfanyl-6-morpholin-4-yl-pyrimidin-2-yl)-phenyl]-3-(4-chloro-3-trifluoromethyl-phenyl)-urea (MTR-0076)
1-[4-(4-Chloro-5-methylsulfanyl-6-morpholin-4-yl-pyrimidin-2-yl)-phenyl]-3-(6-chloro-pyridin-3-yl)-urea (MTR-0077)
N-[4-(4-Chloro-5-methylsulfanyl-6-morpholin-4-yl-pyrimidin-2-yl)-phenyl]-acetamide (MTR-0078)
2-{4-[3-(6-Chloro-pyridin-3-yl)-ureido]-phenyl}-5-ethoxy-6-morpholin-4-yl-pyrimidine-4-carboxylic acid ethyl ester (MTR-0079)
5-Ethoxy-2-[4-(3-ethyl-ureido)-phenyl]-6-morpholin-4-yl-pyrimidine-4-carboxylic acid ethyl ester (MTR-0081)
[4-(4-Chloro-5-methylsulfanyl-6-morpholin-4-yl-pyrimidin-2-yl)-phenyl]-urea (MTR-0083)
4-(4-Chloro-5-methylsulfanyl-6-morpholin-4-yl-pyrimidin-2-yl)-1H-indazole (MTR-0084)
Methanesulfonic acid 3-(4-chloro-5-methylsulfanyl-6-morpholin-4-yl-pyrimidin-2-yl)-phenyl ester (MTR-0086)
1-[4-(4-Chloro-5-methylsulfanyl-6-morpholin-4-yl-pyrimidin-2-yl)-phenyl]-3-phenyl-urea (MTR-0091)
3-(4-Chloro-5-methanesulfonyl-6-morpholin-4-yl-pyrimidin-2-yl)-phenol (MTR-0094)
N-[4-(4-Chloro-5-methylsulfanyl-6-morpholin-4-yl-pyrimidin-2-yl)-phenyl]-methane sulfonamide (MTR-0096)
4-(4-Chloro-5-methylsulfanyl-6-morpholin-4-yl-pyrimidin-2-yl)-phenol (MTR-0098)
Methanesulfonic acid 4-(4-chloro-5-methylsulfanyl-6-morpholin-4-yl-pyrimidin-2-yl)-phenyl ester (MTR-0100)
5-Ethoxy-6-morpholin-4-yl-2-[4-(3-phenyl-thioureido)-phenyl]-pyrimidine-4-carboxylic acid ethyl ester (MTR-0102)
2-(4-Benzenesulfonylamino-phenyl)-5-ethoxy-6-morpholin-4-yl-pyrimidine-4-carboxylic acid ethyl ester (MTR-0103)
1-(2-Chloro-ethyl)-3-[4-(4-chloro-5-methylsulfanyl-6-morpholin-4-yl-pyrimidin-2-yl)-phenyl]-urea (MTR-0108)
5-Ethoxy-2-(4-hydroxy-phenyl)-6-morpholin-4-yl-pyrimidine-4-carboxylic acid ethyl ester (MTR-0111)
5-Ethoxy-2-(4-ethylcarbamoyloxy-phenyl)-6-morpholin-4-yl-pyrimidine-4-carboxylic acid ethyl ester (MTR-0112)
5-Ethoxy-6-morpholin-4-yl-2-(4-phenylcarbamoyloxy-phenyl)-pyrimidine-4-carboxylic acid ethyl ester (MTR-0113)
(2-Chloro-ethyl)-carbamic acid 4-(4-chloro-5-methylsulfanyl-6-morpholin-4-yl-pyrimidin-2-yl)-phenyl ester (MTR-0114)
Benzenesulfonic acid 4-(4-chloro-5-methylsulfanyl-6-morpholin-4-yl-pyrimidin-2-yl)-phenyl ester (MTR-0115)
3-(5-Methoxy-4-morpholin-4-yl-pyrimidin-2-yl)-phenol (MTR-0116)
5-Ethoxy-6-morpholin-4-yl-2-[4-(3-phenyl-ureido)-phenyl]-pyrimidine-4-carboxylic acid (MTR-0118)
N-[4-(4-Chloro-5-methylsulfanyl-6-morpholin-4-yl-pyrimidin-2-yl)-phenyl]-benzenesulfonamide (MTR-0119)
5-Ethoxy-6-morpholin-4-yl-2-[4-(3-phenyl-ureido)-phenyl]-pyrimidine-4-carboxylic acid diethylamide (MTR-0120)
5-Ethoxy-6-morpholin-4-yl-2-(4-ureido-phenyl)-pyrimidine-4-carboxylic acid ethyl ester (MTR-0121)
1-[4-(4-Chloro-5-methylsulfanyl-6-morpholin-4-yl-pyrimidin-2-yl)-phenyl]-3-(4-dimethylamino-phenyl)-urea (MTR-0123)
1-{4-[5-Ethoxy-4-(morpholine-4-carbonyl)-6-morpholin-4-yl-pyrimidin-2-yl]-phenyl}-3-phenyl-urea (MTR-0124)
5-Ethoxy-6-morpholin-4-yl-2-[4-(3-phenyl-ureido)-phenyl]-pyrimidine-4-carboxylic acid amide (MTR-0125)
Phenyl-carbamic acid 4-(5-methoxy-4-morpholin-4-yl-pyrimidin-2-yl)-phenyl ester (MTR-0127)
1-[4-(5-Methoxy-4-morpholin-4-yl-pyrimidin-2-yl)-phenyl]-3-phenyl-urea (MTR-0128)
1-Ethyl-3-[4-(5-methoxy-4-morpholin-4-yl-pyrimidin-2-yl)-phenyl]-urea (MTR-0129)
Ethyl-carbamic acid 4-(5-methoxy-4-morpholin-4-yl-pyrimidin-2-yl)-phenyl ester (MTR-0130)
4-(4-Chloro-5-methylsulfanyl-6-morpholin-4-yl-pyrimidin-2-yl)-benzenesulfonamide (MTR-0131)
1-[4-(4-Chloro-5-methylsulfanyl-6-morpholin-4-yl-pyrimidin-2-yl)-phenyl]-3-ethyl-urea (MTR-0132)
5-(4-Chloro-5-methylsulfanyl-6-morpholin-4-yl-pyrimidin-2-yl)-pyridin-2-ylamine (MTR-0133)
1-[5-(4-Chloro-5-methylsulfanyl-6-morpholin-4-yl-pyrimidin-2-yl)-pyridin-2-yl]-3-phenyl-urea (MTR-0134)
1-[4-(4-Chloro-5-methylsulfanyl-6-morpholin-4-yl-pyrimidin-2-yl)-phenyl]-3-(4-fluoro-phenyl)-urea (MTR-0135)
1-[5-(4-Chloro-5-methylsulfanyl-6-morpholin-4-yl-pyrimidin-2-yl)-pyridin-2-yl]-3-ethyl-urea (MTR-0136)
1-[4-(4-Chloro-5-methylsulfanyl-6-morpholin-4-yl-pyrimidin-2-yl)-phenyl]-3-(3-fluoro-phenyl)-urea (MTR-0137)

1-[4-(4-Chloro-5-methylsulfanyl-6-morpholin-4-yl-pyrimidin-2-yl)-phenyl]-3-(3,4-difluoro-phenyl)-urea (MTR-0138)

5-Ethoxy-6-morpholin-4-yl-2-[4-(3-phenyl-ureido)-phenyl]-pyrimidine-4-carboxylic acid (2-morpholin-4-yl-ethyl)-amide (MTR-0139)

5-Ethoxy-6-morpholin-4-yl-2-[4-(3-phenyl-ureido)-phenyl]-pyrimidine-4-carboxylic acid (2-pyrrolidin-1-yl-ethyl)-amide (MTR-0140)

1-{4-[5-Ethoxy-4-morpholin-4-yl-6-(pyrrolidine-1-carbonyl)-pyrimidin-2-yl]-phenyl}-3-phenyl-urea (MTR-0141)

1-{4-[5-Ethoxy-4-morpholin-4-yl-6-(piperidine-1-carbonyl)-pyrimidin-2-yl]-phenyl}-3-phenyl-urea (MTR-0142)

1-[5-(4-Chloro-5-methylsulfanyl-6-morpholin-4-yl-pyrimidin-2-yl)-pyridin-2-yl]-3-(3-fluoro-phenyl)-urea (MTR-0143)

5-Ethoxy-6-morpholin-4-yl-2-[4-(3-phenyl-ureido)-phenyl]-pyrimidine-4-carboxylic acid (2-diethylamino-ethyl)-amide (MTR-0144)

1-{4-[5-Ethoxy-4-(4-methanesulfonyl-piperazine-1-carbonyl)-6-morpholin-4-yl-pyrimidin-2-yl]-phenyl}-3-phenyl-urea (MTR-0145)

2-(6-Amino-pyridin-3-yl)-5-ethoxy-6-morpholin-4-yl-pyrimidine-4-carboxylic acid ethyl ester (MTR-0146)

5-Ethoxy-2-{4-[3-(3-fluoro-phenyl)-ureido]-phenyl}-6-morpholin-4-yl-pyrimidine-4-carboxylic acid ethyl ester (MTR-0147)

5-Ethoxy-6-morpholin-4-yl-2-[6-(3-phenyl-ureido)-pyridin-3-yl]-pyrimidine-4-carboxylic acid ethyl ester (MTR-0148)

5-Ethoxy-2-{4-[3-(4-fluoro-phenyl)-ureido]-phenyl}-6-morpholin-4-yl-pyrimidine-4-carboxylic acid ethyl ester (MTR-0149)

2-{4-[3-(3,4-Difluoro-phenyl)-ureido]-phenyl}-5-ethoxy-6-morpholin-4-yl-pyrimidine-4-carboxylic acid ethyl ester (MTR-0150)

1-(4-Fluoro-phenyl)-3-[4-(5-methoxy-4-morpholin-4-yl-pyrimidin-2-yl)-phenyl]-urea (MTR-0152)

4-(5-Methoxy-4-morpholin-4-yl-pyrimidin-2-yl)-phenylamine (MTR-0153)

4-(5-Methylsulfanyl-4-morpholin-4-yl-pyrimidin-2-yl)-phenylamine (MTR-0154)

4-(5-Methylsulfanyl-4-morpholin-4-yl-pyrimidin-2-yl)-phenol (MTR-0155)

5-Ethoxy-2-{6-[3-(4-fluoro-phenyl)-ureido]-pyridin-3-yl}-6-morpholin-4-yl-pyrimidine-4-carboxylic acid ethyl ester (MTR-0156)

2-{6-[3-(3,4-Difluoro-phenyl)-ureido]-pyridin-3-yl}-5-ethoxy-6-morpholin-4-yl-pyrimidine-4-carboxylic acid ethyl ester (MTR-0157)

5-Ethoxy-2-{6-[3-(3-fluoro-phenyl)-ureido]-pyridin-3-yl}-6-morpholin-4-yl-pyrimidine-4-carboxylic acid ethyl ester (MTR-0158)

1-Ethyl-3-[4-(5-methylsulfanyl-4-morpholin-4-yl-pyrimidin-2-yl)-phenyl]-urea (MTR-0159)

4-[5-Ethoxy-4-(4-methanesulfonyl-piperazin-1-ylmethyl)-6-morpholin-4-yl-pyrimidin-2-yl]-1H-indazole (MTR-0160)

4-[5-Ethoxy-4-(4-methanesulfonyl-piperazin-1-ylmethyl)-6-morpholin-4-yl-pyrimidin-2-yl]-phenylamine (MTR-0161)

1-[4-(5-Methylsulfanyl-4-morpholin-4-yl-pyrimidin-2-yl)-phenyl]-3-phenyl-urea (MTR-0162)

4-(5-Methylsulfanyl-4-morpholin-4-yl-pyrimidin-2-yl)-benzenesulfonamide (MTR-0163)

1-(3-Fluoro-phenyl)-3-[4-(5-methoxy-4-morpholin-4-yl-pyrimidin-2-yl)-phenyl]-urea (MTR-0164)

1-(3,4-Difluoro-phenyl)-3-[4-(5-methoxy-4-morpholin-4-yl-pyrimidin-2-yl)-phenyl]-urea (MTR-0165)

[2-(4-Amino-phenyl)-5-ethoxy-6-morpholin-4-yl-pyrimidin-4-yl]-methanol (MTR-0166)

1-(4-Fluoro-phenyl)-3-[4-(5-methoxy-4-morpholin-4-yl-pyrimidin-2-yl)-phenyl]-thio urea (MTR-0167)

1-(3-Fluoro-phenyl)-3-[4-(5-methoxy-4-morpholin-4-yl-pyrimidin-2-yl)-phenyl]-thio urea (MTR-0168)

1-{4-[5-Ethoxy-4-(4-methanesulfonyl-piperazin-1-ylmethyl)-6-morpholin-4-yl-pyrimidin-2-yl]-phenyl}-3-phenyl-urea (MTR-0169)

4-[5-Ethoxy-4-(4-methyl-piperazin-1-ylmethyl)-6-morpholin-4-yl-pyrimidin-2-yl]-1H-indazole (MTR-0170)

4-[5-Ethoxy-4-(4-methyl-piperazin-1-ylmethyl)-6-morpholin-4-yl-pyrimidin-2-yl]-phenylamine (MTR-0171)

1-{4-[5-Ethoxy-4-(4-methyl-piperazin-1-ylmethyl)-6-morpholin-4-yl-pyrimidin-2-yl]-phenyl}-3-phenyl-urea (MTR-0172)

1-{4-[4-(4-Methanesulfonyl-piperazin-1-yl)-5-methylsulfanyl-6-morpholin-4-yl-pyrimidin-2-yl]-phenyl}-3-phenyl-urea (MTR-0173)

4-(5-Ethoxy-4-morpholin-4-yl-6-morpholin-4-ylmethyl-pyrimidin-2-yl)-1H-indazole (MTR-0174)

4-(5-Ethoxy-4-morpholin-4-yl-6-morpholin-4-ylmethyl-pyrimidin-2-yl)-phenylamine (MTR-0175)

1-[4-(5-Ethoxy-4-morpholin-4-yl-6-morpholin-4-ylmethyl-pyrimidin-2-yl)-phenyl]-3-phenyl-urea (MTR-0176)

1-(3,4-Difluoro-phenyl)-3-[4-(5-methylsulfanyl-4-morpholin-4-yl-pyrimidin-2-yl)-phenyl]-urea (MTR-0177)

1-(4-Fluoro-phenyl)-3-[4-(5-methylsulfanyl-4-morpholin-4-yl-pyrimidin-2-yl)-phenyl]-urea (MTR-0178)

3-[5-Ethoxy-4-(4-methanesulfonyl-piperazin-1-ylmethyl)-6-morpholin-4-yl-pyrimidin-2-yl]-phenol (MTR-0180)

2-(4-Amino-phenyl)-5-methoxy-6-morpholin-4-yl-pyrimidine-4-carboxylic acid ethyl ester (MTR-0181)

5-Methoxy-6-morpholin-4-yl-2-[4-(3-phenyl-ureido)-phenyl]-pyrimidine-4-carboxylic acid ethyl ester (MTR-0182)

5-Methoxy-6-morpholin-4-yl-2-[4-(3-phenyl-ureido)-phenyl]-pyrimidine-4-carboxylic acid (MTR-0183)

1-{4-[5-Methoxy-4-(morpholine-4-carbonyl)-6-morpholin-4-yl-pyrimidin-2-yl]-phenyl}-3-phenyl-urea (MTR-0184)

1-{4-[4-(4-Methanesulfonyl-piperazine-1-carbonyl)-5-methoxy-6-morpholin-4-yl-pyrimidin-2-yl]-phenyl}-3-phenyl-urea (MTR-0185)

1-{4-[5-Ethoxy-4-(4-methyl-piperazine-1-carbonyl)-6-morpholin-4-yl-pyrimidin-2-yl]-phenyl}-3-phenyl-urea (MTR-0186)

[2-(4-Amino-phenyl)-5-methylsulfanyl-6-morpholin-4-yl-pyrimidin-4-yl]-acetic acid methyl ester (MTR-0187)

{5-Methylsulfanyl-6-morpholin-4-yl-2-[4-(3-phenyl-ureido)-phenyl]-pyrimidin-4-yl}-acetic acid methyl ester (MTR-0188)

{5-Methylsulfanyl-6-morpholin-4-yl-2-[4-(3-phenyl-ureido)-phenyl]-pyrimidin-4-yl}-acetic acid (MTR-0189)

2-{5-Methylsulfanyl-6-morpholin-4-yl-2-[4-(3-phenyl-ureido)-phenyl]-pyrimidin-4-yl}-acetamide (MTR-0192)

1-[4-(5-Ethoxy-4-morpholin-4-yl-6-piperidin-1-ylmethyl-pyrimidin-2-yl)-phenyl]-3-phenyl-urea (MTR-0193)

1-[4-(4-Chloro-5-methylsulfanyl-6-morpholin-4-yl-pyrimidin-2-yl)-phenyl]-3-methyl-urea (MTR-0195)

1-[4-(4-Chloro-5-methylsulfanyl-6-morpholin-4-yl-pyrimidin-2-yl)-phenyl]-3-morpholin-4-yl-urea (MTR-0196)

1-[4-(4-Chloro-5-methylsulfanyl-6-morpholin-4-yl-pyrimidin-2-yl)-phenyl]-3-pyridin-3-yl-urea (MTR-0197)
1-[4-(4-Chloro-5-methylsulfanyl-6-morpholin-4-yl-pyrimidin-2-yl)-phenyl]-3-(2-morpholin-4-yl-ethyl)-urea (MTR-0198)
1-[4-(4-Chloro-5-methylsulfanyl-6-morpholin-4-yl-pyrimidin-2-yl)-phenyl]-3-[4-(2-dimethylamino-ethoxy)-phenyl]-urea (MTR-0199)
1-[4-(4-Chloro-5-methylsulfanyl-6-morpholin-4-yl-pyrimidin-2-yl)-phenyl]-3-thiazol-2-yl-urea (MTR-0200)
1-[4-(4-Chloro-5-methylsulfanyl-6-morpholin-4-yl-pyrimidin-2-yl)-phenyl]-3-(4-methyl-piperazin-1-yl)-urea (MTR-0201)
5-Ethoxy-2-[4-(3-methyl-ureido)-phenyl]-6-morpholin-4-yl-pyrimidine-4-carboxylic acid ethyl ester (MTR-0202)
5-Ethoxy-2-{4-[(morpholine-4-carbonyl)-amino]-phenyl}-6-morpholin-4-yl-pyrimidine-4-carboxylic acid ethyl ester (MTR-0203)
2-{4-[3-(3-Dimethylamino-propyl)-ureido]-phenyl}-5-ethoxy-6-morpholin-4-yl-pyrimidine-4-carboxylic acid ethyl ester (MTR-0204)
5-Ethoxy-6-morpholin-4-yl-2-[4-(3-pyridin-3-yl-ureido)-phenyl]-pyrimidine-4-carboxylic acid ethyl ester (MTR-0205)
5-Ethoxy-2-{4-[3-(4-methyl-piperazin-1-yl)-ureido]-phenyl}-6-morpholin-4-yl-pyrimidine-4-carboxylic acid ethyl ester (MTR-0206)
1-[4-(5-Methylsulfanyl-4-morpholin-4-yl-pyrimidin-2-yl)-phenyl]-3-(2-morpholin-4-yl-ethyl)-urea (MTR-0207)
1-(3-Dimethylamino-propyl)-3-[4-(5-methylsulfanyl-4-morpholin-4-yl-pyrimidin-2-yl)-phenyl]-urea (MTR-0208)
1-(4-Methyl-piperazin-1-yl)-3-[4-(5-methylsulfanyl-4-morpholin-4-yl-pyrimidin-2-yl)-phenyl]-urea (MTR-0209)
1-Methyl-3-[4-(5-methylsulfanyl-4-morpholin-4-yl-pyrimidin-2-yl)-phenyl]-urea (MTR-0210)
1-[4-(4-Chloro-5-methylsulfanyl-6-morpholin-4-yl-pyrimidin-2-yl)-phenyl]-3-(3-fluoro-4-morpholin-4-yl-phenyl)-urea (MTR-0211)
4-{3-[4-(4-Chloro-5-methylsulfanyl-6-morpholin-4-yl-pyrimidin-2-yl)-phenyl]-ureido}-benzoic acid ethyl ester (MTR-0212)
1-[4-(4-Chloro-5-methylsulfanyl-6-morpholin-4-yl-pyrimidin-2-yl)-phenyl]-3-[4-(3-oxo-morpholin-4-yl)-phenyl]-urea (MTR-0213)
1-[4-(4-Chloro-5-methylsulfanyl-6-morpholin-4-yl-pyrimidin-2-yl)-phenyl]-3-(3-trifluoromethyl-phenyl)-urea (MTR-0214)
1-[4-(4-Chloro-5-methylsulfanyl-6-morpholin-4-yl-pyrimidin-2-yl)-phenyl]-3-[4-(4-methyl-piperazin-1-yl)-phenyl]-urea (MTR-0215)
1-[4-(4-Chloro-5-methylsulfanyl-6-morpholin-4-yl-pyrimidin-2-yl)-phenyl]-3-(4-thio morpholin-4-yl-phenyl)-urea (MTR-0216)
5-Ethoxy-6-morpholin-4-yl-2-{4-[3-(2-morpholin-4-yl-ethyl)-ureido]-phenyl}-pyrimidine-4-carboxylic acid ethyl ester (MTR-0217)
5-Ethoxy-6-morpholin-4-yl-2-(2-phenylamino-1H-benzoimidazol-5-yl)-pyrimidine-4-carboxylic acid ethyl ester (MTR-0218)
5-Ethoxy-6-morpholin-4-yl-2-[4-(3-morpholin-4-yl-ureido)-phenyl]-pyrimidine-4-carboxylic acid ethyl ester (MTR-0219)
5-Ethoxy-6-morpholin-4-yl-2-[4-(3-thiazol-2-yl-ureido)-phenyl]-pyrimidine-4-carboxylic acid ethyl ester (MTR-0220)
5-Ethoxy-2-{4-[3-(3-fluoro-4-morpholin-4-yl-phenyl)-ureido]-phenyl}-6-morpholin-4-yl-pyrimidine-4-carboxylic acid ethyl ester (MTR-0221)
5-Ethoxy-6-morpholin-4-yl-2-(4-{3-[4-(3-oxo-morpholin-4-yl)-phenyl]-ureido}-phenyl)-pyrimidine-4-carboxylic acid ethyl ester (MTR-0222)
5-Ethoxy-6-morpholin-4-yl-2-{4-[3-(3-trifluoromethyl-phenyl)-ureido]-phenyl}-pyrimidine-4-carboxylic acid ethyl ester (MTR-0223)
1-[4-(5-Methylsulfanyl-4-morpholin-4-yl-pyrimidin-2-yl)-phenyl]-3-morpholin-4-yl-urea (MTR-0224)
1-[4-(5-Methylsulfanyl-4-morpholin-4-yl-pyrimidin-2-yl)-phenyl]-3-pyridin-3-yl-urea (MTR-0225)
1-(3-Fluoro-4-morpholin-4-yl-phenyl)-3-[4-(5-methylsulfanyl-4-morpholin-4-yl-pyrimidin-2-yl)-phenyl]-urea (MTR-0226)
1-[4-(5-Methylsulfanyl-4-morpholin-4-yl-pyrimidin-2-yl)-phenyl]-3-[4-(3-oxo-morpholin-4-yl)-phenyl]-urea (MTR-0227)
1-[4-(5-Methoxy-4-morpholin-4-yl-pyrimidin-2-yl)-phenyl]-3-pyridin-3-yl-urea (MTR-0228)
1-[4-(5-Methoxy-4-morpholin-4-yl-pyrimidin-2-yl)-phenyl]-3-methyl-urea (MTR-0229)
5-Ethoxy-6-morpholin-4-yl-2-[4-(3-pyridin-2-yl-ureido)-phenyl]-pyrimidine-4-carboxylic acid ethyl ester (MTR-0230)
5-Ethoxy-2-(4-{3-[4-(4-methyl-piperazin-1-yl)-phenyl]-ureido}-phenyl)-6-morpholin-4-yl-pyrimidine-4-carboxylic acid ethyl ester (MTR-0231)
5-Ethoxy-6-morpholin-4-yl-2-{4-[3-(4-thiomorpholin-4-yl-phenyl)-ureido]-phenyl}-pyrimidine-4-carboxylic acid ethyl ester (MTR-0232)
5-Ethoxy-6-morpholin-4-yl-2-{4-[3-(4-morpholin-4-yl-phenyl)-ureido]-phenyl}-pyrimidine-4-carboxylic acid ethyl ester (MTR-0233)
2-{4-[3-(2-Amino-phenyl)-thioureido]-phenyl}-5-ethoxy-6-morpholin-4-yl-pyrimidine-4-carboxylic acid ethyl ester (MTR-0234)
1-[4-(4-Chloro-5-methylsulfanyl-6-morpholin-4-yl-pyrimidin-2-yl)-phenyl]-3-(4-morpholin-4-yl-phenyl)-urea (MTR-0235)
1-[4-(4-Chloro-5-methylsulfanyl-6-morpholin-4-yl-pyrimidin-2-yl)-phenyl]-3-[6-(4-methyl-piperazin-1-yl)-pyridin-3-yl]-urea (MTR-0236)
1-[4-(4-Chloro-5-methylsulfanyl-6-morpholin-4-yl-pyrimidin-2-yl)-phenyl]-3-(6-morpholin-4-yl-pyridin-3-yl)-urea (MTR-0237)
1-{4-[4-(4-Methyl-piperazin-1-yl)-5-methylsulfanyl-6-morpholin-4-yl-pyrimidin-2-yl]-phenyl}-3-pyridin-3-yl-urea (MTR-0238)
1-(3,4-Dimethoxy-phenyl)-3-[4-(5-methoxy-4-morpholin-4-yl-pyrimidin-2-yl)-phenyl]-urea (MTR-0239)
1-[4-(5-Methoxy-4-morpholin-4-yl-pyrimidin-2-yl)-phenyl]-3-(3-trifluoromethyl-phenyl)-urea (MTR-0240)
1-[4-(5-Methoxy-4-morpholin-4-yl-pyrimidin-2-yl)-phenyl]-3-[4-(3-oxo-morpholin-4-yl)-phenyl]-urea (MTR-0241)
1-(3-Fluoro-4-morpholin-4-yl-phenyl)-3-[4-(5-methoxy-4-morpholin-4-yl-pyrimidin-2-yl)-phenyl]-urea (MTR-0242)
2-[4-(1H-Benzoimidazol-2-ylamino)-phenyl]-5-ethoxy-6-morpholin-4-yl-pyrimidine-4-carboxylic acid ethyl ester (MTR-0243)
2-{4-[3-(4-Carbamoyl-phenyl)-ureido]-phenyl}-5-ethoxy-6-morpholin-4-yl-pyrimidine-4-carboxylic acid ethyl ester (MTR-0244)

5-Ethoxy-6-morpholin-4-yl-2-[4-(3-pyridin-3-yl-ureido)-phenyl]-pyrimidine-4-carboxylic acid (MTR-0245)
1-[4-(4-Methyl-piperazin-1-yl)-phenyl]-3-[4-(5-methylsulfanyl-4-morpholin-4-yl-pyrimidin-2-yl)-phenyl]-urea (MTR-0246)
1-[4-(5-Methylsulfanyl-4-morpholin-4-yl-pyrimidin-2-yl)-phenyl]-3-(4-thiomorpholin-4-yl-phenyl)-urea (MTR-0247)
1-[4-(5-Methylsulfanyl-4-morpholin-4-yl-pyrimidin-2-yl)-phenyl]-3-(4-morpholin-4-yl-phenyl)-urea (MTR-0248)
1-[4-(5-Methylsulfanyl-4-morpholin-4-yl-pyrimidin-2-yl)-phenyl]-3-thiazol-2-yl-urea (MTR-0249)
2-{4-[3-(3-Acetylamino-phenyl)-ureido]-phenyl}-5-ethoxy-6-morpholin-4-yl-pyrimidine-4-carboxylic acid ethyl ester (MTR-0250)
2-{4-[3-(3-Carbamoyl-phenyl)-ureido]-phenyl}-5-ethoxy-6-morpholin-4-yl-pyrimidine-4-carboxylic acid ethyl ester (MTR-0251)
5-Ethoxy-6-morpholin-4-yl-2-(4-{3-[3-(2,2,2-trifluoroacetylamino)-phenyl]-ureido}-phenyl)-pyrimidine-4-carboxylic acid ethyl ester (MTR-0252)
1-{4-[5-Ethoxy-4-(morpholine-4-carbonyl)-6-morpholin-4-yl-pyrimidin-2-yl]-phenyl}-3-pyridin-3-yl-urea (MTR-0253)
1-[4-(4-Chloro-5-methylsulfanyl-6-morpholin-4-yl-pyrimidin-2-yl)-phenyl]-3-pyridin-2-yl-urea (MTR-0254)
2-{3-[4-(4-Chloro-5-methylsulfanyl-6-morpholin-4-yl-pyrimidin-2-yl)-phenyl]-ureido}-thiophene-3-carboxylic acid methyl ester (MTR-0255)
1-Benzo[1,3]dioxol-5-yl-3-[4-(4-chloro-5-methylsulfanyl-6-morpholin-4-yl-pyrimidin-2-yl)-phenyl]-urea (MTR-0256)
4-{3-[4-(4-Chloro-5-methylsulfanyl-6-morpholin-4-yl-pyrimidin-2-yl)-phenyl]-ureido}-benzamide (MTR-0257)
1-[4-(4-Chloro-5-methylsulfanyl-6-morpholin-4-yl-pyrimidin-2-yl)-phenyl]-3-(3,4-dimethoxy-phenyl)-urea (MTR-0258)
1-[4-(5-Methoxy-4-morpholin-4-yl-pyrimidin-2-yl)-phenyl]-3-(2-morpholin-4-yl-ethyl)-urea (MTR-259)
1-[4-(5-Methoxy-4-morpholin-4-yl-pyrimidin-2-yl)-penta-2,4-dienyl]-3-(4-methyl-piperazin-1-yl)-urea (MTR-0260)
1-[4-(5-Methoxy-4-morpholin-4-yl-pyrimidin-2-yl)-phenyl]-3-(4-morpholin-4-yl-phenyl)-urea (MTR-0261)
1-[4-(5-Methoxy-4-morpholin-4-yl-pyrimidin-2-yl)-phenyl]-3-(4-thiomorpholin-4-yl-phenyl)-urea (MTR-0262)
1-[4-(5-Methylsulfanyl-4-morpholin-4-yl-pyrimidin-2-yl)-phenyl]-3-(3-trifluoromethyl-phenyl)-urea (MTR-0263)
4-{3-[4-(5-Methylsulfanyl-4-morpholin-4-yl-pyrimidin-2-yl)-phenyl]-ureido}-benzoic acid ethyl ester (MTR-0264)
1-[4-(5-Methylsulfanyl-4-morpholin-4-yl-pyrimidin-2-yl)-phenyl]-3-(6-morpholin-4-yl-pyridin-3-yl)-urea (MTR-0265)
1-[6-(4-Methyl-piperazin-1-yl)-pyridin-3-yl]-3-[4-(5-methylsulfanyl-4-morpholin-4-yl-pyrimidin-2-yl)-phenyl]-urea (MTR-0266)
4-{3-[4-(5-Methylsulfanyl-4-morpholin-4-yl-pyrimidin-2-yl)-phenyl]-ureido}-benzamide (MTR-0267)
1-[4-(4-Chloro-5-methylsulfanyl-6-morpholin-4-yl-pyrimidin-2-yl)-phenyl]-3-[5-(4-methyl-piperazin-1-yl)-pyridin-2-yl]-urea (MTR-0268)
N-(3-{3-[4-(4-Chloro-5-methylsulfanyl-6-morpholin-4-yl-pyrimidin-2-yl)-phenyl]-ureido}-phenyl)-2,2,2-trifluoro-acetamide (MTR-0269)
N-(3-{3-[4-(4-Chloro-5-methylsulfanyl-6-morpholin-4-yl-pyrimidin-2-yl)-phenyl]-ureido}-phenyl)-acetamide (MTR-0270)
1-[4-(4-Chloro-5-methylsulfanyl-6-morpholin-4-yl-pyrimidin-2-yl)-phenyl]-3-[4-(4-methyl-piperazine-1-carbonyl)-phenyl]-urea (MTR-0271)
[4-(4-Chloro-5-methylsulfanyl-6-morpholin-4-yl-pyrimidin-2-yl)-phenyl]-carbamic acid phenyl ester (MTR-0272)
5-Ethoxy-6-morpholin-4-yl-2-{4-[3-(4-sulfamoyl-phenyl)-ureido]-phenyl}-pyrimidine-4-carboxylic acid ethyl ester (MTR-0273)
5-Ethoxy-2-(4-{3-[4-(4-methyl-piperazine-1-carbonyl)-phenyl]-ureido}-phenyl)-6-morpholin-4-yl-pyrimidine-4-carboxylic acid ethyl ester (MTR-0274)
5-Ethoxy-2-(4-{3-[6-(4-methyl-piperazin-1-yl)-pyridin-3-yl]-ureido}-phenyl)-6-morpholin-4-yl-pyrimidine-4-carboxylic acid ethyl ester (MTR-0275)
5-Ethoxy-6-morpholin-4-yl-2-{4-[3-(6-morpholin-4-yl-pyridin-3-yl)-ureido]-phenyl}-pyrimidine-4-carboxylic acid ethyl ester (MTR-0276)
2-(4-{3-[4-(2-Dimethylamino-ethylcarbamoyl)-phenyl]-ureido}-phenyl)-5-ethoxy-6-morpholin-4-yl-pyrimidine-4-carboxylic acid ethyl ester (MTR-0277)
5-Ethoxy-2-(4-{3-[4-(morpholine-4-carbonyl)-phenyl]-ureido}-phenyl)-6-morpholin-4-yl-pyrimidine-4-carboxylic acid ethyl ester (MTR-0278)
{4-[5-Ethoxy-4-(morpholine-4-carbonyl)-6-morpholin-4-yl-pyrimidin-2-yl]-phenyl}-carbamic acid phenyl ester (MTR-0279)
1-{4-[5-Ethoxy-4-(morpholine-4-carbonyl)-6-morpholin-4-yl-pyrimidin-2-yl]-phenyl}-3-[4-(3-oxo-morpholin-4-yl)-phenyl]-urea (MTR-0280)
[4-(5-Methoxy-4-morpholin-4-yl-pyrimidin-2-yl)-phenyl]-carbamic acid phenyl ester (MTR-0281)
4-{3-[4-(5-Methoxy-4-morpholin-4-yl-pyrimidin-2-yl)-phenyl]-ureido}-benzamide (MTR-0282)
4-{3-[4-(5-Methoxy-4-morpholin-4-yl-pyrimidin-2-yl)-phenyl]-ureido}-benzenesulfonamide (MTR-0283)
4-(5-Methoxy-4-morpholin-4-yl-pyrimidin-2-yl)-2-nitro-phenylamine (MTR-0284)
1-(2-Amino-phenyl)-3-[4-(5-methoxy-4-morpholin-4-yl-pyrimidin-2-yl)-phenyl]-thio urea (MTR-0285)
[4-(5-Methylsulfanyl-4-morpholin-4-yl-pyrimidin-2-yl)-phenyl]-urea (MTR-0286)
1-(2-Amino-phenyl)-3-[4-(5-methylsulfanyl-4-morpholin-4-yl-pyrimidin-2-yl)-phenyl]-thiourea (MTR-0287)
4-{3-[4-(5-Methylsulfanyl-4-morpholin-4-yl-pyrimidin-2-yl)-phenyl]-ureido}-benzenesulfonamide (MTR-0288)
(1H-Benzoimidazol-2-yl)-[4-(5-methylsulfanyl-4-morpholin-4-yl-pyrimidin-2-yl)-phenyl]-amine (MTR-0289)
[4-(5-Methylsulfanyl-4-morpholin-4-yl-pyrimidin-2-yl)-phenyl]-carbamic acid phenyl ester (MTR-0290)
1-(6-Bromo-pyridin-3-yl)-3-[4-(4-chloro-5-methylsulfanyl-6-morpholin-4-yl-pyrimidin-2-yl)-phenyl]-urea (MTR-0291)
1-(2-Amino-phenyl)-3-[4-(4-chloro-5-methylsulfanyl-6-morpholin-4-yl-pyrimidin-2-yl)-phenyl]-thiourea (MTR-0292)
4-{3-[4-(4-Chloro-5-methylsulfanyl-6-morpholin-4-yl-pyrimidin-2-yl)-phenyl]-thioureido}-benzoic acid (MTR-0293)
5-Ethoxy-2-(4-{3-[5-(4-methyl-piperazin-1-yl)-pyridin-2-yl]-ureido}-phenyl)-6-morpholin-4-yl-pyrimidine-4-carboxylic acid ethyl ester (MTR-0294)
5-Ethoxy-2-{4-[3-(2-methoxycarbonyl-thiophen-3-yl)-ureido]-phenyl}-6-morpholin-4-yl-pyrimidine-4-carboxylic acid ethyl ester (MTR-0296)

5-Ethoxy-2-{4-[3-(1H-indazol-4-yl)-ureido]-phenyl}-6-morpholin-4-yl-pyrimidine-4-carboxylic acid ethyl ester (MTR-0297)
5-Ethoxy-2-{4-[3-(4-methyl-1H-benzotriazol-5-yl)-ureido]-phenyl}-6-morpholin-4-yl-pyrimidine-4-carboxylic acid ethyl ester (MTR-0298)
5-Ethoxy-6-morpholin-4-yl-2-{4-[3-(2-oxo-2,3-dihydro-benzooxazol-5-yl)-ureido]-phenyl}-pyrimidine-4-carboxylic acid ethyl ester (MTR-0299)
2-(4-Amino-3-fluoro-phenyl)-5-ethoxy-6-morpholin-4-yl-pyrimidine-4-carboxylic acid ethyl ester (MTR-0300)
5-Ethoxy-2-(3-fluoro-4-phenoxycarbonylamino-phenyl)-6-morpholin-4-yl-pyrimidine-4-carboxylic acid ethyl ester (MTR-0301)
5-Ethoxy-2-(3-fluoro-4-{3-[4-(3-oxo-morpholin-4-yl)-phenyl]-ureido}-phenyl)-6-morpholin-4-yl-pyrimidine-4-carboxylic acid ethyl ester (MTR-0302)
1-[4-(4-Chloro-5-methylsulfanyl-6-morpholin-4-yl-pyrimidin-2-yl)-phenyl]-3-pyridin-3-yl-thiourea (MTR-0303)
1-[4-(4-Chloro-5-methylsulfanyl-6-morpholin-4-yl-pyrimidin-2-yl)-phenyl]-3-[4-(3-oxo-morpholin-4-yl)-phenyl]-thiourea (MTR-0304)
(1H-Benzoimidazol-2-yl)-[4-(4-chloro-5-methylsulfanyl-6-morpholin-4-yl-pyrimidin-2-yl)-phenyl]-amine (MTR-0305)
1-[4-(4-Chloro-5-methylsulfanyl-6-morpholin-4-yl-pyrimidin-2-yl)-phenyl]-3-isopropyl-urea (MTR-0306)
[4-(4-Chloro-5-methylsulfanyl-6-morpholin-4-yl-pyrimidin-2-yl)-phenyl]-carbamic acid (MTR-0307)
1-[4-(4-Chloro-5-methylsulfanyl-6-morpholin-4-yl-pyrimidin-2-yl)-phenyl]-3-[4-(morpholine-4-carbonyl)-phenyl]-urea (MTR-0308)
4-(5-Methoxy-4-morpholin-4-yl-pyrimidin-2-yl)-benzene-1,2-diamine (MTR-0309)
(1H-Benzoimidazol-2-yl)-[4-(5-methoxy-4-morpholin-4-yl-pyrimidin-2-yl)-phenyl]-amine (MTR-0310)
5-(5-Methoxy-4-morpholin-4-yl-pyrimidin-2-yl)-1H-benzoimidazol-2-ylamine (MTR-0311)
1-[4-(2-Dimethylamino-ethoxy)-phenyl]-3-[4-(5-methoxy-4-morpholin-4-yl-pyrimidin-2-yl)-phenyl]-urea (MTR-0312)
3-{3-[4-(5-Methoxy-4-morpholin-4-yl-pyrimidin-2-yl)-phenyl]-ureido}-benzamide (MTR-0313)
1-[4-(5-Methoxy-4-morpholin-4-yl-pyrimidin-2-yl)-phenyl]-3-thiazol-2-yl-urea (MTR-0314)
1-(3,4-Dimethoxy-phenyl)-3-[4-(5-methylsulfanyl-4-morpholin-4-yl-pyrimidin-2-yl)-phenyl]-urea (MTR-0315)
4-{3-[4-(5-Methylsulfanyl-4-morpholin-4-yl-pyrimidin-2-yl)-phenyl]-ureido}-benzoic acid (MTR-0316)
1-Benzo[1,3]dioxol-5-yl-3-[4-(5-methylsulfanyl-4-morpholin-4-yl-pyrimidin-2-yl)-phenyl]-urea (MTR-0317)
1-[5-(4-Methyl-piperazin-1-yl)-pyridin-2-yl]-3-[4-(5-methylsulfanyl-4-morpholin-4-yl-pyrimidin-2-yl)-phenyl]-urea (MTR-0318)
1-[4-(5-Methylsulfanyl-4-morpholin-4-yl-pyrimidin-2-yl)-phenyl]-3-[4-(3-oxo-morpholin-4-yl)-phenyl]-thiourea (MTR-0319)
2-(4-Amino-2-fluoro-phenyl)-5-ethoxy-6-morpholin-4-yl-pyrimidine-4-carboxylic acid ethyl ester (MTR-0320)
5-Ethoxy-2-(2-fluoro-4-phenoxycarbonylamino-phenyl)-6-morpholin-4-yl-pyrimidine-4-carboxylic acid ethyl ester (MTR-0321)
5-Ethoxy-2-(2-fluoro-4-{3-[4-(3-oxo-morpholin-4-yl)-phenyl]-ureido}-phenyl)-6-morpholin-4-yl-pyrimidine-4-carboxylic acid ethyl ester (MTR-0322)
4-{3-[4-(5-Ethoxy-4-morpholin-4-yl-pyrimidin-2-yl)-phenyl]-ureido}-benzamide (MTR-0323)
1-[4-(5-Ethoxy-4-morpholin-4-yl-pyrimidin-2-yl)-phenyl]-3-(4-thiomorpholin-4-yl-phenyl)-urea (MTR-0324)
1-[4-(5-Ethoxy-4-morpholin-4-yl-pyrimidin-2-yl)-phenyl]-3-[4-(3-oxo-morpholin-4-yl)-phenyl]-urea (MTR-0325)
4-{3-[4-(5-Ethoxy-4-morpholin-4-yl-pyrimidin-2-yl)-phenyl]-ureido}-benzenesulfonamide (MTR-0326)
1-[4-(4-Chloro-5-methylsulfanyl-6-morpholin-4-yl-pyrimidin-2-yl)-phenyl]-2-fluoro-phenylamino-urea (MTR-0327)
1-[4-(4-Chloro-5-methylsulfanyl-6-morpholin-4-yl-pyrimidin-2-yl)-phenyl]-3-(5-morpholin-4-yl-pyridin-2-yl)-urea (MTR-0328)
1-(4-Amino-phenyl)-3-[4-(4-chloro-5-methylsulfanyl-6-morpholin-4-yl-pyrimidin-2-yl)-phenyl]-urea (MTR-0329)
1-tert-Butyl-3-[4-(4-chloro-5-methylsulfanyl-6-morpholin-4-yl-pyrimidin-2-yl)-phenyl]-urea (MTR-0330)
1-[4-(4-Chloro-5-methylsulfanyl-6-morpholin-4-yl-pyrimidin-2-yl)-phenyl]-amino-urea (MTR-0331)
4-(4-Chloro-5-methylsulfanyl-6-morpholin-4-yl-pyrimidin-2-yl)-2-fluoro-phenylamine (MTR-0332)
1-tert-Butylamino-3-[4-(4-chloro-5-methylsulfanyl-6-morpholin-4-yl-pyrimidin-2-yl)-phenyl]-urea (MTR-0333)
1-[4-(5-Methoxy-4-morpholin-4-yl-pyrimidin-2-yl)-phenyl]-3-[5-(4-methyl-piperazin-1-yl)-pyridin-2-yl]-urea (MTR-0334)
1-[4-(5-Methoxy-4-morpholin-4-yl-pyrimidin-2-yl)-phenyl]-3-[4-(3-oxo-morpholin-4-yl)-phenyl]-thiourea (MTR-0335) [4-(5-Methoxy-4-morpholin-4-yl-pyrimidin-2-yl)-phenyl]-urea (MTR-0336)
1-[4-(5-Methoxy-4-morpholin-4-yl-pyrimidin-2-yl)-phenyl]-3-[4-(4-methyl-piperazin-1-yl)-phenyl]-urea (MTR-0337)
1-[4-(5-Methoxy-4-morpholin-4-yl-pyrimidin-2-yl)-phenyl]-3-[6-(4-methyl-piperazin-1-yl)-pyridin-3-yl]-urea (MTR-0338)
1-Isopropyl-3-[4-(5-methoxy-4-morpholin-4-yl-pyrimidin-2-yl)-phenyl]-urea (MTR-0339)
1-(6-Bromo-pyridin-3-yl)-3-[4-(5-methylsulfanyl-4-morpholin-4-yl-pyrimidin-2-yl)-phenyl]-urea (MTR-0340)
1-Isopropyl-3-[4-(5-methylsulfanyl-4-morpholin-4-yl-pyrimidin-2-yl)-phenyl]-urea (MTR-0341)
1-tert-Butyl-3-[4-(5-methylsulfanyl-4-morpholin-4-yl-pyrimidin-2-yl)-phenyl]-urea (MTR-0342)
1-[4-(2-Dimethylamino-ethoxy)-phenyl]-3-[4-(5-methylsulfanyl-4-morpholin-4-yl-pyrimidin-2-yl)-phenyl]-urea (MTR-0343)
2-{4-[3-(4-Carbamoyl-phenyl)-ureido]-3-fluoro-phenyl}-5-ethoxy-6-morpholin-4-yl-pyrimidine-4-carboxylic acid ethyl ester (MTR-0344)
2-{4-[3-(4-Carbamoyl-phenyl)-ureido]-2-fluoro-phenyl}-5-ethoxy-6-morpholin-4-yl-pyrimidine-4-carboxylic acid ethyl ester (MTR-0345)
1-[4-(4-Chloro-5-methylsulfanyl-6-morpholin-4-yl-pyrimidin-2-yl)-phenyl]-3-(1H-indazol-4-yl)-urea (MTR-0346)
N-(4-{3-[4-(4-Chloro-5-methylsulfanyl-6-morpholin-4-yl-pyrimidin-2-yl)-phenyl]-ureido}-phenyl)-methanesulfonamide (MTR-0347)
1,3-Bis-[4-(4-chloro-5-methylsulfanyl-6-morpholin-4-yl-pyrimidin-2-yl)-phenyl]-urea (MTR-0349)
1-(4-Amino-phenyl)-3-[4-(5-methoxy-4-morpholin-4-yl-pyrimidin-2-yl)-phenyl]-urea (MTR-0350)
4-{3-[4-(5-Methoxy-4-morpholin-4-yl-pyrimidin-2-yl)-phenyl]-ureido}-benzoic acid (MTR-0351)
1-(6-Bromo-pyridin-3-yl)-3-[4-(5-methoxy-4-morpholin-4-yl-pyrimidin-2-yl)-phenyl]-urea (MTR-0352)

1-[4-(5-Methoxy-4-morpholin-4-yl-pyrimidin-2-yl)-phenyl]-3-(6-morpholin-4-yl-pyridin-3-yl)-urea (MTR-0353)
[4-(4-Chloro-5-methylsulfanyl-6-morpholin-4-yl-pyrimidin-2-yl)-2-fluoro-phenyl]-carbamic acid phenyl Ester (MTR-0354)
1-[4-(4-Chloro-5-methylsulfanyl-6-morpholin-4-yl-pyrimidin-2-yl)-2-fluoro-phenyl]-3-[4-(3-oxo-morpholin-4-yl)-phenyl]-urea (MTR-0355)
[4-(4-Chloro-5-methylsulfanyl-6-morpholin-4-yl-pyrimidin-2-yl)-2-fluoro-phenyl]-urea (MTR-0356)
4-(4-Chloro-5-methylsulfanyl-6-morpholin-4-yl-pyrimidin-2-yl)-2-fluoro-phenylamine (MTR-0357)
4-{3-[4-(4-Chloro-5-methylsulfanyl-6-morpholin-4-yl-pyrimidin-2-yl)-phenyl]-ureido}-benzenesulfonamide (MTR-0358)
1-[4-(4-Chloro-5-methylsulfanyl-6-morpholin-4-yl-pyrimidin-2-yl)-3-fluoro-phenyl]-3-[4-(3-oxo-morpholin-4-yl)-phenyl]-urea (MTR-0359)
4-(5-Methylsulfanyl-4-morpholin-4-yl-6-pyridin-4-yl-pyrimidin-2-yl)-phenylamine (MTR-0360)
2-[4-(3-Benzo[1,3]dioxol-5-yl-ureido)-phenyl]-5-ethoxy-6-morpholin-4-yl-pyrimidine-4-carboxylic acid ethyl ester (MTR-0361)
5-Ethoxy-2-{4-[3-(4-ethoxycarbonyl-phenyl)-ureido]-phenyl}-6-morpholin-4-yl-pyrimidine-4-carboxylic acid ethyl ester (MTR-0362)
2-(4-{3-[4-(2-Dimethylamino-ethoxy)-phenyl]-ureido}-phenyl)-5-ethoxy-6-morpholin-4-yl-pyrimidine-4-carboxylic acid ethyl ester (MTR-0363)
4-(3-{4-[5-Ethoxy-4-(morpholine-4-carbonyl)-6-morpholin-4-yl-pyrimidin-2-yl]-phenyl}-ureido)-benzamide (MTR-0364)
5-Ethoxy-2-{4-[3-(4-methanesulfonyl-phenyl)-ureido]-phenyl}-6-morpholin-4-yl-pyrimidine-4-carboxylic acid ethyl ester (MTR-0365)
5-Ethoxy-2-[4-(3-isopropyl-ureido)-phenyl]-6-morpholin-4-yl-pyrimidine-4-carboxylic acid ethyl ester (MTR-0366)
2-[4-(3-tert-Butyl-ureido)-phenyl]-5-ethoxy-6-morpholin-4-yl-pyrimidine-4-carboxylic acid ethyl ester (MTR-0367)
N-(4-{3-[4-(5-Ethoxy-4-morpholin-4-yl-pyrimidin-2-yl)-phenyl]-ureido}-phenyl)-acetamide (MTR-0368)
5-Ethoxy-2-{4-[3-(4-methanesulfonylamino-phenyl)-ureido]-phenyl}-6-morpholin-4-yl-pyrimidine-4-carboxylic acid ethyl ester (MTR-0369)
2-{4-[3-(4-Acetylamino-phenyl)-ureido]-phenyl}-5-ethoxy-6-morpholin-4-yl-pyrimidine-4-carboxylic acid ethyl ester (MTR-0370)
N-(4-{3-[4-(4-Chloro-5-methylsulfanyl-6-morpholin-4-yl-pyrimidin-2-yl)-phenyl]-ureido}-phenyl)-acetamide (MTR-0371)
1-[4-(4-Chloro-5-methylsulfanyl-6-morpholin-4-yl-pyrimidin-2-yl)-phenyl]-3-(2-oxo-2,3-dihydro-benzooxazol-5-yl)-urea (MTR-0372)
6-Chloro-5-methylsulfanyl-4-morpholin-4-yl-[2,5']bipyrimidinyl-2'-ylamine (MTR-0373)
1,3-Bis-[4-(5-methylsulfanyl-4-morpholin-4-yl-pyrimidin-2-yl)-phenyl]-urea (MTR-0374)
3-Fluoro-4-(5-methylsulfanyl-4-morpholin-4-yl-pyrimidin-2-yl)-phenylamine (MTR-0375)
N-(4-{3-[4-(5-Methylsulfanyl-4-morpholin-4-yl-pyrimidin-2-yl)-phenyl]-ureido}-phenyl)-methanesulfonamide (MTR-0376)
N-(3-{3-[4-(5-Methylsulfanyl-4-morpholin-4-yl-pyrimidin-2-yl)-phenyl]-ureido}-phenyl)-acetamide (MTR-0377)
1-[3-Fluoro-4-(5-methylsulfanyl-4-morpholin-4-yl-pyrimidin-2-yl)-phenyl]-3-[4-(3-oxo-morpholin-4-yl)-phenyl]-urea (MTR-0378)
N-(4-{3-[3-Fluoro-4-(5-methylsulfanyl-4-morpholin-4-yl-pyrimidin-2-yl)-phenyl]-ureido}-phenyl)-acetamide (MTR-0379)
N-(4-{3-[4-(5-Methylsulfanyl-4-morpholin-4-yl-pyrimidin-2-yl)-phenyl]-ureido}-phenyl)-acetamide (MTR-0380)
1-[4-(5-Methanesulfonyl-4-morpholin-4-yl-pyrimidin-2-yl)-phenyl]-3-[4-(3-oxo-morpholin-4-yl)-phenyl]-urea (MTR-0381)
1-[4-(5-Methoxy-4-morpholin-4-yl-pyrimidin-2-yl)-phenyl]-3-[4-(morpholine-4-carbonyl)-phenyl]-urea (MTR-0382)
2-Fluoro-4-(5-methoxy-4-morpholin-4-yl-pyrimidin-2-yl)-phenylamine (MTR-0383)
3-Fluoro-4-(5-methoxy-4-morpholin-4-yl-pyrimidin-2-yl)-phenylamine (MTR-0384)
4-{3-[2-Fluoro-4-(5-methoxy-4-morpholin-4-yl-pyrimidin-2-yl)-phenyl]-ureido}-benzamide (MTR-0385)
1-[4-(5-Methoxy-4-morpholin-4-yl-pyrimidin-2-yl)-phenyl]-3-pyridin-2-yl-urea (MTR-0386)
1-[4-(4-Chloro-5-methylsulfanyl-6-morpholin-4-yl-pyrimidin-2-yl)-phenyl]-3-(4-methanesulfonyl-phenyl)-urea (MTR-0387)
[4-(5-Methylsulfanyl-4-morpholin-4-yl-6-pyridin-4-yl-pyrimidin-2-yl)-phenyl]-urea (MTR-0388)
1-(6-Chloro-5-methylsulfanyl-4-morpholin-4-yl-[2,5']bipyrimidinyl-2'-yl)-3-[4-(3-oxo-morpholin-4-yl)-phenyl]-urea (MTR-0389)
[4-(5-Methylsulfanyl-4-morpholin-4-yl-6-pyridin-4-yl-pyrimidin-2-yl)-phenyl]-carbamic acid phenyl ester (MTR-0390)
1-[4-(5-Methylsulfanyl-4-morpholin-4-yl-6-pyridin-4-yl-pyrimidin-2-yl)-phenyl]-3-[4-(3-oxo-morpholin-4-yl)-phenyl]-urea (MTR-0391)
4-{3-[4-(5-Methylsulfanyl-4-morpholin-4-yl-6-pyridin-4-yl-pyrimidin-2-yl)-phenyl]-ureido}-benzamide (MTR-0392)
N-(4-{3-[4-(5-Ethoxy-4-morpholin-4-yl-pyrimidin-2-yl)-phenyl]-ureido}-phenyl)-methanesulfonamide (MTR-0394)
1-[4-(5-Ethoxy-4-morpholin-4-yl-pyrimidin-2-yl)-phenyl]-3-(2-oxo-2,3-dihydro-benzooxazol-5-yl)-urea (MTR-0395)
4-(5-Ethoxy-4-pyridin-4-yl-pyrimidin-2-yl)-phenylamine (MTR-0396)
[4-(5-Ethoxy-4-pyridin-4-yl-pyrimidin-2-yl)-phenyl]-carbamic acid phenyl ester (MTR-0397)
1-[4-(5-Ethoxy-4-pyridin-4-yl-pyrimidin-2-yl)-phenyl]-3-[4-(3-oxo-morpholin-4-yl)-phenyl]-urea (MTR-0398)
1-[4-(5-Ethoxy-4-pyridin-4-yl-pyrimidin-2-yl)-phenyl]-3-phenyl-urea (MTR-0399)
4-{3-[4-(5-Ethoxy-4-pyridin-4-yl-pyrimidin-2-yl)-phenyl]-ureido}-benzamide (MTR-0400)
1-[4-(5-Methanesulfinyl-4-morpholin-4-yl-pyrimidin-2-yl)-phenyl]-3-[4-(3-oxo-morpholin-4-yl)-phenyl]-urea (MTR-0401)
2'-Amino-5-ethoxy-6-morpholin-4-yl-[2,5']bipyrimidinyl-4-carboxylic acid ethyl ester (MTR-0402)
5-Ethoxy-6-morpholin-4-yl-2'-{3-[4-(3-oxo-morpholin-4-yl)-phenyl]-ureido}-[2,5']bipyrimidinyl-4-carboxylic acid ethyl ester (MTR-0403)
1-(4-Methanesulfonyl-phenyl)-3-[4-(5-methylsulfanyl-4-morpholin-4-yl-pyrimidin-2-yl)-phenyl]-urea (MTR-0404)

1-[2-Fluoro-4-(5-methoxy-4-morpholin-4-yl-pyrimidin-2-yl)-phenyl]-3-[4-(3-oxo-morpholin-4-yl)-phenyl]-urea (MTR-0405)
1-[3-Fluoro-4-(5-methoxy-4-morpholin-4-yl-pyrimidin-2-yl)-phenyl]-3-[4-(3-oxo-morpholin-4-yl)-phenyl]-urea (MTR-0406)
4-{3-[3-Fluoro-4-(5-methoxy-4-morpholin-4-yl-pyrimidin-2-yl)-phenyl]-ureido}-benzamide (MTR-0407)
1-[4-(5-Methoxy-4-morpholin-4-yl-pyrimidin-2-yl)-phenyl]-3-pyridin-3-yl-thiourea (MTR-0408)
4-{3-[4-(4-Chloro-5-methylsulfanyl-6-morpholin-4-yl-pyrimidin-2-yl)-2-fluoro-phenyl]-ureido}-benzamide (MTR-0409)
4-{3-[4-(4-Chloro-5-methylsulfanyl-6-morpholin-4-yl-pyrimidin-2-yl)-2-fluoro-phenyl]-ureido}-benzenesulfonamide (MTR-0410)
4-{3-[4-(4-Chloro-5-methylsulfanyl-6-morpholin-4-yl-pyrimidin-2-yl)-3-fluoro-phenyl]-ureido}-benzamide (MTR-0411)
4-{3-[4-(4-Chloro-5-methylsulfanyl-6-morpholin-4-yl-pyrimidin-2-yl)-3-fluoro-phenyl]-ureido}-benzenesulfonamide (MTR-0412)
1-[4-(4-Chloro-5-methylsulfanyl-6-morpholin-4-yl-pyrimidin-2-yl)-phenyl]-3-[4-(4-methanesulfonyl-piperazin-1-yl)-phenyl]-urea (MTR-0413)
N-(5-{3-[4-(4-Chloro-5-methylsulfanyl-6-morpholin-4-yl-pyrimidin-2-yl)-phenyl]-ureido}-pyridin-2-yl)-acetamide (MTR-0415)
2'-[3-(4-Carbamoyl-phenyl)-ureido]-5-ethoxy-6-morpholin-4-yl-[2,5']bipyrimidinyl-4-carboxylic acid ethyl ester (MTR-0417)
2'-[3-(4-Acetylamino-phenyl)-ureido]-5-ethoxy-6-morpholin-4-yl-[2,5']bipyrimidinyl-4-carboxylic acid ethyl ester (MTR-0418)
5-Ethoxy-2-(4-{3-[4-(4-methanesulfonyl-piperazin-1-yl)-phenyl]-ureido}-phenyl)-6-morpholin-4-yl-pyrimidine-4-carboxylic acid ethyl ester (MTR-0419)
1-[4-(5-Ethoxy-4-morpholin-4-yl-pyrimidin-2-yl)-phenyl]-3-[4-(4-methanesulfonyl-piperazin-1-yl)-phenyl]-urea (MTR-0420)
1-[4-(5-Ethoxy-4-morpholin-4-yl-pyrimidin-2-yl)-phenyl]-3-[4-(morpholine-4-carbon yl)-phenyl]-urea (MTR-0421)
1-[4-(5-Ethoxy-4-morpholin-4-yl-pyrimidin-2-yl)-phenyl]-3-(2-oxo-2,3-dihydro-benzooxazol-6-yl)-urea (MTR-0422)
5-Ethoxy-6-morpholin-4-yl-2-{4-[3-(2-oxo-2,3-dihydro-benzooxazol-6-yl)-ureido]-phenyl}-pyrimidine-4-carboxylic acid ethyl ester (MTR-0423)
1-[4-(5-Ethoxy-4-morpholin-4-yl-pyrimidin-2-yl)-phenyl]-3-(4-methanesulfonyl-phenyl)-urea (MTR-0424)
5-(5-Ethoxy-4-morpholin-4-yl-pyrimidin-2-yl)-1,3-dihydro-benzoimidazol-2-one (MTR-0425)
N-(3-{3-[4-(5-Methoxy-4-morpholin-4-yl-pyrimidin-2-yl)-phenyl]-ureido}-phenyl)-acetamide (MTR-0426)
N-(3-Dimethylamino-propyl)-4-{3-[4-(5-methoxy-4-morpholin-4-yl-pyrimidin-2-yl)-phenyl]-ureido}-benzamide (MTR-0427)
5-Methoxy-4-morpholin-4-yl-[2,5']bipyrimidinyl-2'-ylamine (MTR-0428)
4-[3-(5-Methoxy-4-morpholin-4-yl-[2,5']bipyrimidinyl-2'-yl)-ureido]-benzamide (MTR-0429)
1-[4-(4-Methanesulfonyl-piperazin-1-yl)-phenyl]-3-[4-(5-methylsulfanyl-4-morpholin-4-yl-pyrimidin-2-yl)-phenyl]-urea (MTR-0430)
5-Methylsulfanyl-4-morpholin-4-yl-[2,5']bipyrimidinyl-2'-ylamine (MTR-0431)
4-[3-(6-Chloro-5-methylsulfanyl-4-morpholin-4-yl-[2,5']bipyrimidinyl-2'-yl)-ureido]-benzenesulfonamide (MTR-0432)
1-[4-(4-Chloro-5-methylsulfanyl-6-morpholin-4-yl-pyrimidin-2-yl)-phenyl]-3-(2-oxo-2,3-dihydro-benzooxazol-6-yl)-urea (MTR-0433)
1-[4-(4-Chloro-5-methylsulfanyl-6-morpholin-4-yl-pyrimidin-2-yl)-phenyl]-3-[4-(morpholine-4-sulfonyl)-phenyl]-urea (MTR-0435)
1-[4-(4-Chloro-5-methylsulfanyl-6-morpholin-4-yl-pyrimidin-2-yl)-phenyl]-3-[4-(4-dimethylamino-piperidine-1-carbonyl)-phenyl]-urea (MTR-0436)
4-(5-Methylsulfanyl-4-morpholin-4-yl-6-pyridin-3-yl-pyrimidin-2-yl)-phenylamine (MTR-0437)
1-[4-(5-Methylsulfanyl-4-morpholin-4-yl-6-pyridin-3-yl-pyrimidin-2-yl)-phenyl]-3-phenyl-urea (MTR-0438)
1-[4-(5-Methylsulfanyl-4-morpholin-4-yl-6-pyridin-3-yl-pyrimidin-2-yl)-phenyl]-3-phenyl-thiourea (MTR-0440)
N-(5-{3-[4-(5-Ethoxy-4-morpholin-4-yl-pyrimidin-2-yl)-phenyl]-ureido}-pyridin-2-yl)-acetamide (MTR-0442)
2-{4-[3-(6-Acetylamino-pyridin-3-yl)-ureido]-phenyl}-5-ethoxy-6-morpholin-4-yl-pyrimidine-4-carboxylic acid ethyl ester (MTR-0443)
N-[3-(5-Ethoxy-4-morpholin-4-yl-pyrimidin-2-yl)-phenyl]-methanesulfonamide (MTR-0444)
N-[3-(5-Ethoxy-4-morpholin-4-yl-pyrimidin-2-yl)-phenyl]-2,4-difluoro-benzenesulfonamide (MTR-0445)
1-[4-(5-Ethoxy-4-morpholin-4-yl-pyrimidin-2-yl)-phenyl]-3-pyridin-4-yl-urea (MTR-0446)
1-[4-(5-Ethoxy-4-pyridin-3-yl-pyrimidin-2-yl)-phenyl]-3-[4-(3-oxo-morpholin-4-yl)-phenyl]-urea (MTR-0447)
4-(5-Methoxy-4-pyridin-4-yl-pyrimidin-2-yl)-phenylamine (MTR-0448)
N-(4-{3-[4-(5-Methoxy-4-morpholin-4-yl-pyrimidin-2-yl)-phenyl]-ureido}-phenyl)-methanesulfonamide (MTR-0449)
1-[4-(5-Methoxy-4-morpholin-4-yl-pyrimidin-2-yl)-phenyl]-3-(2-oxo-2,3-dihydro-benzooxazol-6-yl)-urea (MTR-0450)
1-(5-Methoxy-4-morpholin-4-yl-[2,5']bipyrimidinyl-2'-yl)-3-[4-(3-oxo-morpholin-4-yl)-phenyl]-urea (MTR-0451)
1-[4-(5-Ethoxy-4-morpholin-4-yl-pyrimidin-2-yl)-phenyl]-3-[4-(morpholine-4-sulfon yl)-phenyl]-urea (MTR-0452)
1-[4-(5-Methylsulfanyl-4-morpholin-4-yl-6-pyridin-4-yl-pyrimidin-2-yl)-phenyl]-3-pyridin-4-yl-urea (MTR-0453)
1-[4-(Morpholine-4-carbonyl)-phenyl]-3-{4-[4-morpholin-4-yl-5-(2-morpholin-4-yl-ethoxy)-pyrimidin-2-yl]-phenyl}-urea (MTR-0454)
1-{4-[4-Morpholin-4-yl-5-(2-morpholin-4-yl-ethoxy)-pyrimidin-2-yl]-phenyl}-3-[4-(3-oxo-morpholin-4-yl)-phenyl]-urea (MTR-0455)
4-(3-{4-[4-Morpholin-4-yl-5-(2-morpholin-4-yl-ethoxy)-pyrimidin-2-yl]-phenyl}-ureido)-benzamide (MTR-0456)
1-[4-(5-Methylsulfanyl-4-morpholin-4-yl-6-pyridin-3-yl-pyrimidin-2-yl)-phenyl]-3-[4-(3-oxo-morpholin-4-yl)-phenyl]-urea (MTR-0457)
1-[4-(5-Methylsulfanyl-4-morpholin-4-yl-pyrimidin-2-yl)-phenyl]-3-(2-oxo-2,3-dihydro-benzooxazol-6-yl)-urea (MTR-0459)
4-(4-Chloro-5-methoxy-6-morpholin-4-yl-pyrimidin-2-yl)-phenylamine (MTR-0460)
1-[4-(5-Methylsulfanyl-4-morpholin-4-yl-pyrimidin-2-yl)-phenyl]-3-[4-(morpholine-4-carbonyl)-phenyl]-urea (MTR-0461)

1-[4-(5-Methylsulfanyl-4-morpholin-4-yl-pyrimidin-2-yl)-phenyl]-3-pyridin-4-yl-urea (MTR-0462)
N-(4-{3-[4-(5-Methylsulfanyl-4-morpholin-4-yl-6-pyridin-3-yl-pyrimidin-2-yl)-phenyl]-ureido}-phenyl)-methanesulfonamide (MTR-0463)
1-[4-(5-Methylsulfanyl-4-morpholin-4-yl-6-pyridin-3-yl-pyrimidin-2-yl)-phenyl]-3-pyridin-3-yl-urea (MTR-0464)
1-[4-(5-Methylsulfanyl-4-morpholin-4-yl-6-pyridin-4-yl-pyrimidin-2-yl)-phenyl]-3-phenyl-urea (MTR-0465)
4-(5-Methylsulfanyl-2,6-di-pyridin-3-yl-pyrimidin-4-yl)-morpholine (MTR-0466)
N-[3-(4-Chloro-5-methylsulfanyl-6-morpholin-4-yl-pyrimidin-2-yl)-phenyl]-methane sulfonamide (MTR-0467)
1-[4-(5-Methylsulfanyl-4-morpholin-4-yl-6-pyridin-4-yl-pyrimidin-2-yl)-phenyl]-3-phenyl-thiourea (MTR-0468)
1-[4-(4-Chloro-5-methylsulfanyl-6-morpholin-4-yl-pyrimidin-2-yl)-phenyl]-3-pyridin-4-yl-urea (MTR-0469)
1-(4-Methanesulfonyl-phenyl)-3-[4-(5-methoxy-4-morpholin-4-yl-pyrimidin-2-yl)-phenyl]-urea (MTR-0470)
1-[4-(5-Methoxy-4-morpholin-4-yl-pyrimidin-2-yl)-phenyl]-3-[4-(morpholine-4-sulfonyl)-phenyl]-urea (MTR-0471)
1-[4-(5-Methoxy-4-morpholin-4-yl-pyrimidin-2-yl)-phenyl]-3-pyridin-4-yl-urea (MTR-0472)
1-[4-(5-Methoxy-4-pyridin-4-yl-pyrimidin-2-yl)-phenyl]-3-[4-(morpholine-4-carbonyl)-phenyl]-urea (MTR-0473)
1-[4-(5-Methoxy-4-pyridin-4-yl-pyrimidin-2-yl)-phenyl]-3-[4-(3-oxo-morpholin-4-yl)-phenyl]-urea (MTR-0474)
1-[4-(4-Chloro-5-methoxy-6-morpholin-4-yl-pyrimidin-2-yl)-phenyl]-3-pyridin-4-yl-urea (MTR-0476)
1-Ethyl-3-[4-(5-methylsulfanyl-4-morpholin-4-yl-6-pyridin-4-yl-pyrimidin-2-yl)-phenyl]-urea (MTR-0477)
1-Methyl-3-[4-(5-methylsulfanyl-4-morpholin-4-yl-6-pyridin-4-yl-pyrimidin-2-yl)-phenyl]-urea (MTR-0478)
1-Isopropyl-3-[4-(5-methylsulfanyl-4-morpholin-4-yl-6-pyridin-4-yl-pyrimidin-2-yl)-phenyl]-urea (MTR-0479)
1-[4-(5-Methoxy-4-pyridin-4-yl-pyrimidin-2-yl)-phenyl]-3-pyridin-4-yl-urea (MTR-0480)
1-{4-[4-Morpholin-4-yl-5-(2-morpholin-4-yl-ethoxy)-pyrimidin-2-yl]-phenyl}-3-pyridin-4-yl-urea (MTR-0481)
4-(5-Methoxy-4-morpholin-4-yl-6-pyridin-4-yl-pyrimidin-2-yl)-phenylamine (MTR-0482)
4-(5-Methoxy-4-morpholin-4-yl-6-(4-aminophenyl-pyrimidin-2-yl)-phenylamine (MTR-0483)
1-[4-(4-Chloro-5-methylsulfanyl-6-morpholin-4-yl-pyrimidin-2-yl)-phenyl]-3-isoxazol-3-yl-urea (MTR-0484)
1-Isoxazol-3-yl-3-[4-(5-methylsulfanyl-4-morpholin-4-yl-6-pyridin-4-yl-pyrimidin-2-yl)-phenyl]-urea (MTR-0485)
N-(5-{3-[4-(5-Methoxy-4-morpholin-4-yl-pyrimidin-2-yl)-phenyl]-ureido}-pyridin-2-yl)-acetamide (MTR-0486)
1-[4-(4-Methanesulfonyl-piperazin-1-yl)-phenyl]-3-[4-(5-methoxy-4-morpholin-4-yl-pyrimidin-2-yl)-phenyl]-urea (MTR-0487)
1-[4-(4-Chloro-5-ethoxy-6-morpholin-4-yl-pyrimidin-2-yl)-phenyl]-3-pyridin-4-yl-urea (MTR-0488)
1-[4-(4-Chloro-5-ethoxy-6-morpholin-4-yl-pyrimidin-2-yl)-phenyl]-3-pyridin-3-yl-urea (MTR-0489)
1-[4-(5-Ethoxy-4-morpholin-4-yl-6-pyridin-3-yl-pyrimidin-2-yl)-phenyl]-3-pyridin-4-yl-urea (MTR-0490)
1-[4-(5-Ethoxy-4-morpholin-4-yl-6-pyridin-3-yl-pyrimidin-2-yl)-phenyl]-3-pyridin-3-yl-urea (MTR-0491)
1-[4-(5-Ethoxy-4-morpholin-4-yl-6-pyridin-4-yl-pyrimidin-2-yl)-phenyl]-3-pyridin-4-yl-urea (MTR-0492)
1-[4-(5-Ethoxy-4-morpholin-4-yl-6-pyridin-4-yl-pyrimidin-2-yl)-phenyl]-3-pyridin-3-yl-urea (MTR-0493)
1-[4-(4-Chloro-5-ethoxy-6-morpholin-4-yl-pyrimidin-2-yl)-phenyl]-3-[4-(3-oxo-morpholin-4-yl)-phenyl]-urea (MTR-0494)
1-[4-(5-Ethoxy-4-morpholin-4-yl-6-pyridin-4-yl-pyrimidin-2-yl)-phenyl]-3-[4-(3-oxo-morpholin-4-yl)-phenyl]-urea (MTR-0495)
1-[4-(5-Ethoxy-4-morpholin-4-yl-6-pyridin-3-yl-pyrimidin-2-yl)-phenyl]-3-[4-(3-oxo-morpholin-4-yl)-phenyl]-urea (MTR-0496)
1-[4-(5-Methoxy-4-morpholin-4-yl-6-pyridin-3-yl-pyrimidin-2-yl)-phenyl]-3-pyridin-3-yl-urea (MTR-0497)
1-[4-(5-Methoxy-4-morpholin-4-yl-6-pyridin-4-yl-pyrimidin-2-yl)-phenyl]-3-pyridin-4-yl-urea (MTR-0498)
1-[4-(5-Methoxy-4-morpholin-4-yl-6-pyridin-4-yl-pyrimidin-2-yl)-phenyl]-3-pyridin-3-yl-urea (MTR-0499)
1-[4-(4-Chloro-5-methoxy-6-morpholin-4-yl-pyrimidin-2-yl)-phenyl]-3-[4-(3-oxo-morpholin-4-yl)-phenyl]-urea (MTR-0500)
1-[4-(5-Methoxy-4-morpholin-4-yl-6-pyridin-4-yl-pyrimidin-2-yl)-phenyl]-3-[4-(3-oxo-morpholin-4-yl)-phenyl]-urea (MTR-0501)
1-[4-(5-Methoxy-4-morpholin-4-yl-6-pyridin-3-yl-pyrimidin-2-yl)-phenyl]-3-[4-(3-oxo-morpholin-4-yl)-phenyl]-urea (MTR-0502)
1-[4-(4-Chloro-5-methoxy-6-morpholin-4-yl-pyrimidin-2-yl)-phenyl]-3-isoxazol-3-yl-urea (MTR-0503)
1-Isoxazol-3-yl-3-[4-(5-methoxy-4-morpholin-4-yl-6-pyridin-4-yl-pyrimidin-2-yl)-phenyl]-urea (MTR-0504)
1-[4-(4-Chloro-5-ethoxy-6-morpholin-4-yl-pyrimidin-2-yl)-phenyl]-3-isoxazol-3-yl-urea (MTR-0505)
1-[4-(5-Ethoxy-4-morpholin-4-yl-6-pyridin-4-yl-pyrimidin-2-yl)-phenyl]-3-isoxazol-3-yl-urea (MTR-0506)
1-Isoxazol-3-yl-3-[4-(5-methoxy-4-morpholin-4-yl-6-pyridin-3-yl-pyrimidin-2-yl)-phenyl]-urea (MTR-0507)
1-[4-(5-Ethoxy-4-morpholin-4-yl-6-pyridin-3-yl-pyrimidin-2-yl)-phenyl]-3-isoxazol-3-yl-urea (MTR-0508)
1-Isoxazol-3-yl-3-[4-(5-methylsulfanyl-4-morpholin-4-yl-6-pyridin-3-yl-pyrimidin-2-yl)-phenyl]-urea (MTR-0509)

or a stereoisomer, or a tautomer, or an N-oxide, or a pharmaceutically acceptable salt, or an ester, or a prodrug, or a hydrate, or a solvate thereof.

The pyrimidine compounds of formula (I), or a stereoisomer, or a tautomer, or an N-oxide, or a pharmaceutically acceptable salt, or an ester, or a prodrug, or a hydrate, or a solvate thereof, may be prepared by any process known to be applicable to the preparation of chemically related compounds.

According to the invention, suitable pharmaceutically acceptable salts of formula (I) include hydrochloride, hydrobromide, hydroiodide, sulfate, phosphate, mesylate, besylate, acetate, oxalate, citrate, lactate, tartrate, succinate, methanesulfonate, trifluoroacetate, and maleate salts. The preferred salt is a hydrochloride salt. When the compounds of the invention bear a free carboxy substituent, the salts include both the above-mentioned acid addition salts and the salts of sodium, potassium, calcium and ammonium. The latter are prepared by treating the free pyrimidine of formula (I), or the acid addition salt thereof, with the corresponding metal base or ammonia.

The pyrimidine compounds of formula (I) may be prepared by any suitable synthetic routes. Examples of the routes can be those set out in Schemes 1 to 10 below.

Scheme 1

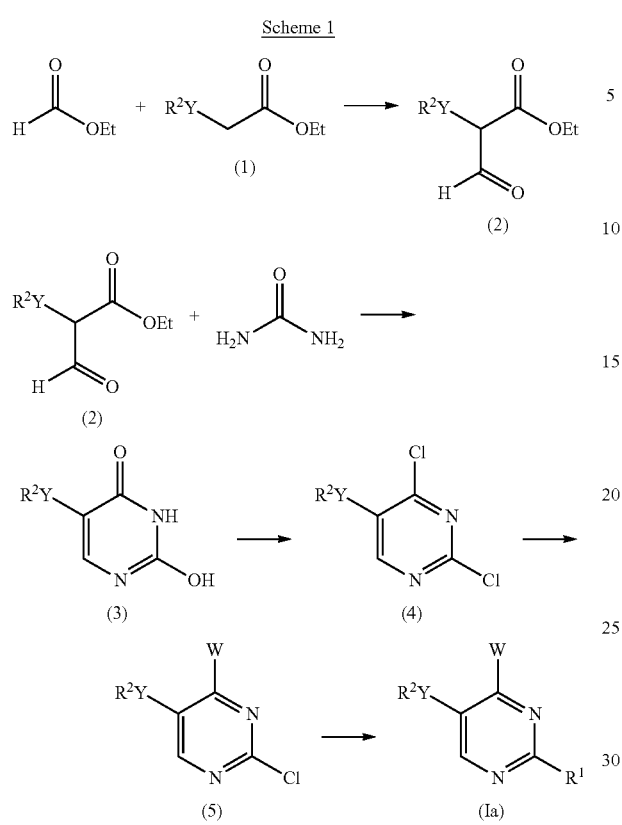

In Scheme 1, $R^1$, $R^2$, Y and W are as defined above for formula (I). A compound of formula (1) which is a known compound or is prepared by methods known in the literature is converted into a compound of formula (2) by treatment with a strong base. The base is typically sodium methoxide, sodium ethoxide, potassium methoxide or potassium ethoxide. A compound of formula (3) is prepared by treatment of the compound of formula (2) with urea in an appropriate solvent such as ethanol. Compounds of formula (4) may be prepared by treating compounds of formula (3) with phosphorous oxychloride in the presence of an N,N-dialkylaniline. Compounds of formula (5) may be prepared by treating compounds of formula (4) with an amine of formula HW in an inert solvent in the presence of a base. Compounds of formula (Ia) may be prepared by the Suzuki coupling of a compound of formula (5) with a boronic acid or a boronic ester.

Scheme 2

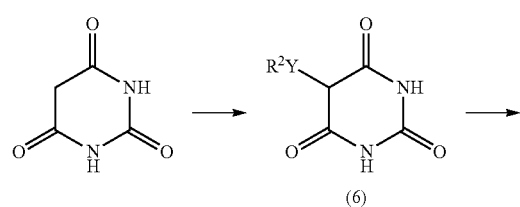

In Scheme 2, $YR^2$=$SCH_3$, Z=Cl or Br, W and $R^1$ are as defined above for formula (I). Compounds of formula (6) may be prepared by treating Barbituric acid with dimethyl sulfoxide. Compounds of formula (7) may be prepared by treating compounds of formula (6) with phosphorous oxychloride or phosphorous oxybromide in the presence of an N,N-dialkylaniline. Compounds of formula (8) may be prepared by treating compounds of formula (7) with an amine of formula HW in an inert solvent in the presence of a base. Compounds of formula (I) may be prepared by the Suzuki coupling of a compound of formula (8) with a boronic acid or a boronic ester.

Scheme 3

In Scheme 3, $YR^2$=$SCH_3$, W and $R^1$ are as defined above for formula (I). The compound of formula (3) wherein $YR^2$=$SCH_3$ is prepared from 5-Iodouracil according to the method in *Organic Letters*, 2007, 9, 1639. Compounds of formula (4) may be prepared by treating compounds of formula (3) with phosphorous oxychloride in the presence of an N,N-dialkylaniline. Compounds of formula (5) may be prepared by treating compounds of formula (4) with an amine of formula HW in an inert solvent in the presence of a base. Compounds of formula (Ia) may be prepared by the Suzuki coupling of a compound of formula (5) with a boronic acid or a boronic ester.

Scheme 4

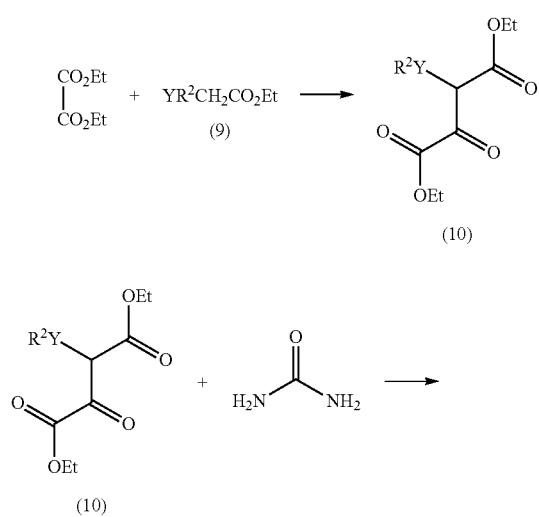

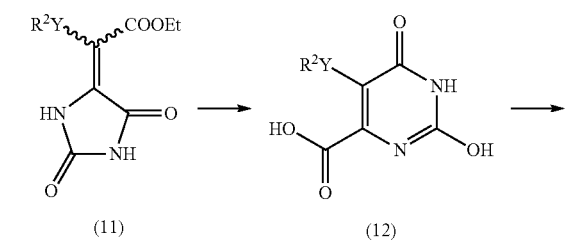

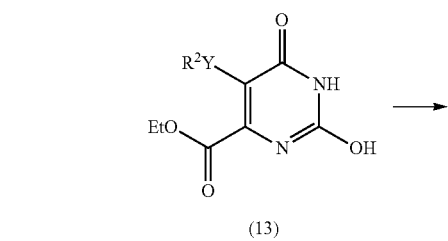

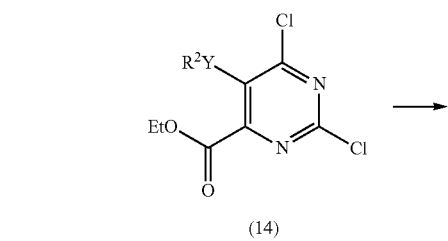

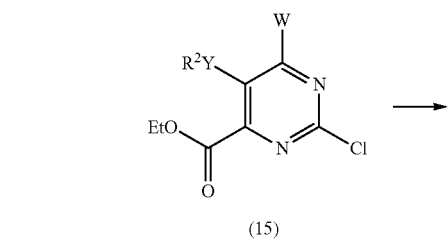

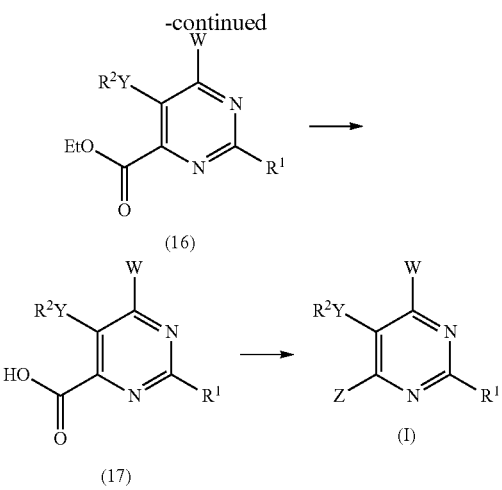

In Scheme 4, $YR^2$=—$OCH_3$ or —OEt, Z=—C(O)$NR_3R_4$, $R^1$ and W are as defined above for formula (I). A compound of formula (9), which is a known compound or is prepared by methods known in the literature, is converted into a compound of formula (10) by treatment with a strong base. The base is typically sodium methoxide, sodium ethoxide, potassium methoxide or potassium ethoxide. A compound of formula (11) is prepared by treatment of the compound of formula (10) with urea in an acid solution 1. Compounds of formula (11) may be converted to compounds of formula (12) in the presence of a base solution. Compounds of formula (13) may be prepared by the acetylation of a compound of formula (12) with a acetyl chloride. Compounds of formula (14) may be prepared by treating compounds of formula (13) with phosphorous oxychloride in the presence of an N,N-dialkylaniline. Compounds of formula (15) may be prepared by treating compounds of formula (14) with an amine of formula HW in an inert solvent in the presence of a base. Compounds of formula (16) may be prepared by the Suzuki coupling of a compound of formula (15) with a boronic acid or a boronic ester. Compounds of formula (17) can be obtained by hydrolysis of compounds of formula (16). Compounds of formula (I) can be prepared by coupling of compounds of formula (17) with an amine by one of the standard methods of amide bond formation.

Scheme 5

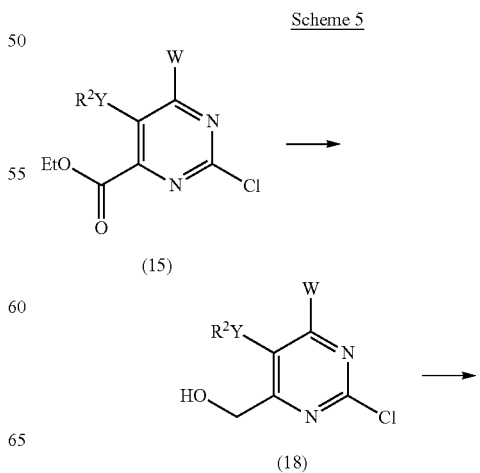

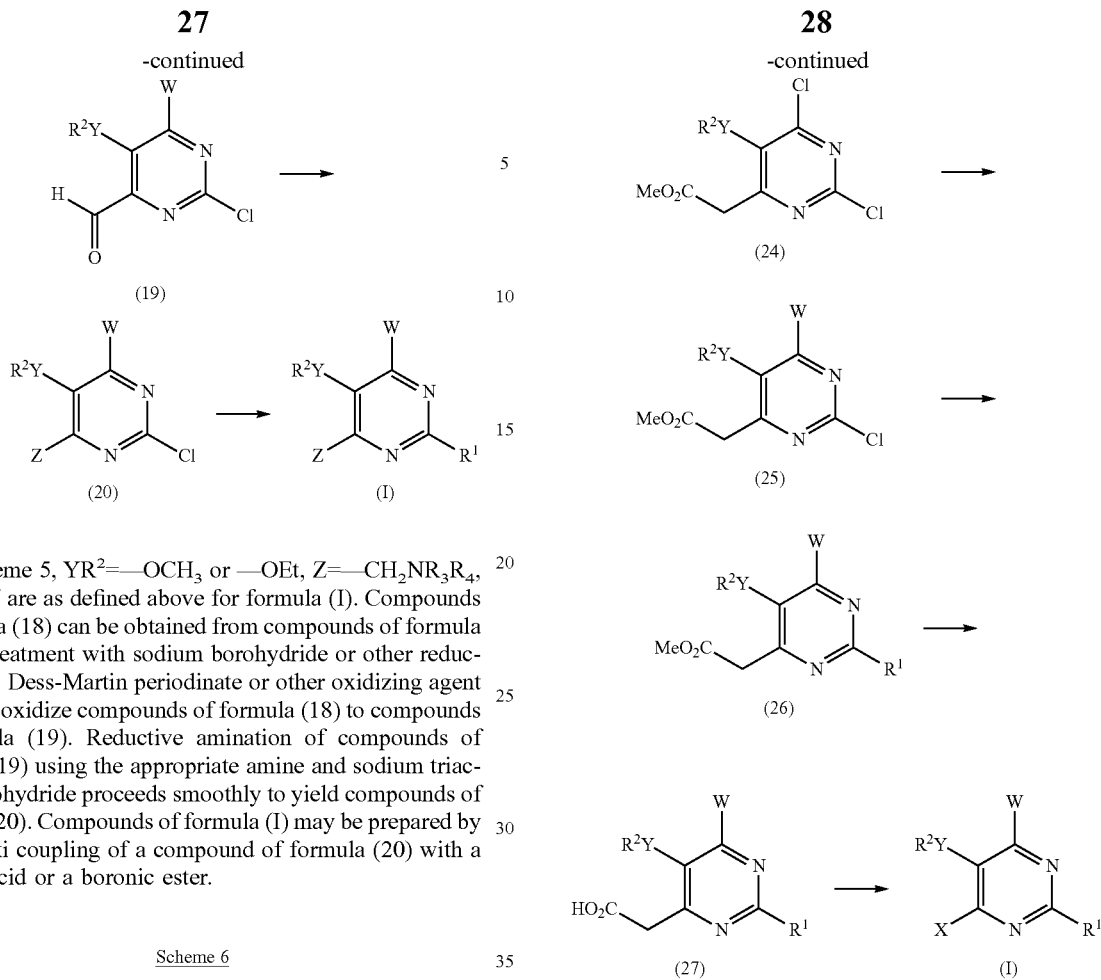

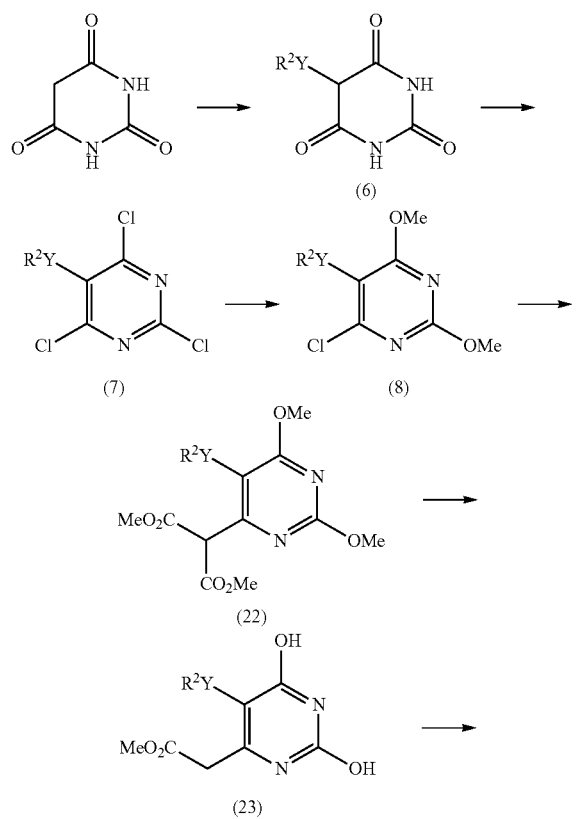

In Scheme 5, $YR^2$=—$OCH_3$ or —OEt, Z=—$CH_2NR_3R_4$, $R^1$ and W are as defined above for formula (I). Compounds of formula (18) can be obtained from compounds of formula (15) by treatment with sodium borohydride or other reducing agent. Dess-Martin periodinate or other oxidizing agent is used to oxidize compounds of formula (18) to compounds of formula (19). Reductive amination of compounds of formula (19) using the appropriate amine and sodium triacetoxyborohydride proceeds smoothly to yield compounds of formula (20). Compounds of formula (I) may be prepared by the Suzuki coupling of a compound of formula (20) with a boronic acid or a boronic ester.

In Scheme 6, $YR^2$=$SCH_3$, Z=—$CH_2C(O)NR_3R_4$, $R^1$ and W are as defined above for formula (I). Compounds of formula (7) may be prepared by the method of scheme 2. Compounds of formula (21) may be prepared by reacting together compounds of formula (7) and sodium methoxide in MeOH. Compounds of formula (22) may be prepared by reacting together compounds of formula (21) and dimethyl malonate in the presence of sodium hydride. Compounds of formula (23) can be obtained by demethylation and decarboxylation of compounds of formula (22) in the presence of an excess of alkali hydroxide. Compounds of formula (24) may be prepared by treating compounds of formula (23) with phosphorous oxychloride or phosphorous oxybromide in the presence of an N,N-dialkylaniline. Compounds of formula (25) may be prepared by treating compounds of formula (24) with an amine of formula HW in an inert solvent in the presence of a base. Compounds of formula (26) may be prepared by the Suzuki coupling of a compound of formula (25) with a boronic acid or a boronic ester. Compounds of formula (27) can be obtained by hydrolysis of compounds of formula (26). Compounds of Formula (I) can be prepared by coupling of compounds of formula (27) with an amine by one of the standard methods of amide bond formation.

29

Scheme 7

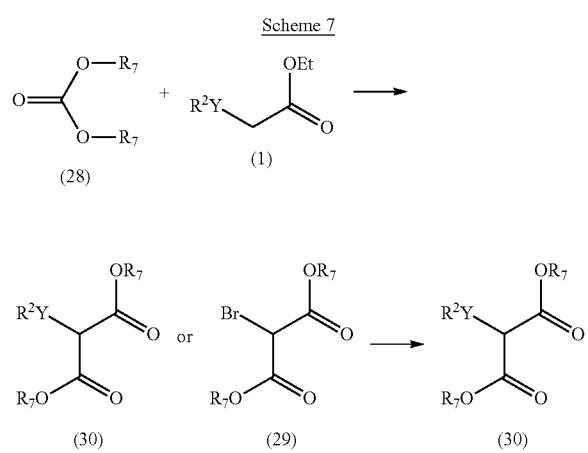

In Scheme 7, $R_7$=OMe, OEt, $YR^2$=OCH$_3$, OEt, Z=Cl, Br, $R^1$ and W are as defined above for formula (I). Compounds of formula (30) are prepared from carbonic acid diethyl ester (28, $R_7$=OEt) according to the method in J. of Heterocyclic Chemistry, 1989, 1261-1271 or from compounds of formula (29) according to the method in J. Med. Chem., 1974, 1197. Compounds of formula (6) are prepared by treating the compounds of formula (30) with urea in an appropriate solvent such as ethanol. Compounds of formula (7) may be prepared by treating compounds of formula (6) with phosphorous oxychloride in the presence of an N,N-dialkylaniline. Compounds of formula (8) may be prepared by treating compounds of formula (7) with an amine of formula HW in an inert solvent in the presence of a base.

30

Compounds of formula (I) may be prepared by the Suzuki coupling of a compound of formula (8) with a boronic acid or a boronic ester.

Scheme 8

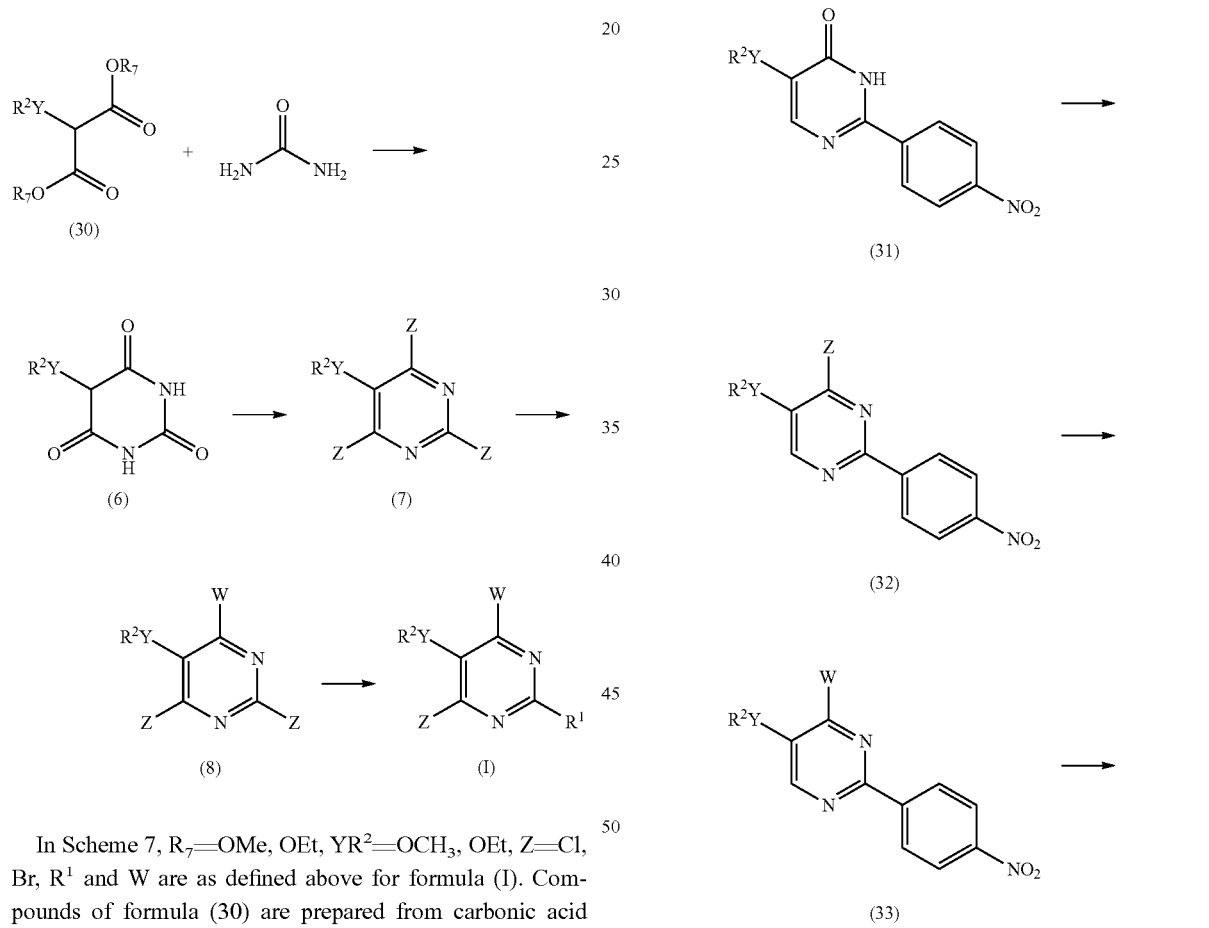

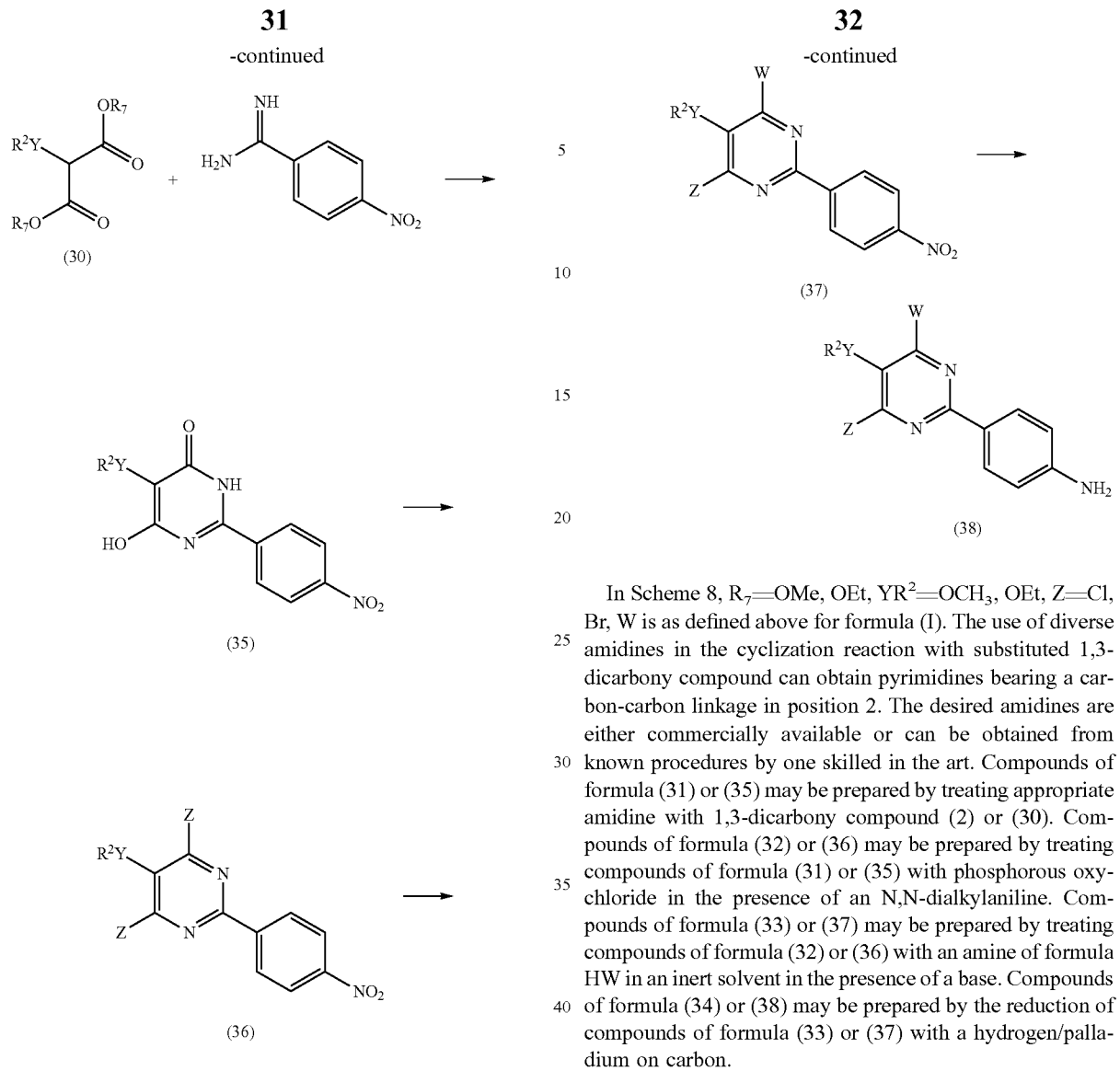

In Scheme 8, $R_7$=OMe, OEt, $YR^2$=OCH$_3$, OEt, Z=Cl, Br, W is as defined above for formula (I). The use of diverse amidines in the cyclization reaction with substituted 1,3-dicarbony compound can obtain pyrimidines bearing a carbon-carbon linkage in position 2. The desired amidines are either commercially available or can be obtained from known procedures by one skilled in the art. Compounds of formula (31) or (35) may be prepared by treating appropriate amidine with 1,3-dicarbony compound (2) or (30). Compounds of formula (32) or (36) may be prepared by treating compounds of formula (31) or (35) with phosphorous oxychloride in the presence of an N,N-dialkylaniline. Compounds of formula (33) or (37) may be prepared by treating compounds of formula (32) or (36) with an amine of formula HW in an inert solvent in the presence of a base. Compounds of formula (34) or (38) may be prepared by the reduction of compounds of formula (33) or (37) with a hydrogen/palladium on carbon.

Scheme 9

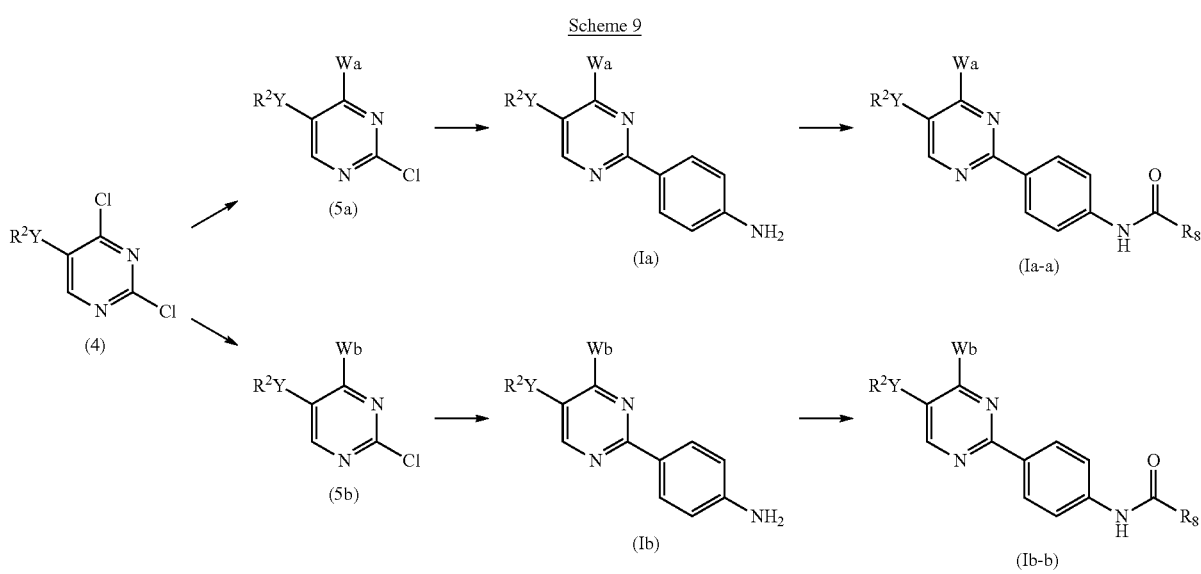

Substitution at the 4-Cl is not limited to an amino group, as described in Scheme 1-8. 4-Cl can also bear a carbon linker. In Scheme 9, $R^2$, Y, W (Wa, Wb), $R_8=NR_3R_4$ are as defined above for formula (I). Each chlorine atom of the compound of formula (4) is selectively replaced at different conditions. Compounds of formula (4) are reacted with different amines (Wa=morpholine or substituted morpholine derivatives) to yield the compound of formula (5a) and with aryl and heteroaryl boronic acid (ester) (Wb) by Suzuki coupling in the presence of palladium catalyst to yield the compound of formula (5b). The second chlorine atom is replaced with 4-aminoaryl and aminoheteroaryl boronic acid(ester) in the presence of palladium catalyst to yield (Ia) and (Ib) respectively. The amino group is converted to the urea derivatives by three different procedures depending upon the availability of the starting material. Some of the examples shown here are converted into the urea derivatives by reacting (Ia) or (Ib) with an appropriately substituted isocyanate or thioisocyanate derivative. Some of the urea derivatives reported here are prepared by reacting (Ia) or (Ib) with triphosgene in presence of tiethylamine and an appropriately substituted primary amine derivative. The corresponding carbamate derivatives are prepared by reacting (Ia), (Ib) or a substituted amine derivative with a phenyl chloroformate reagent. The phenyl N-substituted carbamates are reacted with different substituted amine, heteroalkyl amine or heteroaryl aniline to yield the compound of formula (Ia-a) or (Ib-b).

Scheme 10

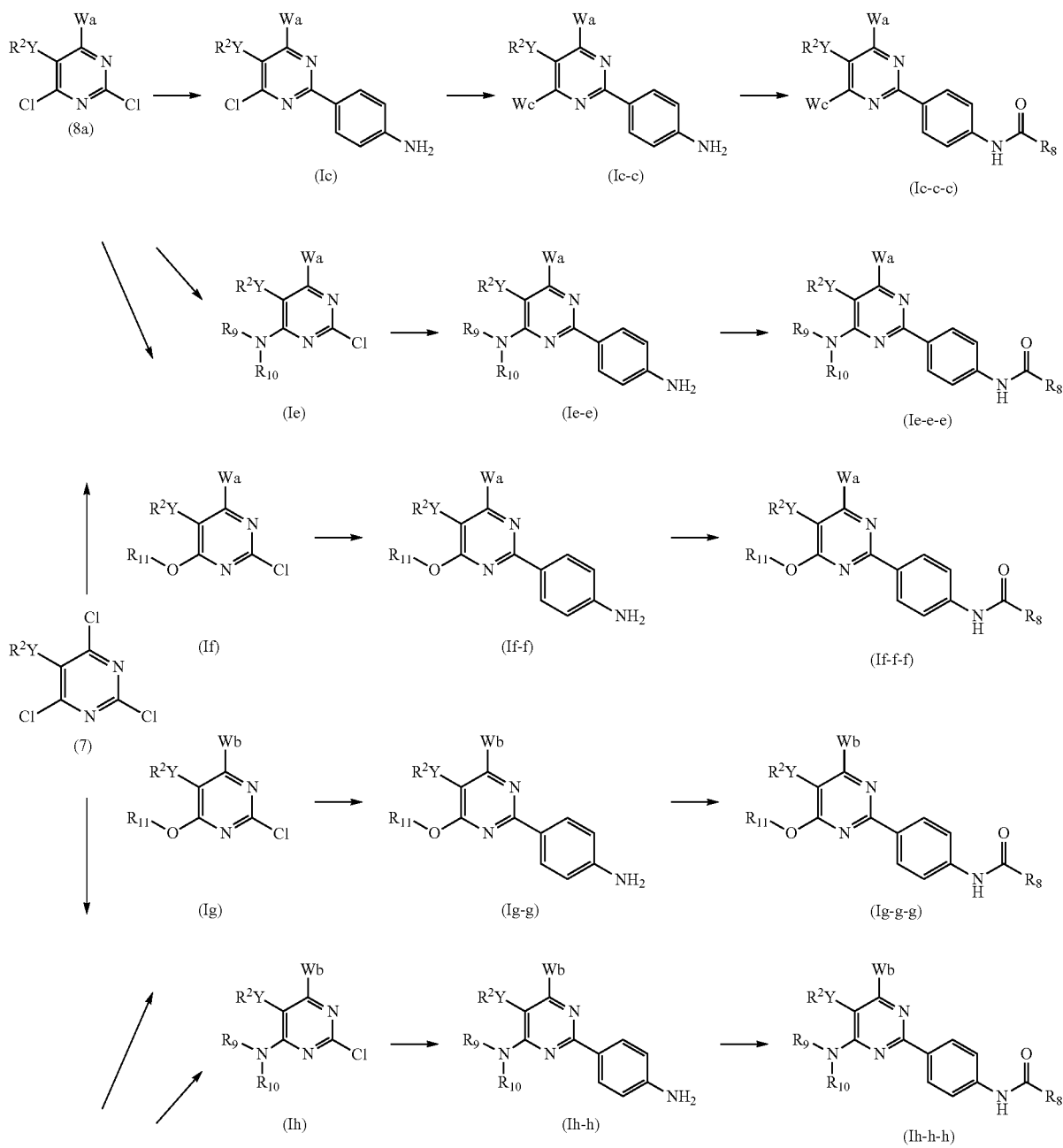

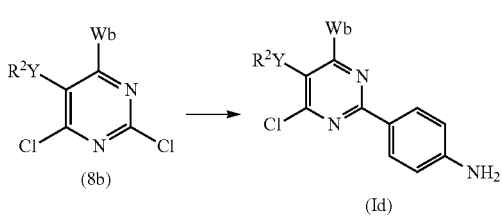 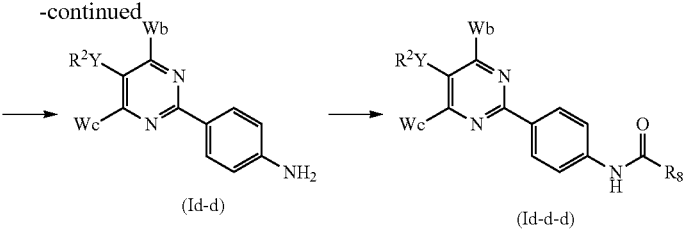

Substitution at the 6-Cl is not limited to an amino group, as described in Scheme 2, 7 and 8. 6-Cl can also bear an oxygen or a carbon linker. In Scheme 10, $R^2$, Y, W(Wa, Wb, Wc) and $R_8=NR_3R_4$ are as defined above for formula (I). Each chlorine atom of the compound of formula (7) is selectively replaced at different conditions. Substitution at the chlorine position is not limited to an amino group. Chlorine position can also bear an oxygen or a carbon linker. 2,4,6-Trisubstituted pyrimidines can be obtained via standard procedure (i.e. SNAr, Mitsunobu, Suzuki, Stille and Heck couplings). Compounds of formula (7) are reacted with different amines (Wa=morpholine or substituted morpholine derivatives) to yield the compound of formula (8a) and with aryl and heteroaryl boronic acid (ester) (Wb) by Suzuki coupling in the presence of palladium catalyst to yield the compound of formula (8b). The second chlorine atom is replaced with 4-aminoaryl and aminoheteroaryl boronic acid(ester) in the presence of palladium catalyst to yield (Ic) and (Id) respectively. The third chlorine atom is replaced with alkyl, alkene, alkyne, aryl or heteroaryl by organomagnesium or organozinc or organoboronic ester reagents to yield (Ic-c) and (Id-d) respectively. The amino group of (Ic-c) and (Id-d) is converted to the urea derivatives by three different procedures as described above (Scheme 9) to yield the compound of formula (Ic-c-c) and (Id-d-d). Compounds of formula (8a) and (8b) also are reacted with different amines and alcohols to give (Ie), (If), (Ie), and (Ih), respectively. Compounds of formula (Ie), (If), (Ig) and (Ih) then underwent the same procedures as described above to yield compounds of formula (Ie-e-e), (If-f-f), (Ig-g-g) and (Ih-h-h).

It has now been found that a series of novel pyrimidine compounds have inhibitory activity against the PI3K enzymes and the class IV kinase mTOR. It is now well understood that deregulation of oncogenes and tumour-suppressor genes contributes to the formation of malignant tumours, for example, by way of increased cell proliferation or increased cell survival. It is also now known that signaling pathways mediated by the PI3K/mTOR families have a central role in a number of cell processes, including proliferation and survival, and deregulation of these pathways is a causative factor in a wide spectrum of human cancers and other diseases.

The compounds of the present invention have been found to be inhibitors of mTOR kinase and PI3 kinase. The pharmacological inhibitors of mTOR kinase and PI3 kinase should be of therapeutic value for treatment of various forms of cancer comprising solid tumors such as carcinomas, sarcomas, leukaemias and lymphoid malignancies. Accordingly, a compound of the present invention can be used to treat a disease or disorder arising from abnormal cell growth, function or behaviour associated with mTOR kinase and PI3 kinase.

Also within the scope of this invention are a pharmaceutical composition that contains an effective amount of at least one of the pyrimidine compounds of formula (I) or a stereoisomer, or a tautomer, or an N-oxide, or a pharmaceutically acceptable salt, or an ester, or a prodrug, or a hydrate, or a solvate thereof together with a pharmaceutically acceptable carrier, a method for treating a PI3K kinase-/mTOR kinase-related disease (e.g., cancer) by administering to a subject in need of this treatment an effective amount of the pyrimidine compounds of formula (I), and a method of decreasing the activity of at least one PI3K kinase and mTOR kinase by contacting the at least one PI3K kinase and mTOR kinase with at least one of the pyrimidine compounds of formula (I).

As used herein, the term "PI3 kinase-/mTOR kinase-related disease" refers to a disease or condition that is characterized by abnormal PI3 and/or mTOR activity or a disease or condition that can be treated with changes to the activity of at least one of PI3 and mTOR. Abnormal PI3 and/or mTOR activity can arise as the result of elevated PI3 and/or mTOR expression level, or presence of PI3 and/or mTOR expression that does not occur in normal conditions. PI3 kinase-/mTOR kinase-related diseases described herein include, but are not limited to, cancer, diabetes, immune disorders, hyper-proliferation disorders, hyperproliferative disorders of the kidney, renal disease, von Hippel-Lindau disease, restenosis, fibrosis, psoriasis, osteoarthritis, rheumatoid arthritis, inflammatory disorders, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering a pyrimidine compound of formula (I) to a subject that has a PI3 kinase-/mTOR kinase-related disease, or has a symptom of or a predisposition toward it, with the purpose to cure, heal, alleviate, relieve, alter, remedy, ameliorate, improve, affect or reduce the risk of the disorder, or the symptoms of or the predisposition toward the disorder. For example, treating cancer refers to treatment resulting in inhibition of cancer growth or cancer cell growth, regression in cancer growth (i.e. reducing the size of a detectable cancer), or disappearance of a cancer. The term "an effective amount" refers to the amount of the active agent that is required to confer the intended therapeutic effect in the subject. Effective amounts may vary, as recognized by those skilled in the art, depending on route of administration, the excipient used, and the possibility of co-usage with other agents. The subject in need of the treatment can be a mammal. The term "mammal" refers to human or nonhuman mammal, for example, dogs, cats, pigs, cows, sheep, goats, horses, rats, or mice.

Cancer that can be treated by the methods of the invention is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, and leukemia. The cancers also include Epidermal Growth Factor Receptor (EGFR) dependent cancers or cancers that resist to EGFR targeting agent.

The compounds described herein can be administered to a mammal in conjunction with radiation therapy, immunotherapy, monoclonal antibody therapy, hormonal therapy, chemotherapy using other agents, and/or surgery. "In conjunction with" means that the therapies do not need to occur at the same time, and can be in succession, or alternate with each other and/or periods of rest and recovery.

In one embodiment, a PI3 kinase-/mTOR kinase-related disease, such as cancer, can be treated with a method comprising administering an effective amount of at least a pyrimidine compound of formula (I) and at least one chemotherapeutic agent to a mammal. Non-limiting examples of chemotherapeutic agent include protein kinase inhibitors other than the compound described herein (e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide), alkylating agents (e.g., melphalan, chlorambucil, busulfan, thiotepa, ifosfamide, carmustine, lomustine, semustine, streptozocin, decarbazine, and cyclophosphamide), mitotic inhibitors, antimetabolites (e.g., capecitibine, gemcitabine, 5-fluorouracil or 5-fluorouracil/leucovorin, fludarabine, cytarabine, mercaptopurine, thioguanine, pentostatin, and methotrexate), cell cycle inhibitors, enzymes, hormones, anti-hormones, growth-factor inhibitors, plant alkaloids and terpenoids, topoisomerase inhibitors (e.g., etoposide, teniposide, camptothecin, topotecan, irinotecan, doxorubicin, and daunorubicin), antitumor antibiotics (e.g., actinomycin D, bleomycin, mitomycin C, adriamycin, daunorubicin, idarubicin, doxorubicin and pegylated liposomal doxorubicin), vinca alkaloids (e.g., vincristine and vinblastin), taxanes (e.g., paclitaxel and docetaxel), platinum agents (e.g., cisplatin, carboplatin, and oxaliplatin), thalidomide and related analogs (e.g., CC-5013 and CC-4047), monoclonal antibodies, antiangiogenic agents, and combinations thereof.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In one embodiment, the pharmaceutical composition of this invention is administered intravenously. The pharmaceutically acceptable carriers may include, but are not limited to, water, Ringer's solution, isotonic sodium chloride solution or phosphate buffered saline, and solutions containing thickening and solubilizing agents, such as glucose, polyethylene glycol, and polypropylene glycol and mixtures thereof.

A sterile injectable composition can be formulated according to techniques known in the art using suitable dispersing or wetting agents and suspending agents. The sterile injectable preparation can also be a sterile injectable solution or suspension in a non-toxic parenterally acceptable diluent or solvent. Among the acceptable vehicles and solvents that can be employed are mannitol, water, Ringer's solution and isotonic sodium chloride solution. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. The composition of the present invention may also be administered in the form of suppositories for rectal administration.

Suitable in vitro assays can be used to preliminarily evaluate the efficacy of the pyrimidine compounds of formula (I) in anticancer activities such as inhibiting growth of tumor cells. The compounds can further be examined for their efficacy in treating cancer. For example, a compound can be administered to an animal (e.g., a mouse model) having cancer and its therapeutic effects then assessed. Based on the results, an appropriate dosage range and administration route can also be determined.

The invention will be further described in the Examples as follows. The examples given below are intended to be illustrative only and not to limit the invention. Any modifications and variations that can be easily made by those skilled in the art fall within the scope of the disclosure of the specification and the appended claims of the present invention.

EXAMPLES

Example 1

Preparation of Compounds of Formula (I) in Scheme 4

2-Ethoxy-Malonic Acid Diethyl Ester

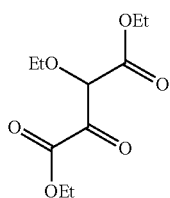

A mixture of diethyl oxalate (39.23 ml, 1.12 eq.) and ethyl ethoxyacetate (34.95 ml, 1 eq.) was added dropwise to a slurry of sodium ethoxide (18.64 g, 1.07 eq.) in toluene (100 ml) at 45-50° C. After dropping, the resulting solution was heated to 70-80° C. for 2 hrs and poured into 70 ml of 14% HCl with cooling. The resultant mixture was extracted with EA and the combined organic layers were washed with brine and dried in vacuo to give 55.86 g (93.7%) of a product.

2-Methoxy-Malonic Acid Diethyl Ester

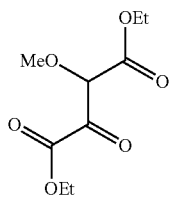

A mixture of diethyl oxalate (27.5 ml, 1 eq.) and methyl methoxyacetate (20 ml, 1 eq.) was added dropwise to a slurry of sodium methoxide (16.4 g, 1.5 eq.) in toluene (350 ml) at 45-50° C. After dropping, the resulting solution was heated to 70-80° C. for 2 hrs and poured into 70 ml of 14% HCl with cooling. The resultant mixture was extracted with EA and the combined organic layers were washed with brine and dried in vacuo to give 16.7 g (40.5%) of a product.

(2,5-Dioxo-imidazolidin-4-ylidene)-ethoxy-acetic acid ethyl ester

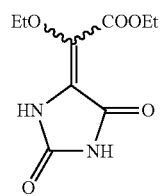

A mixture of diethyl 2-ethoxy-3-oxo-succinate (55.86 g, 1 eq) and urea (14.41 g, 1 eq.) was refluxed for 2.5 h in 1 M HCl-AcOH (1200 ml, 5 eq.) and allowed to become cool. The cooled mixture was evaporated to dryness. The residues were dissolved in MeOH, heated aside for crystallization. After crystallization, the precipitates were filtered to give a product which was an off-white solid (15.11 g, 27.5%).

$^1$H NMR (500 MHz, DMSO-$d_6$): δ1.21-1.27 (m, 6H), 3.82-3.86 (m, 2H), 4.24-4.29 (m, 2H), 9.79 (s, 1H), 11.33 (s, 1H)

(2,5-Dioxo-imidazolidin-4-ylidene)-methoxy-acetic acid ethyl ester

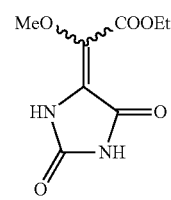

$^1$H NMR (500 MHz, DMSO-$d_6$): δ1.23-1.28 (m, 3H), 3.61 (s, 3H), 4.25-4.29 (m, 2H), 9.85 (s, 1H), 11.39 (s, 1H)

5-Ethoxy-2,6-dihydroxy-pyrimidine-4-carboxylic acid

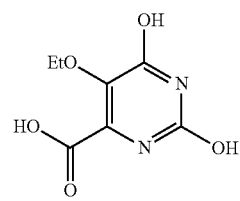 [SMILES: CCOc1c(O)nc(O)nc1C(=O)O]

(2,5-dioxo-imidazolidin-4-ylidene)-ethoxy-acetic acid ethyl ester (16.02 g, 1 eq.) was dissolved in aq. 1 N KOH (281 ml, 4 eq.) and refluxed for 3.5 hrs. The mixture was cooled to 0° C. and carefully acidified with conc. HCl. After overnight cooling (4° C.), it led to the formation of white precipitate. The mixture was filtered and the precipitate was dried in vacuo. The product obtained was a white solid (7.76 g, 55%).

$^1$H NMR (500 MHz, DMSO-$d_6$): δ1.17-1.23 (m, 3H), 3.89-3.93 (m, 2H), 10.60 (s, 1H), 11.42 (s, 1H)

2,6-Dihydroxy-5-methoxy-pyrimidine-4-carboxylic acid

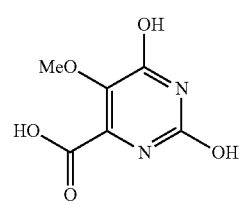 [SMILES: COc1c(O)nc(O)nc1C(=O)O]

$^1$H NMR (500 MHz, DMSO-$d_6$): δ3.61 (s, 3H), 10.53 (s, 1H), 11.39 (s, 1H)

5-Ethoxy-2,6-dihydroxy-pyrimidine-4-carboxylic acid ethyl ester

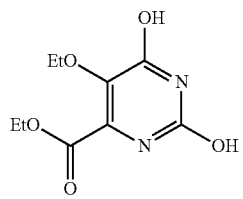 [SMILES: CCOC(=O)c1nc(O)nc(O)c1OCC]

Acetyl chloride (100 ml, 36 eq.) was added dropwise to absolute EtOH (780 ml) at 0° C. After stirring the resulting solution for 20 min at r.t., 5-ethoxy-2,6-dihydroxy-pyrimidine-4-carboxylic acid (7.76 g, 1 eq.) was added in one portion and the mixture was refluxed overnight. The volatiles were evaporated in vacuo to give 5-ethoxy-2,6-dihydroxy-pyrimidine-4-carboxylic acid ethyl ester as an off-white solid (8.85 g, 100%).

$^1$H NMR (500 MHz, DMSO-$d_6$): δ1.18-1.30 (m, 6H), 3.91-3.95 (m, 2H), 4.25-4.31 (m, 2H), 10.74 (s, 1H), 11.51 (s, 1H)

5-Methoxy-2,6-dihydroxy-pyrimidine-4-carboxylic acid ethyl ester

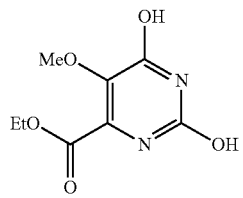 [SMILES: CCOC(=O)c1nc(O)nc(O)c1OC]

$^1$H NMR (500 MHz, DMSO-$d_6$): δ1.23-1.30 (m, 3H), 365 (s, 3H), 4.27-4.32 (m, 2H), 10.80 (s, 1H), 11.54 (s, 1H)

2,6-Dichloro-5-ethoxy-pyrimidine-4-carboxylic acid ethyl ester

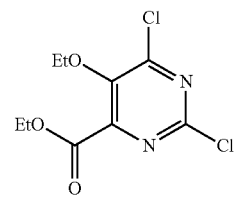 [SMILES: CCOC(=O)c1nc(Cl)nc(Cl)c1OCC]

N,N-dimethylaniline (6.85 ml) was added to a stirred solution of 5-ethoxy-2,6-dihydroxy-pyrimidine-4-carboxylic acid ethyl ester (8.85 g) in POCl$_3$ (265 ml) and the mixture was refluxed overnight. Excess POCl$_3$ was evaporated in vacuo and the residue was poured into ice-water and extracted with ether. The combined ethereal layers were washed with brine, dried and evaporated in vacuo. Purification by flash chromatography gave a product (8.33 g, 81%).

$^1$H NMR (500 MHz, DMSO-$d_6$): δ1.23-1.35 (m, 3H), 4.13-4.18 (m, 2H), 4.39-4.43 (m, 2H)

2,6-Dichloro-5-methoxy-pyrimidine-4-carboxylic acid ethyl ester

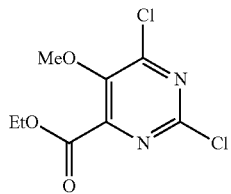 [SMILES: CCOC(=O)c1nc(Cl)nc(Cl)c1OC]

$^1$H NMR (500 MHz, DMSO-$d_6$): δ1.26-1.35 (m, 3H), 3.93 (s, 3H), 4.40-4.48 (m, 2H)

2-Chloro-5-ethoxy-6-morpholin-4-yl-pyrimidine-4-carboxylic acid ethyl ester

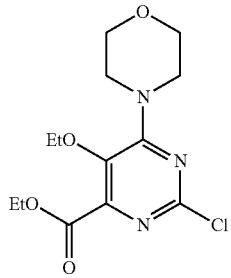 [SMILES: CCOC(=O)c1nc(Cl)nc(N2CCOCC2)c1OCC]

2,6-dichloro-5-ethoxy-pyrimidine-4-carboxylic acid ethyl ester (2 g, 1 eq.) was stirred in toluene (80 ml) and a solution of morpholine (0.73 ml, 1.1 eq.) in toluene (20 ml) was added dropwise in about 10 minutes at −10~0° C., after stirring the resulting solution for 3 h at r.t. Water was added and extracted with EA. The combined organic layers were washed with brine, dried and evaporated in vacuo. Purification by flash chromatography gave a product (1.79 g, 75%).

$^1$H NMR (500 MHz, CDCl$_3$-$d_1$): δ1.33-1.41 (m, 6H), 3.76-3.78 (m, 4H), 3.87-3.89 (m, 4H), 3.92-3.96 (m, 2H), 4.39-4.43 (m, 2H)

2-Chloro-5-methoxy-6-morpholin-4-yl-pyrimidine-4-carboxylic acid ethyl ester

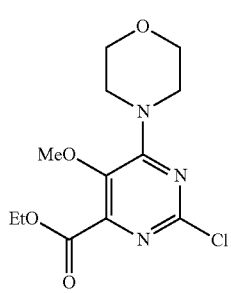 [SMILES: CCOC(=O)c1nc(Cl)nc(N2CCOCC2)c1OC]

$^1$H NMR (500 MHz, CDCl$_3$-$d_1$): δ1.38-1.42 (m, 3H), 3.74 (s, 3H), 3.77-3.79 (m, 4H), 3.87-3.89 (m, 4H), 4.40-4.44 (m, 2H)

5-Ethoxy-2-(3-hydroxy-phenyl)-6-morpholin-4-yl-pyrimidine-4-carboxylic acid ethyl ester

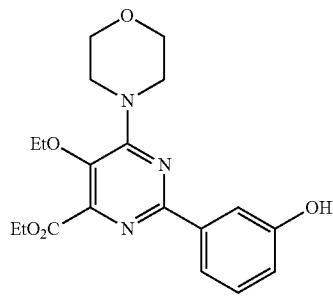 [SMILES: CCOC(=O)c1nc(-c2cccc(O)c2)nc(N2CCOCC2)c1OCC]

A mixture of 2-chloro-5-ethoxy-6-morpholine-4-yl-pyrimidine-4-carboxylic acid ethyl ester (152 mg, 1 eq.), 3-(4,4,5,5-tetramethyl-1,3,2-dioxaborolan-2-yl)phenol (137.9 mg, 1.3 eq.), dioxane (6 ml), $H_2O$ (1 ml), $Pd(PPh_3)_4$ (56 mg, 0.1 eq.) and sodium carbonate (102 mg, 2 eq.) was heated to reflux overnight. The solvent was removed in vacuo. The residue was extracted with EA, and the organic layer washed with brine and dried. The crude was purified by chromatography to give a product (99.6 mg, 55%).

$^1$H NMR (500 MHz, $CDCl_3$-$d_1$): δ1.36-1.39 (m, 3H), 1.44-1.46 (m, 3H), 3.85-3.87 (m, 4H), 3.91-3.93 (m, 4H), 3.99-4.03 (m, 2H), 4.46-4.50 (m, 2H), 6.94-6.95 (m, 1H), 7.27-7.33 (m, 1H), 7.82-7.83 (m, 1H), 7.91-7.92 (m, 1H)

Compounds of the following Examples were synthesized following the synthetic method described above. The bronic acids or bronic esters are readily recognizable by one skilled in the art and are commercially available from Aldrich, Acros Organics and Maybridge Chemical Company Ltd.

5-Ethoxy-2-(4-hydroxy-3-methoxy-phenyl)-6-morpholin-4-yl-pyrimidine-4-carboxylic acid ethyl ester

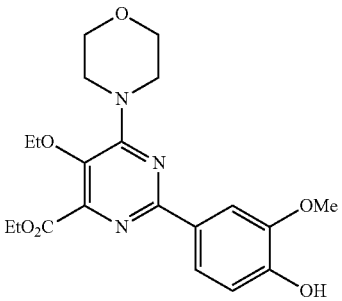 [SMILES: CCOC(=O)c1nc(-c2ccc(O)c(OC)c2)nc(N2CCOCC2)c1OCC]

$^1$H NMR (500 MHz, $CDCl_3$-$d_1$): δ1.33-1.36 (m, 3H), 1.42-1.45 (m, 3H), 3.82-3.88 (m, 8H), 3.96-3.99 (m, 5H), 4.47-4.49 (m, 2H), 5.84 (s, 1H), 6.94-6.96 (m, 1H), 7.89-7.91 (m, 2H)

5-Ethoxy-2-(3-fluoro-4-methoxy-phenyl)-6-morpholin-4-yl-pyrimidine-4-carboxylic acid ethyl ester

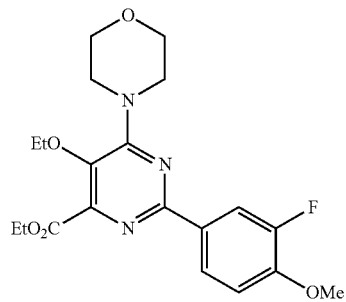 [SMILES: CCOC(=O)c1nc(-c2ccc(OC)c(F)c2)nc(N2CCOCC2)c1OCC]

$^1$H NMR (500 MHz, $CDCl_3$-$d_1$): δ1.34-1.36 (m, 3H), 1.42-1.45 (m, 3H), 3.82-3.84 (m, 4H), 3.88-3.89 (m, 4H), 3.95 (s, 3H), 3.94-4.00 (m, 2H), 4.44-4.49 (m, 2H), 6.96-6.99 (m, 1H), 8.04-8.11 (m, 2H)

2-(3-Amino-phenyl)-5-ethoxy-6-morpholin-4-yl-pyrimidine-4-carboxylic acid ethyl ester

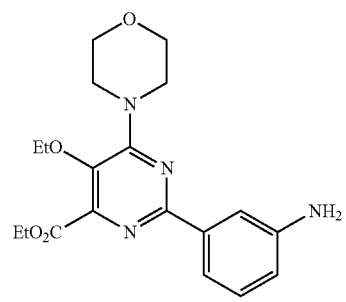 [SMILES: CCOC(=O)c1nc(-c2cccc(N)c2)nc(N2CCOCC2)c1OCC]

$^1$H NMR (500 MHz, $CDCl_3$-$d_1$): δ1.34-1.36 (m, 3H), 1.42-1.44 (m, 3H), 3.74 (s, 2H), 3.81-3.84 (m, 4H), 3.88-3.90 (m, 4H), 3.96-4.00 (m, 2H), 4.44-4.49 (m, 2H), 6.75-6.76 (m, 1H), 7.20-7.26 (m, 1H), 7.68-7.74 (m, 1H)

2-(3,5-Difluoro-phenyl)-5-ethoxy-6-morpholin-4-yl-pyrimidine-4-carboxylic acid ethyl ester

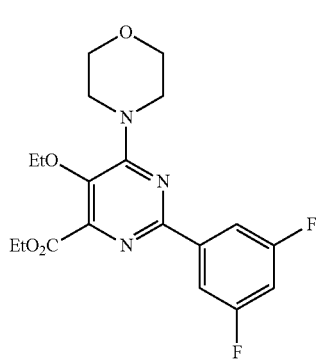 [SMILES: CCOC(=O)c1nc(-c2cc(F)cc(F)c2)nc(N2CCOCC2)c1OCC]

$^1$H NMR (500 MHz, $CDCl_3$-$d_1$): δ1.35-1.38 (m, 3H), 1.43-1.46 (m, 3H), 3.83-3.84 (m, 4H), 3.89-3.91 (m, 4H), 3.98-4.02 (m, 2H), 4.45-4.50 (m, 2H), 6.84-6.88 (m, 1H), 7.84-7.86 (m, 2H)

5-Ethoxy-2-(1H-indol-6-yl)-6-morpholin-4-yl-pyrimidine-4-carboxylic acid ethyl ester

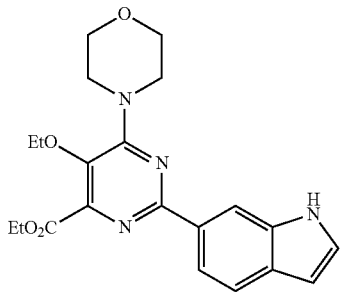 [SMILES: CCOC(=O)c1nc(-c2ccc3cc[nH]c3c2)nc(N2CCOCC2)c1OCC]

¹H NMR (500 MHz, CDCl₃-d₁): δ1.34-1.37 (m, 3H), 1.43-1.46 (m, 3H), 3.84-3.86 (m, 4H), 3.91-3.93 (m, 4H), 3.98-4.02 (m, 2H), 4.46-4.50 (m, 2H), 6.57 (s, 1H), 7.26-7.28 (m, 1H), 7.65-7.66 (m, 1H), 8.13-8.14 (m, 1H), 8.33 (s, 1H), 8.45 (s, 1H)

5-Ethoxy-2-(1H-indol-5-yl)-6-morpholin-4-yl-pyrimidine-4-carboxylic acid ethyl ester

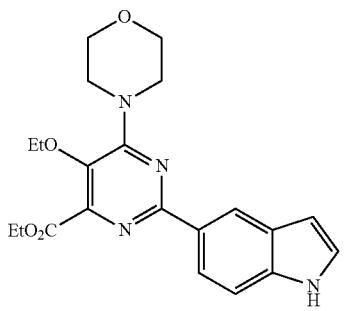 [SMILES: CCOC(=O)c1nc(-c2ccc3[nH]ccc3c2)nc(N2CCOCC2)c1OCC]

¹H NMR (500 MHz, CDCl₃-d₁): δ1.34-1.37 (m, 3H), 1.43-1.46 (m, 3H), 3.84-3.86 (m, 4H), 3.91-3.93 (m, 4H), 3.97-4.02 (m, 2H), 4.46-4.50 (m, 2H), 6.63 (s, 1H), 7.21-7.22 (m, 1H), 7.39-7.41 (m, 1H), 8.23-8.28 (m, 2H), 8.67 (s, 1H)

5-Ethoxy-2-(1H-indazol-4-yl)-6-morpholin-4-yl-pyrimidine-4-carboxylic acid ethyl ester

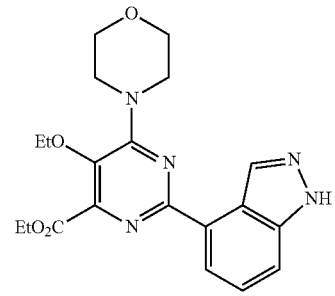

¹H NMR (500 MHz, CDCl₃-d₁): δ1.37-1.40 (m, 3H), 1.46-1.49 (m, 3H), 3.87-3.88 (m, 4H), 3.93-3.95 (m, 4H), 4.03-4.07 (m, 2H), 4.48-4.52 (m, 2H), 7.45-7.48 (m, 1H), 7.58-7.59 (m, 1H), 8.21-8.22 (m, 1H), 8.98 (s, 1H)

2-Benzo[1,3]dioxol-5-yl-5-ethoxy-6-morpholin-4-yl-pyrimidine-4-carboxylic acid ethyl ester

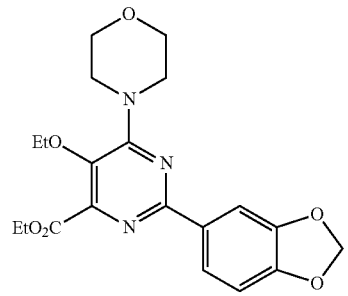 [SMILES: CCOC(=O)c1nc(-c2ccc3c(c2)OCO3)nc(N2CCOCC2)c1OCC]

¹H NMR (500 MHz, CDCl₃-d₁): δ1.33-1.36 (m, 3H), 1.42-1.45 (m, 3H), 3.82-3.83 (m, 4H), 3.87-3.88 (m, 4H), 3.95-3.99 (m, 2H), 4.44-4.48 (m, 2H), 6.00 (s, 1H), 6.84-6.86 (m, 1H), 7.81 (s, 1H), 7.92-7.94 (m, 1H)

5-Ethoxy-2-(2-fluoro-3-methoxy-phenyl)-6-morpholin-4-yl-pyrimidine-4-carboxylic acid ethyl ester

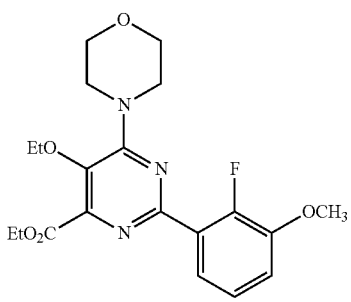 [SMILES: CCOC(=O)c1nc(-c2cccc(OC)c2F)nc(N2CCOCC2)c1OCC]

¹H NMR (500 MHz, CDCl₃-d₁): δ1.35-1.38 (m, 3H), 1.41-1.44 (m, 3H), 3.79-3.80 (m, 4H), 3.90-3.92 (m, 4H), 3.98-4.03 (m, 2H), 4.43-4.47 (m, 2H), 7.00-7.04 (m, 1H), 7.10-7.13 (m, 1H), 7.57-7.59 (m, 1H)

2-(4-Amino-phenyl)-5-ethoxy-6-morpholin-4-yl-pyrimidine-4-carboxylic acid ethyl ester

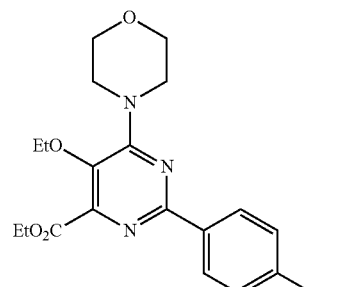

¹H NMR (500 MHz, CDCl₃-d₁): δ1.32-1.35 (m, 3H), 1.42-1.44 (m, 3H), 3.82-3.87 (m, 10H), 3.94-3.99 (m, 2H), 4.43-4.48 (m, 2H), 6.68-6.70 (m, 2H), 8.15-8.16 (m, 2H)

5-Methoxy-2-(3-hydroxy-phenyl)-6-morpholin-4-yl-pyrimidine-4-carboxylic acid ethyl ester

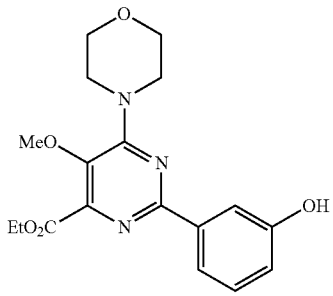 [SMILES: CCOC(=O)c1nc(-c2cccc(O)c2)nc(N2CCOCC2)c1OC]

¹H NMR (500 MHz, CDCl₃-d₁): δ1.44-1.47 (m, 3H), 3.81 (s, 3H), 3.86-3.88 (m, 4H), 3.91-3.93 (m, 4H), 4.47-4.51 (m, 2H), 5.33 (s, 1H), 6.94-6.95 (m, 1H), 7.29-7.34 (m, 1H), 7.82-7.83 (m, 1H), 7.91-7.93 (m, 1H)

5-Methoxy-2-(1H-indazol-4-yl)-6-morpholin-4-yl-pyrimidine-4-carboxylic acid ethyl ester

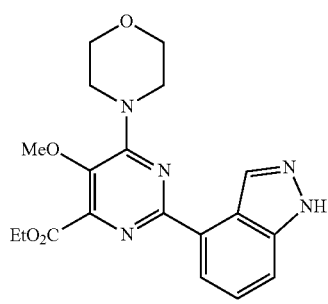 [SMILES: CCOC(=O)c1nc(-c2cccc3[nH]ncc23)nc(N2CCOCC2)c1OC]

¹H NMR (500 MHz, CDCl₃-d₁): δ1.45-1.48 (m, 3H), 3.83 (s, 3H), 3.87-3.87 (m, 4H), 3.92-3.94 (m, 4H), 4.48-4.53 (m, 2H), 7.44-7.47 (m, 1H), 7.58-7.60 (m, 1H), 8.20-8.21 (m, 1H), 8.98 (m, 1H)

2-(4-hydroxy-phenyl)-5-ethoxy-6-morpholin-4-yl-pyrimidine-4-carboxylic acid ethyl ester

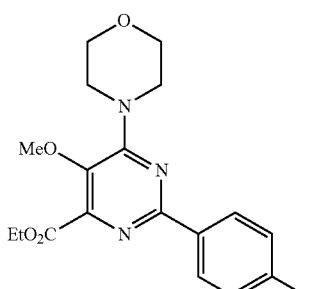

¹H NMR (500 MHz, CDCl₃-d₁): δ1.33-1.36 (m, 3H), 1.41-1.43 (m, 3H), 3.82-3.84 (m, 4H), 3.86-3.89 (m, 4H), 3.95-3.99 (m, 2H), 4.43-4.47 (m, 2H), 5.79 (s, 1H), 6.84-6.86 (m, 2H), 8.21-8.22 (m, 2H)

2-(6-Amino-pyridin-3-yl)-5-ethoxy-6-morpholin-4-yl-pyrimidine-4-carboxylic acid ethyl ester

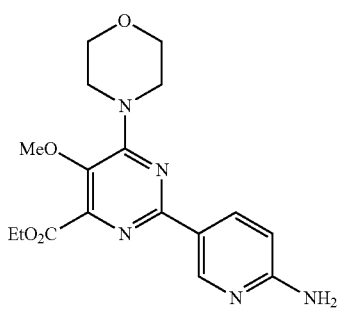

¹H NMR (500 MHz, CDCl₃-d₁): δ1.33-1.36 (m, 3H), 1.42-1.45 (m, 3H), 3.81-3.83 (m, 4H), 3.87-3.88 (m, 4H), 3.95-3.99 (m, 2H), 4.44-4.48 (m, 2H), 4.67 (s, 2H), 6.51-6.52 (m, 1H), 8.34-8.36 (m, 1H), 9.01-9.02 (m, 1H)

5-Ethoxy-6-morpholin-4-yl-2-[4-(3-phenyl-ureido)-phenyl]-pyrimidine-4-carboxylic acid ethyl ester

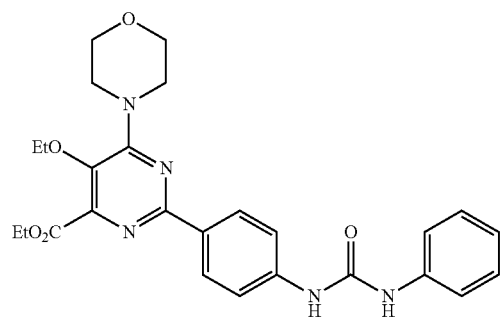

Phenyl isocyanate (0.22 ml, 1.5 eq.) was added to a stirred solution of 2-(4-Amino-phenyl)-5-ethoxy-6-morpholin-4-yl-pyrimidine-4-carboxylic acid ethyl ester (500 mg, 1 eq.) in toluene (25 ml) and the mixture was reacted for 4 h at 80° C. The reaction mixture was cooled, the solvent was removed in vacuo, and the residue was washed with EA and filtered to give a product (550 mg, 83%).

¹H NMR (500 MHz, Acetone-d₆): δ1.31-1.40 (m, 6H), 3.81-3.83 (m, 4H), 3.88-3.90 (m, 4H), 3.98-4.03 (m, 2H), 4.39-4.43 (m, 2H), 6.98-7.01 (m, 1H), 7.27-7.30 (m, 2H), 7.54-7.56 (m, 2H), 7.62-7.64 (m, 2H), 8.17 (s, 1H), 8.27-8.29 (m, 2H), 8.33 (s, 1H)

5-Ethoxy-2-[4-(3-ethyl-ureido)-phenyl]-6-morpholin-4-yl-pyrimidine-4-carboxylic acid ethyl ester

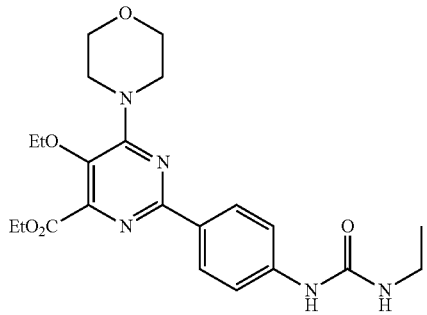 [SMILES: CCNC(=O)Nc1ccc(-c2nc(C(=O)OCC)c(OCC)c(N3CCOCC3)n2)cc1]

Ethyl isocyanate (0.012 ml, 1.4 eq.) was added to a stirred solution of 2-(4-amino-phenyl)-5-ethoxy-6-morpholin-4-yl-pyrimidine-4-carboxylic acid ethyl ester (40 mg, 1 eq.) in toluene (2 ml) and the mixture was reacted overnight at 80° C.

The reaction mixture was extracted with EA, washed with brine. The crude was purified by chromatography to give a product (12 mg, 25.2%).

$^1$H NMR (500 MHz, Acetone-$d_6$): δ1.10-1.13 (m, 3H), 1.31-1.39 (m, 6H), 3.25 (m, 2H), 3.81-3.82 (m, 4H), 3.86-3.87 (m, 4H), 4.00-4.01 (m, 2H), 4.39-4.41 (m, 2H), 5.85 (m, 1H), 7.55-7.57 (m, 2H), 8.09 (s, 1H), 8.21-8.23 (m, 2H)

The urea compounds of the following Examples were synthesized following the synthetic method described above by the different isocycanate that are commercially available.

2-{3-[3-(4-Chloro-3-trifluoromethyl-phenyl)-ureido]-phenyl}-5-ethoxy-6-morpholin-4-yl-pyrimidine-4-carboxylic acid ethyl ester

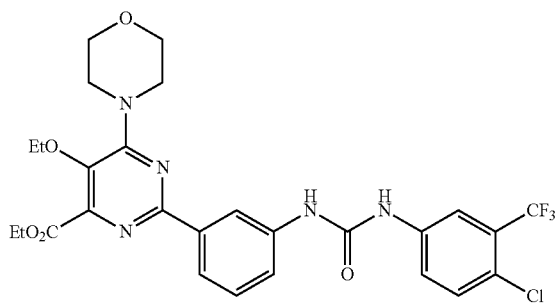 [SMILES: CCOC(=O)c1nc(-c2cccc(NC(=O)Nc3ccc(Cl)c(C(F)(F)F)c3)c2)nc(N2CCOCC2)c1OCC]

$^1$H NMR (500 MHz, Acetone-$d_6$): δ1.32-1.35 (m, 3H), 1.38-1.41 (m, 3H), 3.81-3.83 (m, 4H), 3.89-3.91 (m, 4H), 4.02-4.05 (m, 2H), 4.40-4.44 (m, 2H), 7.38-7.41 (m, 1H), 7.55-7.57 (m, 1H), 7.76-7.79 (m, 1H), 7.82-7.84 (m, 2H), 8.01-8.03 (m, 1H), 8.16-8.17 (m, 1H), 8.36 (s, H), 8.43 (s, 1H), 8.58 (s, 1H)

5-Ethoxy-6-morpholin-4-yl-2-[3-(3-phenyl-ureido)-phenyl]-pyrimidine-4-carboxylic acid ethyl ester

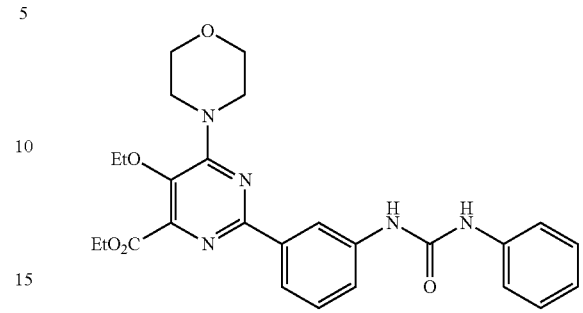

$^1$H NMR (500 MHz, Acetone-$d_6$): δ1.32-1.34 (m, 3H), 1.38-1.41 (m, 3H), 3.81-3.83 (m, 4H), 3.89-3.91 (m, 4H), 4.02-4.05 (m, 2H), 4.41-4.44 (m, 2H), 6.99 (m, 1H), 7.26-7.30 (m, 2H), 7.55-7.57 (m, 2H), 7.84-7.86 (m, 1H), 7.98-8.00 (m, 1H), 8.15 (s, 1H), 8.27 (s, 1H), 8.34-8.36 (m, 1H)

2-{4-[3-(4-Chloro-3-trifluoromethyl-phenyl)-ureido]-phenyl}-5-ethoxy-6-morpholin-4-yl-pyrimidine-4-carboxylic acid ethyl ester

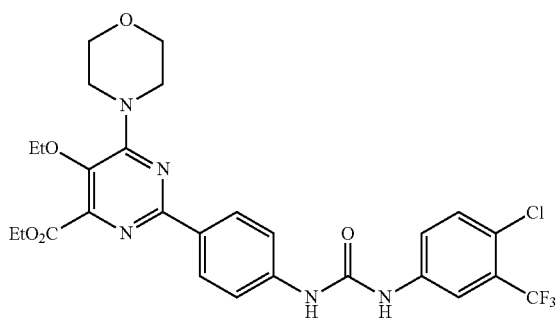 [SMILES: CCOC(=O)c1nc(-c2ccc(NC(=O)Nc3ccc(Cl)c(C(F)(F)F)c3)cc2)nc(N2CCOCC2)c1OCC]

$^1$H NMR (500 MHz, Acetone-$d_6$): δ1.33-1.42 (m, 6H), 3.83-3.85 (m, 4H), 3.90-3.92 (m, 4H), 4.03-4.05 (m, 2H), 4.41-4.45 (m, 2H), 7.58-7.60 (m, 1H), 7.64-7.66 (m, 2H), 7.78-7.80 (m, 1H), 8.18 (m, 1H), 8.31-8.32 (m, 2H), 8.52 (s, 1H), 8.63 (s, 1H)

5-Ethoxy-2-{4-[3-(3-fluoro-phenyl)-ureido]-phenyl}-6-morpholin-4-yl-pyrimidine-4-carboxylic acid ethyl ester

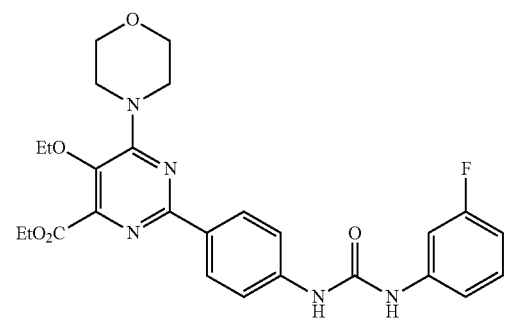

¹H NMR (500 MHz, Acetone-d₆): δ1.32-1.34 (m, 3H), 1.37-1.40 (m, 3H), 3.81-3.83 (m, 4H), 3.88-3.90 (m, 4H), 4.00-4.02 (m, 2H), 4.40-4.42 (m, 2H), 6.70-6.80 (m, 1H), 7.10-7.20 (m, 1H), 7.21-7.31 (m, 1H), 7.62-7.64 (m, 3H), 8.28-8.30 (m, 2H), 8.38 (s, 2H)

5-Ethoxy-2-{4-[3-(4-fluoro-phenyl)-ureido]-phenyl}-6-morpholin-4-yl-pyrimidine-4-carboxylic acid ethyl ester

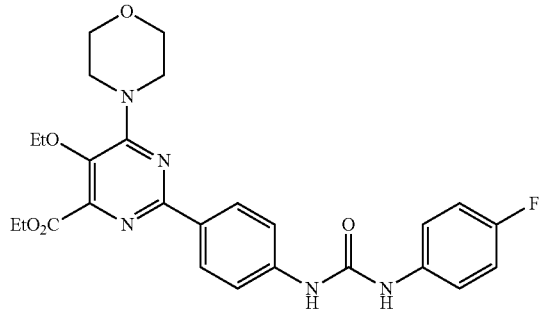 [SMILES: CCOC(=O)c1nc(-c2ccc(NC(=O)Nc3ccc(F)cc3)cc2)nc(N2CCOCC2)c1OCC]

¹H NMR (500 MHz, Acetone-d₆): δ1.30-1.35 (m, 3H), 1.38-1.41 (m, 3H), 3.81-3.84 (m, 4H), 3.88-3.90 (m, 4H), 4.01-4.04 (m, 2H), 4.40-4.44 (m, 2H), 7.06-7.10 (m, 2H), 7.56-7.64 (m, 4H), 8.22-8.34 (m, 3H)

2-{4-[3-(3,4-Difluoro-phenyl)-ureido]-phenyl}-5-ethoxy-6-morpholin-4-yl-pyrimidine-4-carboxylic acid ethyl ester

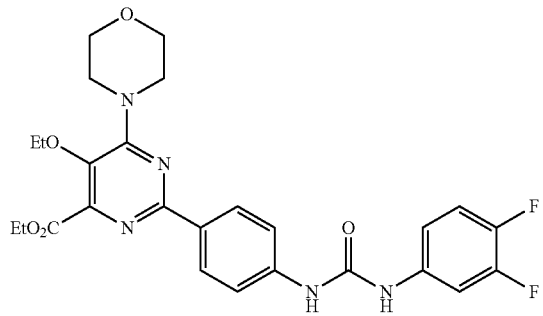

¹H NMR (500 MHz, Acetone-d₆): δ1.30-1.35 (m, 3H), 1.38-1.41 (m, 3H), 3.82-3.84 (m, 4H), 3.89-3.91 (m, 4H), 4.00-4.04 (m, 2H), 4.40-4.44 (m, 2H), 7.20-7.25 (m, 2H), 7.62-7.64 (m, 2H), 7.80-7.90 (m, 1H), 8.29-8.30 (m, 2H), 8.38 (s, 1H)

2-{4-[3-(6-Chloro-pyridin-3-yl)-ureido]-phenyl}-5-ethoxy-6-morpholin-4-yl-pyrimidine-4-carboxylic acid ethyl ester

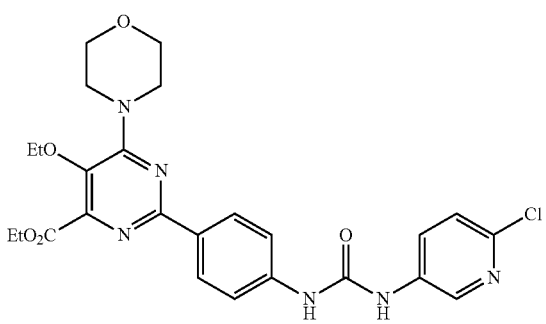 [SMILES: CCOC(=O)c1nc(-c2ccc(NC(=O)Nc3ccc(Cl)nc3)cc2)nc(N2CCOCC2)c1OCC]

¹H NMR (500 MHz, Acetone-d₆): δ1.31-1.40 (m, 6H), 3.80-3.82 (m, 4H), 3.88-3.90 (m, 4H), 4.00-4.03 (m, 2H), 4.39-4.43 (m, 2H), 7.37-7.39 (m, 1H), 7.62-7.64 (m, 2H), 8.11-8.13 (m, 1H), 8.28-8.30 (m, 2H), 8.47-8.49 (m, 1H)

5-Ethoxy-6-morpholin-4-yl-2-(4-ureido-phenyl)-pyrimidine-4-carboxylic acid ethyl ester

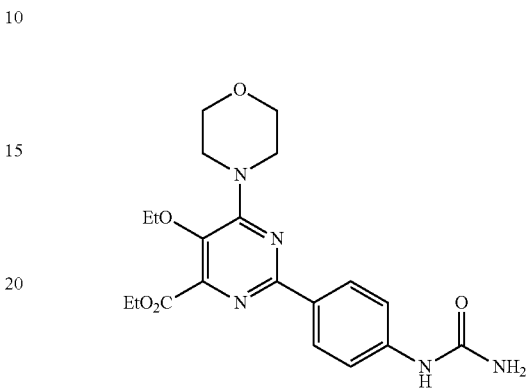

Trimethylsilyl isocyanate (0.1 ml, 5 eq.) was added to a stirred solution of 2-(4-amino-phenyl)-5-ethoxy-6-morpholin-4-yl-pyrimidine-4-carboxylic acid ethyl ester (60 mg, 1 eq.) in THF (2 ml) and the mixture was reacted to reflux overnight. The reaction mixture was extracted with EA and washed with brine. The crude was purified by chromatography to give a product (26.2 mg, 40%).

¹H NMR (500 MHz, Acetone-d₆): δ1.31-1.40 (m, 6H), 3.80-3.82 (m, 4H), 3.86-3.88 (m, 4H), 3.99-4.02 (m, 2H), 4.38-4.42 (m, 2H), 5.55 (s, 2H), 7.57-7.59 (m, 2H), 8.22-8.24 (m, 2H), 8.31 (s, 1H)

5-Ethoxy-6-morpholin-4-yl-2-[6-(3-phenyl-ureido)-pyridin-3-yl]-pyrimidine-4-carboxylic acid ethyl ester

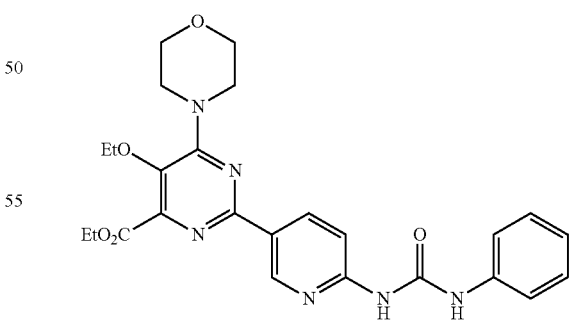

¹H NMR (500 MHz, Acetone-d₆) δ1.33-1.36 (m, 3H), 1.39-1.41 (m, 3H), 3.82-3.84 (m, 4H), 3.92-3.94 (m, 4H), 4.02-4.04 (m, 2H), 4.42-4.44 (m, 2H), 7.00-7.10 (m, 1H), 7.31-7.34 (m, 3H), 8.55-8.65 (m, 1H), 8.90-9.00 (s, 1H), 9.24-9.25 (m, 1H), 11.40 (s, 1H)

5-Ethoxy-2-{6-[3-(4-fluoro-phenyl)-ureido]-pyridin-3-yl}-6-morpholin-4-yl-pyrimidine-4-carboxylic acid ethyl ester

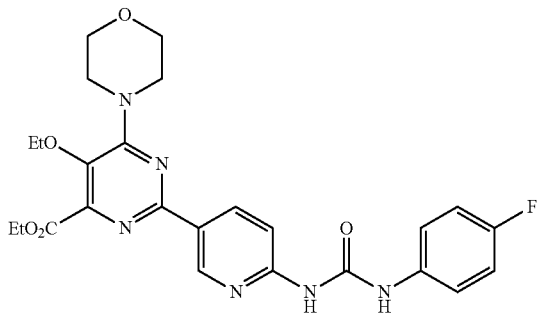

$^1$H NMR (500 MHz, Acetone-$d_6$): δ1.32-1.41 (m, 6H), 3.82-3.84 (m, 4H), 3.92-3.94 (m, 4H), 4.02-4.05 (m, 2H), 4.41-4.45 (m, 2H), 7.08-7.12 (m, 2H), 7.35-7.36 (m, 1H), 7.71-7.73 (m, 2H), 8.59-8.61 (m, 1H), 8.97 (s, 1H), 9.23-9.24 (m, 1H), 11.51 (s, 1H)

2-{6-[3-(3,4-Difluoro-phenyl)-ureido]-pyridin-3-yl}-5-ethoxy-6-morpholin-4-yl-pyrimidine-4-carboxylic acid ethyl ester

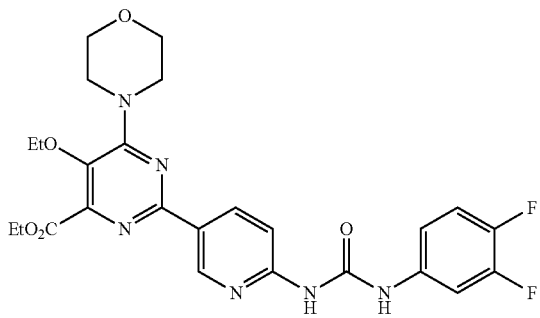 [SMILES: CCOC(=O)c1nc(-c2ccc(NC(=O)Nc3ccc(F)c(F)c3)nc2)nc(N2CCOCC2)c1OCC]

$^1$H NMR (500 MHz, Acetone-$d_6$): δ1.33-1.41 (m, 6H), 3.82-3.83 (m, 4H), 3.92-3.93 (m, 4H), 4.00-4.05 (m, 2H), 4.41-4.45 (m, 2H), 7.25-7.38 (m, 3H), 7.89-7.92 (m, 1H), 8.60-8.62 (m, 1H), 9.06 (s, 1H), 9.24 (s, 1H), 11.78 (s, 1H)

5-Ethoxy-2-{6-[3-(3-fluoro-phenyl)-ureido]-pyridin-3-yl}-6-morpholin-4-yl-pyrimidine-4-carboxylic acid ethyl ester

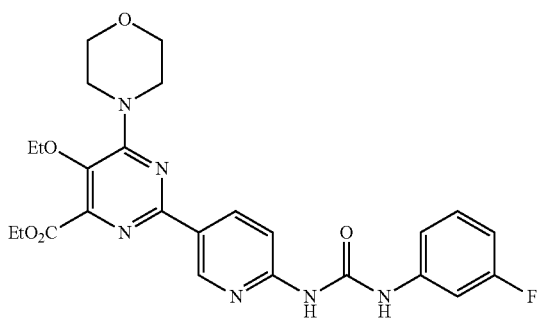 [SMILES: CCOC(=O)c1nc(-c2ccc(NC(=O)Nc3cccc(F)c3)nc2)nc(N2CCOCC2)c1OCC]

$^1$H NMR (500 MHz, Acetone-$d_6$): δ1.32-1.41 (m, 6H), 3.82-3.84 (m, 4H), 3.92-3.94 (m, 4H), 4.00-4.05 (m, 2H), 4.41-4.45 (m, 2H), 6.79-6.82 (m, 1H), 7.33-7.38 (m, 3H), 7.73-7.75 (m, 1H), 8.60-8.63 (m, 1H), 9.03 (s, 1H), 9.26 (s, 1H)

5-Ethoxy-6-morpholin-4-yl-2-[4-(3-phenyl-thioureido)-phenyl]-pyrimidine-4-carboxylic acid ethyl ester

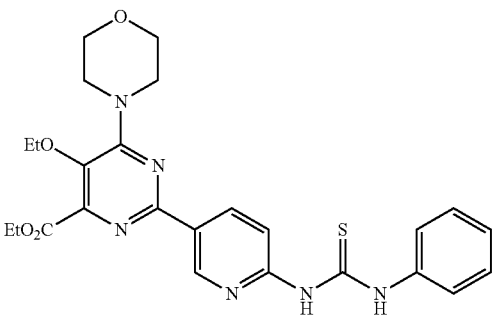 [SMILES: CCOC(=O)c1nc(-c2ccc(NC(=S)Nc3ccccc3)nc2)nc(N2CCOCC2)c1OCC]

Phenyl isothiocyanate (0.02 ml, 1.5 eq.) was added to a stirred solution of 2-(4-amino-phenyl)-5-ethoxy-6-morpholin-4-yl-pyrimidine-4-carboxylic acid ethyl ester (40 mg, 1 eq.) in CHCl$_3$ (3 ml) and the mixture was reacted overnight at r.t. The reaction mixture was extracted with EA and washed with brine. The crude was purified by chromatography to give a product (32.6 mg, 60%).

$^1$H NMR (500 MHz, Acetone-$d_6$): δ1.32-1.40 (m, 6H), 3.81-3.83 (m, 4H), 3.89-3.91 (m, 4H), 4.01-4.04 (m, 2H), 4.39-4.43 (m, 2H), 7.16-7.19 (m, 1H), 7.35-7.38 (m, 2H), 7.55-7.57 (m, 2H), 7.67-7.70 (m, 2H), 8.30-8.32 (m, 2H), 9.19 (s, 1H), 9.23 (s, 1H)

2-(4-Benzenesulfonylamino-phenyl)-5-ethoxy-6-morpholin-4-yl-pyrimidine-4-carboxylic acid ethyl ester

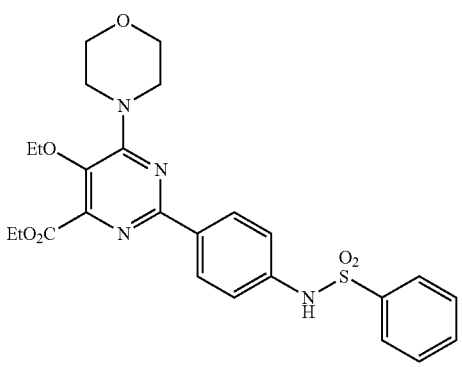 [SMILES: CCOC(=O)c1nc(-c2ccc(NS(=O)(=O)c3ccccc3)cc2)nc(N2CCOCC2)c1OCC]

Phenyl sulfonyl chloride (0.02 ml, 1.3 eq.), Et$_3$N (1 drop) was added to a stirred solution of 2-(4-amino-phenyl)-5-ethoxy-6-morpholin-4-yl-pyrimidine-4-carboxylic acid ethyl ester (40 mg, 1 eq.) in CH$_2$Cl$_2$ (2 ml) and the mixture was reacted overnight at r.t. The reaction mixture was extracted with EA and washed with brine. The crude was purified by chromatography to give a product (13 mg, 23.7%).

¹H NMR (500 MHz, CDCl₃-d₁): δ1.33-1.36 (m, 3H), 1.40-1.44 (m, 3H), 3.81-3.87 (m, 8H), 4.10-4.14 (m, 2H), 4.43-4.47 (m, 2H), 6.79 (s, 1H), 7.12-7.13 (m, 2H), 7.41-7.44 (m, 2H), 7.51-7.53 (m, 1H), 7.77-7.79 (m, 2H), 8.20-8.22 (m, 2H)

5-Ethoxy-2-(4-ethylcarbamoyloxy-phenyl)-6-morpholin-4-yl-pyrimidine-4-carboxylic acid ethyl ester

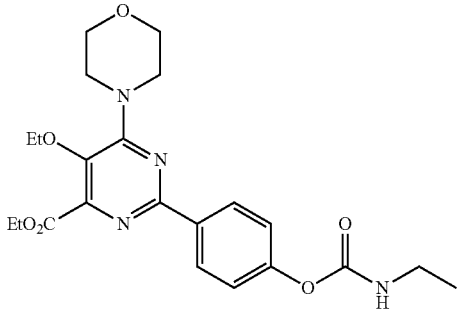 [SMILES: CCNC(=O)Oc1ccc(-c2nc(C(=O)OCC)c(OCC)c(N3CCOCC3)n2)cc1]

Ethyl isocyanate (0.013 ml, 1.5 eq.) was added to a stirred solution of 2-(4-hydroxy-phenyl)-5-ethoxy-6-morpholin-4-yl-pyrimidine-4-carboxylic acid ethyl ester (40 mg, 1 eq.) in toluene (3 ml) and the mixture was reacted to reflux overnight. The reaction mixture was extracted with EA and washed with brine. The crude was purified by chromatography to give a product (12 mg, 25.2%).

¹H NMR (500 MHz, CDCl₃-d₁): δ1.23-1.27 (m, 3H), 1.34-1.37 (m, 3H), 1.39-1.45 (m, 3H), 3.31-3.34 (m, 2H), 3.82-3.83 (m, 4H), 3.88-3.89 (m, 4H), 3.96-4.11 (m, 2H), 4.44-4.49 (m, 2H), 5.07 (s, 1H), 7.17-7.19 (m, 2H), 8.31-8.33 (m, 2H)

5-Ethoxy-6-morpholin-4-yl-2-(4-phenylcarbamoyloxy-phenyl)-pyrimidine-4-carboxylic acid ethyl ester

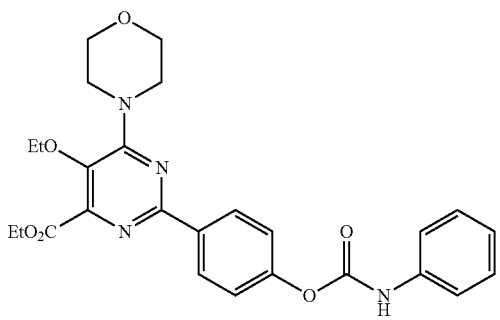 [SMILES: CCOC(=O)c1nc(-c2ccc(OC(=O)Nc3ccccc3)cc2)nc(N2CCOCC2)c1OCC]

¹H NMR (500 MHz, Acetone-d₆): δ1.32-1.40 (m, 6H), 3.81-3.83 (m, 4H), 3.90-3.92 (m, 4H), 4.02-4.05 (m, 2H), 4.40-4.44 (m, 2H), 7.07-7.10 (m, 1H), 7.30-7.37 (m, 4H), 7.62-7.64 (m, 2H), 8.39-8.40 (m, 2H), 9.28 (s, 1H)

5-Ethoxy-6-morpholin-4-yl-2-[4-(3-phenyl-ureido)-phenyl]-pyrimidine-4-carboxylic acid amide

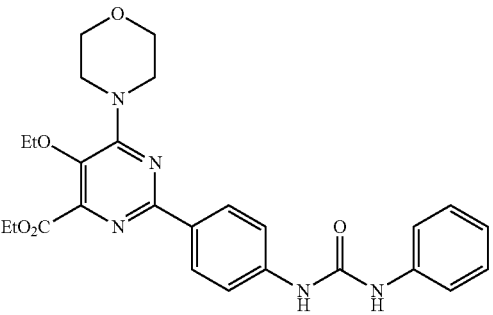 [SMILES: CCOc1c(C(=O)O)nc(-c2ccc(NC(=O)Nc3ccccc3)cc2)nc1N1CCOCC1]

5-ethoxy-6-4-morpholin-yl-2-[(3-4-phenyl-ureido)-phenyl]-pyrimidine-4-carboxylic acid ethyl ester (50 mg, 1 eq.), 7N NH₃/MeOH (9 ml) and THF (0.5 ml) were placed in high pressure reacted bottle and reacted to reflux for 2 days. The reaction mixture was cooled, solvent removed in vacuo, and the residue washed with heating MeOH and filtered to give a product (37.7 mg, 80%).

¹H NMR (500 MHz, DMSO-d₆): δ1.25-1.28 (m, 3H), 3.75-3.76 (m, 4H), 3.80-3.81 (m, 4H), 3.92-3.96 (m, 2H), 6.97-6.99 (m, 1H), 7.27-7.31 (m, 2H), 7.46-7.47 (m, 2H), 7.54-7.55 (m, 2H), 7.60 (s, 1H), 7.95 (s, 1H), 8.21-8.3 (m, 2H), 8.70 (s, 1H), 8.90 (s, 1H)

5-Ethoxy-6-morpholin-4-yl-2-[4-(3-phenyl-ureido)-phenyl]-pyrimidine-4-carboxylic acid

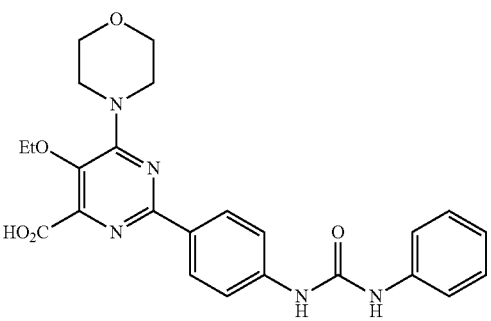

1N KOH (10.5 ml, 5 eq.) was added to a stirred solution of 5-ethoxy-6-morpholin-4-yl-2-[4-(3-phenyl-ureido)-phenyl]-pyrimidine-4-carboxylic acid ethyl ester (1.03 g, 1 eq.) in MeOH (10 ml) and the mixture was refluxed for 4 h. The mixture was cooled to 0° C. and carefully acidified with conc. HCl. The mixture was filtered and the precipitate was dried in vacuo, and a product was obtained as a white solid (0.93 g, 97%).

¹H NMR (500 MHz, DMSO-d₆): δ1.25-1.28 (m, 3H), 3.75-3.76 (m, 4H), 3.81-3.82 (m, 4H), 3.90-3.95 (m, 2H), 6.96-6.99 (m, 1H), 7.27-7.30 (m, 2H), 7.46-7.48 (m, 2H), 7.55-7.57 (m, 2H), 8.17-8.19 (m, 2H), 9.09 (s, 1H), 9.29 (s, 1H)

Potassium salt of 5-ethoxy-6-morpholin-4-yl-2-[4-(3-phenyl-ureido)-phenyl]-pyrimidine-4-carboxylic acid

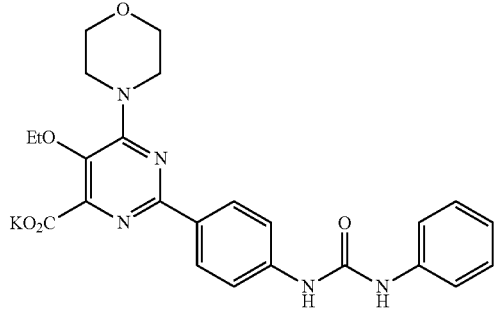

1N KOH (5 ml, 5 eq.) was added to a stirred solution of 5-ethoxy-6-morpholin-4-yl-2-[4-(3-phenyl-ureido)-phenyl]-pyrimidine-4-carboxylic acid ethyl ester (500 mg, 1 eq.) in MeOH (5 ml) and the mixture was refluxed for 4 h. The mixture was cooled to r.t. and filtered. The precipitate was washed with MeOH and dried in vacuo, and a product was obtained as a white solid (400 mg, 78%).

$^1$H NMR (500 MHz, DMSO-$d_6$): δ1.23-1.26 (m, 3H), 3.74 (m, 8H), 4.01-4.03 (m, 2H), 6.94-6.95 (m, 1H), 7.25-7.28 (m, 2H), 7.55-7.57 (m, 2H), 7.69-7.70 (m, 2H), 8.19-8.20 (m, 2H), 10.17 (s, 1H), 10.30 (s, 1H)

5-Ethoxy-6-morpholin-4-yl-2-[4-(3-phenyl-ureido)-phenyl]-pyrimidine-4-carboxylic acid diethylamide

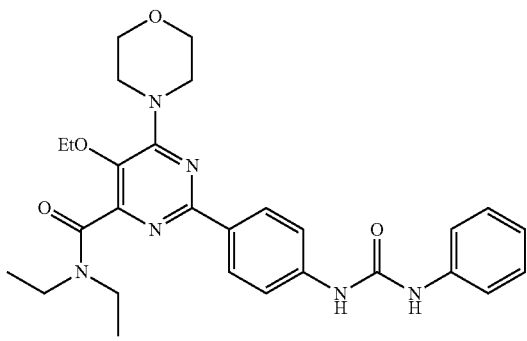 [SMILES: CCOc1c(C(=O)N(CC)CC)nc(-c2ccc(NC(=O)Nc3ccccc3)cc2)nc1N1CCOCC1]

EDC (50 mg, 1.5 eq.), HOBT (40 mg, 1.5 eq.), Et$_2$NH (0.0275 ml, 1.5 eq.) and Et3N (0.05 ml, 2.0 eq.) were added to a stirred solution of 5-ethoxy-6-morpholin-4-yl-2-[4-(3-phenyl-ureido)-phenyl]-pyrimidine-4-carboxylic acid (80 mg, 1 eq.) in dry DMF (2 ml) and the mixture reacted overnight at r.t. The mixture was quenched with H$_2$O, extracted with EA, and washed with brine. The crude was purified by chromatography to give a product (43 mg, 48%).

$^1$H NMR (500 MHz, DMSO-$d_6$): δ1.07-1.10 (m, 3H), 1.15-1.18 (m, 3H), 1.22-1.24 (m, 3H), 3.14-3.16 (m, 2H), 3.45-3.46 (m, 2H), 3.76-3.81 (m, 4H), 3.87-3.90 (m, 4H), 4.02-4.03 (m, 2H), 6.98-6.99 (m, 1H), 7.27-7.30 (m, 2H), 7.45-7.47 (m, 2H), 7.54-7.56 m, 2H), 8.17-8.19 (m, 2H), 8.71 (s, 1H), 8.90 (s, 1H)

1-{4-[5-Ethoxy-4-(morpholine-4-carbonyl)-6-morpholin-4-yl-pyrimidin-2-yl]-phenyl}-3-phenyl-urea

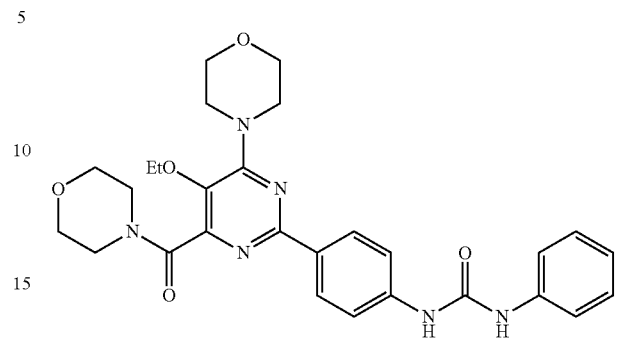

$^1$H NMR (500 MHz, DMSO-$d_6$): δ1.25-1.27 (m, 3H), 3.28-3.30 (m, 2H), 3.56-3.57 (m, 2H), 3.67 (m, 4H), 3.76-3.82 (m, 8H), 3.90-3.91 (m, 2H), 6.98 (m, 1H), 7.28-7.31 (m, 2H), 7.46-7.47 (m, 2H), 7.54-7.56 (m, 2H), 8.17-8.18 (m, 2H), 8.71 (s, 1H), 8.90 (s, 1H)

1-{4-[5-Ethoxy-4-morpholin-4-yl-6-(pyrrolidine-1-carbonyl)-pyrimidin-2-yl]-phenyl}-3-phenyl-urea

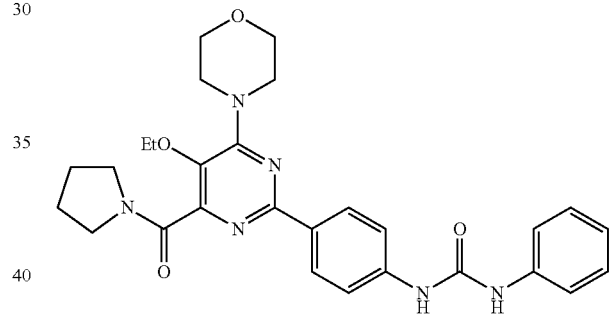

$^1$H NMR (500 MHz, DMSO-$d_6$): δ1.21-1.24 (m, 3H), 1.84-1.88 (m, 4H), 3.25-3.27 (m, 2H), 3.47-3.49 (m, 2H), 3.75-3.81 (m, 8H), 3.90-3.91 (m, 2H), 6.98 (m, 1H), 7.29-7.30 (m, 2H), 7.45-7.47 (m, 2H), 7.53-7.55 (m, 2H), 8.16-8.18 (m, 2H), 8.70 (s, 1H), 8.90 (s, 1H) 1-{4-[5-Ethoxy-4-morpholin-4 yl-6-(piperidine-1-carbonyl)-pyrimidin-2-yl]-phenyl}3-phenyl-urea

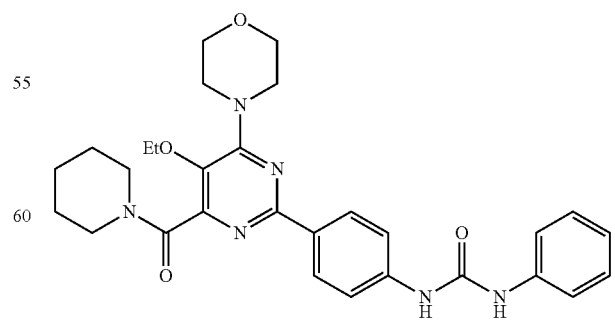

$^1$H NMR (500 MHz, DMSO-$d_6$): δ1.23-1.26 (m, 3H), 1.50-1.64 (m, 6H), 3.20 (m, 2H), 3.62 (m, 2H), 3.76-3.80

(m, 8H), 3.87-3.91 (m, 2H), 6.97-6.99 (m, 1H), 7.27-7.30 (m, 2H), 7.45-7.47 (m, 2H), 7.53-7.55 (m, 2H), 8.16-8.18 (m, 2H), 8.76 (s, 1H), 8.95 (s, 1H)

1-{4-[5-Ethoxy-4-(4-methanesulfonyl-piperazine-1-carbonyl)-6-morpholin-4-yl-pyrimidin-2-yl]-phenyl}-3-phenyl-urea

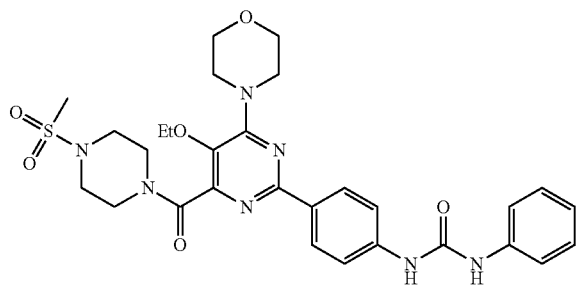 [SMILES: CCOc1c(C(=O)N2CCN(S(C)(=O)=O)CC2)nc(-c2ccc(NC(=O)Nc3ccccc3)cc2)nc1N1CCOCC1]

$^1$H NMR (500 MHz, DMSO-d$_6$): δ1.24-1.27 (m, 3H), 2.95 (s, 3H), 3.13 (m, 2H), 3.23 (m, 2H), 3.40 (m, 2H), 3.77-3.82 (m, 10H), 3.88-3.92 (m, 2H), 6.98 (m, 1H), 7.27-7.30 (m, 2H), 7.46-7.47 (m, 2H), 7.54-7.55 (m, 2H), 8.17-8.19 (m, 2H), 8.71 (s, 1H), 8.91 (s, 1H)

5-Ethoxy-6-morpholin-4-yl-2-[4-(3-phenyl-ureido)-phenyl]-pyrimidine-4-carboxylic acid(2-morpholin-4-yl-ethyl)-amide

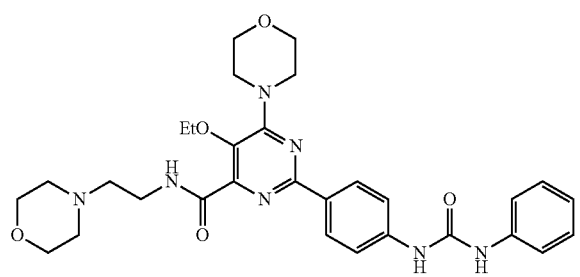 [SMILES: CCOc1c(C(=O)NCCN2CCOCC2)nc(-c2ccc(NC(=O)Nc3ccccc3)cc2)nc1N1CCOCC1]

$^1$H NMR (500 MHz, DMSO-d$_6$): δ1.23-1.27 (m, 6H), 2.36-2.63 (m, 6H), 3.3-3.41 (m, 4H), 3.59-3.60 (m, 4H), 3.74-3.75 (m, 4H), 3.81-3.82 (m, 4H), 3.92-3.95 (m, 2H), 6.97-6.99 (m, 1H), 7.27-7.30 (m, 2H), 7.46-7.48 (m, 2H), 7.54-7.56 (m, 2H), 8.22-8.24 (m, 2H), 8.54-8.57 (m, 1H), 8.70 (s, 1H), 8.91 (s, 1H)

5-Ethoxy-6-morpholin-4-yl-2-[4-(3-phenyl-ureido)-phenyl]-pyrimidine-4-carboxylic acid (2-pyrrolidin-1-yl-ethyl)-amide

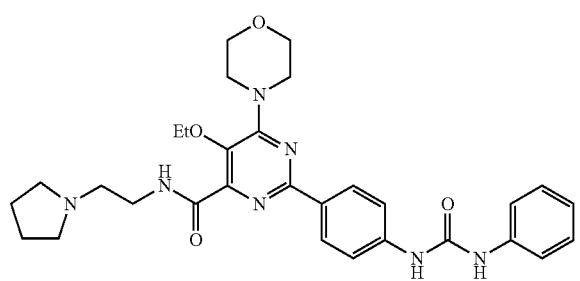 [SMILES: CCOc1c(C(=O)NCCN2CCCC2)nc(-c2ccc(NC(=O)Nc3ccccc3)cc2)nc1N1CCOCC1]

$^1$H NMR (500 MHz, DMSO-d$_6$): δ1.24-1.27 (m, 6H), 1.70 (m, 4H), 2.57-2.60 (m, 4H), 3.75-3.76 (m, 4H), 3.81-3.82 (m, 4H), 3.90-3.95 (m, 2H), 6.96-6.99 (m, 1H), 7.27-7.30 (m, 2H), 7.47-7.49 (m, 2H), 7.56-7.57 (m, 2H), 8.20-8.22 (m, 2H), 8.55-8.57 (m, 1H), 9.10 (s, 1H), 9.30 (s, 1H)

5-Ethoxy-6-morpholin-4-yl-2-[4-(3-phenyl-ureido)-phenyl]-pyrimidine-4-carboxylic acid (2-diethyl-amino-ethyl)-amide

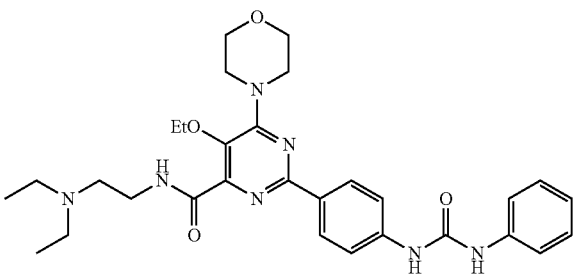 [SMILES: CCOc1c(C(=O)NCCN(CC)CC)nc(-c2ccc(NC(=O)Nc3ccccc3)cc2)nc1N1CCOCC1]

$^1$H NMR (500 MHz, DMSO-d$_6$): δ0.98-1.01 (m, 6H), 1.24-1.27 (m, 3H), 2.54-2.58 (m, 8H), 3.75-3.76 (m, 4H), 3.81-3.82 (m, 4H), 3.92-3.95 (m, 2H), 6.98 (m, 1H), 7.27-7.30 (m, 2H), 7.46-7.48 (m, 2H), 7.55-7.56 (m, 2H), 8.21-8.23 (m, 2H), 8.50 (m, 1H), 9.00 (s, 1H), 9.20 (s, 1H)

5-Methoxy-6-morpholin-4-yl-2-[4-(3-phenyl-ureido)-phenyl]-pyrimidine-4-carboxylic acid ethyl ester

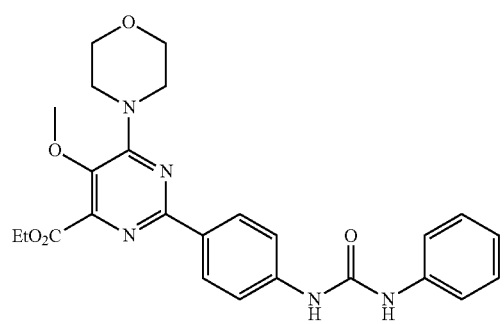 [SMILES: CCOC(=O)c1nc(-c2ccc(NC(=O)Nc3ccccc3)cc2)nc(N2CCOCC2)c1OC]

$^1$H NMR (500 MHz, CDCl$_3$-d$_1$): δ1.42-1.44 (m, 3H), 3.76 (s, 3H), 3.81-3.873 (m, 8H), 4.45-4.50 (m, 2H), 7.05-7.07 (m, 1H), 7.12 (s, 1H), 7.22 (m, 1H), 7.27-7.33 (m, 4H), 7.37-7.39 (m, 2H), 8.20-8.21 (m, 2H)

5-Methoxy-6-morpholin-4-yl-2-[4-(3-phenyl-ureido)-phenyl]-pyrimidine-4-carboxylic acid

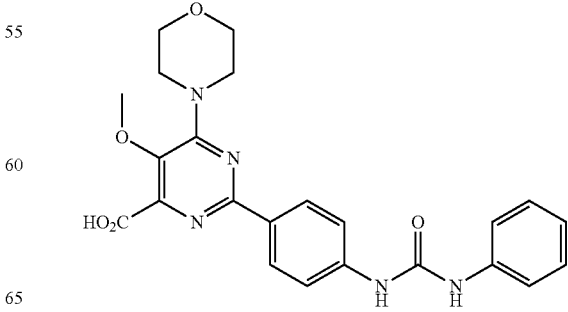

¹H NMR (500 MHz, DMSO-d₆): δ3.72 (s, 3H), 3.77-3.82 (m, 8H), 6.99-7.00 (m, 1H), 7.28-7.30 (m, 2H), 7.46-7.48 (m, 2H), 7.55-7.57 (m, 2H), 8.18-8.19 (m, 2H), 8.78 (s, 1H), 8.98 (s, 1H)

1-{4-[5-Methoxy-4-(morpholine-4-carbonyl)-6-morpholin-4-yl-pyrimidin-2-yl]-phenyl}-3-phenyl-urea

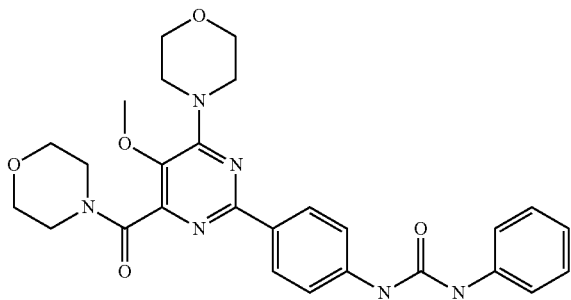

¹H NMR (500 MHz, DMSO-d₆): δ3.28 (m, 2H), 3.33 (m, 4H), 3.56 (m, 2H), 3.67-3.68 (m, 7H), 3.76-3.82 (m, 8H), 6.98-6.99 (m, 1H), 7.28-7.30 (m, 2H), 7.46-7.47 (m, 2H), 7.54-7.56 (m, 2H), 8.17-8.19 (m, 2H), 8.71 (s, 1H), 8.91 (s, 1H)

1-{4-[4-(4-Methanesulfonyl-piperazine-1-carbonyl)-5-methoxy-6-morpholin-4-yl-pyrimidin-2-yl]-phenyl}-3-phenyl-urea

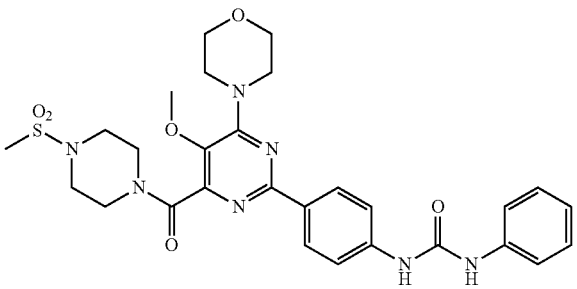 [SMILES: COc1c(C(=O)N2CCN(S(C)(=O)=O)CC2)nc(-c2ccc(NC(=O)Nc3ccccc3)cc2)nc1N1CCOCC1]

¹H NMR (500 MHz, DMSO-d6): δ2.95 (s, 3H), 3.12 (m, 2H), 3.24 (m, 2H), 3.39 (m, 2H), 3.68 (s, 3H), 3.77-3.82 (m, 10H), 6.97-6.99 (m, 1H), 7.27-7.30 (m, 2H), 7.46-7.47 (m, 2H), 7.54-7.56 (m, 2H), 8.17-8.19 (m, 2H), 8.71 (s, 1H), 8.91 (s, 1H)

1-{4-[5-Ethoxy-4-(4-methyl-piperazine-1-carbonyl)-6-morpholin-4-yl-pyrimidin-2-yl]-phenyl}-3-phenyl-urea

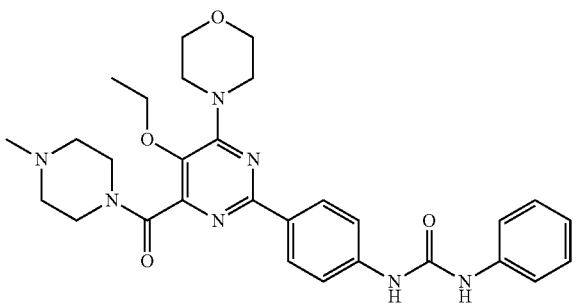 [SMILES: CCOc1c(C(=O)N2CCN(C)CC2)nc(-c2ccc(NC(=O)Nc3ccccc3)cc2)nc1N1CCOCC1]

¹H NMR (500 MHz, DMSO-d₆): δ1.23-1.27 (m, 6H), 2.20 (s, 3H), 2.29 (m, 2H), 2.37-2.38 (m, 2H), 3.24-3.26 (m, 2H), 3.65 (m, 2H), 3.76-3.81 (m, 8H), 3.87-3.91 (m, 2H), 6.97-6.99 (m, 1H), 7.27-7.30 (m, 2H), 7.46-7.47 (m, 2H), 7.54-7.56 (m, 2H), 8.16-8.18 (m, 2H), 8.731 (s, 1H), 8.93 (s, 1H)

5-Ethoxy-6-morpholin-4-yl-2-(4-phenoxycarbonylamino-phenyl)-pyrimidine-4-carboxylic acid ethyl ester

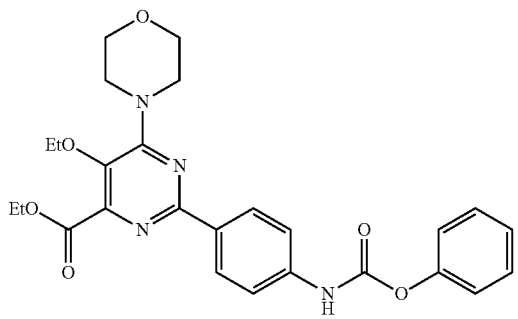 [SMILES: CCOC(=O)c1nc(-c2ccc(NC(=O)Oc3ccccc3)cc2)nc(N2CCOCC2)c1OCC]

Phenyl chloroformate (0.95 ml, 1.5 eq.) was added to a stirred solution of 2-(4-Amino-phenyl)-5-ethoxy-6-morpholin-4-yl-pyrimidine-4-carboxylic acid ethyl ester (1.15 g, 1 eq.) in EA (20 ml) and NaHCO₃ (sat) (20 ml). The mixture was reacted at room temperature for 2 hrs. The reaction mixture was diluted with NaHCO₃ (sat) and extracted with EA. The organic solution was washed with brine, was dried (MgSO₄), filtered and concentrated under reduced pressure to give a crude carbamate (1.21 g, 80%).

5-Ethoxy-2-[4-(3-methyl-ureido)-phenyl]-6-morpholin-4-yl-pyrimidine-4-carboxylic acid ethyl ester

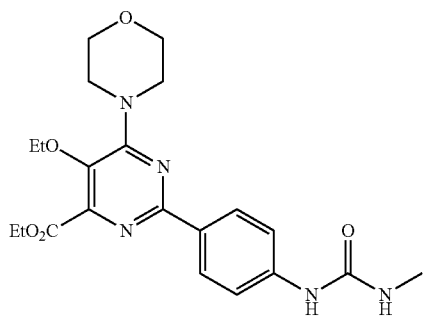 [SMILES: CCOC(=O)c1nc(-c2ccc(NC(=O)NC)cc2)nc(N2CCOCC2)c1OCC]

2M Methyl amine (1.1 ml, 10 eq.) was added to a stirred solution of 5-ethoxy-6-morpholin-4-yl-2-(4-phenoxycarbonylamino-phenyl)-pyrimidine-4-carboxylic acid ethyl ester (110 mg, 1 eq.) in dioxane (3 ml), and the mixture was reacted at 80° C. overnight. The reaction mixture was concentrated and purified by flash chromatography to give a product (47.5 mg, 50%).

¹H NMR (500 MHz, CDCl₃-d₁): δ1.33-1.35 (m, 3H), 1.40-1.43 (m, 3H), 2.73-2.75 (m, 3H), 3.81-3.82 (m, 4H), 3.86-3.87 (m, 4H), 3.94-3.98 (m, 2H), 4.43-4.48 (m, 2H), 5.25 (s, 1H), 7.2 (s, 1H), 7.36-7.37 (m, 2H), 8.21-8.22 (m, 2H)

5-Ethoxy-2-{4-[(morpholine-4-carbonyl)-amino]-phenyl}-6-morpholin-4-yl-pyrimidine-4-carboxylic acid ethyl ester

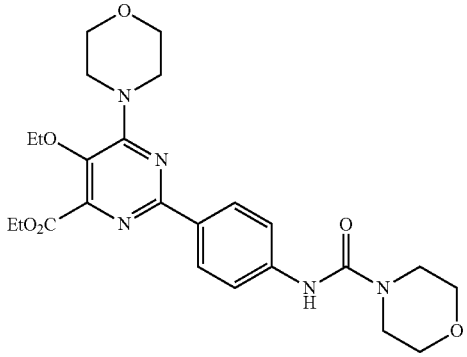 [SMILES: CCOC(=O)c1nc(-c2ccc(NC(=O)N3CCOCC3)cc2)nc(N2CCOCC2)c1OCC]

Morpholine (0.071 ml, 4 eq.) was added to a stirred solution of 5-ethoxy-6-morpholin-4-yl-2-(4-phenoxycarbonylamino-phenyl)-pyrimidine-4-carboxylic acid ethyl ester (100 mg, 1 eq.) and $Et_3N$ (0.085 ml, 3 eq.) in dioxane (3 ml), the mixture was reacted at 80° C. overnight. The reaction mixture was concentrated, and purified by flash chromatography to give a product (59 mg, 60%).

$^1$H NMR (500 MHz, $CDCl_3$-$d_1$): δ1.33-1.36 (m, 3H), 1.42-1.44 (m, 3H), 3.49-3.51 (m, 4H), 3.74-3.75 (m, 4H), 3.83-3.84 (m, 4H), 3.87-3.88 (m, 4H), 3.95-3.99 (m, 2H), 4.44-4.48 (m, 2H), 6.45 (s, 1H), 7.42-7.43 (m, 2H), 8.26-8.28 (m, 2H)

The urea compounds of the following examples were synthesized following the synthetic method described above by the appropriate amine with 5-ethoxy-6-morpholin-4-yl-2-(4-phenoxycarbonylamino-phenyl)-pyrimidine-4-carboxylic acid ethyl ester.

2-{4-[3-(3-Dimethylamino-propyl)-ureido]-phenyl}-5-ethoxy-6-morpholin-4-yl-pyrimidine-4-carboxylic acid ethyl ester

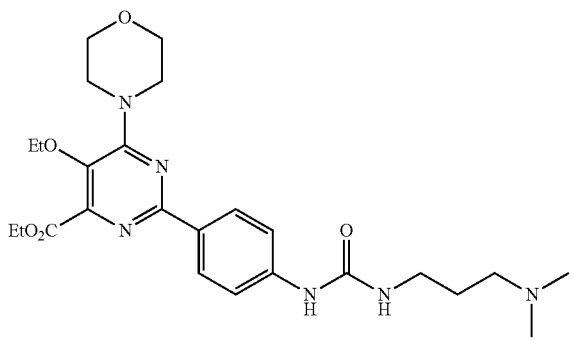 [SMILES: CCOC(=O)c1nc(-c2ccc(NC(=O)NCCCN(C)C)cc2)nc(N2CCOCC2)c1OCC]

$^1$H NMR (500 MHz, $CDCl_3$-$d_1$): δ1.33-1.36 (m, 3H), 1.41-1.44 (m, 3H), 1.66-1.69 (m, 2H), 2.20-2.22 (s, 6H), 2.39-2.41 (m, 2H), 3.34 (s, 2H), 3.81-3.83 (m, 4H), 3.87-3.89 (m, 4H), 3.96-3.99 (m, 2H), 4.43-4.47 (m, 2H), 7.40-7.42 (m, 2H), 8.24-8.26 (m, 2H)

5-Ethoxy-6-morpholin-4-yl-2-[4-(3-pyridin-3-yl-ureido)-phenyl]-pyrimidine-4-carboxylic acid ethyl ester

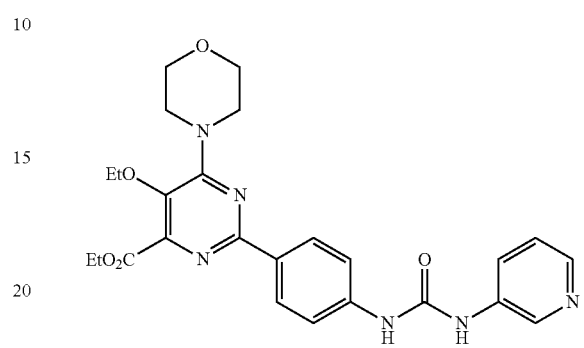

$^1$H NMR (500 MHz, DMSO-$d_6$): δ1.25-1.27 (m, 3H), 1.32-1.35 (m, 3H), 3.75-3.76 (m, 4H), 3.82-3.83 (m, 4H), 3.89-3.93 (m, 2H), 4.35-4.40 (m, 2H), 7.32-7.34 (m, 1H), 7.56-7.58 (m, 2H), 7.95-7.97 (m, 1H), 8.17-8.21 (m, 3H), 8.61 (s, 1H), 8.91 (s, 1H), 9.01 (s, 1H)

5-Ethoxy-2-{4-[3-(4-methyl-piperazin-1-yl)-ureido]-phenyl}-6-morpholin-4-yl-pyrimidine-4-carboxylic acid ethyl ester

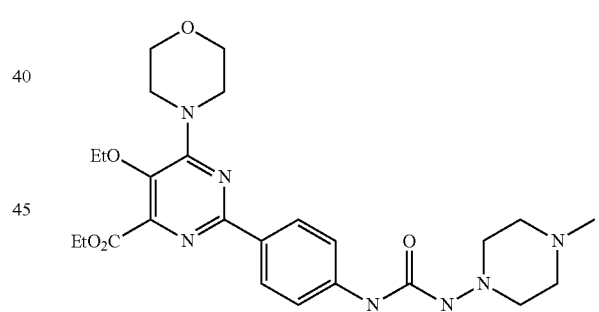

4-methyl-piperazin-1-ylamine (0.52 ml, 2 eq.) was added to a stirred solution of 5-ethoxy-6-morpholin-4-yl-2-(4-phenoxycarbonylamino-phenyl)-pyrimidine-4-carboxylic acid ethyl ester (100 mg, 1 eq.) and $Et_3N$ (0.085 ml, 3 eq.) in dioxane (3 ml), the mixture was reacted at 80° C. overnight. The reaction mixture was concentrated, and purified by flash chromatography to give a product (49.2 mg, 45%).

$^1$H NMR (500 MHz, $CDCl_3$-$d_1$): δ1.32-1.35 (m, 3H), 1.41-1.44 (m, 3H), 2.34 (s, 3H), 2.46-2.49 (m, 4H), 3.54-3.56 (m, 4H), 3.81-3.83 (m, 4H), 3.87-3.88 (m, 4H), 4.10-4.12 (m, 2H), 4.44-4.46 (m, 2H), 6.67 (s, 1H), 7.41-7.43 (m, 2H), 8.24-8.25 (m, 2H)

5-Ethoxy-6-morpholin-4-yl-2-{4-[3-(2-morpholin-4-yl-ethyl)-ureido]-phenyl}-pyrimidine-4-carboxylic acid ethyl ester

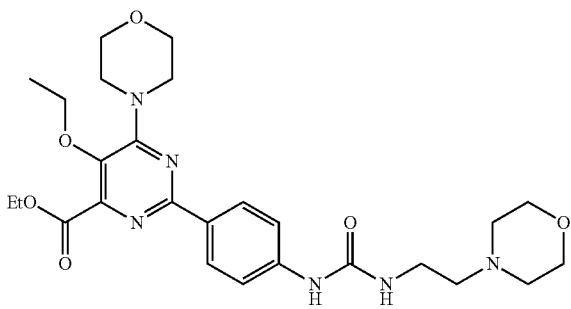 [SMILES: CCOC(=O)c1nc(-c2ccc(NC(=O)NCCN3CCOCC3)cc2)nc(N2CCOCC2)c1OCC]

¹H NMR (500 MHz, CDCl₃-d₁): δ1.33-1.36 (m, 3H), 1.41-1.44 (m, 3H), 2.48 (s, 4H), 2.52-2.54 (m, 2H), 3.36-3.38 (m, 2H), 3.70 (s, 4H), 3.82-3.83 (m, 4H), 3.87-3.89 (m, 4H), 3.96-3.99 (m, 2H), 4.43-4.47 (m, 2H), 5.34 (s, 1H), 7.39-7.41 (m, 2H), 8.26-8.28 (m, 2H)

5-Ethoxy-6-morpholin-4-yl-2-[4-(3-morpholin-4-yl-ureido)-phenyl]-pyrimidine-4-carboxylic acid ethyl ester

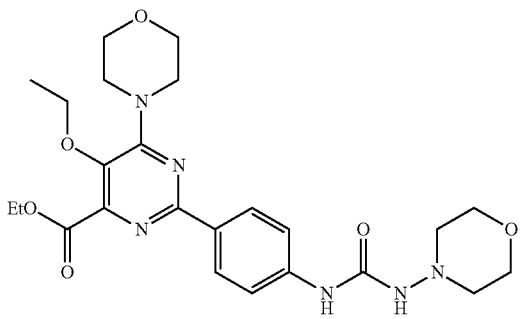

¹H NMR (500 MHz, CDCl₃-d₁): δ1.33-1.35 (m, 3H), 1.41-1.44 (m, 3H), 3.49-3.51 (m, 4H), 3.74-3.75 (m, 4H), 3.81-3.83 (m, 4H), 3.87-3.88 (m, 4H), 3.95-3.99 (m, 2H), 4.43-4.48 (m, 2H), 6.50 (s, 1H), 7.41-7.43 (m, 2H), 8.25-8.27 (m, 2H)

5-Ethoxy-6-morpholin-4-yl-2-[4-(3-thiazol-2-yl-ureido)-phenyl]-pyrimidine-4-carboxylic acid ethyl ester

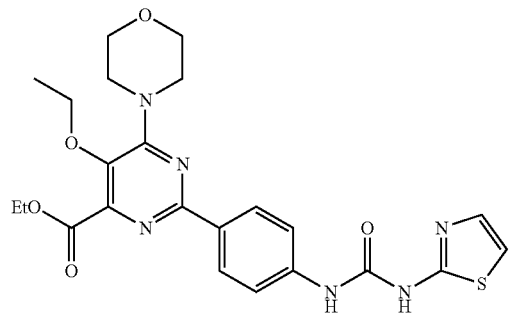 [SMILES: CCOC(=O)c1nc(-c2ccc(NC(=O)Nc3nccs3)cc2)nc(N2CCOCC2)c1OCC]

¹H NMR (500 MHz, DMSO-d₆): δ1.25-1.28 (m, 3H), 1.32-1.35 (m, 3H), 3.75-3.76 (m, 4H), 3.82-3.83 (m, 4H), 3.89-3.93 (m, 2H), 4.35-4.40 (m, 2H), 7.13 (s, 1H), 7.38-7.39 (m, 1H), 7.58-7.60 (m, 2H), 8.19-8.21 (m, 2H), 9.21 (s, 1H)

5-Ethoxy-2-{4-[3-(3-fluoro-4-morpholin-4-yl-phenyl)-ureido]-phenyl}-6-morpholin-4-yl-pyrimidine-4-carboxylic acid ethyl ester

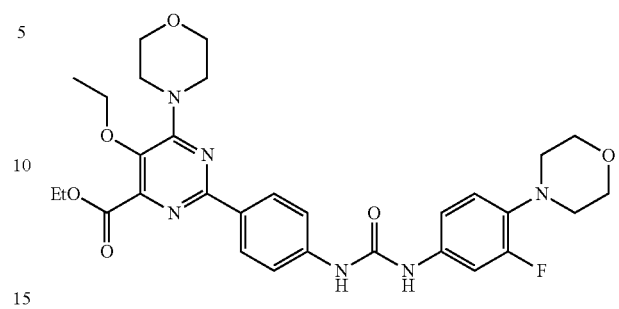

¹H NMR (500 MHz, CDCl₃-d₁): δ1.33-1.36 (m, 3H), 1.42-1.45 (m, 3H), 2.99-3.01 (m, 4H), 3.82-3.84 (m, 4H), 3.85 (m, 4H), 3.87-3.88 (m, 4H), 3.95-3.99 (m, 2H), 4.45-4.50 (m, 2H), 6.81-6.84 (m, 1H), 6.94-6.97 (m, 2H), 7.07 (s, 1H), 7.17-7.20 (m, 1H), 7.35-7.37 (m, 2H), 8.21-8.23 (m, 2H)

5-Ethoxy-6-morpholin-4-yl-2-(4-{3-[4-(3-oxo-morpholin-4-yl)-phenyl]-ureido}-phenyl)-pyrimidine-4-carboxylic acid ethyl ester

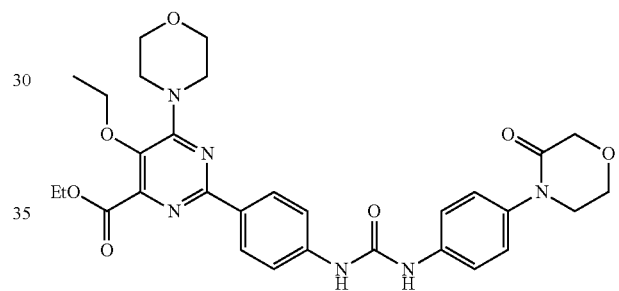

¹H NMR (500 MHz, DMSO-d₆): δ1.25-1.28 (m, 3H), 1.32-1.35 (m, 3H), 3.70-3.71 (m, 2H), 3.75-3.76 (m, 4H), 3.82-3.83 (m, 4H), 3.89-3.93 (m, 2H), 3.96 (m, 2H), 4.18 (m, 2H), 4.35-4.40 (m, 2H), 7.29-7.31 (2H), 7.48-7.50 (m, 2H), 7.55-7.57 (m, 2H), 8.17-8.18 (m, 2H), 8.24 (s, 1H), 8.97 (s, 1H)

5-Ethoxy-6-morpholin-4-yl-2-{4-[3-(3-trifluoromethyl-phenyl)-ureido]-phenyl}-pyrimidine-4-carboxylic acid ethyl ester

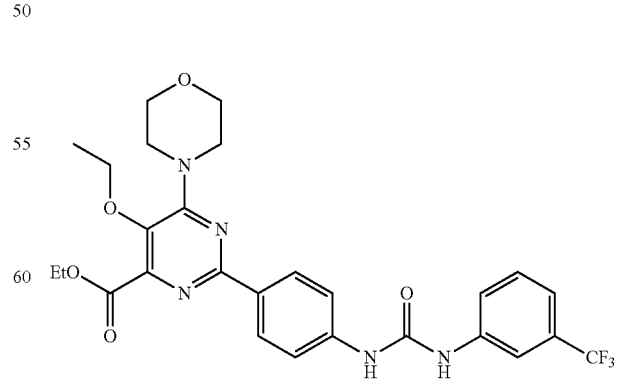

¹H NMR (500 MHz, CDCl₃-d₁): δ1.33-1.36 (m, 3H), 1.42-1.45 (m, 3H), 3.80-3.81 (m, 4H), 3.86 (m, 4H), 3.94-

3.98 (m, 2H), 4.47-4.51 (m, 2H), 7.20-7.22 (m, 1H), 7.29-7.32 (m, 3H), 7.53-7.55 (m, 3H), 7.70 (s, 1H), 8.11-8.12 (m, 2H)

5-Ethoxy-6-morpholin-4-yl-2-[4-(3-pyridin-2-yl-ureido)-phenyl]-pyrimidine-4-carboxylic acid ethyl ester

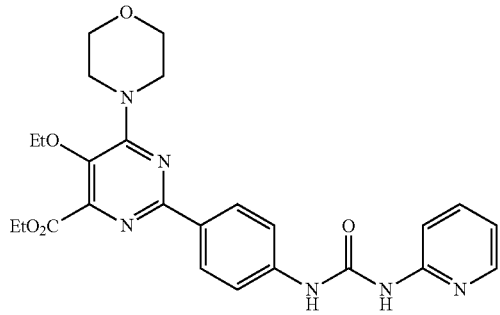 [SMILES: CCOC(=O)c1nc(-c2ccc(NC(=O)Nc3ccccn3)cc2)nc(N2CCOCC2)c1OCC]

$^1$H NMR (500 MHz, DMSO-d$_6$): δ1.25-1.28 (m, 3H), 1.32-1.35 (m, 3H), 3.76 (m, 4H), 3.82-3.83 (m, 4H), 3.91-3.92 (m, 2H), 4.38-4.39 (m, 2H), 7.04 (m, 1H), 7.53-7.54 (m, 1H), 7.62-7.63 (m, 2H), 7.77 (m, 1H), 8.19-8.20 (m, 2H), 8.30 (m, 1H), 9.49 (s, 1H), 10.68 (s, 1H)

5-Ethoxy-2-(4-{3-[4-(4-methyl-piperazin-1-yl)-phenyl]-ureido}-phenyl)-6-morpholin-4-yl-pyrimidine-4-carboxylic acid ethyl ester

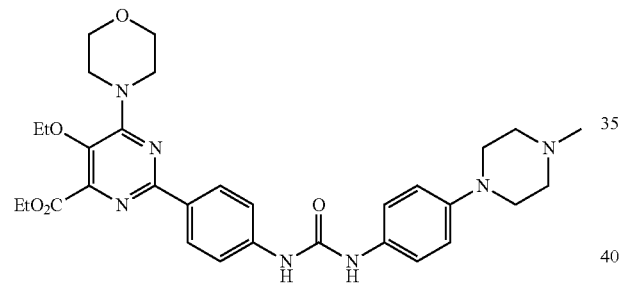

$^1$H NMR (500 MHz, DMSO-d$_6$): δ1.21-1.24 (m, 3H), 1.28-1.31 (m, 3H), 2.17 (s, 3H), 2.41 (m, 4H), 3.01 (s, 4H), 3.71 (m, 4H), 3.77 (m, 4H), 3.86-3.87 (m, 2H), 4.33-4.34 (m, 2H), 6.83-6.85 (m, 2H), 7.25-7.27 (m, 2H), 7.48-7.50 (m, 2H), 8.10-8.12 (m, 2H), 8.43 (s, 1H), 8.81 (s, 1H)

5-Ethoxy-6-morpholin-4-yl-2-{4-[3-(4-thiomorpholin-4-yl-phenyl)-ureido]-phenyl}-pyrimidine-4-carboxylic acid ethyl ester

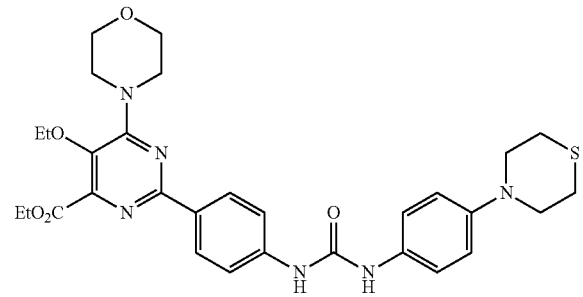 [SMILES: CCOC(=O)c1nc(-c2ccc(NC(=O)Nc3ccc(N4CCSCC4)cc3)cc2)nc(N2CCOCC2)c1OCC]

$^1$H NMR (500 MHz, DMSO-d$_6$): δ1.24-1.28 (m, 3H), 1.32-1.35 (m, 3H), 2.67-2.69 (m, 4H), 3.38-3.40 (m, 4H), 3.01 (m, 4H), 3.75-3.76 (m, 4H), 3.81-3.82 (m, 4H), 3.89-3.93 (m, 2H), 4.36-4.40 (m, 2H), 6.88-6.89 (m, 2H), 7.31-7.32 (m, 2H), 7.53-7.55 (m, 2H), 8.15-8.16 (m, 2H), 8.48 (s, 1H), 8.85 (s, 1H)

5-Ethoxy-6-morpholin-4-yl-2-{4-[3-(4-morpholin-4-yl-phenyl)-ureido]-phenyl}-pyrimidine-4-carboxylic acid ethyl ester

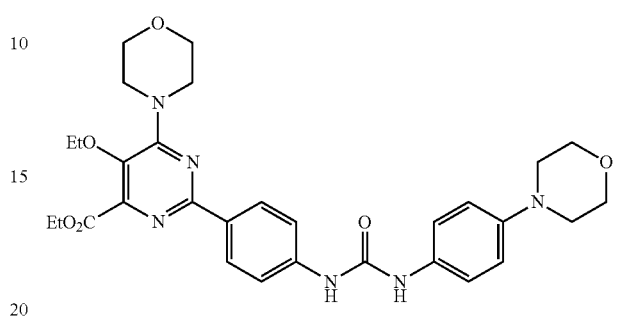

$^1$H NMR (500 MHz, DMSO-d$_6$): δ1.24-1.28 (m, 3H), 1.32-1.35 (m, 3H), 3.01-3.03 (m, 4H), 3.72-3.75 (m, 8H), 3.81-3.82 (m, 4H), 3.89-3.93 (m, 2H), 4.36-4.40 (m, 2H), 6.88-6.90 (m, 2H), 7.31-7.32 (m, 2H), 7.52-7.54 (m, 2H), 8.15-8.16 (m, 2H), 8.47 (s, 1H), 8.84 (s, 1H)

2-{4-[3-(2-Amino-phenyl)-thioureido]-phenyl}-5-ethoxy-6-morpholin-4-yl-pyrimidine-4-carboxylic acid ethyl ester

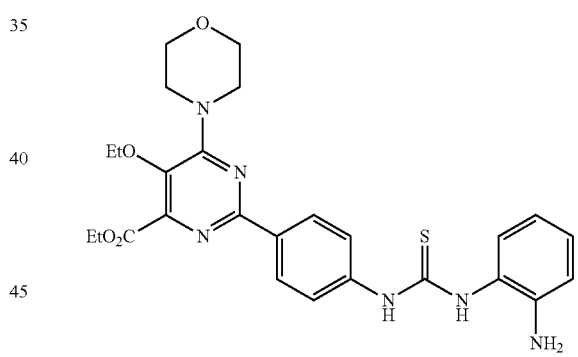

To a stirred solution of 1,1-thiocarbonyldiimidazole (216.5 mg, 1.5 eq.), imidazole (164.52 mg, 3 eq.) and CH$_3$CN (10 ml) at 0° C., 2-(4-amino-phenyl)-5-ethoxy-6-morpholin-4-yl-pyrimidine-4-carboxylic acid ethyl ester (300 mg, 1 eq.) dissolved in CH$_3$CN (10 ml) was added dropwise over 10 min. After 10 min, the cooling bath was removed. After 3 h, benzene-1,2-diamine (175.2 mg, 2 eq.) was added and the reaction was heated to 50° C. for 3 h, and then stirred at ambient temperature for 16 h. The solvent was removed by evaporation. The residue was chromatographed to give a thiourea (120 mg, 29%)

$^1$H NMR (500 MHz, DMSO-d$_6$): δ1.25-1.28 (m, 3H), 1.32-1.35 (m, 3H), 3.75-3.76 (m, 4H), 3.82-3.83 (m, 4H), 3.89-3.93 (m, 2H), 4.36-4.40 (m, 2H), 6.56-6.59 (m, 1H), 6.75-6.76 (m, 1H), 6.96-6.99 (m, 1H), 7.09-7.10 (m, 1H), 7.68-7.69 (m, 2H), 8.17-8.19 (m, 2H), 9.17 (s, 1H), 9.82 (s, 1H)

2-[4-(1H-Benzoimidazol-2-ylamino)-phenyl]-5-ethoxy-6-morpholin-4-yl-pyrimidine-4-carboxylic acid ethyl ester

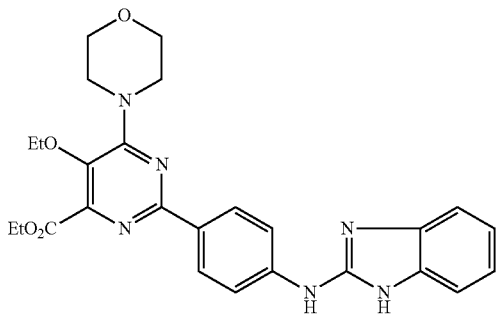 [SMILES: CCOC(=O)c1nc(-c2ccc(Nc3nc4ccccc4[nH]3)cc2)nc(N2CCOCC2)c1OCC]

A solution of thiourea (120 mg, 1 eq.) in THF (5 ml) and DCC (56.85 mg, 1.2 eq.) was heated under reflux with stirring for 4 h. The cooled solution was stirred overnight and filtered to give a product (33.7 mg, 30%).

$^1$H NMR (500 MHz, DMSO-d$_6$): δ1.25-1.28 (m, 3H), 1.32-1.35 (m, 3H), 3.75-3.77 (m, 4H), 3.82-3.83 (m, 4H), 3.89-3.93 (m, 2H), 4.36-4.40 (m, 2H), 7.00-7.03 (m, 2H), 7.30-7.32 (m, 2H), 7.37-7.39 (m, 2H), 7.85-7.86 (m, 2H), 8.20-8.21 (m, 2H), 9.76 (s, 1H), 11.00 (s, 1H)

2-{4-[3-(4-Carbamoyl-phenyl)-ureido]-phenyl}-5-ethoxy-6-morpholin-4-yl-pyrimidine-4-carboxylic acid ethyl ester

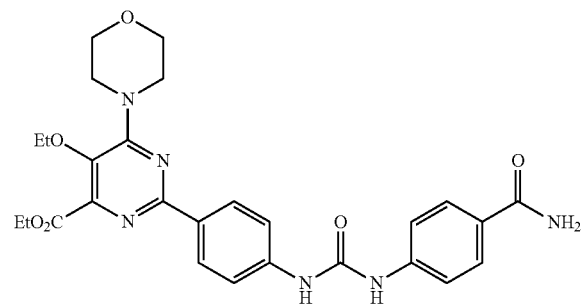 [SMILES: CCOC(=O)c1nc(-c2ccc(NC(=O)Nc3ccc(C(N)=O)cc3)cc2)nc(N2CCOCC2)c1OCC]

$^1$H NMR (500 MHz, DMSO-d$_6$): δ1.25-1.28 (m, 3H), 1.32-1.35 (m, 3H), 3.76 (m, 4H), 3.81-3.82 (m, 4H), 3.91-3.92 (m, 2H), 4.36-4.40 (m, 2H), 7.21 (m, 1H), 7.52-7.58 (m, 4H), 7.82-7.84 (m, 3H), 8.18-8.19 (m, 2H), 8.99 (s, 1H), 9.05 (s, 1H)

5-Ethoxy-6-morpholin-4-yl-2-[4-(3-pyridin-3-yl-ureido)-phenyl]-pyrimidine-4-carboxylic acid

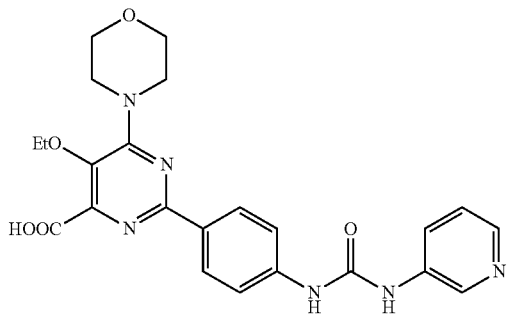 [SMILES: CCOc1c(C(=O)O)nc(-c2ccc(NC(=O)Nc3cccnc3)cc2)nc1N1CCOCC1]

$^1$H NMR (500 MHz, DMSO-d$_6$): δ1.26-1.28 (m, 3H), 3.75-3.76 (m, 4H), 3.81-3.82 (m, 4H), 3.91-3.95 (m, 2H), 4.37-4.39 (m, 2H), 7.56-7.60 (m, 2H), 7.89 (m, 1H), 8.18-8.23 (m, 2H), 8.32-8.34 (m, 1H), 8.48-8.49 (m, 1H), 9.08 (m, 1H), 9.77 (s, 1H), 10.23 (s, 1H)

2-{4-[3-(3-Acetylamino-phenyl)-ureido]-phenyl}-5-ethoxy-6-morpholin-4-yl-pyrimidine-4-carboxylic acid ethyl ester

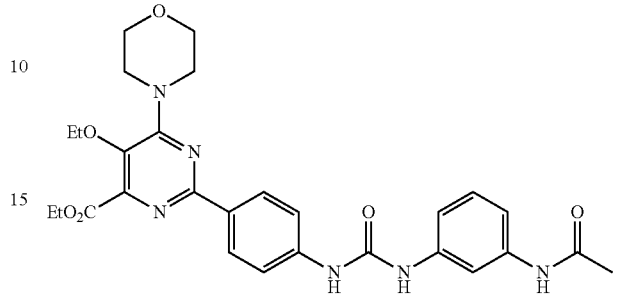

$^1$H NMR (500 MHz, DMSO-d$_6$): δ1.25-1.28 (m, 3H), 1.32-1.35 (m, 3H), 2.04 (s, 3H), 3.75-3.76 (m, 4H), 3.81-3.82 (m, 4H), 3.89-3.93 (m, 2H), 4.36-4.40 (m, 2H), 7.17-7.21 (m, 3H), 7.54-7.56 (m, 2H), 7.79 (m, 1H), 8.16-8.18 (m, 2H), 8.76 (s, 1H), 8.85 (s, 1H), 9.94 (s, 1H)

2-{4-[3-(3-Carbamoyl-phenyl)-ureido]-phenyl}-5-ethoxy-6-morpholin-4-yl-pyrimidine-4-carboxylic acid ethyl ester

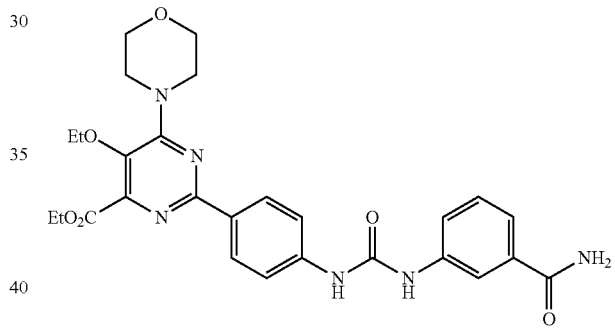

$^1$H NMR (500 MHz, DMSO-d$_6$): δ1.25-1.28 (m, 3H), 1.32-1.35 (m, 3H), 3.75-3.76 (m, 4H), 3.81-3.82 (m, 4H), 3.90-3.92 (m, 2H), 4.37-4.38 (m, 2H), 7.35 (m, 2H), 7.47-7.48 (m, 1H), 7.56-7.58 (m, 2H), 7.63-7.64 (m, 1H), 7.91-7.94 (m, 2H), 9.17-8.19 (m, 2H), 8.86 (s, 1H), 8.99 (s, 1H)

5-Ethoxy-6-morpholin-4-yl-2-(4-{3-[3-(2,2,2-trifluoro-acetylamino)-phenyl]-ureido}-phenyl)-pyrimidine-4-carboxylic acid ethyl ester

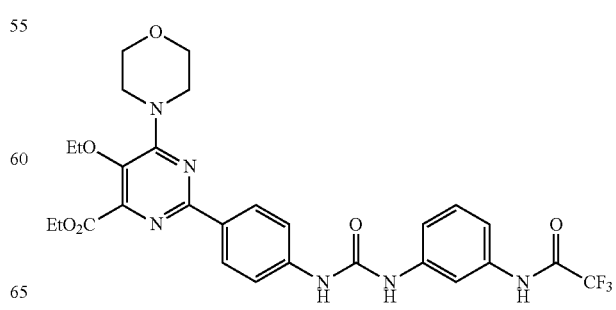

¹H NMR (500 MHz, DMSO-d₆): δ1.24-1.28 (m, 3H), 1.32-1.35 (m, 3H), 2.67-2.69 (m, 4H), 3.38-3.40 (m, 4H), 3.01 (m, 4H), 3.75-3.76 (m, 4H), 3.81-3.82 (m, 4H), 3.89-3.93 (m, 2H), 4.36-4.40 (m, 2H), 7.57-7.59 (m, 3H), 7.72-7.74 (m, 1H), 7.84-7.85 (m, 1H), 8.18-8.20 (m 2H), 8.58 (s, 1H), 9.11 (s, 1H), 9.27 (s, 1H)

1-{4-[5-Ethoxy-4-(morpholine-4-carbonyl)-6-morpholin-4-yl-pyrimidin-2-yl]-phenyl}-3-pyridin-3-yl-urea

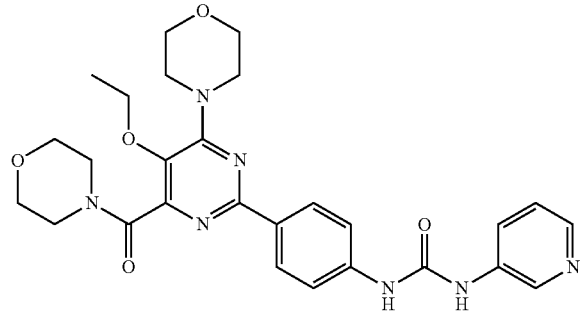 [SMILES: CCOc1c(C(=O)N2CCOCC2)nc(-c2ccc(NC(=O)Nc3cccnc3)cc2)nc1N1CCOCC1]

¹H NMR (500 MHz, DMSO-d₆): δ1.24-1.27 (m, 3H), 3.28-3.29 (m, 2H), 3.55-3.57 (m 2H), 3.66 (m, 4H), 3.76 (m, 4H), 3.81 (m, 4H), 3.88-3.92 (m, 2H), 7.32-7.35 (m, 1H), 7.55-7.57 (m, 2H), 7.95-7.97 (m, 1H), 8.17-8.21 (m, 3H), 8.61-8.62 (m, 1H), 8.95 (s, 1H), 9.10 (s, 1H)

5-Ethoxy-6-morpholin-4-yl-2-{4-[3-(4-sulfamoyl-phenyl)-ureido]-phenyl}-pyrimidine-4-carboxylic acid ethyl ester

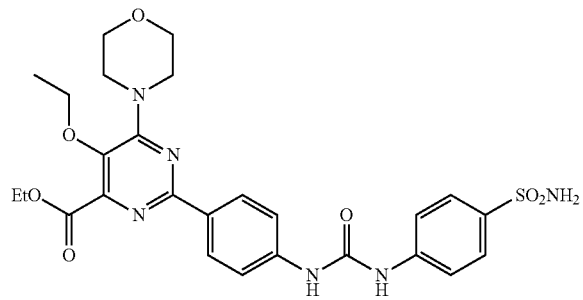 [SMILES: CCOC(=O)c1nc(-c2ccc(NC(=O)Nc3ccc(S(N)(=O)=O)cc3)cc2)nc(N2CCOCC2)c1OCC]

¹H NMR (500 MHz, DMSO-d₆): δ1.25-1.28 (m, 3H), 1.32-1.35 (m, 3H), 3.75-3.76 (m, 4H), 3.81-3.82 (m, 4H), 3.89-3.93 (m, 2H), 4.36-4.40 (m, 2H), 7.22 (s, 1H), 7.56-7.58 (m, 2H), 7.62-7.63 (m, 2H), 7.73-7.75 (m, 2H), 8.18-8.19 (m, 2H), 9.12 (s, 1H), 9.18 (s, 1H)

2-{4-[3-(4-Carboxy-phenyl)-ureido]-phenyl}-5-ethoxy-6-morpholin-4-yl-pyrimidine-4-carboxylic acid ethyl-ester

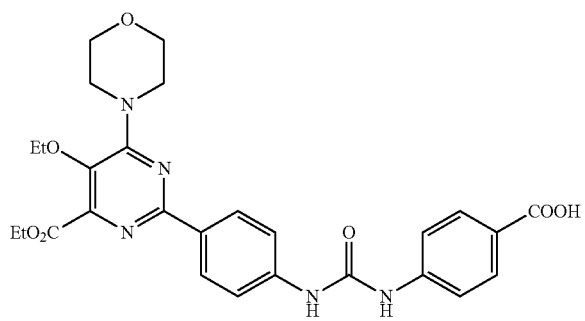 [SMILES: CCOC(=O)c1nc(-c2ccc(NC(=O)Nc3ccc(C(=O)O)cc3)cc2)nc(N2CCOCC2)c1OCC]

¹H NMR (500 MHz, DMSO-d₆): δ1.25-1.28 (m, 3H), 1.32-1.35 (m, 3H), 3.75-3.76 (m, 4H), 3.81-3.82 (m, 4H), 3.89-3.93 (m, 2H), 4.36-4.40 (m, 2H), 7.56 (m, 4H), 7.86-7.88 (, 2H), 8.16-8.18 (m, 2H), 9.26 (s, 1H), 9.33 (s, 1H)

5-Ethoxy-2-(4-{3-[4-(4-methyl-piperazine-1-carbonyl)-phenyl]-ureido}-phenyl)-6-morpholin-4-yl-pyrimidine-4-carboxylic acid ethyl ester

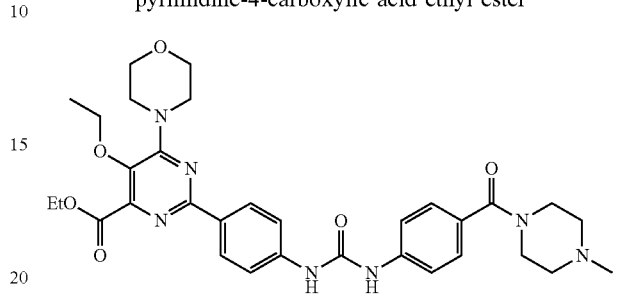

EDC (53.7 mg, 1.5 eq.), HOBT (42.9 mg, 1.5 eq.), 1-methyl-piperazine (0.03 ml, 1.5 eq.) and Et₃N (0.053 ml, 2.0 eq.) were added to a stirred solution of 2-{4-[3-(4-carboxy-phenyl)-ureido]-phenyl}-5-ethoxy-6-morpholin-4-yl-pyrimidine-4-carboxylic acid ethyl ester (80 mg, 1 eq.) in dry DMF (2 ml) and the mixture reacted overnight at r.t. The mixture was quenched with H₂O, extracted with EA, and washed with brine. The crude was purified by chromatography to give a product (34.5 mg, 30%).

¹H NMR (500 MHz, DMSO-d₆): δ1.25-1.28 (m, 3H), 1.32-1.35 (m, 3H), 2.19 (s, 3H), 2.31 (m, 4H), 3.50 (m, 4H), 3.75-3.76 (m, 4H), 3.82 (m, 4H), 3.89-3.93 (m, 2H), 4.35-4.40 (m, 2H), 7.32-7.34 (m, 2H), 7.52-7.57 (m, 4H), 8.16-8.18 (m 2H), 9.27 (s, 1H), 9.29 (s, 1H).

5-Ethoxy-2-(4-{3-[6-(4-methyl-piperazin-1-yl)-pyridin-3-yl]-ureido}-phenyl)-6-morpholin-4-yl-pyrimidine-4-carboxylic acid ethyl ester

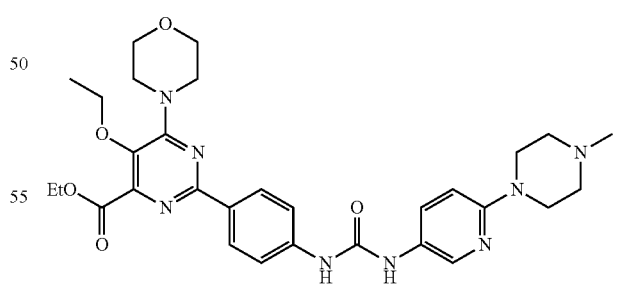

¹H NMR (500 MHz, DMSO-d₆): δ1.25-1.28 (m, 3H), 1.32-1.35 (m, 3H), 2.22 (s, 3H), 2.42 (m, 4H), 3.40 (m, 4H), 3.75-3.76 (m, 4H), 3.81-3.82 (m, 4H), 3.89-3.92 (m, 2H), 4.35-4.39 (m, 2H), 6.81-6.82 (m, 1H), 7.53-7.54 (m, 2H), 7.69-7.70 (m, 1H), 8.14-8.16 (m, 3H), 8.52 (s, 1H), 8.99 (s, 1H)

5-Ethoxy-6-morpholin-4-yl-2-{4-[3-(6-morpholin-4-yl-pyridin-3-yl)-ureido]-phenyl}-pyrimidine-4-carboxylic acid ethyl ester

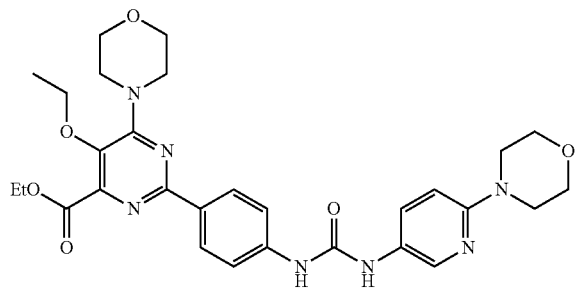 [SMILES: CCOC(=O)c1nc(-c2ccc(NC(=O)Nc3ccc(N4CCOCC4)nc3)cc2)nc(N2CCOCC2)c1OCC]

$^1$H NMR (500 MHz, DMSO-d$_6$): δ1.25-1.28 (m, 3H), 1.32-1.35 (m, 3H), 3.71 (m, 4H), 3.75 (m, 4H), 3.82 (m, 4H), 3.89-3.91 (m, 2H), 4.35-4.40 (m, 2H), 6.82-6.84 (m, 1H), 7.53-7.55 (m, 2H), 7.72-7.74 (m, 1H), 8.15-8.18 (m, 3H), 8.51 (s, 1H), 8.96 (s, 1H)

2-(4-{3-[4-(2-Dimethylamino-ethylcarbamoyl)-phenyl]-ureido}-phenyl)-5-ethoxy-6-morpholin-4-yl-pyrimidine-4-carboxylic acid ethyl ester

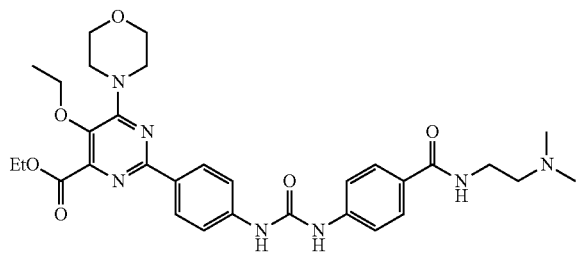 [SMILES: CCOC(=O)c1nc(-c2ccc(NC(=O)Nc3ccc(C(=O)NCCN(C)C)cc3)cc2)nc(N2CCOCC2)c1OCC]

$^1$H NMR (500 MHz, DMSO-d$_6$): δ1.25-1.28 (m, 3H), 1.32-1.35 (m, 3H), 2.17 (s, 6H), 2.37-2.39 (m, 2H), 3.75-3.76 (m, 4H), 3.82 (m, 4H), 3.89-3.93 (m, 2H), 4.35-4.40 (m, 2H), 7.54-7.59 (m 4H), 7.77-7.79 (m, 2H), 8.16-8.18 (m, 3H), 9.5 (b, 2H)

5-Ethoxy-2-(4-{3-[4-(morpholine-4-carbonyl)-phenyl]-ureido}-phenyl)-6-morpholin-4-yl-pyrimidine-4-carboxylic acid ethyl ester

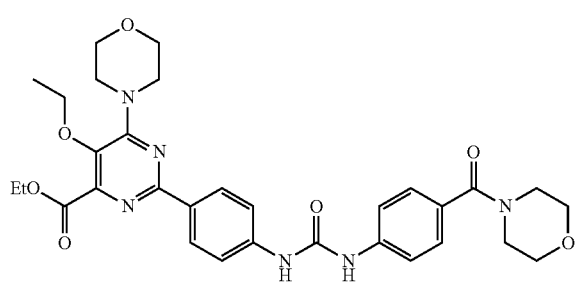 [SMILES: CCOC(=O)c1nc(-c2ccc(NC(=O)Nc3ccc(C(=O)N4CCOCC4)cc3)cc2)nc(N2CCOCC2)c1OCC]

$^1$H NMR (500 MHz, DMSO-d$_6$): δ1.25-1.28 (m, 3H), 1.32-1.35 (m, 3H), 3.50 (m, 4H), 3.59 (m, 4H), 3.75-3.76 (m, 4H), 3.82 (m, 4H), 3.89-3.93 (m, 2H), 4.35-4.40 (m, 2H), 7.35-7.38 (m, 2H), 7.52-7.57 (m, 4H), 8.17-8.18 (m, 2H), 8.95 (s, 1H), 8.99 (s, 1H)

{4-[5-Ethoxy-4-(morpholine-4-carbonyl)-6-morpholin-4-yl-pyrimidin-2-yl]-phenyl}-carbamic acid phenyl ester

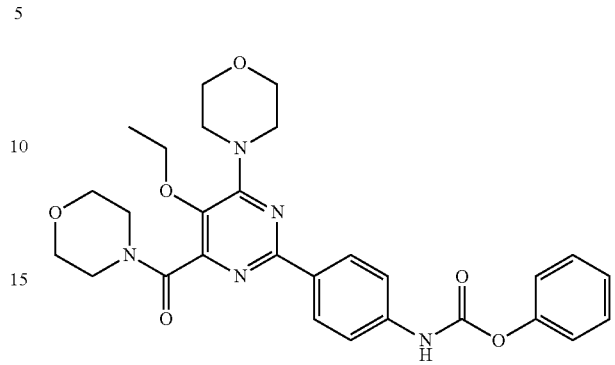

$^1$H NMR (500 MHz, DMSO-d$_6$): δ1.24-1.27 (m, 3H), 3.28-3.30 (m, 2H), 3.55-3.57 (m, 2H), 3.66 (s, 4H), 3.75-3.76 (m, 4H), 3.80-3.82 (m, 2H), 3.88-3.92 (m, 2H), 7.24-7.29 (m, 3H), 7.42-7.46 (m, 2H), 7.60-7.62 (m, 2H), 8.20-8.22 (m, 2H), 10.45 (s, 1H)

1-{4-[5-Ethoxy-4-(morpholine-4-carbonyl)-6-morpholin-4-yl-pyrimidin-2-yl]-phenyl}-3-[4-(3-oxo-morpholin-4-yl)-phenyl]-urea

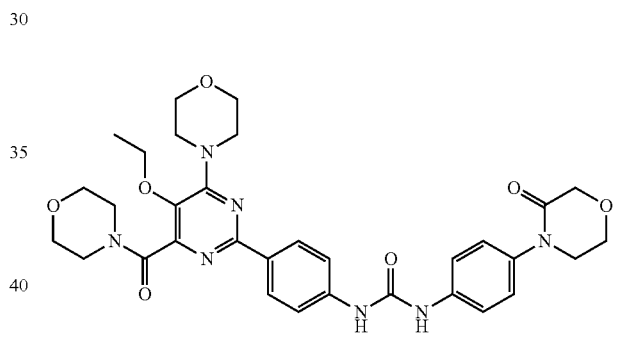

$^1$H NMR (500 MHz, DMSO-d$_6$): δ1.24-1.27 (m, 3H), 3.29 (m, 2H), 3.56 (m, 2H), 3.67-3.69 (m, 6H), 3.75-3.96 (m, 12H), 4.18 (s, 2H), 7.28-7.30 (m 2H), 7.47-7.50 (m, 2H), 7.54-7.56 (m, 2H), 8.16-8.18 (m, 2H), 8.80 (s, 1H), 8.94 (s, 1H)

5-Ethoxy-2-(4-{3-[5-(4-methyl-piperazin-1-yl)-pyridin-2-yl]-ureido}-phenyl)-6-morpholin-4-yl-pyrimidine-4-carboxylic acid ethyl ester

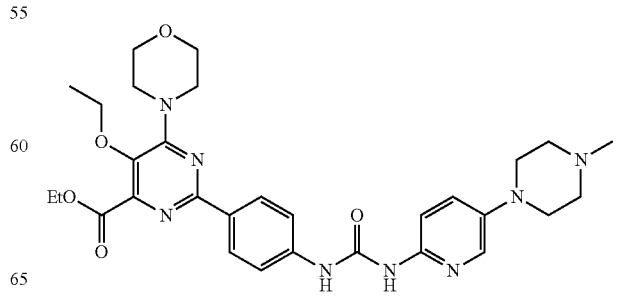

¹H NMR (500 MHz, DMSO-d₆): δ1.25-1.28 (m, 3H), 1.32-1.35 (m, 3H), 2.22 (s, 3H), 2.46 (m, 4H), 3.10 (s, 4H), 3.75-3.76 (m, 4H), 3.81-3.83 (m, 4H), 3.89-3.93 (m, 2H), 4.35-4.39 (m, 2H), 7.44-7.46 (m, 2H), 7.59-7.60 (m, 2H), 7.96 (s, 1H), 8.17-8.19 (m, 2H), 9.21 (s, 1H), 10.5 (b, 1H)

5-Ethoxy-2-{4-[3-(2-methoxycarbonyl-thiophen-3-yl)-ureido]-phenyl}-6-morpholin-4-yl-pyrimidine-4-carboxylic acid ethyl ester

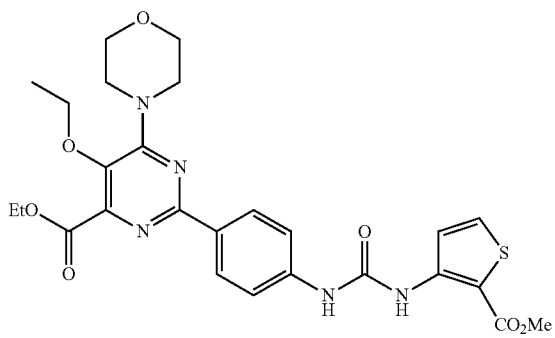 [SMILES: CCOC(=O)c1nc(-c2ccc(NC(=O)Nc3ccsc3C(=O)OC)cc2)nc(N2CCOCC2)c1OCC]

¹H NMR (500 MHz, CDCl₃-d₁): δ1.33-1.36 (m, 3H), 1.42-1.45 (m, 3H), 3.83-3.88 (m, 11H), 3.96-4.00 (m, 2H), 4045-4.49 (m, 2H), 7.19 (m, 1H), 7.46-7.51 (m, 3H), 8.05 (s, 1H), 8.29-8.31 (m, 2H), 9.72 (s, 1H)

5-Ethoxy-2-{4-[3-(1H-indazol-4-yl)-ureido]-phenyl}-6-morpholin-4-yl-pyrimidine-4-carboxylic acid ethyl ester

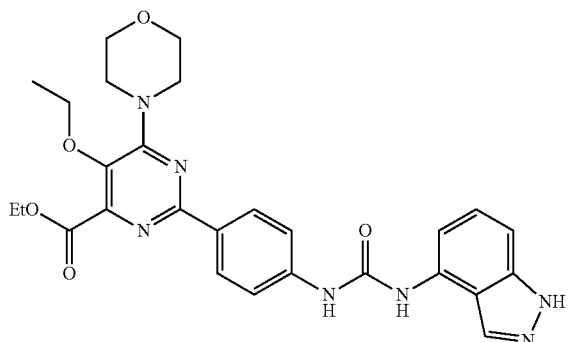

¹H NMR (500 MHz, DMSO-d₆): δ1.24-1.28 (m, 3H), 1.32-1.35 (m, 3H), 3.75-3.76 (m, 4H), 3.82-3.83 (m, 4H), 3.89-3.92 (m, 2H), 4.36-4.40 (m, 2H), 7.14-7.16 (m, 1H), 7.25-7.28 (m, 1H), 7.60-7.61 (m, 2H), 7.66-7.67 (m, 1H), 8.13 (s, 1H), 8.19-8.21 (m, 2H), 8.99 (s, 1H), 9.12 (m, 1H), 13.1 (s, 1H)

5-Ethoxy-2-{4-[3-(4-methyl-1H-benzotriazol-5-yl)-ureido]-phenyl}-6-morpholin-4-yl-pyrimidine-4-carboxylic acid ethyl ester

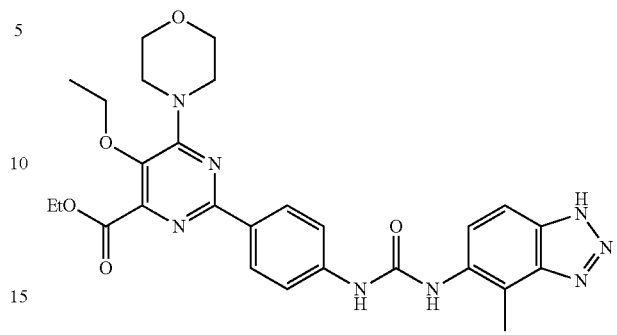

¹H NMR (500 MHz, DMSO-d₆): δ1.24-1.28 (m, 3H), 1.32-1.35 (m, 3H), 2.38 (s, 3H), 3.75-3.76 (m, 4H), 3.82-3.83 (m, 4H), 3.89-3.92 (m, 2H), 4.36-4.40 (m, 2H), 7.24-7.26 (m, 1H), 7.60-7.62 (m, 2H), 7.67-7.69 (m, 1H), 8.17-8.18 (m, 2H), 8.57 (s, 1H), 9.44 (s, 1H)

5-Ethoxy-6-morpholin-4-yl-2-{4-[3-(2-oxo-2,3-dihydro-benzooxazol-5-yl)-ureido]-phenyl}-pyrimidine-4-carboxylic acid ethyl ester

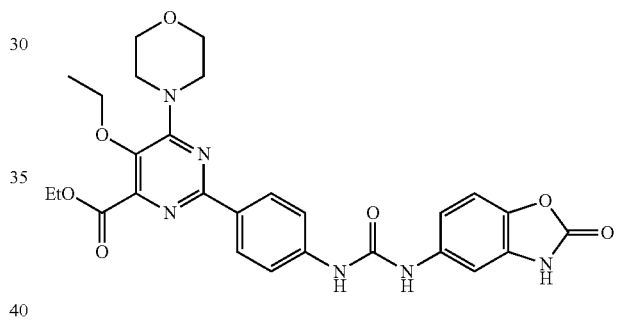

¹H NMR (500 MHz, DMSO-d₆): δ1.24-1.28 (m, 3H) 1.32-1.35 (m, 3H), 3.75-6.76 (m, 4H) 3.82-3.83 (m, 4H), 3.89-3.92 (m, 2H), 4.36-4.40 (m, 2H), 6.90-6.93 (m, 1H), 7.17-7.19 (m, 1H), 7.49 (s, 1H), 7.54 (m, 2H), 8.15-8.17 (m, 2H), 8.82 (s, 1H), 8.95 (s, 1H)

2-(4-Amino-3-fluoro-phenyl)-5-ethoxy-6-morpholin-4-yl-pyrimidine-4-carboxylic acid ethyl ester

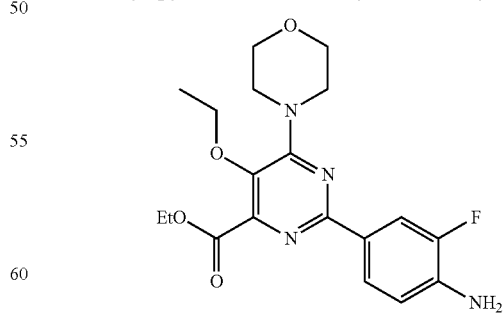

¹H NMR (500 MHz, CDCl₃-d₁): δ1.30-1.33 (m, 3H), 1.39-1.42 (m, 3H), 3.79-3.80 (m, 4H), 3.83-3.84 (m, 4H), 3.92-3.94 (m, 4H), 4.42-4.44 (m, 2H), 6.75 (m, 1H), 7.93-7.94 (m, 2H)

5-Ethoxy-2-(3-fluoro-4-phenoxycarbonylamino-phenyl)-6-morpholin-4-yl-pyrimidine-4-carboxylic acid ethyl ester

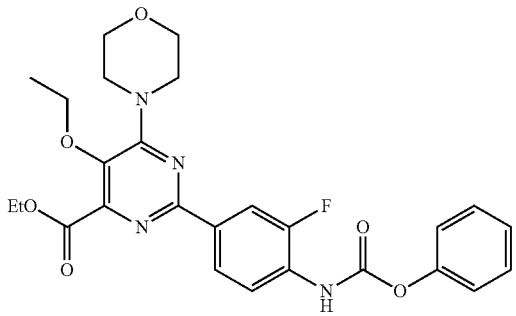 [SMILES: CCOC(=O)c1nc(-c2ccc(NC(=O)Oc3ccccc3)c(F)c2)nc(N2CCOCC2)c1OCC]

$^1$H NMR (500 MHz, CDCl$_3$-d$_1$): δ1.33-1.36 (m, 3H), 1.42-1.45 (m, 3H), 3.82-3.84 (m, 4H), 3.88-3.90 (m, 4H), 3.96-4.00 (m, 2H), 4.44-4.48 (m, 2H), 7.20-7.22 (m, 4H), 7.26-7.27 (m, 1H), 7.39-7.42 (m, 2H), 8.09-8.15 (m, 3H)

5-Ethoxy-2-(3-fluoro-4-{3-[4-(3-oxo-morpholin-4-yl)-phenyl]-ureido}-phenyl)-6-morpholin-4-yl-pyrimidine-4-carboxylic acid ethyl ester

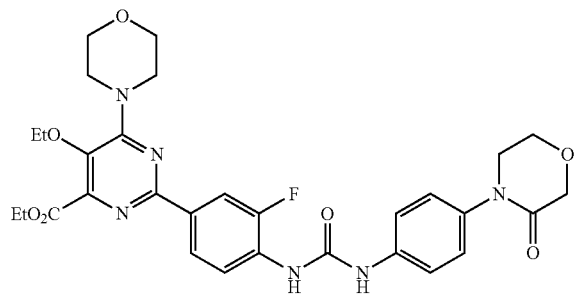 [SMILES: CCOC(=O)c1nc(-c2ccc(NC(=O)Nc3ccc(N4CCOCC4=O)cc3)c(F)c2)nc(N2CCOCC2)c1OCC]

$^1$H NMR (500 MHz, DMSO-d$_6$): δ1.24-1.28 (m, 3H), 1.32-1.35 (m, 3H), 3.70 (m, 2H), 3.75-3.76 (m, 4H), 3.82-3.83 (m, 4H), 3.89-3.92 (m, 2H), 3.93-3.96 (m, 2H), 4.18 (s, 2H), 4.36-4.40 (m, 2H), 7.30-7.32 (m, 2H), 7.48-7.49 (m, 2H), 7.98-8.04 (m, 2H), 8.29-8.32 (m, 1H), 8.80 (s, 1H), 9.22 (s, 1H)

2-(4-Amino-2-fluoro-phenyl)-5-ethoxy-6-morpholin-4-yl-pyrimidine-4-carboxylic acid ethyl ester

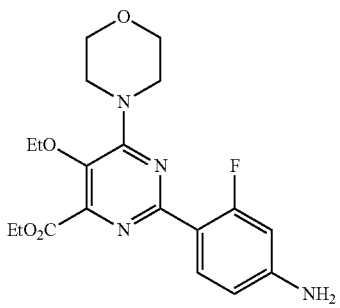 [SMILES: CCOC(=O)c1nc(-c2ccc(N)cc2F)nc(N2CCOCC2)c1OCC]

$^1$H NMR (500 MHz, CDCl$_3$-d$_1$): δ1.32-1.35 (m, 3H), 1.39-1.42 (m, 3H), 3.79-3.80 (m, 4H), 3.85-3.87 (m, 4H), 3.94-3.99 (m, 4H), 4.41-4.46 (m, 2H), 6.37-6.39 (m, 1H), 6.45-6.47 (m, 1H), 7.89-7.92 (m, 1H)

5-Ethoxy-2-(2-fluoro-4-phenoxycarbonylamino-phenyl)-6-morpholin-4-yl-pyrimidine-4-carboxylic acid ethyl ester

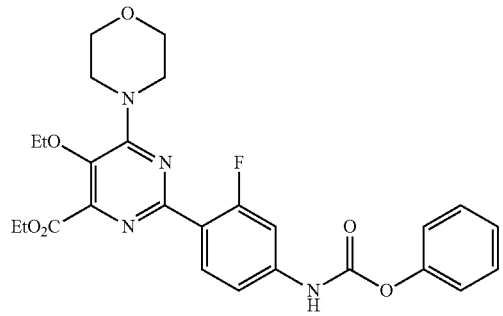 [SMILES: CCOC(=O)c1nc(-c2ccc(NC(=O)Oc3ccccc3)cc2F)nc(N2CCOCC2)c1OCC]

$^1$H NMR (500 MHz, CDCl$_3$-d$_1$): δ1.33-1.36 (m, 3H), 1.42-1.45 (m, 3H), 3.82-3.84 (m, 4H), 3.88-3.90 (m, 4H), 3.96-4.00 (m, 2H), 4.44-4.48 (m, 2H), 7.13-7.14 (m, 2H), 7.18-7.20 (m, 2H), 7.39-7.48 (m, 3H), 8.04-8.07 (m, 1H)

5-Ethoxy-2-(2-fluoro-4-{3-[4-(3-oxo-morpholin-4-yl)-phenyl]-ureido}-phenyl)-6-morpholin-4-yl-pyrimidine-4-carboxylic acid ethyl ester

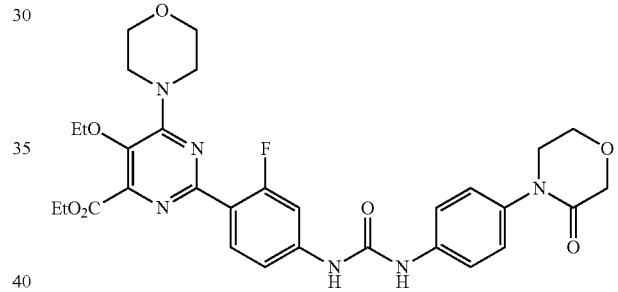

$^1$H NMR (500 MHz, DMSO-d$_6$): δ1.24-1.28 (m, 3H), 1.30-1.33 (m, 3H), 3.69-3.80 (m, 10H), 3.89-3.97 (m, 4H), 4.18 (s, 2H), 4.34-4.39 (m, 2H), 7.19-7.21 (m, 1H), 7.29-7.31 (m, 2H), 7.47-7.49 (m, 2H), 7.55-7.58 (m, 1H), 7.91 (m, 1H), 8.88 (s, 1H), 9.13 (s, 1H)

2-{4-[3-(4-Carbamoyl-phenyl)-ureido]-3-fluoro-phenyl}-5-ethoxy-6-morpholin-4-yl-pyrimidine-4-carboxylic acid ethyl ester

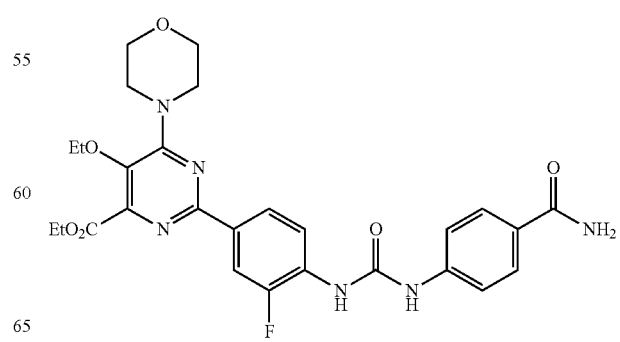

¹H NMR (500 MHz, DMSO-d₆): δ1.25-1.28 (m, 3H), 1.32-1.35 (m, 3H), 3.75-3.76 (m, 4H), 3.81-3.82 (m, 4H), 3.89-3.93 (m, 2H), 4.36-4.40 (m, 2H), 7.21 (m, 1H), 7.51-7.53 (m, 2H), 7.85-7.85 (m, 3H), 7.99-8.05 (m, 3H), 8.29-8.32 (m, 1H), 8.87 (s, 1H), 9.39 (s, 1H)

2-{4-[3-(4-Carbamoyl-phenyl)-ureido]-2-fluoro-phenyl}-5-ethoxy-6-morpholin-4-yl-pyrimidine-4-carboxylic acid ethyl ester

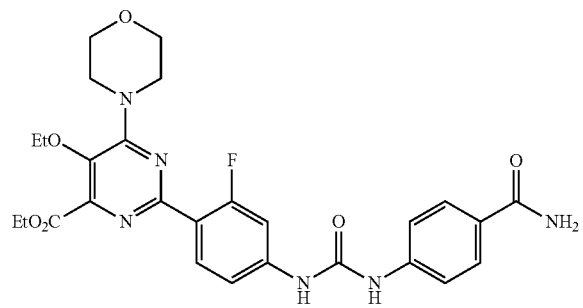 [SMILES: CCOC(=O)c1nc(-c2ccc(NC(=O)Nc3ccc(C(N)=O)cc3)cc2F)nc(N2CCOCC2)c1OCC]

¹H NMR (500 MHz, DMSO-d₆): δ1.24-1.28 (m, 3H), 1.30-1.33 (m, 3H), 3.73-3.74 (m, 10H), 3.79-3.80 (m, 4H), 3.90-3.94 (m, 2H), 4.34-4.38 (m, 2H), 7.21-7.22 (m, 2H), 7.59 (m, 3H), 7.82-7.84 (m, 3H), 7.93-7.96 (m, 1H), 9.05 (s, 1H), 9.20 (s, 1H)

2-[4-(3-Benzo[1,3]dioxol-5-yl-ureido)-phenyl]-5-ethoxy-6-morpholin-4-yl-pyrimidine-4-carboxylic acid ethyl ester

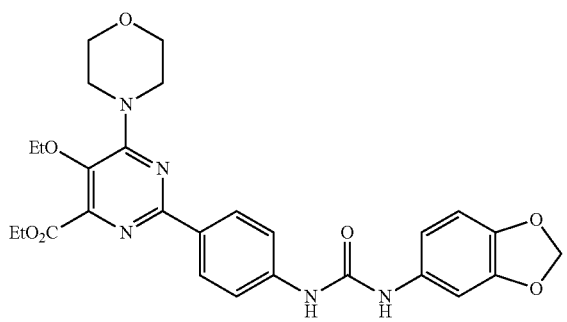 [SMILES: CCOC(=O)c1nc(-c2ccc(NC(=O)Nc3ccc4c(c3)OCO4)cc2)nc(N2CCOCC2)c1OCC]

¹H NMR (500 MHz, DMSO-d₆): δ1.24-1.28 (m, 3H), 1.32-1.35 (m, 3H), 3.75 (m, 4H), 3.82 (m, 4H), 3.90-3.91 (m, 4H), 4.37-4.38 (m, 2H), 5.98 (s, 2H), 6.77 (m, 1H), 6.83 (m, 1H), 7.21 (s, 1H), 7.52-7.53 (m, 2H), 8.15-8.17 (m, 2H), 8.60 (s, 1H), 8.87 (s, 1H)

5-Ethoxy-2-{4-[3-(4-ethoxycarbonyl-phenyl)-ureido]-phenyl}-6-morpholin-4-yl-pyrimidine-4-carboxylic acid ethyl ester

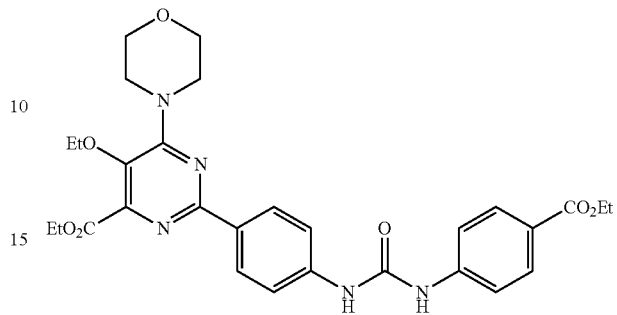

¹H NMR (500 MHz, DMSO-d₆): δ1.24-1.28 (m, 3H), 1.29-1.33 (m, 6H), 3.75 (m, 4H), 3.82 (m, 4H), 3.90-3.91 (m, 4H), 4.37-4.38 (m, 2H), 5.98 (s, 2H), 7.55-7.60 (m, 4H), 7.88-7.90 (m, 2H), 8.17-8.19 (m, 2H), 9.06 (s, 1H), 9.15 (s, 1H)

2-(4-{3-[4-(2-Dimethylamino-ethoxy)-phenyl]-ureido}-phenyl)-5-ethoxy-6-morpholin-4-yl-pyrimidine-4-carboxylic acid ethyl ester

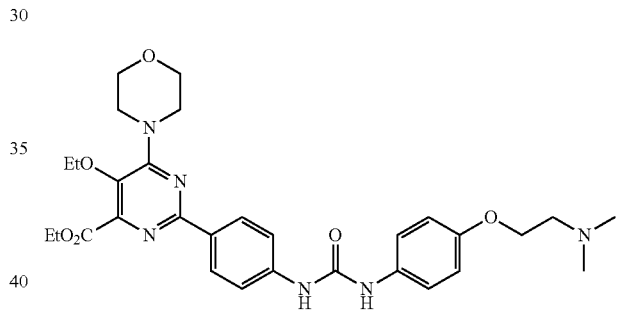

¹H NMR (500 MHz, DMSO-d₆): δ1.24-1.28 (m, 3H), 1.29-1.33 (m, 3H), 2.20 (s, 6H), 2.59 (m, 2H), 3.75 (m, 4H), 3.82 (m, 4H), 3.90-3.91 (m, 4H), 3.99-4.03 (m, 2H), 4.37-4.38 (m, 2H), 6.86 (m, 2H), 7.35-7.37 (m, 0.86 (m, 2H), 7.35-7.37 (m, 2H), 7.53-7.55 (m, 2H), 8.14-8.16 (m, 2H), 8.71 (s, 1H), 9.04 (s, 1H)

4-(3-{4-[5-Ethoxy-4-(morpholine-4-carbonyl)-6-morpholin-4-yl-pyrimidin-2-yl]-phenyl}-ureido)-benzamide

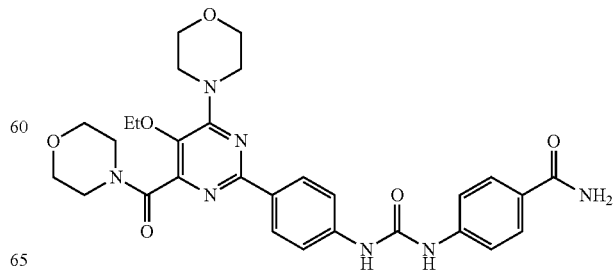

¹H NMR (500 MHz, DMSO-d₆): δ1.24-1.28 (m, 3H), 3.28 (m, 2H), 3.56 (m, 2H), 3.67 (m, 4H), 3.75 (m, 4H), 3.82 (m, 4H), 3.88-3.92 (m, 2H), 7.19 (m, 1H), 7.51-7.56 (m, 4H), 7.81-7.83 (m, 3H), 8.17-8.19 (m, 2H), 8.98 (s, 1H), 9.02 (s, 1H)

5-Ethoxy-2-{4-[3-(4-methanesulfonyl-phenyl)-ureido]-phenyl}-6-morpholin-4-yl-pyrimidine-4-carboxylic acid ethyl ester

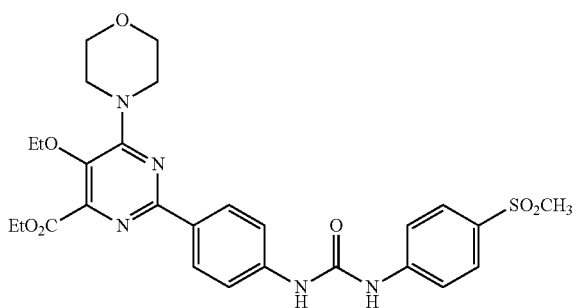 [SMILES: CCOC(=O)c1nc(-c2ccc(NC(=O)Nc3ccc(S(C)(=O)=O)cc3)cc2)nc(N2CCOCC2)c1OCC]

¹H NMR (500 MHz, DMSO-d₆): δ1.24-1.28 (m, 3H), 1.32-1.35 (m, 3H), 3.16 (s, 3H), 3.75-3.76 (m, 4H), 3.82-3.83 (m, 4H), 3.90-3.93 (m, 2H), 4.35-4.39 (m, 2H), 7.56-7.58 (m, 2H), 7.69-7.71 (m, 2H), 7.82 (m, 2H), 8.18-8.19 (m, 2H), 9.10 (m, 1H), 9.25 (s, 1H)

5-Ethoxy-2-[4-(3-isopropyl-ureido)-phenyl]-6-morpholin-4-yl-pyrimidine-4-carboxylic acid ethyl ester

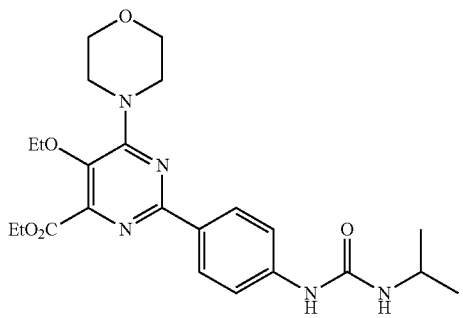 [SMILES: CCOC(=O)c1nc(-c2ccc(NC(=O)NC(C)C)cc2)nc(N2CCOCC2)c1OCC]

¹H NMR (500 MHz, CDCl₃-d₁): δ1.14-1.15 (m, 6H), 1.32-1.35 (m, 3H), 1.41-1.43 (m, 3H), 3.81-3.82 (m, 4H), 3.87 (m, 4H), 3.94-3.99 (m, 2H), 4.44-4.47 (m, 2H), 4.83-4.85 (m, 1H), 6.77 (s, 1H), 7.34-7.36 (m, 2H), 8.22-8.24 (m, 2H)

2-[4-(3-tert-Butyl-ureido)-phenyl]-5-ethoxy-6-morpholin-4-yl-pyrimidine-4-carboxylic acid ethyl ester

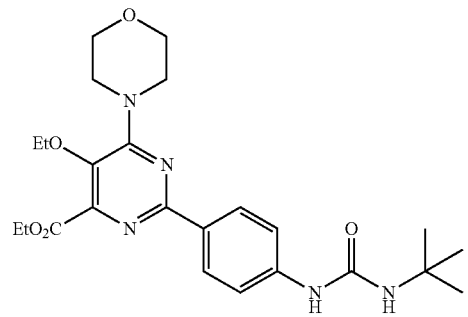 [SMILES: CCOC(=O)c1nc(-c2ccc(NC(=O)NC(C)(C)C)cc2)nc(N2CCOCC2)c1OCC]

¹H NMR (500 MHz, CDCl₃-d₁): δ1.32-1.36 (m, 12H), 1.41-1.44 (m, 3H), 3.81-3.82 (m, 4H), 3.86-3.87 (m, 4H), 3.94-3.99 (m, 2H), 4.44-4.47 (m, 2H), 4.77 (m, 1H), 6.46 (m, 1H), 7.31-7.33 (m, 2H), 8.22-8.24 (m, 2H)

5-Ethoxy-2-{4-[3-(4-methanesulfonylamino-phenyl)-ureido]-phenyl}-6-morpholin-4-yl-pyrimidine-4-carboxylic acid ethyl ester

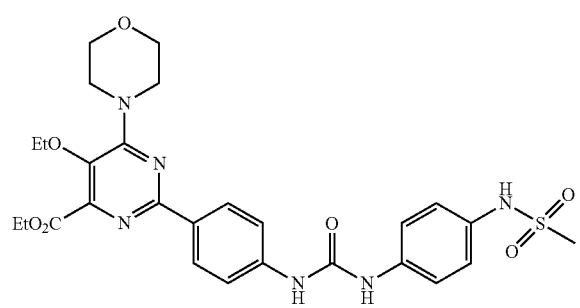 [SMILES: CCOC(=O)c1nc(-c2ccc(NC(=O)Nc3ccc(NS(C)(=O)=O)cc3)cc2)nc(N2CCOCC2)c1OCC]

¹H NMR (500 MHz, DMSO-d₆): δ1.26-1.27 (m, 3H), 1.32-1.34 (m, 3H), 2.92 (s, 3H), 3.75-3.76 (m, 4H), 3.81-3.82 (m, 4H), 3.88-3.93 (m, 2H), 4.35-4.39 (m, 2H), 7.14-7.16 (m, 2H), 7.42-7.43 (m, 2H), 7.53-7.55 (m, 2H0, 8.15-8.17 (m, 2H), 8.71 (s, 1H), 8.90 (s, 1H), 9.46 (s, 1H)

2-{4-[3-(4-Acetylamino-phenyl)-ureido]-phenyl}-5-ethoxy-6-morpholin-4-yl-pyrimidine-4-carboxylic acid ethyl ester

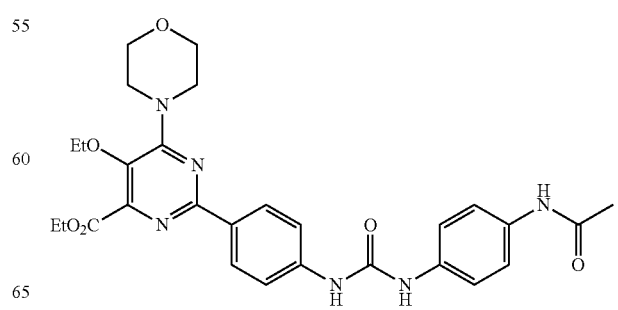

¹H NMR (500 MHz, DMSO-d₆): δ1.25-1.27 (m, 3H), 1.32-1.34 (m, 3H), 2.01 (s, 3H), 3.75-3.76 (m, 4H), 3.81-3.82 (m, 4H), 3.88-3.93 (m, 2H), 4.35-4.39 (m, 2H), 7.36-7.78 (m, 2H), 7.48-7.49 (m, 2H), 7.53-7.55 (m, 2H), 8.15-8.16 (m, 2H), 8.66 (s, 1H), 8.91 (s, 1H), 9.83 (m, 1H)

5-Ethoxy-6-morpholin-4-yl-2'-{3-[4-(3-oxo-morpholin-4-yl)-phenyl]-ureido}-[2,5']bipyrimidinyl-4-carboxylic acid ethyl ester

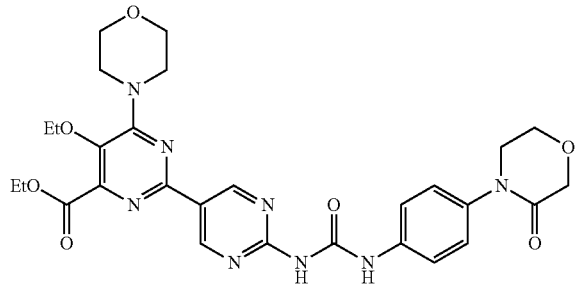 [SMILES: CCOC(=O)c1nc(-c2cnc(NC(=O)Nc3ccc(N4CCOCC4=O)cc3)nc2)nc(N2CCOCC2)c1OCC]

¹H NMR (500 MHz, DMSO-d₆): δ1.19-1.22 (m, 3H), 1.26-1.29 (m, 3H), 3.69-3.73 (m, 6H), 3.86-3.96 (m, 8H), 4.17 (s, 2H), 4.34-4.38 (m, 2H), 7.33-7.34 (m, 2H), 7.66-7.68 (m, 2H), 9.34 (s, 2H), 10.50 (s, 1H), 11.58 (s, 1H)

2'-[3-(4-Carbamoyl-phenyl)-ureido]-5-ethoxy-6-morpholin-4-yl-[2,5']bipyrimidinyl-4-carboxylic acid ethyl ester

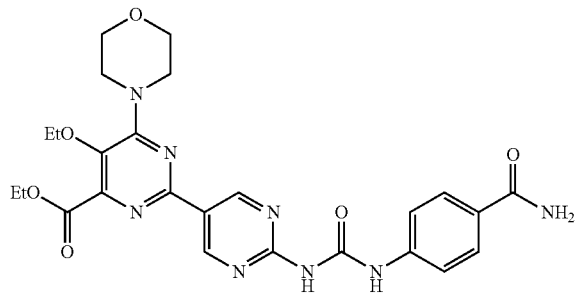 [SMILES: CCOC(=O)c1nc(-c2cnc(NC(=O)Nc3ccc(C(N)=O)cc3)nc2)nc(N2CCOCC2)c1OCC]

¹H NMR (500 MHz, DMSO-d₆): δ1.24-1.29 (m, 3H), 1.32-1.35 (m, 3H), 3.76-3.77 (m, 4H), 3.88-3.95 (m, 6H), 4.36-4.41 (m, 2H), 7.26 (s, 1H), 7.73-7.75 (m, 2H), 7.86-7.90 (m, 3H), 9.38 (s, 2H), 10.62 (s, 1H), 11.81 (s, 1H)

2'-[3-(4-Acetylamino-phenyl)-ureido]-5-ethoxy-6-morpholin-4-yl-[2,5']bipyrimidinyl-4-carboxylic acid ethyl ester

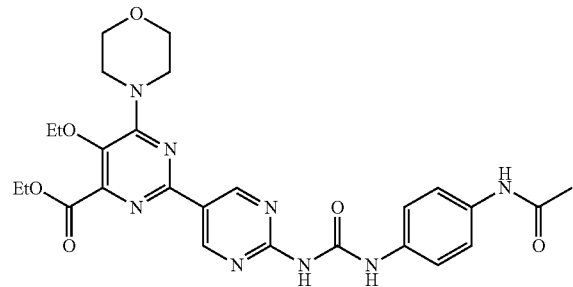 [SMILES: CCOC(=O)c1nc(-c2cnc(NC(=O)Nc3ccc(NC(C)=O)cc3)nc2)nc(N2CCOCC2)c1OCC]

¹H NMR (500 MHz, DMSO-d₆): δ1.24-1.29 (m, 3H), 1.32-1.35 (m, 3H), 2.05 (s, 3H), 3.76-3.77 (m, 4H), 3.88-3.95 (m, 6H), 4.36-4.41 (m, 2H), 7.55 (m, 4H), 9.35 (s, 2H), 9.89 (s, 1H), 10.46 (s, 1H), 11.45 (s, 1H)

5-Ethoxy-2-(4-{3-[4-(4-methanesulfonyl-piperazin-1-yl)-phenyl]-ureido}-phenyl)-morpholin-4-yl-pyrimidine-4-carboxylic acid ethyl ester

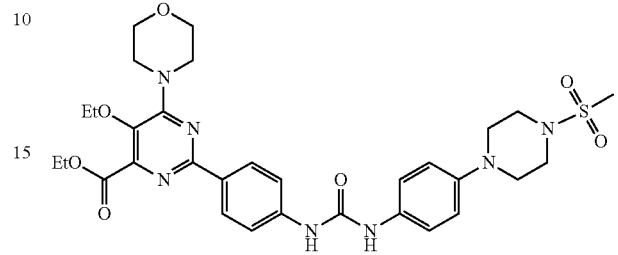

¹H NMR (500 MHz, DMSO-d₆): δ1.25-1.27 (m, 3H), 1.32-1.34 (m, 3H), 2.92 (s, 3H), 3.15-3.16 (m, 4H), 3.23-3.25 (m, 4H), 3.75-3.76 (m, 4H), 3.81-3.82 (m, 4H), 3.88-3.93 (m, 2H), 4.35-4.39 (m, 2H), 6.92-6.94 (m, 2H), 7.33-7.35 (m, 2H), 7.53-7.54 (m, 2H), 8.14-8.16 (m, 2H), 8.53 (s, 1H), 8.86 (s, 1H)

5-Ethoxy-6-morpholin-4-yl-2-{4-[3-(2-oxo-2,3-dihydro-benzooxazol-6-yl)-ureido]-phenyl}-pyrimidine-4-carboxylic acid ethyl ester

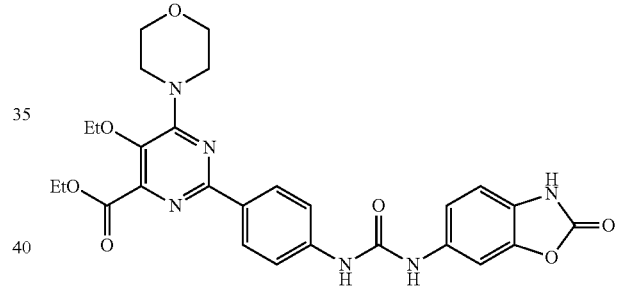

¹H NMR (500 MHz, DMSO-d₆): δ1.25-1.27 (m, 3H), 1.32-1.34 (m, 3H), 3.75 (m, 4H), 3.83 (m, 4H), 3.90-3.91 (m, 2H), 4.35-4.39 (m, 2H), 6.98-6.99 (m, 1H), 7.05-7.07 (m, 1H), 7.54-7.56 (m, 3H), 8.15-8.17 (m, 2H), 8.93 (s, 1H), 9.09 (s, 1H)

2-{4-[3-(6-Acetylamino-pyridin-3-yl)-ureido]-phenyl}-5-ethoxy-6-morpholin-4-yl-pyrimidine-4-carboxylic acid ethyl ester

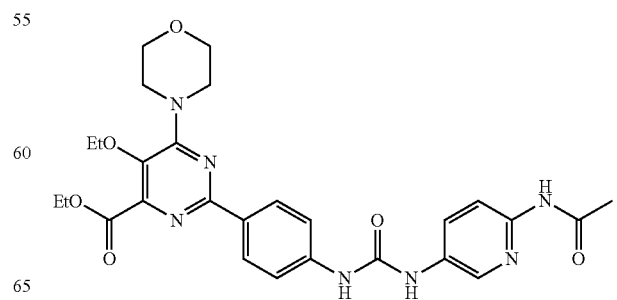

¹H NMR (500 MHz, DMSO-d₆): δ1.20-1.23 (m, 3H), 1.27-1.30 (m, 3H), 2.02 (s, 3H), 3.71-3.72 (m, 4H), 3.78 (m, 4H), 3.84-3.87 (m, 2H), 4.32-4.34 (m, 2H), 7.50-7.52 (m, 2H), 7.77-7.79 (m, 1H), 7.96 (m, 1H), 8.11-8.13 (m, 2H), 8.38 (s, 1H), 8.75 (s, 1H), 9.01 (s, 1H)

Example 2

Preparation of Compounds of Formula (I) in Scheme 5

[2-(4-Amino-phenyl)-5-ethoxy-6-morpholin-4-yl-pyrimidin-4-yl]-methanol

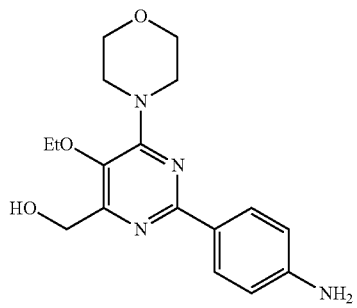 [SMILES: CCOc1c(CO)nc(-c2ccc(N)cc2)nc1N1CCOCC1]

NaBH₄ (192 mg, 5 eq.) was added to a stirred solution of 2-(4-amino-phenyl)-5-ethoxy-6-morpholin-4-yl-pyrimidine-4-carboxylic acid ethyl ester (378 mg, 1 eq.) in EtOH (12 ml) and the mixture reacted to reflux overnight. The mixture was quenched with H₂O, the solvent removed in vacuo, and the residue extracted with EA and washed with brine. The crude was purified by chromatography to give a product (267 mg, 80%).

¹H NMR (500 MHz, CDCl₃-d): δ1.33-1.36 (m, 3H), 3.80-3.90 (m, 10H), 4.30 (s, 1H), 4.71 (s, 2H), 6.71-6.73 (m, 2H), 8.17-8.19 (m, 2H)

(2-Chloro-5-ethoxy-6-morpholin-4-yl-pyrimidin-4-yl)-methanol

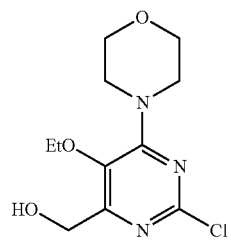

NaBH₄ (0.64 g, 4 eq.) was added to a stirred solution of 2-chloro-5-ethoxy-6-morpholine-4-yl-pyrimidine-4-carboxylic acid ethyl ester (1.34 g, 1 eq.) in EtOH (20 ml) and the mixture reacted to reflux for 2 h. The mixture was quenched with H₂O, the solvent was removed in vacuo, and the residue was extracted with EA, washed with brine, and concentrated to give a product (1.13 g, 97.3%).

¹H NMR (500 MHz, CDCl₃-d₁): δ1.34-1.37 (m, 3H), 3.37 (s, 1H), 3.77-3.84 (m, 10H), 4.63-4.64 (m, 2H)

(2-Chloro-5-ethoxy-6-morpholin-4-yl-pyrimidine-4-carbaldehyde

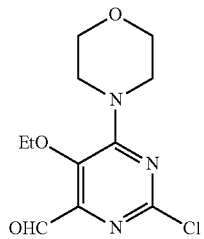 [SMILES: CCOc1c(C=O)nc(Cl)nc1N1CCOCC1]

To a suspension of Dess-Martin periodinane in CH₂Cl₂ (15%, 11.2 ml, 1.1 eq) was added to a stirred solution of (2-chloro-5-ethoxy-6-morpholin-4-yl-pyrimidin-4-yl)-methanol (1.13 g, 1 eq.) in CH₂Cl₂ (20 ml) and the mixture was reacted at r.t. for 2 h. The mixture was quenched with NaHCO₃ (sat), extracted with EA, and washed with brine. The crude was purified by chromatography to give a product (1.08 g, 80.8%).

¹H NMR (500 MHz, CDCl₃-d₁) δ1.38-1.43 (m, 3H), 3.77-4.01 (m, 10H), 10.06 (s, 1H)

4-[2-Chloro-5-ethoxy-6-(4-methanesulfonyl-piperazin-1-ylmethyl)-pyrimidin-4-yl]-morpholine

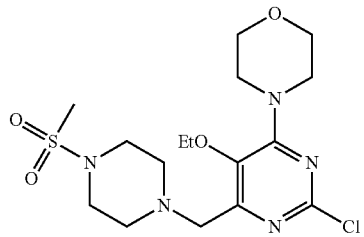 [SMILES: CCOc1c(CN2CCN(S(C)(=O)=O)CC2)nc(Cl)nc1N1CCOCC1]

A mixture of 2-chloro-5-ethoxy-6-morpholine-4-yl-pyrimidine-4-carboxylic acid ethyl ester (271.7 mg, 1 eq.), 1-methanesulfonyl-1-piperazine (197 mg, 1.2 eq.) and trimethylorthoformate (0.33 ml, 3 eq.) was stirred in 1,2-dichloroethane (6 ml) for 6 h at room temperature. To this was added sodium triacetoxyborohydride (530 mg, 2.5 eq.) and the reaction mixture was stirred overnight at room temperature. The mixture was then quenched with brine, exacted with CH₂Cl₂, and dried, and the solvent was removed in vacuo. The residue was triturated with EA/Hex to yield 4-[2-chloro-5-ethoxy-6-(4-methanesulfonyl-piperazin-1-yl-methyl)-pyrimidin-4-yl]-morpholine as a white solid (336 mg, 80%).

¹H NMR (500 MHz, CDCl₃-d₁): δ1.35-1.38 (m, 3H), 2.69-2.70 (m, 4H), 2.77 (s, 3H), 3.26 (m, 4H), 3.59 (s, 2H), 3.79-3.86 (m, 10H)

3-[5-Ethoxy-4-(4-methanesulfonyl-piperazin-1-ylmethyl)-6-morpholin-4-yl-pyrimidin-2-yl]-phenol

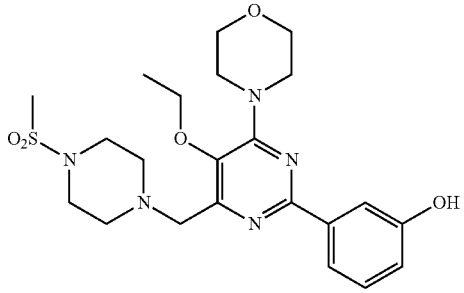 [SMILES: CCOc1c(CN2CCN(S(C)(=O)=O)CC2)nc(-c2cccc(O)c2)nc1N1CCOCC1]

$^1$H NMR (500 MHz, DMSO-d$_6$): δ1.31-1.34 (m, 3H), 2.66 (m, 4H), 2.86 (s, 3H), 3.10 (m, 4H), 3.61 (s, 2H), 3.74 (m, 8H), 3.90-3.93 (m, 2H), 6.82-6.84 (m, 1H), 7.23-7.26 (m, 1H), 7.71 (m, 2H), 9.50 (s, 1H)

4-[2-Chloro-5-ethoxy-6-(4-methyl-piperazin-1-ylmethyl)-pyrimidin-4-yl]-morpholine

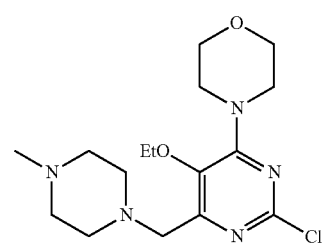 [SMILES: CCOc1c(CN2CCN(C)CC2)nc(Cl)nc1N1CCOCC1]

$^1$H NMR (500 MHz, CDCl$_3$-d$_1$): δ1.34-1.37 (m, 3H), 2.75 (s, 3H), 2.98 (m, 4H), 3.18 (m, 4H), 3.65 (s, 2H), 3.79-3.82 (m, 10H)

4-[2-Chloro-5-ethoxy-6-(4-morpholin-1-ylmethyl)-pyrimidin-4-yl]-morpholine

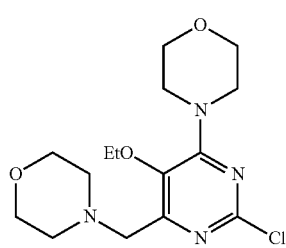 [SMILES: CCOc1c(CN2CCOCC2)nc(Cl)nc1N1CCOCC1]

A mixture of 2-chloro-5-ethoxy-6-morpholine-4-yl-pyrimidine-4-carboxylic acid ethyl ester (878 mg, 1 eq.), morpholine (0.34 ml, 1.2 eq.) and trimethylorthoformate (1.06 ml, 3 eq.) was stirred in 1,2-dichloroethane (20 ml) for 6 hrs at room temperature. To this was added sodium triacetoxyborohydride (1.71 g, 2.5 eq.) and the reaction mixture was stirred overnight at room temperature. The mixture was then quenched with brine, exacted with CH$_2$Cl$_2$, and dried, and the solvent was removed in vacuo. The crude was purified by chromatography to give a product (1.0 g, 91%).

$^1$H NMR (500 MHz, CDCl$_3$-d$_1$): δ1.33-1.36 (m, 3H), 2.56 (m, 4H), 3.50 (s, 2H), 3.68-3.69 (m, 4H), 3.77 (s, 8H), 3.86-3.90 (m, 2H)

4-[5-Ethoxy-4-(4-methanesulfonyl-piperazin-1-ylmethyl)-6-morpholin-4-yl-pyrimidin-2-yl]-1H-indazole

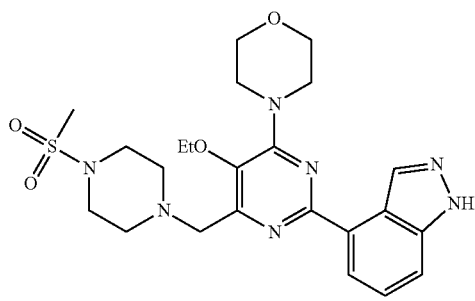 [SMILES: CCOc1c(CN2CCN(S(C)(=O)=O)CC2)nc(-c2cccc3[nH]ncc23)nc1N1CCOCC1]

$^1$H NMR (500 MHz, CDCl$_3$-d$_1$): δ1.39-1.42 (m, 3H), 2.79 (s, 3H), 2.83-2.84 (m, 4H), 3.30 (m, 4H), 3.81 (s, 2H), 3.86-3.88 (m, 8H), 3.95-3.99 (m, 2H), 7.46-7.49 (m, 1H), 7.57-7.58 (m, 1H), 8.20-8.21 (m, 1H), 9.01 (s, 1H)

4-[5-Ethoxy-4-(4-methanesulfonyl-piperazin-1-ylmethyl)-6-morpholin-4-yl-pyrimidin-2-yl]-phenylamine

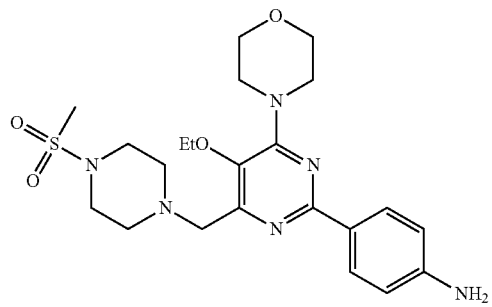 [SMILES: CCOc1c(CN2CCN(S(C)(=O)=O)CC2)nc(-c2ccc(N)cc2)nc1N1CCOCC1]

$^1$H NMR (500 MHz, CDCl$_3$-d$_1$): δ1.34-1.39 (m, 3H), 2.78 (s, 3H), 2.79-2.83 (m, 4H), 3.28 (m, 4H), 3.71 (s, 2H), 3.78-3.83 (m, 8H), 3.89-3.92 (m, 2H), 6.70-6.72 (m, 2H), 8.13-8.15 (m, 2H)

4-[5-Ethoxy-4-(4-methyl-piperazin-1-ylmethyl)-6-morpholin-4-yl-pyrimidin-2-yl]-1H-indazole

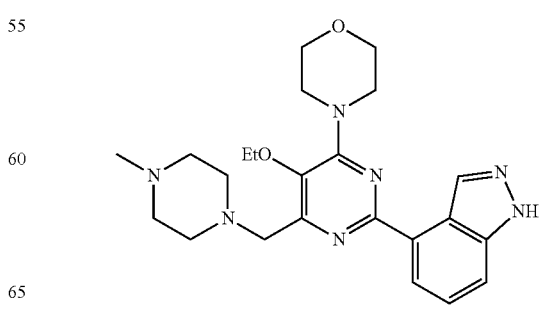

¹H NMR (500 MHz, CDCl₃-d₁): δ1.38-1.41 (m, 3H), 2.33 (s, 3H), 2.57 (m, 4H), 2.79 (m, 4H), 3.77 (s, 2H), 3.85-3.88 (m, 8H), 3.97-4.01 (m, 2H), 7.44-7.47 (m, 1H), 7.55-7.56 (m, 1H), 8.20-8.21 (m, 1H), 9.02 (s, 1H)

4-[5-Ethoxy-4-(4-methyl-piperazin-1-ylmethyl)-6-morpholin-4-yl-pyrimidin-2-yl]-phenylamine

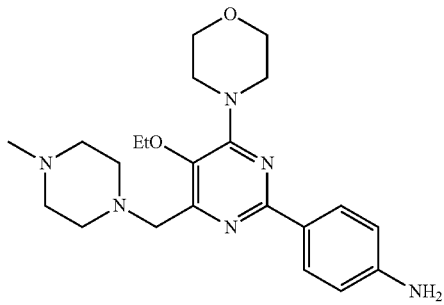 [SMILES: CCOc1c(CN2CCN(C)CC2)nc(-c2ccc(N)cc2)nc1N1CCOCC1]

¹H NMR (500 MHz, CDCl₃-d₁) δ1.34-1.36 (m, 3H), 2.31 (s, 3H), 2.52 (m, 4H), 2.73 (m, 4H), 3.66 (s, 2H), 3.77-3.83 (m, 8H), 3.89-3.93 (m, 2H), 6.69-6.71 (m, 2H), 8.15-8.17 (m, 2H)

4-(5-Ethoxy-4-morpholin-4-yl-6-morpholin-4-ylmethyl-pyrimidin-2-yl)-1H-indazole

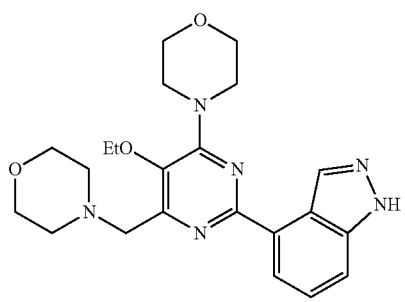 [SMILES: CCOc1c(CN2CCOCC2)nc(-c2cccc3[nH]ncc23)nc1N1CCOCC1]

¹H NMR (500 MHz, CDCl₃-d₁): δ1.38-1.41 (m, 3H), 2.72 (m, 4H), 3.75-3.76 (m, 6H), 3.85-3.88 (m, 8H), 3.99-4.03 (m, 2H), 7.46-7.47 (m, 1H), 7.54-7.56 (m, 1H), 8.21-8.22 (m, 1H), 9.03 (s, 1H)

4-(5-Ethoxy-4-morpholin-4-yl-6-morpholin-4-ylmethyl-pyrimidin-2-yl)-phenylamine

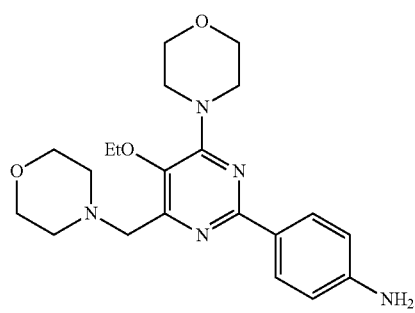 [SMILES: CCOc1c(CN2CCOCC2)nc(-c2ccc(N)cc2)nc1N1CCOCC1]

¹H NMR (500 MHz, CDCl₃-d₁): δ1.34-1.39 (m, 3H), 2.68 (m, 4H), 3.64 (s, 2H), 3.72-3.73 (m, 4H), 3.78-3.83 (m, 8H), 3.91-3.95 (m, 2H), 6.69-6.70 (m, 2H), 8.15-8.16 (m, 2H)

1-{4-[5-Ethoxy-4-(4-methanesulfonyl-piperazin-1-ylmethyl)-6-morpholin-4-yl-pyrimidin-2-yl]-phenyl}-3-phenyl-urea

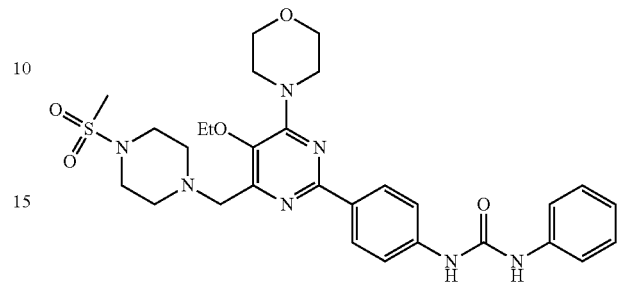

¹H NMR (500 MHz, CDCl₃-d₁): δ1.35-1.38 (m, 3H), 2.73 (s, 3H), 2.77 (m, 4H), 3.24 (m, 4H), 3.71 (s, 2H), 3.81-3.82 (m, 8H), 3.87-3.92 (m, 2H), 7.05 (m, 1H), 7.32-7.45 (m, 6H), 8.21-8.22 (m, 2H)

1-{4-[5-Ethoxy-4-(4-methyl-piperazin-1-ylmethyl)-6-morpholin-4-yl-pyrimidin-2-yl]-phenyl}-3-phenyl-urea

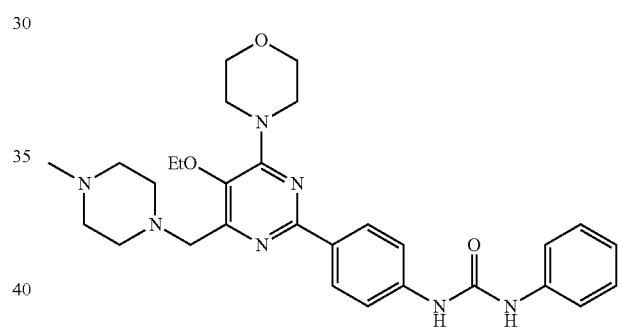

¹H NMR (500 MHz, DMSO-d₆): δ1.30-1.33 (m, 3H), 2.16 (s, 3H), 2.36-2.63 (m, 8H), 3.53 (s, 2H), 3.74 (m, 8H), 3.91-3.93 (m, 2H), 6.98-6.99 (m, 1H), 7.27-7.30 (m, 2H), 7.46-7.47 (m, 2H), 7.53-7.53 (m, 2H), 8.18-8.20 (m, 2H), 8.83 (s, 1H), 9.00 (s, 1H)

1-[4-(5-Ethoxy-4-morpholin-4-yl-6-morpholin-4-ylmethyl-pyrimidin-2-yl)-phenyl]-3-phenyl-urea

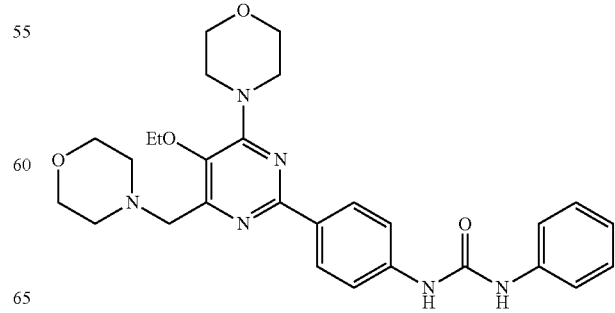

¹H NMR (500 MHz, CDCl₃-d₁): δ1.35-1.38 (m, 3H), 2.65 (s, 4H), 3.66 (s, 2H), 3.69-3.71 (m, 4H), 3.80-3.82 (m, 8H), 3.90-3.95 (m, 2H), 7.02-7.05 (m, 1H), 7.23-7.37 (m, 6H), 8.21-8.23 (m, 2H)

1-[4-(5-Ethoxy-4-morpholin-4-yl-6-morpholin-4-ylmethyl-pyrimidin-2-yl)-phenyl]-3-phenyl-urea hydrochloride

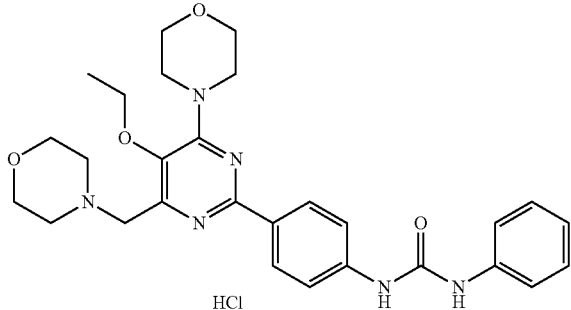 [SMILES: CCOc1c(CN2CCOCC2)nc(-c2ccc(NC(=O)Nc3ccccc3)cc2)nc1N1CCOCC1 ; Cl]

¹H NMR (500 MHz, DMSO-d₆): δ1.33-1.36 (m, 3H), 3.48-3.96 (m, 18H), 4.58 (s, 2H), 6.97-6.99 (m, 1H), 7.27-7.30 (m, 2H), 7.46-7.48 (m, 2H), 7.58-7.60 (m, 2H), 8.29-8.31 (m, 2H), 9.40 (s, 1H), 9.64 (s, 1H)

1-[4-(5-Ethoxy-4-morpholin-4-yl-6-piperidin-1-ylmethyl-pyrimidin-2-yl)-phenyl]-3-D phenyl-urea

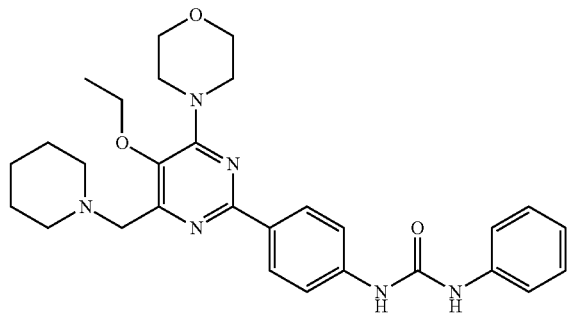 [SMILES: CCOc1c(CN2CCCCC2)nc(-c2ccc(NC(=O)Nc3ccccc3)cc2)nc1N1CCOCC1]

¹H NMR (500 MHz, CDCl₃-d₁): δ1.33-1.40 (m, 5H), 1.56-1.58 (m, 4H), 2.60 (m, 4H), 3.64 (s, 2H), 3.77-3.80 (m, 8H), 3.86-3.90 (m, 2H), 6.93-6.96 (m, 1H), 7.16-7.19 (m, 2H), 7.26-7.28 (m, 2H), 7.31-7.33 (m, 2H), 7.92 (s, 1H), 8.03 (s, 1H), 8.14-8.16 (m, 2H)

1-[4-(5-Ethoxy-4-morpholin-4-yl-6-piperidin-1-ylmethyl-pyrimidin-2-yl)-phenyl]-3-Phenyl-urea hydrochloride

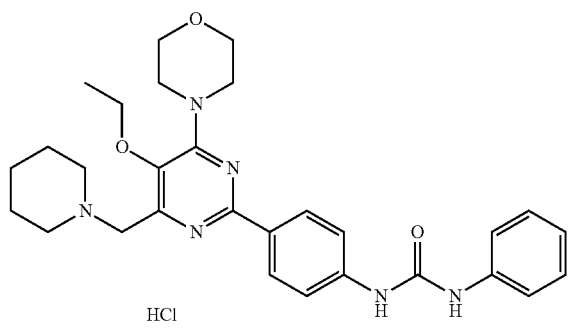 [SMILES: CCOc1c(CN2CCCCC2)nc(-c2ccc(NC(=O)Nc3ccccc3)cc2)nc1N1CCOCC1 ; Cl]

¹H NMR (500 MHz, DMSO-d₆): δ1.33-1.36 (m, 3H), 1.86 (m, 4H), 2.08 (m, 2H), 3.14 (m, 2H), 3.58 (m, 2H), 3.76-3.81 (m, 8H), 3.88-3.91 (m, 2H), 4.48 (s, 2H), 6.95-6.98 (m, 1H), 7.26-7.29 (m, 2H), 7.46-7.47 (m, 2H), 7.58-7.60 (m, 2H), 8.29-8.31 (m, 2H), 9.51 (s, 1H), 9.77 (s, 1H)

Example 3

Preparation of Compounds of Formula (I) in Scheme 1

5-Methoxy-pyrimidine-2,4-diol

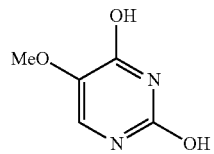

A mixture of methyl methoxylacetate (15 ml, 1.0 eq) and ethyl formate (12.18 ml, 1.0 eq) was added dropwise to slurry of sodium methoxide (8.17 g, 1.0 eq) in toluene (100 ml) at ice both. After dropping at room temperature and stirring overnight, the resulting solution was dried in vacuo. Then a mixture of residue, urea (9.09 g, 1.0 eq) and NaOMe (4.10 g, 0.5 eq) in EtOH (100 ml) was refluxed at 110° C. for 4 hrs. After the solvent was dried in vacuo, water and cone. HCl solution (5<pH<4) were added. After formation of white precipitate, the mixture was filtered and dried solid in vacuo. A product was obtained as a white solid (5.14 g, 23.88%)

¹H NMR (500 MHz, DMSO-d₆): δ7.01 (s, 1H), 3.54 (s, 3H)

2,4-Dichloro-5-methoxy-pyrimidine

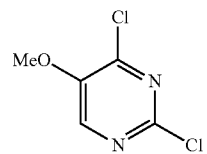

In ice bath, dimethyl-phenyl-amine (6.58 ml, 51.65 mmol, 0.5 eq) was added dropwise to a slurry of 5-methoxy-pyrimidine-2,4-diol (14.68 g, 1.0 eq) in POCl₃ (47.42 ml, 5.0 eq) and refluxed overnight. Excess POCl₃ was evaporated in vacuo and the residue was poured into ice-water. After formation of pink precipitates, the mixture was filtered and dried solid in vacuo. A product was obtained as a white solid (3.89 g, 20.83%)

¹H NMR (500 MHz, CDCl₃-d₁): δ8.18 (s, 1H), 4.01 (s, 3H)

4-(2-Chloro-5-methoxy-pyrimidin-4-yl)-morpholine

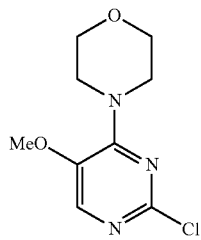 [SMILES: COc1cnc(Cl)nc1N1CCOCC1]

2,4-Dichloro-5-methoxy-pyrimidin (3.2 g, 1.0 eq) was stirred in toluene (20 ml) and a solution of morpholine (2.34 ml, 1.5 eq) in toluene (20 ml) was added dropwise at −10~0° C. After stirring the resulting solution overnight at r.t., NH4Cl(aq) was added and the solution was extracted with EA. The combined organic layers were washed with brine, dried and evaporated in vacuo. A product was obtained as a white solid (3.80 g, 93.08%)

$^1$H NMR (500 MHz, CDCl$_3$-d$_1$): δ7.71 (s, 1H), 3.84 (s, 3H), 3.82 (t, 4H), 3.76 (t, 4H)

4-[5-Methoxy-2-(3-nitro-phenyl)-pyrimidin-4-yl]-morpholine

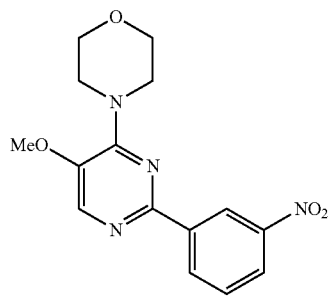 [SMILES: COc1cnc(-c2cccc([N+](=O)[O-])c2)nc1N1CCOCC1]

A mixture of 4-(2-chloro-5-methoxy-pyrimidin-4-yl)-morpholine (0.2 g, 1.0 eq), 3-nitrophenyl boronic acid (0.17 g, 1.2 eq), (PPh$_3$)$_4$Pd (0.10 g, 0.1 eq) and 2 M Na$_2$CO$_3$ (1.3 ml, 3.0 eq) was heated at 80° C. and refluxed overnight. The solvent was removed in vacuo, and the residue was extracted with EA and water. The combined organic layers were washed with brine, dried and evaporated in vacuo. The crude was purified by chromatography to give a yellow solid (0.11 g, 39.97%).

$^1$H NMR (500 MHz, CDCl$_3$-d$_1$): δ9.13 (s, 1H), 8.65 (d, 1H), 8.24 (d, 1H), 8.03 (s, 1H), 7.60 (t, 1H), 3.93 (s, 3H), 3.88 (d, 4H), 3.85 (d, 4H)

4-(5-Methoxy-4-morpholin-4-yl-pyrimidin-2-yl)-phenylamine

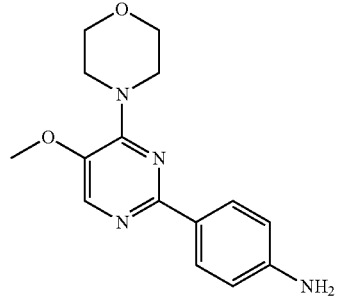 [SMILES: COc1cnc(-c2ccc(N)cc2)nc1N1CCOCC1]

$^1$H NMR (500 MHz, CDCl$_3$-d$_1$): δ8.12 (d, 2H), 7.98 (s, 1H), 6.70 (d, 2H), 3.86 (s, 3H), 3.82 (s, 8H)

4-(5-Methoxy-4-morpholin-4-yl-pyrimidin-2-yl)-phenol

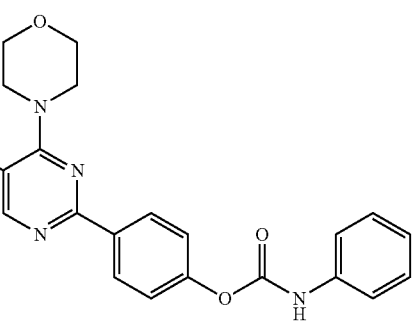

$^1$H NMR (500 MHz, CDCl$_3$-d$_1$): δ8.20 (d, 2H), 7.96 (s, 1H), 6.91 (d, 2H), 3.89 (s, 3H), 3.84 (m, 4H), 3.83 (m, 4H)

Phenyl-carbamic acid 4-(5-methoxy-4-morpholin-4-yl-pyrimidin-2-yl)-phenyl ester Phenyl isocyanate (0.03 ml, 2.0 eq) was added to a solution of 4-(5-methoxy-4-morpholin-4-yl-pyrimidin-2-yl)-phenol (0.05 g, 1.0 eq) in dioxane (6 ml) and heated at 80° C. for 20 hrs. The solvent was removed in vacuo, and the residue was extracted with EA and water. The combined organic layers were washed with brine, dried and evaporated in vacuo. The crude was purified by chromatography to give a white solid (0.07 g, 24.03%).

¹H NMR (500 MHz, CDCl₃-d₁): δ8.34 (d, 2H), 8.02 (s, 1H), 7.45 (d, 2H), 7.33 (t, 2H), 7.27 (s, 1H), 7.12 (m, 1H), 6.90 (s, 1H), 3.90 (s, 3H), 3.86 (m, 4H), 3.84 (m, 4H), 3.70 (s, 1H)

1-[4-(5-Methoxy-4-morpholin-4-yl-pyrimidin-2-yl)-phenyl]-3-phenyl-urea

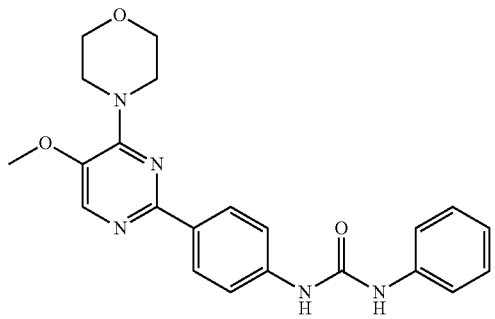 [SMILES: COc1cnc(-c2ccc(NC(=O)Nc3ccccc3)cc2)nc1N1CCOCC1]

¹H NMR (500 MHz, CDCl₃-d₁): δ8.19 (d, 2H), 7.95 (s, 1H), 7.37 (d, 2H), 7.33 (d, 2H), 7.27 (m, 2H), 7.23 (s, 1H), 7.19 (s, 1H), 7.05 (m, 1H), 3.86 (s, 3H), 3.83 (m, 4H), 3.83 (m, 4H)

1-Ethyl-3-[4-(5-methoxy-4-morpholin-4-yl-pyrimidin-2-yl)-phenyl]-urea

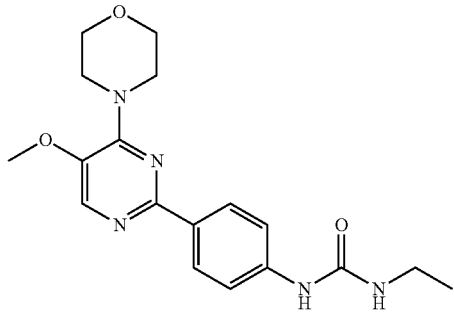 [SMILES: CCNC(=O)Nc1ccc(-c2ncc(OC)c(N3CCOCC3)n2)cc1]

¹H NMR (500 MHz, CDCl₃-d₁): δ8.24 (d, 2H), 8.00 (s, 1H), 7.34 (d, 2H), 6.35 (s, 1H), 4.72 (s, 1H), 3.89 (s, 3H), 3.83 (s, 4H), 3.30 (m, 2H), 1.15 (m, 3H)

1-(4-Fluoro-phenyl)-3-[4-(5-methoxy-4-morpholin-4-yl-pyrimidin-2-yl)-phenyl]-urea

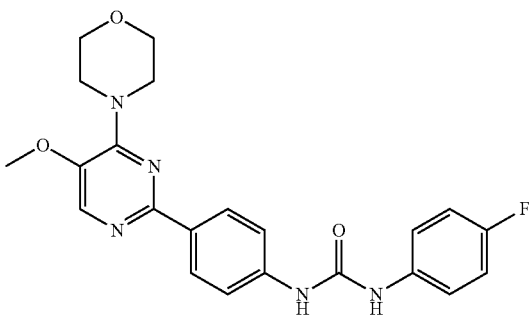 [SMILES: COc1cnc(-c2ccc(NC(=O)Nc3ccc(F)cc3)cc2)nc1N1CCOCC1]

¹H NMR (500 MHz, CDCl₃-d₁): δ8.25 (d, 2H), 7.99 (s, 1H), 7.39 (d, 2H), 7.32 (m, 2H), 7.03 (m, 2H), 6.69 (s, 1H), 6.67 (s, 1H), 3.89 (s, 3H), 3.84 (s, 8H)

1-(3-Fluoro-phenyl)-3-[4-(5-methoxy-4-morpholin-4-yl-pyrimidin-2-yl)-phenyl]-urea

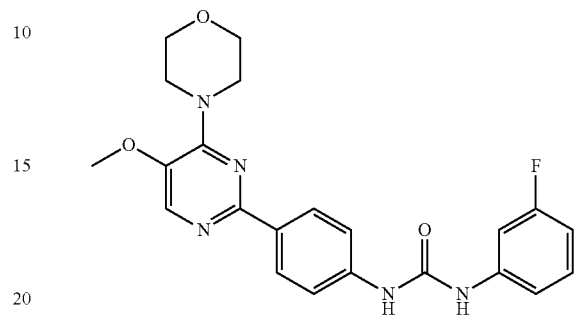

¹H NMR (500 MHz, CDCl₃-d₁): δ8.27 (d, 2H), 8.00 (s, 1H), 7.39 (d, 2H), 7.30 (m, 1H), 7.24 (m, 1H), 7.00 (m, 1H), 6.80 (s, 1H), 6.78 (m, 1H), 6.60 (s, 1H), 3.89 (s, 3H), 3.84 (s, 8H)

1-(3,4-Difluoro-phenyl)-3-[4-(5-methoxy-4-morpholin-4-yl-pyrimidin-2-yl)-phenyl]-urea

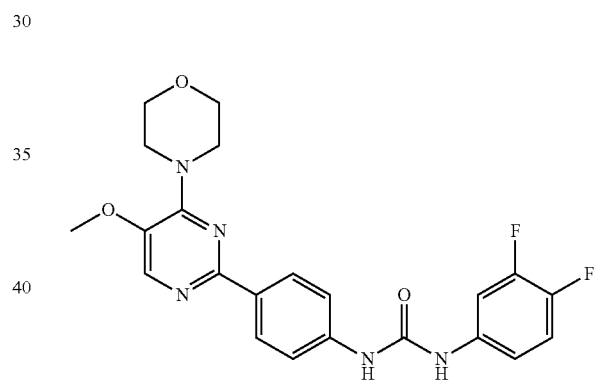

¹H NMR (500 MHz, CDCl₃-d₁): δ8.27 (d, 2H), 8.00 (s, 1H), 7.42 (m, 1H), 7.39 (d, 2H), 7.00 (m, 1H), 6.97 (m, 1H), 6.75 (s, 1H), 6.68 (s, 1H), 3.89 (s, 3H), 3.84 (s, 8H)

1-(4-Fluoro-phenyl)-3-[4-(5-methoxy-4-morpholin-4-yl-pyrimidin-2-yl)-phenyl]-thio urea

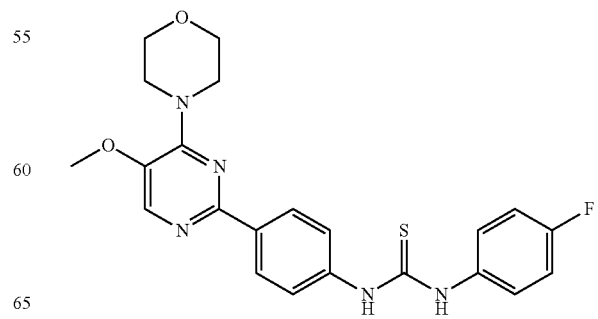

¹H NMR (500 MHz, CDCl₃-d₁): δ8.35 (d, 2H), 8.01 (s, 1H), 7.82 (m, 1H), 7.70 (m, 1H), 7.40 (d, 2H), 7.37 (d, 2H), 7.0 (d, 2H), 3.91 (s, 3H), 3.84 (s, 8H)

1-(3-Fluoro-phenyl)-3-[4-(5-methoxy-4-morpholin-4-yl-pyrimidin-2-yl)-phenyl]-thio urea

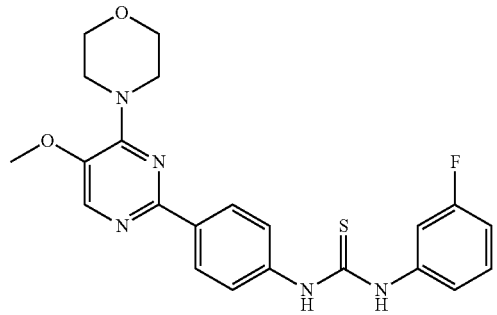

¹H NMR (500 MHz, CDCl₃-d₁): δ8.36 (d, 2H), 8.02 (s, 1H), 7.41 (d, 2H), 7.33 (m, 2H), 7.26 (s, 1H), 7.11 (m, 1H), 6.94 (m, 1H), 3.91 (s, 3H), 3.84 (s, 8H)

1-[4-(5-Methoxy-4-morpholin-4-yl-pyrimidin-2-yl)-phenyl]-3-pyridin-3-yl-urea

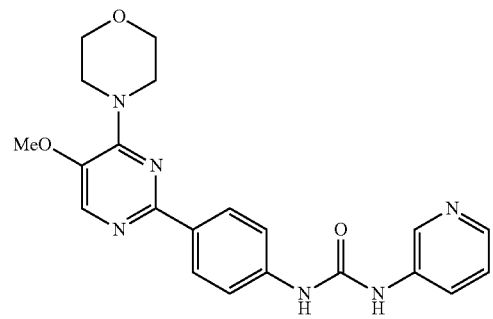 [SMILES: COc1cnc(-c2ccc(NC(=O)Nc3cccnc3)cc2)nc1N1CCOCC1]

¹H NMR (500 MHz, DMSO-d₆): δ9.18 (s, 1H), 9.09 (s, 1H), 8.62 (d, 1H), 8.17-8.19 (t, 3H), 8.13 (s, 1H), 7.95-7.97 (d, 1H), 7.54-7.56 (d, 2H), 7.30-7.33 (m, 1H), 3.87 (s, 1H), 3.73-3.74 (m, 8H)

1-[4-(5-Methoxy-4-morpholin-4-yl-pyrimidin-2-yl)-phenyl]-3-methyl-urea

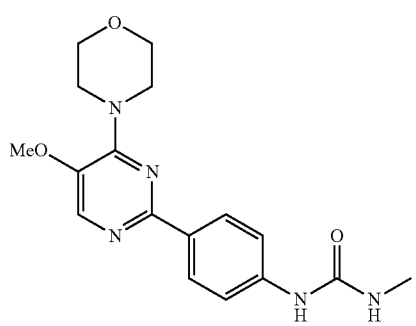 [SMILES: CNC(=O)Nc1ccc(-c2ncc(OC)c(N3CCOCC3)n2)cc1]

¹H NMR (500 MHz, DMSO-d₆): δ9.35 (s, 1H), 8.19-8.21 (d, 2H), 7.71-7.73 (d, 3H), 6.42 (s, 1H), 4.22 (s, 4H), 3.94 (s, 3H), 3.87 (s, 4H), 2.84 (s, 3H)

1-(3,4-Dimethoxy-phenyl)-3-[4-(5-methoxy-4-morpholin-4-yl-pyrimidin-2-yl)-phenyl]-urea

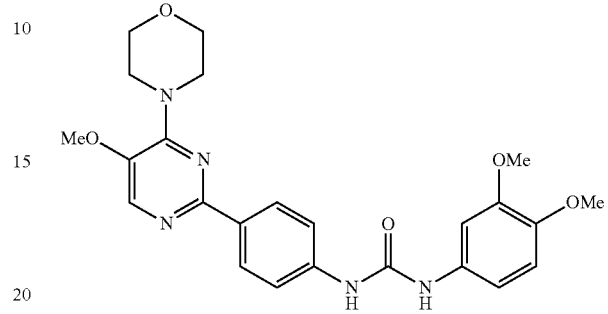

¹H NMR (500 MHz, DMSO-d₆): δ9.18 (s, 1H), 8.89 (s, 1H), 8.13-8.17 (m, 3H), 7.52-7.54 (d, 2H), 7.23 (s, 1H), 6.87-6.89 (m, 2H), 3.87 (s, 3H), 3.70-3.74 (m, 14H)

1-[4-(5-Methoxy-4-morpholin-4-yl-pyrimidin-2-yl)-phenyl]-3-(3-trifluoromethyl-phenyl)-urea

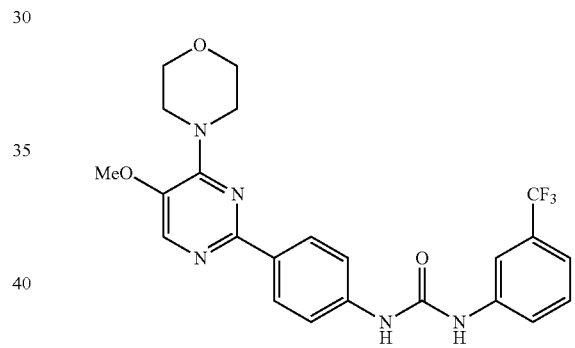

¹H NMR (500 MHz, DMSO-d₆): δ9.10 (s, 1H), 9.01 (s, 1H), 8.18-8.19 (d, 2H), 8.14 (s, 1H), 8.02 (s, 1H), 7.50-7.53 (m, 4H), 7.31-7.32 (d, 1H), 3.87 (s, 3H), 3.73 (m, 8H)

1-[4-(5-Methoxy-4-morpholin-4-yl-pyrimidin-2-yl)-phenyl]-3-[4-(3-oxo-morpholin-4-yl)-phenyl]-urea

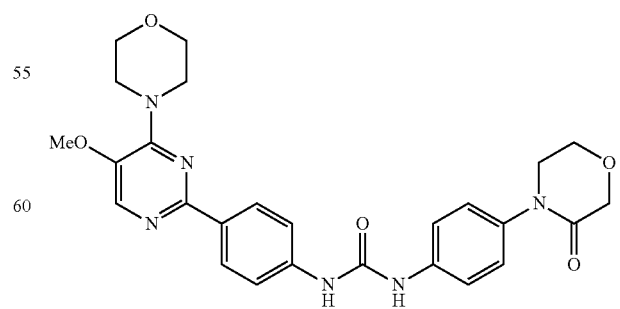

¹H NMR (500 MHz, DMSO-d₆): δ9.11 (s, 1H), 8.98 (s, 1H), 8.17-8.18 (d, 2H), 8.14 (s, 1H), 7.53-7.54 (d, 2H), 7.48-7.50 (d, 2H), 7.28-7.29 (d, 2H), 4.18 (s, 2H), 3.96 (s, 2H), 3.87 (s, 3H), 3.69-3.74 (m, 10H)

1-(3-Fluoro-4-morpholin-4-yl-phenyl)-3-[4-(5-methoxy-4-morpholin-4-yl-pyrimidin-2-yl)-phenyl]-urea

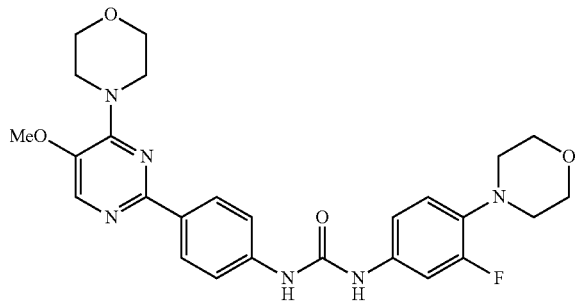 [SMILES: COc1cnc(-c2ccc(NC(=O)Nc3ccc(N4CCOCC4)c(F)c3)cc2)nc1N1CCOCC1]

¹H NMR (500 MHz, DMSO-d₆): δ9.11 (s, 1H), 8.98 (s, 1H), 8.16-8.17 (d, 2H), 8.13 (s, 1H), 7.51-7.53 (d, 2H), 7.47-7.44 (s, 1H), 7.08-7.09 (m, 1H), 6.95-6.99 (m, 1H), 3.87 (s, 3H), 3.73-3.74 (m, 12H), 2.92-2.94 (m, 4H)

1-[4-(5-Methoxy-4-morpholin-4-yl-pyrimidin-2-yl)-phenyl]-3-(2-morpholin-4-yl-ethyl)-urea

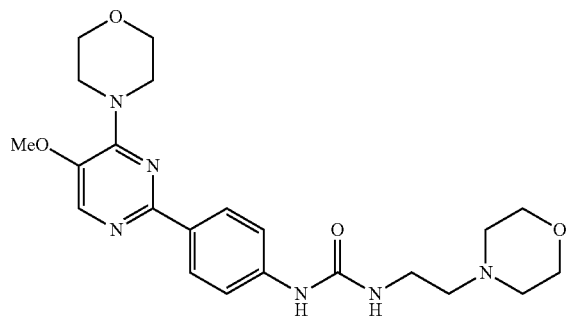

¹H NMR (500 MHz, DMSO-d₆): δ8.91 (s, 1H), 8.10-8.12 (d, 3H), 7.45-7.46 (d, 2H), 6.25 (s, 1H), 3.86 (s, 3H), 3.72 (s, 8H), 3.58-3.60 (m, 4H), 3.19-3.22 (m, 2H), 2.36-2.39 (m, 6H)

1-[4-(5-Methoxy-4-morpholin-4-yl-pyrimidin-2-yl)-phenyl]-3-(4-methyl-piperazin-1-yl)-urea

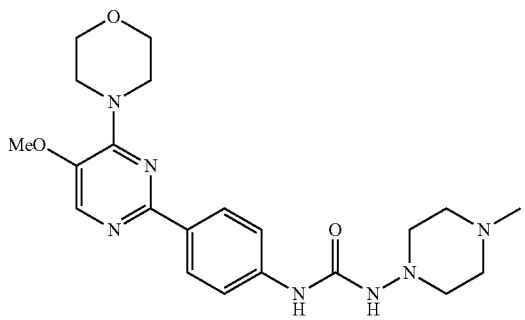 [SMILES: COc1cnc(-c2ccc(NC(=O)NN3CCN(C)CC3)cc2)nc1N1CCOCC1]

¹H NMR (500 MHz, DMSO-d₆): δ8.60 (s, 1H), 8.12-8.14 (d, 2H), 8.12 (s, 1H), 7.77 (s, 1H), 7.60-7.62 (d, 2H), 3.86 (s, 3H), 3.73 (s, 8H), 2.58-2.74 (m, 8H), 2.19 (s, 3H)

1-[4-(5-Methoxy-4-morpholin-4-yl-pyrimidin-2-yl)-phenyl]-3-(4-morpholin-4-yl-phenyl-urea

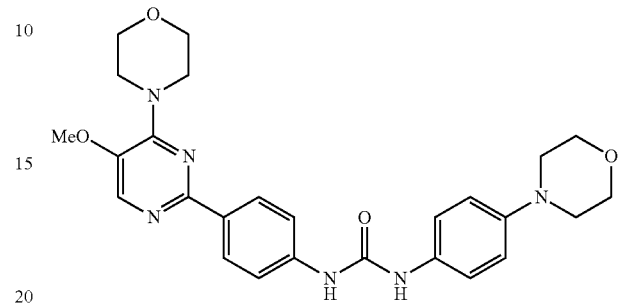

¹H NMR (500 MHz, DMSO-d₆): δ8.85 (s, 1H), 8.56 (s, 1H), 8.15-8.17 (d, 2H), 8.13 (s, 1H), 7.50-7.52 (d, 2H), 7.31-7.33 (d, 2H), 6.88-6.90 (d, 2H), 3.87 (s, 3H), 3.72-3.74 (m, 12H), 3.01-3.03 (m, 4H).

1-[4-(5-Methoxy-4-morpholin-4-yl-pyrimidin-2-yl)-phenyl]-3-(4-thiomorpholin-4-yl-phenyl)-urea

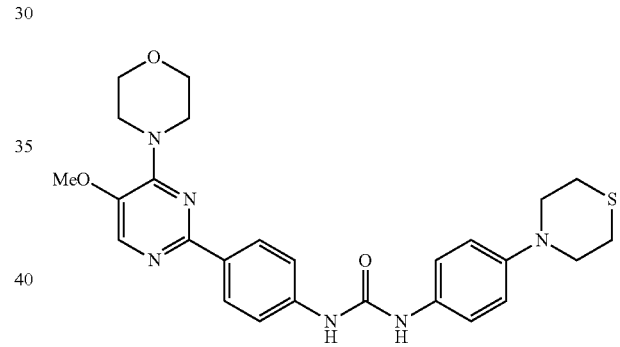

¹H NMR (500 MHz, DMSO-d₆): δ8.89 (s, 1H), 8.59 (s, 1H), 8.15-8.17 (d, 2H), 8.13 (s, 1H), 7.50-7.52 (d, 2H), 7.31-7.32 (d, 2H), 6.87-6.89 (d, 2H), 3.87 (s, 3H), 3.73-3.74 (m, 8H), 3.38-3.39 (m, 4H), 2.67-2.69 (m, 4H).

[4-(5-Methoxy-4-morpholin-4-yl-pyrimidin-2-yl)-phenyl]-carbamic acid phenyl ester

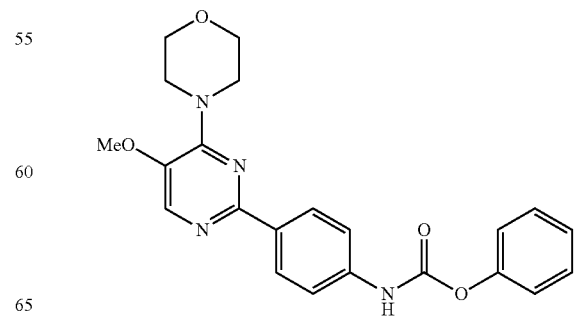

A mixture of 4-(5-methoxy-4-morpholin-4-yl-pyrimidin-2-yl)-phenylamine (1.50 g, 1.0 eq.) and sodium bicarbonate solution (6 ml) in ethyl acetate (6 ml) stirring 5 min. After dropping phenyl chloroformate (0.98 ml, 1.2 eq) for 4 hrs at room temperature. The resultant mixture extracted with EA and the combined organic layers were washed with brine and dried in vacuo to give a light brown solid (1.80 g, 40.5%) as the product.

$^1$H NMR (500 MHz, CDCl$_3$-d$_1$): δ8.36-8.38 (d, 2H), 7.95 (s, 1H), 7.61-7.63 (d, 2H), 7.39-7.42 (m, 3H), 7.26 (s, 1H), 7.19-7.25 (m, 2H), 4.02 (s, 4H), 3.90 (s, 3H), 3.85-3.86 (m, 4H)

4-{3-[4-(5-Methoxy-4-morpholin-4-yl-pyrimidin-2-yl)-phenyl]-ureido}-benzamide

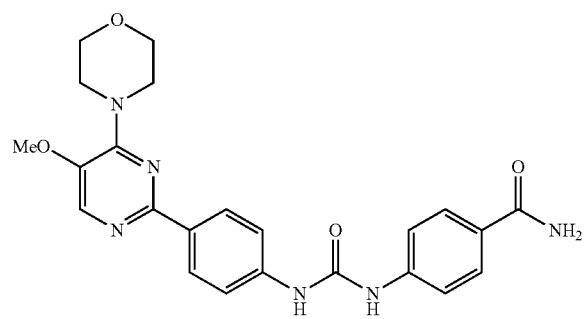 [SMILES: COc1cnc(-c2ccc(NC(=O)Nc3ccc(C(N)=O)cc3)cc2)nc1N1CCOCC1]

$^1$H NMR (500 MHz, DMSO-d$_6$): δ9.40-9.60 (m, 2H), 8.17-8.19 (d, 2H), 8.14 (s, 1H), 7.80-7.82 (d, 3H), 7.53-7.56 (m, 4H), 7.18 (s, 1H), 3.87 (s, 3H), 3.73-3.74 (m, 8H).

4-{3-[4-(5-Methoxy-4-morpholin-4-yl-pyrimidin-2-yl)-phenyl]-ureido}-benzenesulfonamide

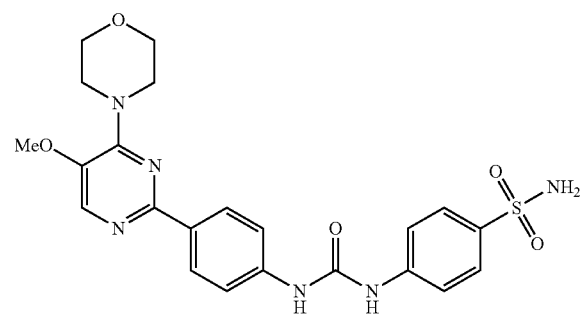

$^1$H NMR (500 MHz, DMSO-d$_6$): δ9.30 (s, 1H), 9.15 (s, 1H), 8.18-8.20 (d, 2H), 8.14 (s, 1H), 7.72-7.74 (d, 2H), 7.62-7.64 (d, 2H), 7.54-7.56 (d, 2H), 7.21 (s, 2H), 3.87 (s, 3H), 3.73-3.74 (m, 8H)

2-Nitro-4-(4,4,5,5-tetramethyl-[1,3,2]dioxaborolan-2-yl)-phenylamine

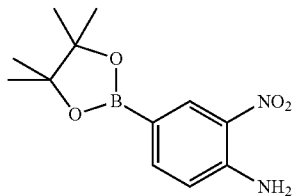 [SMILES: CC1(C)OB(c2ccc(N)c([N+](=O)[O-])c2)OC1(C)C]

$^1$H NMR (500 MHz, CDCl$_3$-d$_1$): δ8.59 (s, 1H), 7.71-7.73 (d, 1H), 6.76-6.78 (d, 1H), 6.20-6.30 (m, 2H), 1.33 (s, 12H).

4-(5-Methoxy-4-morpholin-4-yl-pyrimidin-2-yl)-2-nitro-phenylamine

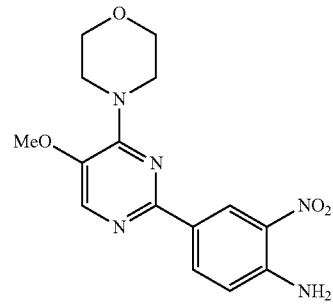 [SMILES: COc1cnc(-c2ccc(N)c([N+](=O)[O-])c2)nc1N1CCOCC1]

A mixture of 4-(2-chloro-5-methoxy-pyrimidin-4-yl)-morpholine (1.0 g, 1 eq.), 2-nitro-4-(4,4,5,5-tetramethyl-[1,3,2]dioxaborolan-2-yl)-phenylamine (1.26 g, 1.1 eq.), dioxane (20 ml), Pd(PPh$_3$)$_4$ (0.05 g, 0.1 eq.) and 2M sodium carbonate (6.53 ml, 3.0 eq.) was heated to reflux overnight. The solvent was removed in vacuo, the residue extracted with EA, and the organic layer washed with brine and dried. The crude was purified by chromatography to give a brown solid (2.08 g, 47.83%).

$^1$H NMR (500 MHz, CDCl$_3$-d$_1$): δ9.06 (s, 1H), 8.32-8.34 (d, 1H), 7.98 (s, 1H), 6.84-6.86 (d, 1H), 6.20 (s, 2H), 3.86 (s, 3H), 3.84 (s, 8H)

1-(2-Amino-phenyl)-3-[4-(5-methoxy-4-morpholin-4-yl-pyrimidin-2-yl)-phenyl]-thio urea

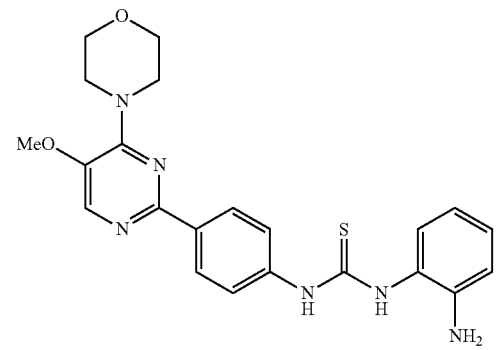

A mixture of di-imidazol-1-yl-methanethione (0.5 g, 1.50 eq.), imidazole (0.03 g, 0.3 eq.) and CH₃CN (7 ml) was added dropwise to 4-(5-methoxy-4-morpholin-4-yl-pyrimidin-2-yl)-phenylamine (0.5 g, 1.0 eq.) in CH₂Cl₂ (5 ml) at 0° C. When S.M. is disappear in TLC, dropping benzene-1,2-diamine (0.37 g, 3.0 eq) to the solution for 3 hrs at 50° C. The solvent was removed in vacuo. The resulting solution was crystallized in a EA solution, and filtered to given a light yellow solid, which was then dried in vacuo to give of a product (0.53 g, 70.18%).

¹H NMR (500 MHz, DMSO-d₆): δ9.80 (s, 1H), 9.20 (s, 1H), 8.18-8.19 (d, 2H), 8.15 (s, 1H), 7.63-7.64 (d, 2H), 7.09-7.10 (m, 1H), 6.95-6.96 (m, 1H), 6.74-6.75 (m, 1H), 6.55-6.58 (m, 1H), 4.92 (s, 2H), 3.88 (s, 3H), 3.72-3.75 (m, 8H).

4-(5-Methoxy-4-morpholin-4-yl-pyrimidin-2-yl)-benzene-1,2-diamine

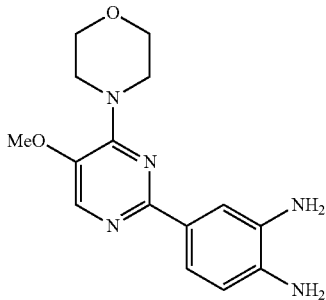

A mixture of 4-(5-methoxy-4-morpholin-4-yl-pyrimidin-2-yl)-2-nitro-phenylamine (0.69 g, 1.0 eq.) and Pd/C (Cat.) in MeOH/EA (10 ml/10 ml) was prepared. The mixture was sharked and H₂ gas was injected to the mixture for 4-6 hrs at room temperature. The mixture was filtered with Celite 454 and dried in vacuo to give a black sold (0.65 g, 99.9%) as a product.

¹H NMR (500 MHz, CDCl₃-d₁): δ8.03 (s, 1H), 7.49 (s, 1H), 7.36-7.38 (m, 1H), 6.50-6.51 (d, 1H), 4.77 (s, 2H), 4.49 (s, 2H), 3.82 (s, 3H), 3.70 (s, 8H).

(1H-Benzoimidazol-2-yl)-[4-(5-methoxy-4-morpholin-4-yl-pyrimidin-2-yl)-phenyl]-amine

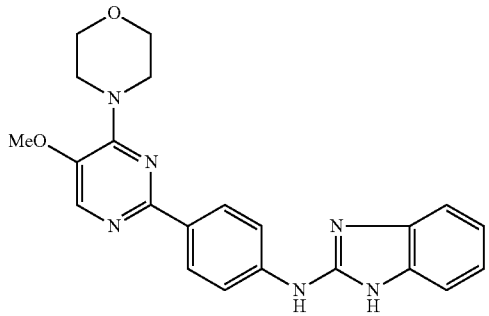

A mixture of 1-(2-Amino-phenyl)-3-[4-(5-methoxy-4-morpholin-4-yl-pyrimidin-2-yl)-phenyl]-thiourea (0.3 g, 1.0 eq.) and DCC (0.18 g, 1.3 eq.) in THF (10 ml) for 9 hrs at 80-90° C. The mixture was dried in vacuo, crystallized in a EA solution, and then filtered to give a white solid (0.18 g, 68.36%), which was then dried in vacuo to give of a product.

¹H NMR (500 MHz, DMSO-d₆): δ11.2 (s, 1H), 9.87 (s, 1H), 8.20-8.22 (d, 2H), 8.14 (s, 1H), 7.82-7.84 (d, 2H), 7.28-7.36 (d, 2H), 7.00 (s, 2H), 3.87 (s, 3H), 3.74 (s, 8H).

5-(5-Methoxy-4-morpholin-4-yl-pyrimidin-2-yl)-1H-benzoimidazol-2-ylamine

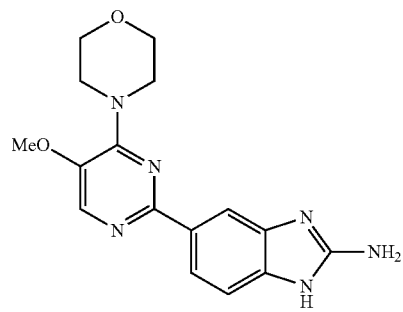 [SMILES: COc1cnc(-c2ccc3[nH]c(N)nc3c2)nc1N1CCOCC1]

A mixture of 4-(5-methoxy-4-morpholin-4-yl-pyrimidin-2-yl)-benzene-1,2-diamine (0.58 g, 1.0 eq.) and ACN/H2O (5 ml/1 ml). In ice bath, cyanogen bromide (0.3 g, 1.5 eq) was added to mixture solution dropwisely. The solution was stirred overnight at room temperature, quenched with a NaHCO₃ (sat.) solution, and then filtered to give a light brown solid (0.32 g, 51.78%), which was dried in vacuo to give a product.

¹H NMR (500 MHz, DMSO-d₆): δ8.12 (s, 1H), 8.06 (s, 1H), 7.93-7.95 (d, 1H), 7.14-7.5 (d, 1H), 6.63 (s, 2H), 3.86 (s, 3H), 3.74 (s, 8H).

1-(4-Dimethylaminomethoxy-phenyl)-3-[4-(5-methoxy-4-morpholin-4-yl-pyrimidin-2-yl)-phenyl]-urea

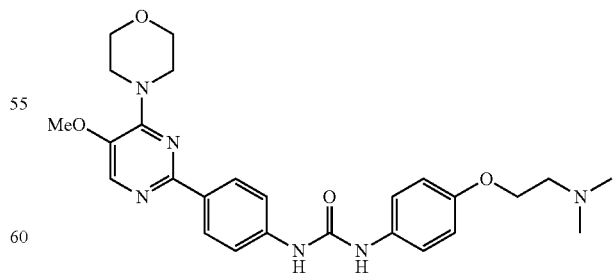

¹H NMR (500 MHz, DMSO-d₆): δ8.86 (s, 1H), 8.60 (s, 1H), 8.15-8.17 (d, 2H), 8.13 (s, 1H), 7.50-7.52 (d, 2H), 7.34-7.36 (d, 2H), 6.87-6.89 (d, 2H), 4.00-4.02 (m, 2H), 3.87 (s, 3H), 3.73-3.74 (m, 8H), 2.63-2.66 (m, 2H), 1.90 (s, 6H)

105

3-{3-[4-(5-Methoxy-4-morpholin-4-yl-pyrimidin-2-yl)-phenyl]-ureido}-benzamide

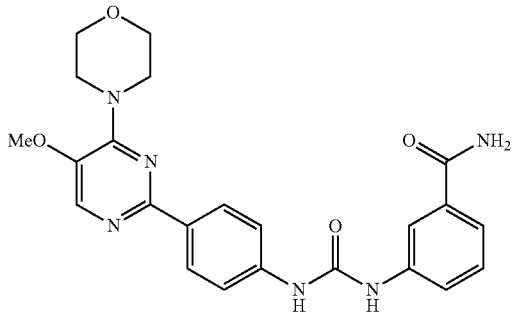 [SMILES: COc1cnc(-c2ccc(NC(=O)Nc3cccc(C(N)=O)c3)cc2)nc1N1CCOCC1]

¹H NMR (500 MHz, DMSO-d₆): δ8.92 (s, 1H), 8.86 (s, 1H), 8.17-8.19 (d, 2H), 8.14 (s, 1H), 7.94 (s, 1H), 7.89 (s, 1H), 7.53-7.55 (d, 2H), 7.46-7.47 (d, 2H), 7.33-7.37 (m, 2H), 3.87 (s, 3H), 3.73-3.74 (m, 8H)

1-[4-(5-Methoxy-4-morpholin-4-yl-pyrimidin-2-yl)-phenyl]-3-thiazol-2-yl-urea

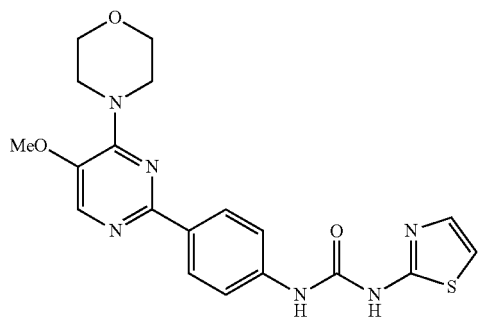

¹H NMR (500 MHz, DMSO-d₆): δ9.15 (s, 1H), 8.20-8.22 (d, 2H), 8.14 (s, 1H), 7.55-7.56 (d, 2H), 7.39 (s, 1H), 7.20 (s, 1H), 3.87 (s, 3H), 3.73-3.74 (m, 8H)

1-[4-(5-Methoxy-4-morpholin-4-yl-pyrimidin-2-yl)-phenyl]-3-[4-(4-methyl-piperazin-1-yl)-phenyl]-urea

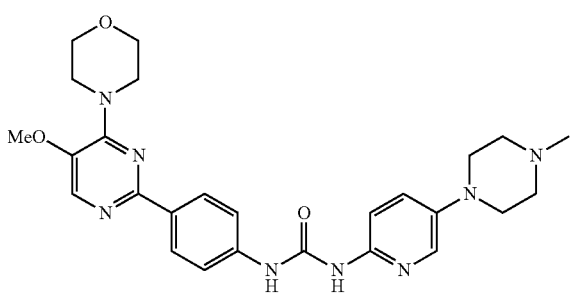 [SMILES: COc1cnc(-c2ccc(NC(=O)Nc3ccc(N4CCN(C)CC4)cn3)cc2)nc1N1CCOCC1]

¹H NMR (500 MHz, DMSO-d₆): δ9.22 (s, 1H), 8.18-8.20 (d, 2H), 8.14 (s, 1H), 7.97 (s, 1H), 7.56-7.58 (d, 2H), 7.47 (s, 2H), 3.87 (s, 3H), 3.73-3.74 (m, 8H), 3.17 (m, 4H), 3.06 (m, 4H), 1.16-1.19 (m, 3H).

106

1-[4-(5-Methoxy-4-morpholin-4-yl-pyrimidin-2-yl)-phenyl]-3-[4-(3-oxo-morpholin-4-yl)-phenyl]-thio-urea

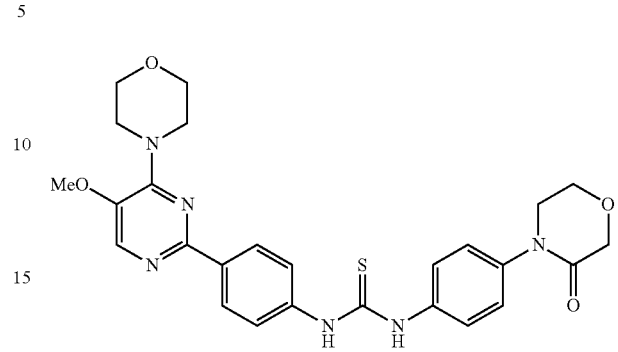

¹H NMR (500 MHz, DMSO-d₆): δ10.00-10.20 (m, 2H), 8.19-8.21 (d, 2H), 8.16 (s, 1H), 7.59-7.60 (d, 2H), 7.51 (s, 2H), 7.33-7.34 (d, 2H), 4.19 (s, 2H), 3.96-3.98 (m, 2H), 3.88 (s, 3H), 3.72-3.75 (m, 8H).

[4-(5-Methoxy-4-morpholin-4-yl-pyrimidin-2-yl)-phenyl]-urea

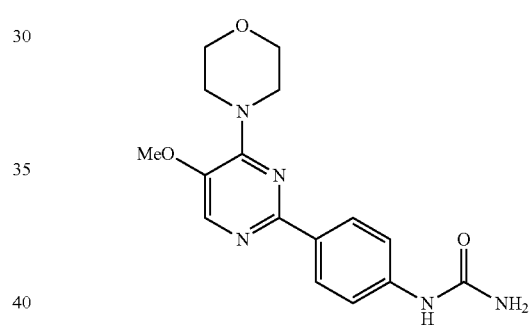

¹H NMR (500 MHz, DMSO-d₆): δ8.70 (s, 1H), 8.12 (s, 1H), 8.12-8.10 (d, 2H), 7.45 (d, 2H), 5.90 (s, 2H), 3.86 (s, 3H), 3.72-3.73 (m, 8H).

[1-[4-(5-Methoxy-4-morpholin-4-yl-pyrimidin-2-yl)-phenyl]-3-[4-(4-methyl-piperazin-1-yl)-phenyl]-urea

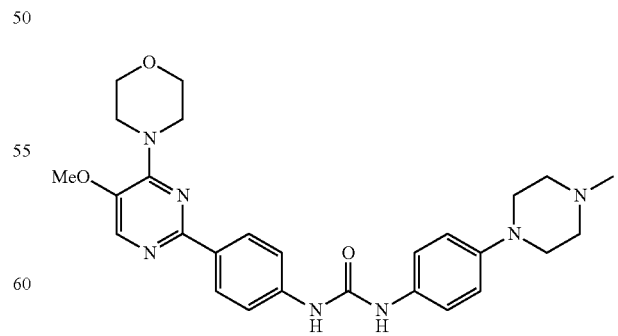

¹H NMR (500 MHz, DMSO-d₆): δ8.95 (s, 1H), 8.75 (s, 1H), 8.15-8.17 (d, 2H), 8.13 (s, 1H), 7.50-7.52 (d, 2H), 7.34-7.36 (d, 2H), 6.93-6.95 (d, 2H), 3.87 (s, 3H), 3.73-3.74 (m, 8H).

107

1-[4-(5-Methoxy-4-morpholin-4-yl-pyrimidin-2-yl)-phenyl]-3-[6-(4-methyl-piperazin-1-yl)-pyridin-3-yl]-urea

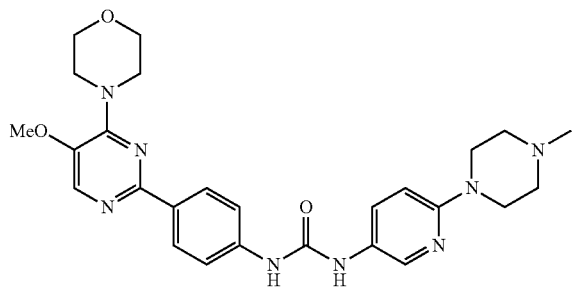

$^1$H NMR (500 MHz, DMSO-d$_6$): δ8.90 (s, 1H), 8.51 (s, 1H), 8.15-8.17 (d, 2H), 8.13 (s, 1H), 7.70-7.72 (m, 1H), 7.50-7.52 (d, 2H), 6.84-6.86 (d, 2H), 3.87 (s, 3H), 3.73-3.74 (m, 8H), 3.30-3.44 (m, 8H), 2.54 (s, 3H).

1-Isopropyl-3-[4-(5-methoxy-4-morpholin-4-yl-pyrimidin-2-yl)-phenyl]-urea

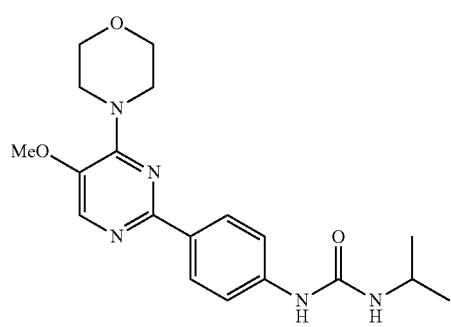

$^1$H NMR (500 MHz, DMSO-d$_6$): δ8.49 (s, 1H), 8.10-8.11 (m, 3H), 7.42-7.44 (d, 2H), 6.05 (s, 1H), 3.86 (s, 3H), 3.72-3.76 (m, 8H), 1.09-1.10 (m, 6H).

1-(4-Amino-phenyl)-3-[4-(5-methoxy-4-morpholin-4-yl-pyrimidin-2-yl)-phenyl]-urea

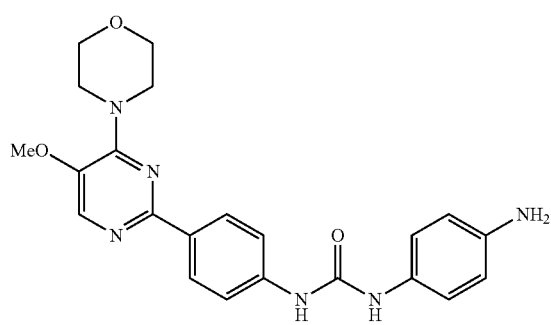 [SMILES: COc1cnc(-c2ccc(NC(=O)Nc3ccc(N)cc3)cc2)nc1N1CCOCC1]

$^1$H NMR (500 MHz, DMSO-d$_6$): δ8.89 (s, 1H), 8.40 (s, 1H), 8.13-8.15 (m, 3H), 7.49-7.51 (d, 2H), 7.08-7.09 (d, 2H), 6.50-6.51 (d, 2H), 4.77 (s, 2H), 3.86 (s, 3H), 3.73-3.74 (m, 8H).

108

4-{3-[4-(5-Methoxy-4-morpholin-4-yl-pyrimidin-2-yl)-phenyl]-ureido}-benzoic acid

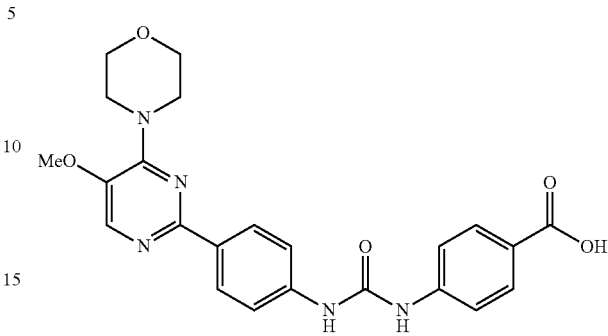

$^1$H NMR (500 MHz, DMSO-d$_6$): δ9.38 (s, 1H), 9.27 (s, 1H), 8.18-8.20 (d, 2H), 8.14 (s, 1H), 7.87-7.88 (d, 2H), 7.55-7.59 (m, 4H), 3.87 (s, 3H), 3.73-3.74 (m, 8H)

1-(6-Bromo-pyridin-3-yl)-3-[4-(5-methoxy-4-morpholin-4-yl-pyrimidin-2-yl)-phenyl]-urea

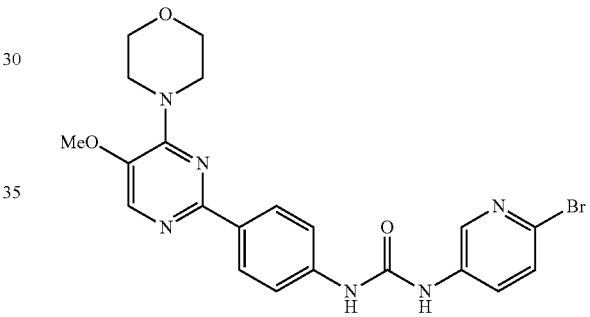

$^1$H NMR (500 MHz, DMSO-d$_6$): δ9.05-9.06 (d, 2H), 8.47 (s, 1H), 8.18-8.20 (d, 2H), 8.14 (s, 1H), 7.90-7.92 (d, 1H), 7.52-7.56 (m, 3H), 3.87 (s, 3H), 3.73-3.74 (m, 8H).

1-[4-(5-Methoxy-4-morpholin-4-yl-pyrimidin-2-yl)-phenyl]-3-(6-morpholin-4-yl-pyridin-3-yl)-urea

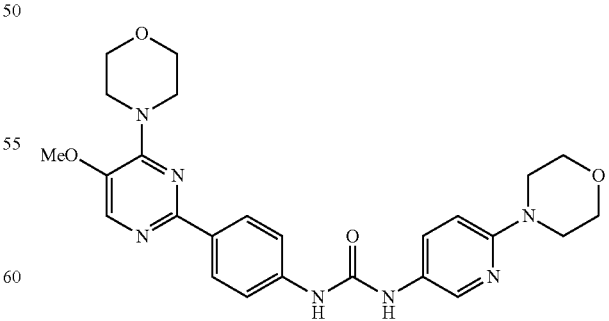

$^1$H NMR (500 MHz, DMSO-d$_6$): δ8.88 (s, 1H), 8.50 (s, 1H), 8.13-8.18 (m, 4H), 7.72-7.74 (m, 2H), 7.50-7.52 (d, 2H), 6.81-6.83 (d, 1H), 3.87 (s, 3H), 3.69-3.74 (m, 12H), 3.30-3.36 (m, 4H).

1-[4-(5-Methoxy-4-morpholin-4-yl-pyrimidin-2-yl)-phenyl]-3-[4-(morpholine-4-carbonyl)-phenyl]-urea

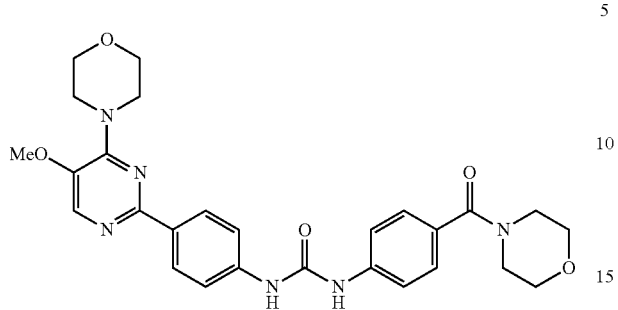

¹H NMR (500 MHz, DMSO-d₆): δ8.95-8.97 (d, 2H), 8.18-8.19 (d, 2H), 8.14 (s, 1H), 7.52-7.54 (m, 4H), 7.36-7.37 (d, 2H), 3.87 (s, 3H), 3.73-3.74 (m, 8H), 3.60 (s, 4H), 3.43-3.48 (m, 4H).

2-Fluoro-4-(5-methoxy-4-morpholin-4-yl-pyrimidin-2-yl)-phenylamine

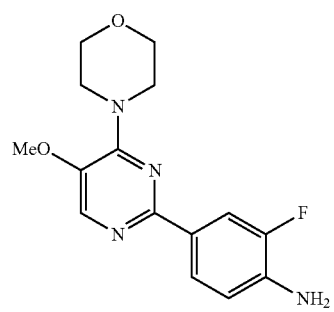

¹H NMR (500 MHz, DMSO-d₆): δ7.91-7.97 (m, 3H), 6.78-6.81 (m, 1H), 3.88 (s, 3H), 3.80-3.84 (m, 8H).

[2-Fluoro-4-(5-methoxy-4-morpholin-4-yl-pyrimidin-2-yl)-phenyl]-carbamic acid phenyl ester

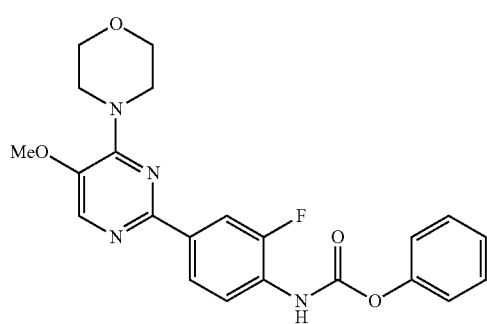 [SMILES: COc1cnc(-c2ccc(NC(=O)Oc3ccccc3)c(F)c2)nc1N1CCOCC1]

¹H NMR (500 MHz, CDCl₃-d₁): δ8.12 (s, 1H), 8.06-8.09 (m, 2H), 7.40-7.43 (m, 3H), 7.27-7.29 (m, 2H), 7.21-7.22 (m, 2H), 3.90 (s, 3H), 3.84 (s, 8H).

3-Fluoro-4-(5-methoxy-4-morpholin-4-yl-pyrimidin-2-yl)-phenylamine

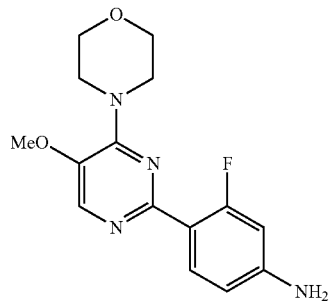

¹H NMR (500 MHz, DMSO-d₆): δ8.02 (s, 1H), 7.84-7.88 (m, 1H), 6.47-6.49 (m, 1H), 6.40-6.43 (m, 1H), 3.88-3.89 (m, 5H), 3.81-3.88 (m, 8H).

[3-Fluoro-4-(5-methoxy-4-morpholin-4-yl-pyrimidin-2-yl)-phenyl]-carbamic acid phenyl ester

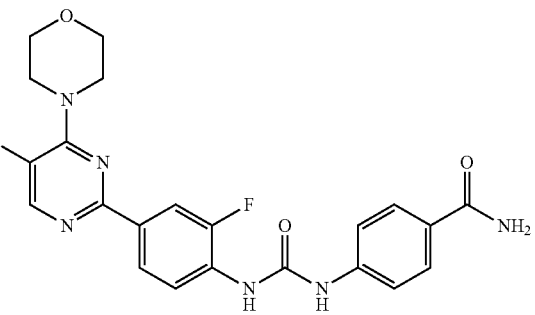

¹H NMR (500 MHz, CDCl₃-d₁): δ7.99-8.04 (m, 2H), 7.39-7.46 (m, 3H), 7.15-7.27 (m, 5H), 3.90 (s, 3H), 3.82 (s, 8H).

4-{3-[2-Fluoro-4-(5-methoxy-4-morpholin-4-yl-pyrimidin-2-yl)-phenyl]-ureido}-benzamide ¹H NMR (500 MHz, DMSO-d₆): δ9.56 (s, 1H), 8.99 (s, 1H), 8.22-8.25 (m, 1H), 8.15 (s, 1H), 7.99-8.05 (m, 2H), 7.82-7.84 (m, 3H), 7.52-7.54 (d, 2H), 7.20 (s, 1H), 3.88 (s, 3H), 3.72-3.75 (m, 8H).

1-[4-(5-Methoxy-4-morpholin-4-yl-pyrimidin-2-yl)-phenyl]-3-pyridin-2-yl-urea

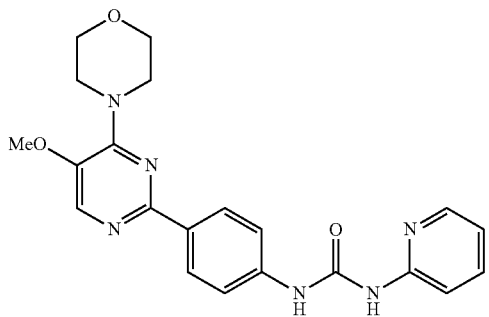 [SMILES: COc1cnc(-c2ccc(NC(=O)Nc3ccccn3)cc2)nc1N1CCOCC1]

¹H NMR (500 MHz, DMSO-d₆): δ10.65 (s, 1H), 9.52 (s, 1H), 8.29 (s, 1H), 8.20-8.21 (d, 2H), 8.14 (s, 1H), 7.74-7.76 (m, 1H), 7.59-7.61 (d, 2H), 7.53-7.54 (m, 1H), 7.01-7.03 (m, 1H), 3.87 (s, 3H), 3.73-3.74 (m, 8H).

1-[2-Fluoro-4-(5-methoxy-4-morpholin-4-yl-pyrimidin-2-yl)-phenyl]-3-[4-(3-oxo-morpholin-4-yl)-phenyl]-urea

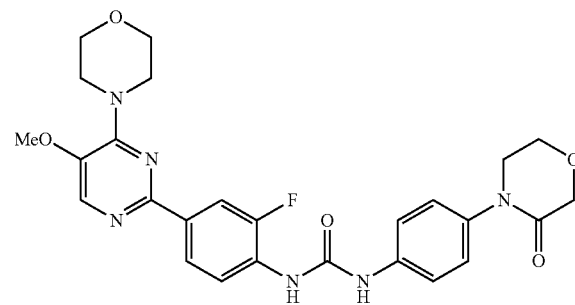 [SMILES: COc1cnc(-c2ccc(NC(=O)Nc3ccc(N4CCOCC4=O)cc3)c(F)c2)nc1N1CCOCC1]

¹H NMR (500 MHz, DMSO-d₆): δ9.50 (s, 1H), 9.01 (s, 1H), 8.21-8.25 (m, 1H), 8.15 (s, 1H), 7.98-8.05 (m, 2H), 7.49-7.51 (d, 2H), 7.29-7.31 (d, 2H), 4.18 (s, 2H), 3.95-3.97 (m, 2H), 3.88 (s, 3H), 3.69-3.76 (m, 10H).

1-[3-Fluoro-4-(5-methoxy-4-morpholin-4-yl-pyrimidin-2-yl)-phenyl]-3-[4-(3-oxo-morpholin-4-yl)-phenyl]-urea

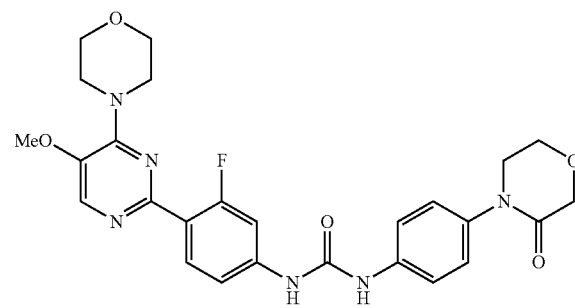 [SMILES: COc1cnc(-c2ccc(NC(=O)Nc3ccc(N4CCOCC4=O)cc3)cc2F)nc1N1CCOCC1]

¹H NMR (500 MHz, DMSO-d₆): δ9.31 (s, 1H), 9.10 (s, 1H), 8.14 (s, 1H), 7.89-7.92 (m, 1H), 7.47-7.54 (m, 3H), 7.26-7.28 (d, 2H), 7.18 (s, 1H), 4.16 (s, 2H), 3.93-3.95 (m, 2H), 3.86 (s, 3H), 3.68-3.70 (m, 10H)

4-{3-[3-Fluoro-4-(5-methoxy-4-morpholin-4-yl-pyrimidin-2-yl)-phenyl]-ureido}-benzamide

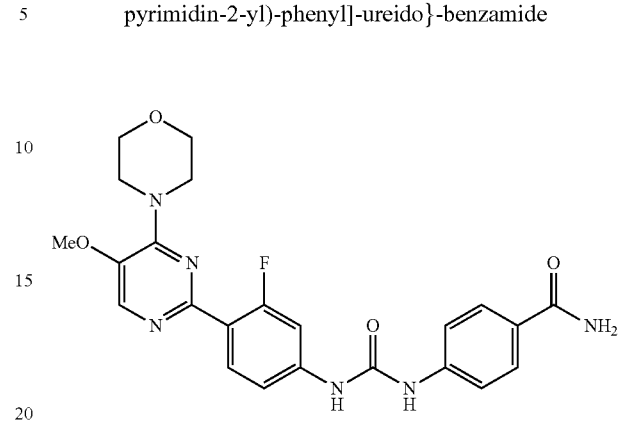

¹H NMR (500 MHz, DMSO-d₆): δ8.16 (s, 1H), 7.92 (s, 1H), 7.80-7.82 (m, 3H), 7.56-7.58 (m, 3H), 7.19-7.30 (m, 2H), 3.88 (s, 3H), 3.71-3.72 (m, 8H), 3.16 (s, 2H).

1-[4-(5-Methoxy-4-morpholin-4-yl-pyrimidin-2-yl)-phenyl]-3-pyridin-3-yl-thiourea

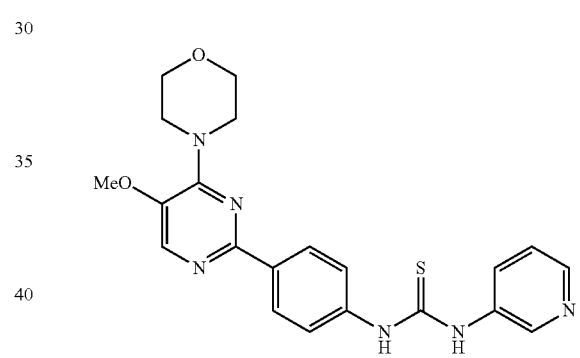

¹H NMR (500 MHz, DMSO-d₆): δ10.30-10.10 (m, 2H), 8.60 (s, 1H), 8.31-8.32 (d, 1H), 8.20-8.22 (m, 2H), 8.16 (s, 1H), 7.94 (s, 1H), 7.58-7.61 (m, 2H), 7.36-7.37 (d, 1H), 3.88 (s, 3H), 3.72-3.76 (m, 8H).

N-(3-{3-[4-(5-Methoxy-4-morpholin-4-yl-pyrimidin-2-yl)-phenyl]-ureido}-phenyl)-acetamide

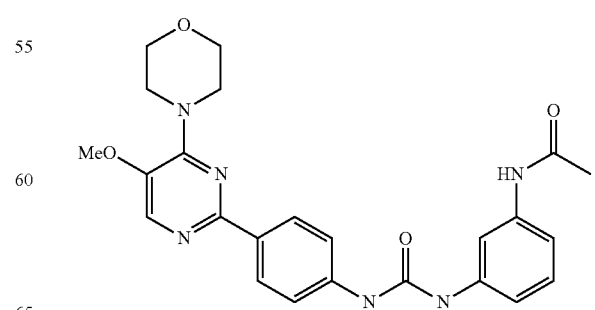

¹H NMR (500 MHz, DMSO-d₆): δ9.92 (s, 1H), 8.92 (s, 1H), 8.75-8.78 (d, 1H), 8.18-8.20 (m, 2H), 8.17 (s, 1H), 7.77 (s, 1H), 7.51-7.55 (m, 2H), 7.18-7.19 (m, 2H), 3.87 (s, 3H), 3.73-3.75 (m, 8H), 1.90 (s, 3H).

N-(3-Dimethylamino-propyl)-4-{3-[4-(5-methoxy-4-morpholin-4-yl-pyrimidin-2-yl)-phenyl]-ureido}-benzamide

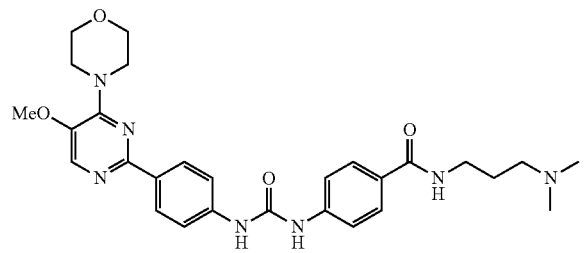 [SMILES: COc1cnc(-c2ccc(NC(=O)Nc3ccc(C(=O)NCCCN(C)C)cc3)cc2)nc1N1CCOCC1]

¹H NMR (500 MHz, DMSO-d₆): δ9.08-9.10 (d, 2H), 8.36 (s, 1H), 8.18-8.19 (d, 2H), 8.14 (s, 1H), 7.77-7.78 (d, 2H), 7.52-7.55 (m, 4H), 3.87 (s, 3H), 3.73-3.74 (m, 8H), 2.26-2.29 (s, 2H), 2.15 (s, 6H), 1.63-1.66 (s, 2H).

5-Methoxy-4-morpholin-4-yl-[2,5']bipyrimidinyl-2'-ylamine

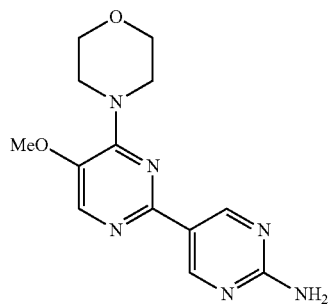

¹H NMR (500 MHz, CDCl₃-d₁): δ9.14 (s, 2H), 7.96 (s, 1H), 5.20 (s, 2H), 3.89 (s, 3H), 3.82 (s, 8H).

(5-Methoxy-4-morpholin-4-yl-[2,5']bipyrimidinyl-2'-yl)-carbamic acid phenyl ester

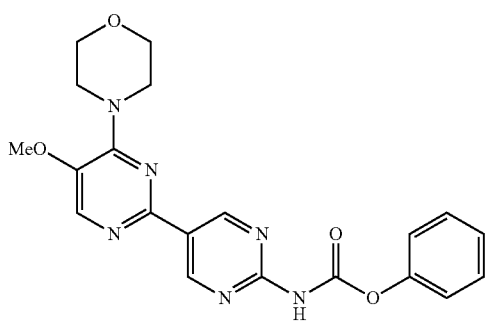 [SMILES: COc1cnc(-c2cnc(NC(=O)Oc3ccccc3)nc2)nc1N1CCOCC1]

¹H NMR (500 MHz, CDCl₃-d₁): δ9.47 (s, 2H), 8.51 (s, 1H), 7.99 (s, 1H), 7.39-7.42 (m, 2H), 7.26-7.29 (m, 3H), 3.91 (s, 3H), 3.80 (s, 8H).

4-{3-[3-Fluoro-4-(5-methoxy-4-morpholin-4-yl-pyrimidin-2-yl)-phenyl]-ureido}-benzamide

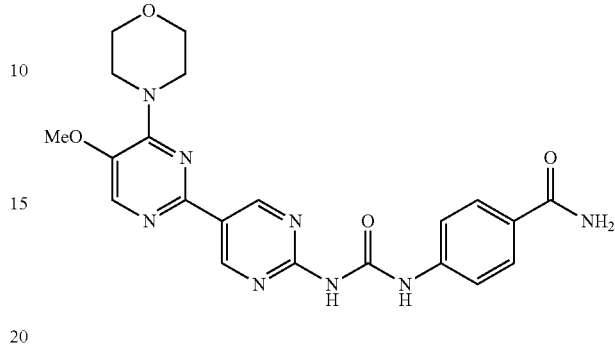

¹H NMR (500 MHz, DMSO-d₆): δ9.39 (s, 2H), 8.19 (s, 1H), 7.86-7.88 (m, 2H), 7.72-7.74 (m, 2H), 7.56-7.57 (m, 1H), 7.25 (s, 1H), 6.50-6.51 (d, 1H), 5.58 (s, 1H), 3.90 (s, 3H), 3.82 (s, 4H), 3.73 (s, 4H).

N-(4-{3-[4-(5-Methoxy-4-morpholin-4-yl-pyrimidin-2-yl)-phenyl]-ureido}-phenyl)-methanesulfonamide

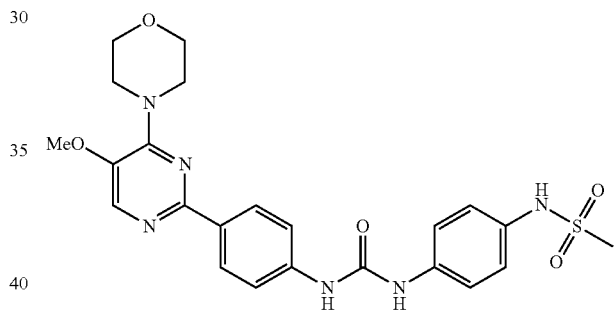

¹H NMR (500 MHz, DMSO-d₆): δ9.09 (s, 1H), 8.91 (s, 1H), 8.16-8.17 (d, 2H), 8.13 (s, 1H), 7.52-7.53 (d, 2H), 7.42-7.44 (d, 2H), 7.13-7.14 (d, 2H), 3.87 (s, 3H), 3.73-3.74 (m, 8H), 2.91 (s, 3H).

1-[4-(5-Methoxy-4-morpholin-4-yl-pyrimidin-2-yl)-phenyl]-3-(2-oxo-2,3-dihydro-benzooxazol-6-yl)-urea

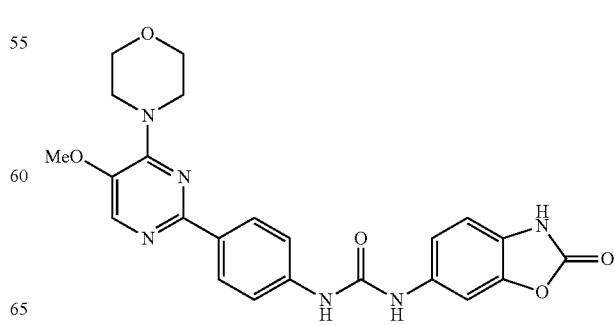

¹H NMR (500 MHz, DMSO-d₆): δ8.99 (s, 1H), 8.92 (s, 1H), 8.16-8.18 (d, 2H), 8.13 (s, 1H), 7.52-7.53 (d, 2H), 7.47 (s, 1H), 7.15-7.16 (d, 1H), 6.90-6.92 (d, 1H), 3.87 (s, 3H), 3.73-3.74 (m, 8H).

1-(5-Methoxy-4-morpholin-4-yl-[2,5']bipyrimidinyl-2'-yl)-3-[4-(3-oxo-morpholin-4-yl)-phenyl]-urea

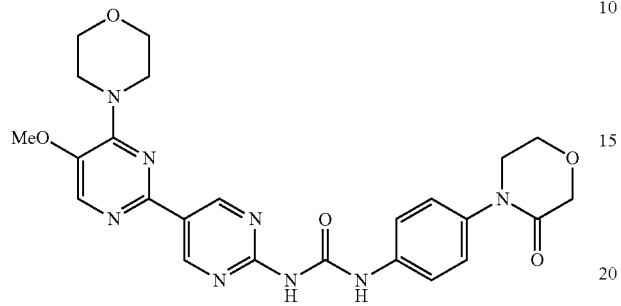

¹H NMR (500 MHz, DMSO-d₆): δ11.59 (s, 1H), 10.47 (s, 1H), 9.37 (s, 2H), 8.18 (s, 1H), 7.67-7.59 (d, 2H), 7.35-7.37 (d, 2H), 4.19 (s, 2H), 3.96-3.98 (m, 2H), 3.90 (s, 3H), 3.81-3.82 (m, 2H), 3.72 (s, 8H).

2-Chloro-4-morpholin-4-yl-pyrimidin-5-ol

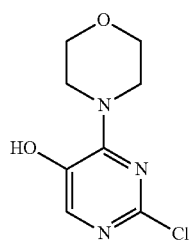 [SMILES: Oc1cnc(Cl)nc1N1CCOCC1]

A mixture of 4-(2-chloro-5-methoxy-pyrimidin-4-yl)-morpholine (5.0 g, 1.0 eq.) and CH₂Cl₂ (20 ml) was added dropwise to a slurry of aluminum chloride (23.22 g, 8.0 eq.) in CH₂Cl₂ (30 ml) in ice bath. After dropping, the resulting solution was stirred overnight at room temperature. The resultant mixture was extracted with EA and the combined organic layers were washed with brine and dried in vacuo to give a light yellow solid (4.18 g, 89.23%) as a product.

¹H NMR (500 MHz, DMSO-d₆): δ10.34 (s, 1H), 7.67 (s, 1H), 3.72-3.73 (m, 4H), 3.65-3.66 (m, 4H).

4-(2-Chloro-5-(2-Morpholin-4ethoxy)-pyrimidin-4-yl)-morpholine

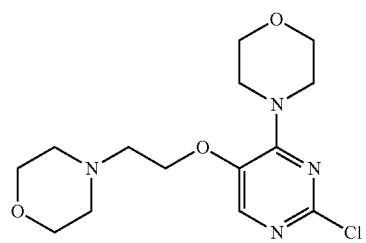 [SMILES: Clc1ncc(OCCN2CCOCC2)c(N2CCOCC2)n1]

A mixture of 2-chloro-4-morpholin-4-yl-pyrimidin-5-ol (0.1 g, 1.0 eq.), 4-(2-chloro-ethyl)-morpholine hydrochloric acid (0.12 g, 1.5 eq.) and K₂CO₃ (0.19 g, 3.0 eq.) in 1,4-dioxane (5 ml) was heated at 90° C. and refluxed overnight. The resultant mixture was extracted with EA and the combined organic layers were washed with brine and dried in vacuo to give a yellow solid (0.18 g, 68.02%) as a product.

¹H NMR (500 MHz, CDCl₃-d₁): δ7.73 (s, 1H), 4.07-4.09 (m, 2H), 3.86-3.88 (m, 4H), 3.76-3.78 (m, 4H), 3.69-3.71 (m, 4H), 2.75-2.77 (m, 2H), 2.50-2.53 (m, 4H).

4-(5-(2-morpholin-4-yl-ethoxy)-4-morpholin-4-yl-pyrimidin-2-yl)-phenylamine

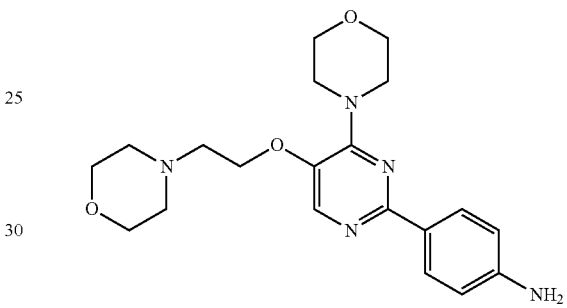

¹H NMR (500 MHz, CDCl₃-d₁): δ8.13-8.15 (d, 2H), 7.97 (s, 1H), 6.71-6.72 (d, 2H), 4.12-4.14 (m, 2H), 3.90-3.91 (m, 4H), 3.87-3.88 (m, 4H), 3.82-3.83 (m, 4H), 2.78-2.80 (m, 2H), 2.50-2.58 (m, 4H).

{4-[4-Morpholin-4-yl-5-(2-morpholin-4-yl-ethoxy)-pyrimidin-2-yl]-phenyl}-carbamic acid phenyl ester

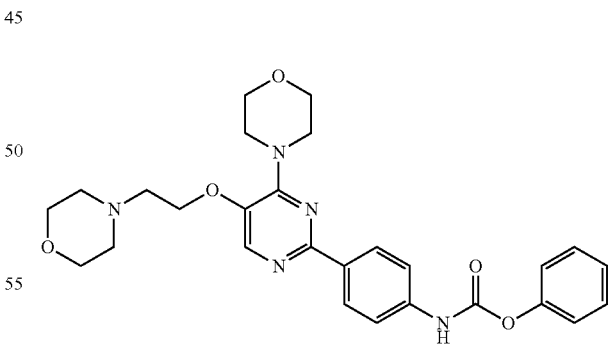

¹H NMR (500 MHz, CDCl₃-d₁): δ8.31-8.32 (d, 2H), 8.01 (s, 1H), 7.53-7.55 (d, 2H), 7.39-7.42 (m, 2H), 7.20-7.26 (m, 3H), 7.09 (s, 1H), 4.22-4.24 (m, 2H), 3.91-3.93 (m, 4H), 3.83-3.85 (m, 4H), 3.77-3.80 (m, 4H), 2.87-2.89 (m, 2H), 2.64-2.66 (m, 4H).

1-[4-(Morpholine-4-carbonyl)-phenyl]-3-{4-[4-morpholin-4-yl-5-(2-morpholin-4-yl-ethoxy)-pyrimidin-2-yl]-phenyl}-urea

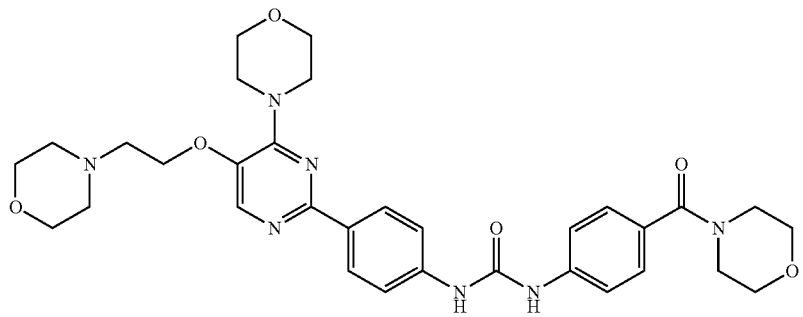 [SMILES: O=C(Nc1ccc(C(=O)N2CCOCC2)cc1)Nc1ccc(-c2ncc(OCCN3CCOCC3)c(N3CCOCC3)n2)cc1]

$^1$H NMR (500 MHz, DMSO-d$_6$): δ9.19-9.21 (d, 2H), 8.17-8.18 (d, 2H), 8.14 (s, 1H), 7.53-7.55 (d, 4H), 7.35-7.37 (d, 2H), 4.17-4.19 (m, 2H), 3.79-3.81 (d, 4H), 3.73 (s, 4H), 3.59 (s, 4H), 3.56 (s, 4H), 3.49 (s, 4H), 2.70-2.71 (d, 2H), 2.36 (s, 4H).

1-{4-[4-Morpholin-4-yl-5-(2-morpholin-4-yl-ethoxy)-pyrimidin-2-yl]-phenyl}-3-[4-(3-oxo-morpholin-4-yl)-phenyl]-urea

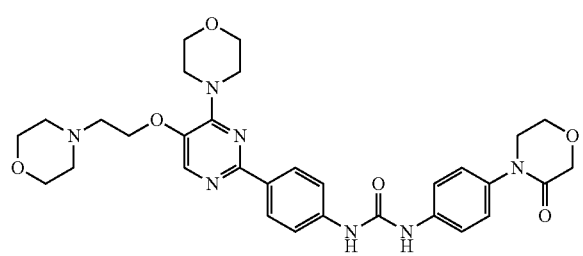 [SMILES: O=C(Nc1ccc(-c2ncc(OCCN3CCOCC3)c(N3CCOCC3)n2)cc1)Nc1ccc(N2CCOCC2=O)cc1]

$^1$H NMR (500 MHz, DMSO-d$_6$): δ9.20 (s, 1H), 9.19 (s, 1H), 8.14-8.18 (m, 3H), 7.53-7.54 (d, 2H), 7.48-7.50 (d, 2H), 7.27-7.29 (d, 2H), 4.18 (s, 4H), 3.95-3.97 (m, 2H), 3.79-3.80 (s, 4H), 3.73 (s, 4H), 3.68-3.70 (m, 2H), 3.55-3.56 (m, 4H), 2.69-2.71 (m, 2H), 2.45 (s, 4H).

4-(3-{4-[4-Morpholin-4-yl-5-(2-morpholin-4-yl-ethoxy)-pyrimidin-2-yl]-phenyl}-ureido)-benzamide

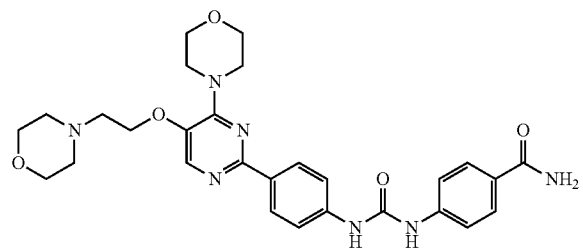 [SMILES: NC(=O)c1ccc(NC(=O)Nc2ccc(-c3ncc(OCCN4CCOCC4)c(N4CCOCC4)n3)cc2)cc1]

$^1$H NMR (500 MHz, DMSO-d$_6$): δ9.30-9.50 (m, 2H), 8.14-8.18 (m, 3H), 7.80-7.82 (m, 3H), 7.53-7.56 (m, 4H), 7.18 (s, 1H), 4.17-4.19 (m, 2H), 3.79-3.80 (m, 4H), 3.73-3.74 (m, 4H), 3.55-3.56 (m, 4H), 2.69-2.71 (m, 2H), 2.36 (s, 4H).

1-{4-[4-Morpholin-4-yl-5-(2-morpholin-4-yl-ethoxy)-pyrimidin-2-yl]-phenyl}-3-pyridin-4-yl-urea

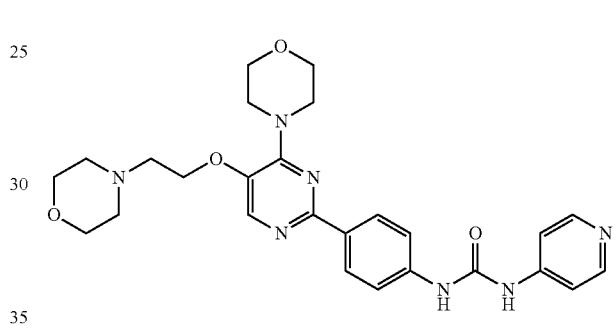

$^1$H NMR (500 MHz, DMSO-d$_6$): δ9.68 (s, 1H), 9.45 (s, 1H), 8.34-8.35 (d, 2H), 8.17-8.19 (d, 2H), 8.15 (s, 1H), 7.54-7.56 (d, 2H), 7.45-7.48 (d, 2H), 4.18 (s, 2H), 3.79-3.80 (m, 4H), 3.73-3.74 (m, 4H), 3.55-3.57 (m, 4H), 2.63-2.64 (m, 2H), 2.50-2.57 (m, 4H).

1-(4-Methanesulfonyl-phenyl)-3-[4-(5-methoxy-4-morpholin-4-yl-pyrimidin-2-yl)-phenyl]-urea

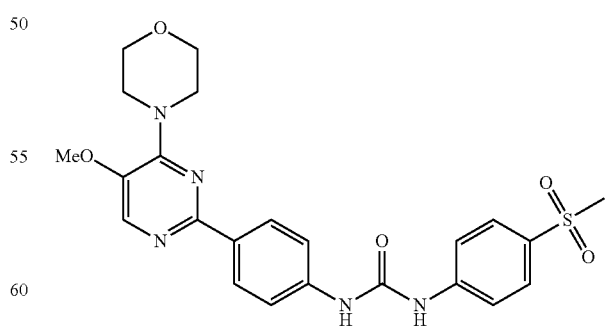

$^1$H NMR (500 MHz, DMSO-d$_6$): δ9.72 (s, 1H), 9.45 (s, 1H), 8.18-8.20 (d, 2H), 8.14 (s, 1H), 7.81-7.82 (d, 2H), 7.71-7.73 (d, 2H), 7.56-7.58 (d, 2H), 3.87 (s, 3H), 3.73-3.74 (m, 8H), 3.15 (s, 3H).

1-[4-(5-Methoxy-4-morpholin-4-yl-pyrimidin-2-yl)-phenyl]-3-[4-(morpholine-4-sulfonyl)-phenyl]-urea

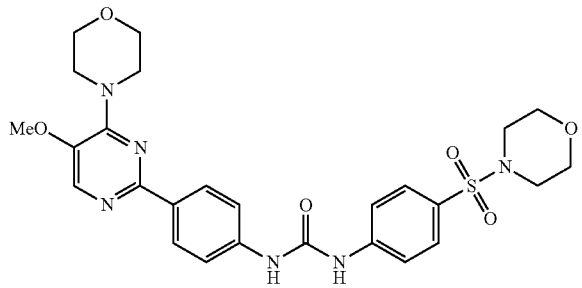

¹H NMR (500 MHz, DMSO-d₆): δ9.52 (s, 1H), 9.23 (s, 1H), 8.19-8.20 (d, 2H), 8.14 (s, 1H), 7.72-7.74 (d, 2H), 7.64-7.66 (d, 2H), 7.55-7.57 (d, 2H), 3.87 (s, 3H), 3.73-3.74 (m, 8H), 3.62-3.64 (m, 4H), 2.84 (m, 4H).

Pyridin-4-yl-carbamic acid phenyl ester

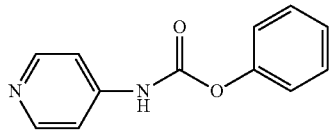 [SMILES: O=C(Nc1ccncc1)Oc1ccccc1]

¹H NMR (500 MHz, CDCl₃-d₁): δ8.50-8.51 (m, 2H), 7.88 (s, 1H), 7.39-7.45 (m, 4H), 7.27-7.28 (m, 1H), 7.17-7.22 (m, 2H).

1-[4-(5-Methoxy-4-morpholin-4-yl-pyrimidin-2-yl)-phenyl]-3-pyridin-4-yl-urea

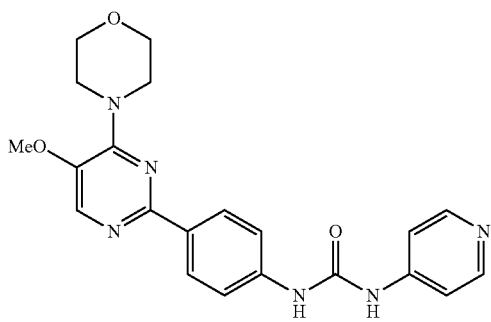

¹H NMR (500 MHz, DMSO-d₆): δ9.32 (s, 1H), 9.22 (s, 1H), 8.35-8.36 (d, 2H), 8.18-8.20 (d, 2H), 8.14 (s, 1H), 7.54-7.55 (d, 2H), 7.44-7.45 (d, 2H), 3.87 (s, 3H), 3.70-3.74 (m, 8H).

1-[4-(4-Methanesulfonyl-piperazin-1-yl)-phenyl]-3-[4-(5-methoxy-4-morpholin-4-yl-pyrimidin-2-yl)-phenyl]-urea

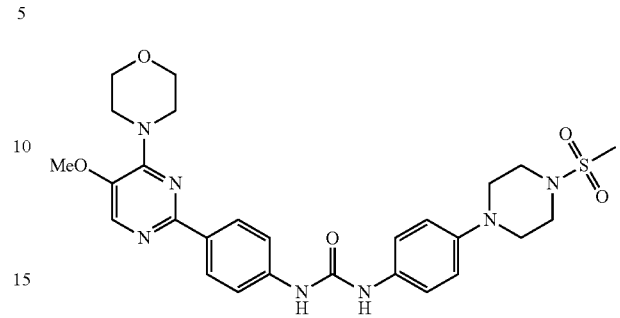

¹H NMR (500 MHz, DMSO-d₆): δ8.85 (s, 1H), 8.57 (s, 1H), 8.13-8.17 (m, 3H), 7.50-7.52 (d, 2H), 7.33-7.34 (d, 2H), 6.92-6.94 (d, 2H), 3.87 (s, 3H), 3.72-3.73 (m, 8H), 3.22-3.24 (m, 4H), 3.15-3.16 (m, 4H), 2.92 (s, 3H).

N-(5-{3-[4-(5-Methoxy-4-morpholin-4-yl-pyrimidin-2-yl)-phenyl]-ureido}-pyridin-2-yl)-acetamide

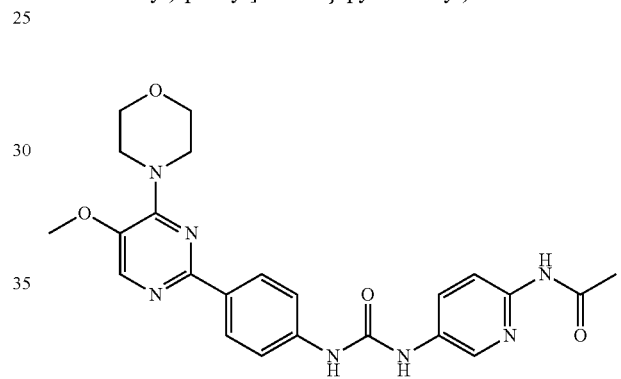

¹H NMR (500 MHz, DMSO-d₆): δ10.37 (s, 1H), 9.01 (s, 1H), 8.82 (s, 1H), 8.42 (d, 1H), 8.14-8.18 (d, 3H), 8.00-8.05 (m, 1H), 7.82-7.83 (m, 1H), 7.52-7.54 (d, 2H), 3.87 (s, 3H), 3.73-3.74 (m, 8H), 2.06 (s, 3H).

5-Ethoxy-pyrimidine-2,4-diol

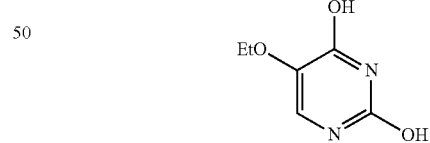

A mixture of ethyl ethoxylacetate (20 g, 1.0 eq) and ethyl formate (11.21 ml, 1.0 eq) was added dropwise to a slurry of sodium ethoxide (10.3 g, 1.0 eq) in toluene (100 ml) in ice both. After dropping at room temperature and stirring overnight, the resulting solution was dried in vacuo. Then a mixture of residue, urea (9.09 g, 1.0 eq) and sodium ethoxide (10.3 g, 1.0 eq) in EtOH (100 ml) was refluxed at 110° C. for 6 hrs. After the solvent was dried in vacuo, water and conc. HCl solution (5<pH<4) were added. After formation of white precipitates, the mixture was filtered and dried solid in vacuo. A product was obtained as a white solid (7.76 g, 32%)

¹H NMR (500 MHz, DMSO-d₆): δ1.20-1.23 (m, 3H), 3.75-3.80 (m, 2H), 5.50 (s, 2H), 7.05 (s, 1H)

2,4-Dichloro-5-ethoxy-pyrimidine

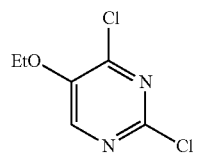 [SMILES: CCOc1cnc(Cl)nc1Cl]

In ice bath, dimethyl-phenyl-amine (5.21 ml, 1.0 eq) was added dropwise to slurry of 5-ethoxy-pyrimidine-2,4-diol (6.45 g, 1.0 eq) in POCl₃ (20 ml, 5.0 eq) and refluxed overnight. Excess POCl₃ was evaporated in vacuo and the residue was poured into ice-water. After formation of precipitates, the mixture was filtered and dried solid in vacuo. A product was obtained as a white solid (2.84 g, 35.57%)

¹H NMR (500 MHz, CDCl₃-d₁): δ1.47-1.50 (m, 3H), 4.16-4.20 (m, 2H), 8.13 (s, 1H)

4-(2-Chloro-5-ethoxy-pyrimidin-4-yl)-morpholine

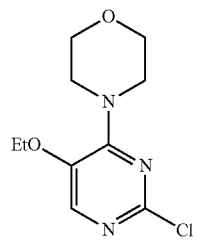 [SMILES: CCOc1cnc(Cl)nc1N1CCOCC1]

2,4-dichloro-5-ethoxy-pyrimidin (2.83 g, 1.0 eq) was stirred in toluene (20 ml) and a solution of morpholine (1.93 ml, 1.5 eq) in toluene (20 ml) was added dropwise at −10~0° C. After stirring the resulting solution overnight at r.t., NH₄Cl(aq) was added to the solution and the solution was extracted with EA. The combined organic layers were washed with brine, dried and evaporated in vacuo. A product was obtained as a white solid (2.7 g, 73.5%).

¹H NMR (500 MHz, CDCl₃-d₁): δ1.41-1.44 (m, 3H), 3.75-3.77 (m, 4H), 3.83-3.85 (m, 4H), 4.01-4.05 (m, 2H), 7.69 (s, 1H)

4-(5-Ethoxy-4-morpholin-4-yl-pyrimidin-2-yl)-phenylamine

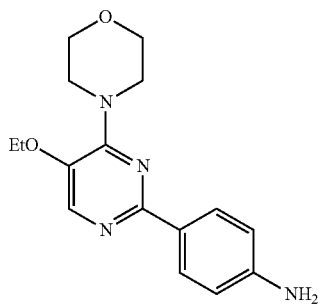 [SMILES: CCOc1cnc(-c2ccc(N)cc2)nc1N1CCOCC1]

¹H NMR (500 MHz, CDCl₃-d₁): δ1.41-1.44 (m, 3H), 3.83 (m, 8H), 4.05-4.09 (m, 2H), 6.70-6.72 (m, 2H), 7.97 (s, 1H), 8.11-8.12 (m, 2H)

[4-(5-Ethoxy-4-morpholin-4-yl-pyrimidin-2-yl)-phenyl]-carbamic acid phenyl ester

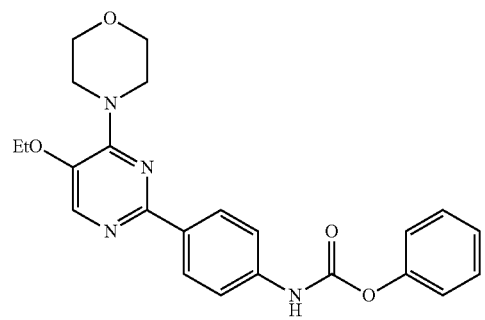 [SMILES: CCOc1cnc(-c2ccc(NC(=O)Oc3ccccc3)cc2)nc1N1CCOCC1]

¹H NMR (500 MHz, DMSO-d₆): δ1.34-1.37 (m, 3H), 3.72-3.78 (m, 8H), 4.09-4.13 (m, 2H), 7.24-7.29 (m, 3H), 7.42-7.46 (m, 2H), 7.58-7.60 (m, 2H), 8.12 (s, 1H), 8.21-8.23 (m, 2H), 10.40 (s, 1H)

4-{3-[4-(5-Ethoxy-4-morpholin-4-yl-pyrimidin-2-yl)-phenyl]-ureido}-benzamide

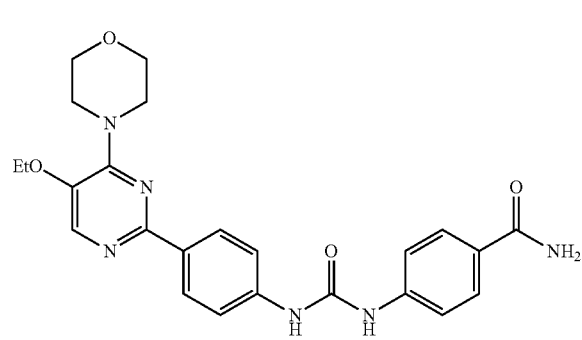 [SMILES: CCOc1cnc(-c2ccc(NC(=O)Nc3ccc(C(N)=O)cc3)cc2)nc1N1CCOCC1]

¹H NMR (500 MHz, DMSO-d₆): δ1.34-1.37 (m, 3H), 3.73-3.78 (m, 8H), 4.10-4.14 (m, 2H), 7.18 (m, 1H), 7.51-7.55 (m, 4H), 7.81-7.83 (m, 3H), 8.12 (s, 1H), 8.18-8.20 (m, 2H), 8.94 (s, 1H), 8.97 (s, 1H)

1-[4-(5-Ethoxy-4-morpholin-4-yl-pyrimidin-2-yl)-phenyl]-3-(4-thiomorpholin-4-yl-phenyl-urea

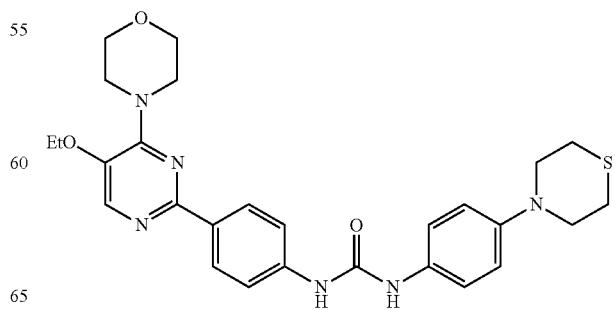

¹H NMR (500 MHz, DMSO-d₆): δ1.34-1.37 (m, 3H), 2.65-2.67 (m, 4H), 3.36-3.37 (m, 4H), 3.71-3.76 (m, 8H), 4.08-4.12 (m, 2H), 6.85-6.87 (m, 2H), 7.30-7.31 (m, 2H), 7.49-7.51 (m, 2H), 8.10-8.14 (m, 3H), 8.57 (s, 1H), 8.85 (s, 1H)

1-[4-(5-Ethoxy-4-morpholin-4-yl-pyrimidin-2-yl)-phenyl]-3-[4-(3-oxo-morpholin-4-yl)-phenyl]-urea

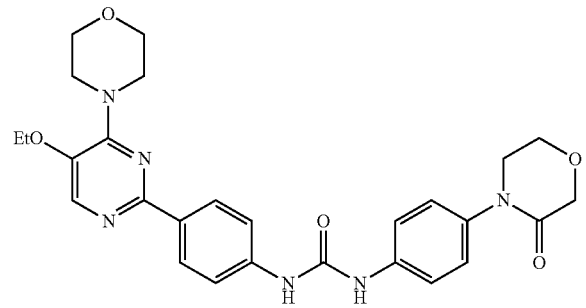 [SMILES: CCOc1cnc(-c2ccc(NC(=O)Nc3ccc(N4CCOCC4=O)cc3)cc2)nc1N1CCOCC1]

¹H NMR (500 MHz, DMSO-d₆): δ1.34-1.37 (m, 3H), 3.68-3.70 (m, 2H), 3.72-3.73 (m, 4H), 3.76-3.78 (m, 4H), 3.95-3.96 (m, 2H), 3.97-4.14 (m, 2H), 4.19 (s, 2H), 7.28-7.30 (m, 2H), 7.47-7.53 (m, 4H), 8.12 (s, 1H), 8.17-8.19 (m, 2H), 8.79 (s, 1H), 8.87 (s, 1H)

4-{3-[4-(5-Ethoxy-4-morpholin-4-yl-pyrimidin-2-yl)-phenyl]-ureido}-benzenesulfonamide

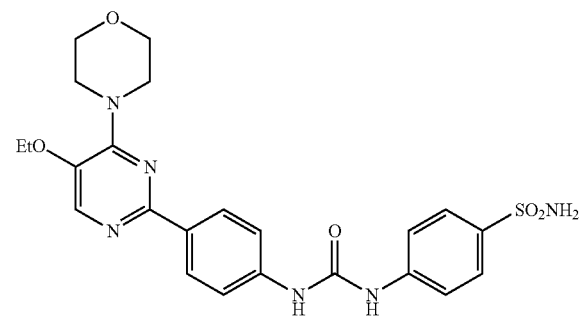 [SMILES: CCOc1cnc(-c2ccc(NC(=O)Nc3ccc(S(N)(=O)=O)cc3)cc2)nc1N1CCOCC1]

¹H NMR (500 MHz, DMSO-d₆): δ1.34-1.37 (m, 3H), 3.73-3.78 (m, 8H), 4.10-4.14 (m, 2H), 7.18 (m, 2H), 7.49-7.50 (m, 4H), 7.57-7.59 (m, 2H), 8.08 (s, 1H), 8.14-8.16 (m, 2H), 8.93 (s, 1H), 9.06 (s, 1H)

N-(4-{3-[4-(5-Ethoxy-4-morpholin-4-yl-pyrimidin-2-yl)-phenyl]-ureido}-phenyl)-acetamide

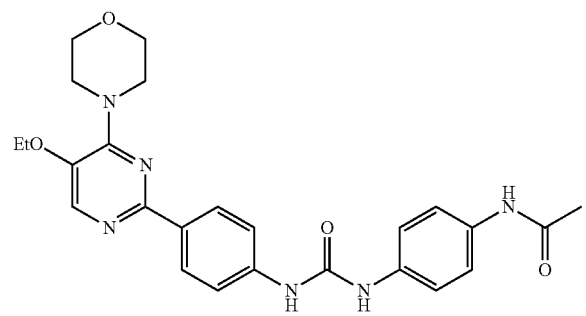

¹H NMR (500 MHz, DMSO-d₆): δ1.34-1.37 (m, 3H), 2.01 (s, 3H), 3.72-3.77 (m, 8H), 4.09-4.14 (m, 2H), 7.36-7.38 (m, 2H), 7.47-7.52 (m, 4H), 8.12 (s, 1H), 8.16-8.18 (m, 2H), 8.64 (s, 1H), 8.83 (s, 1H), 9.82 (s, 1H)

N-(4-{3-[4-(5-Ethoxy-4-morpholin-4-yl-pyrimidin-2-yl)-phenyl]-ureido}-phenyl)-methanesulfonamide

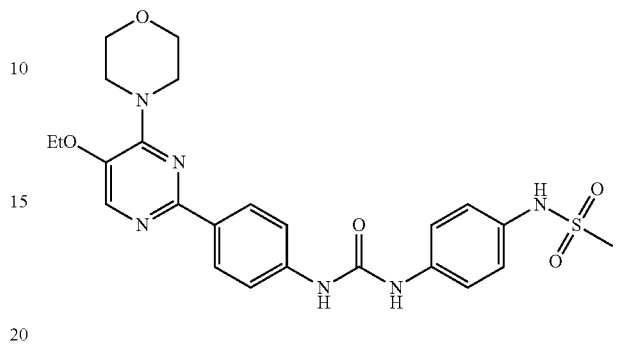

¹H NMR (500 MHz, DMSO-d₆): δ1.34-1.37 (m, 3H), 2.92 (s, 3H), 3.72-3.77 (m, 8H), 4.09-4.14 (m, 2H), 7.36-7.38 (m, 2H), 7.14-7.16 (m, 2H), 7.41-7.43 (m, 2H), 7.50-7.52 (m, 2H), 8.12 (s, 1H), 8.16-8.18 (m, 2H), 8.70 (s, 1H), 8.82 (s, 1H), 9.45 (s, 1H)

1-[4-(5-Ethoxy-4-morpholin-4-yl-pyrimidin-2-yl)-phenyl]-3-(2-oxo-2,3-dihydro-benzooxazol-5-yl)-urea

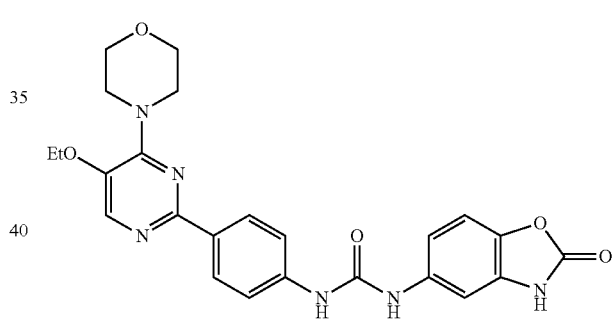

¹H NMR (500 MHz, DMSO-d₆): δ1.34-1.37 (m, 3H), 3.72-3.77 (m, 8H), 4.09-4.14 (m, 2H), 6.92 (m, 1H), 7.16-7.17 (m, 1H), 7.49-7.53 (m, 2H), 8.12 (s, 1H), 8.17-8.18 (m, 2H), 8.83 (s, 1H), 8.89 (s, 1H)

1-[4-(5-Ethoxy-4-morpholin-4-yl-pyrimidin-2-yl)-phenyl]-3-[4-(4-methanesulfonyl-piperazin-1-yl)-phenyl]-urea

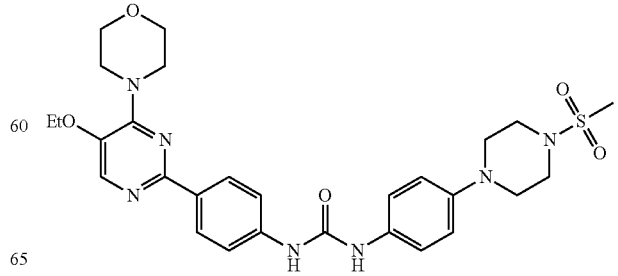

¹H NMR (500 MHz, DMSO-d₆): δ1.34-1.37 (m, 3H), 2.92 (s, 1H), 3.15-3.16 (m, 4H_, 3.23-3.24 (m, 4H), 3.72-3.73 (m, 4H), 3.76-3.77 (m, 4H), 4.09-4.13 (m, 4H), 6.92-6.94 (m, 2H), 7.33-7.35 (m, 2H), 7.50-7.52 (m, 2H), 8.11 (s, 1H), 8.15-8.17 (m, 2H), 8.57 (s, 1H), 8.84 (s, 1H)

1-[4-(5-Ethoxy-4-morpholin-4-yl-pyrimidin-2-yl)-phenyl]-3-[4-(morpholine-4-carbon yl)-phenyl]-urea

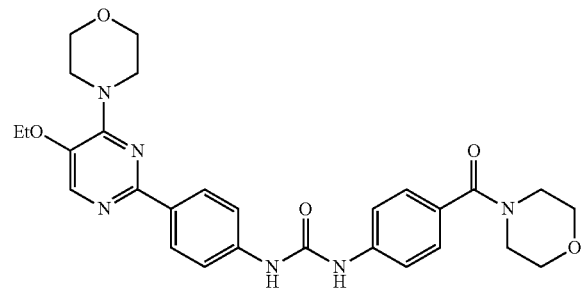 [SMILES: CCOc1cnc(-c2ccc(NC(=O)Nc3ccc(C(=O)N4CCOCC4)cc3)cc2)nc1N1CCOCC1]

¹H NMR (500 MHz, DMSO-d₆): δ1.34-1.37 (m, 3H), 3.42-3.43 (m, 4H), 3.49 (m, 4H), 3.72-3.73 (m, 4H), 3.76-3.77 (m, 4H), 4.09-4.13 (m, 2H), 7.35-7.37 (m, 2H), 7.51-7.54 (m, 4H), 8.12 (s, 1H), 8.17-8.19 (m, 2H), 8.92-8.96 (m, 2H)

1-[4-(5-Ethoxy-4-morpholin-4-yl-pyrimidin-2-yl)-phenyl]-3-(2-oxo-2,3-dihydro-benzooxazol-6-yl)-urea

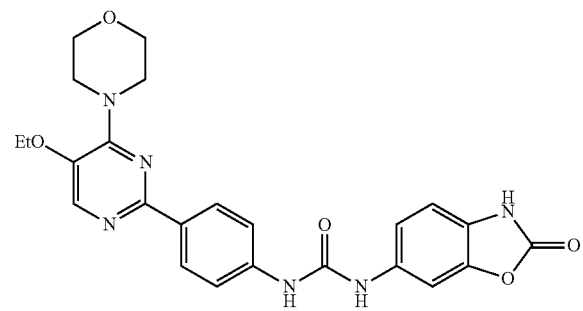 [SMILES: CCOc1cnc(-c2ccc(NC(=O)Nc3ccc4[nH]c(=O)oc4c3)cc2)nc1N1CCOCC1]

¹H NMR (500 MHz, DMSO-d₆): δ1.34-1.37 (m, 3H), 3.73-3.74 (m, 4H), 3.76-3.77 (m, 4H), 4.10-4.14 (m, 2H), 6.99-7.01 (m, 1H), 7.06-7.08 (m, 1H), 7.51-7.53 (m, 2H), 7.58 (m, 1H), 8.12 (s, 1H), 8.16-8.18 (m, 2H), 8.73 (s, 1H), 8.73 (s, 1H), 11.46 (s, 1H)

1-[4-(5-Ethoxy-4-morpholin-4-yl-pyrimidin-2-yl)-phenyl]-3-(4-methanesulfonyl-phenyl)-urea

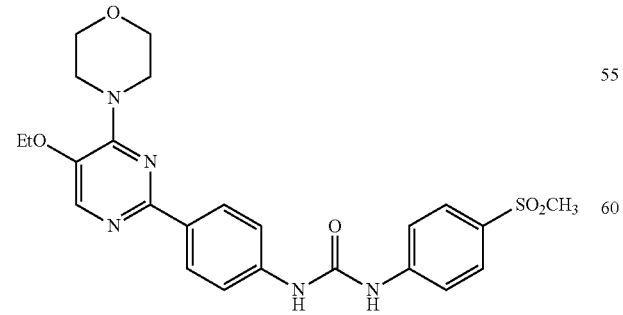

¹H NMR (500 MHz, DMSO-d₆): δ1.34-1.37 (m, 3H), 3.16 (s, 3H), 3.73-3.74 (m, 4H), 3.77-3.78 (m, 4H), 4.10-4.14 (m, 2H), 7.54-7.56 (m, 2H), 7.69-7.71 (m, 2H), 7.82-7.84 (m, 2H), 8.12 (s, 1H), 8.19-8.20 (m, 2H), 9.03 (s, 1H), 9.25 (s, 1H)

5-(5-Ethoxy-4-morpholin-4-yl-pyrimidin-2-yl)-1,3-dihydro-benzoimidazol-2-one

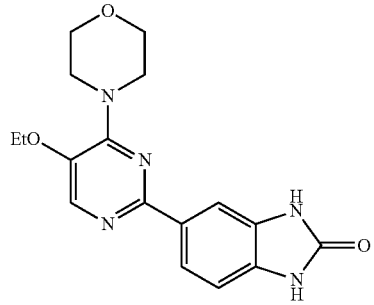 [SMILES: CCOc1cnc(-c2ccc3[nH]c(=O)[nH]c3c2)nc1N1CCOCC1]

¹H NMR (500 MHz, DMSO-d₆): δ1.34-1.37 (m, 3H), 3.16 (s, 3H), 3.73-3.74 (m, 4H), 3.77-3.78 (m, 4H), 4.10-4.14 (m, 2H), 6.95-6.97 (m, 1H), 7.83 (m, 1H), 7.93-7.94 (m, 1H), 8.11 (s, 1H)

N-(5-{3-[4-(5-Ethoxy-4-morpholin-4-yl-pyrimidin-2-yl)-phenyl]-ureido}-pyridin-2-yl)-acetamide

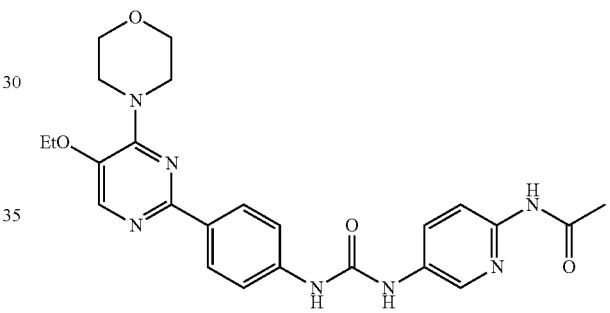

¹H NMR (500 MHz, DMSO-d₆): δ1.34-1.37 (m, 3H), 2.09 (s, 3H), 3.73-3.74 (m, 4H), 3.77-3.78 (m, 4H), 4.10-4.14 (m, 2H), 7.52-7.54 (m, 2H), 7.81-7.83 (m, 1H), 8.00-8.02 (m, 1H), 8.12 (s, 1H), 8.17-8.18 (m, 2H), 8.42-8.43 (m, 1H), 8.75 (s, 1H), 8.94 (s, 1H), 10.38 (s, 1H)

N-[3-(5-Ethoxy-4-morpholin-4-yl-pyrimidin-2-yl)-phenyl]-methanesulfonamide

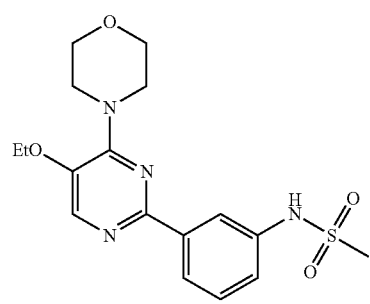 [SMILES: CCOc1cnc(-c2cccc(NS(C)(=O)=O)c2)nc1N1CCOCC1]

¹H NMR (500 MHz, DMSO-d₆): δ1.35-1.37 (m, 3H), 2.99 (s, 3H), 3.73-3.74 (m, 4H), 3.77-3.78 (m, 4H), 4.13-4.14 (m, 2H), 7.26-7.28 (m, 1H), 7.38-7.41 (m, 1H), 7.97-7.99 (m, 1H), 8.16-8.18 (m, 2H), 9.83 (s, 1H)

N-[3-(5-Ethoxy-4-morpholin-4-yl-pyrimidin-2-yl)-phenyl]-2,4-difluoro-benzenesulfonamide

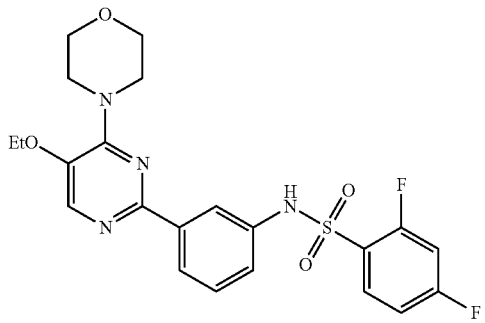 [SMILES: CCOc1cnc(-c2cccc(NS(=O)(=O)c3ccc(F)cc3F)c2)nc1N1CCOCC1]

¹H NMR (500 MHz, DMSO-d₆): δ1.33-1.37 (m, 3H), 3.71-3.75 (m, 8H), 4.09-4.13 (m, 2H), 7.14-7.15 (m, 1H), 7.22-7.26 (m, 1H), 7.29-7.32 (m, 1H), 7.49-7.53 (m, 1H), 7.88-7.92 (m, 2H), 8.04 (s, 1H), 8.12 (s, 1H), 10.74 (s, 1H)

1-[4-(5-Ethoxy-4-morpholin-4-yl-pyrimidin-2-yl)-phenyl]-3-pyridin-4-yl-urea

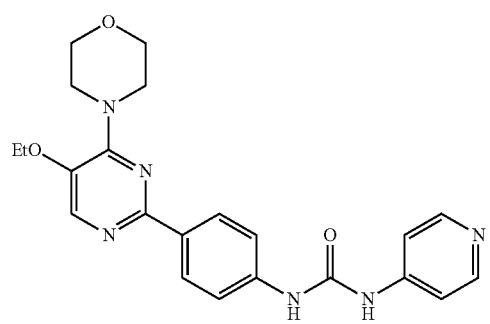 [SMILES: CCOc1cnc(-c2ccc(NC(=O)Nc3ccncc3)cc2)nc1N1CCOCC1]

¹H NMR (500 MHz, DMSO-d₆): δ1.33-1.37 (m, 3H), 3.71-3.72 (m, 4H), 3.76-3.77 (m, 4H), 4.08-4.12 (m, 2H), 7.44-7.45 (m, 2H), 7.52-7.54 (m, 2H), 8.11 (s, 1H), 8.18-8.19 (m, 2H), 8.35 (m, 1H), 9.04 (s, 1H), 9.15 (s, 1H)

1-[4-(5-Ethoxy-4-morpholin-4-yl-pyrimidin-2-yl)-phenyl]-3-pyridin-4-yl-urea hydrochloride

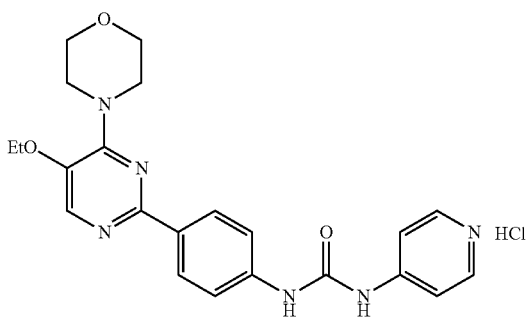 [SMILES: CCOc1cnc(-c2ccc(NC(=O)Nc3ccncc3)cc2)nc1N1CCOCC1 ; Cl]

¹H NMR (500 MHz, DMSO-d₆): δ1.33-1.37 (m, 3H), 3.71-3.72 (m, 4H), 3.76-3.77 (m, 4H), 4.08-4.12 (m, 2H), 7.44-7.45 (m, 2H), 7.52-7.54 (m, 2H), 8.11 (s, 1H), 8.18-8.19 (m, 2H), 8.35 (m, 1H), 9.04 (s, 1H), 9.15 (s, 1H)

1-[4-(5-Ethoxy-4-morpholin-4-yl-pyrimidin-2-yl)-phenyl]-3-[4-(morpholine-4-sulfon yl)-phenyl]-urea

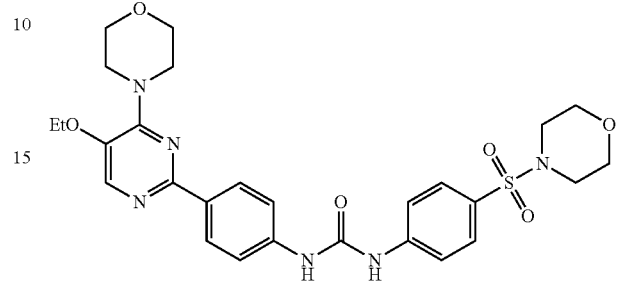

¹H NMR (500 MHz, DMSO-d₆): δ1.33-1.37 (m, 3H), 2.84 (m, 4H), 3.63 (m, 4H), 3.73-3.74 (m, 4H), 3.77-3.78 (m, 4H), 4.10-4.14 (m, 2H), 7.54 (m, 2H), 7.64-7.66 (m, 2H), 7.71-7.73 (m, 2H), 8.13 (s, 1H), 8.19-8.20 (m, 2H), 9.05 (s, 1H), 9.29 (s, 1H)

Example 4

Preparation of Compounds of Formula (I) in Scheme 2

2,4,6-Trichloro-5-methylsulfanyl-pyrimidine

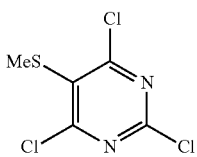 [SMILES: CSc1c(Cl)nc(Cl)nc1Cl]

Barbituric acid (5.2 g, 40.6 mmol.), 3.5 ml of DMSO, 20 ml of acetic acid, and 6.0 ml of aceticanhydride were heated progressively to 90-100° C. This temperature was maintained for 4 hr and then 130 ml of water were added to the mixture. After cooling and filtering, the precipitate was washed with acetone. The dimethylsulfonium-substituted barbituric acid weighed 6.1 g (80.1%).

¹H NMR (500 MHz, DMSO-d6): δ10.14 (s, 2H), 2.96 (s, 6H)

The above product (5.2 g, 27.5 mmol.) was reacted with 30 ml of phosphorus oxychloride and 5.0 ml of dimethylaniline. After heating for 24 hr under reflux, the reaction mixture was subjected to hydrolysis in iced salt water. The reaction mixture was subjected to filtration and the resulting solid was washed with water. After drying in vacuo, a product of 4.5 g (60.1%) was obtained.

¹H NMR (500 MHz, CDCl₃-d₁): δ2.80 (s, 3H)

4-(2,6-Dichloro-5-methylsulfanyl-pyrimidin-4-yl)-morpholine

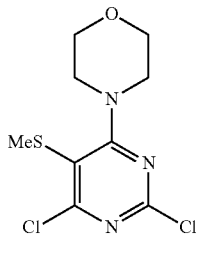 [SMILES: CSc1c(Cl)nc(Cl)nc1N1CCOCC1]

A mixture of 2,4,6-trichloro-5-methylsulfanyl-pyrimidine (4.0 g, 17.4 mmol.), morpholine (2.3 g, 26.1 mmol, 1.5 eq.) and THF (20 ml) was stirred at room temperature for 2.0 hr. The reaction mixture was dried and the solvent was evaporated. Thereafter, a 0.1 N HCl washing free morpholine was added to the solution. The solution was extracted with EA and the EA in the solution was removed by evaporation. A crude product was obtained. Purification of the crude by flash chromatography on silica gel (Hexane/EtOAc 6:1) gave a gray solid of 2.34 g (48.2%).

$^1$H NMR (500 MHz, CDCl$_3$-d$_1$): δ3.89 (t, 4H), 3.80 (t, 4H), 2.32 (s, 3H)

4-(4-Chloro-5-methylsulfanyl-6-morpholin-4-yl-pyrimidin-2-yl)-phenylamine

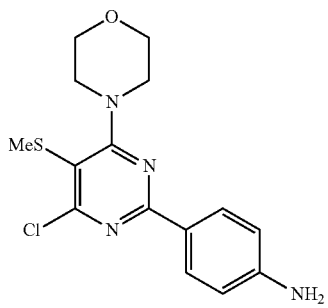

A mixture of 4-(2,6-dichloro-5-methylsulfanyl-pyrimidin-4-yl)-morpholine (200 mg, 0.71 mmol.), 4-(4,4,5,5-tetramethyl-[1,3,2]dioxaborolan-2-yl)-aniline) (172.0 mg, 0.781 mmol.), (PPh$_3$)$_4$Pd (437 mg, 0.07 mmol.), 2M Na$_2$CO$_3$ (1.0 ml, 2.13 mmol, 3.0 eq.) and dioxane (15.0 ml) was added to the reaction vessel which was flushed with argon. The reaction mixture was stirred at 90° C. for 12 hrs and then dried so that the solvent was evaporated. The reaction mixture was partitioned between EA and water. The organic layers were collected, washed with brine, dried over MgSO$_4$, filtered and evaporated in vacuo. The resulting residue was purified by flash chromatography on silica gel (Hexane/EtOAc 3:2) to give a pale yellow solid of 102 mg (42.3%).

$^1$H NMR (500 MHz, DMSO-d$_6$): δ8.19 (d, 2H), 6.72 (d, 2H), 3.85 (s, 8H), 2.35 (s, 3H).

4-[6-Chloro-2-(3-methoxy-phenyl)-5-methylsulfanyl-pyrimidin-4-yl]-morpholine

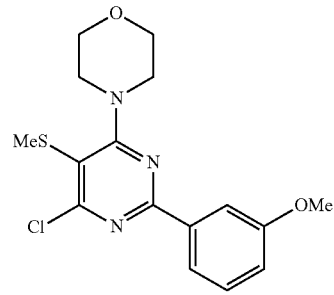 [SMILES: COc1cccc(-c2nc(Cl)c(SC)c(N3CCOCC3)n2)c1]

$^1$H NMR (500 MHz, CDCl$_3$-d$_1$): δ7.96 (d, 1H), 7.90 (d, 1H), 7.36 (t, 1H), 7.01 (d, 1H), 3.87 (m, 11H), 2.36 (s, 3H)

4-(4-Chloro-5-methylsulfanyl-6-morpholin-4-yl-pyrimidin-2-yl)-phenol

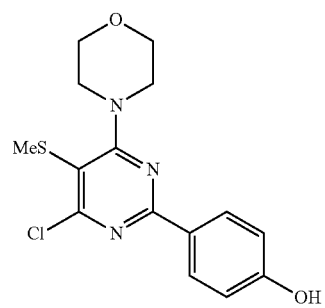 [SMILES: CSc1c(Cl)nc(-c2ccc(O)cc2)nc1N1CCOCC1]

$^1$H NMR (500 MHz, CDCl$_3$-d$_1$): δ8.27 (d, 2H), 6.88 (d, 2H), 5.08 (s, 1H), 3.86 (s, 8H), 2.35 (s, 3H)

3-(4-Chloro-5-methylsulfanyl-6-morpholin-4-yl-pyrimidin-2-yl)-phenol

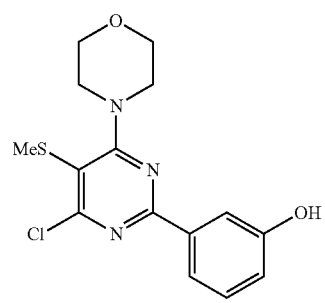 [SMILES: CSc1c(Cl)nc(-c2cccc(O)c2)nc1N1CCOCC1]

$^1$H NMR (500 MHz, CDCl$_3$-d$_1$): δ7.93 (d, 1H), 7.82 (dd, 1H), 7.32 (t, 1H), 6.96 (m, 1H), 5.31 (b, 1H), 3.87 (q, 8H), 2.36 (s, 3H)

131

4-(4-Chloro-5-methylsulfanyl-6-morpholin-4-yl-pyrimidin-2-yl)-benzenesulfonamide

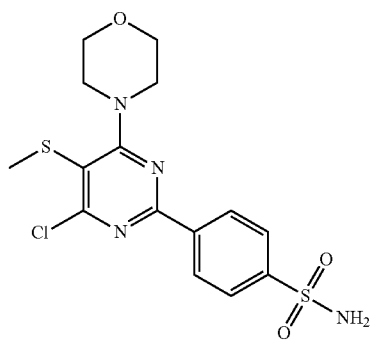 [SMILES: CSc1c(Cl)nc(-c2ccc(S(N)(=O)=O)cc2)nc1N1CCOCC1]

$^1$H NMR (500 MHz, Acetone-d$_6$): δ8.52 (d, 2H), 7.99 (d, 2H), 6.71 (s, 2H), 3.83 (t, 8H), 2.41 (s, 3H)

5-(4-Chloro-5-methylsulfanyl-6-morpholin-4-yl-pyrimidin-2-yl)-pyridin-2-ylamine

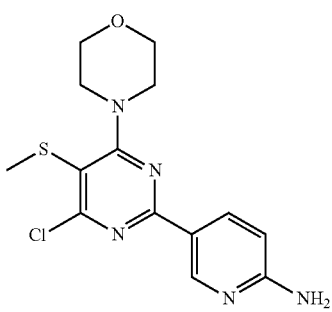

$^1$H NMR (500 MHz, CDCl$_3$-d$_1$): δ9.05 (d, 1H), 8.36 (dd, 1H), 6.53 (s, 1H), 4.87 (b, 2H), 3.85 (t, 8H), 2.35 (s, 3H)

5-(4-Chloro-5-methylsulfanyl-6-morpholin-4-yl-pyrimidin-2-yl)-1H-indole

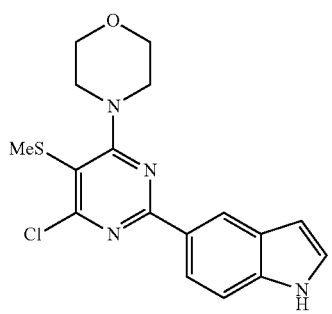 [SMILES: CSc1c(Cl)nc(-c2ccc3[nH]ccc3c2)nc1N1CCOCC1]

$^1$H NMR (500 MHz, CDCl$_3$-d$_1$): δ8.72 (d, 1H), 8.28-8.24 (dd, 2H), 7.43-7.41 (d, 1H), 7.25 (dd, 1H), 7.25-7.24 (d, 1H), 3.89 (m, 8H), 2.37 (s, 3H)

132

4-(4-Chloro-5-methylsulfanyl-6-morpholin-4-yl-pyrimidin-2-yl)-1H-indazole

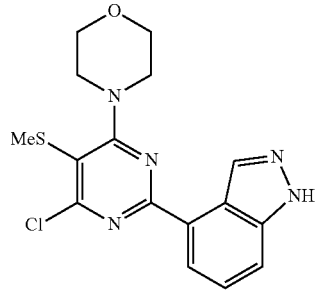 [SMILES: CSc1c(Cl)nc(-c2cccc3[nH]ncc23)nc1N1CCOCC1]

$^1$H NMR (500 MHz, CDCl$_3$-d$_1$): δ8.98 (s, 1H), 8.30 (d, 1H), 7.64 (d, 1H), 7.49 (s, 1H), 3.91 (s, 8H), 2.41 (s, 1H)

N-[4-(4-Chloro-5-methylsulfanyl-6-morpholin-4-yl-pyrimidin-2-yl)-phenyl]-methane sulfonamide

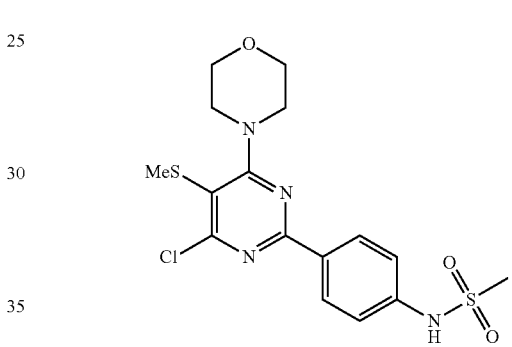

A mixture of 4-(4-chloro-5-methylsulfanyl-6-morpholin-4-yl-pyrimidin-2-yl)-phenylamine (30 mg, 0.091 mmol.), methanesulfonyl chloride (15.5 mg, 0.136 mmol, 1.5 eq.) and CH$_2$Cl$_2$ was added to the reaction vessel and flushed with argon. The reaction mixture was stirred at r.t. for 2 hrs. The reaction mixture was partitioned between CH$_2$Cl$_2$ and NaHCO$_3$ $_{(aq)}$, the organic layer was washed with brine, dried over MgSO$_4$, filtered and evaporated in vacuo. A white solid of 30.3 mg (82.1%) was obtained as the product.

$^1$H NMR (500 MHz, CDCl$_3$-d$_1$): δ8.34 (d, 2H), 7.26 (d, 1H), 6.72 (s, 1H), 3.87 (d, 8H), 3.06 (s, 3H), 2.35 (t, 3H)

N-[4-(4-Chloro-5-methylsulfanyl-6-morpholin-4-yl-pyrimidin-2-yl)-phenyl]-acetamide

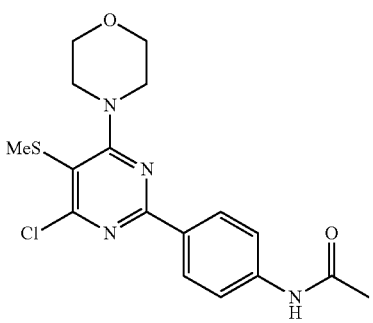 [SMILES: CSc1c(Cl)nc(-c2ccc(NC(C)=O)cc2)nc1N1CCOCC1]

¹H NMR (500 MHz, CDCl₃-d₁): δ10.25 (s, 1H), 8.21 (d, 2H), 7.72 (d, 2H), 3.84 (t, 4H), 3.84 (t, 4H), 3.75 (t, 4H), 2.33 (s, 3H), 2.08 (s, 3H)

N-[4-(4-Chloro-5-methylsulfanyl-6-morpholin-4-yl-pyrimidin-2-yl)-phenyl]-benzenesulfonamide

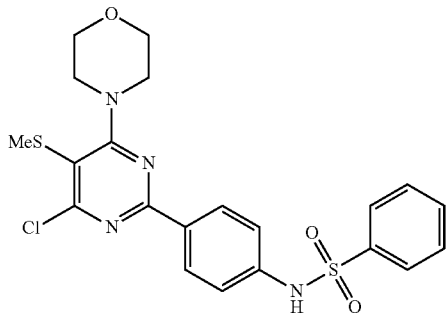 [SMILES: CSc1c(Cl)nc(-c2ccc(NS(=O)(=O)c3ccccc3)cc2)nc1N1CCOCC1]

¹H NMR (500 MHz, CDCl₃-d₁): δ8.24 (d, 2H), 7.80 (t, 2H), 7.53 (t, 1H), 7.44 (t, 2H), 7.14 (d, 2H), 6.75 (s, 1H), 3.84 (d, 8H), 2.34 (d, 3H)

Methanesulfonic acid-4-(4-chloro-5-methylsulfanyl-6-morpholin-4-yl-pyrimidin-2-yl)-phenyl ester

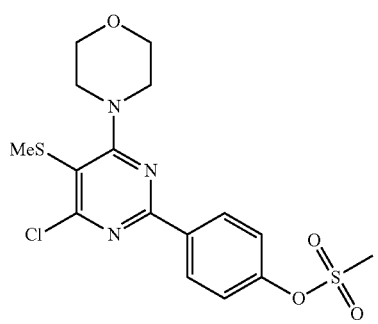 [SMILES: CSc1c(Cl)nc(-c2ccc(OS(C)(=O)=O)cc2)nc1N1CCOCC1]

¹H NMR (500 MHz, CDCl₃-d₁): δ8.42 (m, 2H), 7.36 (q, 2H), 3.86 (m, 8H), 3.17 (s, 3H), 2.37 (s, 3H)

Benzenesulfonic acid-4-(4-chloro-5-methylsulfanyl-6-morpholin-4-yl-pyrimidin-2-yl)-phenyl ester

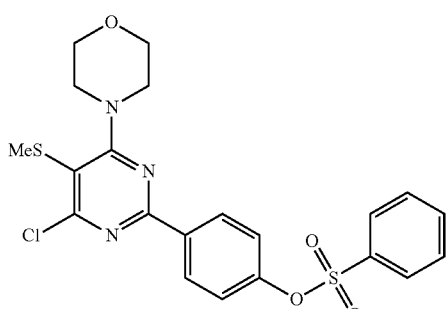

¹H NMR (500 MHz, CDCl₃-d₁): δ8.29-8.27 (d, 2H), 7.84-7.83 (d, 2H), 7.68-7.65 (d, 1H), 7.53-7.50 (d, 2H), 7.05-7.04 (s, 1H), 3.86 (t, 8H), 3.18 (s, 3H), 2.36 (s, 3H)

Methanesulfonic acid-3-(4-chloro-5-methylsulfanyl-6-morpholin-4-yl-pyrimidin-2-yl)-phenyl ester

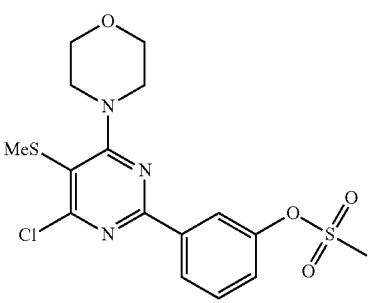 [SMILES: CSc1c(Cl)nc(-c2cccc(OS(C)(=O)=O)c2)nc1N1CCOCC1]

¹H NMR (500 MHz, CDCl₃-d₁): δ8.33 (d, 1H), 8.23 (d, 1H), 7.49 (d, 1H), 7.42 (d, 1H), 3.86 (t, 8H), 3.18 (s, 3H), 2.36 (s, 3H)

1-[4-(4-Chloro-5-methylsulfanyl-6-morpholin-4-yl-pyrimidin-2-yl)-phenyl]-3-(4-chloro-3-trifluoromethyl-phenyl)-urea

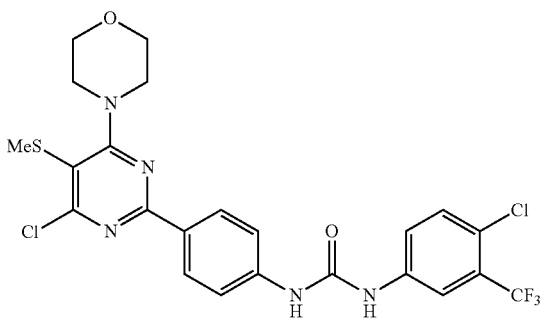 [SMILES: CSc1c(Cl)nc(-c2ccc(NC(=O)Nc3ccc(Cl)c(C(F)(F)F)c3)cc2)nc1N1CCOCC1]

A mixture of 4-(4-chloro-5-methylsulfanyl-6-morpholin-4-yl-pyrimidin-2-yl)-phenylamine (40 mg, 0.118 mmol.), 2-chloro-4-isocyanato-1-trifluoro methyl-benzene (39 mg, 0.178 mmol.), CH₂Cl₂ (1.0 ml), and toluene (2.0 ml) was added to a reaction vessel which was flushed with argon. The reaction mixture was stirred at 90° C. for 16 hrs. After cooling and filtering, the precipitate was washed with a minor portion of CH₂Cl₂ again to give a white solid of 26.7 mg (40.3%).

¹H NMR (500 MHz, Acetone-d₆): δ8.66 (s, 1H), 8.59 (s, 1H), 8.30 (dd, 2H), 8.16 (d, 1H), 7.77 (dd, 1H), 7.66 (dd, 2H), 7.56 (d, 1H), 3.90 (t, 4H), 3.82 (t, 4H), 2.39 (s, 3H)

135

1-[4-(4-Chloro-5-methylsulfanyl-6-morpholin-4-yl-pyrimidin-2-yl)-phenyl]-3-(2-chloro-pyridin-4-yl)-urea

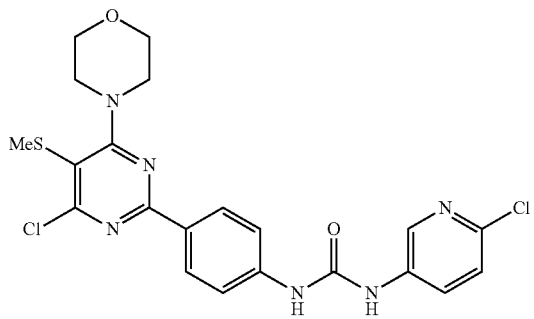 [SMILES: CSc1c(Cl)nc(-c2ccc(NC(=O)Nc3ccc(Cl)nc3)cc2)nc1N1CCOCC1]

$^1$H NMR (500 MHz, Acetone-d$_6$): δ8.72 (s, 1H), 8.61 (s, 1H), 8.50 (d, 2H), 8.32 (s, 1H), 7.67 (d, 2H), 7.38 (d, 1H), 3.91 (t, 4H), 3.82 (t, 4H), 2.39 (s, 3H)

1-[4-(4-Chloro-5-methylsulfanyl-6-morpholin-4-yl-pyrimidin-2-yl)-phenyl]-3-phenyl-urea

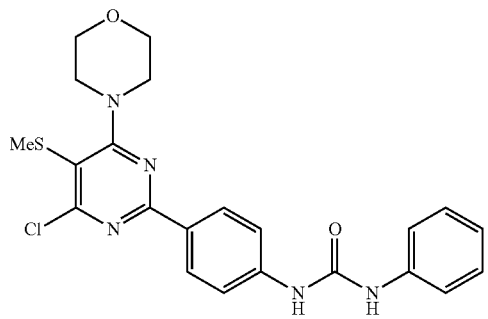 [SMILES: CSc1c(Cl)nc(-c2ccc(NC(=O)Nc3ccccc3)cc2)nc1N1CCOCC1]

$^1$H NMR (500 MHz, CDCl$_3$-d$_1$): δ8.27 (d, 2H), 7.43 (d, 2H), 7.34 (t, 4H), 7.12 (s, 1H), 7.05 (s, 1H), 6.90 (s, 1H), 3.96 (d, 8H), 2.35 (s, 3H)

1-[4-(4-Chloro-5-methylsulfanyl-6-morpholin-4-yl-pyrimidin-2-yl)-phenyl]-3-(4-dimethylamino-phenyl)-urea

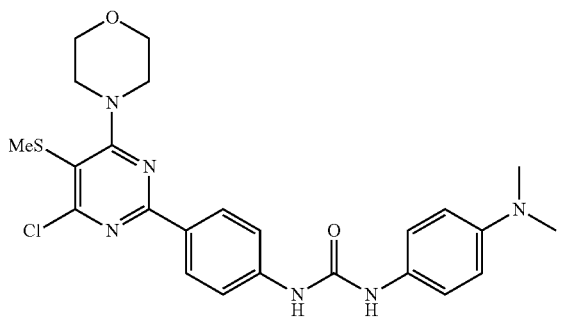 [SMILES: CSc1c(Cl)nc(-c2ccc(NC(=O)Nc3ccc(N(C)C)cc3)cc2)nc1N1CCOCC1]

136

$^1$H NMR (500 MHz, CDCl$_3$-d$_1$): δ8.31 (b, 1H), 8.29 (s, 1H), 7.89 (b, 1H), 8.27 (s, 1H), 7.91 (s, 1H), 7.66 (d, 2H), 7.36 (d, 2H), 6.73 (d, 2H), 3.90 (t, 4H), 3.82 (t, 4H), 2.80 (d, 6H), 2.39 (s, 3H)

1-[4-(4-Chloro-5-methylsulfanyl-6-morpholin-4-yl-pyrimidin-2-yl)-phenyl]-3-(4-fluoro-phenyl)-urea

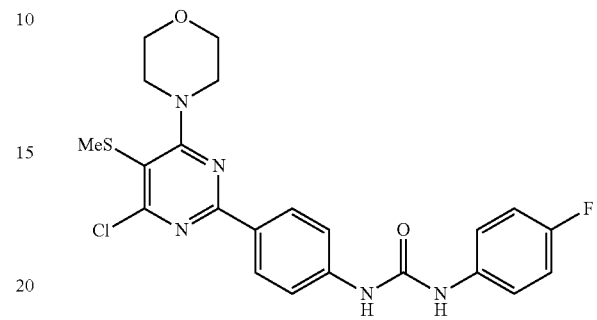

$^1$H NMR (500 MHz, DMSO-d$_6$): δ9.04 (s, 1H), 8.82 (s, 1H) 8.21-8.19 (d, 2H), 7.58 (d, 2H), 7.49-7.46 (dd, 2H), 7.15-7.11 (t, 2H), 3.84 (d, 4H), 3.76 (d, 4H), 2.36 (s, 3H)

1-[4-(4-Chloro-5-methylsulfanyl-6-morpholin-4-yl-pyrimidin-2-yl)-phenyl]-3-(3-fluoro-phenyl)-urea

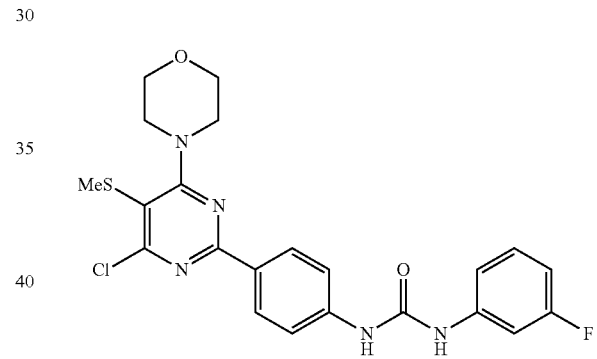

$^1$H NMR (500 MHz, Acetone-d$_6$): δ8.56 (s, 1H), 8.52 (s, 1H), 8.31-8.30 (d, 2H) 7.68-7.66 (d, 2H), 7.62-7.60 (d, 1H), 7.30-7.29 (d, 2H), 7.20 (s, 1H), 3.71 (t, 4H), 3.82 (t, 4H), 2.39 (s, 3H).

1-[4-(4-Chloro-5-methylsulfanyl-6-morpholin-4-yl-pyrimidin-2-yl)-phenyl]-3-(3,4-difluoro-phenyl)-urea

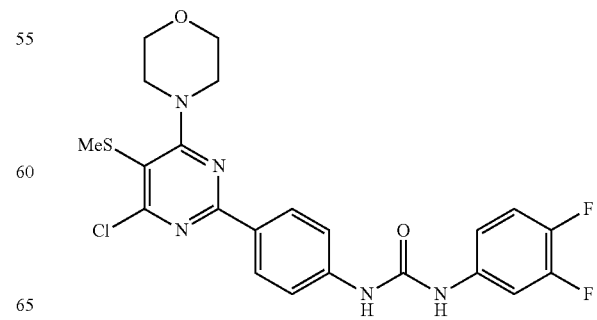

¹H NMR (500 MHz, Acetone-d₆): δ8.77 (s, 1H), 8.73 (s, 2H), 8.30 (d, 2H), 7.82 (m, 1H), 7.66 (d, 2H), 7.21 (m, 1H), 3.91 (t, 4H), 3.82 (t, 4H), 2.39 (s, 3H)

[4-(4-Chloro-5-methylsulfanyl-6-morpholin-4-yl-pyrimidin-2-yl)-phenyl]-urea

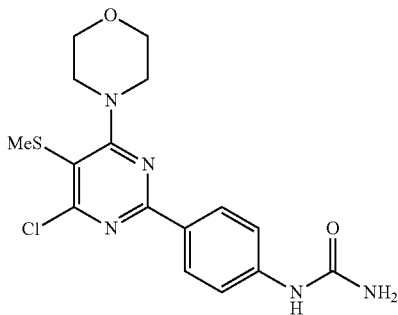 [SMILES: CSc1c(Cl)nc(-c2ccc(NC(N)=O)cc2)nc1N1CCOCC1]

Trimethylsilyl isocyanate (136 mg, 5 eq.) was added to a stirred solution of 4-(4-Chloro-5-methylsulfanyl-6-morpholin-4-yl-pyrimidin-2-yl)-phenylamine (80 mg, 0.237 mmol.) in THF (2.0 ml) and the mixture was reacted to reflux for 16 hrs. The reaction mixture was extracted with EA and washed with brine. The crude was purified by Chromatography (Hexane/EtOAc 1:1) to give a product 28.1 mg (31.2%).

¹H NMR (500 MHz, CDCl₃-d₁): δ8.58 (s, 1H), 8.33 (s, 2H), 7.66 (s, 2H), 6.42 (b, 2H), 3.92 (t, 4H), 3.82 (t, 4H), 2.39 (s, 3H)

1-(2-Chloro-ethyl)-3-[4-(4-chloro-5-methylsulfanyl-6-morpholin-4-yl-pyrimidin-2-yl)-phenyl]-urea

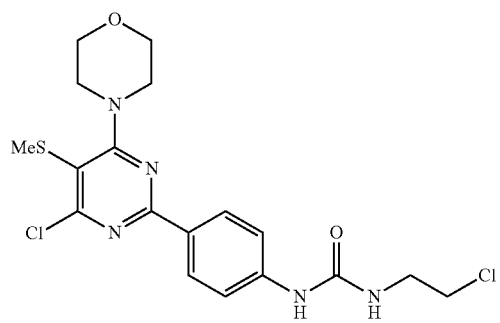 [SMILES: CSc1c(Cl)nc(-c2ccc(NC(=O)NCCCl)cc2)nc1N1CCOCC1]

¹H NMR (500 MHz, CDCl₃-d₁): δ8.26 (d, 2H), 7.40 (d, 2H), 7.12 (s, 1H), 5.58 (t, 1H), 3.86 (d, 8H), 3.62 (m, 4H), 2.35 (s, 3H)

1-[4-(4-Chloro-5-methylsulfanyl-6-morpholin-4-yl-pyrimidin-2-yl)-phenyl]-3-ethyl-urea

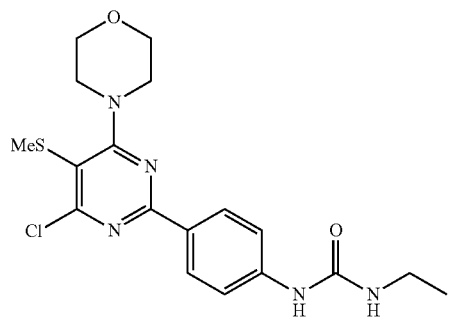 [SMILES: CCNC(=O)Nc1ccc(-c2nc(Cl)c(SC)c(N3CCOCC3)n2)cc1]

¹H NMR (500 MHz, CDCl₃-d₁): δ8.26 (d, 2H), 7.39 (d, 2H), 6.97 (s, 1H), 5.05 (b, 1H), 3.85 (d, 8H), 3.29 (d, 2H), 2.35 (s, 3H), 1.15 (t, 3H)

1-[5-(4-Chloro-5-methylsulfanyl-6-morpholin-4-yl-pyrimidin-2-yl)-pyridin-2-yl]-3-phenyl-urea

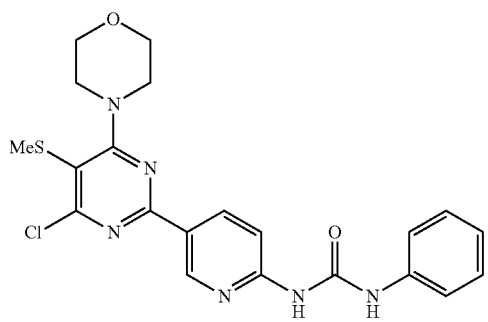 [SMILES: CSc1c(Cl)nc(-c2ccc(NC(=O)Nc3ccccc3)nc2)nc1N1CCOCC1]

¹H NMR (500 MHz, DMSO-d₆): δ10.4 (s, 1H), 9.76 (s, 1H), 9.14 (s, 1H), 8.50 (dd, 1H), 7.66 (d, 1H), 7.55 (d, 2H), 7.32 (t, 2H), 7.04 (s, 1H), 3.87 (t, 4H), 3.76 (t, 4H), 2.36 (d, 3H)

1-[5-(4-Chloro-5-methylsulfanyl-6-morpholin-4-yl-pyrimidin-2-yl)-pyridin-2-yl]-3-(3-fluoro-phenyl)-urea

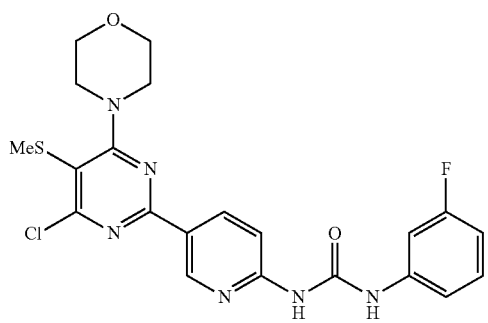 [SMILES: CSc1c(Cl)nc(-c2ccc(NC(=O)Nc3cccc(F)c3)nc2)nc1N1CCOCC1]

¹H NMR (500 MHz, CDCl₃-d₁): δ12.1 (s, 1H), 9.25 (s, 1H), 8.57 (dd, 1H), 8.44 (s, 1H), 7.59 (d, 1H), 7.28 (dd, 2H), 6.90 (s, 1H), 6.80 (s, 1H), 3.88 (t, 8H), 2.38 (s, 3H)

1-[5-(4-Chloro-5-methylsulfanyl-6-morpholin-4-yl-pyrimidin-2-yl)-pyridin-2-yl]-3-ethyl-urea

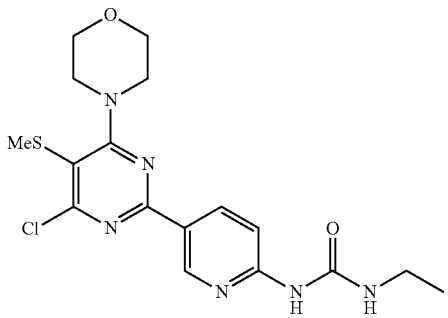 [SMILES: CCNC(=O)Nc1ccc(-c2nc(Cl)c(SC)c(N3CCOCC3)n2)cn1]

$^1$H NMR (500 MHz, DMSO-d$_6$): δ9.52 (s, 1H), 9.04 (s, 1H), 8.41 (dd, 1H), 8.00 (b, 1H), 7.51 (d, 1H), 3.85 (t, 4H), 3.75 (t, 4H), 3.20 (t, 2H), 2.34 (s, 3H), 1.10 (t, 3H)

1-[4-(4-Chloro-5-methylsulfanyl-6-morpholin-4-yl-pyrimidin-2-yl)-phenyl]-imidazolidin-2-one

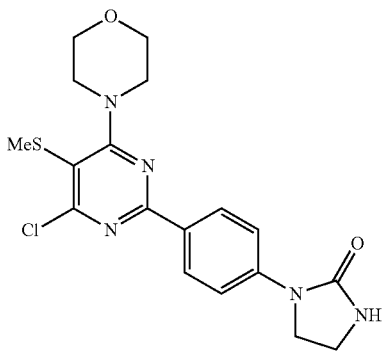 [SMILES: CSc1c(Cl)nc(-c2ccc(N3CCNC3=O)cc2)nc1N1CCOCC1]

A mixture of 1-(2-chloro-ethyl)-3-[4-(4-chloro-5-methylsulfanyl-6-morpholin-4-yl-pyrimidin-2-yl)-phenyl]-urea (20 mg, 0.045 mmol.), 10% NaOH (0.5 ml), THF (2.0 ml), and H$_2$O (1.0 ml) was added to a vessel. The reaction mixture was stirred at 80° C. for 8 hr and then dried, and the solvent was evaporated. The reaction mixture was partitioned between EA and 0.1N HCl, the organic layer was washed with brine, dried over MgSO$_4$, filtered and evaporated in vacuo. The resulting residue was purified by flash chromatography on silica gel (Hexane/EtOAc 3:1) to give a gray solid of 11.4 mg (62.3%).

$^1$H NMR (500 MHz, CDCl$_3$-d$_1$): δ8.33 (d, 2H), 7.64 (d, 2H), 4.88 (s, 1H), 4.01 (m, 2H), 3.87 (t, 8H), 3.66 (m, 2H), 2.36 (s, 3H)

(2-Chloro-ethyl)-carbamic acid 4-(4-chloro-5-methylsulfanyl-6-morpholin-4-yl-pyrimidin-2-yl)-phenyl ester

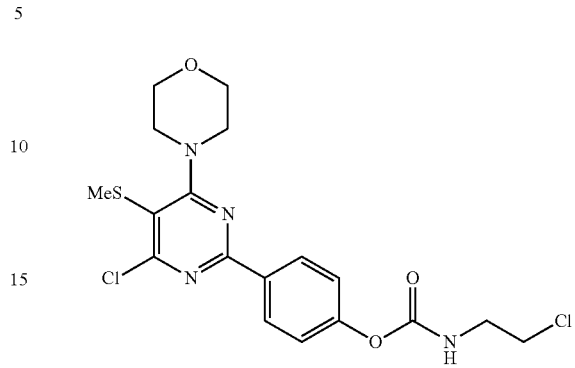

A mixture of 4-(4-chloro-5-methylsulfanyl-6-morpholin-4-yl-pyrimidin-2-yl)-phenol (80.0 mg, 0.236 mmol), 1-chloro-2-isocyanato-ethane (43.1 mg, 0.354 mmol, eq=1.5.), toluene and CH$_2$Cl$_2$ was added to the reaction vessel and flushed with argon. The reaction mixture was stirred at 80° C. for 16 hrs and then dried, and the solvent was evaporated. The reaction mixture was partitioned between EA and water, the organic layer was washed with brine, dried over MgSO$_4$, filtered and evaporated in vacuo. The resulting residue was purified by flash chromatography on silica gel (Hexane/EtOAc 2:1) to give a gray solid of 58.9 mg (58.1%)

$^1$H NMR (500 MHz, CDCl$_3$-d$_1$): δ8.36 (d, 2H), 7.23 (d, 2H), 5.50 (s, 1H), 3.87 (d, 8H), 3.70 (t, 2H), 3.64 (dd, 2H), 2.36 (s, 3H)

[4-(4-Chloro-5-methylsulfanyl-6-morpholin-4-yl-pyrimidin-2-yl)-phenyl]-carbamic acid phenyl ester

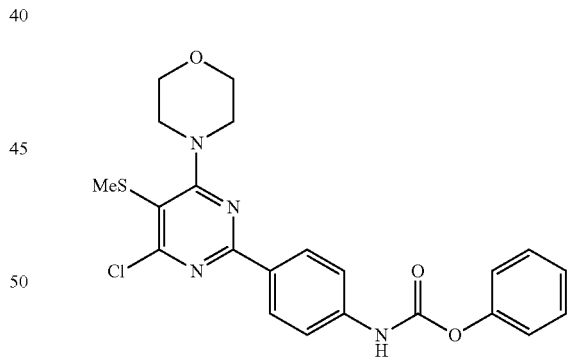

A mixture of 4-(4-chloro-5-methylsulfanyl-6-morpholin-4-yl-pyrimidin-2-yl)-phenylamine (915 mg, 2.717 mmol.) in EA (20 ml) and NaHCO$_3$ (20 ml) the reaction was stirred at r.t. then added dropwise to slurry of phenyl chloroformate (851 mg, 0.543 mmol, 2.0 eq) at reaction for 2 hr. The reaction mixture was partitioned between EA/NaHCO$_3$, the organic layer was washed with brine, dried over MgSO$_4$, filtered and evaporated in vacuo. The residue was recrystallized by (Hexane/EtOAc) to give a pale yellow product of 1056 mg (85.1%).

$^1$H NMR (500 MHz, CDCl$_3$-d$_1$): δ8.35-8.33 (d, 2H), 7.54-7.52 (d, 2H), 7.41-7.38 (dd, 2H), 7.26-7.18 (m, 4H), 3.87 (s, 8H), 2.36 (s, 3H)

141

[4-(4-Chloro-5-methylsulfanyl-6-morpholin-4-yl-pyrimidin-2-yl)-2-fluoro-phenyl]-carbamic acid phenyl ester

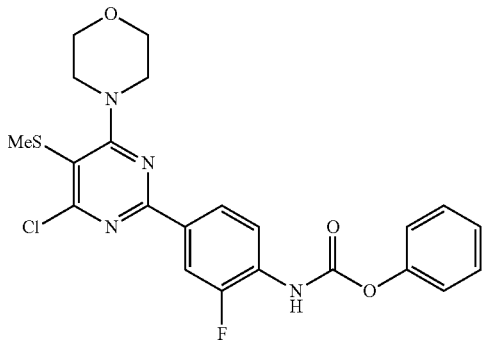 [SMILES: CSc1c(Cl)nc(-c2ccc(NC(=O)Oc3ccccc3)c(F)c2)nc1N1CCOCC1]

$^1$H NMR (500 MHz, CDCl$_3$-d$_1$): δ8.18 (b, 1H), 8.14-8.11 (m, 2H), 7.43-7.40 (dd, 2H), 7.35 (s, 1H), 7.28-7.26 (s, 1H), 7.22-7.20 (s, 2H), 3.88-3.87 (s, 4H), 2.36 (s, 3H)

1-[4-(4-Chloro-5-methylsulfanyl-6-morpholin-4-yl-pyrimidin-2-yl)-phenyl]-3-methyl-urea

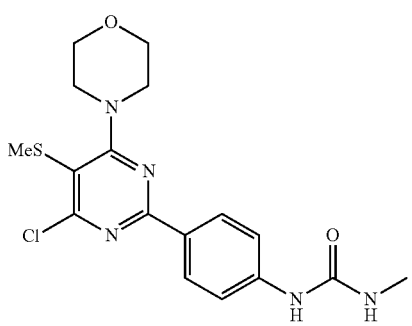 [SMILES: CNC(=O)Nc1ccc(-c2nc(Cl)c(SC)c(N3CCOCC3)n2)cc1]

$^1$H NMR (500 MHz, DMSO-d$_6$): δ8.28 (d, 2H), 7.40 (d, 2H), 6.82 (b, 1H), 5.91 (b, 1H), 3.85 (d, 8H), 2.86 (d, 3H), 2.35 (s, 3H)

1-[4-(4-Chloro-5-methylsulfanyl-6-morpholin-4-yl-pyrimidin-2-yl)-phenyl]-3-morpholin-4-yl-urea

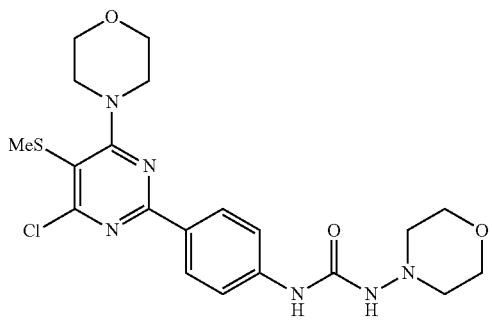 [SMILES: CSc1c(Cl)nc(-c2ccc(NC(=O)NN3CCOCC3)cc2)nc1N1CCOCC1]

142

$^1$H NMR (500 MHz, CDCl$_3$-d$_1$): δ8.32-8.31 (d, 2H), 8.23 (s, 1H), 7.59-7.57 (d, 2H), 5.87 (s, 1H), 4.01 (b, 2H), 3.87-3.87 (d, 8H), 3.72 (b, 2H), 3.09 (b, 2H), 2.77 (b, 2H), 2.36 (s, 3H)

1-[4-(4-Chloro-5-methylsulfanyl-6-morpholin-4-yl-pyrimidin-2-yl)-phenyl]-3-pyridin-3-yl-urea

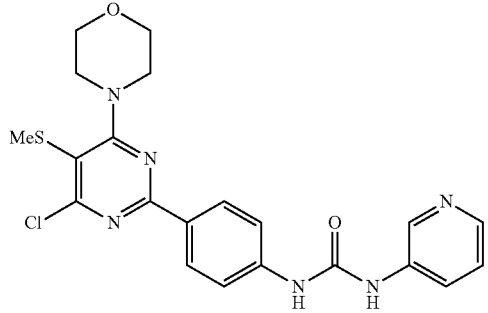 [SMILES: CSc1c(Cl)nc(-c2ccc(NC(=O)Nc3cccnc3)cc2)nc1N1CCOCC1]

$^1$H NMR (500 MHz, DMSO-d$_6$): δ9.31 (s, 1H), 9.10 (s, 1H), 8.63 (d, 1H), 8.20 (t, 3H), 7.95 (dd, 1H), 7.55 (d, 2H), 7.32 (s, 1H), 3.84 (d, 4H), 3.77 (d, 4H), 2.36 (s, 3H)

1-[4-(4-Chloro-5-methylsulfanyl-6-morpholin-4-yl-pyrimidin-2-yl)-phenyl]-3-pyridin-4-yl-urea

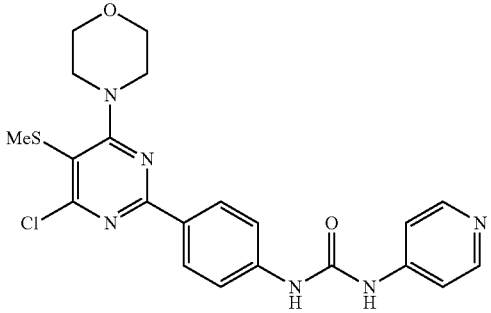 [SMILES: CSc1c(Cl)nc(-c2ccc(NC(=O)Nc3ccncc3)cc2)nc1N1CCOCC1]

$^1$H NMR (500 MHz, DMSO-d$_6$): δ9.27-9.25 (d, 2H), 8.38-8.36 (d, 2H), 8.23-8.22 (d, 2H), 7.61-7.59 (d, 2H), 7.46-7.45 (d, 2H), 3.85-3.84 (d, 4H), 3.77-3.75 (d, 4H), 2.34 (s, 3H)

1-[4-(4-Chloro-5-methylsulfanyl-6-morpholin-4-yl-pyrimidin-2-yl)-phenyl]-3-(2-morpholin-4-yl-ethyl)-urea

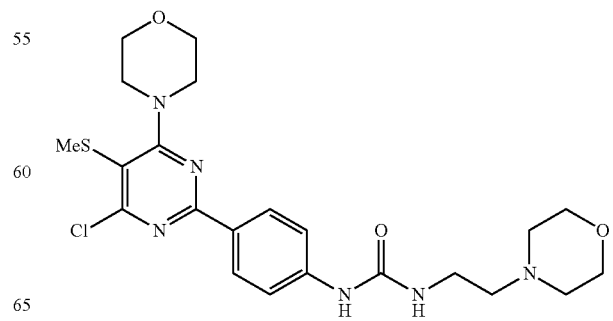

¹H NMR (500 MHz, CDCl₃-d₁): δ8.25 (d, 2H), 7.89 (b, 1H), 7.44 (d, 2H), 5.88 (b, 1H), 3.85 (d, 8H), 3.65 (t, 4H), 3.55 (dd, 2H), 2.51 (d, 2H), 2.47 (s, 4H), 2.34 (s, 3H)

1-[4-(4-Chloro-5-methylsulfanyl-6-morpholin-4-yl-pyrimidin-2-yl)-phenyl]-3-[4-(2-dimethylamino-ethoxy)-phenyl]-urea ¹H NMR (500 MHz, DMSO-d₆): δ8.32-8.30 (d, 2H), 8.25 (d, 1H), 7.58-7.56 (d, 2H), 5.54 (b, 1H), 3.87-3.85 (d, 8H), 3.09 (b, 2H), 2.89 (b, 2H), 2.65 (b, 2H), 2.35 (s, 3H), 2.34 (b, 2H) 2.17 (s, 3H)

1-[4-(4-Chloro-5-methylsulfanyl-6-morpholin-4-yl-pyrimidin-2-yl)-phenyl]-3-(3-fluoro-4-morpholin-4-yl-phenyl)-urea

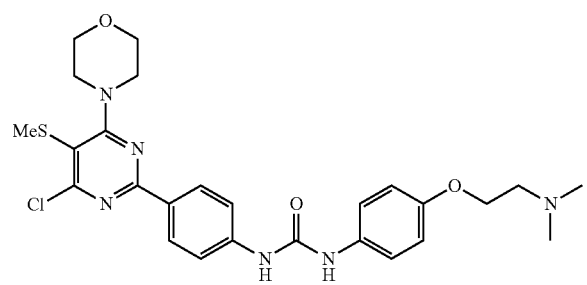 [SMILES: CSc1c(Cl)nc(-c2ccc(NC(=O)Nc3ccc(OCCN(C)C)cc3)cc2)nc1N1CCOCC1]

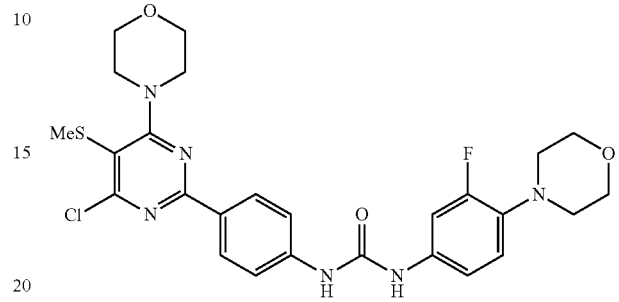

¹H NMR (500 MHz, DMSO-d₆): δ9.63 (s, 1H), 9.31 (s, 1H), 8.19-8.18 (d, 2H), 7.59-7.57 (d, 2H), 7.44-7.42 (d, 2H), 6.97-6.95 (d, 2H), 4.45 (s, 2H), 3.90 (s, 2H), 3.84-3.38 (dd, 8H), 3.24 (s, 6H), 2.34 (s, 3H)

1-[4-(4-Chloro-5-methylsulfanyl-6-morpholin-4-yl-pyrimidin-2-yl)-phenyl]-3-thiazol-2-yl-urea ¹H NMR (500 MHz, DMSO-d₆): δ9.16 (s, 1H), 8.93 (s, 1H), 8.20-8.19 (d, 2H), 7.59-7.57 (d, 2H), 7.47-7.44 (d, 1H), 7.10-7.08 (d, 1H), 7.00 (d, 1H), 3.84-3.83 (d, 4H), 3.76-3.72 (dd, 8H), 2.94-2.93 (d, 4H), 2.34 (s, 3H)

4-{3-[4-(4-Chloro-5-methylsulfanyl-6-morpholin-4-yl-pyrimidin-2-yl)-phenyl]-ureido}-benzoic acid ethyl ester

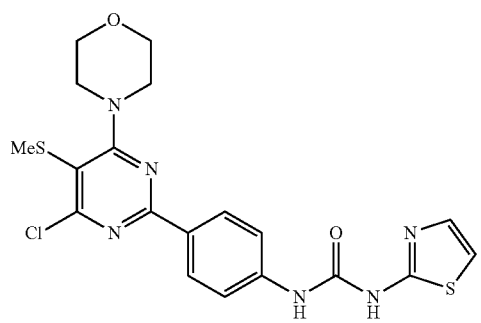 [SMILES: CSc1c(Cl)nc(-c2ccc(NC(=O)Nc3nccs3)cc2)nc1N1CCOCC1]

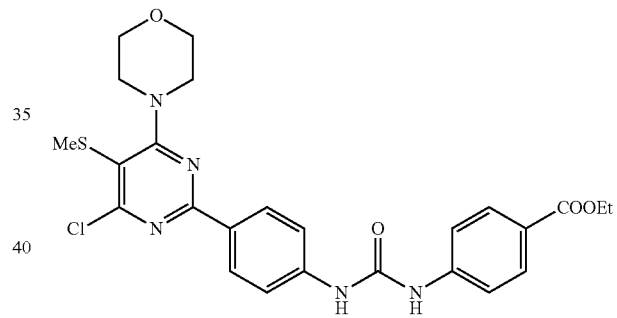

¹H NMR (500 MHz, DMSO-d₆): δ11.01 (b, 1H), 9.72 (b, 1H), 8.23 (d, 2H), 7.65 (d, 2H), 7.35 (s, 1H), 7.11 (s, 1H), 3.84 (d, 4H), 3.77 (d, 4H), 2.36 (s, 3H)

1-[4-(4-Chloro-5-methylsulfanyl-6-morpholin-4-yl-pyrimidin-2-yl)-phenyl]-3-[6-(4-m ethyl-piperazin-1-yl)-pyridin-3-yl]-urea ¹H NMR (500 MHz, CDCl₃-d₁): δ8.17 (t, 2H), 8.09 (s, 1H), 8.01 (s, 1H), 7.90 (d, 2H), 7.43 (t, 4H), 4.33 (dd, 2H), 3.86 (s, 4H), 3.83 (s, 4H), 2.34 (s, 3H), 1.36 (dd, 3H)

1-[4-(4-Chloro-5-methylsulfanyl-6-morpholin-4-yl-pyrimidin-2-yl)-phenyl]-3-[4-(3-oxo-morpholin-4-yl)-phenyl]-urea

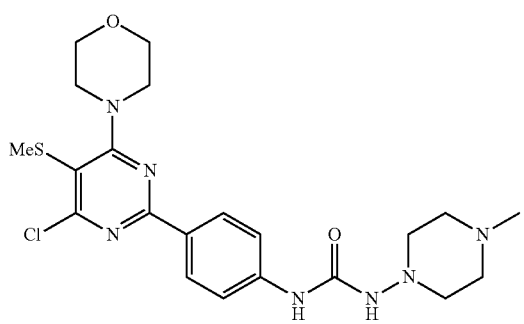 [SMILES: CSc1c(Cl)nc(-c2ccc(NC(=O)NN3CCN(C)CC3)cc2)nc1N1CCOCC1]

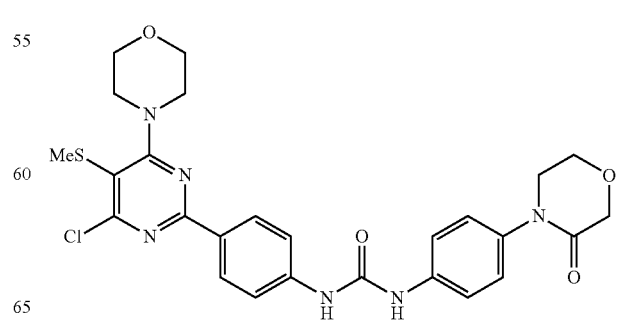

¹H NMR (500 MHz, DMSO-d₆): δ9.18 (s, 1H), 8.98 (d, 1H), 8.21-8.19 (d, 2H), 7.61-7.59 (d, 2H), 7.51-7.49 (d, 2H), 7.30-7.28 (d, 2H), 4.18 (s, 2H), 3.97-3.95 (dd, 2H), 3.84-3.76 (d, 4H), 3.76-3.75 (d, 4H), 3.70-3.68 (dd, 2H), 2.36 (s, 3H)

1-[4-(4-Chloro-5-methylsulfanyl-6-morpholin-4-yl-pyrimidin-2-yl)-phenyl]-3-(3-trifluoromethyl-phenyl)-urea

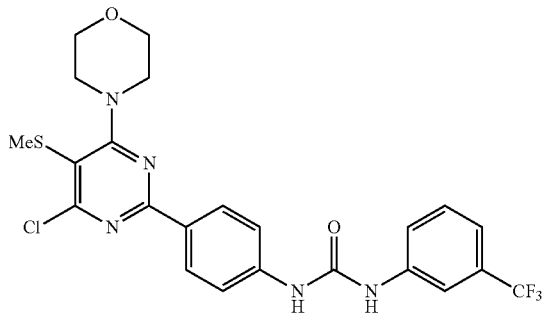 [SMILES: CSc1c(Cl)nc(-c2ccc(NC(=O)Nc3cccc(C(F)(F)F)c3)cc2)nc1N1CCOCC1]

¹H NMR (500 MHz, DMSO-d₆): δ9.19-9.18 (d, 2H), 8.23-8.21 (d, 2H), 8.03 (s, 1H) 7.62-7.58 (t, 3H), 7.54-7.53 (d, 1H), 7.34-7.33 (d, 1H), 3.84-3.83 (d, 4H), 3.77-3.75 (d, 4H), 2.34 (s, 3H)

1-[4-(4-Chloro-5-methylsulfanyl-6-morpholin-4-yl-pyrimidin-2-yl)-phenyl]-3-[4-(4-methyl-piperazin-1-yl)-phenyl]-urea

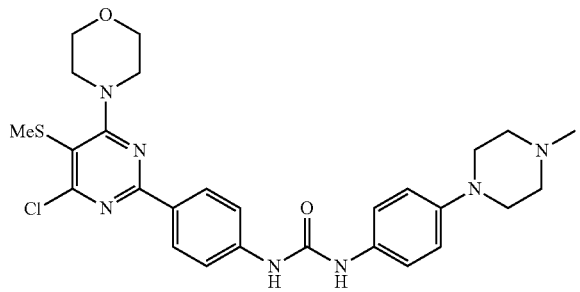 [SMILES: CSc1c(Cl)nc(-c2ccc(NC(=O)Nc3ccc(N4CCN(C)CC4)cc3)cc2)nc1N1CCOCC1]

¹H NMR (500 MHz, DMSO-d₆): δ9.02 (s, 1H), 8.60 (s, 1H), 8.19-8.18 (d, 2H), 7.58-7.56 (d, 2H), 7.31-7.30 (d, 2H), 6.89-6.87 (d, 2H), 3.84-3.83 (d, 4H), 3.76-3.75 (d, 4H), 3.05 (s, 4H), 2.45-2.44 (d, 4H), 2.36-2.34 (d, 3H), 2.34 (s, 3H)

1-[4-(4-Chloro-5-methylsulfanyl-6-morpholin-4-yl-pyrimidin-2-yl)-phenyl]-3-(4-thiomorpholin-4-yl-phenyl)-urea

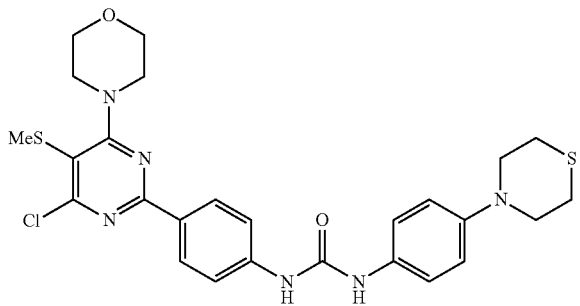 [SMILES: CSc1c(Cl)nc(-c2ccc(NC(=O)Nc3ccc(N4CCOCC4)cc3)cc2)nc1N1CCOCC1]

¹H NMR (500 MHz, DMSO-d₆): δ9.03 (s, 1H), 8.61 (s, 1H), 8.20-8.18 (d, 2H), 7.58-7.56 (d, 2H), 7.33-7.31 (d, 2H), 6.89-6.87 (d, 2H), 3.84-3.83 (d, 4H), 3.76-3.75 (d, 4H), 3.40-3.38 (s, 4H), 2.69-2.67 (d, 4H), 2.32 (s, 3H)

1-[4-(4-Chloro-5-methylsulfanyl-6-morpholin-4-yl-pyrimidin-2-yl)-phenyl]-3-(4-morpholin-4-yl-phenyl)-urea

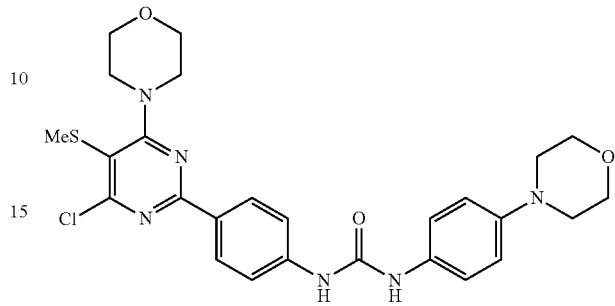

¹H NMR (500 MHz, DMSO-d₆): δ8.96 (s, 1H), 8.54 (s, 1H), 8.16-8.14 (d, 2H), 7.54-7.52 (d, 2H), 7.29-7.28 (d, 2H), 6.86-6.84 (d, 2H), 3.80-3.79 (d, 4H), 3.72-3.69 (d, 8H), 2.99-2.97 (d, 4H), 2.32 (s, 3H)

1-[4-(4-Chloro-5-methylsulfanyl-6-morpholin-4-yl-pyrimidin-2-yl)-phenyl]-3-[6-(4-methyl-piperazin-1-yl)-pyridin-3-yl]-urea

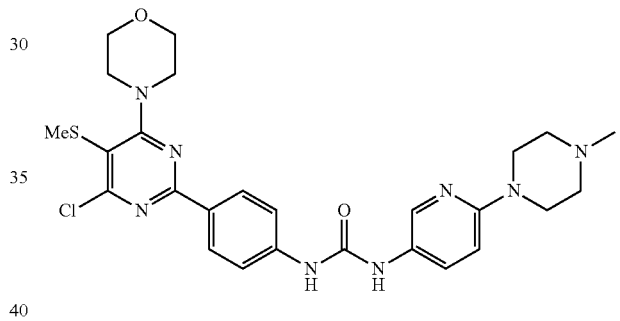

¹H NMR (500 MHz, DMSO-d₆): δ9.12 (s, 1H), 8.60 (s, 1H), 8.20-8.18 (d, 2H), 8.16 (d, 1H), 7.70-7.60 (d, 1H), 7.58-7.56 (d, 2H), 6.82-6.81 (d, 1H), 3.84-3.83 (d, 4H), 3.76-3.75 (d, 4H), 3.43-3.39 (d, 4H), 2.40-2.39 (d, 4H), 2.38-2.36 (d, 3H), 2.30 (s, 3H)

1-[4-(4-Chloro-5-methylsulfanyl-6-morpholin-4-yl-pyrimidin-2-yl)-phenyl]-3-(6-morpholin-4-yl-pyridin-3-yl)-urea

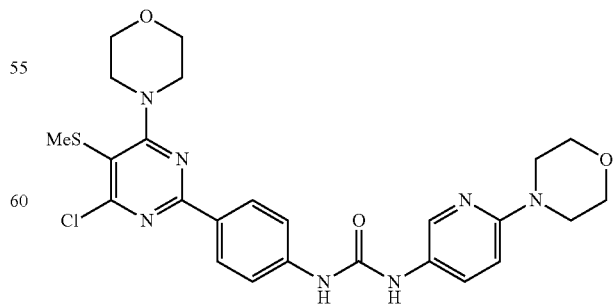

¹H NMR (500 MHz, DMSO-d₆): δ9.21 (s, 1H), 8.72 (s, 1H), 8.20-8.18 (d, 3H), 7.74-7.72 (d, 1H), 7.59-7.57 (d, 2H), 6.84-6.82 (d, 1H), 3.84-3.83 (d, 4H), 3.76-3.75 (d, 4H), 3.71-3.69 (d, 4H), 3.32-3.30 (d, 4H), 2.34 (s, 3H)

1-[4-(4-Chloro-5-methylsulfanyl-6-morpholin-4-yl-pyrimidin-2-yl)-phenyl]-3-pyridin-2-yl-urea

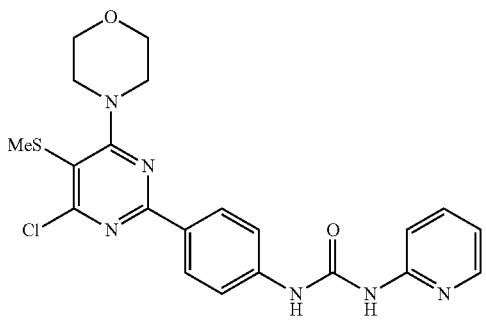 [SMILES: CSc1c(Cl)nc(-c2ccc(NC(=O)Nc3ccccn3)cc2)nc1N1CCOCC1]

¹H NMR (500 MHz, DMSO-d₆): δ10.73 (s, 1H), 9.53 (s, 1H), 8.30-8.29 (d, 1H), 8.24-8.22 (d, 2H), 7.78-7.75 (dd, 1H), 7.67-7.65 (d, 2H), 7.56-7.55 (d, 1H), 7.05-7.02 (d, 1H), 3.85-3.84 (d, 4H), 3.77-3.76 (d, 4H), 2.36-2.34 (s, 3H)

2-{3-[4-(4-Chloro-5-methylsulfanyl-6-morpholin-4-yl-pyrimidin-2-yl)-phenyl]-ureido}-thiophene-3-carboxylic acid methyl ester

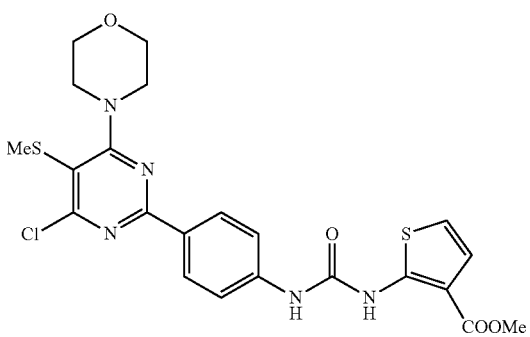 [SMILES: COC(=O)c1ccsc1NC(=O)Nc1ccc(-c2nc(Cl)c(SC)c(N3CCOCC3)n2)cc1]

¹H NMR (500 MHz, CDCl₃-d₁): δ9.72 (s, 1H), 8.32-8.30 (d, 2H), 8.06-8.05 (d, 1H), 7.57-7.55 (dd, 2H), 7.48-7.46 (d, 1H), 3.91 (s, 4H), 3.90-3.88 (d, 3H), 3.87-3.86 (d, 4H), 2.36 (s, 3H)

1-Benzo[1,3]dioxol-5-yl-3-[4-(4-chloro-5-methylsulfanyl-6-morpholin-4-yl-pyrimidin-2-yl)-phenyl]-urea

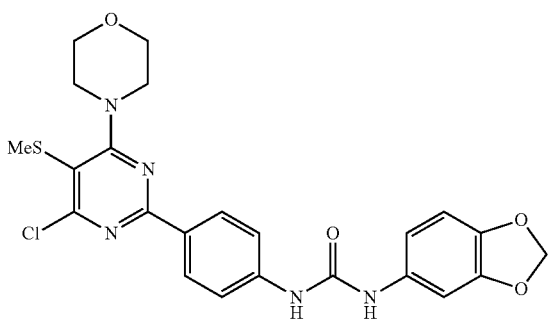 [SMILES: CSc1c(Cl)nc(-c2ccc(NC(=O)Nc3ccc4c(c3)OCO4)cc2)nc1N1CCOCC1]

¹H NMR (500 MHz, DMSO-d₆): δ9.13 (s, 1H), 8.82 (s, 1H), 8.20-8.18 (d, 2H), 7.58-7.56 (d, 2H), 7.21 (s, 1H), 6.84-6.78 (dd, 2H), 5.97 (s, 2H), 3.84-3.83 (d, 4H), 3.76-3.76 (d, 4H), 2.36-2.34 (s, 3H)

4-{3-[4-(4-Chloro-5-methylsulfanyl-6-morpholin-4-yl-pyrimidin-2-yl)-phenyl]-ureido}-benzamide

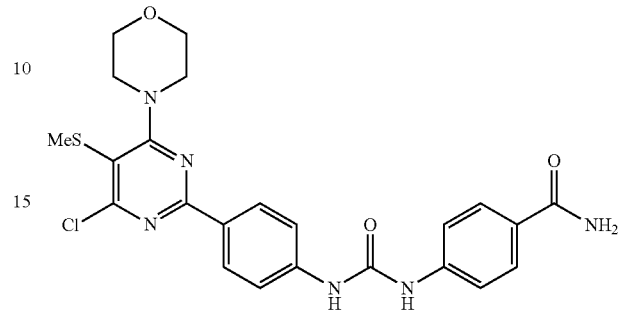

¹H NMR (500 MHz, DMSO-d₆): δ9.13 (s, 1H), 9.04 (s, 1H), 8.23-8.21 (d, 2H), 7.84-7.82 (d, 3H), 7.61-7.59 (d, 2H), 7.54-7.52 (d, 2H), 7.20 (b, 1H), 3.85-3.84 (d, 4H) 3.77-3.76 (d, 4H), 2.34 (s, 3H)

1-[4-(4-Chloro-5-methylsulfanyl-6-morpholin-4-yl-pyrimidin-2-yl)-phenyl]-3-(3,4-dimethoxy-phenyl)-urea

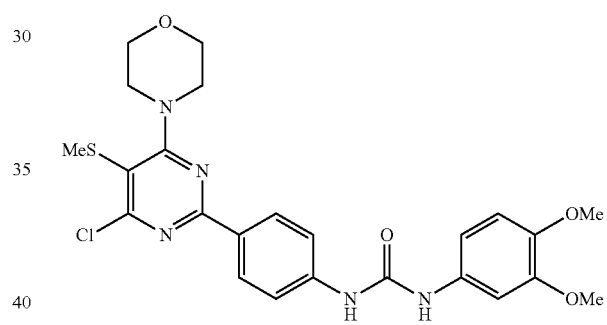

¹H NMR (500 MHz, DMSO-d₆): δ8.94 (s, 1H), 8.60 (s, 1H), 8.21-8.19 (d, 2H), 7.59-7.57 (d, 2H), 7.21 (s, 1H), 6.88-6.87 (s, 2H), 3.84 (s, 3H), 3.75 (s, 8H), 3.71 (s, 3H), 2.36 (s, 3H)

1-[4-(4-Chloro-5-methylsulfanyl-6-morpholin-4-yl-pyrimidin-2-yl)-phenyl]-3-[5-(4-methyl-piperazin-1-yl)-pyridin-2-yl]-urea

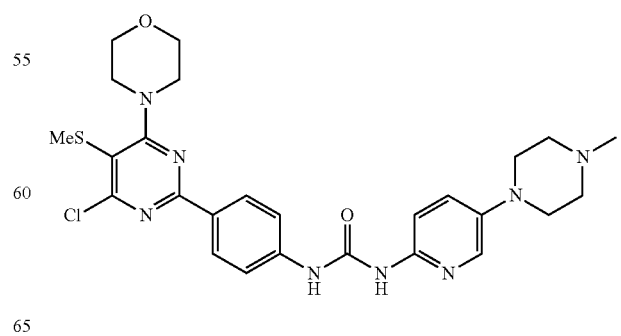

¹H NMR (500 MHz, DMSO-d₆): δ10.82 (b, 1H), 9.26 (s, 1H), 8.22-8.20 (d, 2H), 7.95 (s, 1H), 7.64-7.63 (d, 2H), 7.46-7.44 (t, 2H), 3.84-3.77 (d, 4H), 3.76-3.75 (d, 4H), 3.10-3.09 (t, 4H), 2.52-2.49 (d, 4H), 2.46-2.45 (s, 3H), 2.34-2.21 (s, 3H)

N-(3-{3-[4-(4-Chloro-5-methylsulfanyl-6-morpholin-4-yl-pyrimidin-2-yl)-phenyl]-ureido}-phenyl)-2,2,2-trifluoro-acetamide

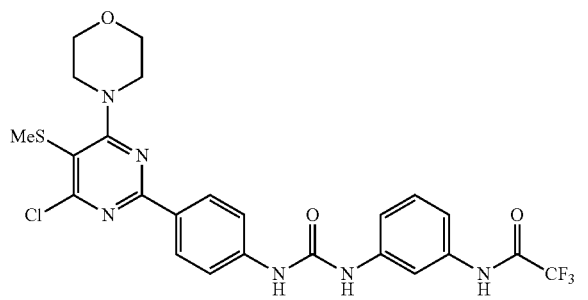

$^1$H NMR (500 MHz, DMSO-d$_6$): δ9.33 (b, 1H), 9.29 (b, 1H), 8.58 (s, 1H), 8.23-8.21 (d, 2H), 7.86-7.85 (d, 1H), 7.79-7.76 (d, 1H), 7.63-7.58 (m, 3H), 3.84-3.76 (d, 4H), 3.75-3.75 (d, 4H), 2.36-2.34 (s, 3H)

N-(3-{3-[4-(4-Chloro-5-methylsulfanyl-6-morpholin-4-yl-pyrimidin-2-yl)-phenyl]-ureido}-phenyl)-acetamide

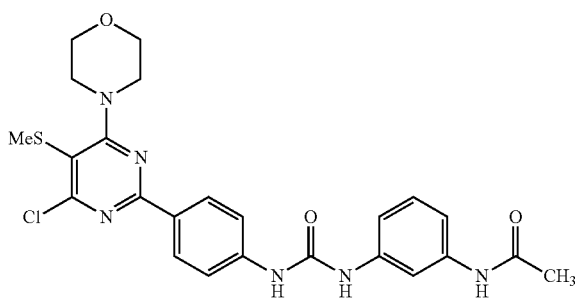 [SMILES: CSc1c(Cl)nc(-c2ccc(NC(=O)Nc3cccc(NC(C)=O)c3)cc2)nc1N1CCOCC1]

$^1$H NMR (500 MHz, DMSO-d$_6$): δ9.93 (s, 1H), 9.05 (s, 1H), 8.91 (s, 1H), 8.21-8.19 (d, 2H), 7.78 (s, 1H), 7.59-7.58 (d, 2H), 7.21-7.17 (dd, 3H), 3.84-3.83 (d, 4H), 3.77-3.76 (d, 4H), 2.36-2.34 (s, 3H), 2.03-1.98 (s, 3H)

1-[4-(4-Chloro-5-methylsulfanyl-6-morpholin-4-yl-pyrimidin-2-yl)-phenyl]-3-[4-(4-methyl-piperazine-1-carbonyl)-phenyl]-urea

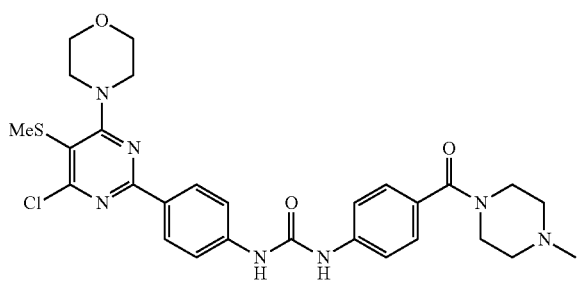 [SMILES: CSc1c(Cl)nc(-c2ccc(NC(=O)Nc3ccc(C(=O)N4CCN(C)CC4)cc3)cc2)nc1N1CCOCC1]

$^1$H NMR (500 MHz, DMSO-d$_6$): δ9.21 (s, 1H), 9.13 (s, 1H), 8.22-8.21 (d, 2H), 7.60-7.59 (d, 2H), 7.54-7.53 (d, 2H), 7.37-7.36 (d, 2H), 3.84 (d, 4H), 3.76 (d, 4H), 3.39-3.35 (d, 4H), 2.50-2.46 (d, 4H), 2.36-2.34 (s, 3H), 2.03-1.98 (s, 3H)

1-(6-Bromo-pyridin-3-yl)-3-[4-(4-chloro-5-methylsulfanyl-6-morpholin-4-yl-pyrimidin-2-yl)-phenyl]-urea

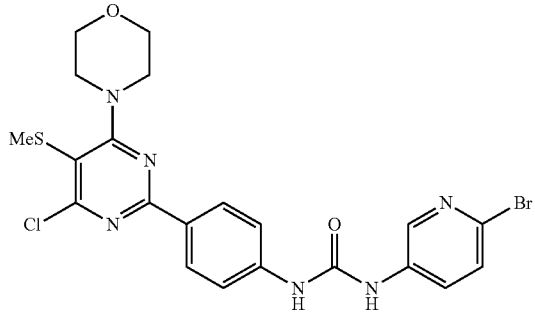 [SMILES: CSc1c(Cl)nc(-c2ccc(NC(=O)Nc3ccc(Br)nc3)cc2)nc1N1CCOCC1]

$^1$H NMR (500 MHz, DMSO-d$_6$): δ9.71 (b, 2H), 8.51-8.50 (d, 1H), 8.22-8.20 (d, 2H), 7.93-7.91 (dd, 1H), 7.62-7.60 (d, 2H), 7.56-7.54 (d, 1H), 3.84-3.76 (d, 4H), 3.76 (s, 4H), 2.36-2.34 (s, 3H)

4-{3-[4-(4-Chloro-5-methylsulfanyl-6-morpholin-4-yl-pyrimidin-2-yl)-phenyl]-ureido}-benzoic acid

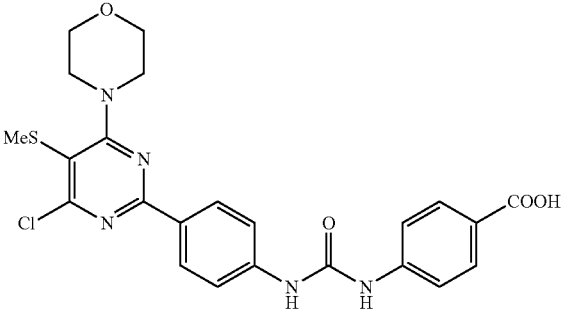 [SMILES: CSc1c(Cl)nc(-c2ccc(NC(=O)Nc3ccc(C(=O)O)cc3)cc2)nc1N1CCOCC1]

$^1$H NMR (500 MHz, DMSO-d$_6$): δ9.39-9.38 (d, 1H), 9.33-9.32 (d, 1H), 8.22-8.20 (d, 2H) 7.90-7.88 (dd, 2H), 7.61-7.59 (dd, 4H), 3.84-3.81 (d, 4H), 3.76-3.74 (d, 4H), 2.33 (s, 3H)

1-(2-Amino-phenyl)-3-[4-(4-chloro-5-methylsulfanyl-6-morpholin-4-yl-pyrimidin-2-yl)-phenyl]-thiourea

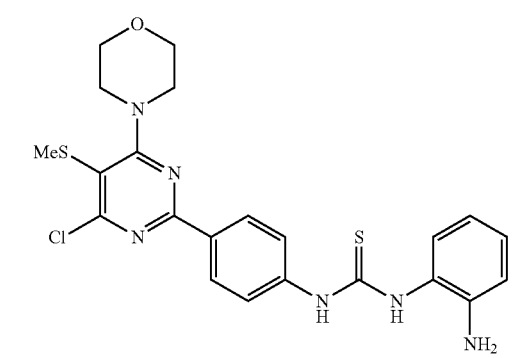 [SMILES: CSc1c(Cl)nc(-c2ccc(NC(=S)Nc3ccccc3N)cc2)nc1N1CCOCC1]

A mixture of bis-(2,5-dihydro-imidazol-1-yl)-methanethione (29.2 mg, 0.164 mmol), imidazole (3.7 mg, 0.05 mmol, 0.5 eq) in CH$_3$CN (5 ml) was stirred at 0° C., then added dropwise to a slurry of 4-(4-chloro-5-methylsulfanyl-6-morpholin-4-yl-pyrimidin-2-yl)-phenylamine (50 mg, 0.109 mmol.). The resulting mixture was reacted 3.0 hrs at r.t. and then benzene-1,2-diamine (23.6 mg, 0.218 mmol, 2.0 eq) was added thereinto. The reaction resulted in a white solid, which was filtered, collected and evaporated in vacuo to give 49.5 mg of a white compound (68.5%).

$^1$H NMR (500 MHz, DMSO-d$_6$): δ10.01 (b, 1H), 9.65 (b, 1H), 8.22-8.20 (d, 2H), 7.75-7.74 (d, 2H), 7.10-7.09 (d, 1H), 6.97-6.95 (d, 1H), 6.75-6.74 (d, 1H), 6.58-6.55 (d, 1H), 4.95 (b, 2H), 3.85-3.84 (d, 4H), 3.76-3.75 (d, 4H), 2.36-2.34 (s, 3H)

1-[4-(4-Chloro-5-methylsulfanyl-6-morpholin-4-yl-pyrimidin-2-yl)-phenyl]-3-pyridin-3-yl-thiourea

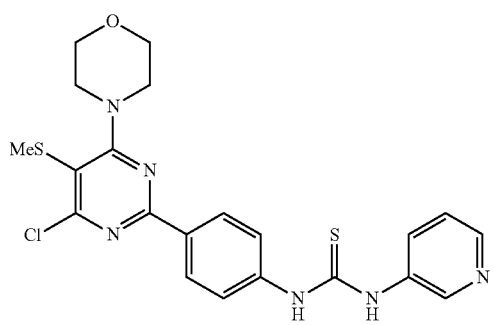 [SMILES: CSc1c(Cl)nc(-c2ccc(NC(=S)Nc3cccnc3)cc2)nc1N1CCOCC1]

$^1$H NMR (500 MHz, DMSO-d$_6$): δ8.63-8.63 (d, 1H), 8.44-8.43 (d, 1H), 8.26-8.24 (d, 2H), 7.98-7.97 (d, 1H), 7.70-7.66 (m, 4H), 7.12-7.04 (d, 1H), 3.86-3.85 (d, 4H), 3.76-3.75 (d, 4H), 2.35 (s, 3H)

1-[4-(4-Chloro-5-methylsulfanyl-6-morpholin-4-yl-pyrimidin-2-yl)-phenyl]-3-[4-(3-oxo-morpholin-4-yl)-phenyl]-thiourea

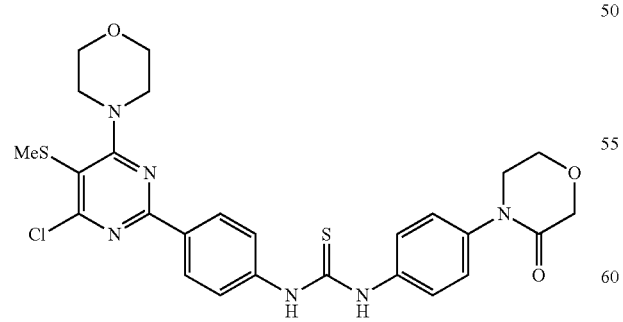

$^1$H NMR (500 MHz, DMSO-d$_6$): δ10.10 (b, 1H), 10.01 (b, 1H), 8.23-8.22 (d, 2H), 7.70-7.68 (d, 2H), 7.53-7.50 (d, 2H), 7.36-7.34 (d, 2H), 4.20-3.98 (d, 2H), 3.97-3.96 (d, 2H), 3.85-3.75 (dd, 4H), 3.74-3.71 (dd, 6H), 2.36-2.34 (s, 3H)

(1H-Benzoimidazol-2-yl)-[4-(4-chloro-5-methylsulfanyl-6-morpholin-4-yl-pyrimidin-2-yl)-phenyl]-amine

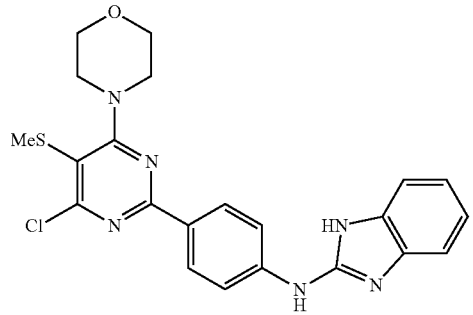 [SMILES: CSc1c(Cl)nc(-c2ccc(Nc3nc4ccccc4[nH]3)cc2)nc1N1CCOCC1]

A mixture of 1-(2-amino-phenyl)-3-[4-(4-chloro-5-methylsulfanyl-6-morpholin-4-yl-pyrimidin-2-yl)-phenyl]-thiourea (120 mg, 1.0 eq.) and DCC (0.18 g, 0.271 mmol, 1.1 eq.) in THF (8 ml) was reacted for 9 hrs at 80-90° C. The resulting mixture was dried in vacuo, crystallized in EA solution, filtered to give a yellow solid (69.5 mg, 62.3%), which was then dried in vacuo to give a product.

$^1$H NMR (500 MHz, DMSO-d$_6$): δ10.78 (b, 1H), 9.98 (s, 1H), 8.25-8.23 (d, 2H), 7.90-7.89 (d, 2H), 7.24-7.20 (d, 2H), 7.02 (s, 2H), 3.85-3.84 (d, 4H), 3.77-3.75 (d, 4H), 2.34 (s, 3H)

1-[4-(4-Chloro-5-methylsulfanyl-6-morpholin-4-yl-pyrimidin-2-yl)-phenyl]-3-isopropyl-urea

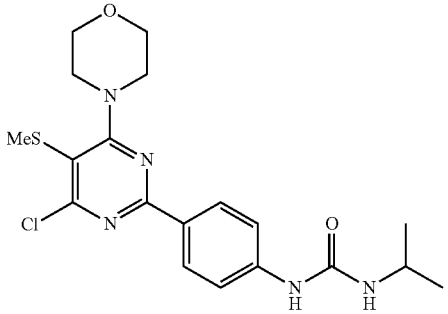

$^1$H NMR (500 MHz, DMSO-d$_6$): δ8.67 (s, 1H), 8.15-8.13 (d, 2H), 7.50-7.49 (d, 2H), 6.02 (s, 1H), 3.84-3.83 (d, 4H), 3.76-3.75 (d, 4H), 2.33 (s, 3H), 1.11-1.09 (s, 6)

1-[4-(4-Chloro-5-methylsulfanyl-6-morpholin-4-yl-pyrimidin-2-yl)-phenyl]-3-[4-(morpholine-4-carbonyl)-phenyl]-urea

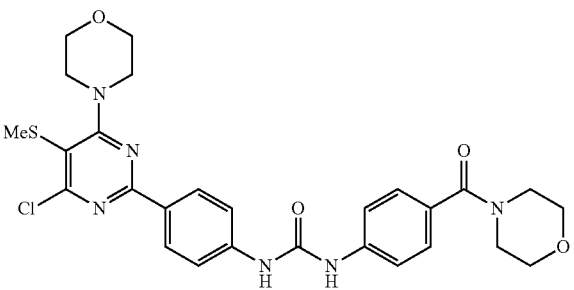 [SMILES: CSc1c(Cl)nc(-c2ccc(NC(=O)Nc3ccc(C(=O)N4CCOCC4)cc3)cc2)nc1N1CCOCC1]

¹H NMR (500 MHz, DMSO-d₆): δ9.34-9.24 (d, 2H), 8.22-8.20 (d, 2H), 7.61-7.60 (d, 2H), 7.55-7.53 (d, 2H), 7.37-7.36 (d, 2H), 3.84-3.83 (d, 4H), 3.77-3.76 (d, 4H), 3.60-3.39 (m, 8H), 2.36-2.34 (s, 3H)

1-[4-(4-Chloro-5-methylsulfanyl-6-morpholin-4-yl-pyrimidin-2-yl)-phenyl]-3-(5-morpholin-4-yl-pyridin-2-yl)-urea

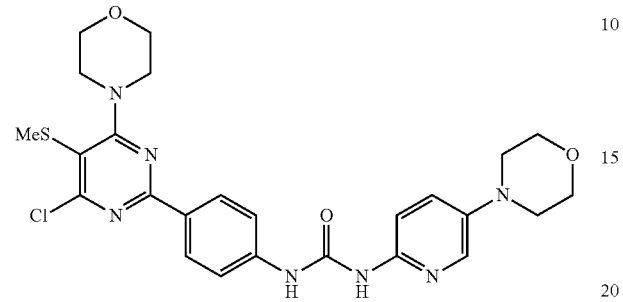

¹H NMR (500 MHz, DMSO-d₆): δ10.31 (b, 1H), 9.27 (s, 1H), 8.23-8.21 (d, 2H), 7.97 (s, 1H), 7.65-7.63 (d, 2H), 7.47 (s, 2H), 3.85-3.83 (d, 4H), 3.77-3.74 (dd, 8H), 3.09-3.07 (d, 4H), 2.49-2.34 (s, 3H)

1-(4-Amino-phenyl)-3-[4-(4-chloro-5-methylsulfanyl-6-morpholin-4-yl-pyrimidin-2-yl)-phenyl]-urea

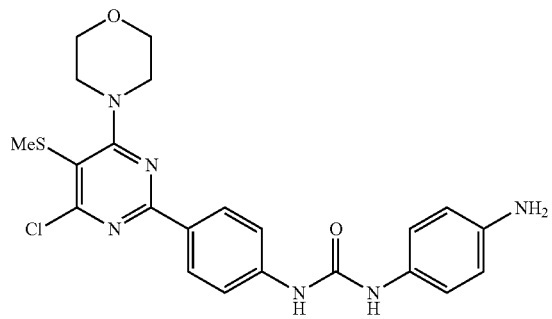 [SMILES: CSc1c(Cl)nc(-c2ccc(NC(=O)Nc3ccc(N)cc3)cc2)nc1N1CCOCC1]

¹H NMR (500 MHz, DMSO-d₆): δ9.09 (s, 1H), 8.48 (s, 1H), 8.18-8.16 (d, 2H), 7.57-7.55 (d, 2H), 7.10-7.08 (d, 2H), 6.52-6.50 (d, 2H), 4.79 (s, 2H), 3.83-3.83 (d, 4H), 3.76-3.75 (d, 4H), 2.49-2.46 (s, 3H)

1-tert-Butyl-3-[4-(4-chloro-5-methylsulfanyl-6-morpholin-4-yl-pyrimidin-2-yl)-phenyl]-urea

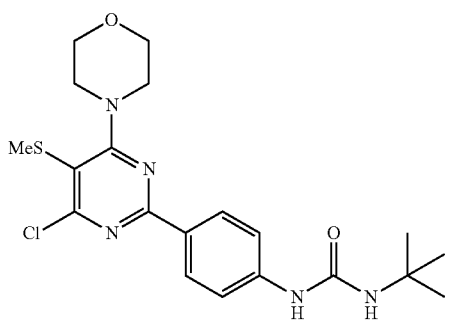

¹H NMR (500 MHz, DMSO-d₆): δ8.60 (s, 1H), 8.14-8.13 (d, 2H), 7.48-7.46 (d, 2H), 6.12 (s, 1H), 3.83-3.81 (d, 4H), 3.76-3.74 (d, 4H), 2.33 (s, 3H), 1.29-1.26 (d, 9H)

4-(4-Chloro-5-methylsulfanyl-6-morpholin-4-yl-pyrimidin-2-yl)-2-fluoro-phenylamine

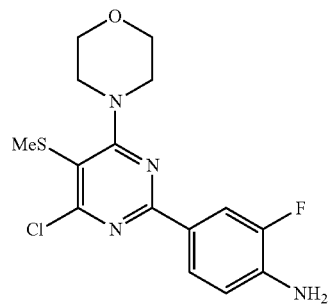

¹H NMR (500 MHz, CDCl₃-d₁): δ8.11-8.06 (dd, 2H), 7.15-7.14 (m, 1H), 3.87-3.86 (d, 8H), 2.36 (s, 3H)

4-(4-Chloro-5-methylsulfanyl-6-morpholin-4-yl-pyrimidin-2-yl)-3-fluoro-phenylamine

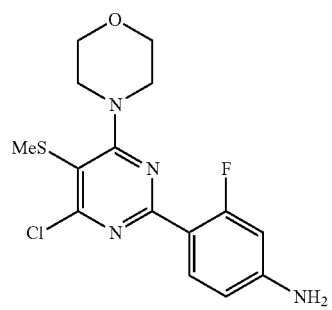 [SMILES: CSc1c(Cl)nc(-c2ccc(N)cc2F)nc1N1CCOCC1]

¹H NMR (500 MHz, CDCl₃-d₁): δ8.04-8.01 (dd, 1H), 6.74-6.72 (d, 1H), 6.67-6.65 (d, 1H), 3.89 (s, 4H), 3.84-3.83 (s, 4H), 2.36 (s, 3H)

6-Chloro-5-methylsulfanyl-4-morpholin-4-yl-[2,5']bipyrimidinyl-2'-ylamine

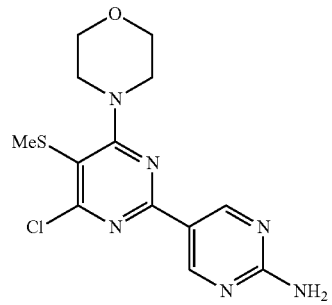 [SMILES: CSc1c(Cl)nc(-c2cnc(N)nc2)nc1N1CCOCC1]

¹H NMR (500 MHz, DMSO-d₆): δ8.99 (s, 2H), 7.35 (s, 2H), 3.84-3.83 (d, 4H), 3.74-3.73 (d, 4H), 2.32 (s, 3H)

1-[4-(4-Chloro-5-methylsulfanyl-6-morpholin-4-yl-pyrimidin-2-yl)-phenyl]-3-(1H-indazol-4-yl)-urea

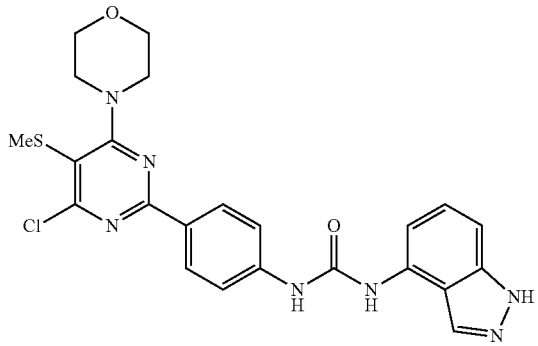 [SMILES: CSc1c(Cl)nc(-c2ccc(NC(=O)Nc3cccc4[nH]ncc34)cc2)nc1N1CCOCC1]

¹H NMR (500 MHz, DMSO-d₆): δ10.45 (s, 1H), 8.55 (s, 1H), 8.29-8.26 (d, 2H), 7.98-7.95 (d, 2H), 7.67 (s, 1H), 7.43-7.41 (d, 1H), 7.26-7.23 (d, 1H), 6.42-6.41 (d, 1H), 6.12 (s, 1H), 3.87-3.85 (d, 4H), 3.77-3.76 (d, 4H), 2.50-2.50 (s, 3H)

N-(4-{3-[4-(4-Chloro-5-methylsulfanyl-6-morpholin-4-yl-pyrimidin-2-yl)-phenyl]-ureido}-phenyl)-methanesulfonamide

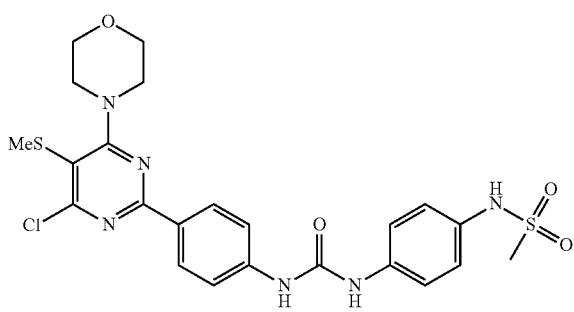 [SMILES: CSc1c(Cl)nc(-c2ccc(NC(=O)Nc3ccc(NS(C)(=O)=O)cc3)cc2)nc1N1CCOCC1]

¹H NMR (500 MHz, DMSO-d₆): δ9.87 (b, 1H), 9.03 (s, 1H), 8.78 (s, 1H), 8.21-8.19 (d, 2H), 7.59-7.57 (d, 2H), 7.44-7.42 (d, 2H), 7.16-7.14 (d, 2H), 3.85-3.83 (d, 4H), 3.77-3.75 (d, 4H), 2.92 (s, 3H), 2.34 (s, 3H)

[4-(4-Chloro-5-methylsulfanyl-6-morpholin-4-yl-pyrimidin-2-yl)-2-fluoro-phenyl]-urea

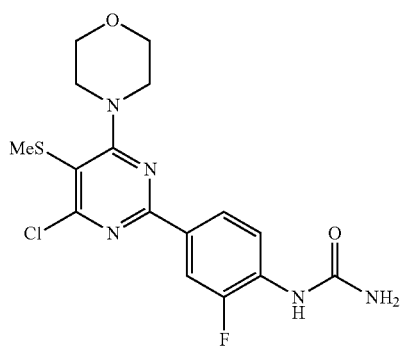 [SMILES: CSc1c(Cl)nc(-c2ccc(NC(N)=O)c(F)c2)nc1N1CCOCC1]

¹H NMR (500 MHz, DMSO-d₆): δ8.64 (s, 1H), 8.34-8.31 (s, 1H), 8.01-7.96 (dd, 2H), 6.34 (s, 2H), 3.84-3.83 (d, 4H), 3.76-3.75 (d, 4H), 2.34 (s, 3H)

1-[4-(4-Chloro-5-methylsulfanyl-6-morpholin-4-yl-pyrimidin-2-yl)-2-fluoro-phenyl]-3-[4-(3-oxo-morpholin-4-yl)-phenyl]-urea

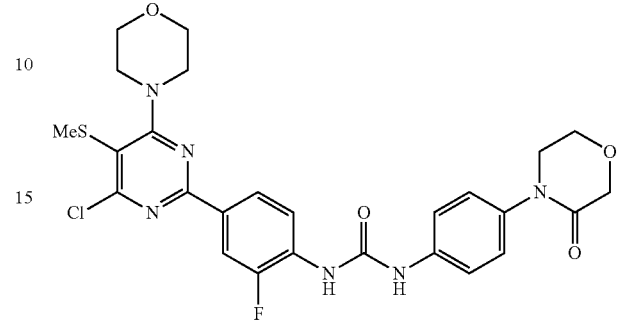

¹H NMR (500 MHz, DMSO-d₆): δ9.31 (s, 1H), 892 (s, 1H), 8.37-8.34 (s, 1H), 8.08-8.51 (d, 2H), 7.50-7.4 (d, 2H), 7.3-7.3 (d, 23H), 4.19 (s, 2H), 3.97-3.95 (s, 2H), 3.85-3.85 (d, 4H), 3.77-3.75 (d, 4H), 3.71-3.69 (s, 2H), 2.34 (s, 3H)\

1-[4-(4-Chloro-5-methylsulfanyl-6-morpholin-4-yl-pyrimidin-2-yl)-3-fluoro-phenyl]-3-[4-(3-oxo-morpholin-4-yl)-phenyl]-urea

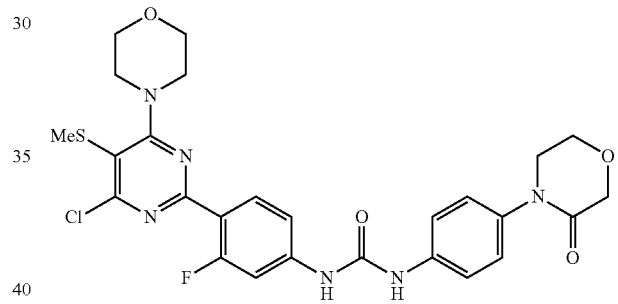

¹H NMR (500 MHz, DMSO-d₆): δ9.34 (s, 1H), 9.03 (s, 1H), 8.05-8.01 (d, 1H), 7.62-7.59 (d, 1H), 7.50-7.46 (d, 2H), 7.31-7.23 (m, 3H), 4.18 (s, 2H), 3.97-3.95 (s, 2H), 3.83-3.82 (d, 4H), 3.75-3.74 (d, 4H), 3.71-3.69 (d, 2H), 2.36-2.34 (s, 3H)

4-{3-[4-(4-Chloro-5-methylsulfanyl-6-morpholin-4-yl-pyrimidin-2-yl)-phenyl]-ureido}-benzenesulfonamide

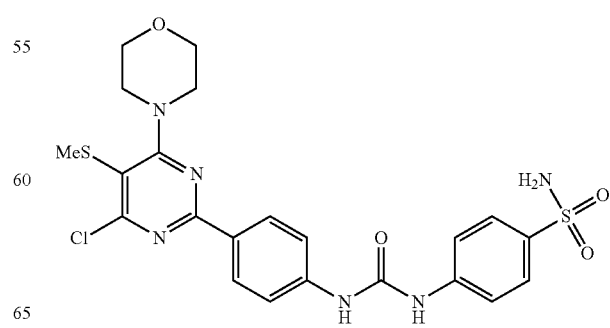

¹H NMR (500 MHz, DMSO-d₆): δ9.14 (s, 2H), 8.23-8.21 (s, 2H), 7.75-7.73 (s, 2H), 7.63-7.62 (d, 2H), 7.61-7.59 (d, 2H), 7.22 (s, 2H), 3.85 (d, 4H), 3.77-3.76 (d, 4H), 2.36 (s, 3H)

N-(4-{3-[4-(4-Chloro-5-methylsulfanyl-6-morpholin-4-yl-pyrimidin-2-yl)-phenyl]-ureido}-phenyl)-acetamide

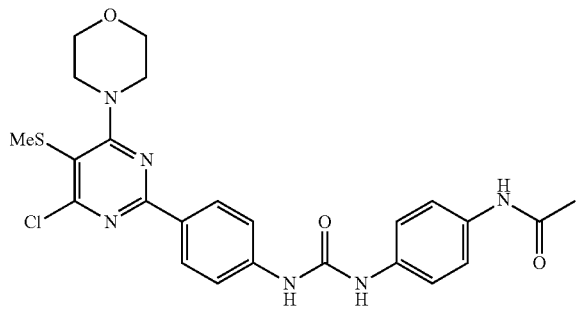 [SMILES: CSc1c(Cl)nc(-c2ccc(NC(=O)Nc3ccc(NC(C)=O)cc3)cc2)nc1N1CCOCC1]

¹H NMR (500 MHz, DMSO-d₆): δ9.83 (s, 1H), 9.03 (s, 1H), 8.72 (s, 1H), 8.20-8.19 (d, 2H), 7.59-7.57 (d, 2H), 7.49-7.48 (d, 2H), 7.38-7.36 (d, 2H), 3.84-3.83 (d, 4H), 3.77-3.76 (d, 4H), 2.36 (s, 3H), 2.01 (s, 3H)

1-[4-(4-Chloro-5-methylsulfanyl-6-morpholin-4-yl-pyrimidin-2-yl)-phenyl]-3-(2-oxo-2,3-dihydro-benzooxazol-5-yl)-urea

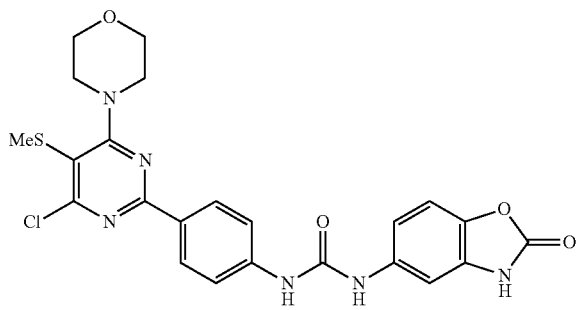 [SMILES: CSc1c(Cl)nc(-c2ccc(NC(=O)Nc3ccc4oc(=O)[nH]c4c3)cc2)nc1N1CCOCC1]

¹H NMR (500 MHz, DMSO-d₆): δ9.16 (s, 1H), 8.95 (s, 1H), 8.21-8.19 (d, 2H), 7.60-7.58 (d, 2H), 7.43 (s, 1H), 7.14-7.12 (s, 1H), 6.92-6.90 (m, 1H), 3.85-3.83 (d, 4H), 3.77-3.76 (d, 4H), 2.36-2.34 (s, 3H)

1-[4-(4-Chloro-5-methylsulfanyl-6-morpholin-4-yl-pyrimidin-2-yl)-phenyl]-3-isoxazol-3-yl-urea

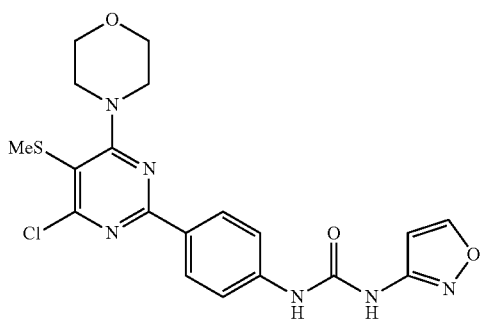 [SMILES: CSc1c(Cl)nc(-c2ccc(NC(=O)Nc3ccon3)cc2)nc1N1CCOCC1]

¹H NMR (500 MHz, DMSO-d₆): δ9.74 (s, 1H), 9.22 (s, 1H), 8.76-8.76 (d, 1H), 8.23-8.21 (d, 2H), 7.63-7.59 (d, 2H), 6.87-6.87 (d, 1H), 3.84-3.83 (d, 4H), 3.77-3.76 (s, 4H), 2.31 (s, 3H)

1-(6-Chloro-5-methylsulfanyl-4-morpholin-4-yl-[2,5']bipyrimidinyl-2'-yl)-3-[4-(3-oxo-morpholin-4-yl)-phenyl]-urea

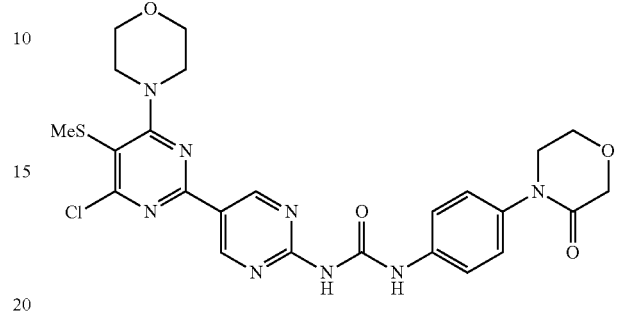

¹H NMR (500 MHz, DMSO-d₆): δ11.57 (s, 1H), 10.24 (b, 1H), 9.39 (d, 2H), 7.70-7.68 (d, 2H), 7.37-7.35 (d, 2H), 4.19-4.18 (d, 2H), 3.98-3.90 (d, 2H), 3.90 (s, 4H), 3.77-3.71 (m, 6H), 2.35 (s, 3H)

4-{3-[4-(4-Chloro-5-methylsulfanyl-6-morpholin-4-yl-pyrimidin-2-yl)-3-fluoro-phenyl]-ureido}-benzamide

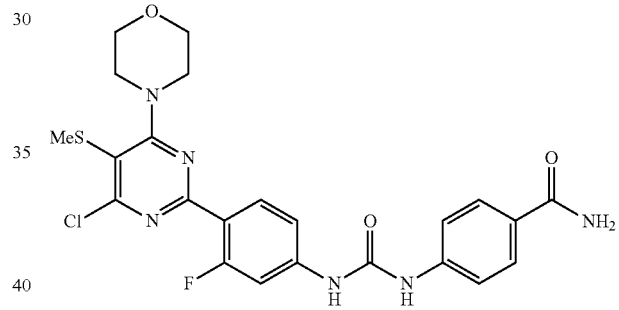

¹H NMR (500 MHz, DMSO-d₆): δ9.35 (s, 1H), 9.16 (s, 1H), 8.04-8.02 (d, 1H), 7.84-7.82 (d, 3H), 7.62-7.52 (m, 3H), 7.26-7.24 (m, 2H), 3.84-3.82 (d, 4H), 3.75-3.73 (d, 4H), 2.35 (s, 3H)

4-{3-[4-(4-Chloro-5-methylsulfanyl-6-morpholin-4-yl-pyrimidin-2-yl)-2-fluoro-phenyl]-ureido}-benzamide

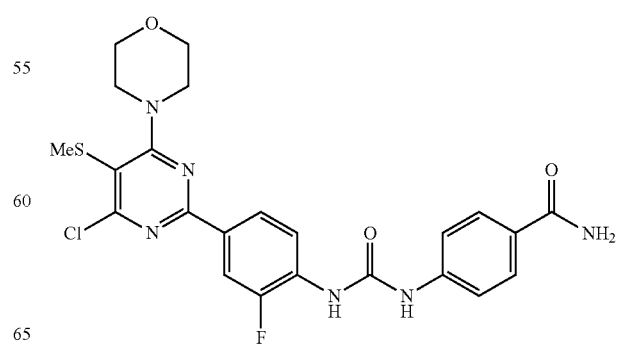

¹H NMR (500 MHz, DMSO-d₆): δ9.45 (s, 1H), 8.97 (s, 1H), 8.37-8.33 (d, 1H), 8.09-8.01 (dd, 2H), 7.85-7.83 (d, 3H), 7.54-7.52 (d, 2H), 7.21 (s, 1H), 3.86-3.85 (d, 4H), 3.77-3.75 (d, 4H), 2.34 (s, 3H)

4-{3-[4-(4-Chloro-5-methylsulfanyl-6-morpholin-4-yl-pyrimidin-2-yl)-2-fluoro-phenyl]-ureido}-benzenesulfonamide

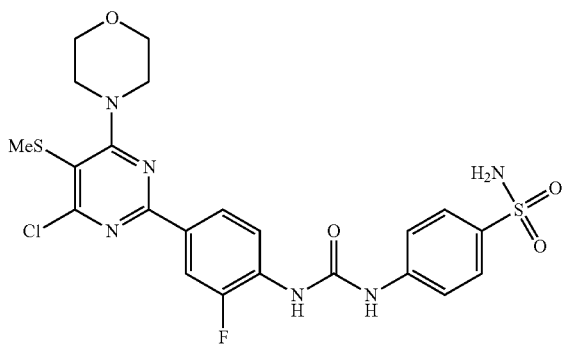 [SMILES: CSc1c(Cl)nc(-c2ccc(NC(=O)Nc3ccc(S(N)(=O)=O)cc3)c(F)c2)nc1N1CCOCC1]

¹H NMR (500 MHz, DMSO-d₆): δ9.62 (s, 1H), 9.01 (s, 1H), 8.33-8.32 (d, 1H), 8.09-8.02 (dd, 2H), 7.76-7.75 (d, 2H), 7.64-7.63 (d, 1H), 7.23 (s, 1H), 3.86-3.85 (d, 4H), 3.77-3.75 (d, 4H), 2.32 (s, 3H)

4-{3-[4-(4-Chloro-5-methylsulfanyl-6-morpholin-4-yl-pyrimidin-2-yl)-3-fluoro-phenyl]-ureido}-benzenesulfonamide

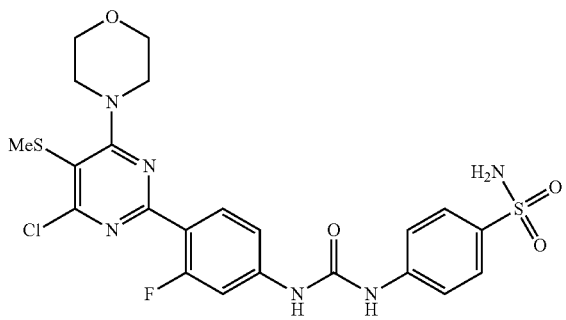 [SMILES: CSc1c(Cl)nc(-c2ccc(NC(=O)Nc3ccc(S(N)(=O)=O)cc3)cc2F)nc1N1CCOCC1]

¹H NMR (500 MHz, DMSO-d₆): δ9.37 (s, 1H), 9.28 (s, 1H), 8.05-8.02 (d, 1H), 7.75-7.73 (d, 2H), 7.63-7.58 (m, 3H), 7.26-7.22 (m, 3H), 3.82-3.81 (d, 4H), 3.73-3.72 (d, 4H), 2.31 (s, 3H)

N-(5-{3-[4-(4-Chloro-5-methylsulfanyl-6-morpholin-4-yl-pyrimidin-2-yl)-phenyl]-ureido}-pyridin-2-yl)-acetamide

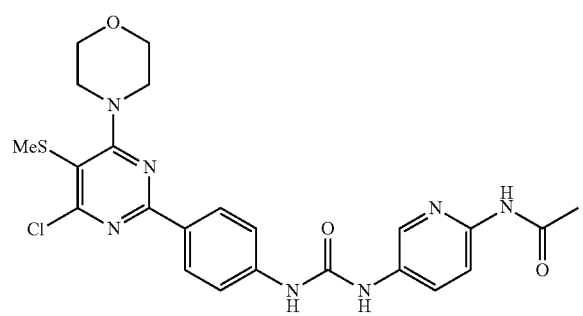 [SMILES: CSc1c(Cl)nc(-c2ccc(NC(=O)Nc3ccc(NC(C)=O)nc3)cc2)nc1N1CCOCC1]

¹H NMR (500 MHz, DMSO-d₆): δ10.38 (s, 1H), 9.20 (s, 1H), 8.90 (s, 1H), 8.43-8.42 (d, 1H), 8.21-8.20 (d, 2H), 7.91-7.89 (d, 1H), 7.84-7.82 (dd, 1H), 7.60-7.59 (d, 2H), 3.84-3.83 (d, 4H), 3.77-3.75 (d, 4H), 2.34 (s, 3H), 2.08-2.06 (d, 3H)

1-[4-(4-Chloro-5-methylsulfanyl-6-morpholin-4-yl-pyrimidin-2-yl)-phenyl]-3-[4-(4-methanesulfonyl-piperazin-1-yl)-phenyl]-urea

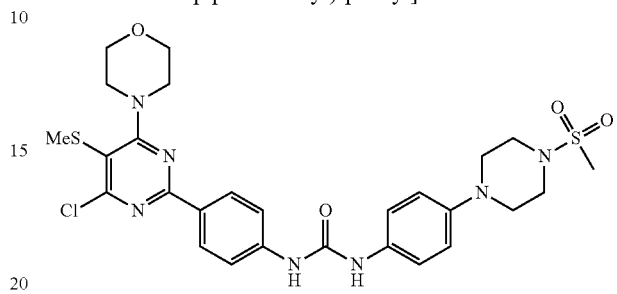

¹H NMR (500 MHz, DMSO-d₆): δ9.01 (s, 1H), 8.61 (s, 1H), 8.20-8.18 (d, 2H), 7.58-7.56 (d, 2H), 7.35-7.33 (d, 2H), 6.94-6.93 (d, 2H), 3.85-3.83 (d, 4H), 3.77-3.75 (d, 4H), 3.25-3.22 (d, 4H), 3.17-3.15 (d, 4H), 2.92 (s, 3H), 2.34 (s, 3H)

4-[3-(6-Chloro-5-methylsulfanyl-4-morpholin-4-yl-[2,5']bipyrimidinyl-2'-yl)-ureido]-benzenesulfonamide

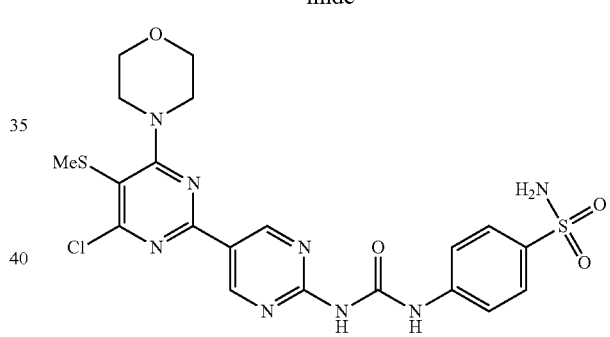

¹H NMR (500 MHz, DMSO-d₆): δ11.85 (s, 1H), 10.75 (s, 1H), 9.41 (s, 2H), 7.87-7.85 (d, 2H), 7.80-7.78 (d, 2H), 7.27 (s, 2H), 3.91-3.90 (d, 4H), 3.77-3.75 (d, 4H), 2.35 (s, 3H)

1-[4-(4-Chloro-5-methylsulfanyl-6-morpholin-4-yl-pyrimidin-2-yl)-phenyl]-3-(2-oxo-2,3-dihydro-benzooxazol-6-yl)-urea

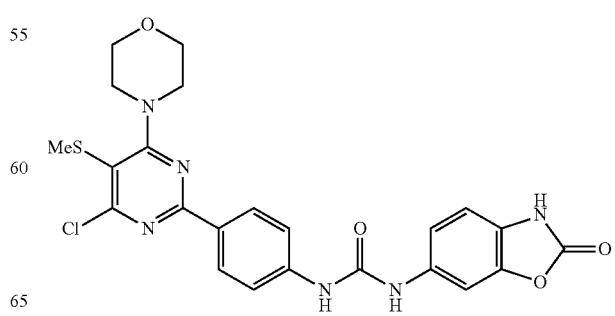

¹H NMR (500 MHz, DMSO-d₆): δ11.49 (s, 1H), 9.07 (s, 1H), 8.87 (s, 1H), 8.21-8.20 (d, 2H), 7.59-7.58 (d, 3H), 7.09-7.07 (d, 1H), 7.02-7.00 (d, 1H), 3.84 (d, 4H), 3.76 (d, 4H), 2.34 (s, 3H)

1-[4-(4-Chloro-5-methylsulfanyl-6-morpholin-4-yl-pyrimidin-2-yl)-phenyl]-3-[4-(morpholine-4-sulfonyl)-phenyl]-urea

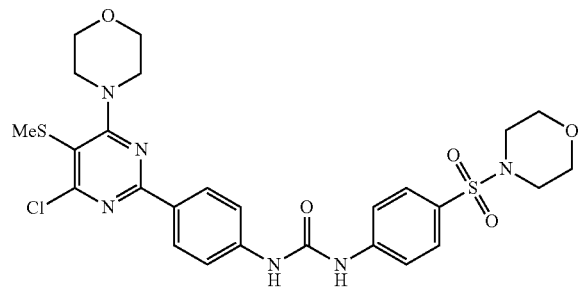 [SMILES: CSc1c(Cl)nc(-c2ccc(NC(=O)Nc3ccc(S(=O)(=O)N4CCOCC4)cc3)cc2)nc1N1CCOCC1]

¹H NMR (500 MHz, DMSO-d₆): δ9.36 (s, 1H), 9.23 (s, 1H), 8.23-8.22 (d, 2H), 7.74-7.72 (d, 2H), 7.67-7.65 (d, 2H), 7.62-7.61 (d, 2H), 3.84 (d, 4H), 3.76 (d, 4H), 3.63 (s, 4H), 2.84 (s, 4H), 2.34 (s, 3H)

1-[4-(4-Chloro-5-methylsulfanyl-6-morpholin-4-yl-pyrimidin-2-yl)-phenyl]-3-[4-(4-dimethylamino-piperidine-1-carbonyl)-phenyl]-urea

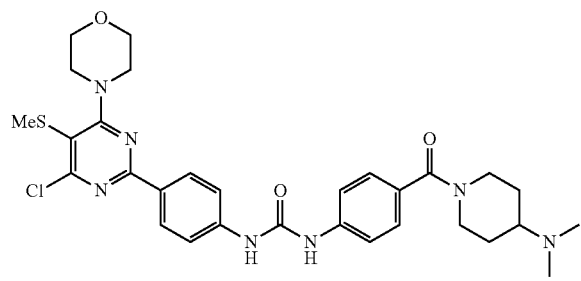 [SMILES: CSc1c(Cl)nc(-c2ccc(NC(=O)Nc3ccc(C(=O)N4CCC(N(C)C)CC4)cc3)cc2)nc1N1CCOCC1]

¹H NMR (500 MHz, DMSO-d₆): δ9.24 (s, 1H), 9.14 (s, 1H), 8.22-8.20 (d, 2H), 7.61-7.59 (d, 2H), 7.54-7.52 (d, 2H), 7.36-7.34 (d, 2H), 3.84-3.83 (d, 4H), 3.77-3.75 (d, 4H), 2.72 (b, 4H), 2.38 (s, 6H), 2.36-2.34 (m, 4H), 1.84 (b, 2H), 1.43-1.41 (b, 2H)

Example 5

Preparation of Compounds of Formula (I) in Scheme 3

5-(Methylthio)pyrimidine-2,4-diol

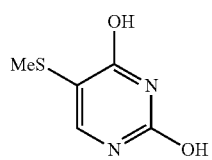

5-iodouracil (476 mg, 2 mmole) was placed in a dry and argon-flushed Schlenk-tube equipped with a magnetic stirring bar and a septum. With vigorous stirring, the substrate was dried for 15 min in high vacuum to exclude the presence of water in the hygroscopic substrate. Then, a solution of LiCl in THF (0.5M; 8 ml; 4 mmole, 2.0 eq) was added and after stirring for some minutes at r.t., the substrate dissolved to give a clear and colourless solution. The solution was cooled to −20° C. and MeMgCl (3M in THF; 1.33 ml, 4 mmole, 2 eq) was added dropwise. After completion of the addition, the resulting clear solution was stirred at −20° C. for 20 min. Afterward, i-PrMgCl (1.32 M in THF; 1.82 ml, 2.40 mmole, 1.20 eq) was added slowly and the resulting mixture was allowed to warm up to room temperature. After one hour, a thick, grayish slurry had formed and the mixture was cooled to −20° C. and S-methyl methanesulfonothioate (328 mg, 2.6 mmole, 1.3 eq) was obtained. Afterwards, the mixture was warmed up to r.t. and stirred at that temperature until TLC indicated completion of the reaction. After quenching with MeOH, the mixture was transferred to a separation funnel containing water (40 ml). By careful addition of 2.0 M HCl, the pH of the mixture was adjusted to ca. 5-6. The aqueous layer was extracted with EA, the combined organic layers were dried (Na₂SO₄) and evaporated. Recrystallization from MeOH afforded the product as a colorless, crystalline solid which was dried in high vacuum (64%).

¹H NMR (500 MHz, DMSO-d₆): δ7.41 (s, 1H), 2.49 (s, 3H)

2,4-Dichloro-5-(methylthio)pyrimidine

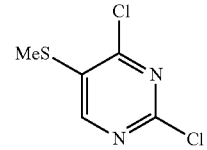

5-(methylthio)pyrimidine-2,4-diol (0.5 g, 3.16 mmole), POCl₃ (3 ml) and dimethylaniline (0.5 ml) were heated to reflux for 12 hrs. The mixture was cooled to 0° C. and carefully poured over ice. The white solid formed was separated by filtration and dried under vacuum to afford the product 2,4-dichloro-5-(methylthio)pyrimidine (0.49 g, 80%).

¹H NMR (500 MHz, CDCl₃-d₁): δ8.29 (s, 1H), 2.55 (s, 3H)

4-(2-Chloro-5-(methylthio)pyrimidin-4-yl)morpholine

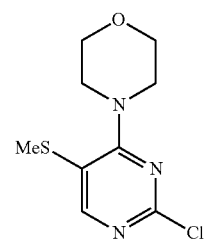 [SMILES: CSc1cnc(Cl)nc1N1CCOCC1]

A solution of the 2,4-dichloro-5-(methylthio)pyrimidine (1.16 g, 6 mmole) in acetone (10 ml) at 0° C. containing Na$_2$CO$_3$ (1.1 eq, 6.6 mmole, 0.7 g) was treated dropwise with a solution of morpholine (1.0 eq, 6.6 mmole, 0.6 ml) in acetone (2 ml) and stirred for 1 hr at 0° C. TLC (EA:Hex=1:2, Rf=0.6) showed completion of the reaction to give two products. The acetone was removed in vacuo, the residue was partitioned between water and EA, and the organic layer was dried (MgSO$_4$) and evaporated in vacuo. Column chromatography (EA/Hex=1/6) gave the product (700 mg, 47%).

$^1$H NMR (500 MHz, CDCl$_3$-d$_1$): δ8.13 (s, 1H), 3.79-3.82 (m, 8H), 2.39 (s, 3H)

4-(5-(Methylthio)-4-morpholinopyrimidin-2-yl)benzenamine

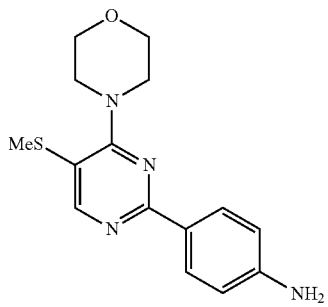

A mixture of 4-(2-chloro-5-(methylthio)pyrimidin-4-yl) morpholine (0.3 g, 1.22 mmole), 4-aminophenylboronic acid pinacol ester (0.58 g, 2.68 mmole), sodium bicarbonate (0.28 g, 2.68 mmole), Pd(PPh$_3$)$_4$ (0.14 g, 0.122 mmole), dioxane (15 ml) and H$_2$O (3.5 ml) was heated to reflux. After 12 hrs, the reaction mixture was cooled, diluted with EA, washed with brine, and dried (MgSO$_4$), and the solvent was removed in vacuo. Purification on silica gel (EA/Hex=1/2) yielded the desired compound (180 mg, 49%).

$^1$H NMR (500 MHz, DMSO-d$_6$): δ 8.33 (s, 1H), 8.01~8.03 (d, 2H), 6.58~6.60 (d, 2H), 5.59 (s, 2H), 3.73~3.74 (d, 4H), 3.64~3.66 (d, 4H), 2.42 (s, 3H)

3-(5-(Methylthio)-4-morpholinopyrimidin-2-yl)phenol

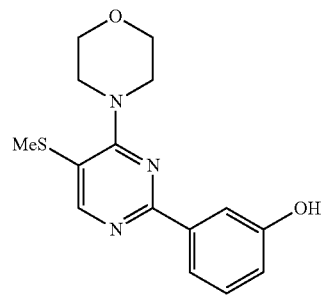 [SMILES: CSc1cnc(-c2cccc(O)c2)nc1N1CCOCC1]

$^1$H NMR (500 MHz, CDCl$_3$-d$_1$): δ8.37 (s, 1H), 7.92~7.94 (d, 2H), 7.85 (s, 1H), 7.30~7.33 (m, 1H), 6.93~6.95 (m, 1H), 3.85~3.87 (m, 4H), 3.79~3.80 (m, 4H), 2.44 (s, 3H)

4-(2-(4-(Methylsulfonyl)phenyl)-5-(methylthio)pyrimidin-4-yl)morpholine

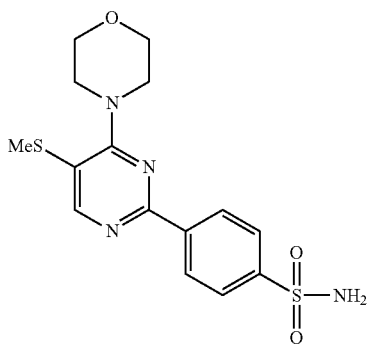 [SMILES: CSc1cnc(-c2ccc(S(N)(=O)=O)cc2)nc1N1CCOCC1]

$^1$H NMR (500 MHz, DMSO-d$_6$): δ 8.46~8.48 (m, 3H), 7.91~7.93 (m, 2H), 7.42 (br, 2H), 3.75~3.77 (m, 4H), 3.68~3.69 (m, 4H), 2.49 (s, 3H)

1-(4-(5-(Methylthio)-4-morpholinopyrimidin-2-yl) phenyl)-3-phenylurea

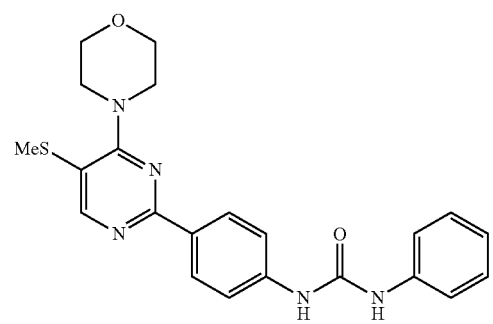 [SMILES: CSc1cnc(-c2ccc(NC(=O)Nc3ccccc3)cc2)nc1N1CCOCC1]

A mixture of 4-(5-(methylthio)-4-morpholinopyrimidin-2-yl)benzeneamine (0.1 g, 0.33 mmole), co-solvent (5 ml, DMF/THF=6/40) and phenyl isocyanate (0.2 ml, 0.92 mmole) was heated to 80° C. After 12 hrs, the reaction mixture was cooled, and the THF removed in vacuo. Then the mixture was diluted with EA, washed with brine, and dried (MgSO$_4$). The solvent was removed in vacuo. Purification of the residue on silica gel (EA/Hex=1/2) yielded the desired compound (42.2 mg, 30.4%).

$^1$H NMR (500 MHz, DMSO-d$_6$): δ 9.01 (s, 1H), 8.82 (s, 1H), 8.41 (s, 1H), 8.24~8.26 (d, 2H) 7.56~7.57 (d, 2H), 7.46~7.47 (d, 2H), 7.27~7.30 (m, 2H), 6.98 (m, 1H), 3.74 (s, 4H), 3.68 (s, 4H), 2.47 (s, 3H)

1-Ethyl-3-(4-(5-(methylthio)-4-morpholinopyrimidin-2-yl)phenyl)urea

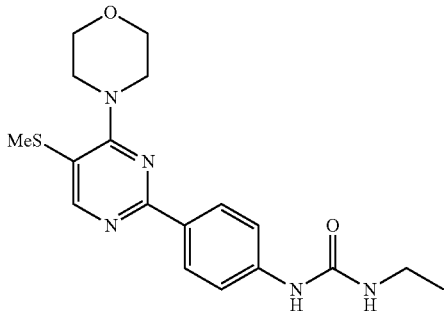 [SMILES: CCNC(=O)Nc1ccc(-c2ncc(SC)c(N3CCOCC3)n2)cc1]

¹H NMR (500 MHz, DMSO-d₆): δ 8.71 (s, 1H), 8.39 (s, 1H), 8.17~8.19 (d, 2H), 7.47~7.49 (d, 2H), 6.20~6.22 (m, 2H), 3.73~3.75 (m, 4H), 3.65~3.67 (m, 4H), 3.10~3.12 (m, 2H), 2.36 (s, 3H), 1.04~1.06 (m, 3H)

1-(3,4-Difluorophenyl)-3-(4-(5-(methylthio)-4-morpholinopyrimidin-2-yl)phenyl)urea

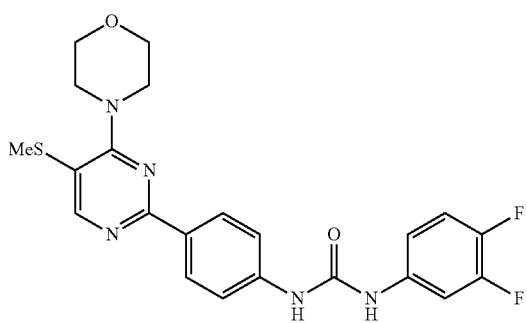 [SMILES: CSc1cnc(-c2ccc(NC(=O)Nc3ccc(F)c(F)c3)cc2)nc1N1CCOCC1]

¹H NMR (500 MHz, DMSO-d₆): δ 9.05 (s, 1H), 9.01 (s, 1H), 8.41 (s, 1H), 8.24~8.26 (d, 2H), 7.67~7.70 (m, 1H), 7.57~7.66 (d, 2H), 7.34~7.36 (m, 1H), 7.13~7.15 (br, 1H), 3.74 (s, 4H), 3.68 (s, 4H), 2.48 (s, 3H)

1-(4-Fluorophenyl)-3-(4-(5-(methylthio)-4-morpholinopyrimidin-2-yl)phenyl)urea

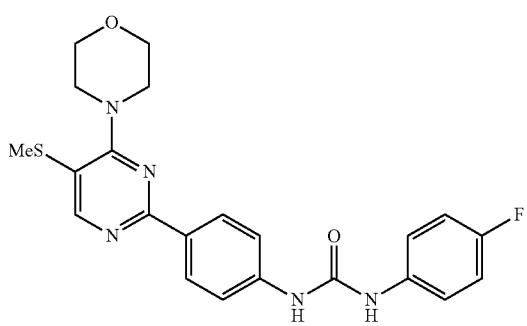 [SMILES: CSc1cnc(-c2ccc(NC(=O)Nc3ccc(F)cc3)cc2)nc1N1CCOCC1]

¹H NMR (500 MHz, DMSO-d₆): δ 8.41 (s, 3H), 8.21~8.23 (d, 2H), 7.57~7.59, (d, 2H), 7.48~7.50 (m, 2H), 7.08~7.12 (m, 2H), 3.75 (s, 4H), 3.67 (s, 4H), 2.47 (s, 3H).

Phenyl 4-(5-(methylthio)-4-morpholinopyrimidin-2-yl)phenylcarbamate

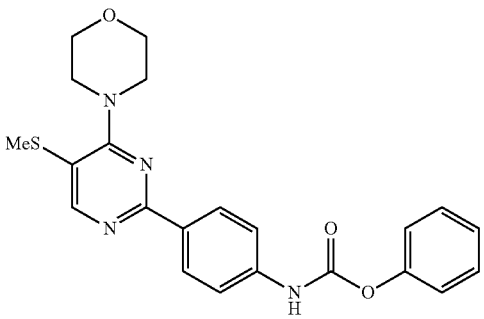 [SMILES: CSc1cnc(-c2ccc(NC(=O)Oc3ccccc3)cc2)nc1N1CCOCC1]

The phenyl chloroformate (0.84 ml, 6.68 mmole, 2.5 eq) was added to a mixture of 4-(5-(methylthio)-4morpholinopyrimidin-2-yl)benzeneamine (0.84 g, 2.18 mmole, 1 eq), NaHCO₃(aq) (1M, 6.3 ml, 6.3 mmole 2.2 eq) and ACN (13 ml) at 0□. The reaction mixture was stirred for 8 hrs and then dried. The reaction mixture was partitioned between EA and water, the organic layer was washed with brine, dried over MgSO₄, filtered and evaporated in vacuo. The resulting residue was purified by flash chromatography on silica gel (Hexane/EtOAc 2:1) to give a yellow solid (80%).
¹H NMR (500 MHz, CDCl₃-d₁): δ8.38 (s, 1H), 8.35~8.36 (d, 2H), 7.53~7.55 (d, 2H), 7.39~7.42 (m, 2H), 7.1~7.2 (m, 3H), 3.79~3.87 (d, 8H), 2.44 (s, 3H)

1-(4-(5-(Methylthio)-4-morpholinopyrimidin-2-yl)phenyl)-3-morpholinourea

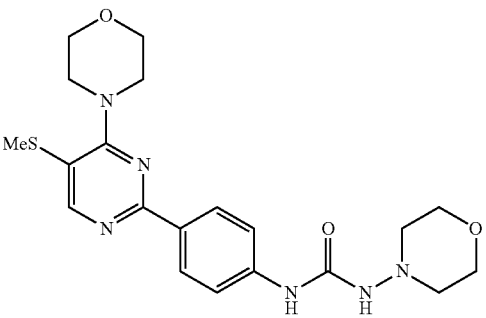 [SMILES: CSc1cnc(-c2ccc(NC(=O)NN3CCOCC3)cc2)nc1N1CCOCC1]

¹H NMR (500 MHz, DMSO-d₆): δ 8.78 (s, 1H), 8.41 (s, 1H), 8.20~8.22 (d, 2H), 7.91 (s, 1H), 7.67~7.69 (d, 2H), 3.66~3.76 (m, 13H), 2.49 (s, 3H)

1-(4-(5-(Methylthio)-4-morpholinopyrimidin-2-yl)phenyl)-3-(pyridin-3-yl)urea

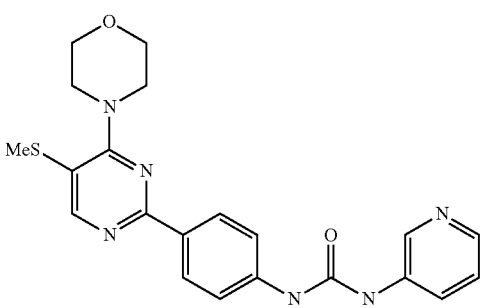

¹H NMR (500 MHz, CD₃OD-d₄): δ8.63 (s, 1H), 8.35 (s, 1H), 8.26~8.28 (d, 2H), 8.19~8.20 (d, 1H), 8.03~8.05 (d, 1H), 7.56~7.57 (d, 2H), 7.37~7.40 (m, 1H), 3.85 (s, 8H), 2.46 (s, 3H)

1-(3-Fluoro-4-morpholinophenyl)-3-(4-(5-(methylthio)-4-morpholinopyrimidin-2-yl)phenyl)urea

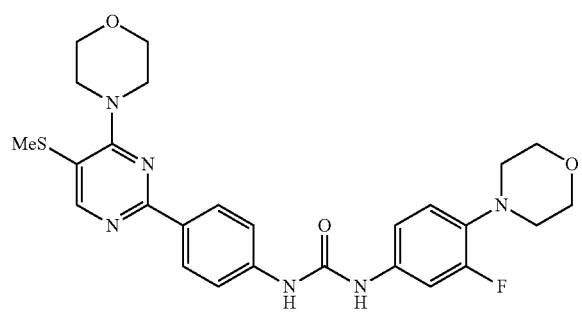 [SMILES: CSc1cnc(-c2ccc(NC(=O)Nc3ccc(N4CCOCC4)c(F)c3)cc2)nc1N1CCOCC1]

¹H NMR (500 MHz, DMSO-d₆): δ 9.07 (s, 1H), 8.91 (s, 1H), 8.41 (s, 1H), 8.23~8.25 (d, 2H), 7.55~7.56 (d, 2H), 7.43~7.44 (d, 1H), 7.07 (d, 1H), 6.98~7.0 (t, 1H), 3.67~3.76 (m, 12H), 2.93~2.94 (s, 4H), 2.48 (s, 3H)

1-(4-(5-(Methylthio)-4-morpholinopyrimidin-2-yl)phenyl)-3-(4-(3-oxomorpholino)phenyl)urea

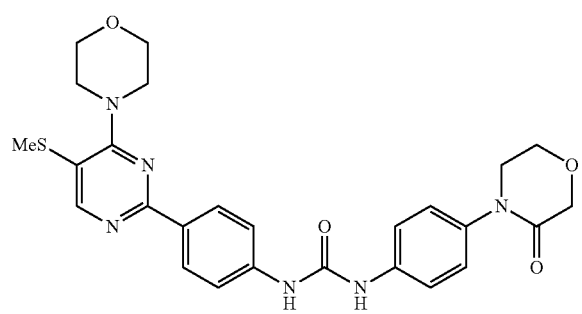 [SMILES: CSc1cnc(-c2ccc(NC(=O)Nc3ccc(N4CCOCC4=O)cc3)cc2)nc1N1CCOCC1]

¹H NMR (500 MHz, DMSO-d₆): δ 9.09 (s, 1H), 8.96 (s, 1H), 8.42 (s, 1H), 8.24~8.26 (d, 2H), 7.56~7.58 (d, 2H), 7.48~7.50 (d, 2H), 7.28~7.30 (d, 2H), 4.18 (s, 2H), 3.95~3.97 (t, 2H), 3.68~3.76 (m, 8H), 2.48 (s, 3H)

1-(4-(4-Methylpiperazin-1-yl)phenyl)-3-(4-(5-(methylthio)-4-morpholinopyrimidin-2-yl)phenyl)urea

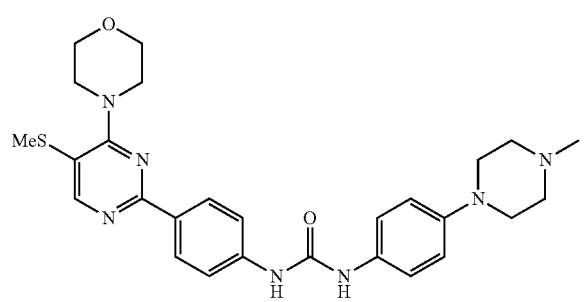 [SMILES: CSc1cnc(-c2ccc(NC(=O)Nc3ccc(N4CCN(C)CC4)cc3)cc2)nc1N1CCOCC1]

¹H NMR (500 MHz, DMSO-d₆): δ 8.94 (s, 1H), 8.58 (s, 1H), 8.41 (s, 1H), 8.22~8.24 (d, 2H), 7.54~7.56 (d, 2H), 7.29~7.31 (d, 2H), 6.86~6.88 (d, 2H), 3.74~3.76 (d, 4H), 3.67~3.68 (d, 4H), 3.03~3.04 (s, 4H), 2.43~2.44 (s, 3H), 2.36 (s, 4H), 2.21 (s, 3H)

1-(4-(5-(Methylthio)-4-morpholinopyrimidin-2-yl)phenyl)-3-(4-thiomorpholinophenyl)urea

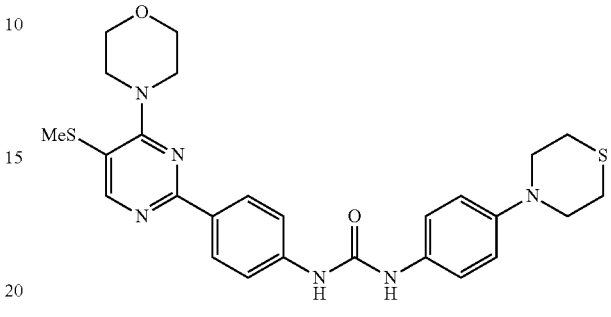

¹H NMR (500 MHz, DMSO-d₆): δ 8.99 (s, 1H), 8.65 (s, 1H), 8.41 (s, 1H), 8.22~8.23 (d, 2H), 7.55~7.57 (d, 2H), 7.31~7.33 (d, 2H), 6.86~6.88 (d, 2H), 3.75~3.76 (d, 4H), 3.67~3.38 (d, 4H), 3.37~3.39 (d, 4H), 2.67~2.68 (d, 4H), 2.47 (s, 3H)

1-(4-(5-(Methylthio)-4-morpholinopyrimidin-2-yl)phenyl)-3-(4-morpholinophenyl)urea

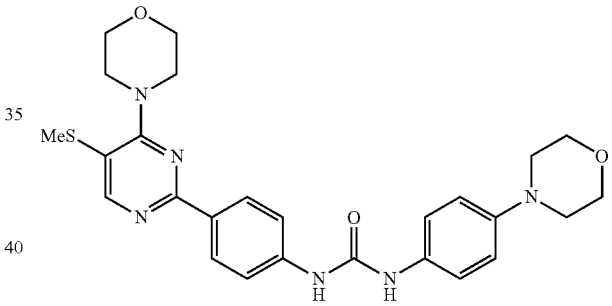

¹H NMR (500 MHz, DMSO-d₆): δ 9.01 (s, 1H), 8.67 (s, 1H), 8.38 (s, 1H), 8.22~8.24 (d, 2H), 7.54~7.56 (d, 2H), 7.28~7.34 (d, 2H), 6.85~6.89 (d, 2H), 3.68~3.76 (m, 8H), 3.67~3.68 (d, 4H), 3.02~3.03 (d, 4H), 2.49 (s, 3H)

1-(4-(5-(Methylthio)-4-morpholinopyrimidin-2-yl)phenyl)-3-(thiazol-2-yl)urea

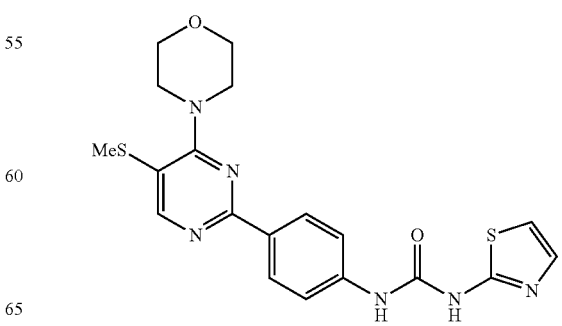

¹H NMR (500 MHz, DMSO-d₆): δ 8.42 (s, 1H), 8.27~8.28 (d, 2H), 7.59~7.67 (d, 2H), 7.38 (s, 1H), 6.85~6.89 (s, 1H), 3.76 (s, 4H), 3.68 (s, 4H), 2.49 (s, 3H)

1-(4-(5-(Methylthio)-4-morpholinopyrimidin-2-yl)phenyl)-3-(3-(trifluoromethyl)phenyl)urea

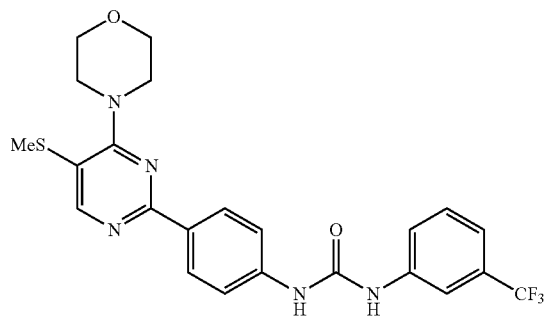

¹H NMR (500 MHz, DMSO-d₆): δ 9.27 (s, 1H), 9.20 (s, 1H), 8.42 (s, 1H), 8.25~8.26 (d, 2H), 8.03 (s, 1H), 7.58~7.59 (d, 3H), 7.50~7.53 (t, 1H), 7.31~7.32 (d, 1H), 3.75 (s, 4H), 3.68 (s, 4H), 2.48 (s, 3H)

Ethyl 4-(3-(4-(5-(methylthio)-4-morpholinopyrimidin-2-yl)phenyl)ureido)benzoate

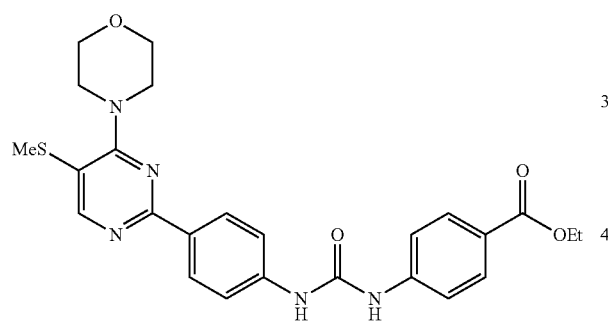

¹H NMR (500 MHz, DMSO-d₆): δ 9.29 (s, 1H), 9.18 (s, 1H), 8.42 (s, 1H), 8.25~8.27 (d, 2H), 7.88~7.90 (d, 2H), 7.57~7.61 (t, 4H), 4.25~4.30 (q, 2H), 3.75~3.76 (d, 4H), 3.67~3.69 (d, 4H), 2.48 (s, 3H), 1.25~1.32 (t, 3H)

1-(4-(5-(Methylthio)-4-morpholinopyrimidin-2-yl)phenyl)-3-(6-morpholinopyridin-3-yl)urea

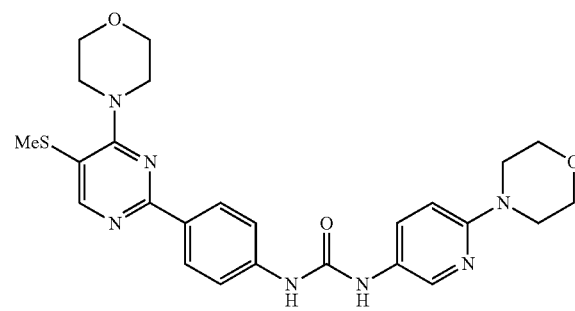 [SMILES: CSc1cnc(-c2ccc(NC(=O)Nc3ccc(N4CCSCC4)cc3)cc2)nc1N1CCOCC1]

¹H NMR (500 MHz, DMSO-d₆): δ 9.01 (s, 1H), 8.67 (s, 1H), 8.41 (s, 1H), 8.19~8.22 (m, 3H), 7.77 (m, 1H), 7.55~7.56 (d, 2H), 6.85~6.89 (d, 1H), 3.75~3.76 (m, 4H), 3.67~3.70 (m, 4H), 2.48 (s, 3H)

1-(6-(4-Methylpiperazin-1-yl)pyridin-3-yl)-3-(4-(5-(methylthio)-4-morpholinopyrimidin-2-yl)phenyl)urea

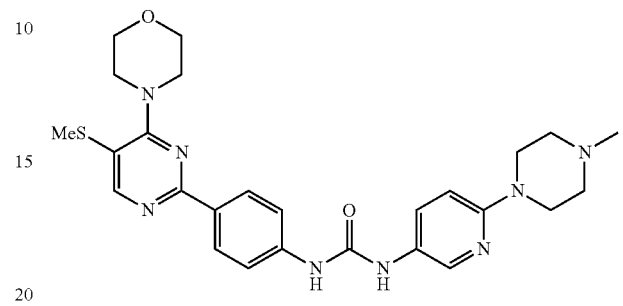

¹H NMR (500 MHz, DMSO-d₆): δ 9.01 (s, 1H), 8.67 (s, 1H), 8.41 (s, 1H), 8.22~8.24 (d, 2H), 8.17 (s, 1H), 7.7 (d, 2H), 7.54~7.56 (d, 2H), 6.85~6.89 (d, 1H), 3.74~3.76 (d, 4H), 3.67~3.68 (d, 4H), 3.37~3.38 (d, 4H), 2.47 (s, 3H), 2.38~2.40 (d, 4H), 2.20 (s, 3H)

4-(3-(4-(5-(Methylthio)-4-morpholinopyrimidin-2-yl)phenyl)ureido)benzamide

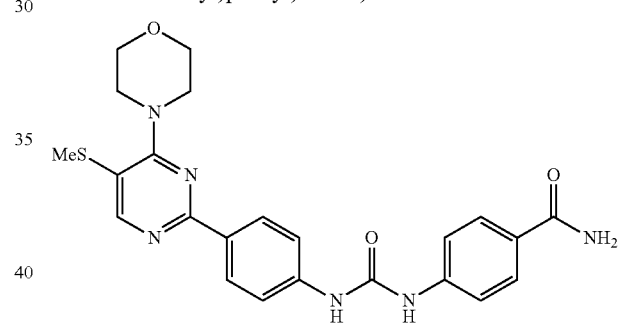

¹H NMR (500 MHz, DMSO-d₆): δ 9.10 (s, 1H), 9.08 (s, 1H), 8.42 (s, 1H), 8.25~8.27 (d, 2H), 7.21~7.83 (m, 3H), 7.57~7.59 (d, 2H), 7.51~7.53 (d, 2H), 7.19 (s, 1H), 3.75~3.76 (d, 4H), 3.67~3.69 (d, 4H), 2.47 (s, 3H)

1-(4-(5-(Methylthio)-4-morpholinopyrimidin-2-yl)phenyl)urea

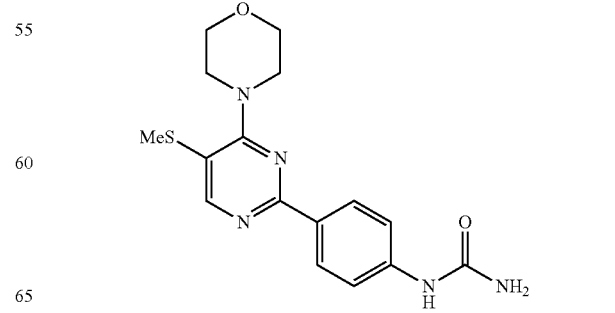

¹H NMR (500 MHz, DMSO-d₆): δ 8.81 (s, 1H), 8.40 (s, 1H), 8.18~8.20 (d, 2H), 7.49~7.50 (d, 2H), 5.96 (d, 2H), 3.74 (s, 4H), 3.67 (s, 4H), 2.46 (s, 3H)

1-(2-Aminophenyl)-3-(4-(5-(methylthio)-4-morpholinopyrimidin-2-yl)phenyl)thiourea

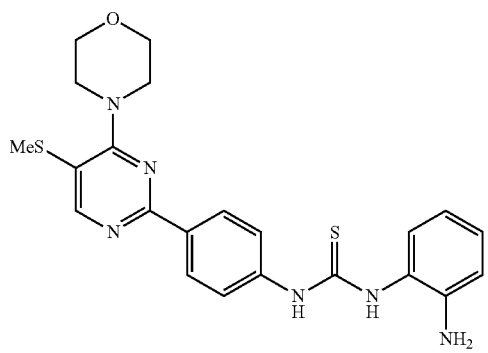 [SMILES: CSc1cnc(-c2ccc(NC(=S)Nc3ccccc3N)cc2)nc1N1CCOCC1]

To a stirred solution of 1,1'-thiocarbonyldiimidazole (0.35 g, 2 mmole), imidazole (27 mg, 0.4 mmole), and CH₃CN (15 ml) at 0° C. was added 4-(5-(methyl-thio)-4-morpholinopyrimidin-2-yl)benzenamine (0.4 g, 1.32 mmole) dissolved in CH₃CN (30 ml) dropwise over 10 minutes. After 10 minutes, the cooling bath was removed. After 3 hours, 1,2-phenylenediamine (0.285 g, 2.64 mmole) was added to the reaction mixture and the reaction mixture was heated to 50° C. for 3 hours and then stirred at ambient temperature for 16 hours. The solvent was removed by evaporation. The residue was chromatographed to give thiourea (10%) as a white solid.

¹H NMR (500 MHz, DMSO-d₆): δ 9.85 (s, 1H), 9.20 (s, 1H), 8.43 (s, 1H), 8.25~8.27 (d, 2H), 7.68~7.70 (d, 2H), 7.09~7.10 (d, 1H), 6.95~6.98 (t, 1H), 6.74~6.76 (d, 1H), 6.55~6.58 (t, 1H), 4.94 (br, 2H), 3.74~3.76 (d, 4H), 3.67~3.69 (d, 4H), 2.49 (s, 3H)

N-(4-(5-(Methylthio)-4-morpholinopyrimidin-2-yl)phenyl)-1H-benzo[d]imidazol-2-amine

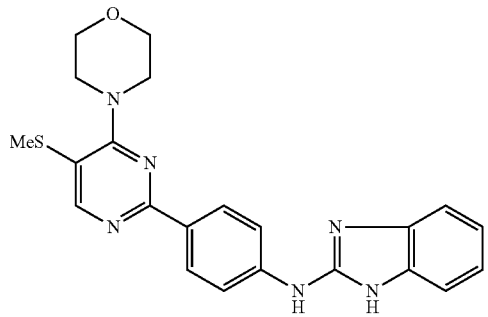 [SMILES: CSc1cnc(-c2ccc(Nc3nc4ccccc4[nH]3)cc2)nc1N1CCOCC1]

A suspension of 1-(2-aminophenyl)-3-(4-(5-(methylthio)-4-morpholinopyrimidin-2-yl)phenyl)thiourea (60 mg, 0.132 mmole) and dicyclohexylcarbodiimide (31 mg, 0.15 mmole) in THF (5 ml) was heated at 64° C. for 20 hr. The cooled mixture was purified by flash chromatography to give a product (40 mg, 73%).

¹H NMR (500 MHz, DMSO-d₆): δ 11.13 (s, 1H), 9.85 (s, 1H), 8.42 (s, 1H), 8.28~8.30 (d, 2H), 7.86~7.88 (d, 2H), 7.31~7.37 (br, 2H), 7.01 (br, 1H), 3.75~3.76 (d, 4H), 3.69~3.70 (d, 4H), 2.47 (s, 3H)

4-(3-(4-(5-(Methylthio)-4-morpholinopyrimidin-2-yl)phenyl)ureido)benzenesulfonamide

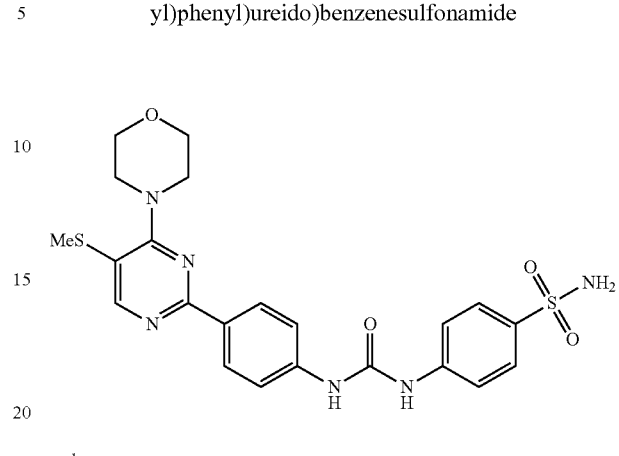

¹H NMR (500 MHz, DMSO-d₆): δ 8.42 (s, 1H), 8.25~8.27 (d, 2H), 7.72~7.74 (d, 2H), 7.63~7.65 (d, 2H), 7.59~7.60 (d, 2H), 7.20 (s, 2H), 3.75~3.76 (d, 4H), 3.68~3.69 (d, 4H)

1-(3,4-Dimethoxyphenyl)-3-(4-(5-(methylthio)-4-morpholinopyrimidin-2-yl)phenyl)urea

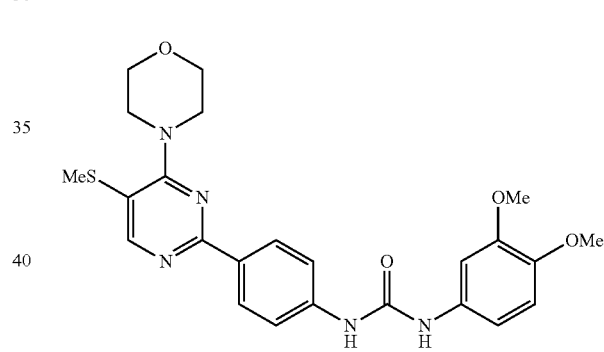

¹H NMR (500 MHz, DMSO-d₆): δ 8.98 (s, 1H), 8.71 (s, 1H), 8.41 (s, 1H), 8.23~8.24 (d, 2H), 7.55~7.57 (d, 2H), 7.21 (s, 1H), 6.87~6.88 (t, 2H), 3.67~3.76 (m, 14H), 2.47 (s, 3H)

4-(3-(4-(5-(Methylthio)-4-morpholinopyrimidin-2-yl)phenyl)ureido)benzoic acid

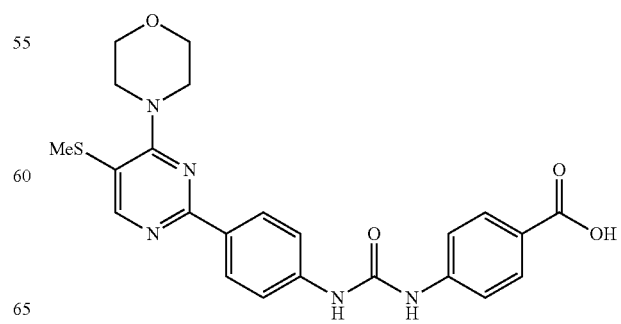

¹H NMR (500 MHz, DMSO-d₆): δ 9.47 (br, 2H), 8.35 (s, 1H), 8.24~8.25 (d, 2H), 7.87~7.88 (d, 2H), 7.63~7.64 (d, 2H), 7.57~7.59 (d, 2H), 3.87 (s, 5H), 3.78 (s, 6H), 1-(Benzo[d][1,3]dioxol-5-yl)-3-(4-(5-(methylthio)-4-morpholinopyrimidin-2-yl)phenyl)urea

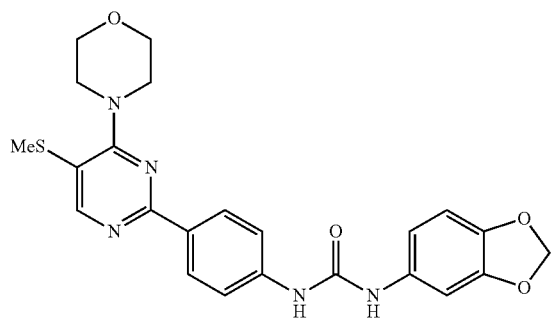 [SMILES: CSc1cnc(-c2ccc(NC(=O)Nc3ccc4c(c3)OCO4)cc2)nc1N1CCOCC1]

¹H NMR (500 MHz, DMSO-d₆): δ 8.44 (s, 1H) 8.26~8.28 (d, 2H), 7.64~7.66 (d, 2H), 7.50~7.54 (t, 3H), 7.33~7.35 (t, 2H), 4.19 (s, 2H), 3.97~3.98 (t, 2H), 3.67~3.76 (m, 7H), 2.51 (s, 3H)

1-(6-Bromopyridin-3-Yl)-3-(4-(5-(methylthio)-4-morpholinopyrimidin-2-yl)phenyl)urea

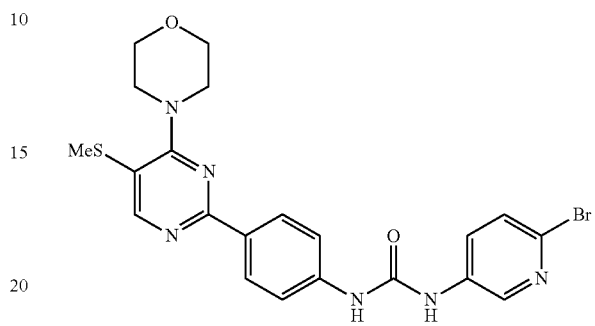

¹H NMR (500 MHz, DMSO-d₆): δ 9.05 (s, 1H), 8.81 (s, 1H), 8.41 (s, 1H) 8.22~8.24 (d, 2H), 7.54~7.56 (d, 2H), 7.21 (s, 1H), 6.82~6.84 (d, 1H), 6.77~6.79 (d, 1H), 5.97 (s, 2H), 3.74~3.75 (d, 4H), 3.67~3.68 (d, 4H), 2.47 (s, 3H)

1-(5-(4-Methylpiperazin-1-yl)pyridin-2-yl)-3-(4-(5-(methylthio)-4-morpholinopyrimidin-2-yl)phenyl)urea

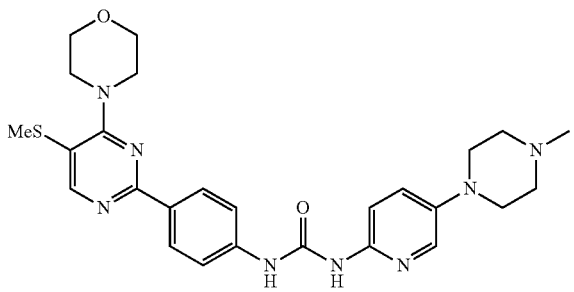 [SMILES: CSc1cnc(-c2ccc(NC(=O)Nc3ccc(N4CCN(C)CC4)cn3)cc2)nc1N1CCOCC1]

¹H NMR (500 MHz, DMSO-d₆): δ 9.20~9.25 (d, 2H), 8.48 (s, 1H), 8.41 (s, 1H), 8.25~8.26 (d, 2H), 7.90~7.92 (d, 1H), 7.54~7.58 (t, 3H), 3.68~3.75 (d, 8H), 2.47 (s, 3H)

1-Isopropyl-3-(4-(5-(methylthio)-4-morpholinopyrimidin-2-yl)phenyl)urea

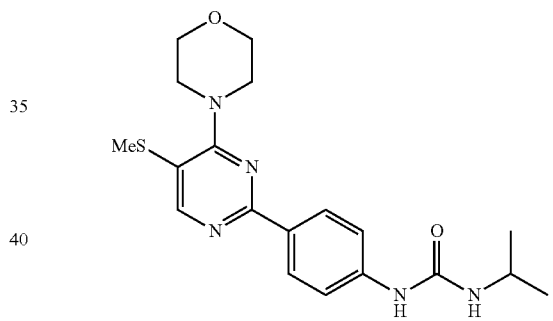

¹H NMR (500 MHz, DMSO-d₆): δ 10.57 (br, 1H), 9.29 (s, 1H), 8.42 (s, 1H) 8.25~8.27 (d, 2H), 7.95 (s, 1H), 7.61~7.62 (d, 2H), 7.45~7.46 (t, 2H), 3.75~3.76 (d, 4H), 3.67~3.68 (d, 4H), 3.56 (d, 4H), 3.08 (s, 4H), 2.47 (s, 3H), 2.21 (s, 3H)

1-(4-(5-(Methylthio)-4-morpholinopyrimidin-2-Yl)phenyl)-3-(4-(3-oxomorpholino)phenyl)thiourea

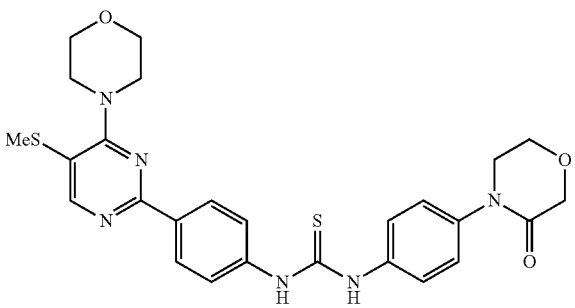

¹H NMR (500 MHz, DMSO-d₆): δ 8.61 (s, 1H), 8.39 (s, 1H), 8.17~8.19 (d, 2H), 7.46~7.48 (d, 2H), 6.14~6.15 (d, 1H), 3.75~3.78 (d, 5H), 3.66~3.67 (d, 4H), 2.46 (s, 3H), 1.09~1.10 (d, 6H)

1-Tert-butyl-3-(4-(5-(methylthio)-4-morpholinopyrimidin-2-yl)phenyl)urea

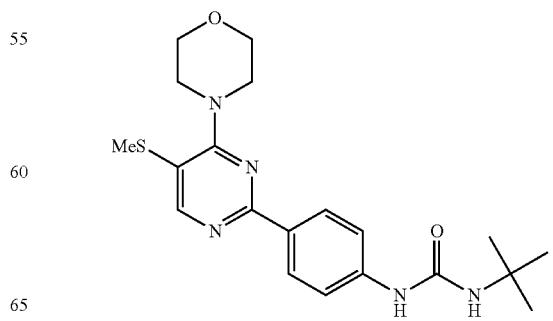

¹H NMR (500 MHz, DMSO-d₆): δ 8.56 (br, 1H), 8.39 (s, 1H), 8.17~8.18 (d, 2H), 7.44~7.46 (d, 2H), 6.14 (br, 1H), 3.74~3.76 (d, 4H), 3.66~3.67 (d, 4H), 2.46 (s, 3H), 1.29 (s, 9H)

1-(4-(2-(Dimethylamino)ethoxy)phenyl)-3-(4-(5-(methylthio)-4-morpholinopyrimidin-2-yl)phenyl)urea

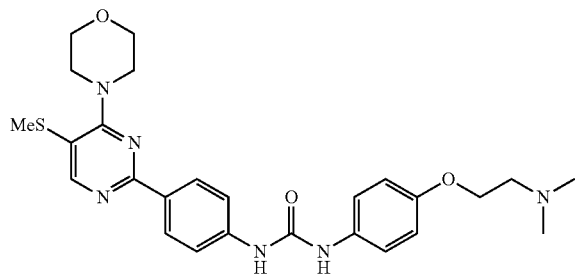 [SMILES: CSc1cnc(-c2ccc(NC(=O)Nc3ccc(OCCN(C)C)cc3)cc2)nc1N1CCOCC1]

¹H NMR (500 MHz, DMSO-d₆): δ 8.97 (s, 1H), 8.62 (s, 1H), 8.41 (s, 1H), 8.22~8.24 (d, 2H), 7.54~7.56 (d, 2H), 7.34~7.36 (d, 2H), 6.86~6.88 (d, 2H), 3.98~4.00 (t, 2H), 3.74~3.76 (d, 4H), 3.67~3.68 (d, 4H), 2.59~2.60 (d, 2H), 2.49 (s, 3H), 2.20 (s, 6H)

1,3-Bis(4-(5-(methylthio)-4-morpholinopyrimidin-2-yl)phenyl)urea

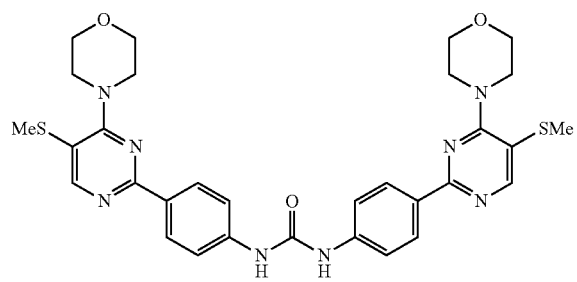 [SMILES: CSc1cnc(-c2ccc(NC(=O)Nc3ccc(-c4ncc(SC)c(N5CCOCC5)n4)cc3)cc2)nc1N1CCOCC1]

¹H NMR (500 MHz, DMSO-d₆): δ 9.24 (s, 1H), 8.42 (s, 1H), 8.25~8.27 (d, 2H), 7.58~7.60 (d, 2H), 3.75~3.76 (d, 4H), 3.68~3.69 (d, 4H)

3-Fluoro-4-(5-(methylthio)-4-morpholinopyrimidin-2-yl)benzenamine

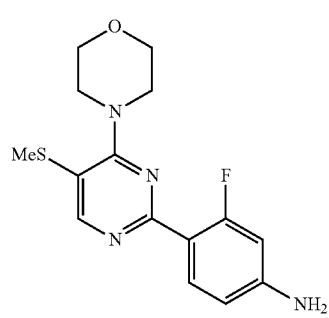 [SMILES: CSc1cnc(-c2ccc(N)cc2F)nc1N1CCOCC1]

¹H NMR (500 MHz, CDCl₃-d₁): δ8.38 (s, 1H), 7.94~7.98 (t, 2H), 7.53~7.55 (d, 2H), 7.39~7.42 (m, 2H), 7.1~7.2 (m, 3H), 3.79~3.87 (d, 8H), 2.44 (s, 3H)

N-(4-(3-(4-(5-(methylthio)-4-morpholinopyrimidin-2-yl)phenyl)ureido)phenyl)methanesulfonamide

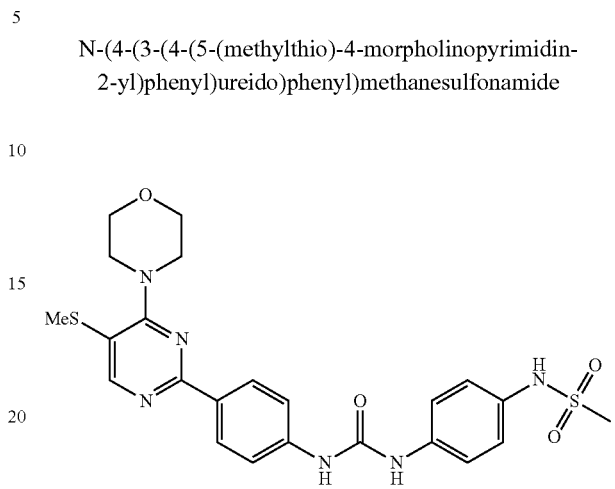

¹H NMR (500 MHz, DMSO-d₆): δ 9.45 (s, 1H), 9.16 (s, 1H), 8.98 (s, 1H), 8.41 (s, 1H), 8.23~8.25 (d, 2H), 7.56~7.57 (d, 2H), 7.42~7.44 (d, 2H), 7.13~7.15 (d, 2H), 3.74~3.75 (d, 4H), 3.67~3.68 (d, 4H), 2.91 (s, 3H), 2.48 (s, 3H)

Phenyl 4-(5-(methylsulfinyl)-4-morpholinopyrimidin-2-yl)phenylcarbamate

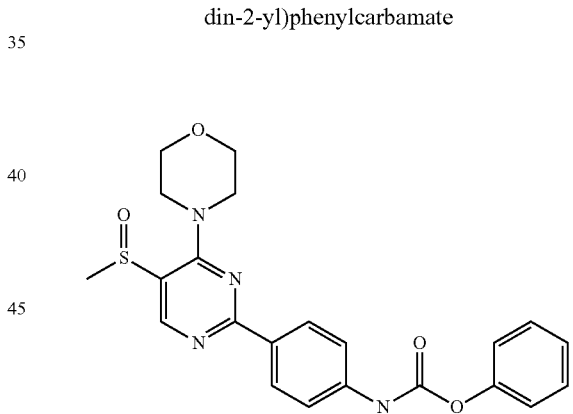

The H₂O₂ (0.32 ml, 3.13 mmole) solution was added to a stirred solution of phenyl 4-(5-(methylthio)-4-morpholinopyrimidin-2-yl)phenylcarbamate (0.54 g, 1.28 mmole), CH₂C₂ (7 ml), Ac₂O (0.13 ml), and silica gel (230~400 mesh, 200 mg). The solution was stirred at room temperature for 2~3 hrs, and quenched with NaHSO₃₍ₐq₎ (70 ml), and NaHCO₃₍ₐq₎ (70 ml), the solvent was removed, the residue was chromatographed to give the product (71%) as a white solid.

¹H NMR (500 MHz, CDCl₃-d₁): δ8.97 (s, 1H), 8.43 (s, 1H), 8.41 (s, 1H), 7.56~7.58 (t, 2H), 7.39~7.42 (t, 2H), 7.17~7.27 (m, 3H), 3.81~3.87 (m, 6H), 3.48~3.68 (m, 2H), 2.79 (s, 3H)

1-(4-(5-(Methylsulfinyl)-4-morpholinopyrimidin-2-yl)phenyl)-3-(4-(3-oxomorpholino)phenyl)urea

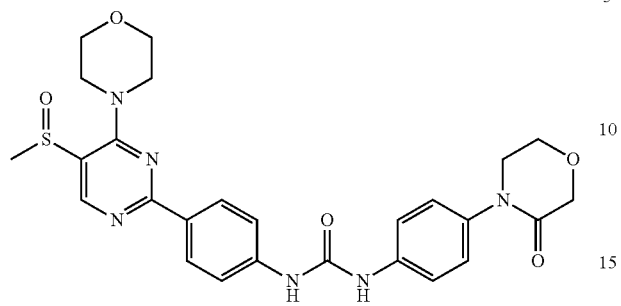

¹H NMR (500 MHz, DMSO-d₆): δ 9.09 (s, 1H), 8.92 (s, 1H), 8.76 (s, 1H), 8.31~8.32 (d, 2H), 7.59~7.61 (d, 2H), 7.48~7.50 (d, 2H), 7.28~7.30 (d, 2H), 4.18 (s, 2H), 3.96 (d, 4H), 3.62~3.73 (m, 10H), 2.79 (s, 3H)

1-(4-(Methylsulfonyl)phenyl)-3-(4-(5-(methylthio)-4-morpholinopyrimidin-2-yl)phenyl)urea

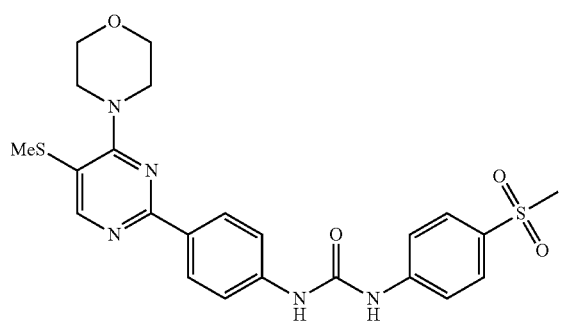 [SMILES: CSc1cnc(-c2ccc(NC(=O)Nc3ccc(S(C)(=O)=O)cc3)cc2)nc1N1CCOCC1]

¹H NMR (500 MHz, DMSO-d₆): δ 9.61 (br, 1H), 9.33 (br, 1H), 8.42 (s, 1H), 8.25~8.27 (d, 2H), 7.81~7.83 (d, 2H), 7.71~7.72 (d, 2H), 7.59~7.61 (d, 2H), 3.75~3.76 (d, 4H), 3.68~3.69 (d, 4H), 3.15 (s, 3H)

1-(4-(4-(Methylsulfonyl)piperazin-1-yl)phenyl)-3-(4-(5-(methylthio)-4-morpholinopyrimidin-2-yl)phenyl)urea

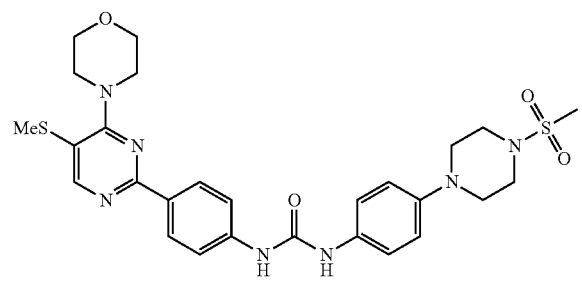 [SMILES: CSc1cnc(-c2ccc(NC(=O)Nc3ccc(N4CCN(S(C)(=O)=O)CC4)cc3)cc2)nc1N1CCOCC1]

¹H NMR (500 MHz, DMSO-d₆): δ 9.38 (br, 1H), 9.02 (br, 1H), 8.41 (s, 1H), 8.21~8.23 (d, 2H), 7.56~7.58 (d, 2H), 7.35~7.37 (d, 2H), 6.91~6.93 (d, 2H), 3.74~3.76 (d, 4H), 3.56~3.68 (d, 4H), 3.24~3.25 (d, 4H), 3.15~3.16 (d, 4H), 2.92 (s, 3H), 2.47 (s, 3H)

5-(Methylthio)-4-morpholino-2,5'-bipyrimidin-2'-amine

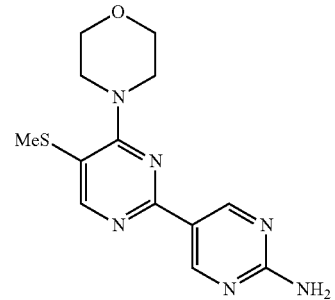

¹H NMR (500 MHz, DMSO-d₆): δ 9.03 (s, 2H), 8.36 (s, 1H), 7.14 (s, 2H), 3.72~3.73 (d, 4H), 3.67~3.68 (d, 4H), 2.49 (s, 3H)

1-(4-(5-(Methylthio)-4-morpholinopyrimidin-2-yl)phenyl)-3-(2-oxo-2,3-dihydrobenzo[d]oxazol-6-yl)urea

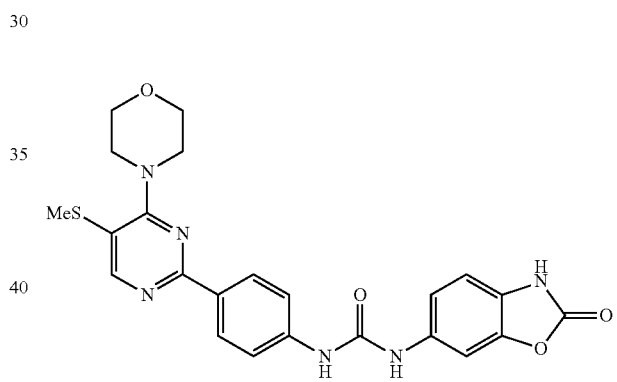

¹H NMR (500 MHz, DMSO-d₆): δ 9.00 (s, 1H), 8.58 (s, 1H), 8.41 (s, 1H), 8.23~8.25 (d, 2H), 7.55~7.57 (d, 3H), 7.05~7.07 (d, 1H), 6.97~6.99 (d, 1H), 3.74~3.76 (d, 4H), 3.67~3.69 (d, 4H), 2.48 (s, 3H)

1-(4-(5-(Methylthio)-4-morpholinopyrimidin-2-yl)phenyl)-3-(4-(morpholine-4-carbonyl)phenyl)urea

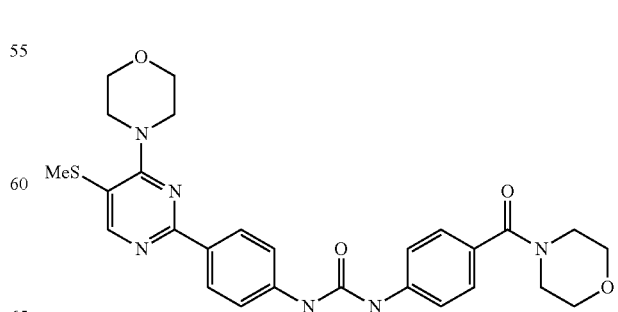

¹H NMR (500 MHz, DMSO-d₆): δ 8.41 (s, 1H), 8.20~8.22 (d, 2H), 7.60~7.66 (m, 4H), 7.31~7.33 (d, 2H), 3.74~3.75 (d, 4H), 3.68 (s, 4H), 3.59 (s, 4H), 3.50 (s, 4H), 2.48 (s, 3H)

1-(4-(5-(Methylthio)-4-morpholinopyrimidin-2-yl) phenyl)-3-(pyridin-4-yl)urea

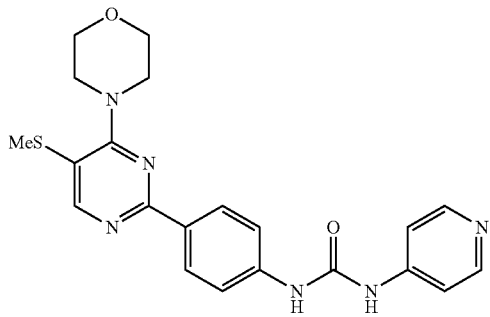 [SMILES: CSc1cnc(-c2ccc(NC(=O)Nc3ccncc3)cc2)nc1N1CCOCC1]

¹H NMR (500 MHz, DMSO-d₆): δ 9.35 (s, 1H), 9.28 (s, 1H), 8.42 (s, 1H), 8.36~8.37 (d, 2H), 8.26~8.27 (d, 2H), 7.57~7.58 (d, 2H), 7.44~7.45 (d, 2H), 3.75~3.76 (d, 4H), 3.67~3.68 (d, 4H), 2.48 (s, 3H)

Example 6

Preparation of Compounds of Formula (I) in Scheme 6

4-Chloro-2,6-dimethoxy-5-methylsulfanyl-pyrimidine

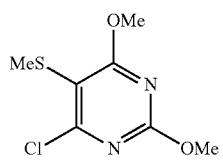 [SMILES: COc1nc(Cl)c(SC)c(OC)n1]

A mixture of 2,4,6-trichloro-5-methylsulfanyl-pyrimidine (5.00 g, 21.73 mmol.) was added dropwise to a slurry of sodium methoxide (2.47 g, 45.65 mmol, 2.1 eq) in MeOH (80 ml) in ice bath at 0° C., then the reaction mixture was stirred at r.t, for 2 hrs and dried, and the solvent was evaporated. The reaction mixture was partitioned between EA and 0.1 N HCl. The organic layer was washed with brine, dried over MgSO₄, filtered and evaporated in vacuo. The resulting residue was purified by flash chromatography on silica gel (Hexane/EtOAc 9:1) to give a gray solid 3.36 g (70.2%).

¹H NMR (500 MHz, CDCl₃-d₁): δ4.07 (s, 3H), 4.00 (s, 3H), 2.33 (s, 3H)

2-(2,6-Dimethoxy-5-methylsulfanyl-pyrimidin-4-yl)-malonic acid dimethyl ester

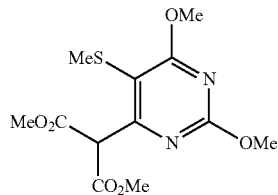

A mixture of 4-chloro-2,6-dimethoxy-5-methylsulfanyl-pyrimidine (3.30 g, 15.0 mmol.) and dimethyl malonate (11.88 g, 90.0 mmol, 6.0 eq.) was added dropwise to slurry of sodium hydride (60% w/w) (3.67 g, 90.0 mmol, 6.0 eq) in DMF (80 ml) in ice bath at 0° C., then the reaction mixture was stirred at 100° C. for 10 hrs and dried, and the solvent was evaporated. The reaction mixture was partitioned between EA and 0.1 N HCl. The organic layer was washed with brine, dried over MgSO₄, filtered and evaporated in vacuo. The resulting residue was purified by flash chromatography on silica gel (Hexane/EtOAc 6:1) to give a pale yellow oil product of 2.85 g (60.2%).

¹H NMR (500 MHz, CDCl₃-d₁): δ5.40 (s, 1H), 4.07 (s, 3H), 3.95 (s, 3H), 3.80 (s, 6H), 2.23 (s, 3H)

(2,6-Dihydroxy-5-methylsulfanyl-pyrimidin-4-yl)-acetic acid methyl ester

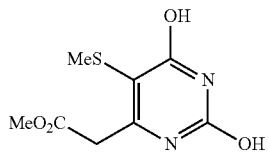 [SMILES: COC(=O)Cc1nc(O)nc(O)c1SC]

A mixture of 2-(2,6-dimethoxy-5-methylsulfanyl-pyrimidin-4-yl)-malonic acid dimethyl ester (2.85 g, 9.0 mmol.) was added dropwise to slurry of HCl (37% w/w) (1.0 ml) in MeOH (50 ml). The reaction mixture was stirred at 100° C. for 24 hr and dried, and the solvent was evaporated in vacuo to give a crude as a pale yellow solid of 1.85 g (89.2%).

¹H NMR (500 MHz, DMSO-d₆): δ11.35 (s, 1H), 11.23 (s, 1H), 3.81 (s, 2H), 3.66 (s, 3H), 2.11 (s, 3H)

(2,6-Dichloro-5-methylsulfanyl-pyrimidin-4-yl)-acetic acid methyl ester

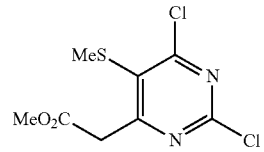

A mixture of (2,6-dihydroxy-5-methylsulfanyl-pyrimidin-4-yl)-acetic acid methyl ester (1.85 g, 9.0 mmol.) was added dropwise to a slurry of POCl₃ (8.0 ml). After the reaction mixture was stirred at 90° C. for 4 hrs, hydrolysis was carried out in iced salt water. The product of the reaction was extracted with EA and then evaporated to remove the EA so as to give a crude. Purification of the crude by flash chromatography on silica gel (Hexane/EtOAc 3:1) gave a brown oil product of 866 mg (40.5%).

¹H NMR (500 MHz, CDCl₃-d₁): δ4.15 (s, 2H), 3.74 (s, 3H), 2.39 (s, 3H)

(2-Chloro-5-methylsulfanyl-6-morpholin-4-yl-pyrimidin-4-yl)-acetic acid methyl ester

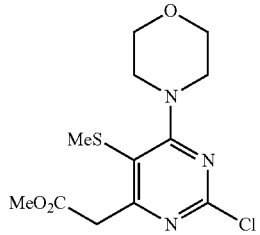 [SMILES: COC(=O)Cc1nc(Cl)nc(N2CCOCC2)c1SC]

A mixture of (2,6-dichloro-5-methylsulfanyl-pyrimidin-4-yl)-acetic acid methyl ester (860 mg, 3.22 mmol.), morpholine (336 mg, 3.86 mmol, 1.2 eq.) and THF (10 ml) was stirred at room temperature for 2.0 hrs. The reaction mixture was dried and the solvent was evaporated. The reaction mixture was subjected to addition of 0.1 N HCl washing free morpholine, extraction with EA and evaporation to remove the EA so as to give a crude. Purification of the crude by flash chromatography on silica gel (Hexane/EtOAc 2:1) gave a gray solid of 427 mg (42.7%).

¹H NMR (500 MHz, CDCl₃-d₁): δ3.99 (s, 2H), 3.80 (dd, 4H), 3.73 (dd, 4H), 3.71 (s, 3H), 2.21 (s, 3H)

[2-(4-Amino-phenyl)-5-methylsulfanyl-6-morpholin-4-yl-pyrimidin-4-yl]-acetic acid methyl ester

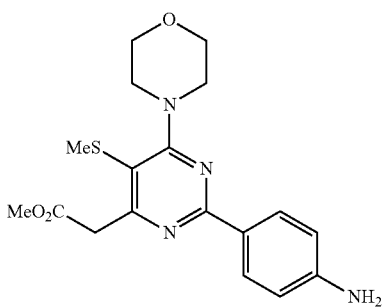 [SMILES: COC(=O)Cc1nc(-c2ccc(N)cc2)nc(N2CCOCC2)c1SC]

A mixture of (2-chloro-5-methylsulfanyl-6-morpholin-4-yl-pyrimidin-4-yl)-acetic acid methyl ester (420 mg, 1.47 mmol.), 4-(4,4,5,5-tetramethyl-[1,3,2]dioxaborolan-2-yl)-aniline) (357 mg, 1.62 mmol.), (PPh₃)₄Pd (170 mg, 0.07 mmol.), 2M Na₂CO₃ (2.2 ml, 4.14 mmol, 3.0 eq.) and dioxane (10 ml) was added a reaction vessel which was flushed with argon. The reaction mixture was stirred at 90° C. for 12 hr then dried, and the solvent was evaporated. The reaction mixture was partitioned between EA and water, the organic layer was washed with brine, dried over MgSO₄, filtered and evaporated in vacuo. The resulting residue was purified by flash chromatography on silica gel (Hexane/EtOAc 3:2) to give a pale yellow solid of 424 mg (43.8%).

¹H NMR (500 MHz, DMSO-d₆): δ7.75 (dd, 2H), 6.70 (dd, 2H), 4.05 (s, 2H), 3.84 (s, 3H), 3.74 (d, 8H), 1.91 (s, 3H)

{5-Methylsulfanyl-6-morpholin-4-yl-2-[4-(3-phenyl-ureido)-phenyl]-pyrimidin-4-yl}-acetic acid methyl ester

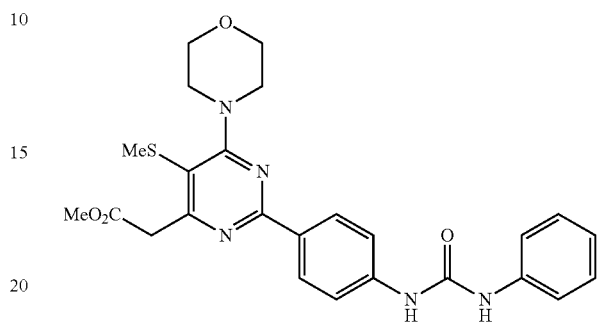

A mixture of [2-(4-amino-phenyl)-5-methylsulfanyl-6-morpholin-4-yl-pyrimidin-4-yl]-acetic acid methyl ester (400 mg, 1.06 mmol.), phenyl isocyanate (254 mg, 2.13 mmol, 2.0 eq) and CH₂Cl₂ (1.0 ml), toluene (2.0 ml) was added a reaction vessel which was flushed with argon. The reaction mixture was stirred at 90° C. for 16 hrs. After cooling and filtering, the precipitate was washed with a minor portion of CH₂Cl₂ again to give a white solid 316 of mg (60.1%).

¹H NMR (500 MHz, DMSO-d₆): δ8.89 (s, 1H), 8.74 (s, 1H), 7.73 (d, 2H), 7.54 (d, 2H), 7.47 (d, 2H), 7.29 (dd, 2H), 6.98 (d, 1H), 4.02 (s, 2H), 3.73 (d, 4H), 3.66 (d, 4H), 3.65 (s, 3H), 2.08 (s, 3H)

{5-Methylsulfanyl-6-morpholin-4-yl-2-[4-(3-phenyl-ureido)-phenyl]-pyrimidin-4-yl}-acetic acid sodium salt

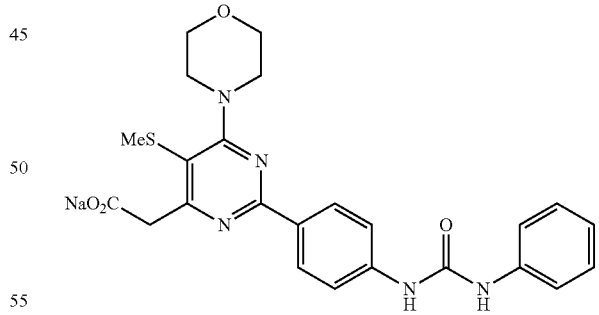

1N NaOH (1.0 ml, 6.0 eq.) was added to a stirred solution of {5-methyl sulfanyl-6-morpholin-4-yl-2-[4-(3-phenyl-ureido)-phenyl]-pyrimidin-4-yl}-acetic acid methyl ester (80 mg, 0.16 mmol.) in MeOH (2.0 ml) and the mixture was refluxed for 4 hrs. The mixture was cooled to r.t. and filtered. The precipitate was washed with MeOH and dried in vacuo to give a white solid of 61 mg (75.2%).

¹H NMR (500 MHz, DMSO-d₆): δ7.59 (d, 2H), 7.48 (d, 2H), 7.38 (d, 2H), 7.00 (t, 2H), 6.54 (t, 1H), 3.69 (dd, 8H), 1.96 (s, 3H)

5-Methylsulfanyl-6-morpholin-4-yl-2-[4-(3-phenyl-ureido)-phenyl]-pyrimidin-4-yl}-acetic acid

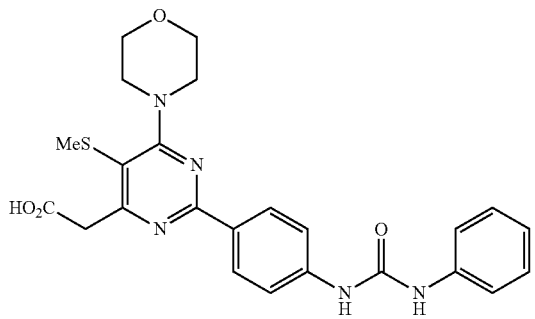 [SMILES: CSc1c(CC(=O)O)nc(-c2ccc(NC(=O)Nc3ccccc3)cc2)nc1N1CCOCC1]

1N NaOH (1.0 ml, 6.0 eq.) was added to a stirred solution of {5-methyl sulfanyl-6-morpholin-4-yl-2-[4-(3-phenyl-ureido)-phenyl]-pyrimidin-4-yl}-acetic acid methyl ester (80 mg, 0.16 mmol.) in MeOH (2.0 ml) and the mixture was refluxed at 0° C. and carefully acidified with conc. HCl. The mixture was filtered and the precipitate was dried in vacuo to give a white solid 64 mg (84.2%).

$^1$H NMR (500 MHz, DMSO-$d_6$): δ9.00 (s, 1H), 8.76 (s, 1H), 7.72 (d, 2H), 7.65-7.46 (m, 4H), 7.29 (t, 2H), 6.99 (t, 1H), 3.93 (s, 2H), 3.72 (d, 4H), 3.65 (d, 4H), 2.08 (s, 3H)

Example 7

Preparation of Formula (I) in Scheme 7

6-Hydroxy-5-methoxy-1H-pyrimidine-2,4-dione

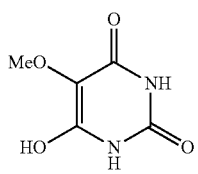

The NaOCH$_3$ (8.5 g, 157 mmole), was added to a stirred solution of dimethyl 2-methoxymalonate (10.2 g, 62.91 mmole), urea (2.5 g, 41.7 mmole), and EtOH (80 ml). The reaction mixture was heated to 100° C. for 4 hrs, then the reaction was evaporated to remove the solvent. Water was added to the mixture and then concentrated HCl was added. The pH of the mixture was adjusted to ca. 3~4. The mixture was filtered and wash water and acetone. After drying in vacuo, it gave a product (99%).

$^1$H NMR (500 MHz, DMSO-$d_6$): δ 8.74 (s, 1H), 3.23 (s, 3H)

2,4,6-Trichloro-5-methoxyprimidine

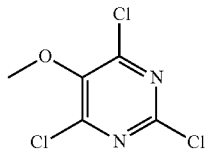

$^1$H NMR (500 MHz, CDCl$_3$-d$_1$): δ3.97 (s, 3H)

4-(2,6-Dichloro-5-methoxypyrimidin-4-yl)morpholine

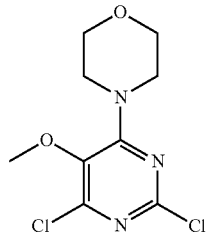 [SMILES: COc1c(Cl)nc(Cl)nc1N1CCOCC1]

$^1$H NMR (500 MHz, CDCl$_3$-d$_1$): δ3.87~3.89 (d, 4H), 3.76~3.78 (d, 4H), 3.73 (s, 3H)

4-(4-chloro-5-methoxy-6-morpholinopyrimidin-2-yl) benzenamine

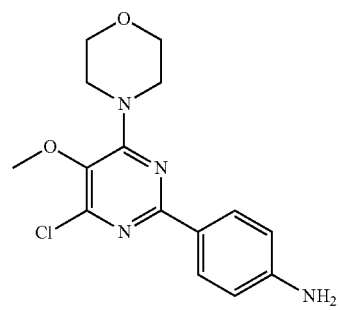 [SMILES: COc1c(Cl)nc(-c2ccc(N)cc2)nc1N1CCOCC1]

$^1$H NMR (500 MHz, DMSO-$d_6$): δ 7.90~7.91 (d, 2H), 6.56~6.58 (d, 2H), 5.65 (br, 2H), 3.79 (s, 4H), 3.73 (s, 4H), 3.67 (s, 3H)

1-[4-(4-Chloro-5-methoxy-6-morpholin-4-yl-pyrimidin-2-yl)-phenyl]-3-pyridin-4-yl-urea

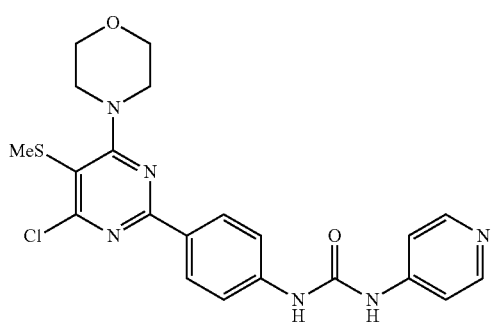 [SMILES: CSc1c(Cl)nc(-c2ccc(NC(=O)Nc3ccncc3)cc2)nc1N1CCOCC1]

$^1$H NMR (500 MHz, DMSO-$d_6$): δ 9.28 (s, 1H), 9.23 (s, 1H), 8.36~8.37 (d, 2H), 8.15~8.17 (d, 2H), 7.56~7.58 (d, 2H), 7.44~7.46 (d, 2H), 3.84~3.86 (d, 4H), 3.74~3.75 (d, 4H), 3.71 (s, 3H)

5-Ethoxy-6-hydroxy-1H-pyrimidine-2,4-dione

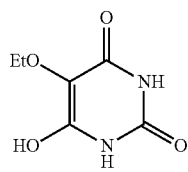

$^1$H NMR (500 MHz, DMSO-d$_6$): δ1.06-1.09 (m, 3H), 3.58-3.61 (m, 2H), 9.00 (s, 2H)

2,4,6-Trichloro-5-ethoxy-pyrimidine

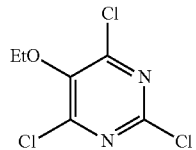

$^1$H NMR (500 MHz, CDCl3-d): δ1.47-1.50 (m, 3H), 4.17-4.21 (m, 2H)

4-(2,6-Dichloro-5-ethoxy-pyrimidin-4-yl)-morpholine

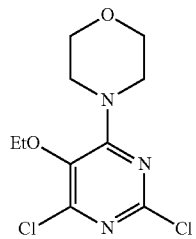 [SMILES: CCOc1c(Cl)nc(Cl)nc1N1CCOCC1]

$^1$H NMR (500 MHz, CDCl$_3$-d$_1$): δ1.38-1.40 (m, 3H), 3.76-3.78 (m, 4H), 3.87-3.89 (m, 4H), 3.91-3.95 (m, 2H)

4-(4-Chloro-5-ethoxy-6-morpholin-4-yl-pyrimidin-2-yl)-phenylamine

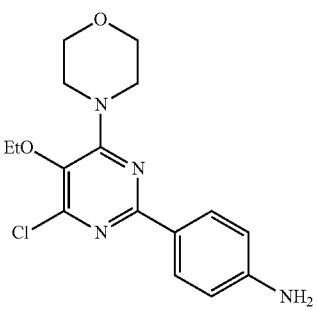 [SMILES: CCOc1c(Cl)nc(-c2ccc(N)cc2)nc1N1CCOCC1]

$^1$H NMR (500 MHz, CDCl3-d$_1$): δ1.38-1.41 (m, 3H), 3.81-3.83 (m, 4H), 3.87-3.89 (m, 4H), 3.94-3.98 (m, 2H), 6.72-6.73 (m, 2H), 8.12-8.14 (m, 2H)

1-[4-(4-Chloro-5-ethoxy-6-morpholin-4-yl-pyrimidin-2-yl)-phenyl]-3-pyridin-4-yl-urea

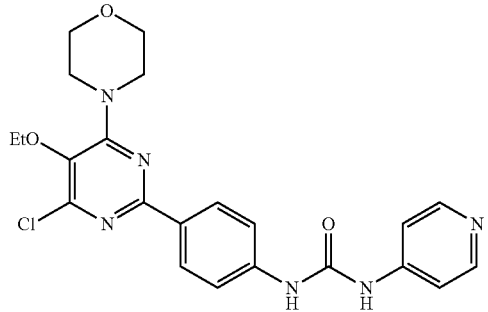 [SMILES: CCOc1c(Cl)nc(-c2ccc(NC(=O)Nc3ccncc3)cc2)nc1N1CCOCC1]

$^1$H NMR (500 MHz, DMSO-d$_6$): δ1.31-1.34 (m, 3H), 3.73-3.75 (m, 4H), 3.84-3.86 (m, 4H), 3.92-3.96 (m, 4H), 7.45-7.46 (m, 2H), 7.57-7.59 (m, 2H), 8.16-8.18 (m, 2H), 8.37-8.38 (m, 2H), 9.17 (s, 1H), 9.20 (s, 1H)

1-[4-(4-Chloro-5-ethoxy-6-morpholin-4-yl-pyrimidin-2-yl)-phenyl]-3-pyridin-3-yl-urea

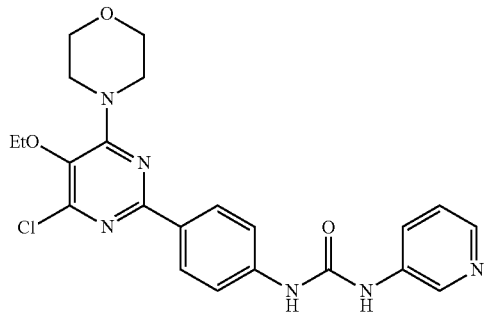 [SMILES: CCOc1c(Cl)nc(-c2ccc(NC(=O)Nc3cccnc3)cc2)nc1N1CCOCC1]

$^1$H NMR (500 MHz, DMSO-d$_6$): δ1.31-1.34 (m, 3H), 3.73-3.75 (m, 4H), 3.84-3.86 (m, 4H), 3.92-3.96 (m, 2H), 7.33-7.34 (m, 1H), 7.56-7.58 (m, 2H), 7.95-7.97 (m, 1H), 8.15-8.17 (m, 2H), 8.21 (m, 1H), 8.62 (s, 1H), 8.92 (s, 1H), 9.10 (s, 1H)

Example 8

Preparation of Compounds of Formula (I) in Scheme 8

5-Methoxy-2-(4-nitro-phenyl)-3H-pyrimidin-4-one

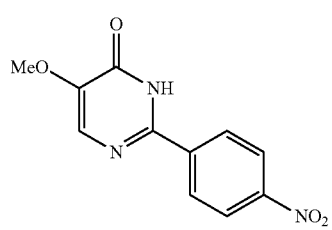 [SMILES: COc1cnc(-c2ccc([N+](=O)[O-])cc2)[nH]c1=O]

A mixture of methyl methoxy acetate (5 mL, 1.0 eq) and ethyl formate (4.07 mL, 1.0 eq) was added dropwise to a slurry of sodium methoxide (5.45 g, 2.0 eq) in toluene (20 mL) in ice both. After dropping at room temperature and stirring overnight, the resulting solution was dried in vacuo. Then a mixture of residue, 4-nitrobenzimide (10.17 g, 1.0 eq) and sodium methoxide (2.72 g, 1.0 eq) in EtOH (80 mL) was refluxed at 110° C. for 6 hrs. After the solvent was dried in vacuo, water and conc. HCl solution (5<pH<4) were added. After formation of white precipitates, the mixture was filtered and dried solid in vacuo. A product was obtained as a white solid (3.21 g, 26%).

4-Chloro-5-methoxy-2-(4-nitro-phenyl)-pyrimidine

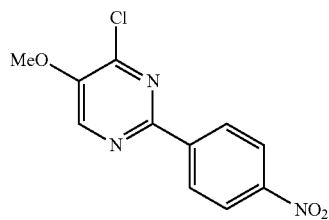 [SMILES: COc1cnc(-c2ccc([N+](=O)[O-])cc2)nc1Cl]

In ice bath, dimethyl-phenyl-amine (1.19 mL, 1.0 eq) was added dropwise to a slurry of 5-Methoxy-2-(4-nitro-phenyl)-3H-pyrimidin-4-one (2.3 g, 1.0 eq) in POCl₃ (4.4 mL, 5.0 eq) and the mixture was refluxed overnight. Excess POCl₃ was evaporated in vacuo and the residue was poured into ice-water. After formation of precipitates, the mixture was filtered and the residue was dried solid in vacuo. A product was obtained as a white solid (2.47 g, 61%).

4-[5-Methoxy-2-(4-nitro-phenyl)-pyrimidin-4-yl]-morpholine

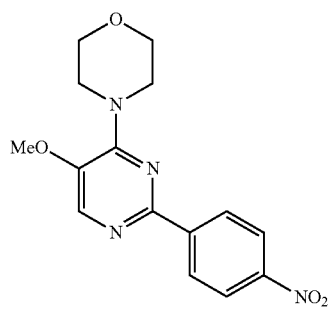

4-chloro-5-methoxy-2-(4-nitro-phenyl)-pyrimidine (1.50 g, 1.0 eq) was stirred in dichloromethane (10 mL) and a solution of morpholine (0.75 mL, 1.5 eq) in dichloromethane (5 mL) was added dropwise to the mixture at 0° C. After stirring, the resulting solution was reacted overnight at r.t., NH₄Cl (aq) was added to the solution and the solution was extracted with dichloromethane. The combined organic layers were washed with brine, dried and evaporated in vacuo. A product was obtained as a white solid (0.73 g, 41%).

$^1$H NMR (500 MHz, DMSO-$d_6$): δ 3.74 (s, 4H), 3.80 (s, 4H), 3.93 (s, 3H), 8.24 (s, 1H), 8.30 (d, 2H), 8.48 (d, 2H)

4-(5-Methoxy-4-morpholin-4-yl-pyrimidin-2-yl)-phenylamine

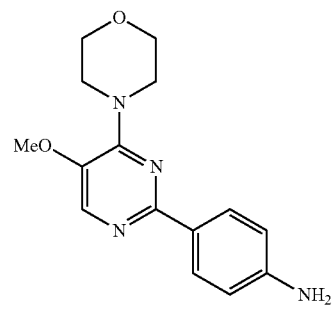 [SMILES: COc1cnc(-c2ccc([N+](=O)[O-])cc2)nc1N1CCOCC1]

4-[5-methoxy-2-(4-nitro-phenyl)-pyrimidin-4-yl]-morpholine (0.2 g, 1 eq) was stirred under hydrogen balloon with palladium on carbon (10 percent, 0.1 g, 0.15 eq) in a mixture of MeOH and EA (1:1, 8 mL) at room temperature overnight. The reaction mixture was then filtered through Celite, volatiles were removed in vacuo, and the residue was purified by flash chromatography to give a white solid (0.15 g, 83%).

$^1$H NMR (500 MHz, DMSO-$d_6$): δ 3.71 (s, 8H), 3.83 (s, 3H), 5.54 (s, 2H), 6.58 (d, 2H), 7.95 (d, 2H), 8.04 (s, 1H)

6-Hydroxy-5-methoxy-2-(4-nitro-phenyl)-3H-pyrimidin-4-one

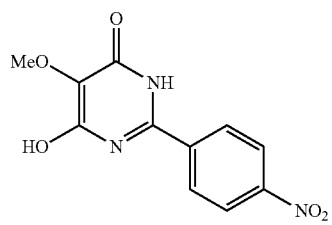 [SMILES: COc1c(O)nc(-c2ccc([N+](=O)[O-])cc2)[nH]c1=O]

The NaOCH₃ (7.8 g, 3 eq) was added to a stirred solution of 1-ethyl 3-methyl 2-methoxymalonate (11 g, 1.3 eq), 4-nitrobenzimidamide hydrochloride (9.6 g, 1 eq) and EtOH (240 ml) and the mixture was refluxed for 8 hrs. After 8 hrs, the solvent was evaporated and water (10~15 ml) was added to the mixture then the mixture was cooled to 0° C. and carefully acidified with conc. HCl. After overnight cooling, it led to the formation of brown precipitates. The mixture was filtered and the precipitates was dried in vacuo to give a brown solid (65%) as a product.

$^1$H NMR (500 MHz, DMSO-$d_6$): δ3.71 (s, 3H), 8.28~8.35 (m, 4H)

4,6-Dichloro-5-methoxy-2-(4-nitro-phenyl)-pyrimidine

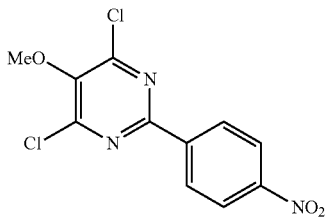 [SMILES: COc1c(Cl)nc(-c2ccc([N+](=O)[O-])cc2)nc1Cl]

The POCl₃ (30 ml, 16.7 eq) was added to a stirred solution of 5-methoxy-2-(4-nitrophenyl)pyrimidine-4,6-diol (5.13 g, 1 eq) and N,N-dimethylaniline (3.2 ml, 1.27 eq) the mixture was refluxed overnight. Excess POCl₃ was evaporated in vacuo and the residue was poured into ice-water to give a solid. The solid was filtered and dried in vacuo to given a brown solid (81%) as a product.

¹H NMR (500 MHz, CDCl₃-d₁): δ4.03 (s, 3H), 8.31~8.32 (d, 2H), 8.54~8.56 (d, 2H)

4-[6-Chloro-5-methoxy-2-(4-nitro-phenyl)-pyrimidin-4-yl]-morpholine

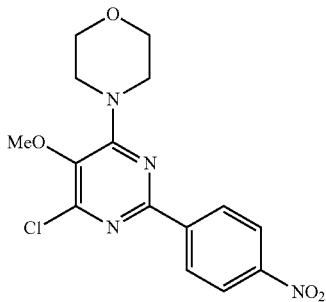

Morpholine (0.6 ml, 2.2 eq) was added to a stirred solution of 4,6-dichloro-5-methoxy-2-(4-nitrophenyl)pyrimidine (0.87 g, 1 eq) in THF, the mixture was stirred at r.t for 4 hrs, the solvent was evaporated, water was added to the solution and the solution was extracted with EA. The combined organic layers were washed with brine, dried and evaporated in vacuo, the product was obtained as a yellow solid (56%).

¹H NMR (500 MHz, CDCl₃-d₁): δ3.08 (s, 3H), 3.84~3.86 (d, 4H), 3.93~3.94 (d, 4H), 8.26~8.27 (d, 2H), 8.46~8.47 (d, 2H)

4-(4-Chloro-5-methoxy-6-morpholin-4-yl-pyrimidin-2-yl)-phenylamine

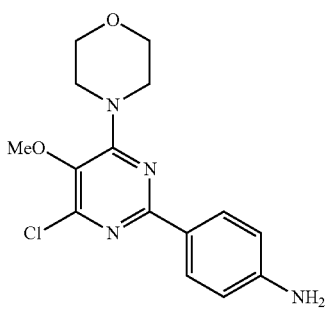

To a stirring solution of 4-(6-chloro-5-methoxy-2-(4-nitrophenyl) yrimidin-4-yl)morpholine (200 mg, 1 eq), and acetic acid (1 ml) in a 25 ml single-necked round-bottomed flask equipped with a magnetic stirrer was added Zn dust (78 mg, 2.1 eq). The mixture was stirred at ambient temperature for 1 hr. The mixture was poured into a solution of saturated NaHCO₃ (34 ml). The mixture was filtered and partitioned between CH₂Cl₂ and water. The organic portion was dried (MgSO₄) and concentrated under reduced pressure. The residue was purified by silica gel to obtain a product (45%), ¹H NMR (500 MHz, DMSO-d₆): δ3.67 (s, 3H), 3.73 (d, 4H), 3.79 (d, 4H), 5.65 (s, 2H), 6.56~6.58 (d, 2H), 7.90~7.91 (d, 2H)

5-Ethoxy-6-hydroxy-2-(4-nitro-phenyl)-3H-pyrimidin-4-one

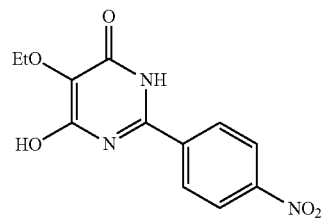 [SMILES: CCOc1c(O)nc(-c2ccc([N+](=O)[O-])cc2)[nH]c1=O]

A mixture of 4-nitrobenzimide (8.0 g, 1.0 eq) and 2-ethoxy-malonic acid diethyl ester (10.54 g, 1.3 eq) and sodium methoxide (6.43 g, 3.0 eq) in EtOH (140 mL) was refluxed at 80° C. for 6 hrs. After the solvent was dried in vacuo, water and cone. HCl solution (5<pH<4) were added. After formation of white precipitates, the mixture was filtered and dried solid in vacuo. A product was obtained as a white solid (1.85 g, 26%).

4,6-Dichloro-5-ethoxy-2-(4-nitro-phenyl)-pyrimidine

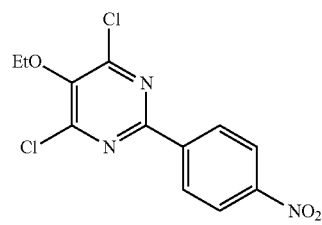 [SMILES: CCOc1c(Cl)nc(-c2ccc([N+](=O)[O-])cc2)nc1Cl]

In ice bath, dimethyl-phenyl-amine (0.94 mL, 1.1 eq) was added dropwise to a slurry of 5-ethoxy-6-hydroxy-2-(4-nitro-phenyl)-3H-pyrimidin-4-one (1.85 g, 1.0 eq) in POCl₃ (6.5 mL, 10.32 eq) and the resulting solution was refluxed overnight. Excess POCl₃ was evaporated in vacuo and the residue was poured into ice-water. After formation of precipitates, the mixture was filtered and dried solid in vacuo. A product was obtained as a white solid (0.5 g, 24%).

¹H NMR (500 MHz, DMSO-d₆): δ 1.42 (t, 3H), 4.25 (q, 2H), 8.39 (d, 2H), 8.48 (d, 2H)

4-[6-Chloro-5-ethoxy-2-(4-nitro-phenyl)-pyrimidin-4-yl]-morpholine

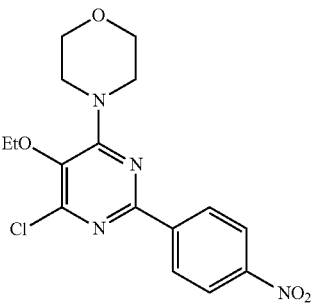

4,6-dichloro-5-ethoxy-2-(4-nitro-phenyl)-pyrimidine (0.50 g, 1.0 eq) was stirred in dichloromethane (10 mL) and a solution of morpholine (0.21 mL, 1.5 eq) in dichloromethane (5 mL) was added dropwise at 0° C. After stirring the resulting solution overnight at r.t., NH$_4$Cl(aq) was added to the solution and the solution was extracted with dichloromethane. The combined organic layers were washed with brine, dried and evaporated in vacuo. A product was obtained as a white solid (0.57 g, 81%).

$^1$H NMR (500 MHz, DMSO-d$_6$): δ 1.34 (t, 3H), 3.76 (t, 4H), 3.89 (t, 4H), 3.98 (q, 2H), 8.32 (d, 2H), 8.45 (d, 2H)

4-(4-Chloro-5-ethoxy-6-morpholin-4-yl-pyrimidin-2-yl)-phenylamine

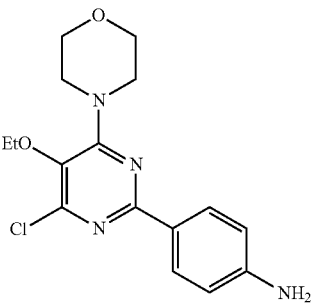

4-[6-chloro-5-ethoxy-2-(4-nitro-phenyl)-pyrimidin-4-yl]-morpholine (0.2 g, 1 eq) was stirred under hydrogen balloon with platinum on carbon (10 percent, 0.11 g, 0.1 eq) in a mixture of MeOH and EA (1:1, 8 mL) at room temperature overnight. The reaction mixture was then filtered through Celite, the volatiles in the mixture was removed in vacuo, and the residue was purified by flash chromatography to give a white solid (0.13 g, 83%).

$^1$H NMR (500 MHz, CDCl$_3$-d$_1$): δ1.41 (t, 3H), 3.81 (t, 4H), 3.88 (t, 4H), 3.96 (q, 2H), 6.75 (d, 2H), 8.14 (d, 2H)

Example 9

Preparation of Compounds of Formula (I) in Scheme 9

2-Chloro-5-methoxy-4-pyridin-4-yl-pyrimidine

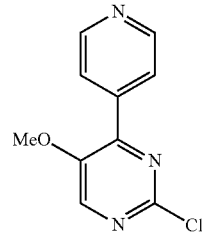 [SMILES: COc1cnc(Cl)nc1-c1ccncc1]

A mixture of 2,4-dichloro-5-methoxy-pyrimidine (3.0 g, 1.0 eq.), 4-pyridinylboronic acid (2.26 g, 1.1 eq.), Pd(PPh$_3$)$_2$Cl$_2$ (0.58 g, 0.05 eq.), K$_3$PO$_4$.H$_2$O (10.67 g, 3.0 eq.), H$_2$O (3 ml) and 1,4-Dioxane (20.0 ml) was heated at 90° C. and refluxed overnight. The solvent was removed in vacuo, and the residue was extracted with EA and water. The combined organic layers was wash with brine, dried and evaporated in vacuo. The crude was purified by chromatography to give a yellow thick liquid (1.83 g, 49.26%).

$^1$H NMR (500 MHz, CDCl3-d$_1$): δ8.76-8.75 (d, 2H), 8.42 (s, 1H), 8.02-8.04 (d, 2H), 4.05 (s, 3H).

4-(5-Methoxy-4-pyridin-4-yl-pyrimidin-2-yl)-phenylamine

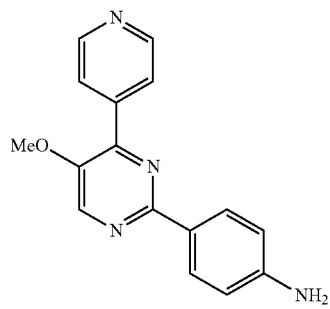 [SMILES: COc1cnc(-c2ccc(N)cc2)nc1-c1ccncc1]

$^1$H NMR (500 MHz, CDCl3-d$_1$): δ8.75-8.76 (m, 2H), 8.55 (s, 1H), 8.26-8.28 (d, 2H), 8.15-8.17 (m, 2H), 6.76-6.78 (d, 2H), 4.00 (s, 3H).

[4-(5-Methoxy-4-pyridin-4-yl-pyrimidin-2-yl)-phenyl]-carbamic acid phenyl ester

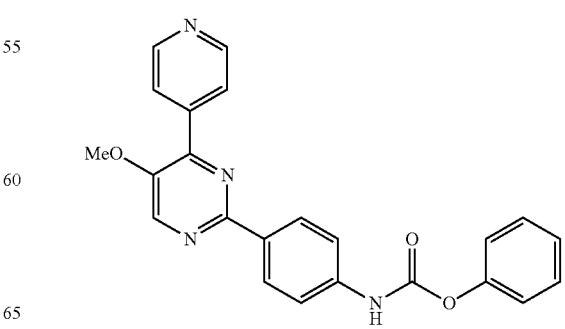

¹H NMR (500 MHz, CDCl3-d₁): δ8.78-8.79 (d, 2H), 8.61 (s, 1H), 8.44-8.45 (d, 2H), 8.22-8.23 (d, 2H), 7.59-7.60 (d, 2H), 7.40-7.43 (m, 2H), 7.21-7.27 (m, 3H), 7.13 (s, 1H), 4.08 (s, 3H).

1-[4-(5-Methoxy-4-pyridin-4-yl-pyrimidin-2-yl)-phenyl]-3-[4-(morpholine-4-carbonyl)-phenyl]-urea

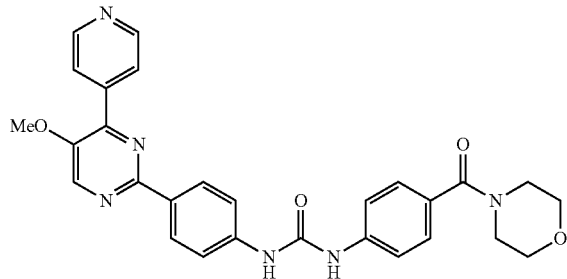

¹H NMR (500 MHz, DMSO-d₆): δ9.94-9.58 (m, 2H), 8.87 (s, 1H), 8.76-8.78 (m, 2H), 8.32-8.34 (m, 2H), 8.12-8.13 (m, 2H), 7.63-7.67 (m, 2H), 7.55-7.56 (m, 2H), 7.38-7.37 (m, 2H), 4.07 (s, 3H), 3.60 (s, 4H), 3.50 (s, 4H).

1-[4-(5-Methoxy-4-pyridin-4-yl-pyrimidin-2-yl)-phenyl]-3-[4-(3-oxo-morpholin-4-yl)-phenyl]-urea

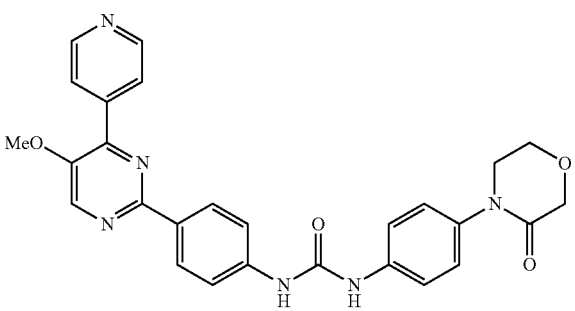 [SMILES: COc1cnc(-c2ccc(NC(=O)Nc3ccc(N4CCOCC4=O)cc3)cc2)nc1-c1ccncc1]

¹H NMR (500 MHz, DMSO-d₆): δ9.32 (s, 1H), 9.12 (s, 1H), 8.86-8.87 (m, 1H), 8.76-8.78 (m, 2H), 8.31-8.34 (m, 2H), 8.12-8.13 (m, 2H), 7.64-7.67 (m, 2H), 7.50-7.52 (m, 2H), 7.28-7.30 (m, 2H), 4.18 (s, 2H), 4.07 (s, 3H), 3.95-3.97 (m, 2H), 3.69-3.71 (m, 2H).

1-[4-(5-Methoxy-4-pyridin-4-yl-pyrimidin-2-yl)-phenyl]-3-pyridin-4-yl-urea

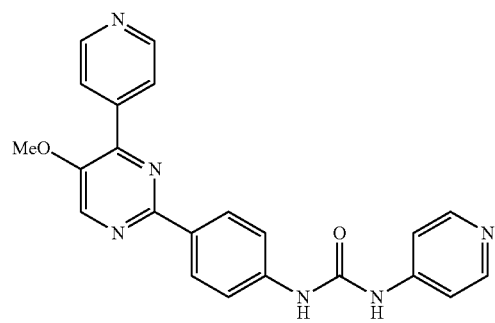 [SMILES: COc1cnc(-c2ccc(NC(=O)Nc3ccncc3)cc2)nc1-c1ccncc1]

¹H NMR (500 MHz, DMSO-d₆): δ9.72 (s, 1H), 9.45 (s, 1H), 8.87 (s, 1H), 8.77-8.78 (m, 2H), 8.33-8.37 (m, 4H), 8.12-8.13 (m, 2H), 7.63-7.65 (d, 2H), 7.46-7.48 (d, 2H), 4.07 (s, 3H).

Example 10

Preparation of Compounds of Formula (I) in Scheme 10

[4-(5-Methylsulfanyl-4-morpholin-4-yl-6-pyridin-4-yl-pyrimidin-2-yl)-phenyl]-carbamic acid phenyl ester

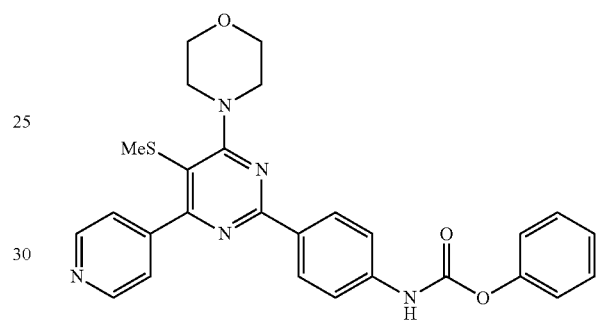

¹H NMR (500 MHz, CDCl₃-d₁): δ8.76-8.73 (d, 2H), 8.45-8.43 (d, 2H), 7.71-7.68 (m, 2H), 7.57-7.55 (d, 2H), 7.42-7.39 (m, 2H), 7.27-7.20 (m, 3H), 3.91-3.90 (s, 8H), 1.62 (s, 3H)

4-(5-Methylsulfanyl-4-morpholin-4-yl-6-pyridin-4-yl-pyrimidin-2-yl)-phenylamine

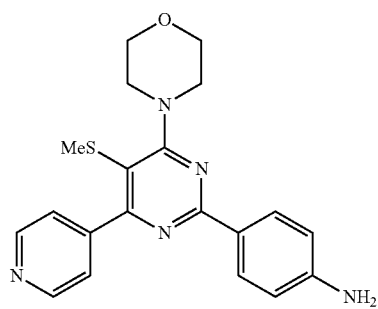 [SMILES: CSc1c(-c2ccncc2)nc(-c2ccc(N)cc2)nc1N1CCOCC1]

¹H NMR (500 MHz, CDCl₃-d₁): δ8.73-8.72 (d, 2H), 8.28-8.26 (d, 2H), 7.69-7.67 (dd, 2H), 6.72-6.71 (s, 2H), 3.95 (s, 2H), 3.89 (s, 8H), 2.04 (s, 3H)

[4-(5-Methylsulfanyl-4-morpholin-4-yl-6-pyridin-4-yl-pyrimidin-2-yl)-phenyl]-urea

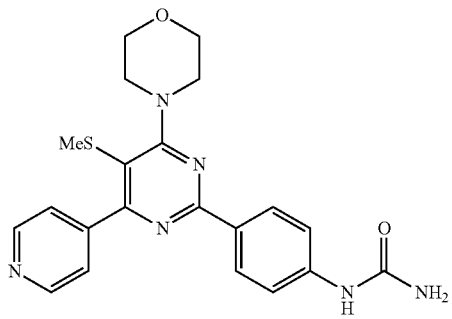 [SMILES: CSc1c(-c2ccncc2)nc(-c2ccc(NC(N)=O)cc2)nc1N1CCOCC1]

¹H NMR (500 MHz, DMSO-d₆): δ8.85 (s, 1H), 8.72-8.71 (d, 2H), 8.24-8.22 (d, 2H), 7.68-7.67 (d, 2H), 7.52-7.50 (d, 2H), 5.96 (s, 2H), 3.87-3.86 (d, 4H), 3.80-3.79 (d, 4H), 2.05 (s, 3H)

1-[4-(5-Methylsulfanyl-4-morpholin-4-yl-6-pyridin-4-yl-pyrimidin-2-yl)-phenyl]-3-[4-(3-oxo-morpholin-4-yl)-phenyl]-urea

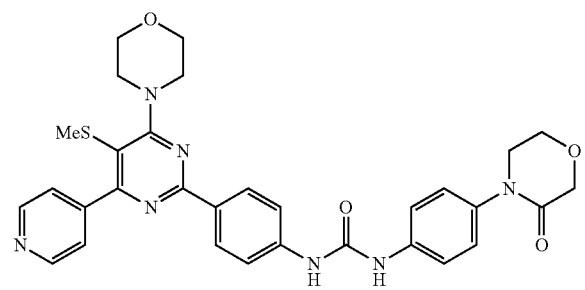 [SMILES: CSc1c(-c2ccncc2)nc(-c2ccc(NC(=O)Nc3ccc(N4CCOCC4=O)cc3)cc2)nc1N1CCOCC1]

¹H NMR (500 MHz, DMSO-d₆): δ9.24 (s, 1H), 9.06 (s, 1H), 8.72-8.71 (d, 2H), 8.29-8.28 (d, 2H), 7.69-7.68 (dd, 2H), 7.61-7.59 (d, 2H), 7.51-7.49 (d, 2H), 7.29-7.27 (d, 2H) 4.18 (s, 2H), 3.96-3.94 (d, 2H), 3.88-3.87 (d, 4H), 3.81-3.80 (d, 4H), 3.70-3.68 (d, 2H), 2.05 (s, 3H)

1-[4-(5-Methylsulfanyl-4-morpholin-4-yl-6-pyridin-4-yl-pyrimidin-2-yl)-phenyl]-3-pyridin-4-yl-urea

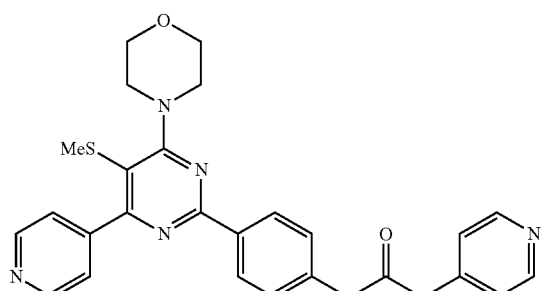

¹H NMR (500 MHz, DMSO-d₆): δ9.34 (s, 1H), 9.29 (s, 1H), 8.73-8.72 (d, 2H), 8.38-8.37 (d, 2H), 8.33-8.31 (d, 2H), 7.69-7.68 (d, 2H), 7.61-7.59 (d, 2H), 7.48-7.46 (d, 2H), 3.88-3.87 (d, 4H), 3.81-3.80 (d, 4H), 2.06 (s, 3H)

4-{3-[4-(5-Methylsulfanyl-4-morpholin-4-yl-6-pyridin-4-yl-pyrimidin-2-yl)-phenyl]-ureido}-benzamide

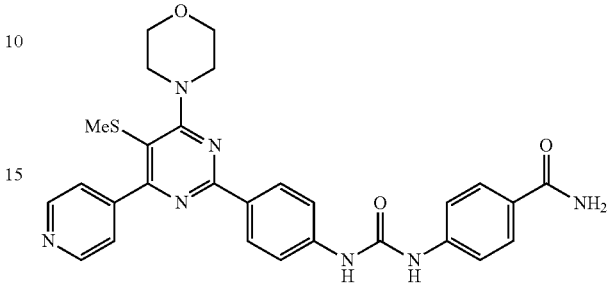

¹H NMR (500 MHz, DMSO-d₆): δ9.40 (b, 1H), 9.34 (b, 1H), 8.72-8.71 (d, 2H), 8.29-8.27 (d, 2H), 7.82-7.80 (d, 3H), 7.69-7.67 (d, 2H), 7.63-7.61 (d, 2H), 7.56-7.54 (d, 2H), 7.14 (s, 1H), 3.87-3.86 (d, 4H), 3.81-3.80 (d, 4H), 2.05 (s, 3H)

1-[4-(5-Methylsulfanyl-4-morpholin-4-yl-6-pyridin-4-yl-pyrimidin-2-yl)-phenyl]-3-phenyl-urea

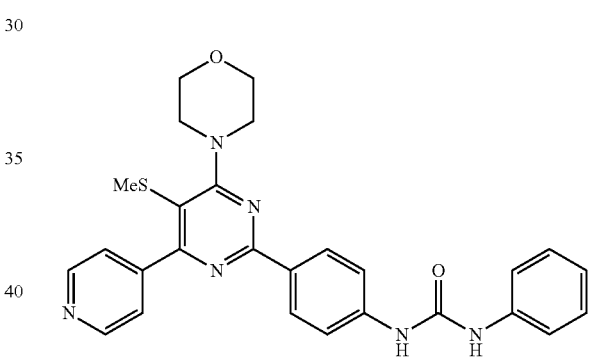

¹H NMR (500 MHz, DMSO-d₆): δ9.07 (s, 1H), 8.83 (s, 1H), 8.73-8.72 (d, 2H), 8.30-8.29 (d, 2H), 7.69-7.68 (d, 2H), 7.59-7.58 (d, 2H), 7.47-7.46 (d, 2H), 7.30-7.27 (d, 2H), 6.98 (s, 1H), 3.88-3.87 (d, 4H), 3.81-3.80 (d, 4H), 2.05 (s, 3H)

1-[4-(5-Methylsulfanyl-4-morpholin-4-yl-6-pyridin-4-yl-pyrimidin-2-yl)-phenyl]-3-phenyl-thiourea

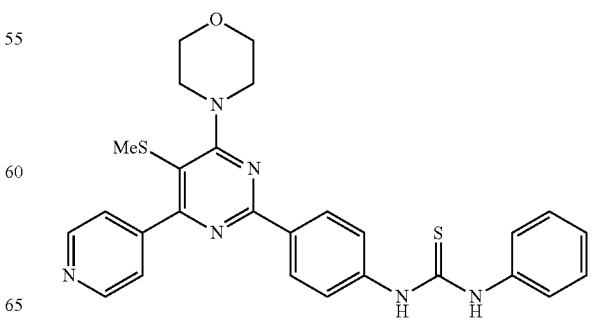

¹H NMR (500 MHz, DMSO-d₆): δ10.0 (b, 1H), 9.99 (b, 1H), 8.73-8.72 (d, 2H), 8.32-8.30 (d, 2H), 7.70-7.66 (m, 4H), 7.50-7.49 (d, 2H), 7.35-7.32 (d, 2H), 7.15-7.12 (d, 1H), 3.89-3.88 (d, 4H), 3.81-3.80 (d, 4H), 2.04 (s, 3H)

1-Ethyl-3-[4-(5-methylsulfanyl-4-morpholin-4-yl-6-pyridin-4-yl-pyrimidin-2-yl)-phenyl]-urea

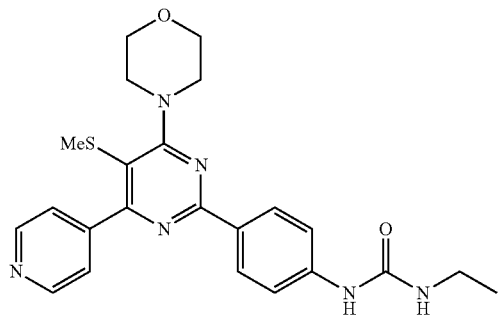 [SMILES: CCNC(=O)Nc1ccc(-c2nc(-c3ccncc3)c(SC)c(N3CCOCC3)n2)cc1]

¹H NMR (500 MHz, DMSO-d₆): δ8.75 (s, 1H), 8.72-8.71 (d, 2H), 8.24-8.22 (d, 2H), 7.68-7.67 (d, 2H), 7.52-7.50 (d, 2H), 6.22-6.19 (t, 1H), 3.87-3.86 (d, 4H), 3.80-3.79 (d, 4H), 3.13-3.10 (dd, 2H), 2.05 (s, 3H), 1.07-1.04 (t, 3H)

1-Methyl-3-[4-(5-methylsulfanyl-4-morpholin-4-yl-6-pyridin-4-yl-pyrimidin-2-yl)-phenyl]-urea

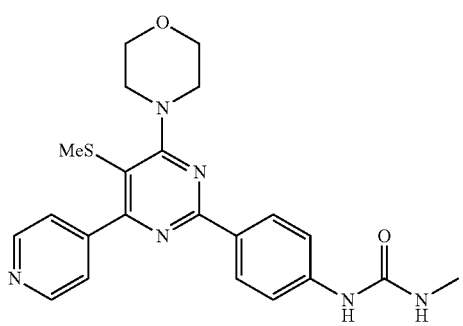 [SMILES: CNC(=O)Nc1ccc(-c2nc(-c3ccncc3)c(SC)c(N3CCOCC3)n2)cc1]

¹H NMR (500 MHz, DMSO-d₆): δ8.90 (s, 1H), 8.72-8.71 (d, 2H), 8.24-8.22 (d, 2H), 7.68-7.67 (d, 2H), 7.52-7.51 (d, 2H), 6.18-6.17 (d, 1H), 3.87-3.86 (d, 4H), 3.79 (d, 4H), 2.65 (s, 3H), 2.05 (s, 3H)

1-Isopropyl-3-[4-(5-methylsulfanyl-4-morpholin-4-yl-6-pyridin-4-yl-pyrimidin-2-yl)-phenyl]-urea

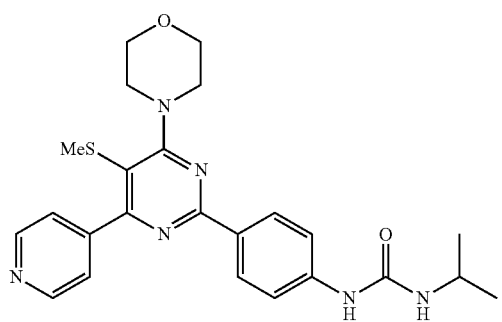 [SMILES: CSc1c(-c2ccncc2)nc(-c2ccc(NC(=O)NC(C)C)cc2)nc1N1CCOCC1]

¹H NMR (500 MHz, DMSO-d₆): δ8.72-8.71 (d, 2H), 8.62 (s, 1H), 8.24-8.22 (d, 2H), 7.68-7.67 (d, 2H), 7.50-7.48 (d, 2H), 6.11-6.10 (d, 1H), 3.87-3.86 (d, 4H), 3.77-3.74 (d, 4H), 2.05 (s, 3H), 1.11-1.10 (t, 6H), 1.00-0.99 (d, 1H)

1-Isoxazol-3-yl-3-[4-(5-methylsulfanyl-4-morpholin-4-yl-6-pyridin-4-yl-pyrimidin-2-yl)-phenyl]-urea

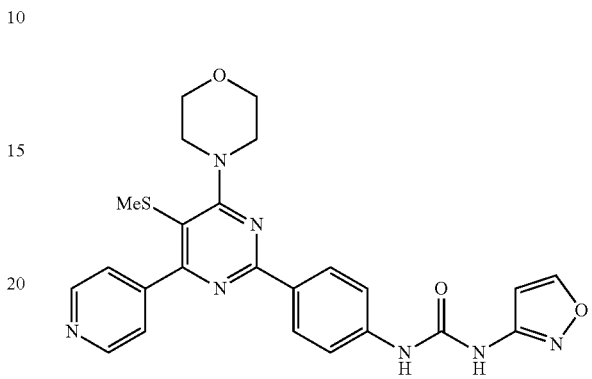

¹H NMR (500 MHz, DMSO-d₆): δ9.74 (s, 1H), 9.22 (s, 1H), 8.75-8.72 (m, 3H), 8.32-8.29 (d, 2H), 7.69-7.68 (d, 2H), 7.62-7.58 (d, 2H), 6.87-6.87 (d, 1H), 3.88-3.87 (d, 4H), 3.81-3.80 (s, 4H), 2.06 (s, 3H)

4-(5-Methylsulfanyl-4,6-di-morpholin-4-yl-pyrimidin-2-yl)-phenylamine

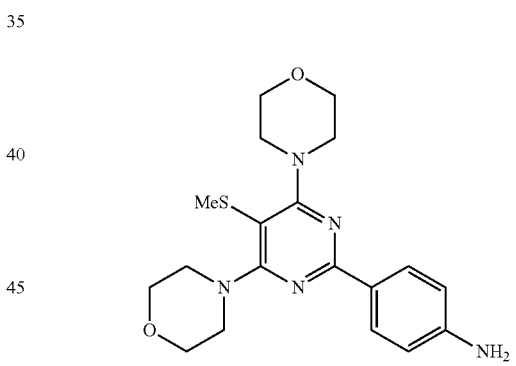

A mixture of 4-(4-chloro-5-methylsulfanyl-6-morpholin-4-yl-pyrimidin-2-yl)-phenylamine (200 mg, 0.594 mmol.), morpholin (103 mg, 1.118 mmol, 2.0 eq), triethylamine (120 mg, 1.118 mmol, 2.0 eq) in dioxane (8 ml) and the mixture was reacted for 16 hrs at 90° C. The reaction mixture was dried and the solvent was removed by evaporation in vacuo. The reaction mixture was partitioned between EA and water. The organic layer was washed with brine, dried over MgSO₄, filtered and evaporated in vacuo. The resulting residue was purified using flash chromatography on silica gel (EA), and recrystallized by (Hexane/EtOAc) to give a gray white 106 mg (46.1%).

¹H NMR (500 MHz, CDCl₃-d₁): δ8.19-8.17 (d, 2H), 6.69-6.68 (d, 2H), 3.88 (s, 2H), 3.84-3.82 (d, 8H), 3.69-3.68 (d, 8H), 2.2 (s, 3H)

1-{4-[4-(4-Methanesulfonyl-piperazin-1-yl)-5-methylsulfanyl-6-morpholin-4-yl-pyrimidin-2-yl]-phenyl}-3-phenyl-urea

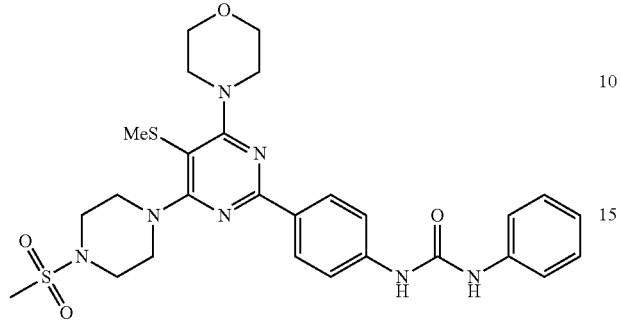

A mixture of 1-[4-(4-chloro-5-methylsulfanyl-6-morpholin-4-yl-pyrimidin-2-yl)-phenyl]-3-phenyl-urea (120 mg, 0.26 mmol.), 1-methanesulfonyl-piperazine (65 mg, 0.39 mmol, 1.5 eq.), triethylamine (40 mg, 0.39 mmol, 1.5 eq.), and DMF (4.0 mil) was added to the reaction vessel and flushed with argon. The reaction mixture was stirred at 80° C. for 5 hrs and then dried, and the solvent was evaporated. The reaction mixture was partitioned between EA and NH$_4$Cl$_{(aq)}$, the organic layer was washed with brine, dried over MgSO$_4$, filtered and evaporated in vacuo. The resulting residue was purified with flash chromatography on silica gel (Hexane/EtOAc 1:1) to give a pale yellow solid of 77.2 mg (50.3%).

$^1$H NMR (500 MHz, DMSO-d$_6$): δ8.87 (s, 1H), 8.73 (s, 1H), 7.57-7.50 (m, 5H), 7.29 (t, 2H), 6.98 (t, 1H), 3.85 (d, 4H), 3.79 (d, 8H), 3.20 (d, 4H), 2.90 (s, 3H), 1.93 (s, 3H)

1-{4-[4-(4-Methyl-piperazin-1-yl)-5-methylsulfanyl-6-morpholin-4-yl-pyrimidin-2-yl]-phenyl}-3-pyridin-3-yl-urea

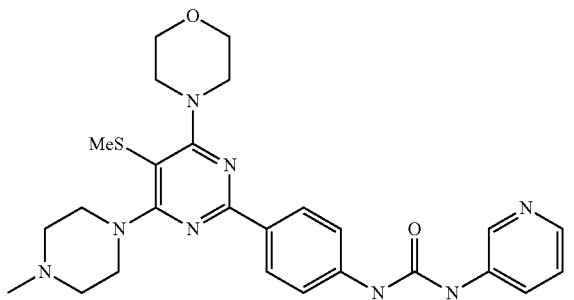

$^1$H NMR (500 MHz, DMSO-d$_6$): δ9.21 (s, 1H), 9.07 (s, 1H), 8.60 (s, 1H), 8.21-8.18 (m, 3H), 7.95 (s, 1H), 7.55-7.53 (d, 2H), 7.31 (d, 1H), 3.72 (b, 4H), 3.60 (s, 8H), 2.44 (b, 4H), 2.21 (s, 3H), 2.14 (s, 3H)

4-(5-Methylsulfanyl-4-morpholin-4-yl-6-pyridin-3-yl-pyrimidin-2-yl)-phenylamine

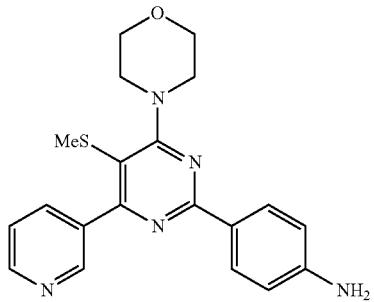 [SMILES: CSc1c(-c2cccnc2)nc(-c2ccc(N)cc2)nc1N1CCOCC1]

$^1$H NMR (500 MHz, CDCl$_3$-d$_1$): δ9.02-9.02 (d, 1H), 8.68-8.67 (dd, 1H), 8.29-8.28 (dd, 2H), 8.14-8.12 (dd, 1H), 7.41-7.38 (s, 1H), 6.73-6.71 (d, 2H), 3.94 (s, 2H), 3.90 (s, 8H), 2.04-2.03 (s, 3H)

1-[4-(5-Methylsulfanyl-4-morpholin-4-yl-6-pyridin-3-yl-pyrimidin-2-yl)-phenyl]-3-phenyl-urea

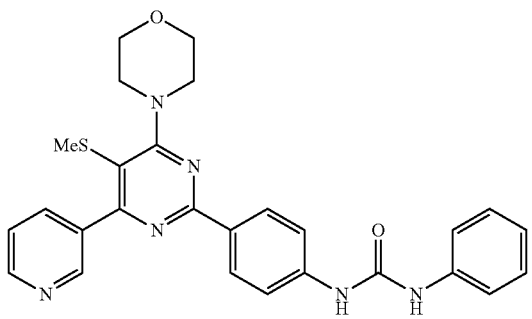

$^1$H NMR (500 MHz, DMSO-d$_6$): δ8.98 (s, 1H), 8.91-8.90 (d, 1H), 8.74 (s, 1H), 8.69-8.67 (dd, 1H), 8.33-8.31 (d, 2H), 8.16-8.14 (d, 1H), 7.60-7.58 (m, 3H), 7.56-7.53 (dd, 2H), 7.47-7.27 (dd, 2H), 6.98 (s, 1H), 3.88-3.87 (d, 4H), 3.81-3.80 (d, 4H), 2.04 (s, 3H)

1-[4-(5-Methylsulfanyl-4-morpholin-4-yl-6-pyridin-3-yl-pyrimidin-2-yl)-phenyl]-3-phenyl-thiourea

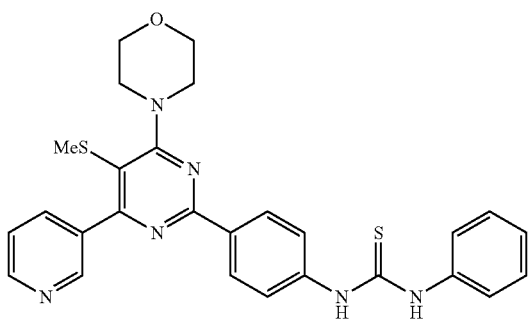 [SMILES: CSc1c(-c2cccnc2)nc(-c2ccc(NC(=S)Nc3ccccc3)cc2)nc1N1CCOCC1]

$^1$H NMR (500 MHz, DMSO-d$_6$): δ10.03 (s, 1H), 9.93 (s, 1H), 8.91-8.91 (d, 1H), 8.68-8.67 (dd, 1H), 8.34-8.32 (d,

2H), 8.16-8.154 (d, 1H), 7.68-7.66 (d, 2H), 7.55-7.49 (m, 3H), 7.36-7.33 (d, 2H), 7.15-7.14 (d, 1H), 3.89-3.88 (d, 4H), 3.81-3.80 (d, 4H), 2.04 (s, 3H)

[4-(5-Methylsulfanyl-4-morpholin-4-yl-6-pyridin-3-yl-pyrimidin-2-yl)-phenyl]-carbamic acid phenyl ester

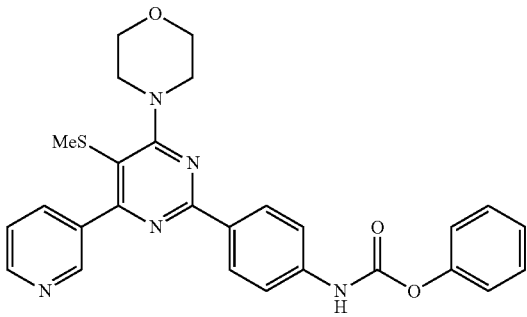 [SMILES: CSc1c(-c2cccnc2)nc(-c2ccc(NC(=O)Oc3ccccc3)cc2)nc1N1CCOCC1]

$^1$H NMR (500 MHz, CDCl$_3$-d$_1$): δ9.06-9.05 (d, 1H), 8.71-8.70 (d, 1H), 8.46-8.44 (d, 2H), 8.17-8.15 (dd, 1H), 7.58-7.56 (d, 2H), 7.43-7.41 (d, 3H), 7.41-7.39 (d, 1H), 7.27-7.20 (m, 3H), 3.92-3.92 (d, 8H), 2.05-2.04 (s, 3H)

1-[4-(5-Methylsulfanyl-4-morpholin-4-yl-6-pyridin-3-yl-pyrimidin-2-yl)-phenyl]-3-[4-(3-oxo-morpholin-4-yl)-phenyl]-urea

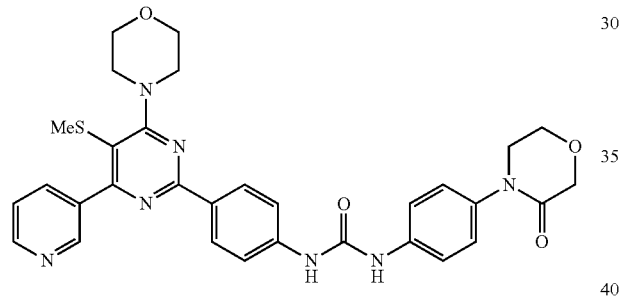

$^1$H NMR (500 MHz, DMSO-d$_6$): δ9.05 (s, 1H), 8.90-8.87 (d, 2H), 8.68-8.67 (d, 1H), 8.33-8.31 (d, 2H), 8.16-8.14 (d, 1H), 7.60-7.56 (m, 3H), 7.55-7.48 (dd, 2H), 7.30-7.28 (d, 2H), 4.18 (s, 2H), 3.97-3.95 (d, 2H), 3.88-3.87 (d, 4H), 3.81-3.80 (d, 4H), 3.70-3.68 (d, 2H), 2.04 (s, 3H)

1-[4-(5-Methylsulfanyl-4-morpholin-4-yl-6-pyridin-3-yl-pyrimidin-2-yl)-phenyl]-3-pyridin-3-yl-urea

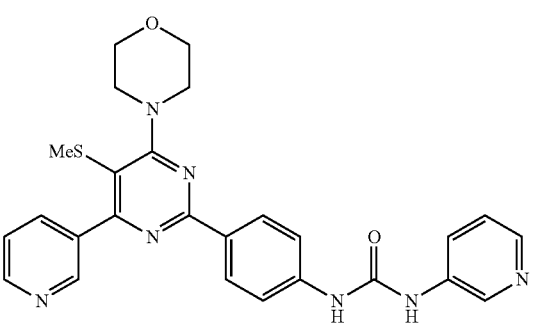 [SMILES: CSc1c(-c2cccnc2)nc(-c2ccc(NC(=O)Nc3cccnc3)cc2)nc1N1CCOCC1]

$^1$H NMR (500 MHz, DMSO-d$_6$): δ9.21 (s, 1H), 9.01 (s, 1H), 8.90 (s, 1H), 8.68-8.67 (d, 1H), 8.62 (d, 1H), 8.33-8.31 (d, 2H), 8.21-8.20 (d, 1H), 8.15-8.14 (d, 1H), 7.97-7.95 (d, 1H), 7.61-7.54 (dd, 2H), 7.34-7.33 (d, 2H), 3.88 (s, 4H), 3.81 (s, 4H), 2.04 (s, 3H)

N-(4-{3-[4-(5-Methylsulfanyl-4-morpholin-4-yl-6-pyridin-3-yl-pyrimidin-2-yl)-phenyl]-ureido}-phenyl)-methanesulfonamide

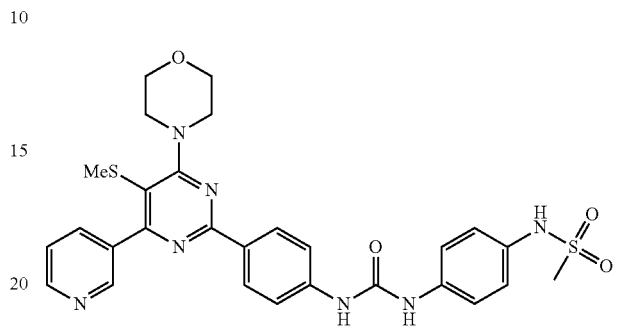

$^1$H NMR (500 MHz, DMSO-d$_6$): δ9.34 (b, 1H), 9.05 (s, 1H), 8.90 (s, 1H), 8.82 (s, 1H), 8.67 (s, 1H), 8.32-8.30 (d, 2H), 8.15-8.14 (d, 1H), 7.59-7.57 (d, 2H), 7.54 (s, 1H), 7.44-7.42 (d, 2H), 7.15-7.14 (d, 2H), 3.87 (s, 4H), 3.80 (s, 4H), 2.91 (s, 3H), 2.04 (s, 3H)

4-(5-Methylsulfanyl-2,6-di-pyridin-3-yl-pyrimidin-4-yl)-morpholine

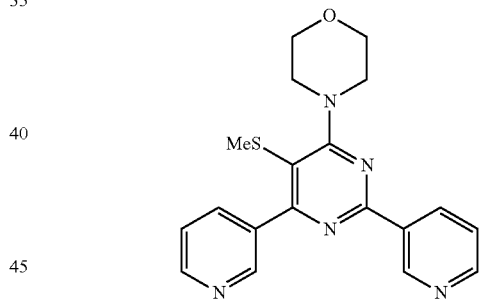

A mixture of 4-(2,6-dichloro-5-methylsulfanyl-pyrimidin-4-yl)-morpholine (200 mg, 0.717 mmol.), 3-(4,4,5,5-tetramethyl-1,3,2-dioxaborolan-2-yl)pyridine (323 mg, 1.577 mmol, 2.2 eq), (PPh$_3$)$_4$Pd (165 mg, 0.2 mmol.), 2M Na$_2$CO$_3$ (2.1 ml, 4.302 mmol, 6.0 eq.) and dioxane (20 ml) was added to a reaction vessel which was then flushed with argon. The reaction mixture was stirred at 90° C. for 16 hrs, and then dried. The solvent was removed by evaporation. The mixture was partitioned between EA and water. The organic layer was collected, washed with brine, dried over MgSO$_4$, filtered and evaporated in vacuo. The resulting residue was purified using flash chromatography on silica gel (Hexane/EtOAc 2:3, few Et3N), recrystallized by (Hexane/EtOAc) to give a pale yellow solid 57.8 mg (22.1%).

$^1$H NMR (500 MHz, CDCl$_3$-d$_1$): δ9.52-9.51 (d, 1H), 8.94-8.94 (d, 1H), 8.70-8.66 (m, 3H), 8.19-8.18 (d, 1H), 7.57-7.53 (dd, 2H), 3.92-3.90 (d, 4H), 3.81-3.80 (d, 4H), 2.05 (s, 3H)

4-(5-Ethoxy-4-morpholin-4-yl-6-pyridin-3-yl-pyrimidin-2-yl)-phenylamine

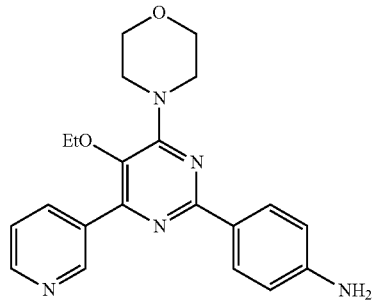 [SMILES: CCOc1c(-c2cccnc2)nc(-c2ccc(N)cc2)nc1N1CCOCC1]

$^1$H NMR (500 MHz, DMSO-d$_6$): δ1.07-1.10 (m, 3H), 3.66-3.70 (m, 2H), 3.78-3.79 (m, 8H), 5.54 (s, 2H), 6.60-6.62 (m, 2H), 7.52-7.54 (m, 1H), 8.06-8.07 (m, 2H), 8.36-8.38 (m, 1H), 8.65-8.66 (m, 1H), 9.17 (s, 1H)

4-(5-Ethoxy-4-morpholin-4-yl-6-pyridin-4-yl-pyrimidin-2-yl)-phenylamine

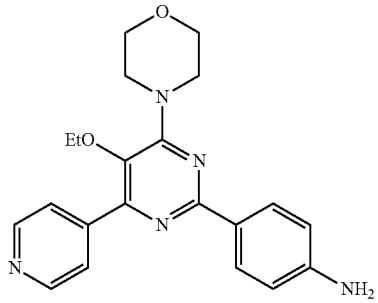

$^1$H NMR (500 MHz, DMSO-d$_6$): δ1.09-1.13 (m, 3H), 3.67-3.71 (m, 2H), 3.78-3.79 (m, 8H), 5.55 (s, 2H), 6.60-6.62 (m, 2H), 7.97-7.98 (m, 2H), 8.05-8.07 (m, 2H), 8.71-8.73 (m, 2H)

1-[4-(5-Ethoxy-4-morpholin-4-yl-6-pyridin-3-yl-pyrimidin-2-yl)-phenyl]-3-pyridin-4-yl-urea

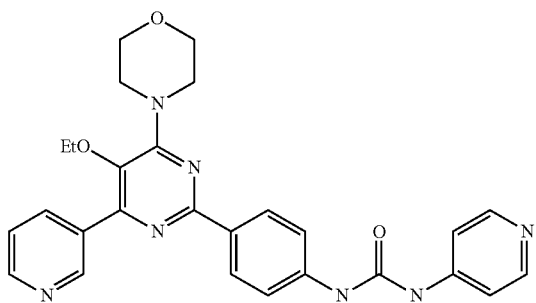

$^1$H NMR (500 MHz, DMSO-d$_6$): δ1.08-1.11 (m, 3H), 3.69-3.73 (m, 2H), 3.79-3.80 (m, 4H), 3.84-3.85 (m, 4H), 7.46-7.47 (m, 2H), 7.56-7.60 (m, 3H), 8.30-8.32 (m, 2H), 8.37-8.41 (m, 3H), 8.67-8.68 (m, 1H), 9.20 (s, 1H), 9.24 (s, 1H), 9.32 (s, 1H)

1-[4-(5-Ethoxy-4-morpholin-4-yl-6-pyridin-3-yl-pyrimidin-2-yl)-phenyl]-3-pyridin-3-yl-urea

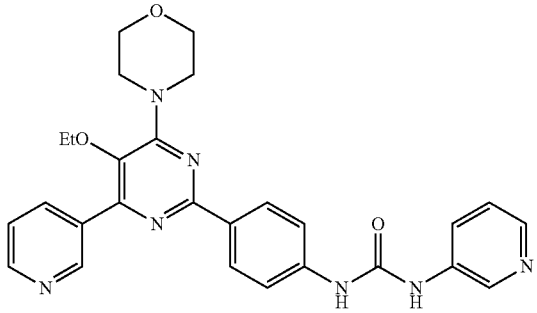 [SMILES: CCOc1c(-c2cccnc2)nc(-c2ccc(NC(=O)Nc3cccnc3)cc2)nc1N1CCOCC1]

$^1$H NMR (500 MHz, DMSO-d$_6$): δ1.08-1.11 (m, 3H), 3.69-3.73 (m, 2H), 3.79-3.80 (m, 4H), 3.84-3.85 (m, 4H), 7.33 (m, 1H), 7.57-7.59 (m, 3H), 7.98 (m, 1H), 8.20-8.21 (m, 1H), 8.29-8.31 (m, 2H), 8.39 (m, 1H), 8.61-8.62 (m, 1H), 8.67-8.68 (m, 1H), 8.89 (s, 1H), 9.07 (s, 1H), 9.19-9.20 (m, 1H)

1-[4-(5-Ethoxy-4-morpholin-4-yl-6-pyridin-4-yl-pyrimidin-2-yl)-phenyl]-3-pyridin-4-yl-urea

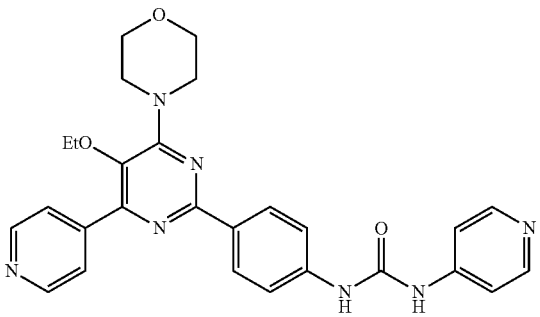 [SMILES: CCOc1c(-c2ccncc2)nc(-c2ccc(NC(=O)Nc3ccncc3)cc2)nc1N1CCOCC1]

$^1$H NMR (500 MHz, DMSO-d$_6$): δ1.11-1.14 (m, 3H), 3.70-3.74 (m, 2H), 3.78-3.79 (m, 4H), 3.84-3.85 (m, 4H), 7.45-7.46 (m, 2H), 7.58-7.59 (m, 2H), 7.99-8.00 (m, 2H), 8.30-8.32 (m, 2H), 8.37-8.38 (m, 2H), 8.74-8.75 (m, 2H), 9.20 (s, 1H), 9.25 (s, 1H)

1-[4-(5-Ethoxy-4-morpholin-4-yl-6-pyridin-4-yl-pyrimidin-2-yl)-phenyl]-3-pyridin-3-yl-urea

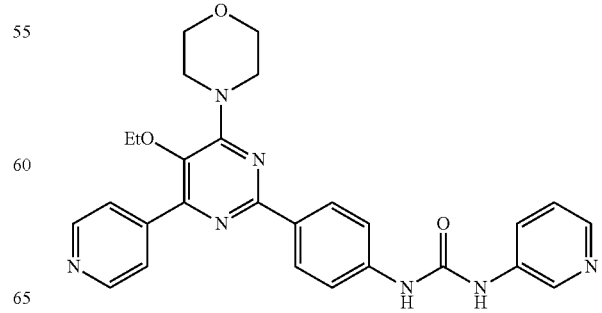

¹H NMR (500 MHz, DMSO-d₆): δ1.11-1.14 (m, 3H), 3.70-3.74 (m, 2H), 3.79-3.80 (m, 4H), 3.84-3.85 (m, 4H), 7.32-7.34 (m, 1H), 7.58-7.59 (m, 2H), 7.95-8.00 (m, 3H), 8.20-8.21 (m, 1H), 8.29-8.31 (m, 2H), 8.61-8.62 (m, 1H), 8.74-8.75 (m, 2H), 8.89 (s, 1H), 9.07 (s, 1H)

[4-(4-Chloro-5-ethoxy-6-morpholin-4-yl-pyrimidin-2-yl)-phenyl]-carbamic acid phenyl ester

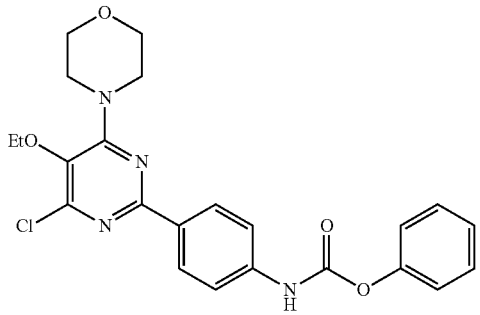 [SMILES: CCOc1c(Cl)nc(-c2ccc(NC(=O)Oc3ccccc3)cc2)nc1N1CCOCC1]

¹H NMR (500 MHz, DMSO-d₆): δ1.31-1.34 (m, 3H), 3.73-3.75 (m, 4H), 3.84-3.86 (m, 4H), 3.91-3.96 (m, 4H), 7.24-7.29 (m, 3H), 7.43-7.46 (m, 2H), 7.61-7.63 (m, 2H), 8.18-8.20 (m, 2H)

[4-(5-Ethoxy-4-morpholin-4-yl-6-pyridin-4-yl-pyrimidin-2-yl)-phenyl]-carbamic acid phenyl ester

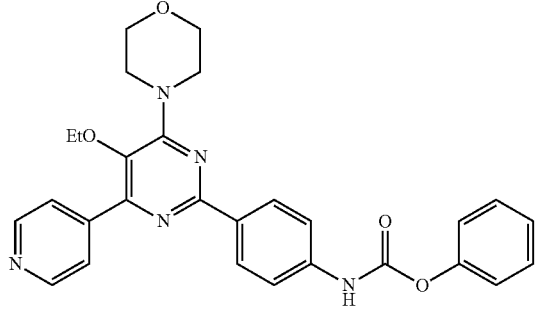 [SMILES: CCOc1c(-c2ccncc2)nc(-c2ccc(NC(=O)Oc3ccccc3)cc2)nc1N1CCOCC1]

¹H NMR (500 MHz, DMSO-d₆): δ1.11-1.13 (m, 3H), 3.70-3.74 (m, 2H), 3.78-3.79 (m, 4H), 3.84-3.85 (m, 4H), 7.24-7.29 (m, 3H), 7.43-7.46 (m, 2H), 7.62-7.64 (m, 2H), 7.99-8.00 (m, 2H), 8.32-8.34 (m, 2H), 8.73-8.74 (m, 2H), 10.46 (s, 1H)

[4-(5-Ethoxy-4-morpholin-4-yl-6-pyridin-3-yl-pyrimidin-2-yl)-phenyl]-carbamic acid phenyl ester

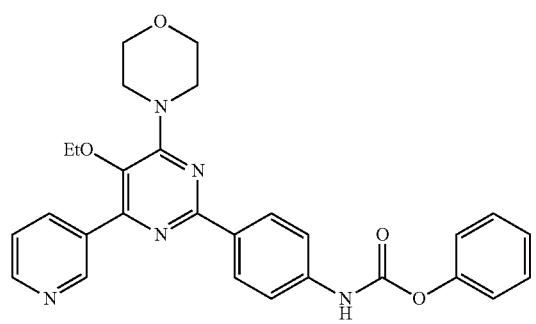

¹H NMR (500 MHz, DMSO-d₆): δ1.08-1.11 (m, 3H), 3.69-3.73 (m, 2H), 3.78-3.79 (m, 4H), 3.84-3.85 (m, 4H), 7.24-7.29 (m, 3H), 7.43-7.46 (m, 2H), 7.53-7.57 (m, 1H), 7.62-7.64 (m, 2H), 8.32-8.34 (m, 2H), 8.39-8.41 (m, 1H), 8.66-8.67 (m, 1H), 9.20 (s, 1H), 10.45 (s, 1H)

1-[4-(4-Chloro-5-ethoxy-6-morpholin-4-yl-pyrimidin-2-yl)-phenyl]-3-[4-(3-oxo-morpholin-4-yl)-phenyl]-urea

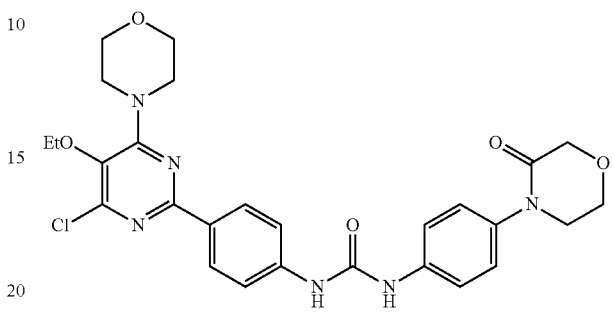

¹H NMR (500 MHz, DMSO-d₆): δ1.31-1.34 (m, 3H), 3.68-3.70 (m, 2H), 3.73-3.75 (m, 4H), 3.83-3.84 (m, 4H), 3.91-3.97 (m, 4H), 4.18 (s, 2H), 7.28-7.30 (m, 2H), 7.48-7.49 (m, 2H), 7.55-7.57 (m, 2H), 8.14-8.16 (m, 2H), 8.84 (s, 1H), 9.00 (s, 1H)

1-[4-(5-Ethoxy-4-morpholin-4-yl-6-pyridin-4-yl-pyrimidin-2-yl)-phenyl]-3-[4-(3-oxo-morpholin-4-yl)-phenyl]-urea

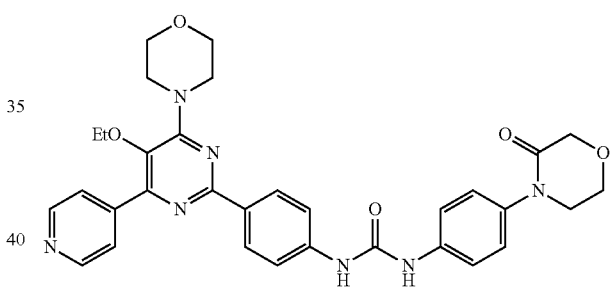

¹H NMR (500 MHz, DMSO-d₆): δ1.11-1.14 (m, 3H), 3.68-3.74 (m, 4H), 3.78-3.79 (m, 4H), 3.84-3.85 (m, 4H), 3.95-3.97 (m, 2H), 4.18 (s, 2H), 7.28-7.30 (m, 2H), 7.48-7.50 (m, 2H), 7.57-7.59 (m, 2H), 7.99-8.00 (m, 2H), 8.28-8.30 (m, 2H), 8.73-8.74 (m, 2H), 8.83 (s, 1H), 8.98 (s, 1H)

1-[4-(5-Ethoxy-4-morpholin-4-yl-6-pyridin-3-yl-pyrimidin-2-yl)-phenyl]-3-[4-(3-oxo-morpholin-4-yl)-phenyl]-urea

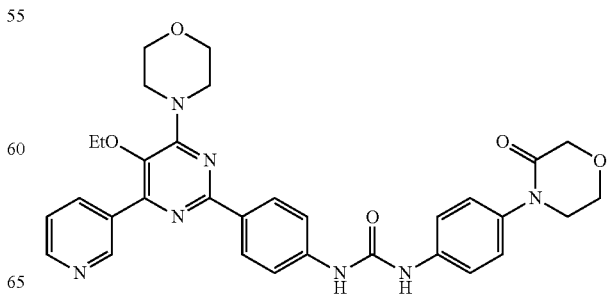

¹H NMR (500 MHz, DMSO-d₆): δ1.08-1.11 (m, 3H), 3.69-3.73 (m, 4H), 3.78-3.79 (m, 4H), 3.84-3.85 (m, 4H), 3.95-3.97 (m, 2H), 4.18 (s, 2H), 7.28-7.30 (m, 2H), 7.48-7.50 (m, 2H), 7.54-7.58 (m, 3H), 8.28-8.30 (m, 2H), 8.39-8.41 (m, 1H), 8.66-8.67 (m, 1H), 8.84 (s, 1H), 8.98 (s, 1H), 9.19-9.20 (m, 1H)

Biological Testing

The compounds of the invention, prepared as described in the examples, were subject to the following series of biological assays. Brief descriptions of different assays are as follows.

(1) Antiproliferation Assay

A549, HCT-116, and A498 cell lines were purchased from the Bioresource Collection and Research Center (BCRC, Taiwan) and cultured in Dulbecco's Modified Eagle Medium (DMEM, Sigma) containing 10% fetal bovine serum (FBS, HyClone). PC-3, U-87 MG, HCC1954 and BT474 cell lines were purchased from the American Type Culture Collection (ATCC, USA). PC-3 was grown in F12K medium (GIBCO) containing 10% FBS. U-87 MG was grown in Eagle's minimum essential medium (MEM, Sigma) supplemented with nonessential amino acids, L-glutamine, sodium pyruvate, and 10% FBS. HCC1954 was grown in RPMI medium (GIBCO) containing 10% FBS. BT-474 was grown in DMEM medium (GIBCO) containing 10% FBS. All cells were incubated in a humidified atmosphere containing 5% $CO_2$ at 37° C.

Cell lines were inoculated to the wells of a 96-well culture plate with 1000-5000 cells per well. The compounds were prepared and used to treat cells with less than 1% DMSO. After 72 hours of drug treatment, the viability of each cell line was examined by CellTiter 96 Aqueous Non-Radioactive Cell Proliferation Assay (Promega). The living cells were detectable by conversion of MTS into aqueous, soluble formazan. MTS/PMS solution was freshly prepared and 20 μl of MTS/PMS solution was added to each well of the 96-well cultured plate. The assay plate was incubated for 3 hours and the absorbance at 490 nm was measured by EMax ELISA Reader (Molecular Devices). The $IC_{50}$ values of compounds were determined after carrying out assays at eight serially diluted concentrations of each compound in triplicate, and are the mean of three separate determinations. The results were analyzed using linear regression software (GraphPad Prism 5; GraphPad Software Inc.).

(2) Immunoblotting

For immunoblotting experiments, A549 cells were inoculated to the wells of a 6-well culture plate and cultured overnight. Cells were incubated with the compound for 30 min and 24 hours and whole cell lysate was harvested by adding 1×SDS Sample Buffer (62.5 mM Tris-HCl (pH 6.8 at 25° C.), 2% w/v SDS, 10% glycerol, 50 mM DTT, and 0.01% w/v bromophenol blue or phenol red). Proteins were separated by SDS-PAGE electrophoresis and transferred to PVDF membrane. Protein expression was immunoblotted by various primary antibodies and detected by Immobilon Western Chemiluminescent HRP Substrate (Millipore). Antibody against Akt, phosphor-Akt (Ser473), phosphor-Akt (Thr308), p70 S6 Kinase, phosphor-p70 S6 Kinase (Thr389), 4E-BP1, and phosphor-4E-BP1 (Thr37/46) were purchased form Cell Signaling Technology.

(3) mTOR Kinase Assay

The activity of the compound against mTOR was examined by measuring the incorporation of $^{33}P$ from $[\gamma\text{-}^{33}P]$-ATP into 4EBP1. His-tagged, recombinant human 4EBP1 was expressed in *E. coli*, purified by nickel-nitrilotriacetic acid (Ni-NTA) resins, and stored at −80° C. Phosphorylation of 4EBP1 by mTOR was assayed in the presence or absence of the compound and performed in a final volume of 25 μl reaction buffer containing 300 ng 4EBP1, 50 ng recombinant mTOR (Invitrogen), 50 mM HEPES (pH 7.5), 1 mM EGTA, 0.01% Polysorbate 20, 10 mM $MnCl_2$, 2.5 mM DTT, 10 μM ATP, and 0.5 μCi $[\gamma\text{-}33P]$-ATP (PerkinElmer) for 30 min at 30° C. The reactions were terminated by adding 3% phosphoric acid. The $^{33}P$ labeled 4EBP1 was transferred onto UniFilter-96 GF/B plate (PerkinElmer) and quantified by Top Count Microplate Scintillation Counter (PerkinElmer). For primary screening of kinase activity inhibition, each test compound was evaluated at 10 M in duplicate. The results were the average of duplicate measurements and expressed as percentage inhibition (compound treatment versus DMSO control). The $IC_{50}$ values of the compounds were determined after carrying out assays at eight serially diluted concentrations of each compound in duplicate. The results were analyzed using linear regression software (GraphPad Prism 5; GraphPad Software Inc.).

(4) PI3K Enzyme Assay

The ability of compounds at 500 nM against phosphatidylinositide 3-kinase (PI3K) was verified by PI3K HTRF Assay. Recombinant PI3K (p110α/p85α) and PI3K (p110β/p85α) were from Millipore. Enzyme reactions were performed according to the manufacturer's suggestions. Briefly, the compounds of interest dissolved in 100% DMSO were dispensed in all wells, following which the mixture of PIP2 and enzyme was added. PI3K (p110α/p85α) and PI3K (p110β/p85α) enzyme reactions were initiated in the presence of 10 μM and 100 μM ATP, respectively, and incubated for 30 min at room temperature. STOP solution prepared 2 hours prior to use was added to stop reactions, and mixed well. Detection solution prepared 2 hours prior to use was added, and incubated at room temperature for 17 hours in the dark. Fluorescence was measures by Packard Fusion Alpha Microplate Analyzer with excitation at 340 nm and emission at 620 nm and 665 nm. HTRF ration was calculated as follows:

$$HTRF\ ratio = \frac{\text{emission at 665 nm}}{\text{emission at 620 nm}} \times 10000$$

Biological Activity

Inhibition of mTOR kinase by various compounds listed above are summarized and shown in Table 1 and Table 2 below. $IC_{50}$ value is defined as the concentration of the test compound which achieves a half-maximal inhibition of the kinase activity.

Inhibition of PI3K alpha and PI3K beta by mTOR compounds at 500 nM are summarized and shown in Table 3.

Effects on cellular proliferation by the various compounds of the present invention are summarized and shown in Table 4 below.

Inhibition effects of compounds of interest on PI3K/Akt/mTOR signal transduction pathway in PC-3 cell are summarized and shown in Table 5 below.

TABLE 1

| Compound | % Inhibition @ 10 μM |
|---|---|
| MTR-0037 | 98% |
| MTR-0043 | 96% |
| MTR-0054 | 81% |
| MTR-0069 | 98% |
| MTR-0073 | 86% |

TABLE 1-continued

| Compound | % Inhibition @ 10 μM |
|---|---|
| MTR-0077 | 87% |
| MTR-0079 | 83% |
| MTR-0081 | 95% |
| MTR-0083 | 99% |
| MTR-0091 | 92% |
| MTR-0098 | 86% |
| MTR-0102 | 81% |
| MTR-0106 | 96% |
| MTR-0108 | 89% |
| MTR-0116 | 81% |
| MTR-0118 | 94% |
| MTR-0120 | 98% |
| MTR-0121 | 94% |
| MTR-0123 | 91% |
| MTR-0124 | 99% |
| MTR-0125 | 96% |
| MTR-0128 | 99% |
| MTR-0129 | 96% |
| MTR-0132 | 98% |
| MTR-0133 | 93% |
| MTR-0135 | 90% |
| MTR-0137 | 84% |
| MTR-0139 | 85% |
| MTR-0141 | 96% |
| MTR-0142 | 98% |
| MTR-0145 | 100% |
| MTR-0147 | 95% |
| MTR-0149 | 93% |
| MTR-0150 | 87% |
| MTR-0152 | 98% |
| MTR-0159 | 97% |
| MTR-162 | 95% |
| MTR-0164 | 91% |
| MTR-0165 | 99% |
| MTR-0167 | 89% |
| MTR-0168 | 91% |
| MTR-0169 | 96% |
| MTR-0172 | 86% |
| MTR-173 | 92% |
| MTR-0176 | 96% |
| MTR-0177 | 84% |
| MTR-0178 | 90% |
| MTR-0182 | 99% |
| MTR-0183 | 95% |
| MTR-0184 | 98% |
| MTR-0185 | 99% |
| MTR-0186 | 96% |
| MTR-0191 | 100% |
| MTR-0193 | 81% |
| MTR-0195 | 101% |
| MTR-0197 | 97% |
| MTR-0198 | 87% |
| MTR-0199 | 99% |
| MTR-0200 | 84% |
| MTR-0202 | 96% |
| MTR-0205 | 100% |
| MTR-0210 | 96% |
| MTR-0211 | 98% |
| MTR-0212 | 85% |
| MTR-0213 | 84% |
| MTR-0215 | 96% |
| MTR-0216 | 94% |
| MTR-0220 | 102% |
| MTR-0221 | 101% |
| MTR-0222 | 93% |
| MTR-0225 | 101% |
| MTR-0226 | 90% |
| MTR-0227 | 99% |
| MTR-0228 | 101% |
| MTR-0229 | 100% |
| MTR-0231 | 97% |
| MTR-0232 | 95% |
| MTR-0233 | 91% |
| MTR-0236 | 98% |
| MTR-0237 | 85% |
| MTR-0238 | 95% |
| MTR-0239 | 89% |
| MTR-0241 | 99% |
| MTR-0242 | 96% |
| MTR-0243 | 92% |
| MTR-0244 | 99% |
| MTR-0245 | 94% |
| MTR-0246 | 96% |
| MTR-0248 | 95% |
| MTR-0249 | 97% |
| MTR-0250 | 98% |
| MTR-0251 | 98% |
| MTR-0252 | 82% |
| MTR-0253 | 99% |
| MTR-0256 | 90% |
| MTR-0257 | 93% |
| MTR-0261 | 98% |
| MTR-0262 | 90% |
| MTR-0264 | 86% |
| MTR-0265 | 96% |
| MTR-0266 | 96% |
| MTR-0267 | 98% |
| MTR-0268 | 97% |
| MTR-0270 | 96% |
| MTR-0271 | 98% |
| MTR-0273 | 99% |
| MTR-0274 | 99% |
| MTR-0275 | 97% |
| MTR-0276 | 82% |
| MTR-0277 | 99% |
| MTR-0278 | 100% |
| MTR-0280 | 95% |
| MTR-0282 | 99% |
| MTR-0283 | 100% |
| MTR-0286 | 93% |
| MTR-0288 | 98% |
| MTR-0289 | 91% |
| MTR-0291 | 89% |
| MTR-0293 | 83% |
| MTR-0297 | 83% |
| MTR-0299 | 97% |
| MTR-0303 | 90% |
| MTR-0304 | 90% |
| MTR-0305 | 82% |
| MTR-0306 | 90% |
| MTR-0307 | 82% |
| MTR-0308 | 93% |
| MTR-0310 | 86% |
| MTR-0312 | 94% |
| MTR-0313 | 98% |
| MTR-0314 | 98% |
| MTR-0316 | 99% |
| MTR-0317 | 93% |
| MTR-0318 | 91% |
| MTR-0319 | 84% |
| MTR-0322 | 94% |
| MTR-0323 | 100% |
| MTR-0324 | 81% |
| MTR-0325 | 100% |
| MTR-0326 | 101% |
| MTR-0328 | 85% |
| MTR-0329 | 97% |
| MTR-0334 | 93% |
| MTR-0335 | 89% |
| MTR-0336 | 89% |
| MTR-0337 | 96% |
| MTR-0338 | 94% |
| MTR-0341 | 83% |
| MTR-0343 | 92% |
| MTR-0344 | 92% |
| MTR-0345 | 95% |
| MTR-0347 | 96% |
| MTR-0350 | 95% |
| MTR-0351 | 99% |
| MTR-0352 | 94% |
| MTR-0353 | 96% |
| MTR-0356 | 82% |
| MTR-0358 | 100% |
| MTR-0360 | 95% |

TABLE 1-continued

| Compound | % Inhibition @ 10 μM |
|---|---|
| MTR-0361 | 95% |
| MTR-0362 | 84% |
| MTR-0363 | 93% |
| MTR-0364 | 100% |
| MTR-0365 | 99% |
| MTR-0366 | 85% |
| MTR-0368 | 97% |
| MTR-0369 | 98% |
| MTR-0370 | 97% |
| MTR-0372 | 96% |
| MTR-0373 | 81% |
| MTR-0376 | 96% |
| MTR-0377 | 97% |
| MTR-0378 | 96% |
| MTR-0380 | 91% |
| MTR-0381 | 92% |
| MTR-0382 | 99% |
| MTR-0385 | 98% |
| MTR-0387 | 96% |
| MTR-0388 | 100% |
| MTR-0391 | 100% |
| MTR-0392 | 102% |
| MTR-0394 | 101% |
| MTR-0398 | 89% |
| MTR-0400 | 85% |
| MTR-0401 | 101% |
| MTR-0403 | 88% |
| MTR-0404 | 97% |
| MTR-0405 | 97% |
| MTR-0406 | 97% |
| MTR-0407 | 96% |
| MTR-0410 | 85% |
| MTR-0411 | 93% |
| MTR-0412 | 98% |
| MTR-0415 | 81% |
| MTR-0419 | 82% |
| MTR-0420 | 92% |
| MTR-0421 | 99% |
| MTR-0423 | 95% |
| MTR-0424 | 100% |
| MTR-0426 | 97% |
| MTR-0427 | 97% |
| MTR-0430 | 86% |
| MTR-0435 | 90% |
| MTR-0436 | 99% |
| MTR-0438 | 99% |
| MTR-0440 | 89% |
| MTR-0442 | 96% |
| MTR-0443 | 100% |
| MTR-0446 | 101% |
| MTR-0449 | 100% |
| MTR-0452 | 100% |
| MTR-0453 | 101% |
| MTR-0454 | 100% |
| MTR-0455 | 100% |
| MTR-0456 | 101% |
| MTR-0457 | 98% |
| MTR-0459 | 88% |
| MTR-0461 | 99% |
| MTR-0462 | 99% |
| MTR-0463 | 97% |
| MTR-0464 | 96% |
| MTR-0465 | 97% |
| MTR-0468 | 97% |
| MTR-0469 | 93% |
| MTR-0470 | 88% |
| MTR-0471 | 94% |
| MTR-0472 | 95% |
| MTR-0474 | 88% |
| MTR-0476 | 99% |
| MTR-0477 | 99% |
| MTR-0478 | 99% |
| MTR-0479 | 95% |
| MTR-0480 | 90% |
| MTR-0481 | 98% |
| MTR-0483 | 88% |
| MTR-0484 | 95% |
| MTR-0485 | 100% |
| MTR-0486 | 88% |
| MTR-0487 | 98% |
| MTR-0488 | 94% |
| MTR-0489 | 96% |
| MTR-0490 | 102% |
| MTR-0491 | 100% |
| MTR-0492 | 100% |
| MTR-0493 | 99% |
| MTR-0494 | 86% |
| MTR-0495 | 100% |
| MTr-0496 | 95% |

TABLE 2

| Compounds | $IC_{50}$ of Kinase [nM] |
|---|---|
| MTR-0069 | 142.6 |
| MTR-0081 | 292.3 |
| MTR-0083 | 107.2 |
| MTR-0106 | 234.9 |
| MTR-0124 | 102.5 |
| MTR-0128 | 253.4 |
| MTR-0132 | 116.3 |
| MTR-0142 | 257.3 |
| MTR-0152 | 206.8 |
| MTR-0165 | 233.2 |
| MTR-0173 | 198.1 |
| MTR-0176 | 210.1 |
| MTR-0182 | 275.3 |
| MTR-0184 | 102.3 |
| MTR-0185 | 223.5 |
| MTR-0195 | 116.4 |
| MTR-0197 | 110.4 |
| MTR-0199 | 161.8 |
| MTR-0202 | 253.6 |
| MTR-0205 | 116.4 |
| MTR-0211 | 226.9 |
| MTR-0215 | 52.5 |
| MTR-0216 | 133.9 |
| MTR-0220 | 72.2 |
| MTR-0221 | 134.6 |
| MTR-0222 | 11.5 |
| MTR-0225 | 101.2 |
| MTR-0226 | 212.6 |
| MTR-0227 | 18.8 |
| MTR-0228 | 82.6 |
| MTR-0229 | 241 |
| MTR-0231 | 105.2 |
| MTR-0232 | 184.7 |
| MTR-0233 | 80.1 |
| MTR-0236 | 80.7 |
| MTR-0238 | 225.2 |
| MTR-0241 | 8.1 |
| MTR-0242 | 107.2 |
| MTR-0244 | 18 |
| MTR-0246 | 228.1 |
| MTR-0248 | 96.4 |
| MTR-0249 | 116.7 |
| MTR-0250 | 150.2 |
| MTR-0251 | 146.1 |
| MTR-0253 | 62.5 |
| MTR-0257 | 74.4 |
| MTR-0261 | 86.8 |
| MTR-0262 | 8 |
| MTR-0265 | 171.9 |
| MTR-0266 | 256.7 |
| MTR-0267 | 109.1 |
| MTR-0268 | 237.7 |
| MTR-0271 | 89.6 |
| MTR-0273 | 81.1 |
| MTR-0274 | 105.6 |
| MTR-0277 | 78.3 |

TABLE 2-continued

| Compounds | IC$_{50}$ of Kinase [nM] |
|---|---|
| MTR-0278 | 67 |
| MTR-0282 | 47.7 |
| MTR-0283 | 30.5 |
| MTR-0288 | 78.9 |
| MTR-0299 | 177 |
| MTR-0303 | 237.9 |
| MTR-0308 | 48.6 |
| MTR-0313 | 214.3 |
| MTR-0314 | 169.7 |
| MTR-0316 | 93.9 |
| MTR-0322 | 93 |
| MTR-0323 | 50.1 |
| MTR-0325 | 24.8 |
| MTR-0326 | 40.9 |
| MTR-0337 | 272.2 |
| MTR-0347 | 174.5 |
| MTR-0351 | 65.7 |
| MTR-0353 | 194.6 |
| MTR-0358 | 26.8 |
| MTR-0364 | 70.4 |
| MTR-0365 | 179.9 |
| MTR-0368 | 83.4 |
| MTR-0369 | 214.1 |
| MTR-0370 | 86 |
| MTR-0372 | 202.4 |
| MTR-0376 | 130.3 |
| MTR-0378 | 133.2 |
| MTR-0380 | 221.2 |
| MTR-0382 | 67.7 |
| MTR-0385 | 215 |
| MTR-0387 | 140.8 |
| MTR-0388 | 79.6 |
| MTR-0391 | 5.4 |
| MTR-0392 | 19.6 |
| MTR-0394 | 70.4 |
| MTR-0401 | 64.8 |
| MTR-0404 | 148.5 |
| MTR-0405 | 49.5 |
| MTR-0406 | 179.7 |
| MTR-0407 | 219.5 |
| MTR-0412 | 136.93 |
| MTR-0420 | 65.7 |
| MTR-0421 | 58.8 |
| MTR-0424 | 30.1 |
| MTR-0426 | 173.9 |
| MTR-0427 | 97.7 |
| MTR-0436 | 69.4 |
| MTR-0438 | 51.1 |
| MTR-0442 | 39 |
| MTR-0443 | 76.8 |
| MTR-0446 | 56.6 |
| MTR-0449 | 79.2 |
| MTR-0452 | 155.1 |
| MTR-0453 | 30.2 |
| MTR-0454 | 110.9 |
| MTR-0455 | 42.3 |
| MTR-0456 | 119.3 |
| MTR-0457 | 5.8 |
| MTR-0461 | 138.2 |
| MTR-0462 | 101.1 |
| MTR-0463 | 47.8 |
| MTR-0464 | 75.1 |
| MTR-0465 | 124.1 |
| MTR-0469 | 193.5 |
| MTR-0471 | 252 |
| MTR-0472 | 117.4 |
| MTR-0476 | 175.9 |
| MTR-0477 | 23.7 |
| MTR-0478 | 25.1 |
| MTR-0481 | 169.3 |
| MTR-0484 | 58.1 |
| MTR-0487 | 86.7 |
| MTR-0488 | 255.5 |
| MTR-0489 | 267.7 |

TABLE 3

| Compound | % inhibition @ 500 nM | |
|---|---|---|
| | p110α | p110β |
| MTR-0043 | 85.40% | 44.80% |
| MTR-0069 | 53.80% | 4.10% |
| MTR-0083 | 44.80% | 9.00% |
| MTR-0091 | 60.90% | 16.20% |
| MTR-0124 | 49.10% | −2.60% |
| MTR-0128 | 85.80% | 17.30% |
| MTR-0133 | 70.00% | 4.50% |
| MTR-0135 | 70.10% | 14.20% |
| MTR-0147 | 52.40% | 1.20% |
| MTR-0152 | 83.00% | 35.70% |
| MTR-0162 | 102.20% | 33.90% |
| MTR-0164 | 84.70% | 42.10% |
| MTR-0165 | 100.80% | 66.20% |
| MTR-0168 | 65.00% | 20.20% |
| MTR-0169 | 52.70% | 3.20% |
| MTR-0173 | 82.10% | 32.40% |
| MTR-0178 | 48.80% | 8.20% |
| MTR-0197 | 59.80% | 20.30% |
| MTR-0205 | 42.60% | 6.00% |
| MTR-0211 | 42.00% | 24.40% |
| MTR-0215 | 53.60% | 24.10% |
| MTR-0222 | 44.30% | 16.50% |
| MTR-0225 | 43.80% | 14.30% |
| MTR-0226 | 45.70% | 25.20% |
| MTR-0227 | 87.00% | 38.20% |
| MTR-0228 | 74.40% | 33.20% |
| MTR-0236 | 61.20% | 17.60% |
| MTR-0241 | 94.80% | 53.70% |
| MTR-0242 | 96.30% | 22.80% |
| MTR-0244 | 60.00% | 26.30% |
| MTR-0246 | 43.30% | 10.90% |
| MTR-0248 | 45.80% | 3.60% |
| MTR-0257 | 95.50% | 62.40% |
| MTR-0261 | 58.40% | 8.80% |
| MTR-0262 | 56.30% | 18.00% |
| MTR-0267 | 83.70% | 54.10% |
| MTR-0270 | 41.10% | 20.00% |
| MTR-0271 | 94.50% | 53.80% |
| MTR-0273 | 50.20% | 28.30% |
| MTR-0274 | 59.00% | 28.40% |
| MTR-0277 | 61.90% | 56.50% |
| MTR-0278 | 58.60% | 31.00% |
| MTR-0282 | 76.80% | 53.90% |
| MTR-0283 | 72.90% | 53.40% |
| MTR-0288 | 79.20% | 32.60% |
| MTR-0299 | 44.30% | 6.70% |
| MTR-0308 | 106.50% | 37.50% |
| MTR-0313 | 86.90% | 30.40% |
| MTR-0316 | 55.90% | 27.90% |
| MTR-0322 | 44.20% | 13.20% |
| MTR-0323 | 90.80% | 49.50% |
| MTR-0325 | 91.50% | 36.90% |
| MTR-0326 | 90.70% | 42.30% |
| MTR-0347 | 80.60% | 63.50% |
| MTR-0351 | 52.30% | 32.00% |
| MTR-0358 | 97.80% | 97.80% |
| MTR-0368 | 101.40% | 60.90% |
| MTR-0370 | 61.80% | 40.80% |
| MTR-0372 | 95.50% | 47.90% |
| MTR-0376 | 79.40% | 47.90% |
| MTR-0378 | 84.50% | 30.00% |
| MTR-0380 | 100.60% | 67.00% |
| MTR-0382 | 95.90% | 53.30% |
| MTR-0385 | 64.00% | 36.80% |
| MTR-0387 | 83.10% | 27.70% |
| MTR-0391 | 51.70% | 29.10% |
| MTR-0392 | 46.60% | 31.30% |
| MTR-0394 | 70.50% | 67.20% |
| MTR-0398 | 47.00% | 21.80% |
| MTR-0401 | 41.70% | 16.20% |
| MTR-0404 | 66.90% | 22.70% |
| MTR-0405 | 52.50% | 23.60% |
| MTR-0406 | 78.40% | 56.90% |
| MTR-0407 | 63.40% | 48.60% |
| MTR-0412 | 82.70% | 53.00% |
| MTR-0420 | 58.60% | 8.30% |

TABLE 3-continued

| Compound | % inhibition @ 500 nM | |
|---|---|---|
| | p110α | p110β |
| MTR-0421 | 98.70% | 51.30% |
| MTR-0424 | 71.50% | 27.10% |
| MTR-0426 | 58.40% | 39.70% |
| MTR-0427 | 71.10% | 76.20% |
| MTR-0436 | 71.50% | 51.90% |
| MTR-0442 | 79.10% | 48.50% |
| MTR-0446 | 66.30% | 40.70% |
| MTR-0449 | 75.40% | 92.50% |
| MTR-0454 | 74.40% | 30.30% |
| MTR-0455 | 48.90% | 19.80% |
| MTR-0456 | 52.60% | 30.60% |
| MTR-0457 | 47.40% | 22.30% |
| MTR-0461 | 93.40% | 46.70% |
| MTR-0462 | 67.90% | 38.30% |
| MTR-0469 | 81.70% | 70.70% |

TABLE 4

| Compound | $IC_{50}$, nM | |
|---|---|---|
| | A549 | PC3 |
| MTR-0124 | 566 ± 12 | 390 ± 9 |
| MTR-0128 | 914 ± 29 | 499 ± 45 |
| MTR-0142 | 488 ± 56 | 416 ± 90 |
| MTR-0145 | 1358 ± 340 | 432 ± 20 |
| MTR-0191 | 373 ± 14 | 374 ± 18 |
| MTR-0197 | 115 ± 2 | 18 ± 1 |
| MTR-0205 | 673 ± 19 | 130 ± 5 |
| MTR-0221 | 710 ± 76 | 327 ± 43 |
| MTR-0222 | 88 ± 17 | 30 ± 7 |
| MTR-0225 | 1535 ± 113 | 333 ± 24 |
| MTR-0227 | 223 ± 20 | 49 ± 3 |
| MTR-0228 | 1029 ± 114 | 193 ± 8 |
| MTR-0241 | 129 ± 5 | 61 ± 4 |
| MTR-0242 | 748 ± 140 | 286 ± 1 |
| MTR-0244 | 891 ± 64 | 70 ± 9 |
| MTR-0246 | 1449 ± 29 | 433 ± 10 |
| MTR-0248 | 145 ± 5 | 178 ± 27 |
| MTR-0250 | 834 ± 37 | 305 ± 24 |
| MTR-0251 | 2062 ± 75 | 456 ± 23 |
| MTR-0253 | 2478 ± 367 | 268 ± 44 |
| MTR-0257 | 501 ± 23 | 119 ± 14 |
| MTR-0261 | 512 ± 25 | 111 ± 2 |
| MTR-0262 | 561 ± 49 | 130 ± 4 |
| MTR-0267 | 3492 ± 156 | 207 ± 7 |
| MTR-0271 | 155 ± 1 | 97 ± 4 |
| MTR-0273 | 660 ± 40 | 162 ± 6 |
| MTR-0274 | 135 ± 11 | 57 ± 2 |
| MTR-0277 | 561 ± 30 | 86 ± 3 |
| MTR-0278 | 67 ± 3 | 39 ± 0 |
| MTR-0280 | 382 ± 23 | 126 ± 8 |
| MTR-0282 | 7571 ± 755 | 148 ± 14 |
| MTR-0283 | 3721 ± 341 | 283 ± 31 |
| MTR-0288 | 3982 ± 275 | 252 ± 27 |
| MTR-0299 | 2499 ± 49 | 384 ± 39 |
| MTR-0303 | 223 ± 8 | 46 ± 1 |
| MTR-0308 | 219 ± 11 | 62 ± 2 |
| MTR-0322 | 302 ± 1 | 109 ± 0 |
| MTR-0323 | 1041 ± 23 | 86 ± 3 |
| MTR-0325 | 53 ± 2 | 16 ± 1 |
| MTR-0326 | 1029 ± 19 | 147 ± 10 |
| MTR-0337 | 457 ± 38 | 154 ± 6 |
| MTR-0347 | 313 ± 3 | 154 ± 8 |
| MTR-0350 | 614 ± 28 | 188 ± 6 |
| MTR-0353 | 557 ± 7 | 396 ± 6 |
| MTR-0358 | 144 ± 1 | 34 ± 1 |
| MTR-0364 | 462 ± 8 | 142 ± 14 |
| MTR-0365 | 74 ± 5 | 23 ± 1 |
| MTR-0368 | 214 ± 2 | 74 ± 2 |
| MTR-0369 | 280 ± 6 | 44 ± 4 |
| MTR-0370 | 287 ± 5 | 92 ± 4 |
| MTR-0372 | 332 ± 20 | 204 ± 7 |

TABLE 4-continued

| Compound | $IC_{50}$, nM | |
|---|---|---|
| | A549 | PC3 |
| MTR-0376 | 595 ± 33 | 142 ± 10 |
| MTR-0377 | 598 ± 18 | 205 ± 6 |
| MTR-0378 | 186 ± 3 | 113 ± 11 |
| MTR-0382 | 74 ± 5 | 19 ± 1 |
| MTR-0385 | 361 ± 13 | 396 ± 6 |
| MTR-0387 | 148 ± 10 | 88 ± 3 |
| MTR-0388 | 250 ± 8 | 136 ± 3 |
| MTR-0391 | 6 ± 0 | 8 ± 0 |
| MTR-0392 | 188 ± 7 | 22 ± 0 |
| MTR-0394 | 431 ± 10 | 71 ± 2 |
| MTR-0398 | 460 ± 28 | 179 ± 14 |
| MTR-0401 | 685 ± 35 | 169 ± 3 |
| MTR-0404 | 273 ± 1 | 109 ± 0 |
| MTR-0405 | 88 ± 6 | 74 ± 2 |
| MTR-0406 | >10000 | 285 ± 5 |
| MTR-0407 | >10000 | 386 ± 16 |
| MTR-0420 | 234 ± 1 | 148 ± 2 |
| MTR-0421 | 87 ± 1 | 37 ± 1 |
| MTR-0424 | 118 ± 2 | 51 ± 1 |
| MTR-0426 | 962 ± 58 | 282 ± 11 |
| MTR-0427 | 1798 ± 52 | 125 ± 2 |
| MTR-0436 | 299 ± 10 | 78 ± 4 |
| MTR-0438 | 116 ± 4 | 48 ± 1 |
| MTR-0442 | 392 ± 15 | 110 ± 10 |
| MTR-0443 | 529 ± 7 | 131 ± 6 |
| MTR-0446 | 379 ± 13 | 130 ± 8 |
| MTR-0449 | 1050 ± 12 | 95 ± 7 |
| MTR-0452 | 82 ± 3 | 32 ± 1 |
| MTR-0453 | 206 ± 1 | 56 ± 2 |
| MTR-0454 | 215 ± 1 | 54 ± 1 |
| MTR-0455 | 309 ± 16 | 72 ± 2 |
| MTR-0456 | 2088 ± 34 | 362 ± 25 |
| MTR-0457 | 11 ± 0.2 | 6.5 ± 0.3 |
| MTR-0461 | 177 ± 3 | 64 ± 2 |
| MTR-0462 | 448 ± 23 | 182 ± 6 |
| MTR-0463 | 222 ± 15 | 32 ± 1 |
| MTR-0464 | 12 ± 0.8 | 2.4 ± 0 |
| MTR-0465 | 197 ± 3 | 137 ± 2 |
| MTR-0469 | 39 ± 2 | 5.7 ± 0 |
| MTR-0471 | | 34 ± 2 |
| MTR-0472 | | 226 ± 19 |
| MTR-0476 | 137 ± 6 | 15 ± 0 |
| MTR-0477 | 122 ± 1 | 102 ± 1 |
| MTR-0478 | 107 ± 4 | 102 ± 1 |
| MTR-0481 | 608 ± 14 | 424 ± 26 |

TABLE 5

| compound | $IC_{50}$ (nM) | | |
|---|---|---|---|
| | p-S6K (mTORC1) | p-Akt S473 (mTORC2) | p-Akt T308 (PI3K) |
| PI-103 | 64.86 | 35.61 | 86.73 |
| GDC-0941 | 451.34 | 11.49 | 158.49 |
| BEZ-235 | <10 | 28.91 | 892.1 |
| Rapamycin | <10 | <10 | >1000 |
| MTR-0227 | 11.64 | 184.73 | 141.29 |
| MTR-0325 | <10 | 74.49 | >1000 |
| MTR-0358 | <10 | 491.45 | >1000 |
| MTR-0391 | <10 | 19.14 | 290.64 |
| MTR-0392 | 35.03 | 17.91 | <10 |
| MTR-0394 | <10 | 11.11 | <10 |

What is claimed is:

1. A method of treating mTOR kinase-/PI3K kinase-related diseases in a subject in need thereof which comprises administering to the subject an effective amount of a compound of formula (I):

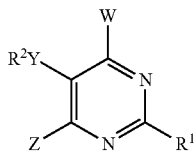

wherein R¹ is selected from:
(i) a group of the following formula:

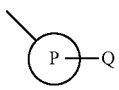

wherein
P is aryl or heteroaryl which is unsubstituted or substituted, when P is a benzoimidazole group, said benzoimidazole group is attached to the pyrimidinyl group in formula (I) through its benzene ring;
Q is selected from —H, —OR, —SR, -Halo, —NR$_3$R$_4$, —OS(O)$_m$R, —OC(O)R, —OC(O)NHR, —S(O)$_m$NR$_3$R$_4$, —NRC(O)R, —NRS(O)$_m$R, —NRC(O)NR$_3$R$_4$, and —NRC(S)NR$_3$R$_4$, wherein each R, R$_3$, and R$_4$ is independently selected from H, C$_1$-C$_6$ alkyl, C$_3$-C$_{10}$ cycloalkyl and a 5- to 12-membered carbocyclic group, aryl or heteroaryl group, the group being unsubstituted or substituted; m is 1 or 2; or R$_3$ and R$_4$, which are the same or different, are each independently selected from H, C$_1$-C$_6$ alkyl which is unsubstituted or substituted, C$_3$-C$_{10}$ cycloalkyl which is unsubstituted or substituted, —C(O)R, —C(O)N(R)$_2$ and —S(O)$_m$R wherein R and m are as defined above, or R$_3$ and R$_4$ together with the nitrogen atom to which they are attached form a saturated 5-, 6- or 7-membered N-containing heterocyclic group which is unsubstituted or substituted;
—C(O)R, —C(O)N(R)$_2$ and —S(O)$_m$R wherein R and m are as defined above;
Y is selected from —O—(CH$_2$)$_n$—, —S—(CH$_2$)$_n$—, and —S(O)$_m$(CH$_2$)$_n$— wherein m is 1 or 2, n is 0 or an integer of 1 to 3, and R² is selected from H or a 5- to 12-membered carbocyclic or heterocyclic group which is unsubstituted or substituted, and a group —NR$_3$R$_4$ wherein R$_3$ and R$_4$ are as defined above;
Z is selected from (i) halo, —(CH$_2$)$_s$COOR, —(CH$_2$)$_s$CHO, —(CH$_2$)CH$_2$OR, —(CH$_2$)$_s$CONR$_3$R$_4$, —(CH$_2$)$_s$CH$_2$NR$_3$R$_4$, —NR$_3$R$_4$ and —O(CH$_2$)$_s$NR$_3$R$_4$ wherein s is 0 or an integer of 1 to 2 and wherein R, R$_3$ and R$_4$ are as defined above; (ii) substituted or unsubstituted heteroaryl, (iii) substituted or unsubstituted heterocyclyl, (iv) substituted or unsubstituted aryl, and (v) substituted or unsubstituted C$_1$-C$_6$-alkyl; and
W is selected from (i) NR$_5$R$_6$, wherein R$_5$ and R$_6$ form, together with the N atom to which they are attached, a morpholine ring which is unsubstituted or substituted, (ii) substituted or unsubstituted heteroaryl, (iii) substituted or unsubstituted heterocyclyl, (iv) substituted or unsubstituted aryl, and (v) substituted or unsubstituted C$_1$-C$_6$-alkyl;
or a stereoisomer, or a tautomer, or an N-oxide, or a pharmaceutically acceptable salt, or an ester, or a prodrug, or a hydrate, or a solvate thereof.

2. A method according to claim 1, wherein the mTOR kinase-/PI3K kinase-related disease is selected from cancer, immune disorders, cardiovascular disease, viral infection, inflammation, metabolism/endocrine function disorders and neurological disorders.

3. A method according to claim 2, wherein the cancer is a Epidermal Growth Factor Receptor (EGFR) dependent cancer or a cancer that resists to EGFR targeting agent.

4. A method according to claim 2, which comprises administering to the subject a further therapeutic agent.

5. A method according to claim 4, wherein the further therapeutic agent is a protein kinase inhibitor, an antibody, an alkylating agent, a mitotic inhibitor, an antimetabolite, a cell cycle inhibitor, an enzyme, a hormone, an anti-hormone, a growth-factor inhibitor, a plant alkaloid and terpenoid, a topoisomerase inhibitor, an antitumor antibiotic, a *vinca* alkaloid, a taxane, a platinum agent, a thalidomide or relative analog, an antiangiogenic agent, or a combination thereof.

6. A method of treating mTOR kinase-/PI3K kinase-related diseases in a subject in need thereof which comprises administering to the subject an effective amount of a compound selected from:
5-Ethoxy-2-(3-hydroxy-phenyl)-6-morpholin-4-yl-pyrimidine-4-carboxylic acid ethyl ester (MTR-0037)
5-Ethoxy-2-(4-hydroxy-3-methoxy-phenyl)-6-morpholin-4-yl-pyrimidine-4-carboxylic acid ethyl ester (MTR-0038)
5-Ethoxy-2-(3-fluoro-4-methoxy-phenyl)-6-morpholin-4-yl-pyrimidine-4-carboxylic acid ethyl ester (MTR-0039)
2-(3-Amino-phenyl)-5-ethoxy-6-morpholin-4-yl-pyrimidine-4-carboxylic acid ethyl ester (MTR-0040)
3-[4-(2-Dimethylamino-ethoxy)-5-methylsulfanyl-6-morpholin-4-yl-pyrimidin-2-yl]-phenol (MTR-0043)
3-[4-(2-Dimethylamino-ethoxy)-5-methylsulfanyl-6-morpholin-4-yl-pyrimidin-2-yl]-phenol (MTR-0046)
3-(5-Methoxy-4-morpholin-4-yl-pyrimidin-2-yl)-phenylamine (MTR-0047)
2-(3,5-Difluoro-phenyl)-5-ethoxy-6-morpholin-4-yl-pyrimidine-4-carboxylic acid ethyl ester (MTR-0053)
5-Ethoxy-2-(1H-indol-5-yl)-6-morpholin-4-yl-pyrimidine-4-carboxylic acid ethyl ester (MTR-0054)
5-Ethoxy-2-(1H-indol-6-yl)-6-morpholin-4-yl-pyrimidine-4-carboxylic acid ethyl ester (MTR-0055)
2-Benzo[1,3]dioxol-5-yl-5-ethoxy-6-morpholin-4-yl-pyrimidine-4-carboxylic acid ethyl ester (MTR-0056)
5-Ethoxy-2-(1H-indazol-4-yl)-6-morpholin-4-yl-pyrimidine-4-carboxylic acid ethyl ester (MTR-0057)
5-Ethoxy-2-(2-fluoro-3-methoxy-phenyl)-6-morpholin-4-yl-pyrimidine-4-carboxylic acid ethyl ester (MTR-0058)
2-{3-[3-(4-Chloro-3-trifluoromethyl-phenyl)-ureido]-phenyl}-5-ethoxy-6-morpholin-4-yl-pyrimidine-4-carboxylic acid ethyl ester (MTR-0059)
5-Ethoxy-6-morpholin-4-yl-2-[3-(3-phenyl-ureido)-phenyl]-pyrimidine-4-carboxylic acid ethyl ester (MTR-0060)
2-(4-Amino-phenyl)-5-ethoxy-6-morpholin-4-yl-pyrimidine-4-carboxylic acid ethyl ester (MTR-0068)
5-Ethoxy-6-morpholin-4-yl-2-[4-(3-phenyl-ureido)-phenyl]-pyrimidine-4-carboxylic acid ethyl ester (MTR-0069)
2-{4-[3-(4-Chloro-3-trifluoromethyl-phenyl)-ureido]-phenyl}-5-ethoxy-6-morpholin-4-yl-pyrimidine-4-carboxylic acid ethyl ester (MTR-0070)

4-(4-Chloro-5-methylsulfanyl-6-morpholin-4-yl-pyrimidin-2-yl)-phenylamine (MTR-0071)
2-(3-Hydroxy-phenyl)-5-methoxy-6-morpholin-4-yl-pyrimidine-4-carboxylic acid ethyl ester (MTR-0073)
5-(4-Chloro-5-methylsulfanyl-6-morpholin-4-yl-pyrimidin-2-yl)-1H-indole (MTR-0074)
2-(1H-Indazol-4-yl)-5-methoxy-6-morpholin-4-yl-pyrimidine-4-carboxylic acid ethyl ester (MTR-0075)
1-[4-(4-Chloro-5-methylsulfanyl-6-morpholin-4-yl-pyrimidin-2-yl)-phenyl]-3-(4-Chloro-3-trifluoromethyl-phenyl)-urea (MTR-0076)
1-[4-(4-Chloro-5-methylsulfanyl-6-morpholin-4-yl-pyrimidin-2-yl)-phenyl]-3-(6-Chloro-pyridin-3-yl)-urea (MTR-0077)
N-[4-(4-Chloro-5-methylsulfanyl-6-morpholin-4-yl-pyrimidin-2-yl)-phenyl]-acetamide (MTR-0078)
2-{4-[3-(6-Chloro-pyridin-3-yl)-ureido]-phenyl}-5-ethoxy-6-morpholin-4-yl-pyrimidine-4-carboxylic acid ethyl ester (MTR-0079)
5-Ethoxy-2-[4-(3-ethyl-ureido)-phenyl]-6-morpholin-4-yl-pyrimidine-4-carboxylic acid ethyl ester (MTR-0081)
[4-(4-Chloro-5-methylsulfanyl-6-morpholin-4-yl-pyrimidin-2-yl)-phenyl]-urea (MTR-0083)
4-(4-Chloro-5-methylsulfanyl-6-morpholin-4-yl-pyrimidin-2-yl)-1H-indazole (MTR-0084)
Methanesulfonic acid 3-(4-chloro-5-methylsulfanyl-6-morpholin-4-yl-pyrimidin-2-yl)-phenyl ester (MTR-0086)
1-[4-(4-Chloro-5-methylsulfanyl-6-morpholin-4-yl-pyrimidin-2-yl)-phenyl]-3-phenyl-urea (MTR-0091)
3-(4-Chloro-5-methanesulfonyl-6-morpholin-4-yl-pyrimidin-2-yl)-phenol (MTR-0094)
N-[4-(4-Chloro-5-methylsulfanyl-6-morpholin-4-yl-pyrimidin-2-yl)-phenyl]-methanesulfonamide (MTR-0096)
4-(4-Chloro-5-methylsulfanyl-6-morpholin-4-yl-pyrimidin-2-yl)-phenol (MTR-0098)
Methanesulfonic acid 4-(4-chloro-5-methylsulfanyl-6-morpholin-4-yl-pyrimidin-2-yl)-phenyl ester (MTR-0100)
5-Ethoxy-6-morpholin-4-yl-2-[4-(3-phenyl-thioureido)-phenyl]-pyrimidine-4-carboxylic acid ethyl ester (MTR-0102)
2-(4-Benzenesulfonylamino-phenyl)-5-ethoxy-6-morpholin-4-yl-pyrimidine-4-carboxylic acid ethyl ester (MTR-0103)
1-(2-Chloro-ethyl)-3-[4-(4-chloro-5-methylsulfanyl-6-morpholin-4-yl-pyrimidin-2-yl)-phenyl]-urea (MTR-0108)
5-Ethoxy-2-(4-hydroxy-phenyl)-6-morpholin-4-yl-pyrimidine-4-carboxylic acid ethyl ester (MTR-0111)
5-Ethoxy-2-(4-ethylcarbamoyloxy-phenyl)-6-morpholin-4-yl-pyrimidine-4-carboxylic acid ethyl ester (MTR-0112)
5-Ethoxy-6-morpholin-4-yl-2-(4-phenylcarbamoyloxy-phenyl)-pyrimidine-4-carboxylic acid ethyl ester (MTR-0113)
(2-Chloro-ethyl)-carbamic acid 4-(4-chloro-5-methylsulfanyl-6-morpholin-4-yl-pyrimidin-2-yl)-phenyl ester (MTR-0114)
Benzenesulfonic acid 4-(4-chloro-5-methylsulfanyl-6-morpholin-4-yl-pyrimidin-2-yl)-phenyl ester (MTR-0115)
3-(5-Methoxy-4-morpholin-4-yl-pyrimidin-2-yl)-phenol (MTR-0116)
5-Ethoxy-6-morpholin-4-yl-2-[4-(3-phenyl-ureido)-phenyl]-pyrimidine-4-carboxylic acid (MTR-0118)
N-[4-(4-Chloro-5-methylsulfanyl-6-morpholin-4-yl-pyrimidin-2-yl)-phenyl]-benzenesulfonamide (MTR-0119)
5-Ethoxy-6-morpholin-4-yl-2-[4-(3-phenyl-ureido)-phenyl]-pyrimidine-4-carboxylic acid diethylamide (MTR-0120)
5-Ethoxy-6-morpholin-4-yl-2-(4-ureido-phenyl)-pyrimidine-4-carboxylic acid ethyl ester (MTR-0121)
1-[4-(4-Chloro-5-methylsulfanyl-6-morpholin-4-yl-pyrimidin-2-yl)-phenyl]-3-(4-dimethylamino-phenyl)-urea (MTR-0123)
1-{4-[5-Ethoxy-4-(morpholine-4-carbonyl)-6-morpholin-4-yl-pyrimidin-2-yl]-phenyl}-3-phenyl-urea (MTR-0124)
5-Ethoxy-6-morpholin-4-yl-2-[4-(3-phenyl-ureido)-phenyl]-pyrimidine-4-carboxylic acid amide (MTR-0125)
Phenyl-carbamic acid 4-(5-methoxy-4-morpholin-4-yl-pyrimidin-2-yl)-phenyl ester (MTR-0127)
1-[4-(5-Methoxy-4-morpholin-4-yl-pyrimidin-2-yl)-phenyl]-3-phenyl-urea (MTR-0128)
1-Ethyl-3-[4-(5-methoxy-4-morpholin-4-yl-pyrimidin-2-yl)-phenyl]-urea (MTR-0129)
Ethyl-carbamic acid 4-(5-methoxy-4-morpholin-4-yl-pyrimidin-2-yl)-phenyl ester (MTR-0130)
4-(4-Chloro-5-methylsulfanyl-6-morpholin-4-yl-pyrimidin-2-yl)-benzenesulfonamide (MTR-0131)
1-[4-(4-Chloro-5-methylsulfanyl-6-morpholin-4-yl-pyrimidin-2-yl)-phenyl]-3-ethyl-urea (MTR-0132)
5-(4-Chloro-5-methylsulfanyl-6-morpholin-4-yl-pyrimidin-2-yl)-pyridin-2-ylamine (MTR-0133)
1-[5-(4-Chloro-5-methylsulfanyl-6-morpholin-4-yl-pyrimidin-2-yl)-pyridin-2-yl]-3-phenyl-urea (MTR-0134)
1-[4-(4-Chloro-5-methylsulfanyl-6-morpholin-4-yl-pyrimidin-2-yl)-phenyl]-3-(4-fluoro-phenyl)-urea (MTR-0135)
1-[5-(4-Chloro-5-methylsulfanyl-6-morpholin-4-yl-pyrimidin-2-yl)-pyridin-2-yl]-3-ethyl-urea (MTR-0136)
1-[4-(4-Chloro-5-methylsulfanyl-6-morpholin-4-yl-pyrimidin-2-yl)-phenyl]-3-(3-fluoro-phenyl)-urea (MTR-0137)
1-[4-(4-Chloro-5-methylsulfanyl-6-morpholin-4-yl-pyrimidin-2-yl)-phenyl]-3-(3,4-difluoro-phenyl)-urea (MTR-0138)
5-Ethoxy-6-morpholin-4-yl-2-[4-(3-phenyl-ureido)-phenyl]-pyrimidine-4-carboxylic acid (2-morpholin-4-yl-ethyl)-amide (MTR-0139)
5-Ethoxy-6-morpholin-4-yl-2-[4-(3-phenyl-ureido)-phenyl]-pyrimidine-4-carboxylic acid (2-pyrrolidin-1-yl-ethyl)-amide (MTR-0140)
1-{4-[5-Ethoxy-4-morpholin-4-yl-6-(pyrrolidine-1-carbonyl)-pyrimidin-2-yl]-phenyl}-3-phenyl-urea (MTR-0141)
1-{4-[5-Ethoxy-4-morpholin-4-yl-6-(piperidine-1-carbonyl)-pyrimidin-2-yl]-phenyl}-3-phenyl-urea (MTR-0142)
1-[5-(4-Chloro-5-methylsulfanyl-6-morpholin-4-yl-pyrimidin-2-yl)-pyridin-2-yl]-3-(3-fluoro-phenyl)-urea (MTR-0143)
5-Ethoxy-6-morpholin-4-yl-2-[4-(3-phenyl-ureido)-phenyl]-pyrimidine-4-carboxylic acid (2-diethylamino-ethyl)-amide (MTR-0144)
1-{4-[5-Ethoxy-4-(4-methanesulfonyl-piperazine-1-carbonyl)-6-morpholin-4-yl-pyrimidin-2-yl]-phenyl}-3-phenyl-urea (MTR-0145)

2-(6-Amino-pyridin-3-yl)-5-ethoxy-6-morpholin-4-yl-pyrimidine-4-carboxylic acid ethyl ester (MTR-0146)

5-Ethoxy-2-{4-[3-(3-fluoro-phenyl)-ureido]-phenyl}-6-morpholin-4-yl-pyrimidine-4-carboxylic acid ethyl ester (MTR-0147)

5-Ethoxy-6-morpholin-4-yl-2-[6-(3-phenyl-ureido)-pyridin-3-yl]-pyrimidine-4-carboxylic acid ethyl ester (MTR-0148)

5-Ethoxy-2-{4-[3-(4-fluoro-phenyl)-ureido]-phenyl}-6-morpholin-4-yl-pyrimidine-4-carboxylic acid ethyl ester (MTR-0149)

2-{4-[3-(3,4-Difluoro-phenyl)-ureido]-phenyl}-5-ethoxy-6-morpholin-4-yl-pyrimidine-4-carboxylic acid ethyl ester (MTR-0150)

1-(4-Fluoro-phenyl)-3-[4-(5-methoxy-4-morpholin-4-yl-pyrimidin-2-yl)-phen yl]-urea (MTR-0152)

4-(5-Methoxy-4-morpholin-4-yl-pyrimidin-2-yl)-phenylamine (MTR-0153)

4-(5-Methylsulfanyl-4-morpholin-4-yl-pyrimidin-2-yl)-phenylamine (MTR-0154)

4-(5-Methylsulfanyl-4-morpholin-4-yl-pyrimidin-2-yl)-phenol (MTR-0155)

5-Ethoxy-2-{6-[3-(4-fluoro-phenyl)-ureido]-pyridin-3-yl}-6-morpholin-4-yl-pyrimidine-4-carboxylic acid ethyl ester (MTR-0156)

2-{6-[3-(3,4-Difluoro-phenyl)-ureido]-pyridin-3-yl}-5-ethoxy-6-morpholin-4-yl-pyrimidine-4-carboxylic acid ethyl ester (MTR-0157)

5-Ethoxy-2-{6-[3-(3-fluoro-phenyl)-ureido]-pyridin-3-yl}-6-morpholin-4-yl-pyrimidine-4-carboxylic acid ethyl ester (MTR-0158)

1-Ethyl-3-[4-(5-methylsulfanyl-4-morpholin-4-yl-pyrimidin-2-yl)-phenyl]-urea (MTR-0159)

4-[5-Ethoxy-4-(4-methanesulfonyl-piperazin-1-ylmethyl)-6-morpholin-4-yl-pyrimidin-2-yl]-1H-indazole (MTR-0160)

4-[5-Ethoxy-4-(4-methanesulfonyl-piperazin-1-ylmethyl)-6-morpholin-4-yl-pyrimidin-2-yl]-phenylamine (MTR-0161)

1-[4-(5-Methylsulfanyl-4-morpholin-4-yl-pyrimidin-2-yl)-phenyl]-3-phenyl-urea (MTR-0162)

4-(5-Methylsulfanyl-4-morpholin-4-yl-pyrimidin-2-yl)-benzenesulfonamide (MTR-0163)

1-(3-Fluoro-phenyl)-3-[4-(5-methoxy-4-morpholin-4-yl-pyrimidin-2-yl)-phenyl]-urea (MTR-0164)

1-(3,4-Difluoro-phenyl)-3-[4-(5-methoxy-4-morpholin-4-yl-pyrimidin-2-yl)-phenyl]-urea (MTR-0165)

[2-(4-Amino-phenyl)-5-ethoxy-6-morpholin-4-yl-pyrimidin-4-yl]-methanol (MTR-0166)

1-(4-Fluoro-phenyl)-3-[4-(5-methoxy-4-morpholin-4-yl-pyrimidin-2-yl)-phen yl]-thiourea (MTR-0167)

1-(3-Fluoro-phenyl)-3-[4-(5-methoxy-4-morpholin-4-yl-pyrimidin-2-yl)-phen yl]-thiourea (MTR-0168)

1-{4-[5-Ethoxy-4-(4-methanesulfonyl-piperazin-1-ylmethyl)-6-morpholin-4-yl-pyrimidin-2-yl]-phenyl}-3-phenyl-urea (MTR-0169)

4-[5-Ethoxy-4-(4-methyl-piperazin-1-ylmethyl)-6-morpholin-4-yl-pyrimidin-2-yl]-1H-indazole (MTR-0170)

4-[5-Ethoxy-4-(4-methyl-piperazin-1-ylmethyl)-6-morpholin-4-yl-pyrimidin-2-yl]-phenylamine (MTR-0171)

1-{4-[5-Ethoxy-4-(4-methyl-piperazin-1-ylmethyl)-6-morpholin-4-yl-pyrimidin-2-yl]-phenyl}-3-phenyl-urea (MTR-0172)

1-{4-[4-(4-Methanesulfonyl-piperazin-1-yl)-5-methylsulfanyl-6-morpholin-4-yl-pyrimidin-2-yl]-phenyl}-3-phenyl-urea (MTR-0173)

4-(5-Ethoxy-4-morpholin-4-yl-6-morpholin-4-ylmethyl-pyrimidin-2-yl)-1H-indazole (MTR-0174)

4-(5-Ethoxy-4-morpholin-4-yl-6-morpholin-4-ylmethyl-pyrimidin-2-yl)-phenylamine (MTR-0175)

1-[4-(5-Ethoxy-4-morpholin-4-yl-6-morpholin-4-ylmethyl-pyrimidin-2-yl)-phenyl]-3-phenyl-urea (MTR-0176)

1-(3,4-Difluoro-phenyl)-3-[4-(5-methylsulfanyl-4-morpholin-4-yl-pyrimidin-2-yl)-phenyl]-urea (MTR-0177)

1-(4-Fluoro-phenyl)-3-[4-(5-methylsulfanyl-4-morpholin-4-yl-pyrimidin-2-yl)-phenyl]-urea (MTR-0178)

3-[5-Ethoxy-4-(4-methanesulfonyl-piperazin-1-ylmethyl)-6-morpholin-4-yl-pyrimidin-2-yl]-phenol (MTR-0180)

2-(4-Amino-phenyl)-5-methoxy-6-morpholin-4-yl-pyrimidine-4-carboxylic acid ethyl ester (MTR-0181)

5-Methoxy-6-morpholin-4-yl-2-[4-(3-phenyl-ureido)-phenyl]-pyrimidine-4-carboxylic acid ethyl ester (MTR-0182)

5-Methoxy-6-morpholin-4-yl-2-[4-(3-phenyl-ureido)-phenyl]-pyrimidine-4-carboxylic acid (MTR-0183)

1-{4-[5-Methoxy-4-(morpholine-4-carbonyl)-6-morpholin-4-yl-pyrimidin-2-yl]-phenyl}-3-phenyl-urea (MTR-0184)

1-{4-[4-(4-Methanesulfonyl-piperazine-1-carbonyl)-5-methoxy-6-morpholin-4-yl-pyrimidin-2-yl]-phenyl}-3-phenyl-urea (MTR-0185)

1-{4-[5-Ethoxy-4-(4-methyl-piperazine-1-carbonyl)-6-morpholin-4-yl-pyrimidin-2-yl]-phenyl}-3-phenyl-urea (MTR-0186)

[2-(4-Amino-phenyl)-5-methylsulfanyl-6-morpholin-4-yl-pyrimidin-4-yl]-acetic acid methyl ester (MTR-0187)

{5-Methylsulfanyl-6-morpholin-4-yl-2-[4-(3-phenyl-ureido)-phenyl]-pyrimidin-4-yl}-acetic acid methyl ester (MTR-0188)

{5-Methylsulfanyl-6-morpholin-4-yl-2-[4-(3-phenyl-ureido)-phenyl]-pyrimidin-4-yl}-acetic acid (MTR-0189)

2-{5-Methylsulfanyl-6-morpholin-4-yl-2-[4-(3-phenyl-ureido)-phenyl]-pyrimidin-4-yl}-acetamide (MTR-0192)

1-[4-(5-Ethoxy-4-morpholin-4-yl-6-piperidin-1-ylmethyl-pyrimidin-2-yl)-phenyl]-3-phenyl-urea (MTR-0193)

1-[4-(4-Chloro-5-methylsulfanyl-6-morpholin-4-yl-pyrimidin-2-yl)-phenyl]-3-methyl-urea (MTR-0195)

1-[4-(4-Chloro-5-methylsulfanyl-6-morpholin-4-yl-pyrimidin-2-yl)-phenyl]-3-morpholin-4-yl-urea (MTR-0196)

1-[4-(4-Chloro-5-methylsulfanyl-6-morpholin-4-yl-pyrimidin-2-yl)-phenyl]-3-pyridin-3-yl-urea (MTR-0197)

1-[4-(4-Chloro-5-methylsulfanyl-6-morpholin-4-yl-pyrimidin-2-yl)-phenyl]-3-(2-morpholin-4-yl-ethyl)-urea (MTR-0198)

1-[4-(4-Chloro-5-methylsulfanyl-6-morpholin-4-yl-pyrimidin-2-yl)-phenyl]-3-[4-(2-dimethylamino-ethoxy)-phenyl]-urea (MTR-0199)

1-[4-(4-Chloro-5-methylsulfanyl-6-morpholin-4-yl-pyrimidin-2-yl)-phenyl]-3-thiazol-2-yl-urea (MTR-0200)

1-[4-(4-Chloro-5-methylsulfanyl-6-morpholin-4-yl-pyrimidin-2-yl)-phenyl]-3-(4-methyl-piperazin-1-yl)-urea (MTR-0201)

5-Ethoxy-2-[4-(3-methyl-ureido)-phenyl]-6-morpholin-4-yl-pyrimidine-4-carboxylic acid ethyl ester (MTR-0202)

5-Ethoxy-2-{4-[(morpholine-4-carbonyl)-amino]-phenyl}-6-morpholin-4-yl-pyrimidine-4-carboxylic acid ethyl ester (MTR-0203)
2-{4-[3-(3-Dimethylamino-propyl)-ureido]-phenyl}-5-ethoxy-6-morpholin-4-yl-pyrimidine-4-carboxylic acid ethyl ester (MTR-0204)
5-Ethoxy-6-morpholin-4-yl-2-[4-(3-pyridin-3-yl-ureido)-phenyl]-pyrimidine-4-carboxylic acid ethyl ester (MTR-0205)
5-Ethoxy-2-{4-[3-(4-methyl-piperazin-1-yl)-ureido]-phenyl}-6-morpholin-4-yl-pyrimidine-4-carboxylic acid ethyl ester (MTR-0206)
1-[4-(5-Methylsulfanyl-4-morpholin-4-yl-pyrimidin-2-yl)-phenyl]-3-(2-morpholin-4-yl-ethyl)-urea (MTR-0207)
1-(3-Dimethylamino-propyl)-3-[4-(5-methylsulfanyl-4-morpholin-4-yl-pyrimidin-2-yl)-phenyl]-urea (MTR-0208)
1-(4-Methyl-piperazin-1-yl)-3-[4-(5-methylsulfanyl-4-morpholin-4-yl-pyrimidin-2-yl)-phenyl]-urea (MTR-0209)
1-Methyl-3-[4-(5-methylsulfanyl-4-morpholin-4-yl-pyrimidin-2-yl)-phenyl]-urea (MTR-0210)
1-[4-(4-Chloro-5-methylsulfanyl-6-morpholin-4-yl-pyrimidin-2-yl)-phenyl]-3-(3-fluoro-4-morpholin-4-yl-phenyl)-urea (MTR-0211)
4-{3-[4-(4-Chloro-5-methylsulfanyl-6-morpholin-4-yl-pyrimidin-2-yl)-phenyl]-ureido}-benzoic acid ethyl ester (MTR-0212)
1-[4-(4-Chloro-5-methylsulfanyl-6-morpholin-4-yl-pyrimidin-2-yl)-phenyl]-3-[4-(3-oxo-morpholin-4-yl)-phenyl]-urea (MTR-0213)
1-[4-(4-Chloro-5-methylsulfanyl-6-morpholin-4-yl-pyrimidin-2-yl)-phenyl]-3-(3-trifluoromethyl-phenyl)-urea (MTR-0214)
1-[4-(4-Chloro-5-methylsulfanyl-6-morpholin-4-yl-pyrimidin-2-yl)-phenyl]-3-[4-(4-methyl-piperazin-1-yl)-phenyl]-urea (MTR-0215)
1-[4-(4-Chloro-5-methylsulfanyl-6-morpholin-4-yl-pyrimidin-2-yl)-phenyl]-3-(4-thiomorpholin-4-yl-phenyl)-urea (MTR-0216)
5-Ethoxy-6-morpholin-4-yl-2-{4-[3-(2-morpholin-4-yl-ethyl)-ureido]-phenyl}-pyrimidine-4-carboxylic acid ethyl ester (MTR-0217)
5-Ethoxy-6-morpholin-4-yl-2-(2-phenylamino-1H-benzoimidazol-5-yl)-pyrimidine-4-carboxylic acid ethyl ester (MTR-0218)
5-Ethoxy-6-morpholin-4-yl-2-[4-(3-morpholin-4-yl-ureido)-phenyl]-pyrimidine-4-carboxylic acid ethyl ester (MTR-0219)
5-Ethoxy-6-morpholin-4-yl-2-[4-(3-thiazol-2-yl-ureido)-phenyl]-pyrimidine-4-carboxylic acid ethyl ester (MTR-0220)
5-Ethoxy-2-{4-[3-(3-fluoro-4-morpholin-4-yl-phenyl)-ureido]-phenyl}-6-morpholin-4-yl-pyrimidine-4-carboxylic acid ethyl ester (MTR-0221)
5-Ethoxy-6-morpholin-4-yl-2-(4-{3-[4-(3-oxo-morpholin-4-yl)-phenyl]-ureido}-phenyl)-pyrimidine-4-carboxylic acid ethyl ester (MTR-0222)
5-Ethoxy-6-morpholin-4-yl-2-{4-[3-(3-trifluoromethyl-phenyl)-ureido]-phenyl}-pyrimidine-4-carboxylic acid ethyl ester (MTR-0223)
1-[4-(5-Methylsulfanyl-4-morpholin-4-yl-pyrimidin-2-yl)-phenyl]-3-morpholin-4-yl-urea (MTR-0224)
1-[4-(5-Methylsulfanyl-4-morpholin-4-yl-pyrimidin-2-yl)-phenyl]-3-pyridin-3-yl-urea (MTR-0225)
1-(3-Fluoro-4-morpholin-4-yl-phenyl)-3-[4-(5-methylsulfanyl-4-morpholin-4-yl-pyrimidin-2-yl)-phenyl]-urea (MTR-0226)
1-[4-(5-Methylsulfanyl-4-morpholin-4-yl-pyrimidin-2-yl)-phenyl]-3-[4-(3-oxo-morpholin-4-yl)-phenyl]-urea (MTR-0227)
1-[4-(5-Methoxy-4-morpholin-4-yl-pyrimidin-2-yl)-phenyl]-3-pyridin-3-yl-urea (MTR-0228)
1-[4-(5-Methoxy-4-morpholin-4-yl-pyrimidin-2-yl)-phenyl]-3-methyl-urea (MTR-0229)
5-Ethoxy-6-morpholin-4-yl-2-[4-(3-pyridin-2-yl-ureido)-phenyl]-pyrimidine-4-carboxylic acid ethyl ester (MTR-0230)
5-Ethoxy-2-(4-{3-[4-(4-methyl-piperazin-1-yl)-phenyl]-ureido}-phenyl)-6-morpholin-4-yl-pyrimidine-4-carboxylic acid ethyl ester (MTR-0231)
5-Ethoxy-6-morpholin-4-yl-2-{4-[3-(4-thiomorpholin-4-yl-phenyl)-ureido]-phenyl}-pyrimidine-4-carboxylic acid ethyl ester (MTR-0232)
5-Ethoxy-6-morpholin-4-yl-2-{4-[3-(4-morpholin-4-yl-phenyl)-ureido]-phenyl}-pyrimidine-4-carboxylic acid ethyl ester (MTR-0233)
2-{4-[3-(2-Amino-phenyl)-thioureido]-phenyl}-5-ethoxy-6-morpholin-4-yl-pyrimidine-4-carboxylic acid ethyl ester (MTR-0234)
1-[4-(4-Chloro-5-methylsulfanyl-6-morpholin-4-yl-pyrimidin-2-yl)-phenyl]-3-(4-morpholin-4-yl-phenyl)-urea (MTR-0235)
1-[4-(4-Chloro-5-methylsulfanyl-6-morpholin-4-yl-pyrimidin-2-yl)-phenyl]-3-[6-(4-methyl-piperazin-1-yl)-pyridin-3-yl]-urea (MTR-0236)
1-[4-(4-Chloro-5-methylsulfanyl-6-morpholin-4-yl-pyrimidin-2-yl)-phenyl]-3-(6-morpholin-4-yl-pyridin-3-yl)-urea (MTR-0237)
1-{4-[4-(4-Methyl-piperazin-1-yl)-5-methylsulfanyl-6-morpholin-4-yl-pyrimidin-2-yl]-phenyl}-3-pyridin-3-yl-urea (MTR-0238)
1-(3,4-Dimethoxy-phenyl)-3-[4-(5-methoxy-4-morpholin-4-yl-pyrimidin-2-yl)-phenyl]-urea (MTR-0239)
1-[4-(5-Methoxy-4-morpholin-4-yl-pyrimidin-2-yl)-phenyl]-3-(3-trifluoromethyl-phenyl)-urea (MTR-0240)
1-[4-(5-Methoxy-4-morpholin-4-yl-pyrimidin-2-yl)-phenyl]-3-[4-(3-oxo-morpholin-4-yl)-phenyl]-urea (MTR-0241)
1-(3-Fluoro-4-morpholin-4-yl-phenyl)-3-[4-(5-methoxy-4-morpholin-4-yl-pyrimidin-2-yl)-phenyl]-urea (MTR-0242)
2-[4-(1H-Benzoimidazol-2-ylamino)-phenyl]-5-ethoxy-6-morpholin-4-yl-pyrimidine-4-carboxylic acid ethyl ester (MTR-0243)
2-{4-[3-(4-Carbamoyl-phenyl)-ureido]-phenyl}-5-ethoxy-6-morpholin-4-yl-pyrimidine-4-carboxylic acid ethyl ester (MTR-0244)
5-Ethoxy-6-morpholin-4-yl-2-[4-(3-pyridin-3-yl-ureido)-phenyl]-pyrimidine-4-carboxylic acid (MTR-0245)
1-[4-(4-Methyl-piperazin-1-yl)-phenyl]-3-[4-(5-methylsulfanyl-4-morpholin-4-yl-pyrimidin-2-yl)-phenyl]-urea (MTR-0246)
1-[4-(5-Methylsulfanyl-4-morpholin-4-yl-pyrimidin-2-yl)-phenyl]-3-(4-thiomorpholin-4-yl-phenyl)-urea (MTR-0247)
1-[4-(5-Methylsulfanyl-4-morpholin-4-yl-pyrimidin-2-yl)-phenyl]-3-(4-morpholin-4-yl-phenyl)-urea (MTR-0248)
1-[4-(5-Methylsulfanyl-4-morpholin-4-yl-pyrimidin-2-yl)-phenyl]-3-thiazol-2-yl-urea (MTR-0249)

2-{4-[3-(3-Acetylamino-phenyl)-ureido]-phenyl}-5-ethoxy-6-morpholin-4-yl-pyrimidine-4-carboxylic acid ethyl ester (MTR-0250)

2-{4-[3-(3-Carbamoyl-phenyl)-ureido]-phenyl}-5-ethoxy-6-morpholin-4-yl-pyrimidine-4-carboxylic acid ethyl ester (MTR-0251)

5-Ethoxy-6-morpholin-4-yl-2-(4-{3-[3-(2,2,2-trifluoro-acetylamino)-phenyl]-ureido}-phenyl)-pyrimidine-4-carboxylic acid ethyl ester (MTR-0252)

1-{4-[5-Ethoxy-4-(morpholine-4-carbonyl)-6-morpholin-4-yl-pyrimidin-2-yl]-phenyl}-3-pyridin-3-yl-urea (MTR-0253)

1-[4-(4-Chloro-5-methylsulfanyl-6-morpholin-4-yl-pyrimidin-2-yl)-phenyl]-3-pyridin-2-yl-urea (MTR-0254)

2-{3-[4-(4-Chloro-5-methylsulfanyl-6-morpholin-4-yl-pyrimidin-2-yl)-phenyl]-ureido}-thiophene-3-carboxylic acid methyl ester (MTR-0255)

1-Benzo[1,3]dioxol-5-yl-3-[4-(4-chloro-5-methylsulfanyl-6-morpholin-4-yl-pyrimidin-2-yl)-phenyl]-urea (MTR-0256)

4-{3-[4-(4-Chloro-5-methylsulfanyl-6-morpholin-4-yl-pyrimidin-2-yl)-phenyl]-ureido}-benzamide (MTR-0257)

1-[4-(4-Chloro-5-methylsulfanyl-6-morpholin-4-yl-pyrimidin-2-yl)-phenyl]-3-(3,4-dimethoxy-phenyl)-urea (MTR-0258)

1-[4-(5-Methoxy-4-morpholin-4-yl-pyrimidin-2-yl)-phenyl]-3-(2-morpholin-4-yl-ethyl)-urea (MTR-259)

1-[4-(5-Methoxy-4-morpholin-4-yl-pyrimidin-2-yl)-penta-2,4-dienyl]-3-(4-methyl-piperazin-1-yl)-urea (MTR-0260)

1-[4-(5-Methoxy-4-morpholin-4-yl-pyrimidin-2-yl)-phenyl]-3-(4-morpholin-4-yl-phenyl)-urea (MTR-0261)

1-[4-(5-Methoxy-4-morpholin-4-yl-pyrimidin-2-yl)-phenyl]-3-(4-thiomorpholin-4-yl-phenyl)-urea (MTR-0262)

1-[4-(5-Methylsulfanyl-4-morpholin-4-yl-pyrimidin-2-yl)-phenyl]-3-(3-trifluoromethyl-phenyl)-urea (MTR-0263)

4-{3-[4-(5-Methylsulfanyl-4-morpholin-4-yl-pyrimidin-2-yl)-phenyl]-ureido}-benzoic acid ethyl ester (MTR-0264)

1-[4-(5-Methylsulfanyl-4-morpholin-4-yl-pyrimidin-2-yl)-phenyl]-3-(6-morpholin-4-yl-pyridin-3-yl)-urea (MTR-0265)

1-[6-(4-Methyl-piperazin-1-yl)-pyridin-3-yl]-3-[4-(5-methylsulfanyl-4-morpholin-4-yl-pyrimidin-2-yl)-phenyl]-urea (MTR-0266)

4-{3-[4-(5-Methylsulfanyl-4-morpholin-4-yl-pyrimidin-2-yl)-phenyl]-ureido}-benzamide (MTR-0267)

1-[4-(4-Chloro-5-methylsulfanyl-6-morpholin-4-yl-pyrimidin-2-yl)-phenyl]-3-[5-(4-methyl-piperazin-1-yl)-pyridin-2-yl]-urea (MTR-0268)

N-(3-{3-[4-(4-Chloro-5-methylsulfanyl-6-morpholin-4-yl-pyrimidin-2-yl)-phenyl]-ureido}-phenyl)-2,2,2-trifluoro-acetamide (MTR-0269)

N-(3-{3-[4-(4-Chloro-5-methylsulfanyl-6-morpholin-4-yl-pyrimidin-2-yl)-phenyl]-ureido}-phenyl)-acetamide (MTR-0270)

1-[4-(4-Chloro-5-methylsulfanyl-6-morpholin-4-yl-pyrimidin-2-yl)-phenyl]-3-[4-(4-methyl-piperazine-1-carbonyl)-phenyl]-urea (MTR-0271)

[4-(4-Chloro-5-methylsulfanyl-6-morpholin-4-yl-pyrimidin-2-yl)-phenyl]-carbamic acid phenyl ester (MTR-0272)

5-Ethoxy-6-morpholin-4-yl-2-{4-[3-(4-sulfamoyl-phenyl)-ureido]-phenyl}-pyrimidine-4-carboxylic acid ethyl ester (MTR-0273)

5-Ethoxy-2-(4-{3-[4-(4-methyl-piperazine-1-carbonyl)-phenyl]-ureido}-phenyl)-6-morpholin-4-yl-pyrimidine-4-carboxylic acid ethyl ester (MTR-0274)

5-Ethoxy-2-(4-{3-[6-(4-methyl-piperazin-1-yl)-pyridin-3-yl]-ureido}-phenyl)-6-morpholin-4-yl-pyrimidine-4-carboxylic acid ethyl ester (MTR-0275)

5-Ethoxy-6-morpholin-4-yl-2-{4-[3-(6-morpholin-4-yl-pyridin-3-yl)-ureido]-phenyl}-pyrimidine-4-carboxylic acid ethyl ester (MTR-0276)

2-(4-{3-[4-(2-Dimethylamino-ethylcarbamoyl)-phenyl]-ureido}-phenyl)-5-ethoxy-6-morpholin-4-yl-pyrimidine-4-carboxylic acid ethyl ester (MTR-0277)

5-Ethoxy-2-(4-{3-[4-(morpholine-4-carbonyl)-phenyl]-ureido}-phenyl)-6-morpholin-4-yl-pyrimidine-4-carboxylic acid ethyl ester (MTR-0278)

{4-[5-Ethoxy-4-(morpholine-4-carbonyl)-6-morpholin-4-yl-pyrimidin-2-yl]-phenyl}-carbamic acid phenyl ester (MTR-0279)

1-{4-[5-Ethoxy-4-(morpholine-4-carbonyl)-6-morpholin-4-yl-pyrimidin-2-yl]-phenyl}-3-[4-(3-oxo-morpholin-4-yl)-phenyl]-urea (MTR-0280)

[4-(5-Methoxy-4-morpholin-4-yl-pyrimidin-2-yl)-phenyl]-carbamic acid phenyl ester (MTR-0281)

4-{3-[4-(5-Methoxy-4-morpholin-4-yl-pyrimidin-2-yl)-phenyl]-ureido}-benzamide (MTR-0282)

4-{3-[4-(5-Methoxy-4-morpholin-4-yl-pyrimidin-2-yl)-phenyl]-ureido}-benzenesulfonamide (MTR-0283)

4-(5-Methoxy-4-morpholin-4-yl-pyrimidin-2-yl)-2-nitro-phenylamine (MTR-0284)

1-(2-Amino-phenyl)-3-[4-(5-methoxy-4-morpholin-4-yl-pyrimidin-2-yl)-phenyl]-thiourea (MTR-0285)

[4-(5-Methylsulfanyl-4-morpholin-4-yl-pyrimidin-2-yl)-phenyl]-urea (MTR-0286)

1-(2-Amino-phenyl)-3-[4-(5-methylsulfanyl-4-morpholin-4-yl-pyrimidin-2-yl)-phenyl]-thiourea (MTR-0287)

4-{3-[4-(5-Methylsulfanyl-4-morpholin-4-yl-pyrimidin-2-yl)-phenyl]-ureido}-benzenesulfonamide (MTR-0288)

(1H-Benzoimidazol-2-yl)-[4-(5-methylsulfanyl-4-morpholin-4-yl-pyrimidin-2-yl)-phenyl]-amine (MTR-0289)

[4-(5-Methylsulfanyl-4-morpholin-4-yl-pyrimidin-2-yl)-phenyl]-carbamic acid phenyl ester (MTR-0290)

1-(6-Bromo-pyridin-3-yl)-3-[4-(4-chloro-5-methylsulfanyl-6-morpholin-4-yl-pyrimidin-2-yl)-phenyl]-urea (MTR-0291)

1-(2-Amino-phenyl)-3-[4-(4-chloro-5-methylsulfanyl-6-morpholin-4-yl-pyrimidin-2-yl)-phenyl]-thiourea (MTR-0292)

4-{3-[4-(4-Chloro-5-methylsulfanyl-6-morpholin-4-yl-pyrimidin-2-yl)-phenyl]-thioureido}-benzoic acid (MTR-0293)

5-Ethoxy-2-(4-{3-[5-(4-methyl-piperazin-1-yl)-pyridin-2-yl]-ureido}-phenyl)-6-morpholin-4-yl-pyrimidine-4-carboxylic acid ethyl ester (MTR-0294)

5-Ethoxy-2-{4-[3-(2-methoxycarbonyl-thiophen-3-yl)-ureido]-phenyl}-6-morpholin-4-yl-pyrimidine-4-carboxylic acid ethyl ester (MTR-0296)

5-Ethoxy-2-{4-[3-(1H-indazol-4-yl)-ureido]-phenyl}-6-morpholin-4-yl-pyrimidine-4-carboxylic acid ethyl ester (MTR-0297)

5-Ethoxy-2-{4-[3-(4-methyl-1H-benzotriazol-5-yl)-ureido]-phenyl}-6-morpholin-4-yl-pyrimidine-4-carboxylic acid ethyl ester (MTR-0298)

5-Ethoxy-6-morpholin-4-yl-2-{4-[3-(2-oxo-2,3-dihydro-benzooxazol-5-yl)-ureido]-phenyl}l-pyrimidine-4-carboxylic acid ethyl ester (MTR-0299)
2-(4-Amino-3-fluoro-phenyl)-5-ethoxy-6-morpholin-4-yl-pyrimidine-4-carboxylic acid ethyl ester (MTR-0300)
5-Ethoxy-2-(3-fluoro-4-phenoxycarbonylamino-phenyl)-6-morpholin-4-yl-pyrimidine-4-carboxylic acid ethyl ester (MTR-0301)
5-Ethoxy-2-(3-fluoro-4-{3-[4-(3-oxo-morpholin-4-yl)-phenyl]-ureido}-phenyl)-6-morpholin-4-yl-pyrimidine-4-carboxylic acid ethyl ester (MTR-0302)
1-[4-(4-Chloro-5-methylsulfanyl-6-morpholin-4-yl-pyrimidin-2-yl)-phenyl]-3-pyridin-3-yl-thiourea (MTR-0303)
1-[4-(4-Chloro-5-methylsulfanyl-6-morpholin-4-yl-pyrimidin-2-yl)-phenyl]-3-[4-(3-oxo-morpholin-4-yl)-phenyl]-thiourea (MTR-0304)
(1H-Benzoimidazol-2-yl)-[4-(4-chloro-5-methylsulfanyl-6-morpholin-4-yl-pyrimidin-2-yl)-phenyl]-amine (MTR-0305)
1-[4-(4-Chloro-5-methylsulfanyl-6-morpholin-4-yl-pyrimidin-2-yl)-phenyl]-3-isopropyl-urea (MTR-0306)
[4-(4-Chloro-5-methylsulfanyl-6-morpholin-4-yl-pyrimidin-2-yl)-phenyl]-carb amic acid (MTR-0307)
1-[4-(4-Chloro-5-methylsulfanyl-6-morpholin-4-yl-pyrimidin-2-yl)-phenyl]-3-[4-(morpholine-4-carbonyl)-phenyl]-urea (MTR-0308)
4-(5-Methoxy-4-morpholin-4-yl-pyrimidin-2-yl)-benzene-1,2-diamine (MTR-0309)
(1H-Benzoimidazol-2-yl)-[4-(5-methoxy-4-morpholin-4-yl-pyrimidin-2-yl)-phenyl]-amine (MTR-0310)
5-(5-Methoxy-4-morpholin-4-yl-pyrimidin-2-yl)-1H-benzoimidazol-2-ylamine (MTR-0311)
1-[4-(2-Dimethylamino-ethoxy)-phenyl]-3-[4-(5-methoxy-4-morpholin-4-yl-pyrimidin-2-yl)-phenyl]-urea (MTR-0312)
3-{3-[4-(5-Methoxy-4-morpholin-4-yl-pyrimidin-2-yl)-phenyl]-ureido}-benzamide (MTR-0313)
1-[4-(5-Methoxy-4-morpholin-4-yl-pyrimidin-2-yl)-phenyl]-3-thiazol-2-yl-urea (MTR-0314)
1-(3,4-Dimethoxy-phenyl)-3-[4-(5-methylsulfanyl-4-morpholin-4-yl-pyrimidin-2-yl)-phenyl]-urea (MTR-0315)
4-{3-[4-(5-Methylsulfanyl-4-morpholin-4-yl-pyrimidin-2-yl)-phenyl]-ureido}-benzoic acid (MTR-0316)
1-Benzo[1,3]dioxol-5-yl-3-[4-(5-methylsulfanyl-4-morpholin-4-yl-pyrimidin-2-yl)-phenyl]-urea (MTR-0317)
1-[5-(4-Methyl-piperazin-1-yl)-pyridin-2-yl]-3-[4-(5-methylsulfanyl-4-morpholin-4-yl-pyrimidin-2-yl)-phenyl]-urea (MTR-0318)
1-[4-(5-Methylsulfanyl-4-morpholin-4-yl-pyrimidin-2-yl)-phenyl]-3-[4-(3-oxo-morpholin-4-yl)-phenyl]-thiourea (MTR-0319)
2-(4-Amino-2-fluoro-phenyl)-5-ethoxy-6-morpholin-4-yl-pyrimidine-4-carboxylic acid ethyl ester (MTR-0320)
5-Ethoxy-2-(2-fluoro-4-phenoxycarbonylamino-phenyl)-6-morpholin-4-yl-pyrimidine-4-carboxylic acid ethyl ester (MTR-0321)
5-Ethoxy-2-(2-fluoro-4-{3-[4-(3-oxo-morpholin-4-yl)-phenyl]-ureido}-phenyl)-6-morpholin-4-yl-pyrimidine-4-carboxylic acid ethyl ester (MTR-0322)
4-{3-[4-(5-Ethoxy-4-morpholin-4-yl-pyrimidin-2-yl)-phenyl]-ureido}-benzamide (MTR-0323)
1-[4-(5-Ethoxy-4-morpholin-4-yl-pyrimidin-2-yl)-phenyl]-3-(4-thiomorpholin-4-yl-phenyl)-urea (MTR-0324)
1-[4-(5-Ethoxy-4-morpholin-4-yl-pyrimidin-2-yl)-phenyl]-3-[4-(3-oxo-morpholin-4-yl)-phenyl]-urea (MTR-0325)
4-{3-[4-(5-Ethoxy-4-morpholin-4-yl-pyrimidin-2-yl)-phenyl]-ureido}-benzenesulfonamide (MTR-0326)
1-[4-(4-Chloro-5-methylsulfanyl-6-morpholin-4-yl-pyrimidin-2-yl)-phenyl]-2-fluoro-phenylamino-urea (MTR-0327)
1-[4-(4-Chloro-5-methylsulfanyl-6-morpholin-4-yl-pyrimidin-2-yl)-phenyl]-3-(5-morpholin-4-yl-pyridin-2-yl)-urea (MTR-0328)
1-(4-Amino-phenyl)-3-[4-(4-chloro-5-methylsulfanyl-6-morpholin-4-yl-pyrimidin-2-yl)-phenyl]-urea (MTR-0329)
1-tert-Butyl-3-[4-(4-chloro-5-methylsulfanyl-6-morpholin-4-yl-pyrimidin-2-yl)-phenyl]-urea (MTR-0330)
1-[4-(4-Chloro-5-methylsulfanyl-6-morpholin-4-yl-pyrimidin-2-yl)-phenyl]-amino-urea (MTR-0331)
4-(4-Chloro-5-methylsulfanyl-6-morpholin-4-yl-pyrimidin-2-yl)-2-fluoro-phenylamine (MTR-0332)
1-tert-Butylamino-3-[4-(4-chloro-5-methylsulfanyl-6-morpholin-4-yl-pyrimidin-2-yl)-phenyl]-urea (MTR-0333)
1-[4-(5-Methoxy-4-morpholin-4-yl-pyrimidin-2-yl)-phenyl]-3-[5-(4-methyl-piperazin-1-yl)-pyridin-2-yl]-urea (MTR-0334)
1-[4-(5-Methoxy-4-morpholin-4-yl-pyrimidin-2-yl)-phenyl]-3-[4-(3-oxo-morpholin-4-yl)-phenyl]-thiourea (MTR-0335)
[4-(5-Methoxy-4-morpholin-4-yl-pyrimidin-2-yl)-phenyl]-urea (MTR-0336)
1-[4-(5-Methoxy-4-morpholin-4-yl-pyrimidin-2-yl)-phenyl]-3-[4-(4-methyl-piperazin-1-yl)-phenyl]-urea (MTR-0337)
1-[4-(5-Methoxy-4-morpholin-4-yl-pyrimidin-2-yl)-phenyl]-3-[6-(4-methyl-piperazin-1-yl)-pyridin-3-yl]-urea (MTR-0338)
1-Isopropyl-3-[4-(5-methoxy-4-morpholin-4-yl-pyrimidin-2-yl)-phenyl]-urea (MTR-0339)
1-(6-Bromo-pyridin-3-yl)-3-[4-(5-methylsulfanyl-4-morpholin-4-yl-pyrimidin-2-yl)-phenyl]-urea (MTR-0340)
1-Isopropyl-3-[4-(5-methylsulfanyl-4-morpholin-4-yl-pyrimidin-2-yl)-phenyl]-urea (MTR-0341)
1-tert-Butyl-3-[4-(5-methylsulfanyl-4-morpholin-4-yl-pyrimidin-2-yl)-phenyl]-urea (MTR-0342)
1-[4-(2-Dimethylamino-ethoxy)-phenyl]-3-[4-(5-methylsulfanyl-4-morpholin-4-yl-pyrimidin-2-yl)-phenyl]-urea (MTR-0343)
2-{4-[3-(4-Carbamoyl-phenyl)-ureido]-3-fluoro-phenyl}-5-ethoxy-6-morpholin-4-yl-pyrimidine-4-carboxylic acid ethyl ester (MTR-0344)
2-{4-[3-(4-Carbamoyl-phenyl)-ureido]-2-fluoro-phenyl}-5-ethoxy-6-morpholin-4-yl-pyrimidine-4-carboxylic acid ethyl ester (MTR-0345)
1-[4-(4-Chloro-5-methylsulfanyl-6-morpholin-4-yl-pyrimidin-2-yl)-phenyl]-3-(1H-indazol-4-yl)-urea (MTR-0346)
N-(4-{3-[4-(4-Chloro-5-methylsulfanyl-6-morpholin-4-yl-pyrimidin-2-yl)-phenyl]-ureido}-phenyl)-methanesulfonamide (MTR-0347)
1,3-Bis-[4-(4-chloro-5-methylsulfanyl-6-morpholin-4-yl-pyrimidin-2-yl)-phen yl]-urea (MTR-0349)
1-(4-Amino-phenyl)-3-[4-(5-methoxy-4-morpholin-4-yl-pyrimidin-2-yl)-phen yl]-urea (MTR-0350)

4-{3-[4-(5-Methoxy-4-morpholin-4-yl-pyrimidin-2-yl)-phenyl]-ureido}-benzoic acid (MTR-0351)
1-(6-Bromo-pyridin-3-yl)-3-[4-(5-methoxy-4-morpholin-4-yl-pyrimidin-2-yl)-phenyl]-urea (MTR-0352)
1-[4-(5-Methoxy-4-morpholin-4-yl-pyrimidin-2-yl)-phenyl]-3-(6-morpholin-4-yl-pyridin-3-yl)-urea (MTR-0353)
[4-(4-Chloro-5-methylsulfanyl-6-morpholin-4-yl-pyrimidin-2-yl)-2-fluoro-phenyl]-carbamic acid phenyl Ester (MTR-0354)
1-[4-(4-Chloro-5-methylsulfanyl-6-morpholin-4-yl-pyrimidin-2-yl)-2-fluoro-phenyl]-3-[4-(3-oxo-morpholin-4-yl)-phenyl]-urea (MTR-0355)
[4-(4-Chloro-5-methylsulfanyl-6-morpholin-4-yl-pyrimidin-2-yl)-2-fluoro-phenyl]-urea (MTR-0356)
4-(4-Chloro-5-methylsulfanyl-6-morpholin-4-yl-pyrimidin-2-yl)-2-fluoro-phenylamine (MTR-0357)
4-{3-[4-(4-Chloro-5-methylsulfanyl-6-morpholin-4-yl-pyrimidin-2-yl)-phenyl]-ureido}-benzenesulfonamide (MTR-0358)
1-[4-(4-Chloro-5-methylsulfanyl-6-morpholin-4-yl-pyrimidin-2-yl)-3-fluoro-phenyl]-3-[4-(3-oxo-morpholin-4-yl)-phenyl]-urea (MTR-0359)
4-(5-Methylsulfanyl-4-morpholin-4-yl-6-pyridin-4-yl-pyrimidin-2-yl)-phenylamine (MTR-0360)
2-[4-(3-Benzo[1,3]dioxol-5-yl-ureido)-phenyl]-5-ethoxy-6-morpholin-4-yl-pyrimidine-4-carboxylic acid ethyl ester (MTR-0361)
5-Ethoxy-2-{4-[3-(4-ethoxycarbonyl-phenyl)-ureido]-phenyl}-6-morpholin-4-yl-pyrimidine-4-carboxylic acid ethyl ester (MTR-0362)
2-(4-{3-[4-(2-Dimethylamino-ethoxy)-phenyl]-ureido}-phenyl)-5-ethoxy-6-morpholin-4-yl-pyrimidine-4-carboxylic acid ethyl ester (MTR-0363)
4-(3-{4-[5-Ethoxy-4-(morpholine-4-carbonyl)-6-morpholin-4-yl-pyrimidin-2-yl]-phenyl}-ureido)-benzamide (MTR-0364)
5-Ethoxy-2-{4-[3-(4-methanesulfonyl-phenyl)-ureido]-phenyl}-6-morpholin-4-yl-pyrimidine-4-carboxylic acid ethyl ester (MTR-0365)
5-Ethoxy-2-[4-(3-isopropyl-ureido)-phenyl]-6-morpholin-4-yl-pyrimidine-4-carboxylic acid ethyl ester (MTR-0366)
2-[4-(3-tert-Butyl-ureido)-phenyl]-5-ethoxy-6-morpholin-4-yl-pyrimidine-4-carboxylic acid ethyl ester (MTR-0367)
N-(4-{3-[4-(5-Ethoxy-4-morpholin-4-yl-pyrimidin-2-yl)-phenyl]-ureido}-phenyl)-acetamide (MTR-0368)
5-Ethoxy-2-{4-[3-(4-methanesulfonylamino-phenyl)-ureido]-phenyl}-6-morpholin-4-yl-pyrimidine-4-carboxylic acid ethyl ester (MTR-0369)
2-{4-[3-(4-Acetylamino-phenyl)-ureido]-phenyl}-5-ethoxy-6-morpholin-4-yl-pyrimidine-4-carboxylic acid ethyl ester (MTR-0370)
N-(4-{3-[4-(4-Chloro-5-methylsulfanyl-6-morpholin-4-yl-pyrimidin-2-yl)-phenyl]-ureido}-phenyl)-acetamide (MTR-0371)
1-[4-(4-Chloro-5-methylsulfanyl-6-morpholin-4-yl-pyrimidin-2-yl)-phenyl]-3-(2-oxo-2,3-dihydro-benzooxazol-5-yl)-urea (MTR-0372)
6-Chloro-5-methylsulfanyl-4-morpholin-4-yl-[2,5']bipyrimidinyl-2'-ylamine (MTR-0373)
1,3-Bis-[4-(5-methylsulfanyl-4-morpholin-4-yl-pyrimidin-2-yl)-phenyl]-urea (MTR-0374)
3-Fluoro-4-(5-methylsulfanyl-4-morpholin-4-yl-pyrimidin-2-yl)-phenylamine (MTR-0375)
N-(4-{3-[4-(5-Methylsulfanyl-4-morpholin-4-yl-pyrimidin-2-yl)-phenyl]-ureido}-phenyl)-methanesulfonamide (MTR-0376)
N-(3-{3-[4-(5-Methylsulfanyl-4-morpholin-4-yl-pyrimidin-2-yl)-phenyl]-ureido}-phenyl)-acetamide (MTR-0377)
1-[3-Fluoro-4-(5-methylsulfanyl-4-morpholin-4-yl-pyrimidin-2-yl)-phenyl]-3-[4-(3-oxo-morpholin-4-yl)-phenyl]-urea (MTR-0378)
N-(4-{3-[3-Fluoro-4-(5-methylsulfanyl-4-morpholin-4-yl-pyrimidin-2-yl)-phenyl]-ureido}-phenyl)-acetamide (MTR-0379)
N-(4-{3-[4-(5-Methylsulfanyl-4-morpholin-4-yl-pyrimidin-2-yl)-phenyl]-ureido}-phenyl)-acetamide (MTR-0380)
1-[4-(5-Methanesulfonyl-4-morpholin-4-yl-pyrimidin-2-yl)-phenyl]-3-[4-(3-oxo-morpholin-4-yl)-phenyl]-urea (MTR-0381)
1-[4-(5-Methoxy-4-morpholin-4-yl-pyrimidin-2-yl)-phenyl]-3-[4-(morpholine-4-carbonyl)-phenyl]-urea (MTR-0382)
2-Fluoro-4-(5-methoxy-4-morpholin-4-yl-pyrimidin-2-yl)-phenylamine (MTR-0383)
3-Fluoro-4-(5-methoxy-4-morpholin-4-yl-pyrimidin-2-yl)-phenylamine (MTR-0384)
4-{3-[2-Fluoro-4-(5-methoxy-4-morpholin-4-yl-pyrimidin-2-yl)-phenyl]-ureido}-benzamide (MTR-0385)
1-[4-(5-Methoxy-4-morpholin-4-yl-pyrimidin-2-yl)-phenyl]-3-pyridin-2-yl-urea (MTR-0386)
1-[4-(4-Chloro-5-methylsulfanyl-6-morpholin-4-yl-pyrimidin-2-yl)-phenyl]-3-(4-methanesulfonyl-phenyl)-urea (MTR-0387)
[4-(5-Methylsulfanyl-4-morpholin-4-yl-6-pyridin-4-yl-pyrimidin-2-yl)-phenyl]-urea (MTR-0388)
1-(6-Chloro-5-methylsulfanyl-4-morpholin-4-yl-[2,5']bipyrimidinyl-2'-yl)-3-[4-(3-oxo-morpholin-4-yl)-phenyl]-urea (MTR-0389)
[4-(5-Methylsulfanyl-4-morpholin-4-yl-6-pyridin-4-yl-pyrimidin-2-yl)-phenyl]-carbamic acid phenyl ester (MTR-0390)
1-[4-(5-Methylsulfanyl-4-morpholin-4-yl-6-pyridin-4-yl-pyrimidin-2-yl)-phenyl]-3-[4-(3-oxo-morpholin-4-yl)-phenyl]-urea (MTR-0391)
4-{3-[4-(5-Methylsulfanyl-4-morpholin-4-yl-6-pyridin-4-yl-pyrimidin-2-yl)-phenyl]-ureido}-benzamide (MTR-0392)
N-(4-{3-[4-(5-Ethoxy-4-morpholin-4-yl-pyrimidin-2-yl)-phenyl]-ureido}-phenyl)-methanesulfonamide (MTR-0394)
1-[4-(5-Ethoxy-4-morpholin-4-yl-pyrimidin-2-yl)-phenyl]-3-(2-oxo-2,3-dihydro-benzooxazol-5-yl)-urea (MTR-0395)
4-(5-Ethoxy-4-pyridin-4-yl-pyrimidin-2-yl)-phenylamine (MTR-0396)
[4-(5-Ethoxy-4-pyridin-4-yl-pyrimidin-2-yl)-phenyl]-carbamic acid phenyl ester (MTR-0397)
1-[4-(5-Ethoxy-4-pyridin-4-yl-pyrimidin-2-yl)-phenyl]-3-[4-(3-oxo-morpholin-4-yl)-phenyl]-urea (MTR-0398)
1-[4-(5-Ethoxy-4-pyridin-4-yl-pyrimidin-2-yl)-phenyl]-3-phenyl-urea (MTR-0399)
4-{3-[4-(5-Ethoxy-4-pyridin-4-yl-pyrimidin-2-yl)-phenyl]-ureido}-benzamide (MTR-0400)
1-[4-(5-Methanesulfinyl-4-morpholin-4-yl-pyrimidin-2-yl)-phenyl]-3-[4-(3-oxo-morpholin-4-yl)-phenyl]-urea (MTR-0401)

2'-Amino-5-ethoxy-6-morpholin-4-yl-[2,5']bipyrimidinyl-4-carboxylic acid ethyl ester (MTR-0402)
5-Ethoxy-6-morpholin-4-yl-2'-{3-[4-(3-oxo-morpholin-4-yl)-phenyl]-ureido}-[2,5']bipyrimidinyl-4-carboxylic acid ethyl ester (MTR-0403)
1-(4-Methanesulfonyl-phenyl)-3-[4-(5-methylsulfanyl-4-morpholin-4-yl-pyrimidin-2-yl)-phenyl]-urea (MTR-0404)
1-[2-Fluoro-4-(5-methoxy-4-morpholin-4-yl-pyrimidin-2-yl)-phenyl]-3-[4-(3-oxo-morpholin-4-yl)-phenyl]-urea (MTR-0405)
1-[3-Fluoro-4-(5-methoxy-4-morpholin-4-yl-pyrimidin-2-yl)-phenyl]-3-[4-(3-oxo-morpholin-4-yl)-phenyl]-urea (MTR-0406)
4-{3-[3-Fluoro-4-(5-methoxy-4-morpholin-4-yl-pyrimidin-2-yl)-phenyl]-ureido}-benzamide (MTR-0407)
1-[4-(5-Methoxy-4-morpholin-4-yl-pyrimidin-2-yl)-phenyl]-3-pyridin-3-yl-thiourea (MTR-0408)
4-{3-[4-(4-Chloro-5-methylsulfanyl-6-morpholin-4-yl-pyrimidin-2-yl)-2-fluoro-phenyl]-ureido}-benzamide (MTR-0409)
4-{3-[4-(4-Chloro-5-methylsulfanyl-6-morpholin-4-yl-pyrimidin-2-yl)-2-fluoro-phenyl]-ureido}-benzenesulfonamide (MTR-0410)
4-{3-[4-(4-Chloro-5-methylsulfanyl-6-morpholin-4-yl-pyrimidin-2-yl)-3-fluoro-phenyl]-ureido}-benzamide (MTR-0411)
4-{3-[4-(4-Chloro-5-methylsulfanyl-6-morpholin-4-yl-pyrimidin-2-yl)-3-fluoro-phenyl]-ureido}-benzenesulfonamide (MTR-0412)
1-[4-(4-Chloro-5-methylsulfanyl-6-morpholin-4-yl-pyrimidin-2-yl)-phenyl]-3-[4-(4-methanesulfonyl-piperazin-1-yl)-phenyl]-urea (MTR-0413)
N-(5-{3-[4-(4-Chloro-5-methylsulfanyl-6-morpholin-4-yl-pyrimidin-2-yl)-phenyl]-ureido}-pyridin-2-yl)-acetamide (MTR-0415)
2'-[3-(4-Carbamoyl-phenyl)-ureido]-5-ethoxy-6-morpholin-4-yl-[2,5']bipyrimidinyl-4-carboxylic acid ethyl ester (MTR-0417)
2'-[3-(4-Acetylamino-phenyl)-ureido]-5-ethoxy-6-morpholin-4-yl-[2,5']bipyrimidinyl-4-carboxylic acid ethyl ester (MTR-0418)
5-Ethoxy-2-(4-{3-[4-(4-methanesulfonyl-piperazin-1-yl)-phenyl]-ureido}-phenyl)-6-morpholin-4-yl-pyrimidine-4-carboxylic acid ethyl ester (MTR-0419)
1-[4-(5-Ethoxy-4-morpholin-4-yl-pyrimidin-2-yl)-phenyl]-3-[4-(4-methanesulfonyl-piperazin-1-yl)-phenyl]-urea (MTR-0420)
1-[4-(5-Ethoxy-4-morpholin-4-yl-pyrimidin-2-yl)-phenyl]-3-[4-(morpholine-4-carbonyl)-phenyl]-urea (MTR-0421)
1-[4-(5-Ethoxy-4-morpholin-4-yl-pyrimidin-2-yl)-phenyl]-3-(2-oxo-2,3-dihydro-benzooxazol-6-yl)-urea (MTR-0422)
5-Ethoxy-6-morpholin-4-yl-2-{4-[3-(2-oxo-2,3-dihydro-benzooxazol-6-yl)-ureido]-phenyl}-pyrimidine-4-carboxylic acid ethyl ester (MTR-0423)
1-[4-(5-Ethoxy-4-morpholin-4-yl-pyrimidin-2-yl)-phenyl]-3-(4-methanesulfon yl-phenyl)-urea (MTR-0424)
5-(5-Ethoxy-4-morpholin-4-yl-pyrimidin-2-yl)-1,3-dihydro-benzoimidazol-2-one (MTR-0425)
N-(3-{3-[4-(5-Methoxy-4-morpholin-4-yl-pyrimidin-2-yl)-phenyl]-ureido}-phenyl)-acetamide (MTR-0426)
N-(3-Dimethylamino-propyl)-4-{3-[4-(5-methoxy-4-morpholin-4-yl-pyrimidin-2-yl)-phenyl]-ureido}-benzamide (MTR-0427)
5-Methoxy-4-morpholin-4-yl-[2,5']bipyrimidinyl-2'-ylamine (MTR-0428)
4-[3-(5-Methoxy-4-morpholin-4-yl-[2,5']bipyrimidinyl-2'-yl)-ureido]-benzamide (MTR-0429)
1-[4-(4-Methanesulfonyl-piperazin-1-yl)-phenyl]-3-[4-(5-methylsulfanyl-4-morpholin-4-yl-pyrimidin-2-yl)-phenyl]-urea (MTR-0430)
5-Methylsulfanyl-4-morpholin-4-yl-[2,5']bipyrimidinyl-2'-ylamine (MTR-0431)
4-[3-(6-Chloro-5-methylsulfanyl-4-morpholin-4-yl-[2,5']bipyrimidinyl-2'-yl)-ureido]-benzenesulfonamide (MTR-0432)
1-[4-(4-Chloro-5-methylsulfanyl-6-morpholin-4-yl-pyrimidin-2-yl)-phenyl]-3-(2-oxo-2,3-dihydro-benzooxazol-6-yl)-urea (MTR-0433)
1-[4-(4-Chloro-5-methylsulfanyl-6-morpholin-4-yl-pyrimidin-2-yl)-phenyl]-3-[4-(morpholine-4-sulfonyl)-phenyl]-urea (MTR-0435)
1-[4-(4-Chloro-5-methylsulfanyl-6-morpholin-4-yl-pyrimidin-2-yl)-phenyl]-3-[4-(4-dimethylamino-piperidine-1-carbonyl)-phenyl]-urea (MTR-0436)
4-(5-Methylsulfanyl-4-morpholin-4-yl-6-pyridin-3-yl-pyrimidin-2-yl)-phenylamine (MTR-0437)
1-[4-(5-Methylsulfanyl-4-morpholin-4-yl-6-pyridin-3-yl-pyrimidin-2-yl)-phenyl]-3-phenyl-urea (MTR-0438)
1-[4-(5-Methylsulfanyl-4-morpholin-4-yl-6-pyridin-3-yl-pyrimidin-2-yl)-phenyl]-3-phenyl-thiourea (MTR-0440)
N-(5-{3-[4-(5-Ethoxy-4-morpholin-4-yl-pyrimidin-2-yl)-phenyl]-ureido}-pyridin-2-yl)-acetamide (MTR-0442)
2-{4-[3-(6-Acetylamino-pyridin-3-yl)-ureido]-phenyl}-5-ethoxy-6-morpholin-4-yl-pyrimidine-4-carboxylic acid ethyl ester (MTR-0443)
N-[3-(5-Ethoxy-4-morpholin-4-yl-pyrimidin-2-yl)-phenyl]-methanesulfonamide (MTR-0444)
N-[3-(5-Ethoxy-4-morpholin-4-yl-pyrimidin-2-yl)-phenyl]-2,4-difluoro-benzenesulfonamide (MTR-0445)
1-[4-(5-Ethoxy-4-morpholin-4-yl-pyrimidin-2-yl)-phenyl]-3-pyridin-4-yl-urea (MTR-0446)
1-[4-(5-Ethoxy-pyridin-3-yl-pyrimidin-2-yl)-phenyl]-3-[4-(3-oxo-morpholin-4-yl)-phenyl]-urea (MTR-0447)
4-(5-Methoxy-4-pyridin-4-yl-pyrimidin-2-yl)-phenylamine (MTR-0448) N-(4-{3-[4-(5-Methoxy-4-morpholin-4-yl-pyrimidin-2-yl)-phenyl]-ureido}-phenyl)-methanesulfonamide (MTR-0449)
1-[4-(5-Methoxy-4-morpholin-4-yl-pyrimidin-2-yl)-phenyl]-3-(2-oxo-2,3-dihydro-benzooxazol-6-yl)-urea (MTR-0450)
1-(5-Methoxy-4-morpholin-4-yl-[2,5']bipyrimidinyl-2'-yl)-3-[4-(3-oxo-morpholin-4-yl)-phenyl]-urea (MTR-0451)
1-[4-(5-Ethoxy-4-morpholin-4-yl-pyrimidin-2-yl)-phenyl]-3-[4-(morpholine-4-sulfonyl)-phenyl]-urea (MTR-0452)
1-[4-(5-Methylsulfanyl-4-morpholin-4-yl-6-pyridin-4-yl-pyrimidin-2-yl)-phen yl]-3-pyridin-4-yl-urea (MTR-0453)
1-[4-(Morpholine-4-carbonyl)-phenyl]-3-{4-[4-morpholin-4-yl-5-(2-morpholin-4-yl-ethoxy)-pyrimidin-2-yl]-phenyl}-urea (MTR-0454)
1-{4-[4-Morpholin-4-yl-5-(2-morpholin-4-yl-ethoxy)-pyrimidin-2-yl]-phenyl}-3-[4-(3-oxo-morpholin-4-yl)-phenyl]-urea (MTR-0455)
4-(3-{4-[4-Morpholin-4-yl-5-(2-morpholin-4-yl-ethoxy)-pyrimidin-2-yl]-phenyl}-ureido)-benzamide (MTR-0456)

1-[4-(5-Methylsulfanyl-4-morpholin-4-yl-6-pyridin-3-yl-pyrimidin-2-yl)-phenyl]-3-[4-(3-oxo-morpholin-4-yl)-phenyl]-urea (MTR-0457)
1-[4-(5-Methylsulfanyl-4-morpholin-4-yl-pyrimidin-2-yl)-phenyl]-3-(2-oxo-2,3-dihydro-benzooxazol-6-yl)-urea (MTR-0459)
4-(4-Chloro-5-methoxy-6-morpholin-4-yl-pyrimidin-2-yl)-phenylamine (MTR-0460)
1-[4-(5-Methylsulfanyl-4-morpholin-4-yl-pyrimidin-2-yl)-phenyl]-3-[4-(morpholine-4-carbonyl)-phenyl]-urea (MTR-0461)
1-[4-(5-Methylsulfanyl-4-morpholin-4-yl-pyrimidin-2-yl)-phenyl]-3-pyridin-4-yl-urea (MTR-0462)
N-(4-{3-[4-(5-Methylsulfanyl-4-morpholin-4-yl-6-pyridin-3-yl-pyrimidin-2-yl)-phenyl]-ureido}-phenyl)-methanesulfonamide (MTR-0463)
1-[4-(5-Methylsulfanyl-4-morpholin-4-yl-6-pyridin-3-yl-pyrimidin-2-yl)-phenyl]-3-pyridin-3-yl-urea (MTR-0464)
1-[4-(5-Methylsulfanyl-4-morpholin-4-yl-6-pyridin-4-yl-pyrimidin-2-yl)-phen yl]-3-phenyl-urea (MTR-0465)
4-(5-Methylsulfanyl-2,6-di-pyridin-3-yl-pyrimidin-4-yl)-morpholine (MTR-0466)
N-[3-(4-Chloro-5-methylsulfanyl-6-morpholin-4-yl-pyrimidin-2-yl)-phenyl]-methanesulfonamide (MTR-0467)
1-[4-(5-Methylsulfanyl-4-morpholin-4-yl-6-pyridin-4-yl-pyrimidin-2-yl)-phenyl]-3-phenyl-thiourea (MTR-0468)
1-[4-(4-Chloro-5-methylsulfanyl-6-morpholin-4-yl-pyrimidin-2-yl)-phenyl]-3-pyridin-4-yl-urea (MTR-0469)
1-(4-Methanesulfonyl-phenyl)-3-[4-(5-methoxy-4-morpholin-4-yl-pyrimidin-2-yl)-phenyl]-urea (MTR-0470)
1-[4-(5-Methoxy-4-morpholin-4-yl-pyrimidin-2-yl)-phenyl]-3-[4-(morpholine-4-sulfonyl)-phenyl]-urea (MTR-0471)
1-[4-(5-Methoxy-4-morpholin-4-yl-pyrimidin-2-yl)-phenyl]-3-pyridin-4-yl-urea (MTR-0472)
1-[4-(5-Methoxy-4-pyridin-4-yl-pyrimidin-2-yl)-phenyl]-3-[4-(morpholine-4-carbonyl)-phenyl]-urea (MTR-0473)
1-[4-(5-Methoxy-4-pyridin-4-yl-pyrimidin-2-yl)-phenyl]-3-[4-(3-oxo-morpholin-4-yl)-phenyl]-urea (MTR-0474)
1-[4-(4-Chloro-5-methoxy-6-morpholin-4-yl-pyrimidin-2-yl)-phenyl]-3-pyridin-4-yl-urea (MTR-0476)
1-Ethyl-3-[4-(5-methylsulfanyl-4-morpholin-4-yl-6-pyridin-4-yl-pyrimidin-2-yl)-phenyl]-urea (MTR-0477)
1-Methyl-3-[4-(5-methylsulfanyl-4-morpholin-4-yl-6-pyridin-4-yl-pyrimidin-2-yl)-phenyl]-urea (MTR-0478)
1-Isopropyl-3-[4-(5-methylsulfanyl-4-morpholin-4-yl-6-pyridin-4-yl-pyrimidin-2-yl)-phenyl]-urea (MTR-0479)
1-[4-(5-Methoxy-4-pyridin-4-yl-pyrimidin-2-yl)-phenyl]-3-pyridin-4-yl-urea (MTR-0480)
1-{4-[4-Morpholin-4-yl-5-(2-morpholin-4-yl-ethoxy)-pyrimidin-2-yl]-phenyl}-3-pyridin-4-yl-urea (MTR-0481)
4-(5-Methoxy-4-morpholin-4-yl-6-pyridin-4-yl-pyrimidin-2-yl)-phenylamine (MTR-0482)
4-(5-Methoxy-4-morpholin-4-yl-6-(4-aminophenyl-pyrimidin-2-yl)-phenylamine (MTR-0483)
1-[4-(4-Chloro-5-methylsulfanyl-6-morpholin-4-yl-pyrimidin-2-yl)-phenyl]-3-isoxazol-3-yl-urea (MTR-0484)
1-Isoxazol-3-yl-3-[4-(5-methylsulfanyl-4-morpholin-4-yl-6-pyridin-4-yl-pyrimidin-2-yl)-phenyl]-urea (MTR-0485)
N-(5-{3-[4-(5-Methoxy-4-morpholin-4-yl-pyrimidin-2-yl)-phenyl]-ureido}-pyridin-2-yl)-acetamide (MTR-0486)
1-[4-(4-Methanesulfonyl-piperazin-1-yl)-phenyl]-3-[4-(5-methoxy-4-morpholin-4-yl-pyrimidin-2-yl)-phenyl]-urea (MTR-0487)
1-[4-(4-Chloro-5-ethoxy-6-morpholin-4-yl-pyrimidin-2-yl)-phenyl]-3-pyridin-4-yl-urea (MTR-0488)
1-[4-(4-Chloro-5-ethoxy-6-morpholin-4-yl-pyrimidin-2-yl)-phenyl]-3-pyridin-3-yl-urea (MTR-0489)
1-[4-(5-Ethoxy-4-morpholin-4-yl-6-pyridin-3-yl-pyrimidin-2-yl)-phenyl]-3-pyridin-4-yl-urea (MTR-0490)
1-[4-(5-Ethoxy-4-morpholin-4-yl-6-pyridin-3-yl-pyrimidin-2-yl)-phenyl]-3-pyridin-3-yl-urea (MTR-0491)
1-[4-(5-Ethoxy-4-morpholin-4-yl-6-pyridin-4-yl-pyrimidin-2-yl)-phenyl]-3-pyridin-4-yl-urea (MTR-0492)
1-[4-(5-Ethoxy-4-morpholin-4-yl-6-pyridin-4-yl-pyrimidin-2-yl)-phenyl]-3-pyridin-3-yl-urea (MTR-0493)
1-[4-(4-Chloro-5-ethoxy-6-morpholin-4-yl-pyrimidin-2-yl)-phenyl]-3-[4-(3-oxo-morpholin-4-yl)-phenyl]-urea (MTR-0494)
1-[4-(5-Ethoxy-4-morpholin-4-yl-6-pyridin-4-yl-pyrimidin-2-yl)-phenyl]-3-[4-(3-oxo-morpholin-4-yl)-phenyl]-urea (MTR-0495)
1-[4-(5-Ethoxy-4-morpholin-4-yl-6-pyridin-3-yl-pyrimidin-2-yl)-phenyl]-3-[4-(3-oxo-morpholin-4-yl)-phenyl]-urea (MTR-0496)
1-[4-(5-Methoxy-4-morpholin-4-yl-6-pyridin-3-yl-pyrimidin-2-yl)-phenyl]-3-pyridin-3-yl-urea (MTR-0497)
1-[4-(5-Methoxy-4-morpholin-4-yl-6-pyridin-4-yl-pyrimidin-2-yl)-phenyl]-3-pyridin-4-yl-urea (MTR-0498)
1-[4-(5-Methoxy-4-morpholin-4-yl-6-pyridin-4-yl-pyrimidin-2-yl)-phenyl]-3-pyridin-3-yl-urea (MTR-0499)
1-[4-(4-Chloro-5-methoxy-6-morpholin-4-yl-pyrimidin-2-yl)-phenyl]-3-[4-(3-oxo-morpholin-4-yl)-phenyl]-urea (MTR-0500)
1-[4-(5-Methoxy-4-morpholin-4-yl-6-pyridin-4-yl-pyrimidin-2-yl)-phenyl]-3-[4-(3-oxo-morpholin-4-yl)-phenyl]-urea (MTR-0501)
1-[4-(5-Methoxy-4-morpholin-4-yl-6-pyridin-3-yl-pyrimidin-2-yl)-phenyl]-3-[4-(3-oxo-morpholin-4-yl)-phenyl]-urea (MTR-0502)
1-[4-(4-Chloro-5-methoxy-6-morpholin-4-yl-pyrimidin-2-yl)-phenyl]-3-isoxazol-3-yl-urea (MTR-0503)
1-Isoxazol-3-yl-3-[4-(5-methoxy-4-morpholin-4-yl-6-pyridin-4-yl-pyrimidin-2-yl)-phenyl]-urea (MTR-0504)
1-[4-(4-Chloro-5-ethoxy-6-morpholin-4-yl-pyrimidin-2-yl)-phenyl]-3-isoxazol-3-yl-urea (MTR-0505)
1-[4-(5-Ethoxy-4-morpholin-4-yl-6-pyridin-4-yl-pyrimidin-2-yl)-phenyl]-3-isoxazol-3-yl-urea (MTR-0506)
1-Isoxazol-3-yl-3-[4-(5-methoxy-4-morpholin-4-yl-6-pyridin-3-yl-pyrimidin-2-yl)-phenyl]-urea (MTR-0507)
1-[4-(5-Ethoxy-4-morpholin-4-yl-6-pyridin-3-yl-pyrimidin-2-yl)-phenyl]-3-isoxazol-3-yl-urea (MTR-0508) and
1-Isoxazol-3-yl-3-[4-(5-methylsulfanyl-4-morpholin-4-yl-6-pyridin-3-yl-pyrimidin-2-yl)-phenyl]-urea (MTR-0509)

or a stereoisomer, or a tautomer, or an N-oxide, or a pharmaceutically acceptable salt, or an ester, or a prodrug, or a hydrate, or a solvate thereof.

7. A method according to claim 6, wherein the mTOR kinase-/PI3K kinase-related disease is selected from cancer, immune disorders, cardiovascular disease, viral infection, inflammation, metabolism/endocrine function disorders and neurological disorders.

8. A method according to claim 7, wherein the cancer is a Epidermal Growth Factor Receptor (EGFR) dependent cancer or a cancer that resists to EGFR targeting agent.

9. A method according to claim 6, which comprises administering to the subject a further therapeutic agent.

10. A method according to claim 9, wherein the further therapeutic agent is a protein kinase inhibitor, an antibody, an alkylating agent, a mitotic inhibitor, an antimetabolite, a cell cycle inhibitor, an enzyme, a hormone, an anti-hormone, a growth-factor inhibitor, a plant alkaloid and terpenoid, a topoisomerase inhibitor, an antitumor antibiotic, a vinca alkaloid, a taxane, a platinum agent, a thalidomide or relative analog, an antiangiogenic agent, or a combination thereof.

\* \* \* \* \*